(12) United States Patent
Lee et al.

(10) Patent No.: US 9,650,379 B2
(45) Date of Patent: May 16, 2017

(54) AZAINDOLE DERIVATIVES AS SELECTIVE HISTONE DEACETYLASE (HDAC) INHIBITORS AND PHARMACEUTICAL COMPOSITIONS COMPRISING THE SAME

(71) Applicant: CHONG KUN DANG PHARMACEUTICAL CORP., Seoul (KR)

(72) Inventors: Changsik Lee, Gyeonggi-do (KR); Hyun-Mo Yang, Gyeonggi-do (KR); Changkon Lee, Gyeonggi-do (KR); Miseon Bae, Gyeonggi-do (KR); Soyoung Kim, Gyeonggi-do (KR); Youngil Choi, Gyeonggi-do (KR); Nina Ha, Gyeonggi-do (KR); Jaekwang Lee, Gyeonggi-do (KR); Jungtaek Oh, Gyeonggi-do (KR); Hyeseung Song, Gyeonggi-do (KR); Ilhyang Kim, Gyeonggi-do (KR); Daekyu Choi, Gyeonggi-do (KR); Jaeki Min, Gyeonggi-do (KR); Hyojin Lim, Gyeonggi-do (KR); Daekwon Bae, Gyeonggi-do (KR)

(73) Assignee: CHONG KUN DANG PHARMACEUTICAL CORP., Seoul (KR)

( * ) Notice: Subject to any disclaimer, the term of this patent is extended or adjusted under 35 U.S.C. 154(b) by 0 days.

(21) Appl. No.: 15/103,597

(22) PCT Filed: Dec. 12, 2014

(86) PCT No.: PCT/IB2014/002768
§ 371 (c)(1),
(2) Date: Jun. 10, 2016

(87) PCT Pub. No.: WO2015/087151
PCT Pub. Date: Jun. 18, 2015

(65) Prior Publication Data
US 2016/0289230 A1 Oct. 6, 2016

(30) Foreign Application Priority Data
Dec. 12, 2013 (KR) .................. 10-2013-0154455

(51) Int. Cl.
C07D 471/06 (2006.01)
A61K 31/437 (2006.01)
C07D 471/04 (2006.01)
C07D 519/00 (2006.01)

(52) U.S. Cl.
CPC ......... *C07D 471/04* (2013.01); *C07D 519/00* (2013.01)

(58) Field of Classification Search
CPC .................................................. C07D 471/06

USPC .................. 546/113; 544/127; 514/300, 254
See application file for complete search history.

(56) References Cited

U.S. PATENT DOCUMENTS

RE38,506 E    4/2004   Breslow et al.

FOREIGN PATENT DOCUMENTS

| EP | 0 847 992 A1 | 6/1998 |
|---|---|---|
| WO | 02/22577 A2 | 3/2002 |
| WO | 02/30879 A2 | 4/2002 |
| WO | 2004/069823 A1 | 8/2004 |
| WO | 2013/052110 A1 | 4/2013 |
| WO | 2013/062344 A1 | 5/2013 |
| WO | 2013/078544 A1 | 6/2013 |

OTHER PUBLICATIONS

International Search Report dated Apr. 8, 2015 for Application No. PCT/IB2014/002768.
Bieliauskas, A.V., et al., "Isoform-selective histone deacetylase inhibitors", Chem. Soc. Rev., 37, 1402-1413, 2008.
Nagma Khan, et al., "Determination of the class and isoform selectivity of small-molecule histone deacetylase inhibitors", Biochem. J., 409,581-589, 2008.
Supriyo Saha et al., "Hydroxamic acid—A novel molecule for anticancer therapy", Journal of Advanced Pharmaceutical Technology & Research, 3, Issue 2, 92-99, Apr.-Jun. 2012.
Brian D. Strahl et al., "The language of covalent histone modifications", Nature 403, 41-45, 2000.
Paul A. Marks et al., "Histone Deacetylases and Cancer: Causes and Therapies", Nature Cancer Rev. 1, 194-202, 2001.
Emanuele, Sonia et al., "Histone deacetylase inhibitors: Apoptotic effects and clinical implications (Review)", International Journal of Oncology 33, 637-646, 2008.
Paul A. Marks et. al., "Histone deacetylase inhibitors as new cancer drugs", Curr Opin. Oncology 13, 477-483, 2001.
Ricky W. Johnstone, "Histone-Deacetylase Inhibitors: Novel Drugs for the Treatment of Cancer", Nat. Rev. Drug. Discov. 1, 287-299, 2002.
Patricia Maiso, et al., "The Histone Deacetylase Inhibitor LBH589 is a Potent Antimyeloma Agent that Overcomes Drug Resistance", Cancer Res 66, 5781-5789, 2006.
Milos Dokmanovic, et al., "Histone Deacetylase Inhibitors: Overview and Perspectives", Mol Cancer Res, 5, 981-989, 2007.

*Primary Examiner* — Charanjit Aulakh
(74) *Attorney, Agent, or Firm* — Ladas & Parry LLP

(57) ABSTRACT

The present invention relates to novel azaindole derivatives, and more particularly, to novel azaindole derivatives having histone deacetylase (HDAC) inhibitory activity, isomers thereof, pharmaceutically acceptable salts thereof, hydrates thereof or solvates thereof, the use thereof for the preparation of pharmaceutical compositions, pharmaceutical compositions containing the same, a method of treating disease using the pharmaceutical compositions, and methods for preparing the novel azaindole derivatives. The novel azaindole derivatives according to the present invention are selective histone deacetylase (HDAC) inhibitors, and may be used as agents for treating malignant tumor diseases, inflammatory diseases, rheumatoid arthritis, and neurodegenerative diseases.

14 Claims, 4 Drawing Sheets

AZAINDOLE DERIVATIVES AS SELECTIVE HISTONE DEACETYLASE (HDAC) INHIBITORS AND PHARMACEUTICAL COMPOSITIONS COMPRISING THE SAME

This application is a 371 of PCT/IB2014/002768, filed on Dec. 12, 2014, which claims priority to Korean patent application number 10-2013-0154455, filed on Dec. 12, 2013.

TECHNICAL FIELD

The present invention relates to novel azaindole derivatives, and more particularly, to novel azaindole derivatives having histone deacetylase (HDAC) inhibitory activity, isomers thereof, pharmaceutically acceptable salts thereof, hydrates thereof or solvates thereof, the use thereof for the preparation of pharmaceutical compositions, pharmaceutical compositions containing the same, a method of treating disease using the pharmaceutical compositions, and methods for preparing the novel azaindole derivatives.

BACKGROUND ART

Compounds according to the present invention are used to inhibit or treat HDAC-mediated diseases. Examples of such diseases include, but are not limited to, cell proliferative diseases such as cancer, autosomal dominant diseases such as Huntington's disease, genetic metabolic diseases such as fibrosis diseases, for example, cystic fibrosis, hepatic fibrosis, kidney fibrosis, pulmonary fibrosis and skin fibrosis, autoimmune diseases such as rheumatoid arthritis, acute/chronic neurological diseases such as diabetes, stroke, hypertrophy such as cardiac hypertrophy, congestive heart failure, amyotrophic lateral sclerosis, glaucoma, ocular diseases (associated with angiogenesis), or Alzheimer's disease.

Transcriptional regulation in cells is a complex biological process. One basic principle in transcriptional regulation is based on the posttranslational modification of histone proteins, namely histone proteins H2A/B, H3 and H4 forming the octameric histone core complex. The complex N-terminal modifications at lysine residues by acetylation or methylation and at serine residues by phosphorylation constitute part of the so called "histone code" (see Strahl & Ellis, Nature 403, 41-45, 2000).

In a simple model, acetylation of positively charged lysine residues reduces affinity to negatively charged DNA, which now becomes accessible for the entry of transcription factors.

Histone acetylation and deacetylation is catalyzed by histone acetyltransferases (HATs) and histone deacetylases (HDACs), respectively. HDACs are associated with transcriptional repressor complexes, switching chromatin to a silence structure, transcriptionally inactive. (see Marks et al., Nature cancer Rev. 1, 194-202, 2001). The opposite is activated by HATs which are associated with transcriptional activator complexes. Three different classes of HDACs have been known so far, namely class I (HDAC 1-3, 8; Mr=42-55 kDa) primarily located in the nucleus and sensitive toward inhibition by Trichostatin A (TSA), class II (HDAC 4-7, 9, 10; Mr=120-130 kDa), which exhibits TSA sensitivity, and class III (SIRT2) that are distinct by their NAD+ dependency and TSA insensitivity.

Histone deacetylase (HDAC) inhibitors constitute a new class of anti-cancer drugs having cell differentiation and apoptosis inducing activity. By targeting histone deacetylases (HDACs), HDAC inhibitors affect Chromatin structure by histone acetylation, inducing reprogramming of a complex transcription, for example, reactivation of tumor suppressor genes and repression of oncogenes. Besides acetylate the N-terminal lysine residue in core histone protein, HDAC inhibitors target non-histone protein, important for cancer biology, including heat-shock-protein 90 (HSP90), tubulin or the p53 tumor suppressor protein. Thus, the medical use of HDAC inhibitors might not be restricted to cancer therapy, since efficacy in animal models for inflammatory diseases, rheumatoid arthritis and neurodegeneration has been shown.

HDAC inhibitors known up to now can be classified according to their structure into four categories: 1) short-chain fatty acids (butyric acid and valproic acid); 2) hydroxamic acids (trichostatin A, SAHA, and LBH-589); 3) cyclic peptides (desipeptide); and 4) benzamides (MS-275, and MGCD-0103) (Emanuele et. al., International Journal of Oncology 33, 637-646, 2008). These many histone deacetylase (HDAC) inhibitors (SAHA, LBH-589 and MS-275 etc.) inhibit cell growth, and effectively induce cell differentiation and apoptosis of various transformed cells not only in culture media but also in animal models (Paul A. Marks et. al., Curr Opin. Oncol. 13, 477-483, 2001). Therefore, HDAC inhibitors such as SAHA, LBH-589 and MS-275 have been assessed in clinical studies for the purpose of treating various cancers (Johnstone. R. W, Nat. Rev. Drug. Discov. 1, 287-299, 2002). Representative compounds, currently known as HDAC inhibitors, include SAHA (U.S. Reissue Pat. No. 38506, Zolinza, Vorinostat), PXD101 (WO 02/30879, Belinostat) and LBH-589 (WO 02/22577, Panobinostat), which are hydroxamate compounds, and MS-275 (EP Patent No. 0847992 Entinostat) and MGCD0103 (WO 04/69823, Mocetinostat), which are benzamide compounds. Among these compounds, SAHA was approved on October 2006 and has been used as an agent for treating CTCL (cutaneous T-cell lymphoma), and indications thereof have been expanded additionally, but it is known that SAHA is insufficient in terms of efficacy and side effects (Maiso et al., Cancer Res 66, 5781-5789, 2006).

Although many HDAC inhibitors have been reported to date, there has been a need for effective HDAC inhibitors that are more efficacious and have less side effects (Dokmanovic, et al. Mol Cancer Res, 5, 981-989, 2007).

DISCLOSURE

Technical Problem

An object of the present invention is to provide novel azaindole derivatives, particularly novel azaindole derivatives having histone deacetylase (HDAC) inhibitory activity, isomers thereof, pharmaceutically acceptable salts thereof, hydrates thereof, or solvates thereof.

Another object of the present invention is to provide the use of novel azaindole derivatives, particularly novel azaindole derivatives having histone deacetylase (HDAC) inhibitory activity, isomers thereof, pharmaceutically acceptable salts thereof, hydrates thereof, or solvates thereof, for the preparation of pharmaceutical compositions, pharmaceutical compositions containing the same, and a method of treating disease using the composition.

Still another object of the present invention is to provide methods for preparing novel azaindole derivatives.

Technical Solution

Novel HDAC Inhibitor Compounds

To achieve the above objects, the present invention provides azaindole derivatives represented by formula I below, isomers thereof, pharmaceutically acceptable salts thereof, hydrates thereof, or solvates thereof.

In a first embodiment of the present invention, the compound of formula I is as follows:

Formula I

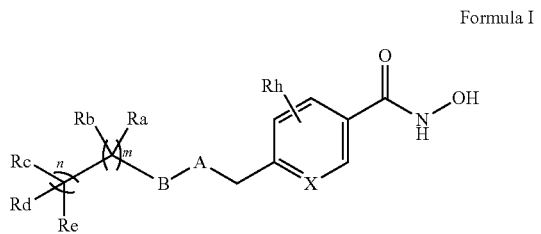

wherein

X is C or N;

Rh is hydrogen, halogen, —$CF_3$, or —$C_{1-5}$ alkyl;

A is selected from the group consisting of

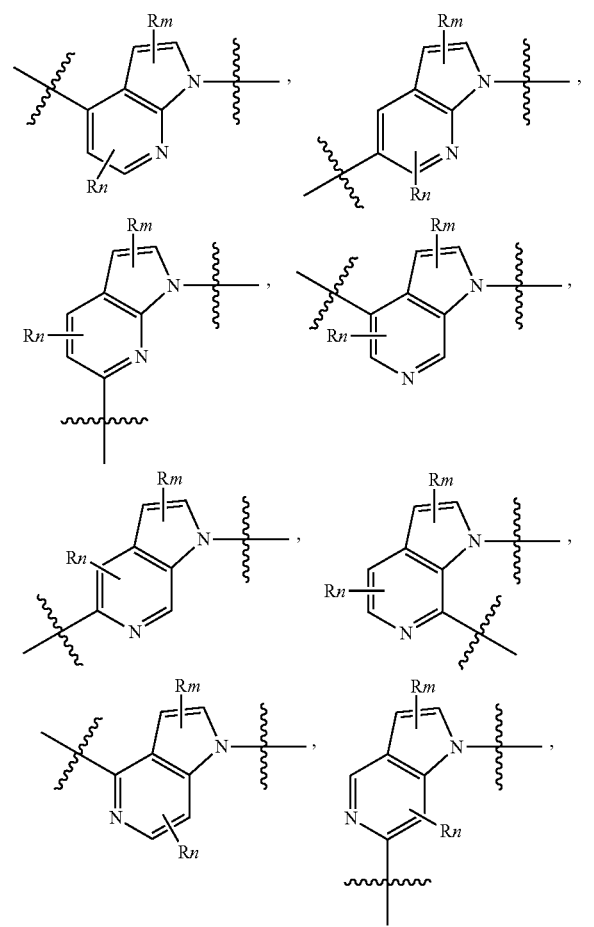

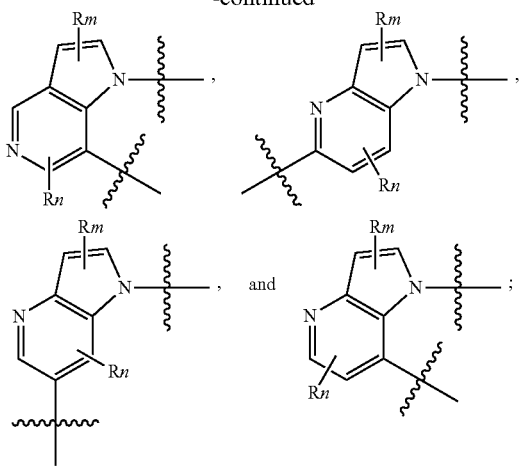

Rm and Rn are each independently hydrogen, halogen, $C_{1-5}$ alkyl, or $C_{3-12}$ cycloalkyl, wherein the $C_{1-5}$ alkyl and $C_{3-12}$ cycloalkyl may each independently be unsubstituted or substituted with halogen, —CN, —$OC_{1-5}$ alkyl or —$C_{1-5}$ alkyl at one or more hydrogen atoms thereof;

B is selected from the group consisting of

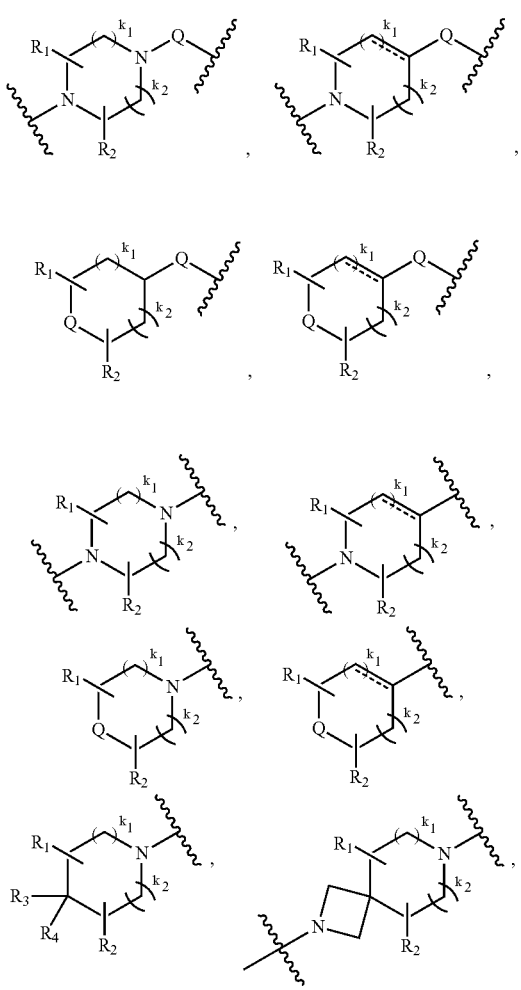

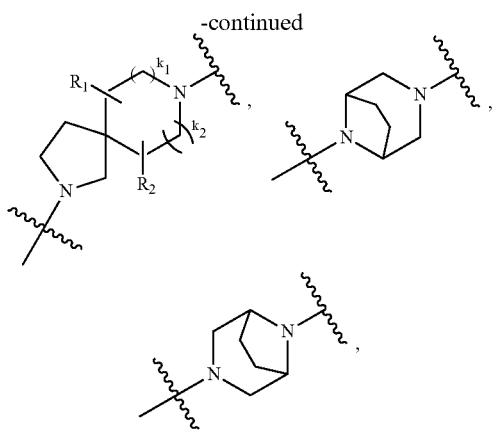

aryl, heteroaryl, $C_{3-12}$ cycloalkyl, and $C_{3-12}$ cycloalkenyl, wherein the aryl, heteroaryl, $C_{3-12}$ cycloalkyl and $C_{3-12}$ cycloalkenyl may each independently be unsubstituted or substituted with halogen, —$C_{1-5}$ alkyl, —$NH_2$, —OH, —$OC_{1-5}$ alkyl or —$CF_3$ at one or more hydrogen atoms thereof, and the dotted line denotes a single or double bond;

Q is aryl, heteroaryl, —$C_{1-5}$ alkyl-aryl, —O-aryl, —$NR_5$-aryl, —$C_{1-5}$ alkyl-heteroaryl, —O-heteroaryl or —$NR_5$-heteroaryl, wherein the aryl and heteroaryl may each independently be unsubstituted or substituted with halogen, —$C_{1-5}$ alkyl, —$NH_2$, —OH, —$OC_{1-5}$ alkyl, —$CF_3$, —$NHC_{1-5}$ alkyl, —$N(C_{1-5}$ alkyl$)_2$ or —$NHSO_2C_{1-5}$ alkyl at one or more carbon atoms thereof;

$R_1$ and $R_2$ are each independently hydrogen, halogen, —$C_{1-5}$ alkyl, —$NH_2$, —OH, —$OC_{1-5}$ alkyl or —$CF_3$;

$R_3$ and $R_4$ are each independently hydrogen, halogen, —$CF_3$, —$C_{1-5}$ alkyl, or —NHCO(O)$C_{1-5}$ alkyl;

$R_5$ is hydrogen or —$C_{1-5}$ alkyl;

$k_1$ and $k_2$ are each independently 0, 1 or 2;

Ra and Rb are each independently hydrogen, halogen, —$C_{1-5}$ alkyl, —$OC_{1-5}$ alkyl, —$C_{3-12}$ cycloalkyl, =O, or —$SO_2$, provided that if any one of Ra and Rb is =O or —$SO_2$, the other one is null, wherein the —$C_{1-5}$ alkyl and —$C_{3-12}$ cycloalkyl may each independently be unsubstituted or substituted with halogen, —CN, —$OC_{1-5}$ alkyl or —$C_{1-5}$ alkyl at one or more hydrogen atoms thereof;

m is 0, 1 or 2;

Rc and Rd are each independently hydrogen, halogen, =O, —$C_{1-5}$ alkyl, —$C_{3-12}$ cycloalkyl, —CO(O)$C_{1-5}$ alkyl, —$C_{1-5}$ alkyl-OH, aryl or heteroaryl, or are linked together to form —$C_{3-12}$ cycloalkyl, provided that if any one of Rc and Rd is =O, the other one is null, wherein the aryl, heteroaryl and $C_{3-12}$ cycloalkyl may each independently be unsubstituted or substituted with halogen, —$CF_3$, —$C_{1-5}$ alkyl or —$OC_{1-5}$ alkyl at one or more hydrogen atoms thereof;

n is 0, 1 or 2; and

Re is hydrogen, halogen, —$CF_3$, —$C_{1-3}$ perfluoroalkyl, —$C_{1-5}$ alkyl, —$OC_{1-5}$ alkyl, —$C_{2-12}$ heterocycloalkyl, —$C_{3-12}$ cycloalkyl, aryl, heteroaryl, —OH, —COOH, —$NH_2$, —$NHC_{1-5}$ alkyl, —$N(C_{1-5}$ alkyl$)_2$, or null, wherein the —$C_{1-5}$ alkyl, —$C_{2-12}$ heterocycloalkyl, —$C_{3-12}$ cycloalkyl, aryl and heteroaryl may each independently be unsubstituted or substituted with halogen, —CN, —$CF_3$, —$OC_{1-5}$ alkyl, —$C_{1-5}$ alkyl, —CO(O)$C_{1-5}$ alkyl, —$C_{2-12}$ heterocycloalkyl, —$C_{1-5}$ alkyl-$C_{2-12}$ heterocycloalkyl, or heteroaryl at one or more hydrogen atoms thereof.

In another embodiment of the present invention, A in formula I may be selected from the group consisting of

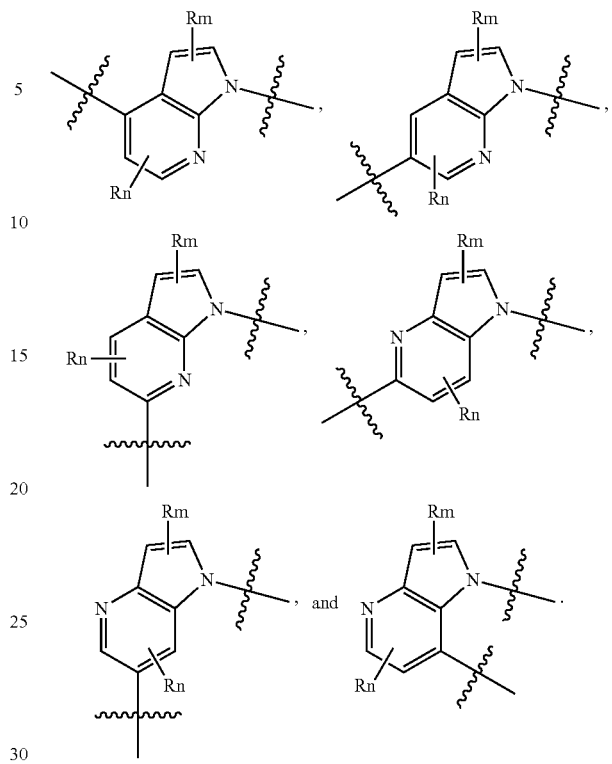

In preferable embodiment of the present invention, A in formula I may be selected from the group consisting of

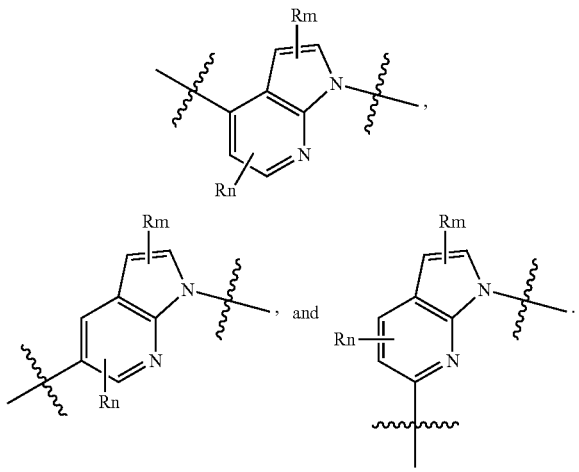

In still another embodiment of the present invention, B in formula I may be selected from the group consisting of

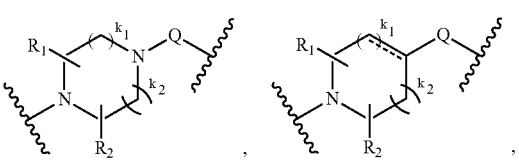

-continued
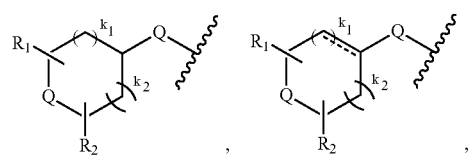
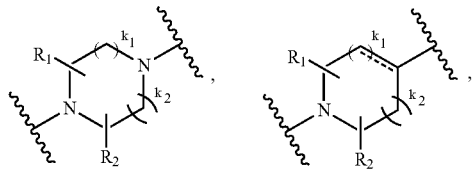
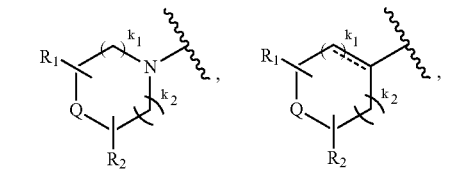

In preferable embodiment of the present invention, B in formula I may be selected from the group consisting of
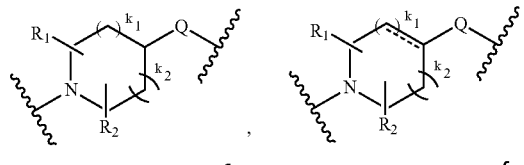
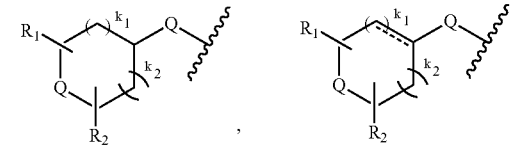
-continued
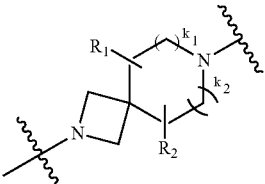
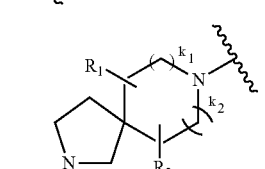
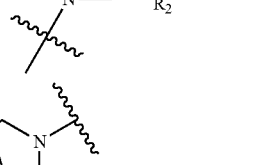
, and
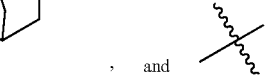
In still another embodiment of the present invention,
X is C;
Rh is hydrogen;
A is selected from the group consisting of
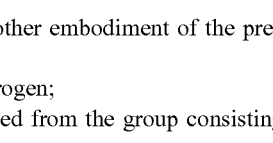
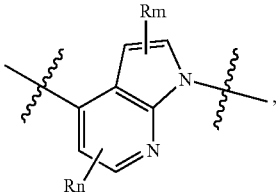
and
B is selected from the group consisting of
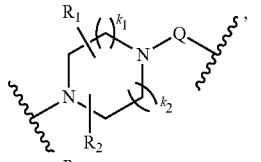
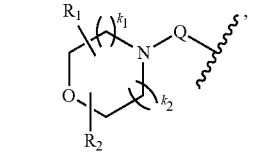

-continued

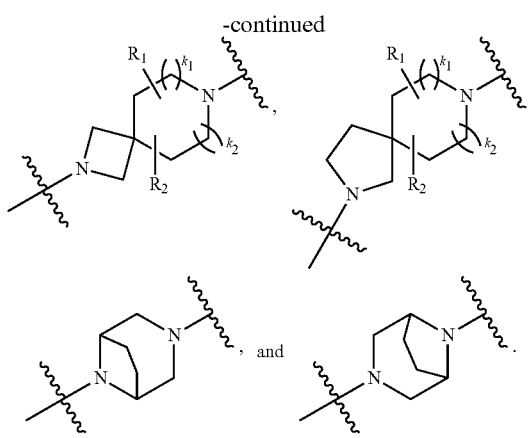

In still another embodiment of the present invention, Ra and Rb are each independently hydrogen or —C$_{1-5}$ alkyl;

m is 0 or 1;
Rc and Rd are each independently hydrogen, —C$_{1-5}$ alkyl, or are linked together to form —C$_{3-12}$ cycloalkyl;
n is 0 or 1; and
Re is hydrogen, halogen, —CF$_3$, —C$_{1-5}$ alkyl, —OH, aryl, or heteroaryl wherein the aryl, or heteroaryl may each independently be unsubstituted or substituted with halogen, —CF$_3$, —OC$_{1-5}$ alkyl, —C$_{2-12}$ heterocycloalkyl, or alkyl-C$_{2-12}$ heterocycloalkyl at one or more hydrogen atoms thereof.

In the present invention, aryl is preferably substituted or unsubstituted phenyl; heteroaryl is substituted or unsubstituted pyridine, pyrimidine, quinoline, pyrazine, pyridazine, pyrrole or pyrazole; C$_{3-12}$ cycloalkyl is substituted or unsubstituted cyclopropyl, cyclobutyl or cyclohexene; and C$_{3-12}$ heterocycloalkyl is substituted or unsubstituted piperidine, morpholine, piperazine or indazole, but the compounds of the present invention are not limited to these examples.

In still another embodiment, the compound of formula I may be selected from the group consisting of the compounds shown in Tables 1 to 15 below.

TABLE 1

| Compound | Structure |
|---|---|
| 103 | 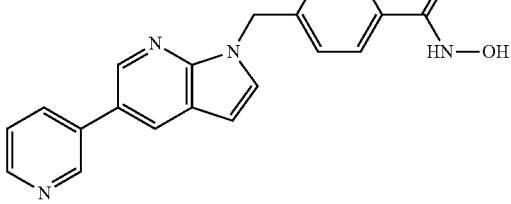 |
| 104 | 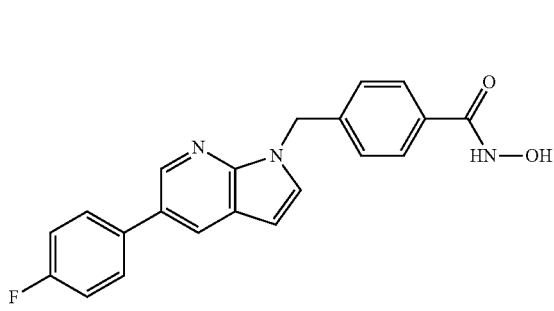 [SMILES: O=C(NO)c1ccc(Cn2ccc3cc(-c4ccc(F)cc4)cnc32)cc1] |
| 124 | 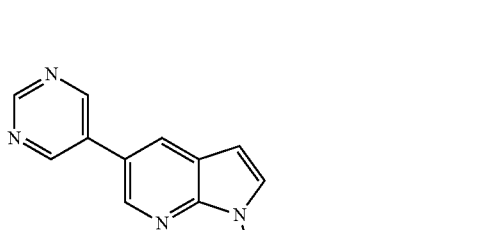 |

TABLE 1-continued

| Compound | Structure |
| --- | --- |
| 125 | 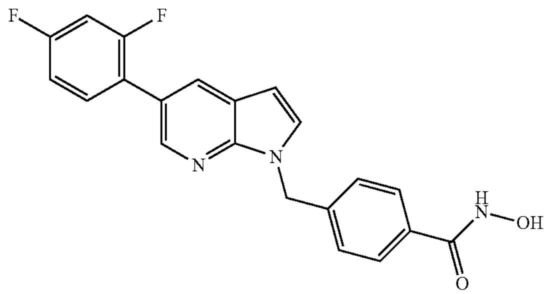 [SMILES: O=C(NO)c1ccc(Cn2ccc3cc(-c4ccc(F)cc4F)cnc32)cc1] |
| 212 | 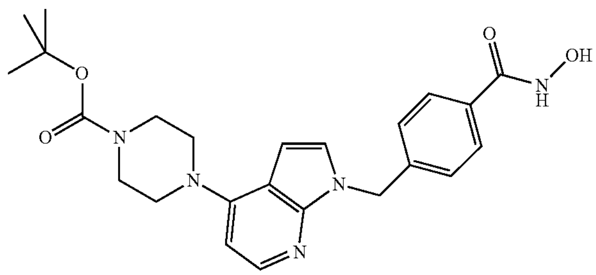 [SMILES: CC(C)(C)OC(=O)N1CCN(c2ccnc3c2ccn3Cc2ccc(C(=O)NO)cc2)CC1] |
| 223 | 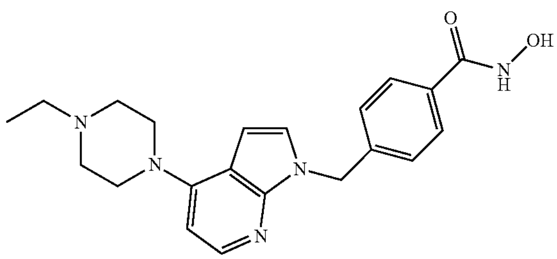 [SMILES: CCN1CCN(c2ccnc3c2ccn3Cc2ccc(C(=O)NO)cc2)CC1] |
| 224 | 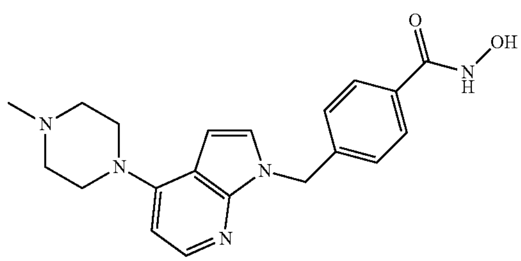 [SMILES: CN1CCN(c2ccnc3c2ccn3Cc2ccc(C(=O)NO)cc2)CC1] |
| 225 | 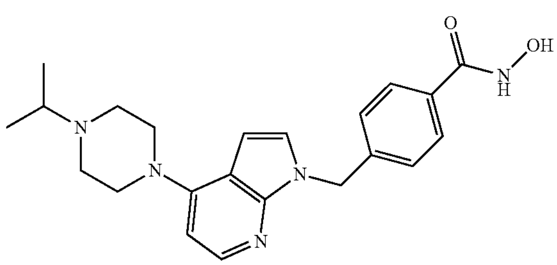 [SMILES: CC(C)N1CCN(c2ccnc3c2ccn3Cc2ccc(C(=O)NO)cc2)CC1] |
| 617 | 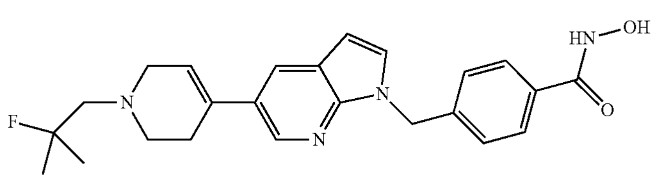 [SMILES: CC(C)(F)CN1CC=C(c2cnc3c(ccn3Cc3ccc(C(=O)NO)cc3)c2)CC1] |

TABLE 1-continued

| Compound | Structure |
|---|---|
| 618 | (structure) |

TABLE 2

| Compound | Structure |
|---|---|
| 629 | (structure) |
| 630 | (structure) |
| 635 | (structure) |
| 636 | (structure) |
| 642 | (structure) |

TABLE 2-continued
| Compound | Structure |
|---|---|
| 645 | 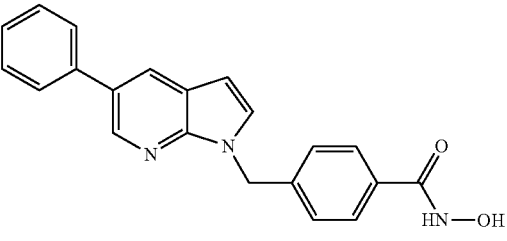 [SMILES: O=C(NO)c1ccc(Cn2ccc3cc(-c4ccccc4)cnc32)cc1] |
| 647 | 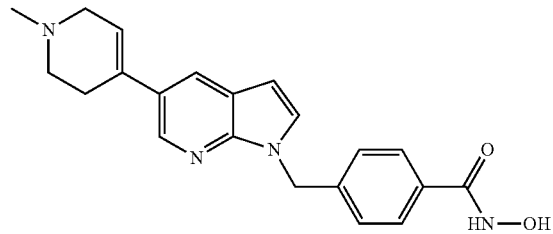 [SMILES: CN1CC=C(c2cnc3c(ccn3Cc3ccc(C(=O)NO)cc3)c2)CC1] |
| 648 | 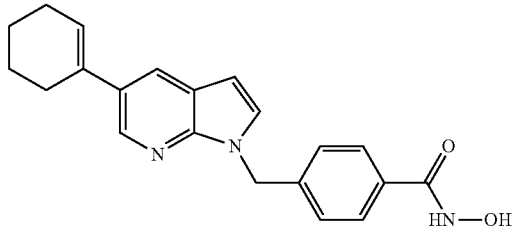 [SMILES: O=C(NO)c1ccc(Cn2ccc3cc(C4=CCCCC4)cnc32)cc1] |
| 649 | 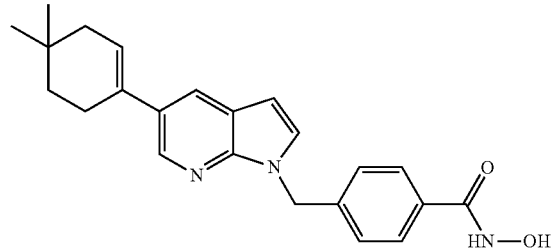 [SMILES: CC1(C)CC=C(c2cnc3c(ccn3Cc3ccc(C(=O)NO)cc3)c2)CC1] |
| 650 | 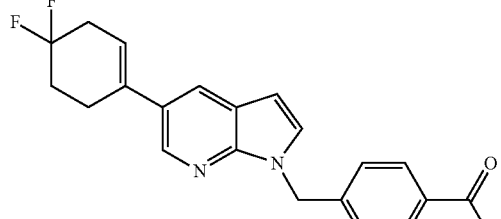 |

TABLE 3
| Compound | Structure |
|---|---|
| 656 | 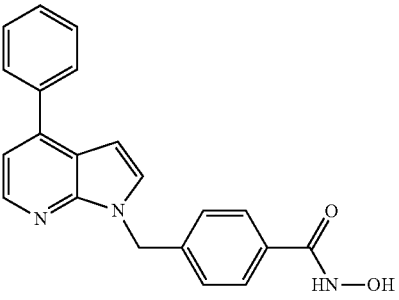 [SMILES: O=C(NO)c1ccc(Cn2ccc3c(-c4ccccc4)ccnc32)cc1] |
| 657 | 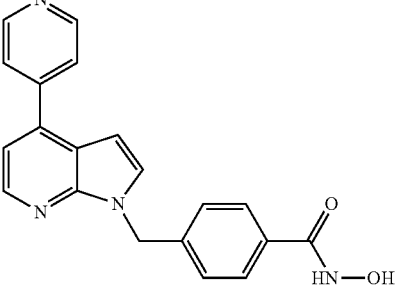 |
| 658 | 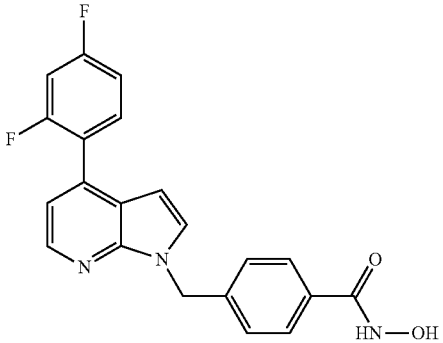 [SMILES: O=C(NO)c1ccc(Cn2ccc3c(-c4ccc(F)cc4F)ccnc32)cc1] |
| 659 | 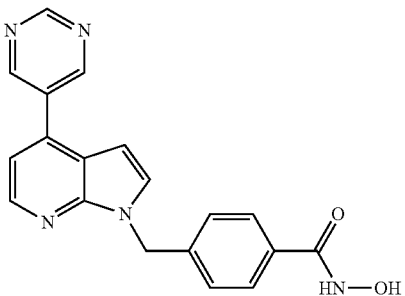 [SMILES: O=C(NO)c1ccc(Cn2ccc3c(-c4cncnc4)ccnc32)cc1] |
| 685 | 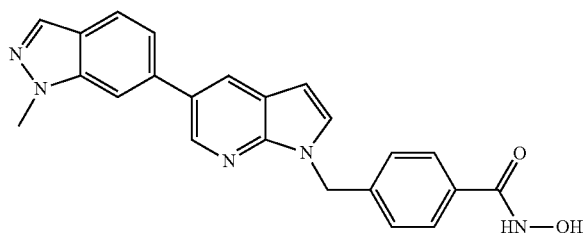 [SMILES: Cn1ncc2ccc(-c3cnc4c(ccn4Cc4ccc(C(=O)NO)cc4)c3)cc21] |

TABLE 3-continued
| Compound | Structure |
|---|---|
| 686 | 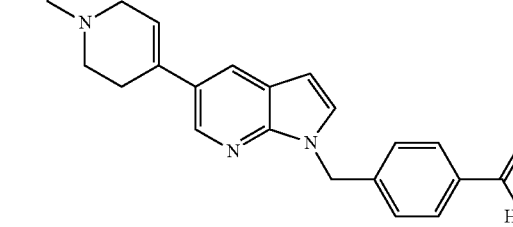 |
| 687 | 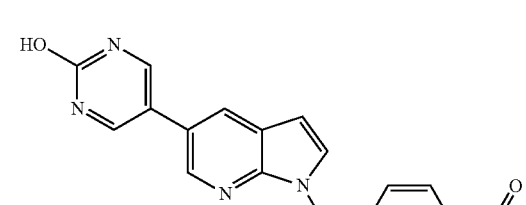 |
| 688 | 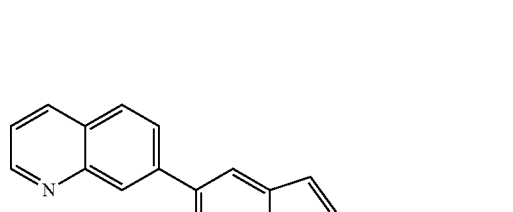 |
| 689 | 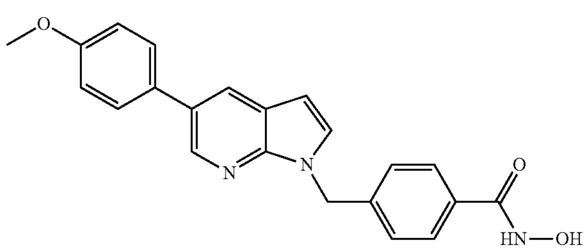 [SMILES: COc1ccc(-c2cnc3c(ccn3Cc3ccc(C(=O)NO)cc3)c2)cc1] |
| 690 | 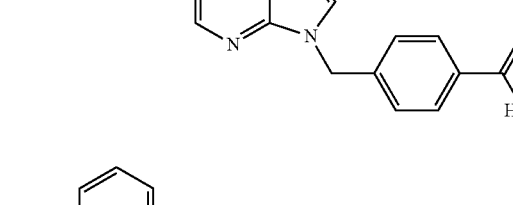 |

TABLE 4

| Compound | Structure |
|---|---|
| 691 | 4-((5-(4-hydroxyphenyl)-1H-pyrrolo[2,3-b]pyridin-1-yl)methyl)-N-hydroxybenzamide |
| 692 | tert-butyl 4-(1-(4-(hydroxycarbamoyl)benzyl)-1H-pyrrolo[2,3-b]pyridin-5-yl)-5,6-dihydropyridine-1(2H)-carboxylate |
| 693 | N-hydroxy-4-((5-(1,2,3,6-tetrahydropyridin-4-yl)-1H-pyrrolo[2,3-b]pyridin-1-yl)methyl)benzamide |
| 694 | tert-butyl 4-(1-(4-(hydroxycarbamoyl)benzyl)-1H-pyrrolo[2,3-b]pyridin-5-yl)piperidine-1-carboxylate |
| 700 | N-hydroxy-4-((4-(4-(5-(trifluoromethyl)pyridin-2-yl)piperazin-1-yl)-1H-pyrrolo[2,3-b]pyridin-1-yl)methyl)benzamide |
| 701 | N-hydroxy-4-((4-(4-(5-(trifluoromethyl)pyrazin-2-yl)piperazin-1-yl)-1H-pyrrolo[2,3-b]pyridin-1-yl)methyl)benzamide |

TABLE 4-continued

| Compound | Structure |
|---|---|
| 702 | 5-ethylpyrimidin-2-yl-piperazinyl-7-azaindole-N-CH2-C6H4-C(O)NHOH |
| 703 | 1-(trifluoromethyl)cyclobutyl-C(O)-piperazinyl-7-azaindole-N-CH2-C6H4-C(O)NHOH |
| 704 | benzyl-piperazinyl-7-azaindole-N-CH2-C6H4-C(O)NHOH |
| 705 | (4-methoxybenzyl)-piperazinyl-7-azaindole-N-CH2-C6H4-C(O)NHOH |

TABLE 5

| Compound | Structure |
|---|---|
| 706 | (4-trifluoromethylbenzyl)-piperazinyl-7-azaindole-N-CH2-C6H4-C(O)NHOH |

TABLE 5-continued

| Compound | Structure |
|---|---|
| 714 | 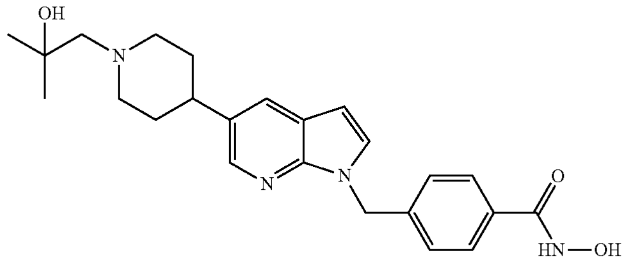 |
| 715 | 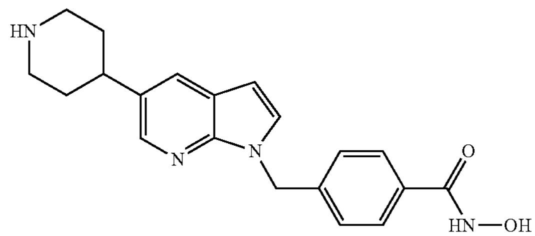 [SMILES: O=C(NO)c1ccc(Cn2ccc3cc(C4=CCNCC4)cnc32)cc1] |
| 721 | 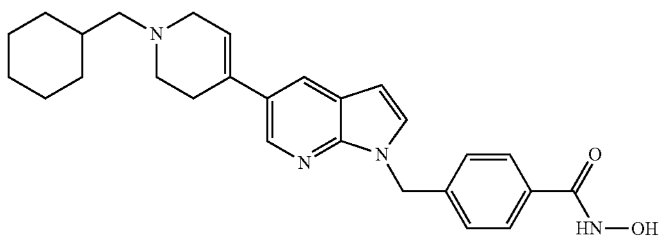 [SMILES: O=C(NO)c1ccc(Cn2ccc3cc(C4=CCN(CC5CCCCC5)CC4)cnc32)cc1] |
| 722 | 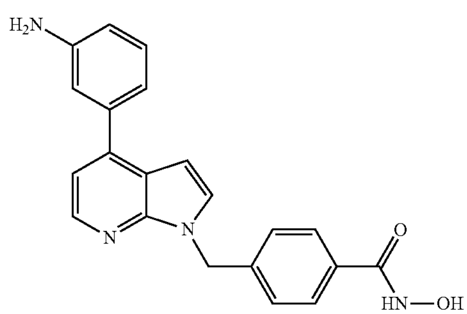 [SMILES: Nc1cccc(-c2ccnc3c2ccn3Cc2ccc(C(=O)NO)cc2)c1] |
| 723 | 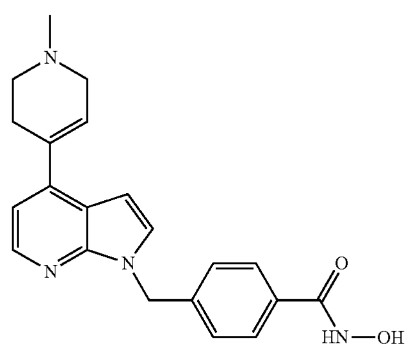 [SMILES: CN1CC=C(c2ccnc3c2ccn3Cc2ccc(C(=O)NO)cc2)CC1] |

TABLE 5-continued

| Compound | Structure |
|---|---|
| 724 | 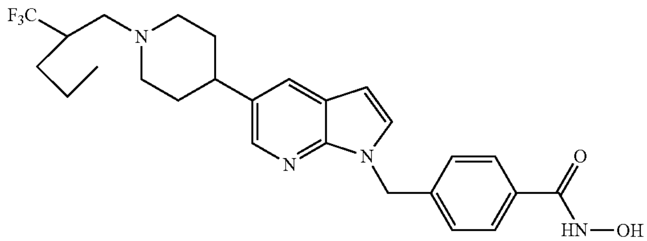 |
| 743 | 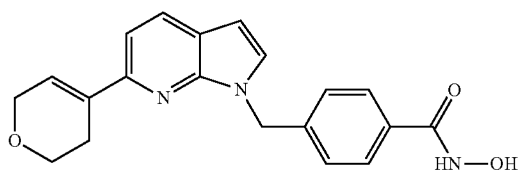 [SMILES: O=C(NO)c1ccc(Cn2ccc3ccc(C4=CCOCC4)nc32)cc1] |
| 744 | 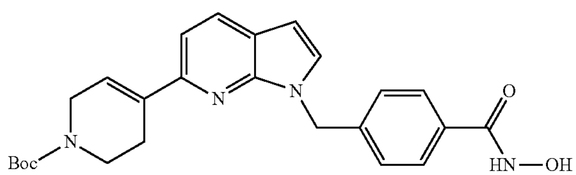 [SMILES: CC(C)(C)OC(=O)N1CC=C(c2ccc3ccn(Cc4ccc(C(=O)NO)cc4)c3n2)CC1] |
| 746 | 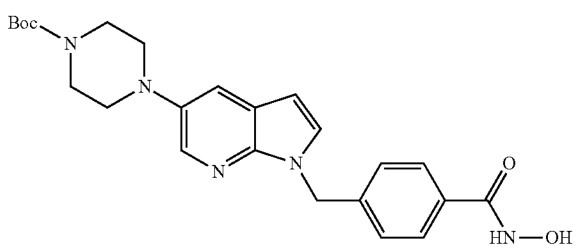 [SMILES: CC(C)(C)OC(=O)N1CCN(c2cnc3c(ccn3Cc3ccc(C(=O)NO)cc3)c2)CC1] |

TABLE 6

| Compound | Structure |
|---|---|
| 757 | 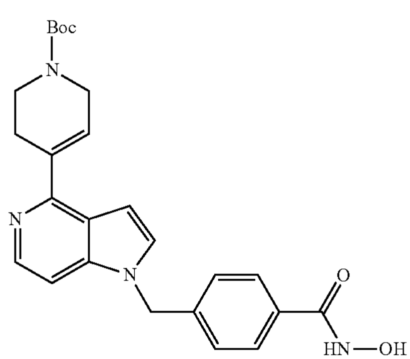 [SMILES: CC(C)(C)OC(=O)N1CC=C(c2nccc3c2ccn3Cc2ccc(C(=O)NO)cc2)CC1] |

TABLE 6-continued

| Compound | Structure |
|---|---|
| 758 | 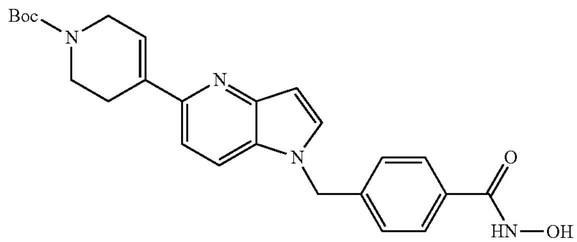 [SMILES: CC(C)(C)OC(=O)N1CC=C(c2ccc3c(ccn3Cc3ccc(C(=O)NO)cc3)n2)CC1] |
| 759 | 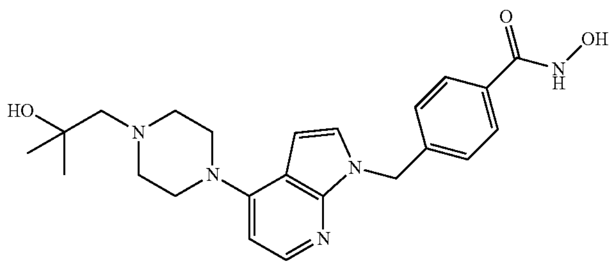 [SMILES: CC(C)(O)CN1CCN(c2ccnc3c2ccn3Cc2ccc(C(=O)NO)cc2)CC1] |
| 760 | 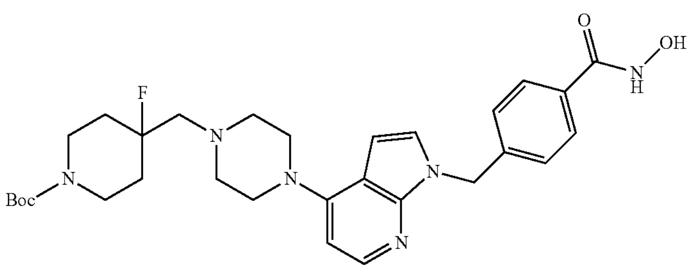 [SMILES: CC(C)(C)OC(=O)N1CCC(F)(CN2CCN(c3ccnc4c3ccn4Cc3ccc(C(=O)NO)cc3)CC2)CC1] |
| 761 | 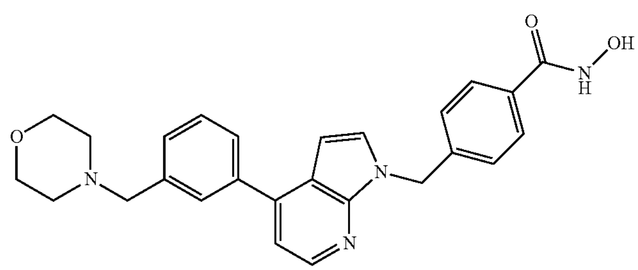 [SMILES: O=C(NO)c1ccc(Cn2ccc3c(-c4cccc(CN5CCOCC5)c4)ccnc32)cc1] |
| 762 | 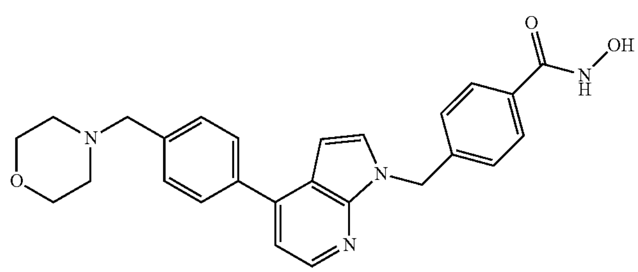 [SMILES: O=C(NO)c1ccc(Cn2ccc3c(-c4ccc(CN5CCOCC5)cc4)ccnc32)cc1] |
| 763 | 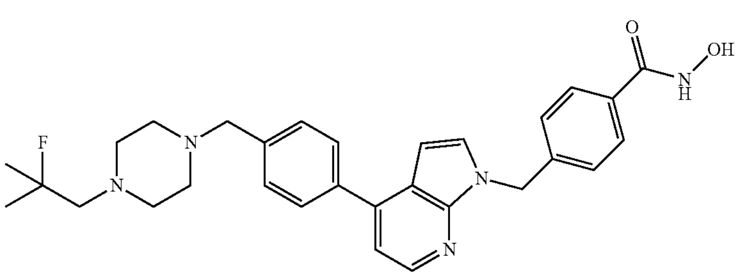 [SMILES: CC(C)(F)CN1CCN(Cc2ccc(-c3ccnc4c3ccn4Cc3ccc(C(=O)NO)cc3)cc2)CC1] |

TABLE 6-continued

| Compound | Structure |
|---|---|
| 764 | 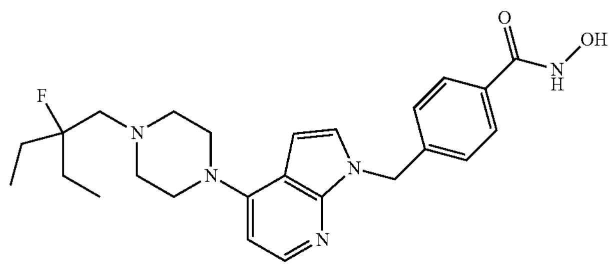 [SMILES: CCC(F)(CC)CN1CCN(c2ccnc3c2ccn3Cc2ccc(C(=O)NO)cc2)CC1] |
| 781 | 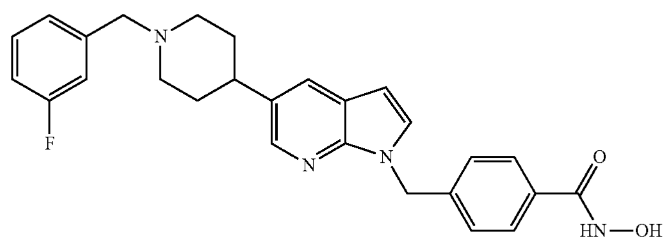 [SMILES: O=C(NO)c1ccc(Cn2ccc3cc(C4CCN(Cc5cccc(F)c5)CC4)cnc32)cc1] |
| 783 | 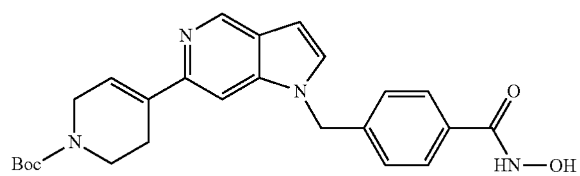 |
| 784 | 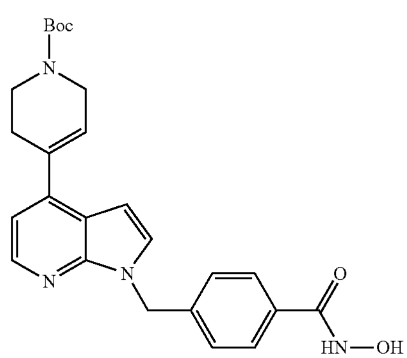 [SMILES: CC(C)(C)OC(=O)N1CC=C(c2ccnc3c2ccn3Cc2ccc(C(=O)NO)cc2)CC1] |
| 785 | 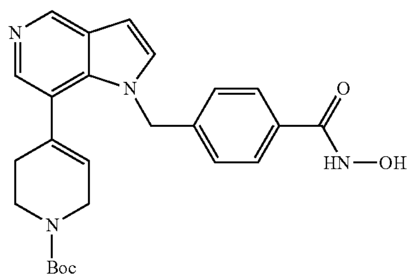 [SMILES: CC(C)(C)OC(=O)N1CC=C(c2cncc3ccn(Cc4ccc(C(=O)NO)cc4)c23)CC1] |

TABLE 7
| Compound | Structure |
| --- | --- |
| 786 | 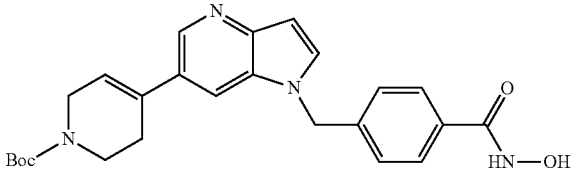 [SMILES: CC(C)(C)OC(=O)N1CC=C(c2cnc3ccn(Cc4ccc(C(=O)NO)cc4)c3c2)CC1] |
| 787 | 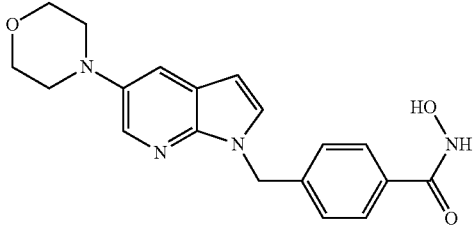 [SMILES: O=C(NO)c1ccc(Cn2ccc3cc(N4CCOCC4)cnc32)cc1] |
| 799 | 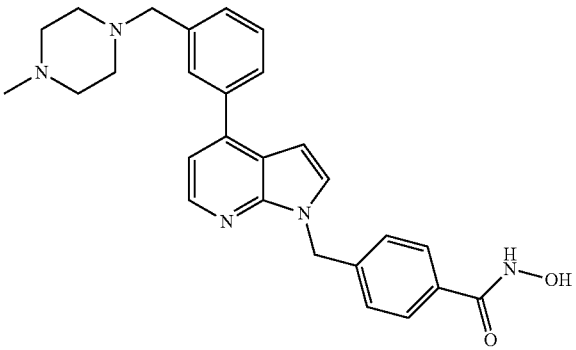 [SMILES: CN1CCN(Cc2cccc(-c3ccnc4c3ccn4Cc3ccc(C(=O)NO)cc3)c2)CC1] |
| 804 | 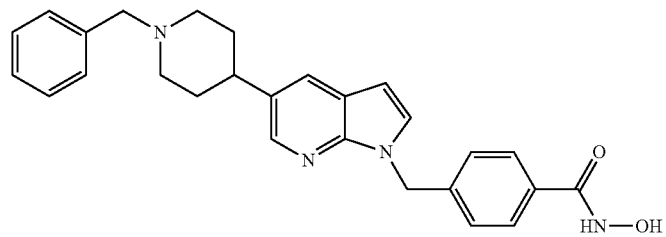 [SMILES: O=C(NO)c1ccc(Cn2ccc3cc(C4CCN(Cc5ccccc5)CC4)cnc32)cc1] |
| 805 | 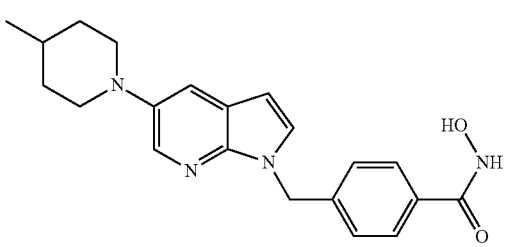 [SMILES: CC1CCN(c2cnc3c(ccn3Cc3ccc(C(=O)NO)cc3)c2)CC1] |
| 806 | 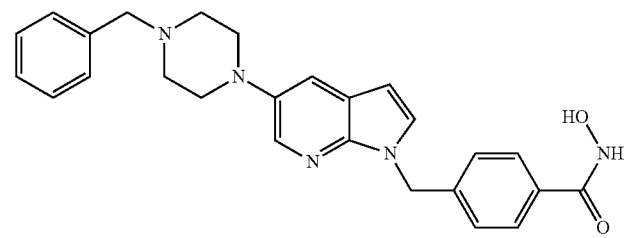 [SMILES: O=C(NO)c1ccc(Cn2ccc3cc(N4CCN(Cc5ccccc5)CC4)cnc32)cc1] |

TABLE 7-continued

| Compound | Structure |
|---|---|
| 807 | 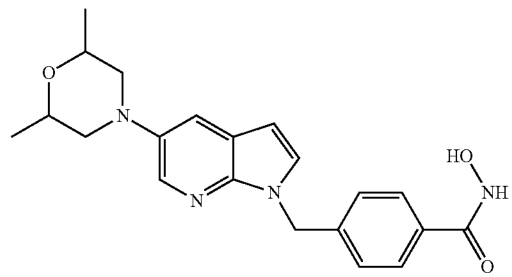 [SMILES: CC1CN(c2cnc3c(ccn3Cc3ccc(C(=O)NO)cc3)c2)CC(C)O1] |
| 808 | 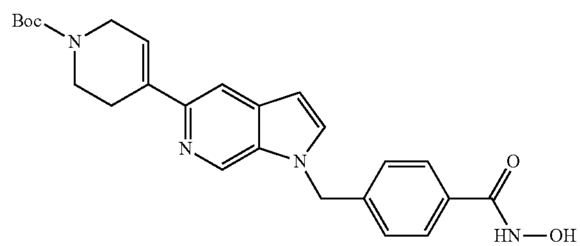 [SMILES: CC(C)(C)OC(=O)N1CC=C(c2cc3ccn(Cc4ccc(C(=O)NO)cc4)c3cn2)CC1] |
| 809 | 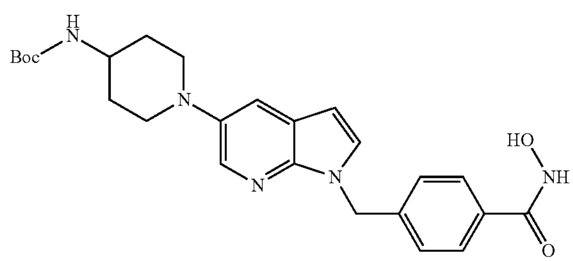 [SMILES: CC(C)(C)OC(=O)NC1CCN(c2cnc3c(ccn3Cc3ccc(C(=O)NO)cc3)c2)CC1] |
| 810 | 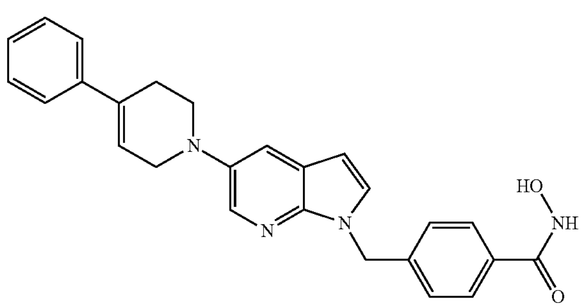 [SMILES: O=C(NO)c1ccc(Cn2ccc3cc(N4CC=C(c5ccccc5)CC4)cnc32)cc1] |
| 812 | 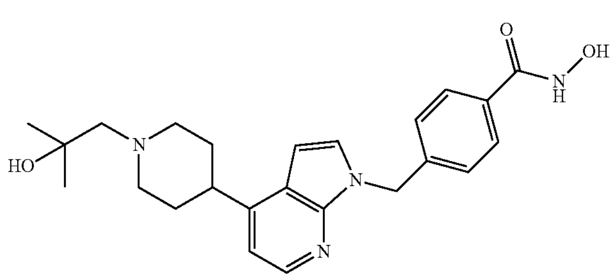 [SMILES: CC(C)(O)CN1CCC(c2ccnc3c2ccn3Cc2ccc(C(=O)NO)cc2)CC1] |

TABLE 7-continued
| Compound | Structure |
|---|---|
| 830 | 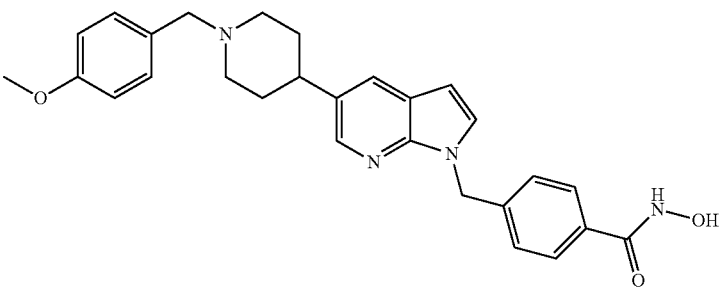 [SMILES: COc1ccc(CN2CCC(c3cnc4c(ccn4Cc4ccc(C(=O)NO)cc4)c3)CC2)cc1] |
TABLE 8
| Compound | Structure |
|---|---|
| 831 | 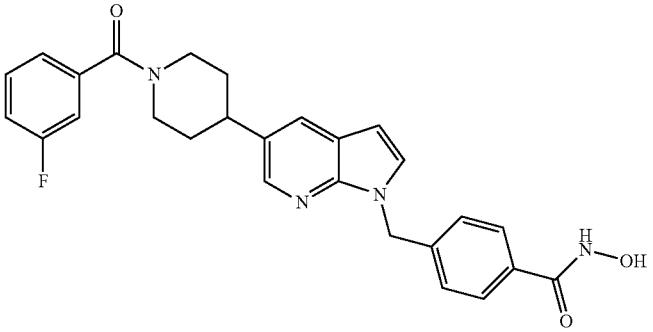 [SMILES: O=C(NO)c1ccc(Cn2ccc3cc(C4CCN(C(=O)c5cccc(F)c5)CC4)cnc32)cc1] |
| 839 | 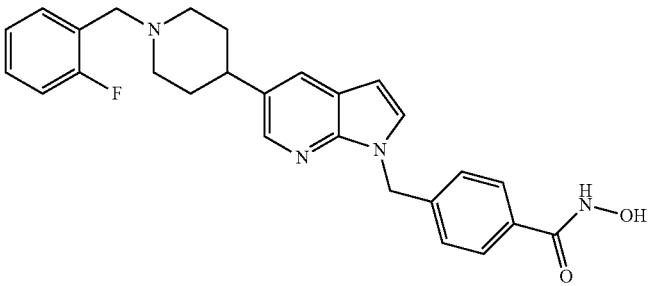 [SMILES: O=C(NO)c1ccc(Cn2ccc3cc(C4CCN(Cc5ccccc5F)CC4)cnc32)cc1] |
| 840 | 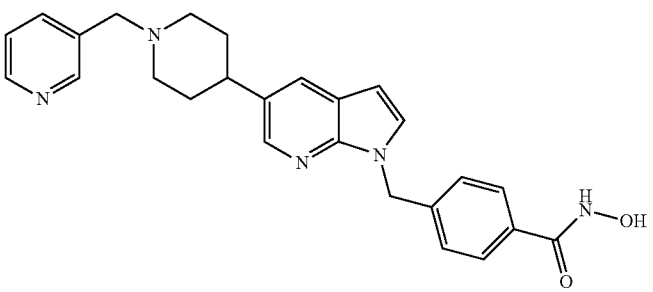 [SMILES: O=C(NO)c1ccc(Cn2ccc3cc(C4CCN(Cc5cccnc5)CC4)cnc32)cc1] |

TABLE 8-continued
| Compound | Structure |
|---|---|
| 841 | 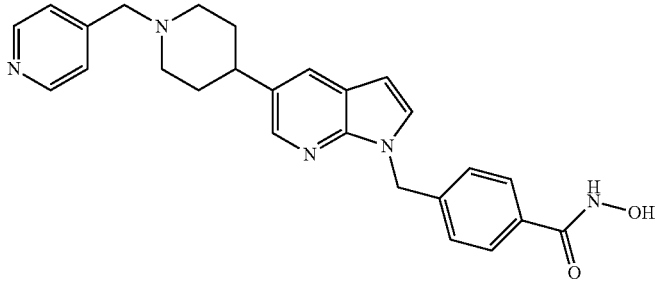 [SMILES: O=C(NO)c1ccc(Cn2ccc3cc(C4CCN(Cc5ccncc5)CC4)cnc32)cc1] |
| 842 | 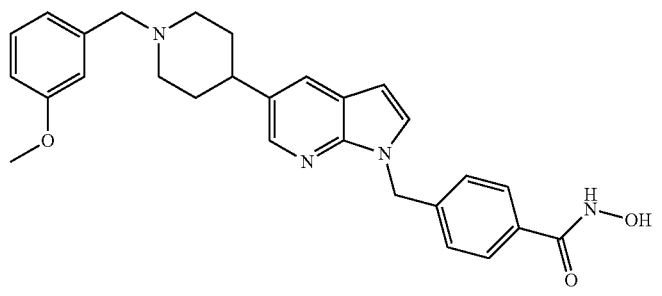 [SMILES: COc1cccc(CN2CCC(c3cnc4c(ccn4Cc4ccc(C(=O)NO)cc4)c3)CC2)c1] |
| 843 | 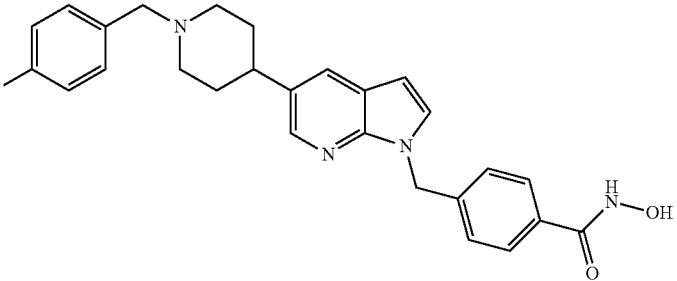 |
| 844 | 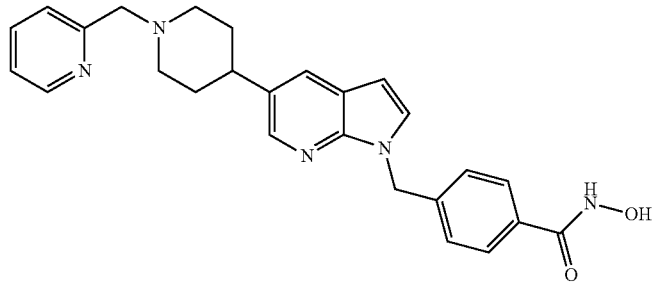 [SMILES: O=C(NO)c1ccc(Cn2ccc3cc(C4CCN(Cc5ccccn5)CC4)cnc32)cc1] |
| 845 | 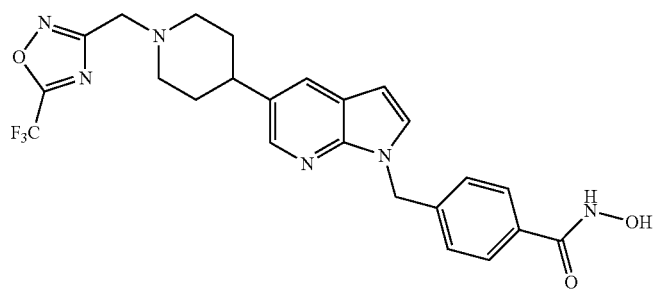 [SMILES: O=C(NO)c1ccc(Cn2ccc3cc(C4CCN(Cc5noc(C(F)(F)F)n5)CC4)cnc32)cc1] |

TABLE 8-continued

| Compound | Structure |
|---|---|
| 846 | 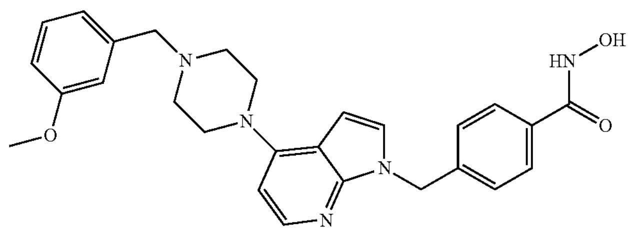 [SMILES: COc1cccc(CN2CCN(c3ccnc4c3ccn4Cc3ccc(C(=O)NO)cc3)CC2)c1] |
| 847 | 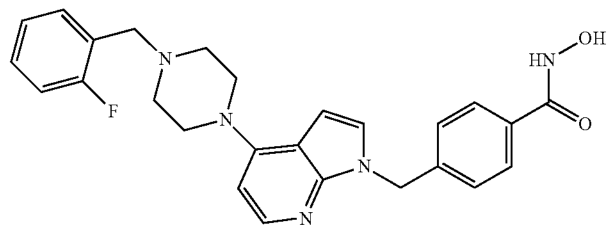 [SMILES: O=C(NO)c1ccc(Cn2ccc3c(N4CCN(Cc5ccccc5F)CC4)ccnc32)cc1] |
| 848 | 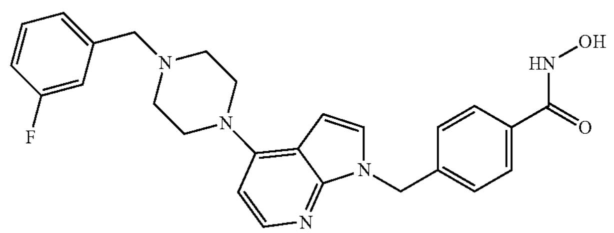 [SMILES: O=C(NO)c1ccc(Cn2ccc3c(N4CCN(Cc5cccc(F)c5)CC4)ccnc32)cc1] |
| 849 | 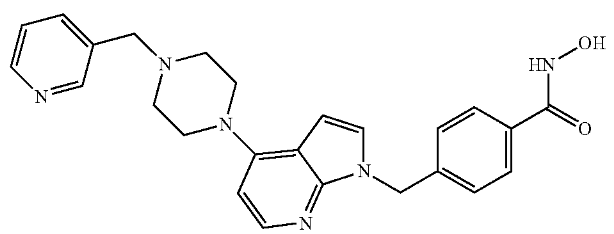 [SMILES: O=C(NO)c1ccc(Cn2ccc3c(N4CCN(Cc5cccnc5)CC4)ccnc32)cc1] |

TABLE 9

| Compound | Structure |
|---|---|
| 850 | 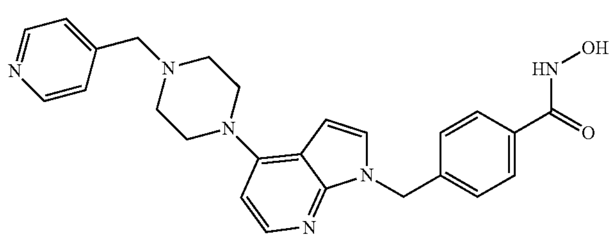 [SMILES: O=C(NO)c1ccc(Cn2ccc3c(N4CCN(Cc5ccncc5)CC4)ccnc32)cc1] |

TABLE 9-continued

| Compound | Structure |
|---|---|
| 851 | 3-fluorobenzyl-piperazinyl-7-azaindole-benzyl-N-hydroxybenzamide |
| 852 | 4-fluorobenzyl-piperazinyl-7-azaindole-benzyl-N-hydroxybenzamide |
| 853 | isobutyl-piperazinyl-7-azaindole-benzyl-N-hydroxybenzamide |
| 854 | 2-fluoro-2-methylpropanoyl-piperidinyl-7-azaindole-benzyl-N-hydroxybenzamide |
| 855 | 2-fluoro-2-methylpropanoyl-piperazinyl-7-azaindole-benzyl-N-hydroxybenzamide |

TABLE 9-continued

| Compound | Structure |
|---|---|
| 856 | 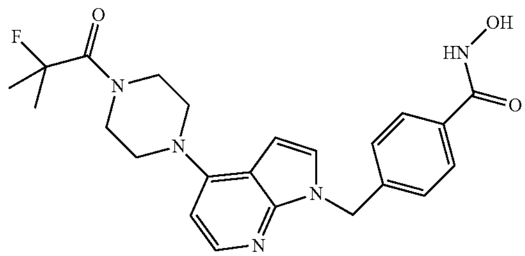 [SMILES: CC(C)(F)C(=O)N1CCN(c2ccnc3c2ccn3Cc2ccc(C(=O)NO)cc2)CC1] |
| 857 | 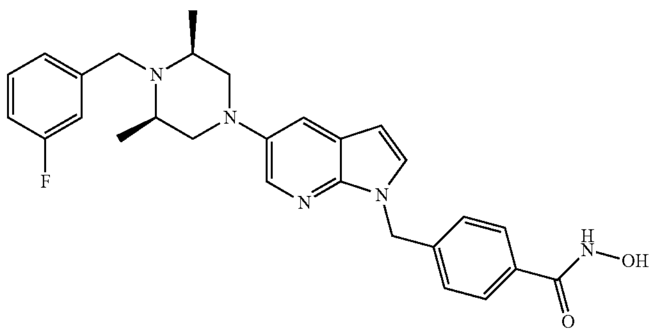 [SMILES: C[C@@H]1CN(c2cnc3c(ccn3Cc3ccc(C(=O)NO)cc3)c2)C[C@H](C)N1Cc1cccc(F)c1] |
| 858 | 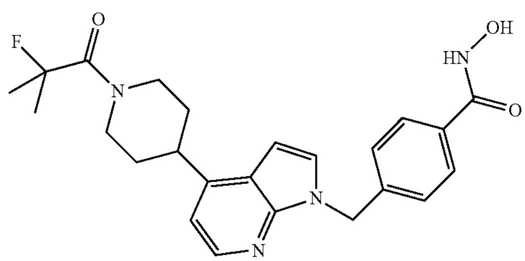 [SMILES: CC(C)(F)C(=O)N1CCC(c2ccnc3c2ccn3Cc2ccc(C(=O)NO)cc2)CC1] |
| 859 | 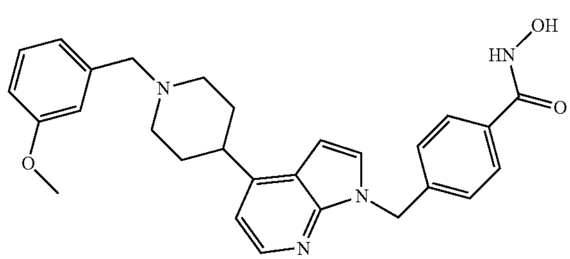 [SMILES: COc1cccc(CN2CCC(c3ccnc4c3ccn4Cc3ccc(C(=O)NO)cc3)CC2)c1] |
| 860 | 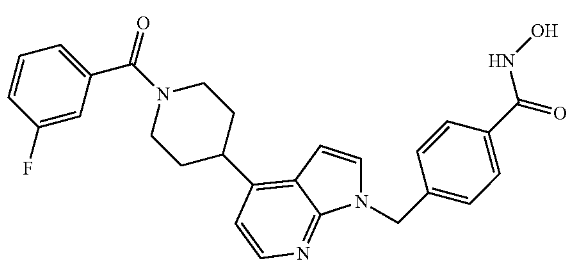 [SMILES: O=C(NO)c1ccc(Cn2ccc3c(C4CCN(C(=O)c5cccc(F)c5)CC4)ccnc32)cc1] |

TABLE 9-continued
| Compound | Structure |
|---|---|
| 861 | 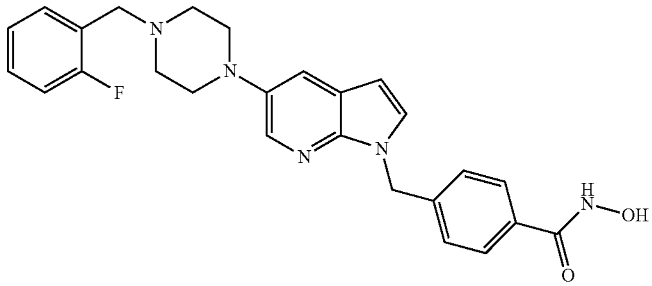 [SMILES: O=C(NO)c1ccc(Cn2ccc3cc(N4CCN(Cc5ccccc5F)CC4)cnc32)cc1] |
TABLE 10
| Compound | Structure |
|---|---|
| 862 | 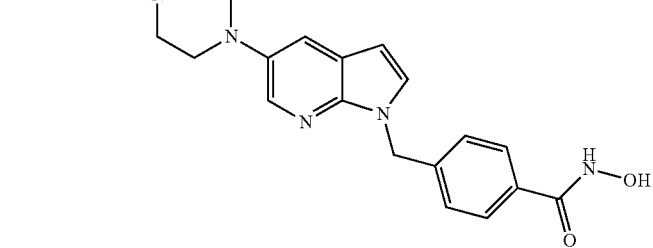 |
| 863 | 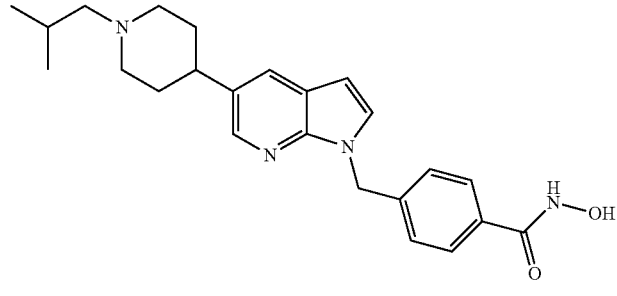 [SMILES: CC(C)CN1CCC(c2cnc3c(ccn3Cc3ccc(C(=O)NO)cc3)c2)CC1] |
| 864 | 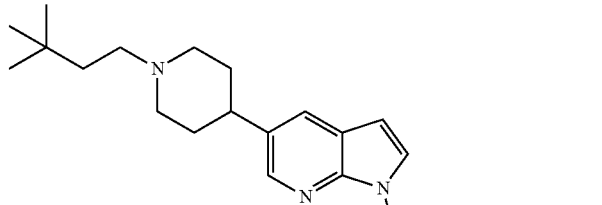 |

TABLE 10-continued

| Compound | Structure |
|---|---|
| 865 | 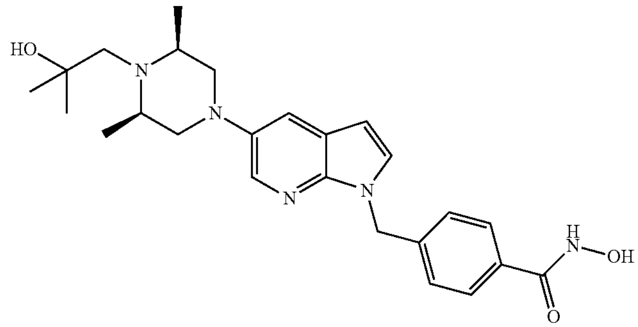 [SMILES: C[C@@H]1CN(c2cnc3c(ccn3Cc3ccc(C(=O)NO)cc3)c2)C[C@H](C)N1CC(C)(C)O] |
| 866 | 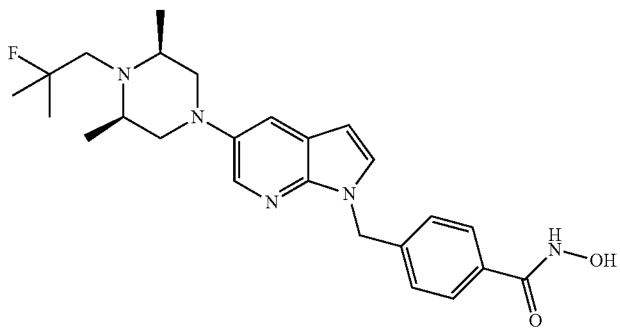 [SMILES: C[C@@H]1CN(c2cnc3c(ccn3Cc3ccc(C(=O)NO)cc3)c2)C[C@H](C)N1CC(C)(C)F] |
| 867 | 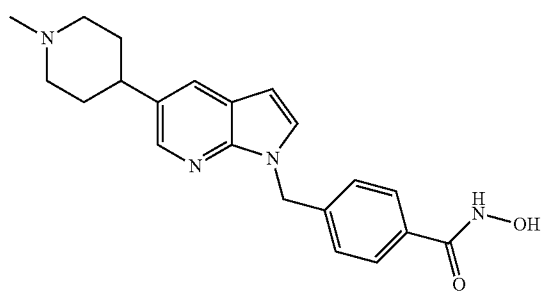 [SMILES: CN1CCC(c2cnc3c(ccn3Cc3ccc(C(=O)NO)cc3)c2)CC1] |
| 868 | 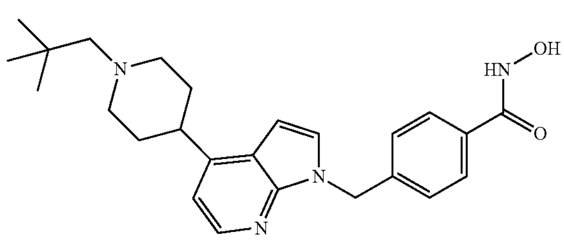 [SMILES: CC(C)(C)CN1CCC(c2ccnc3c2ccn3Cc2ccc(C(=O)NO)cc2)CC1] |
| 869 | 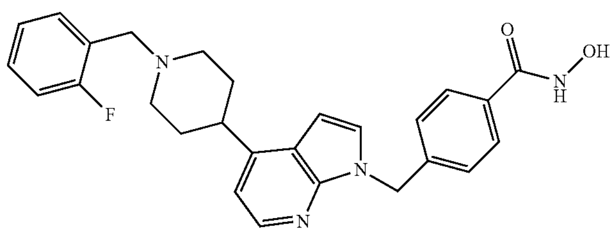 [SMILES: O=C(NO)c1ccc(Cn2ccc3c(C4CCN(Cc5ccccc5F)CC4)ccnc32)cc1] |

TABLE 10-continued

| Compound | Structure |
|---|---|
| 870 | 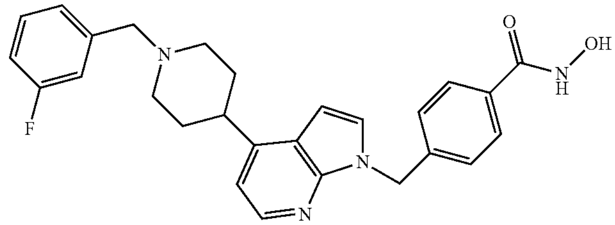 [SMILES: O=C(NO)c1ccc(Cn2ccc3c(C4CCN(Cc5cccc(F)c5)CC4)ccnc32)cc1] |
| 871 | 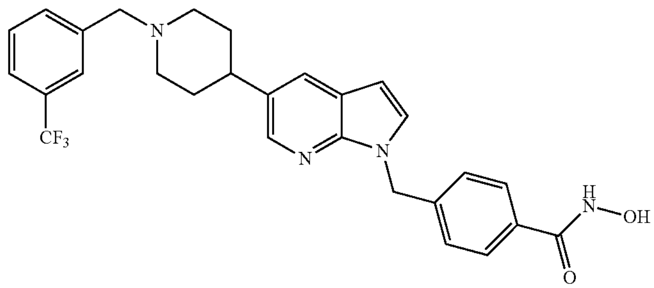 [SMILES: O=C(NO)c1ccc(Cn2ccc3cc(C4CCN(Cc5cccc(C(F)(F)F)c5)CC4)cnc32)cc1] |
| 872 | 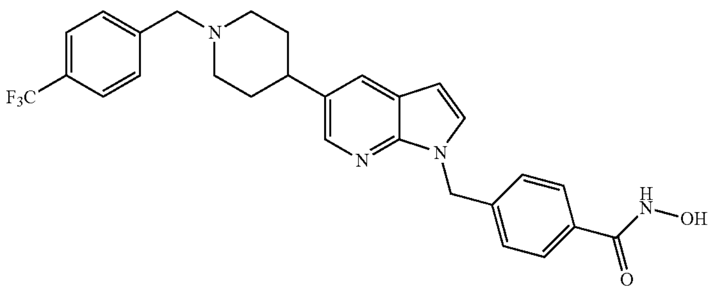 [SMILES: O=C(NO)c1ccc(Cn2ccc3cc(C4CCN(Cc5ccc(C(F)(F)F)cc5)CC4)cnc32)cc1] |
| 873 | 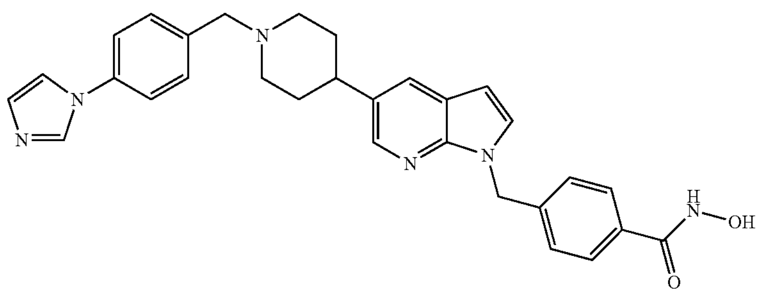 [SMILES: O=C(NO)c1ccc(Cn2ccc3cc(C4CCN(Cc5ccc(-n6ccnc6)cc5)CC4)cnc32)cc1] |

TABLE 11

| Compound | Structure |
|---|---|
| 874 | 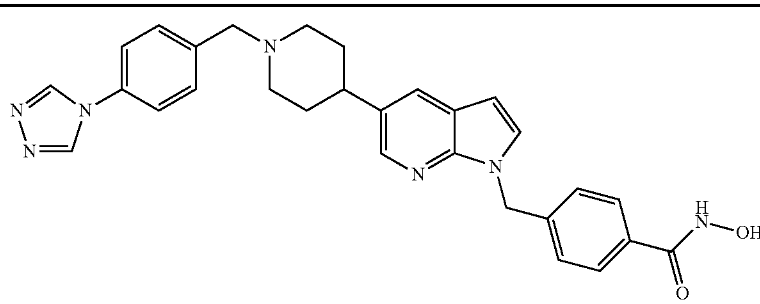 |

TABLE 11-continued
| Compound | Structure |
|---|---|
| 875 | 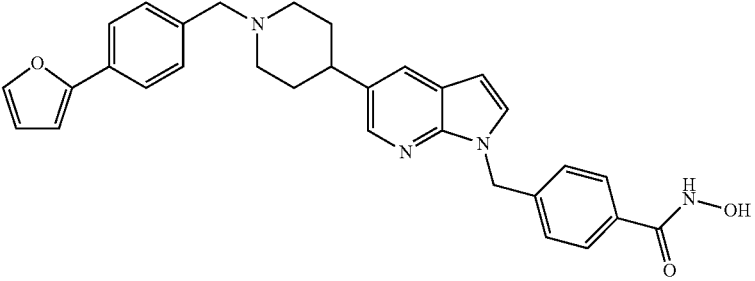 [SMILES: O=C(NO)c1ccc(Cn2ccc3cc(C4CCN(Cc5ccc(-c6ccco6)cc5)CC4)cnc32)cc1] |
| 876 | 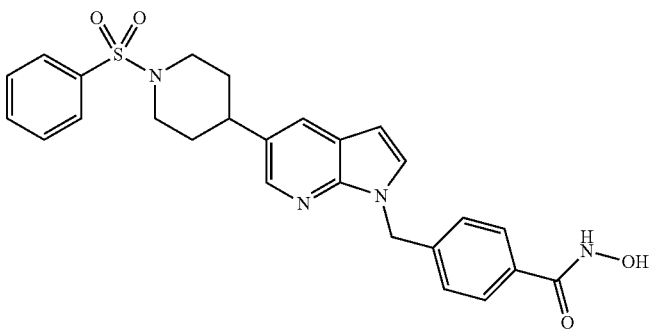 [SMILES: O=C(NO)c1ccc(Cn2ccc3cc(C4CCN(S(=O)(=O)c5ccccc5)CC4)cnc32)cc1] |
| 877 | 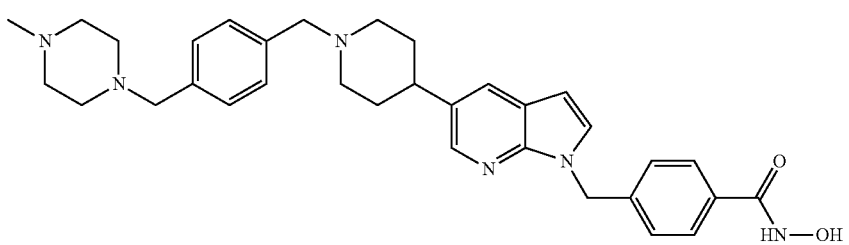 [SMILES: CN1CCN(Cc2ccc(CN3CCC(c4cnc5c(ccn5Cc5ccc(C(=O)NO)cc5)c4)CC3)cc2)CC1] |
| 878 | 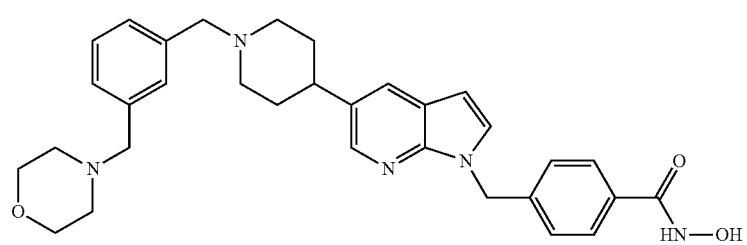 [SMILES: O=C(NO)c1ccc(Cn2ccc3cc(C4CCN(Cc5cccc(CN6CCOCC6)c5)CC4)cnc32)cc1] |
| 879 | 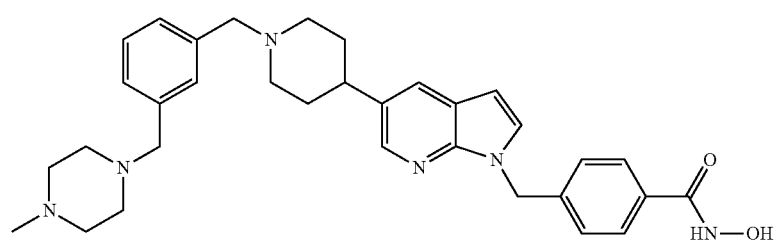 [SMILES: CN1CCN(Cc2cccc(CN3CCC(c4cnc5c(ccn5Cc5ccc(C(=O)NO)cc5)c4)CC3)c2)CC1] |
| 880 | 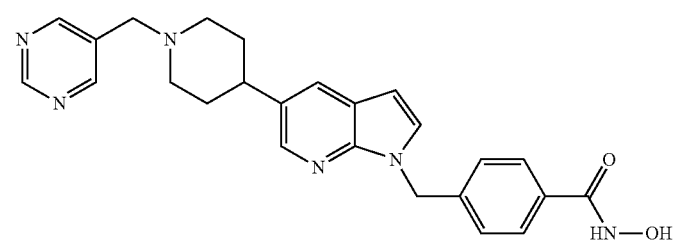 [SMILES: O=C(NO)c1ccc(Cn2ccc3cc(C4CCN(Cc5cncnc5)CC4)cnc32)cc1] |

TABLE 11-continued
| Compound | Structure |
|---|---|
| 881 | 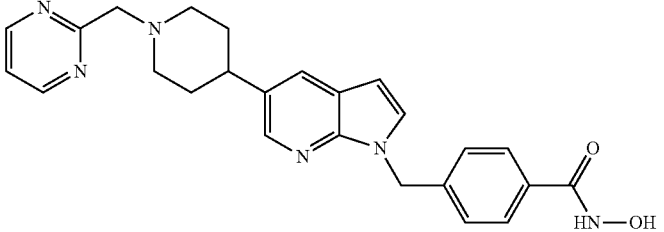 [SMILES: O=C(NO)c1ccc(Cn2ccc3cc(C4CCN(Cc5ncccn5)CC4)cnc32)cc1] |
| 882 | 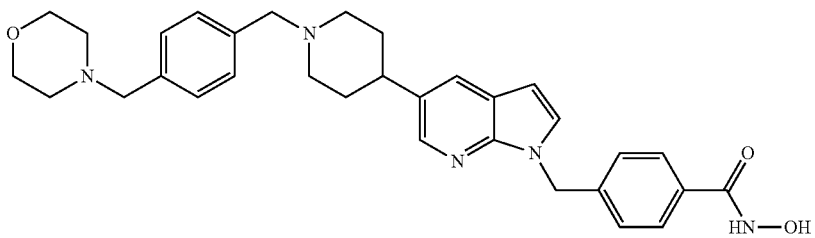 [SMILES: O=C(NO)c1ccc(Cn2ccc3cc(C4CCN(Cc5ccc(CN6CCOCC6)cc5)CC4)cnc32)cc1] |
| 883 | 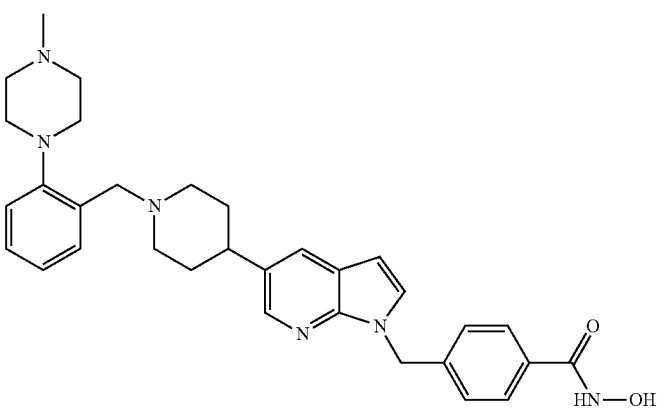 [SMILES: CN1CCN(c2ccccc2CN2CCC(c3cnc4c(ccn4Cc4ccc(C(=O)NO)cc4)c3)CC2)CC1] |
| 884 | 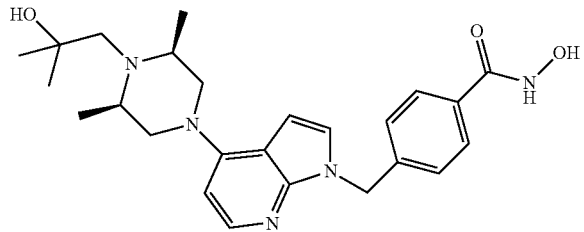 [SMILES: C[C@@H]1CN(c2ccnc3c2ccn3Cc2ccc(C(=O)NO)cc2)C[C@H](C)N1CC(C)(C)O] |
| 885 | 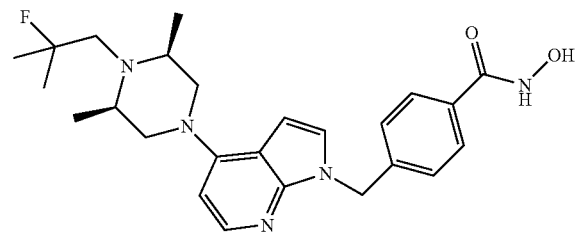 [SMILES: C[C@@H]1CN(c2ccnc3c2ccn3Cc2ccc(C(=O)NO)cc2)C[C@H](C)N1CC(C)(C)F] |

TABLE 12
| Compound | Structure |
|---|---|
| 886 | 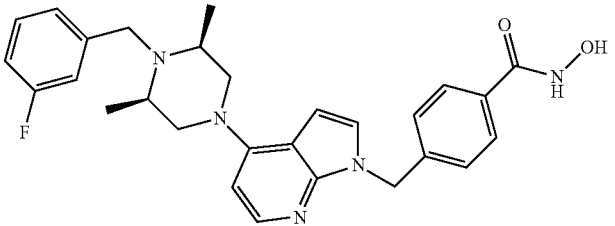 [SMILES: C[C@@H]1CN(c2ccnc3c2ccn3Cc2ccc(C(=O)NO)cc2)C[C@H](C)N1Cc1cccc(F)c1] |
| 895 | 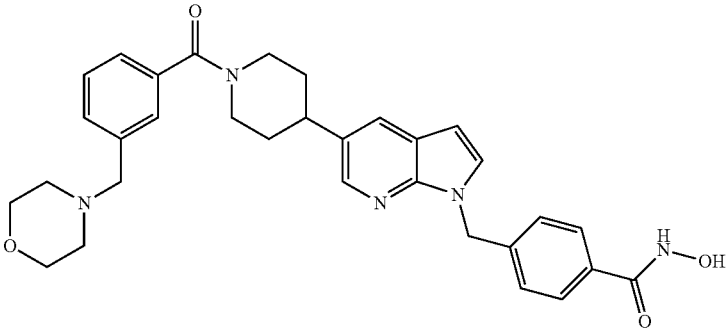 [SMILES: O=C(NO)c1ccc(Cn2ccc3cc(C4CCN(C(=O)c5cccc(CN6CCOCC6)c5)CC4)cnc32)cc1] |
| 896 | 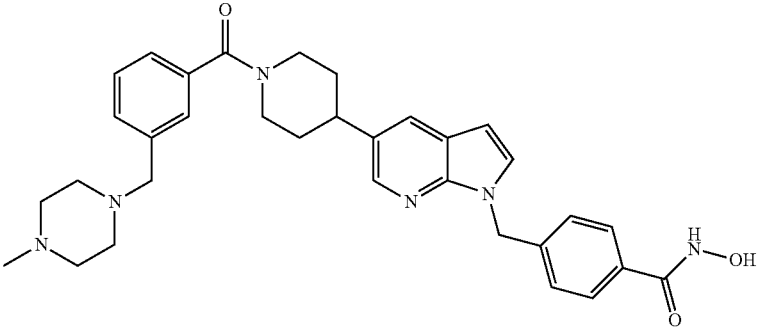 [SMILES: CN1CCN(Cc2cccc(C(=O)N3CCC(c4cnc5c(ccn5Cc5ccc(C(=O)NO)cc5)c4)CC3)c2)CC1] |
| 897 | 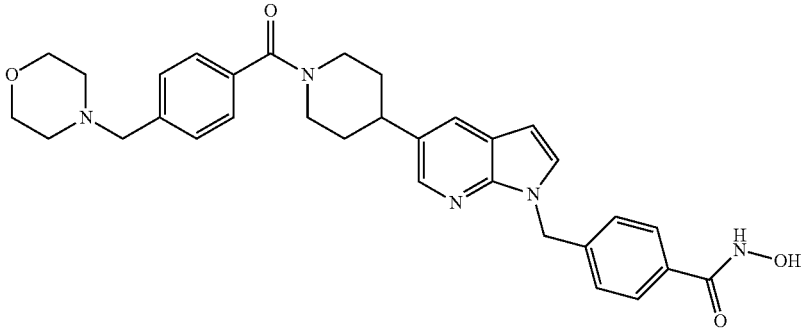 [SMILES: O=C(NO)c1ccc(Cn2ccc3cc(C4CCN(C(=O)c5ccc(CN6CCOCC6)cc5)CC4)cnc32)cc1] |
| 898 | 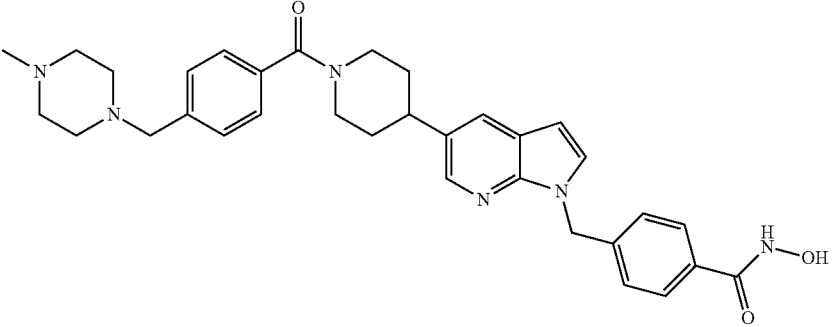 [SMILES: CN1CCN(Cc2ccc(C(=O)N3CCC(c4cnc5c(ccn5Cc5ccc(C(=O)NO)cc5)c4)CC3)cc2)CC1] |

TABLE 12-continued
| Compound | Structure |
|---|---|
| 917 | 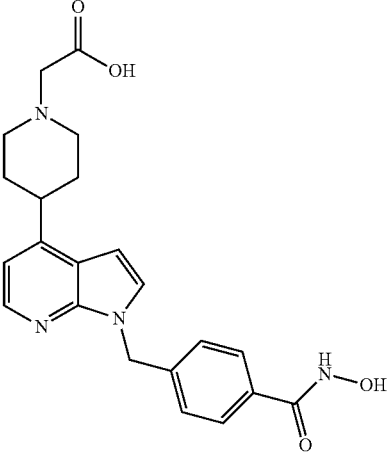 [SMILES: O=C(O)CN1CCC(c2ccnc3c2ccn3Cc2ccc(C(=O)NO)cc2)CC1] |
| 927 | 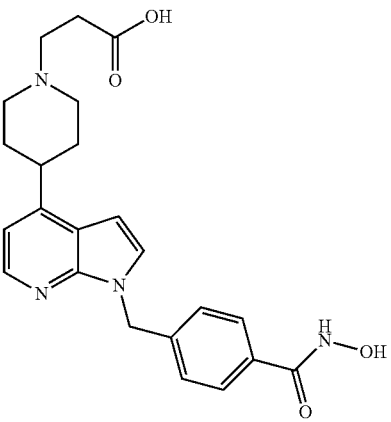 [SMILES: O=C(O)CCN1CCC(c2ccnc3c2ccn3Cc2ccc(C(=O)NO)cc2)CC1] |
| 930 | 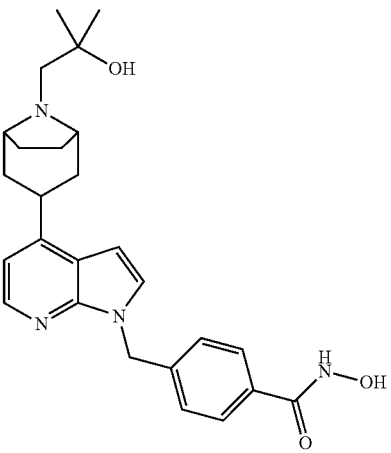 [SMILES: CC(C)(O)CN1C2CCC1CC(c1ccnc3c1ccn3Cc1ccc(C(=O)NO)cc1)C2] |

TABLE 12-continued
| Compound | Structure |
|---|---|
| 945 | 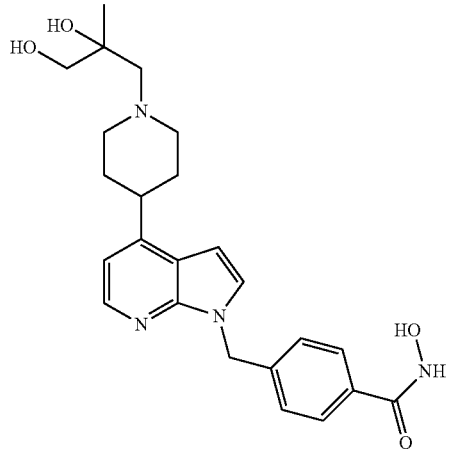 [SMILES: CC(O)(CO)CN1CCC(c2ccnc3c2ccn3Cc2ccc(C(=O)NO)cc2)CC1] |
| 946 | 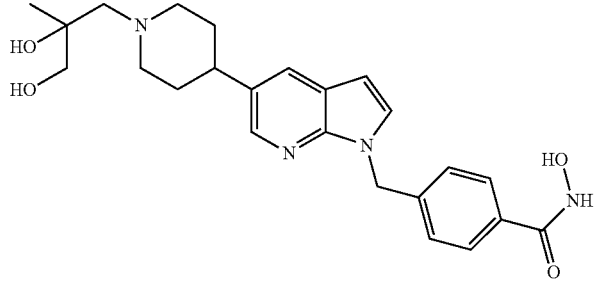 [SMILES: CC(O)(CO)CN1CCC(c2cnc3c(ccn3Cc3ccc(C(=O)NO)cc3)c2)CC1] |
| 956 | 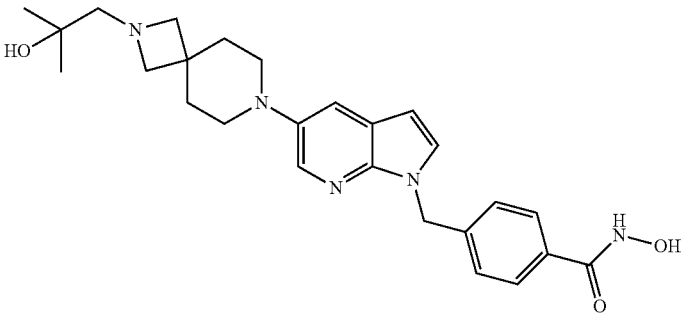 [SMILES: CC(C)(O)CN1CC2(CCN(c3cnc4c(ccn4Cc4ccc(C(=O)NO)cc4)c3)CC2)C1] |
| 957 | 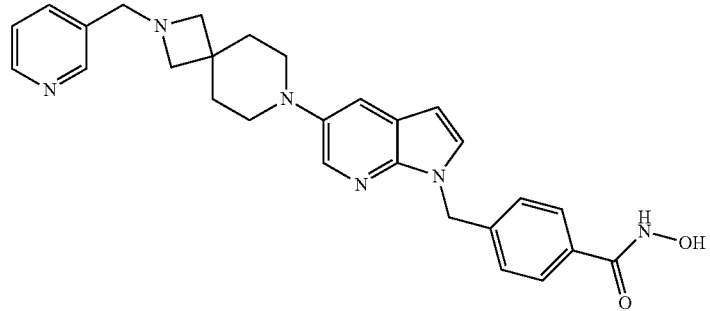 [SMILES: O=C(NO)c1ccc(Cn2ccc3cc(N4CCC5(CC4)CN(Cc4cccnc4)C5)cnc32)cc1] |

TABLE 13

| Compound | Structure |
|---|---|
| 959 | 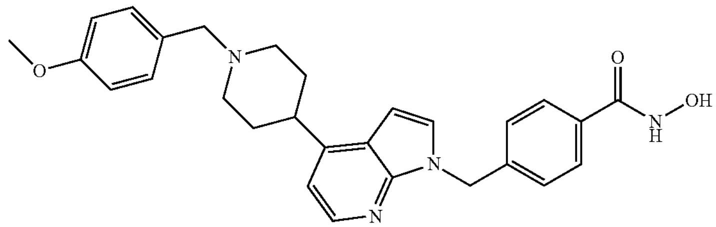 [SMILES: COc1ccc(CN2CCC(c3ccnc4c3ccn4Cc3ccc(C(=O)NO)cc3)CC2)cc1] |
| 966 | 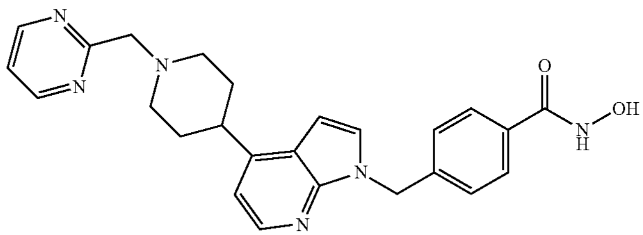 [SMILES: O=C(NO)c1ccc(Cn2ccc3c(C4CCN(Cc5ncccn5)CC4)ccnc32)cc1] |
| 984 | 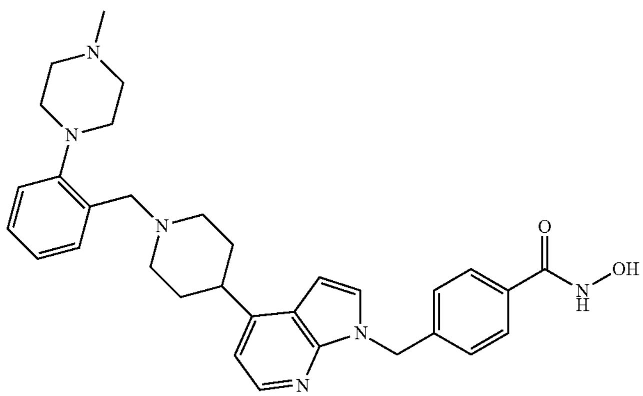 [SMILES: CN1CCN(c2ccccc2CN2CCC(c3ccnc4c3ccn4Cc3ccc(C(=O)NO)cc3)CC2)CC1] |
| 985 | 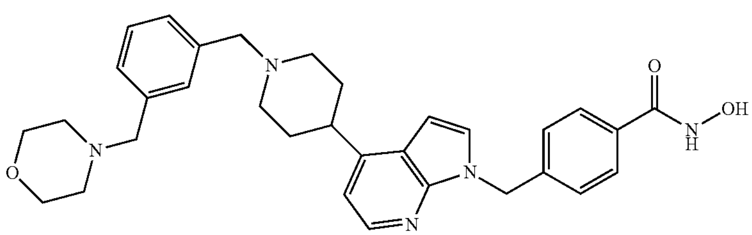 [SMILES: O=C(NO)c1ccc(Cn2ccc3c(C4CCN(Cc5cccc(CN6CCOCC6)c5)CC4)ccnc32)cc1] |
| 986 | 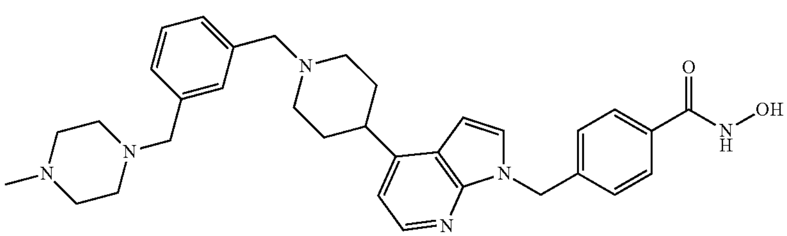 [SMILES: CN1CCN(Cc2cccc(CN3CCC(c4ccnc5c4ccn5Cc4ccc(C(=O)NO)cc4)CC3)c2)CC1] |
| 987 | 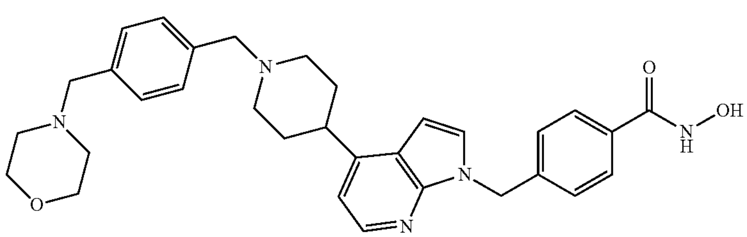 [SMILES: O=C(NO)c1ccc(Cn2ccc3c(C4CCN(Cc5ccc(CN6CCOCC6)cc5)CC4)ccnc32)cc1] |

TABLE 13-continued

| Compound | Structure |
|---|---|
| 988 | 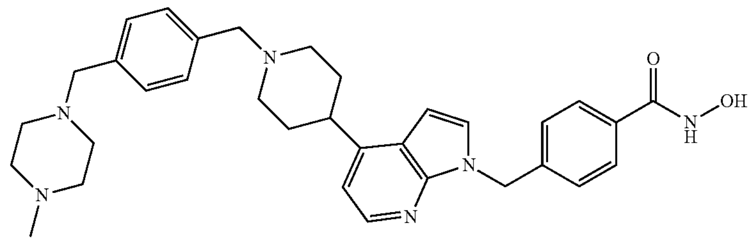 [SMILES: CN1CCN(Cc2ccc(CN3CCC(c4ccnc5c4ccn5Cc4ccc(C(=O)NO)cc4)CC3)cc2)CC1] |
| 990 | 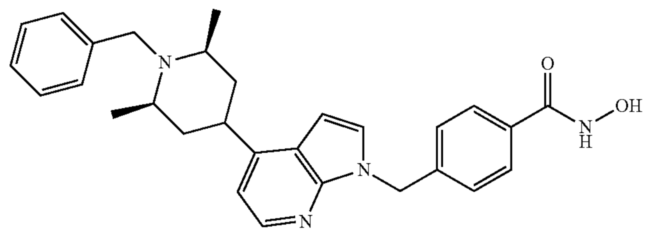 [SMILES: C[C@@H]1CC(c2ccnc3c2ccn3Cc2ccc(C(=O)NO)cc2)C[C@H](C)N1Cc1ccccc1] |
| 991 | 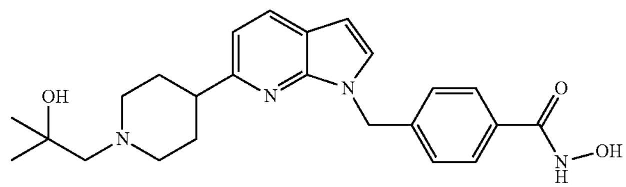 [SMILES: CC(C)(O)CN1CCC(c2ccc3ccn(Cc4ccc(C(=O)NO)cc4)c3n2)CC1] |
| 992 | 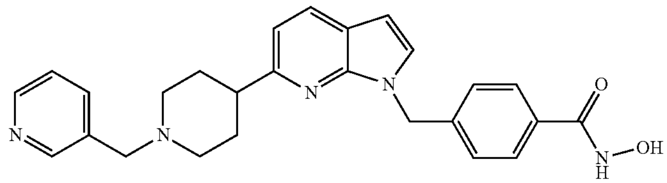 [SMILES: O=C(NO)c1ccc(Cn2ccc3ccc(C4CCN(Cc5cccnc5)CC4)nc32)cc1] |
| 1003 | 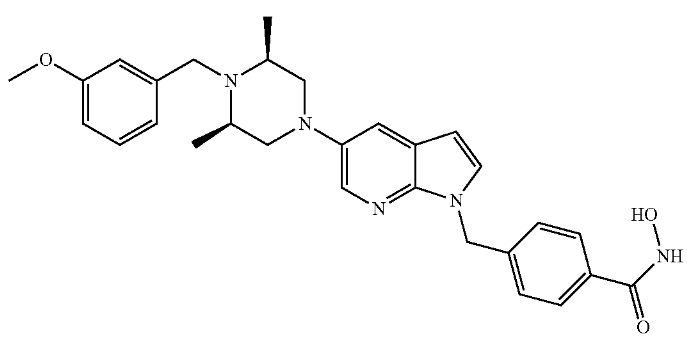 [SMILES: COc1cccc(CN2[C@H](C)CN(c3cnc4c(ccn4Cc4ccc(C(=O)NO)cc4)c3)C[C@@H]2C)c1] |
| 1004 | 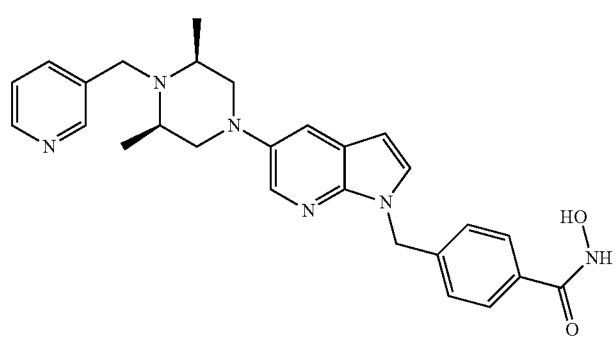 [SMILES: C[C@@H]1CN(c2cnc3c(ccn3Cc3ccc(C(=O)NO)cc3)c2)C[C@H](C)N1Cc1cccnc1] |

TABLE 14

| Compound | Structure |
|---|---|
| 1005 | 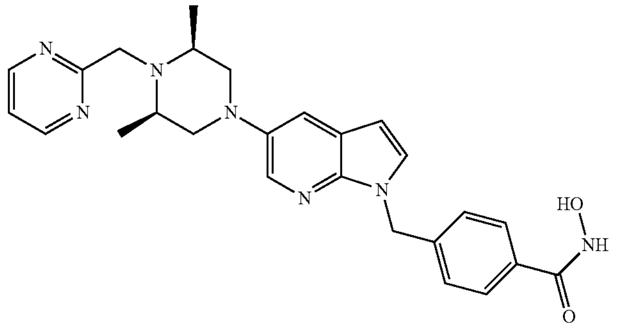 [SMILES: C[C@@H]1CN(c2cnc3c(ccn3Cc3ccc(C(=O)NO)cc3)c2)C[C@H](C)N1Cc1ncccn1] |
| 1014 | 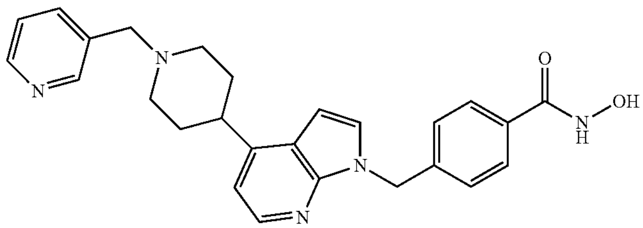 [SMILES: O=C(NO)c1ccc(Cn2ccc3c(C4CCN(Cc5cccnc5)CC4)ccnc32)cc1] |
| 1015 | 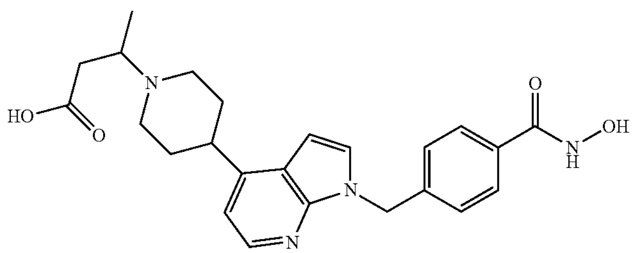 [SMILES: CC(CC(=O)O)N1CCC(c2ccnc3c2ccn3Cc2ccc(C(=O)NO)cc2)CC1] |
| 1017 | 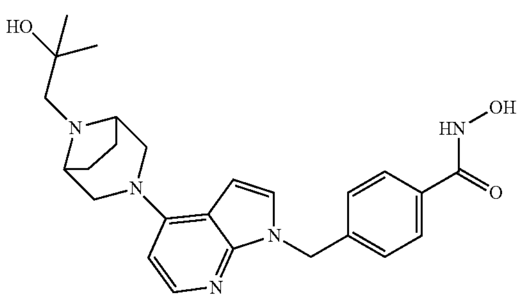 [SMILES: CC(C)(O)CN1C2CCC1CN(c1ccnc3c1ccn3Cc1ccc(C(=O)NO)cc1)C2] |
| 1018 | 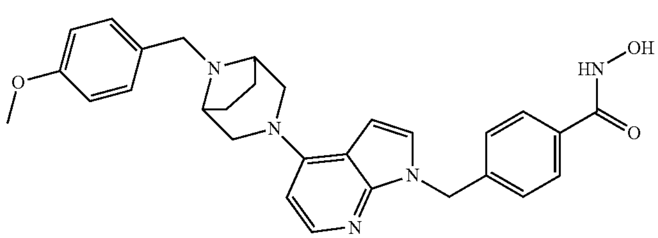 [SMILES: COc1ccc(CN2C3CCC2CN(c2ccnc4c2ccn4Cc2ccc(C(=O)NO)cc2)C3)cc1] |
| 1019 | 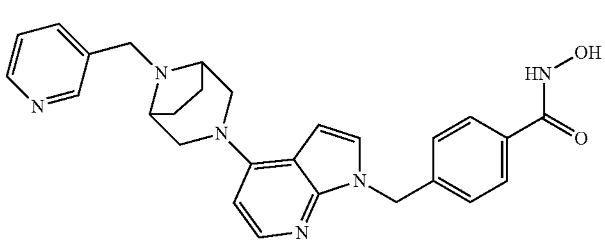 [SMILES: O=C(NO)c1ccc(Cn2ccc3c(N4CC5CCC(C4)N5Cc4cccnc4)ccnc32)cc1] |

TABLE 14-continued
| Compound | Structure |
| --- | --- |
| 1020 | 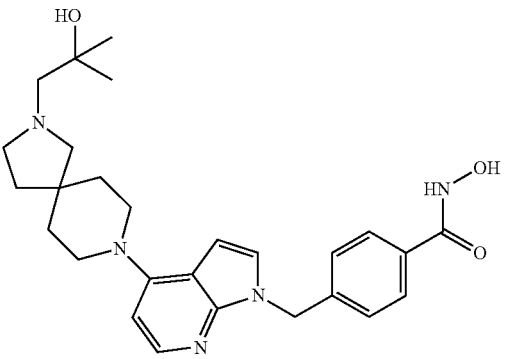 [SMILES: CC(C)(O)CN1CCC2(CCN(c3ccnc4c3ccn4Cc3ccc(C(=O)NO)cc3)CC2)C1] |
| 1021 | 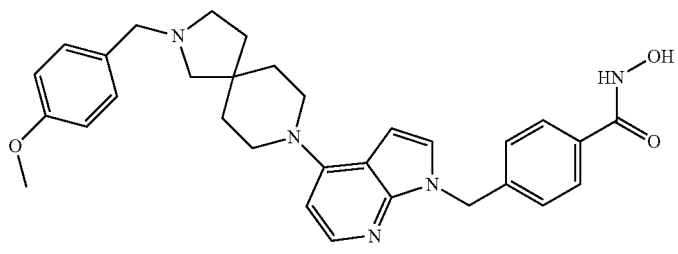 [SMILES: COc1ccc(CN2CCC3(CCN(c4ccnc5c4ccn5Cc4ccc(C(=O)NO)cc4)CC3)C2)cc1] |
| 1022 | 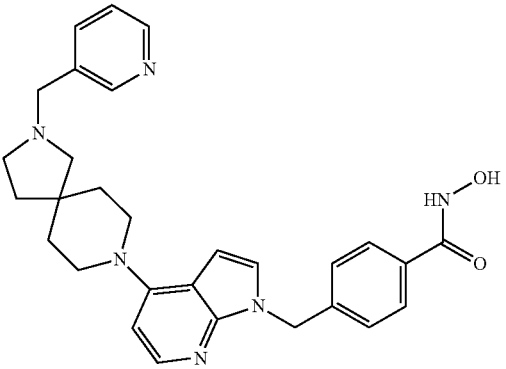 [SMILES: O=C(NO)c1ccc(Cn2ccc3c(N4CCC5(CCN(Cc6cccnc6)C5)CC4)ccnc32)cc1] |
| 1023 | 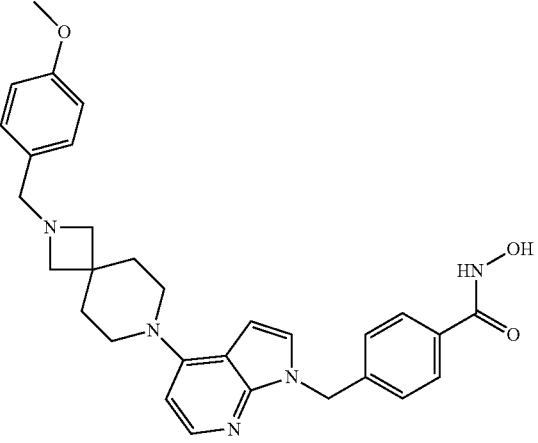 [SMILES: COc1ccc(CN2CC3(CCN(c4ccnc5c4ccn5Cc4ccc(C(=O)NO)cc4)CC3)C2)cc1] |

TABLE 14-continued

| Compound | Structure |
|---|---|
| 1024 | 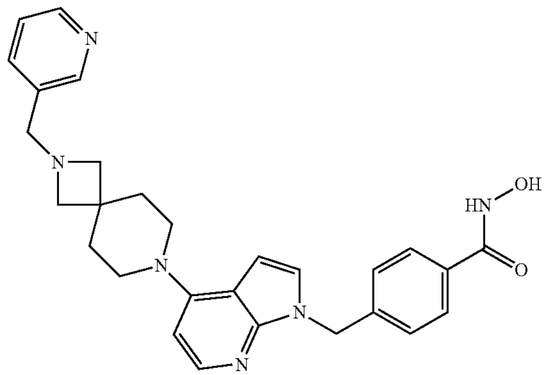 [SMILES: O=C(NO)c1ccc(Cn2ccc3c(N4CCC5(CC4)CN(Cc4cccnc4)C5)ccnc32)cc1] |
| 1025 | 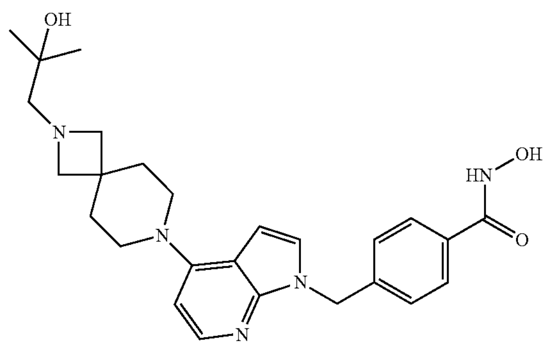 [SMILES: CC(C)(O)CN1CC2(CCN(c3ccnc4c3ccn4Cc3ccc(C(=O)NO)cc3)CC2)C1] |

TABLE 15

| Compound | Structure |
|---|---|
| 1028 | 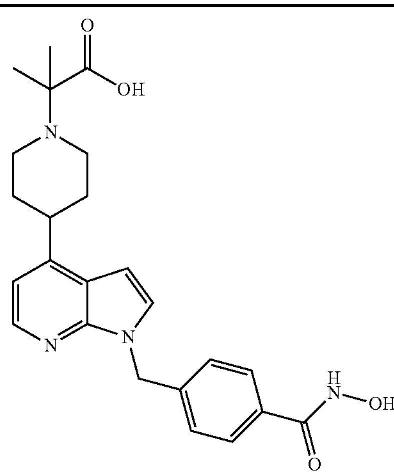 |
| 1098 | 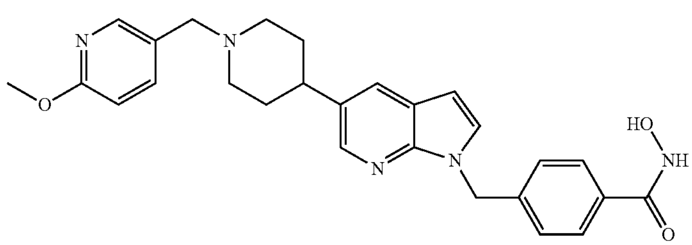 [SMILES: COc1ccc(CN2CCC(c3cnc4c(ccn4Cc4ccc(C(=O)NO)cc4)c3)CC2)cn1] |

TABLE 15-continued
| Compound | Structure |
|---|---|
| 1101 | 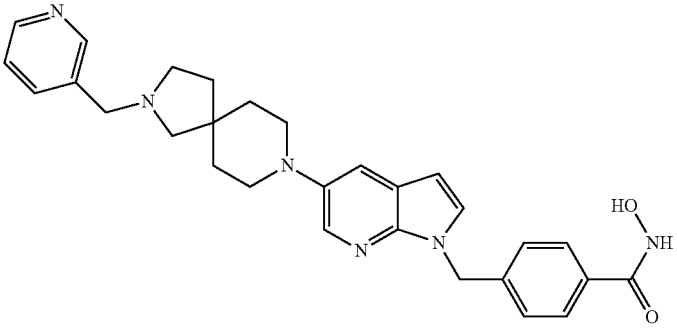 [SMILES: O=C(NO)c1ccc(Cn2ccc3cc(N4CCC5(CCN(Cc6cccnc6)C5)CC4)cnc32)cc1] |
| 1125 | 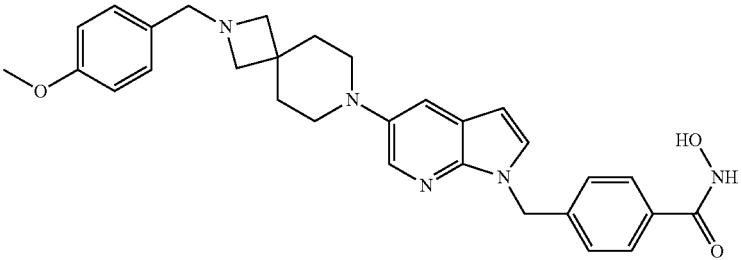 [SMILES: COc1ccc(CN2CC3(CCN(c4cnc5c(ccn5Cc5ccc(C(=O)NO)cc5)c4)CC3)C2)cc1] |
| 1126 | 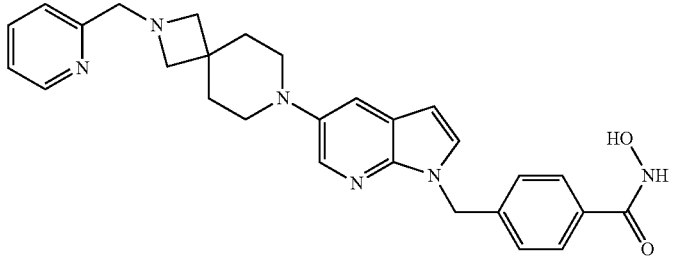 [SMILES: O=C(NO)c1ccc(Cn2ccc3cc(N4CCC5(CC4)CN(Cc4ccccn4)C5)cnc32)cc1] |
In still another embodiment of the present invention, the compound of formula I is preferably selected from the group consisting of the compounds shown in Tables 16 to 19 below.
TABLE 16
| Compound | Structure |
|---|---|
| 223 | 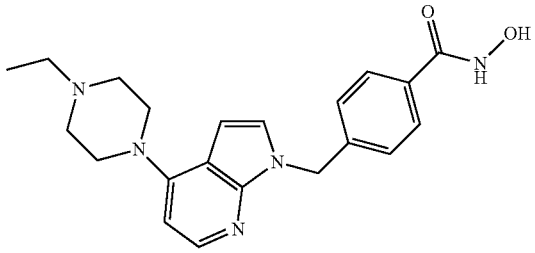 [SMILES: CCN1CCN(c2ccnc3c2ccn3Cc2ccc(C(=O)NO)cc2)CC1] |

TABLE 16-continued

| Compound | Structure |
| --- | --- |
| 224 | 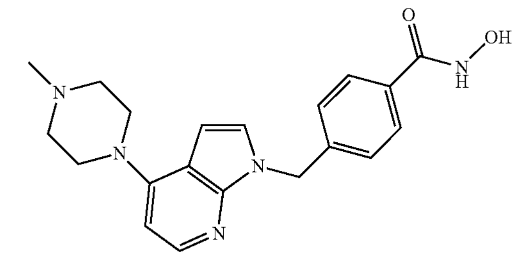 [SMILES: CN1CCN(c2ccnc3c2ccn3Cc2ccc(C(=O)NO)cc2)CC1] |
| 225 | 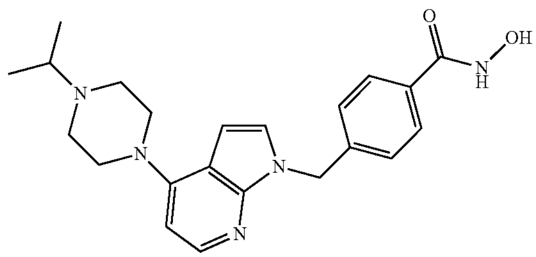 [SMILES: CC(C)N1CCN(c2ccnc3c2ccn3Cc2ccc(C(=O)NO)cc2)CC1] |
| 618 | 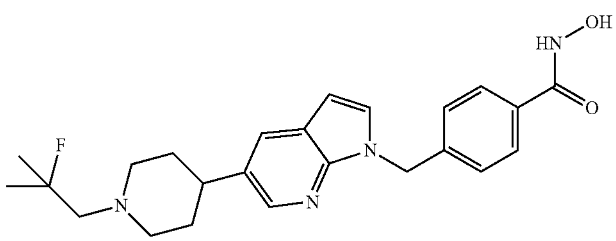 [SMILES: CC(C)(F)CN1CCC(c2cnc3c(ccn3Cc3ccc(C(=O)NO)cc3)c2)CC1] |
| 635 | 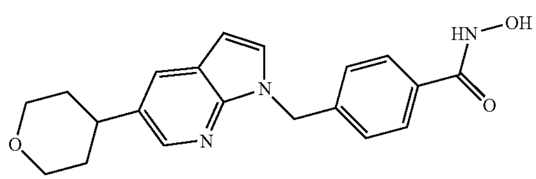 [SMILES: O=C(NO)c1ccc(Cn2ccc3cc(C4CCOCC4)cnc32)cc1] |
| 636 | 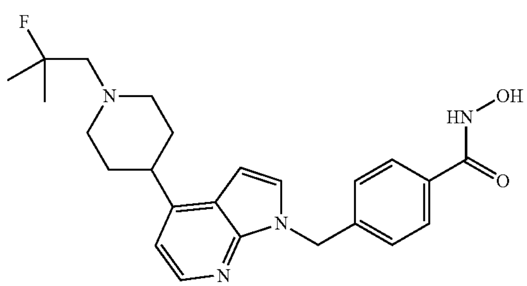 [SMILES: CC(C)(F)CN1CCC(c2ccnc3c2ccn3Cc2ccc(C(=O)NO)cc2)CC1] |
| 642 | 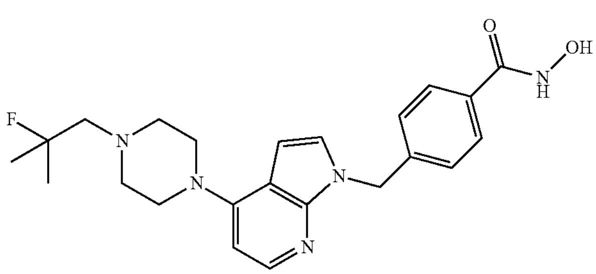 [SMILES: CC(C)(F)CN1CCN(c2ccnc3c2ccn3Cc2ccc(C(=O)NO)cc2)CC1] |

TABLE 16-continued
| Compound | Structure |
|---|---|
| 704 | 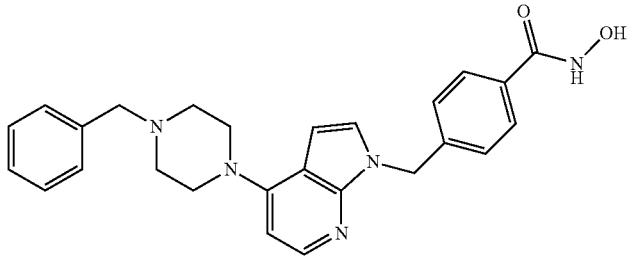 [SMILES: O=C(NO)c1ccc(Cn2ccc3c(N4CCN(Cc5ccccc5)CC4)ccnc32)cc1] |
| 705 | 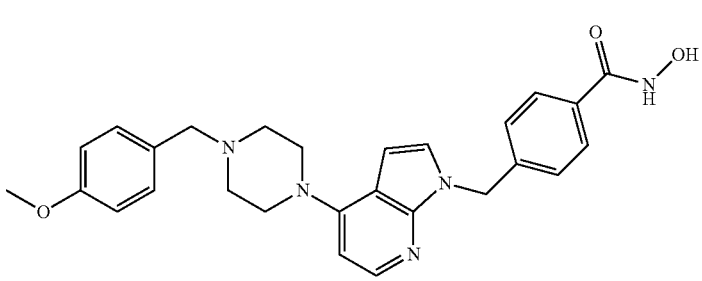 [SMILES: COc1ccc(CN2CCN(c3ccnc4c3ccn4Cc3ccc(C(=O)NO)cc3)CC2)cc1] |
| 706 | 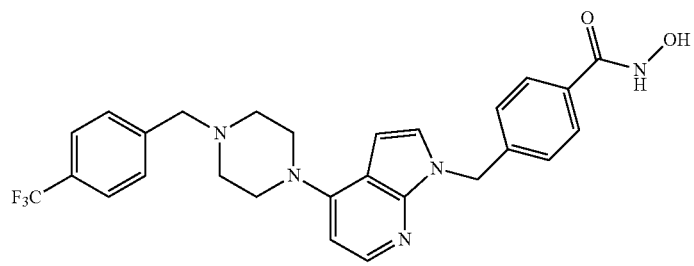 [SMILES: O=C(NO)c1ccc(Cn2ccc3c(N4CCN(Cc5ccc(C(F)(F)F)cc5)CC4)ccnc32)cc1] |
| 714 | 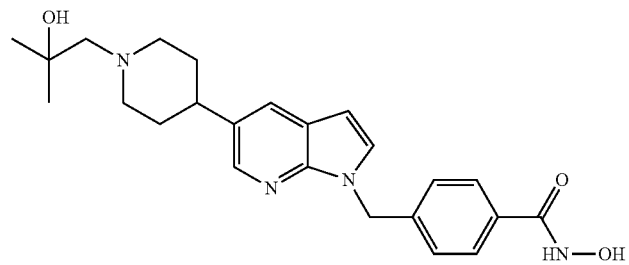 [SMILES: CC(C)(O)CN1CCC(c2cnc3c(ccn3Cc3ccc(C(=O)NO)cc3)c2)CC1] |
| 724 | 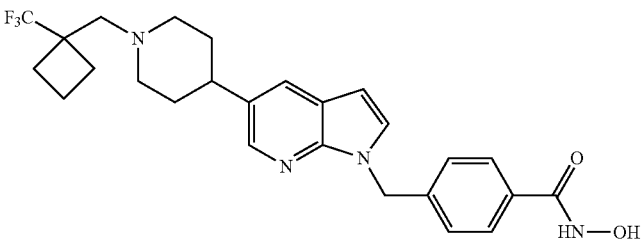 [SMILES: O=C(NO)c1ccc(Cn2ccc3cc(C4CCN(CC5(C(F)(F)F)CCC5)CC4)cnc32)cc1] |

TABLE 17
| Compound | Structure |
|---|---|
| 781 | 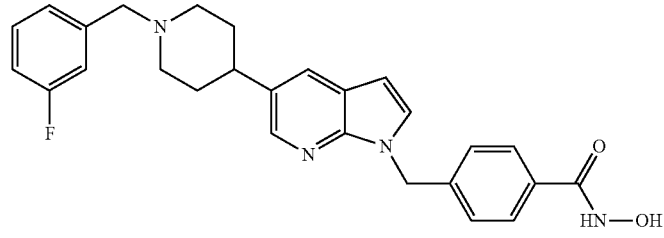 [SMILES: O=C(NO)c1ccc(Cn2ccc3cc(C4CCN(Cc5cccc(F)c5)CC4)cnc32)cc1] |
| 806 | 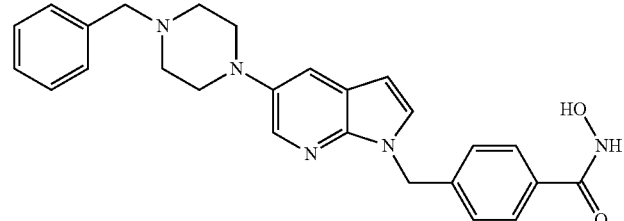 |
| 830 | 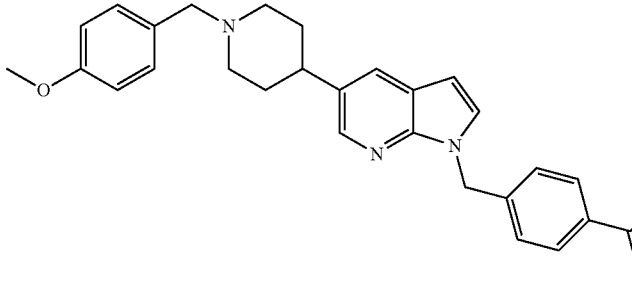 |
| 840 | 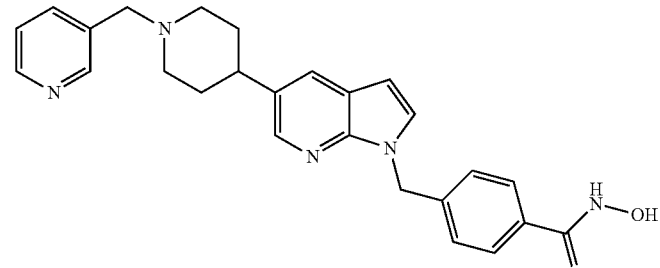 |
| 841 | 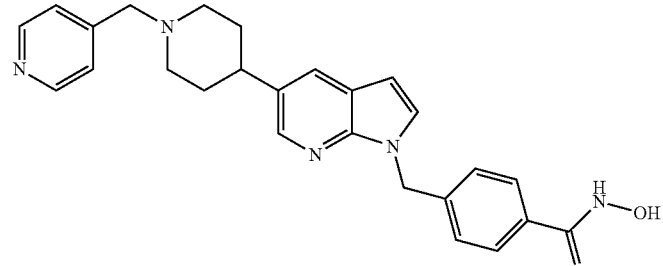 |

TABLE 17-continued

| Compound | Structure |
|---|---|
| 842 | (structure) |
| 843 | (structure) |
| 844 | (structure) |
| 846 | (structure) |
| 848 | (structure) |

TABLE 17-continued
| Compound | Structure |
|---|---|
| 851 | 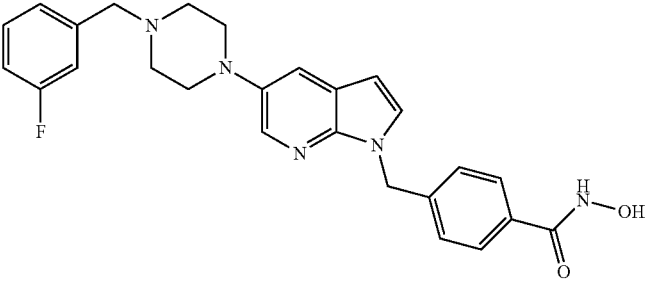 [SMILES: O=C(NO)c1ccc(Cn2ccc3cc(N4CCN(Cc5cccc(F)c5)CC4)cnc32)cc1] |
| 852 | 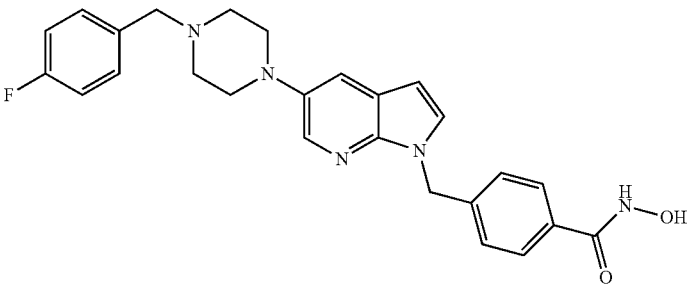 [SMILES: O=C(NO)c1ccc(Cn2ccc3cc(N4CCN(Cc5ccc(F)cc5)CC4)cnc32)cc1] |
TABLE 18
| Compound | Structure |
|---|---|
| 853 | 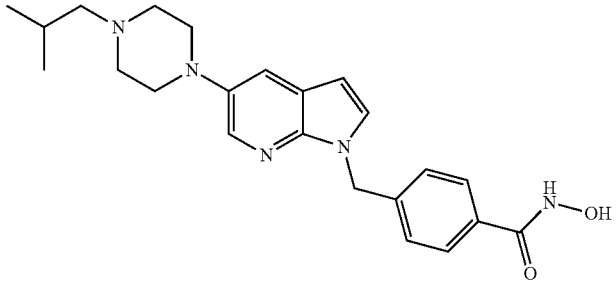 [SMILES: CC(C)CN1CCN(c2cnc3c(ccn3Cc3ccc(C(=O)NO)cc3)c2)CC1] |
| 857 | 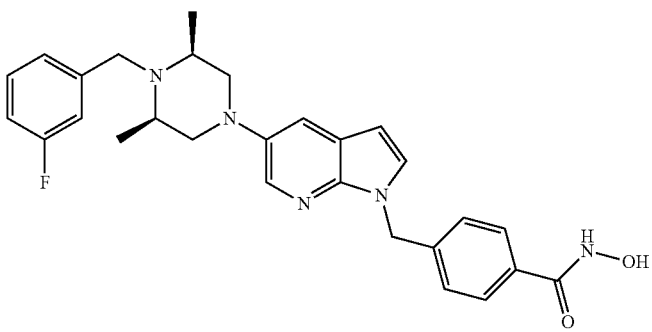 [SMILES: C[C@@H]1CN(c2cnc3c(ccn3Cc3ccc(C(=O)NO)cc3)c2)C[C@H](C)N1Cc1cccc(F)c1] |

татлица TABLE 18-continued
| Compound | Structure |
|---|---|
| 862 | 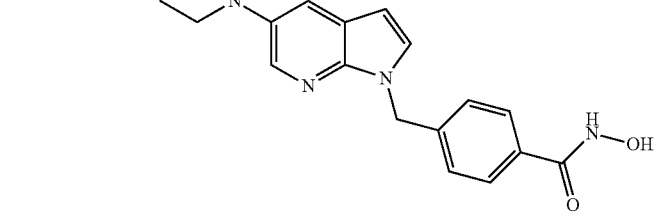 |
| 863 | 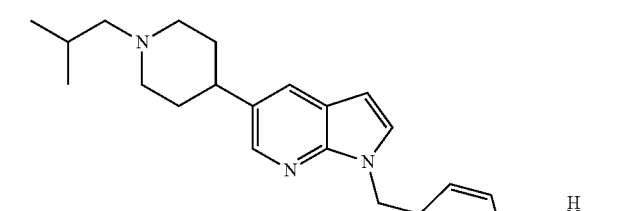 |
| 864 | 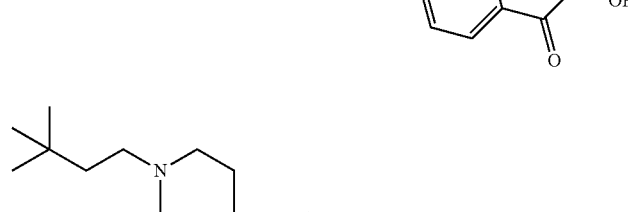 |
| 865 | 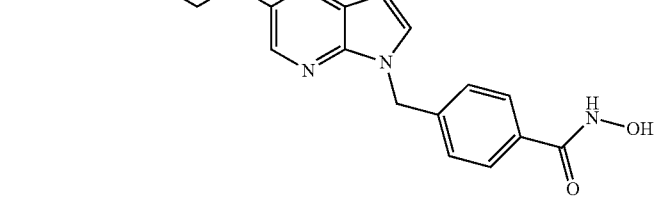 |
| 878 | 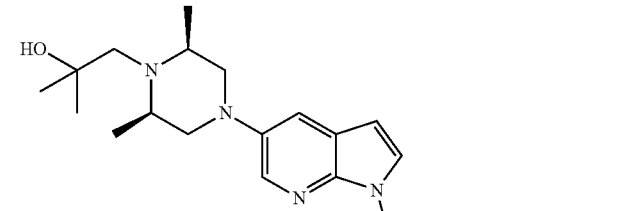 |

TABLE 18-continued
| Compound | Structure |
|---|---|
| 879 | 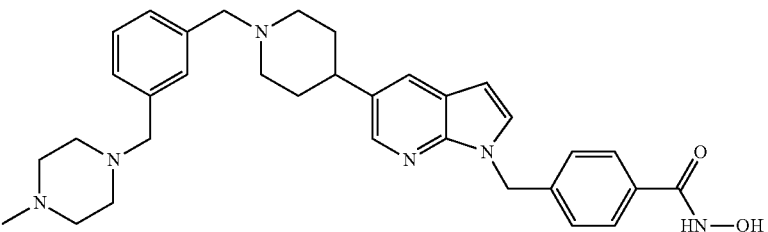 [SMILES: CN1CCN(Cc2cccc(CN3CCC(c4cnc5c(ccn5Cc5ccc(C(=O)NO)cc5)c4)CC3)c2)CC1] |
| 881 | 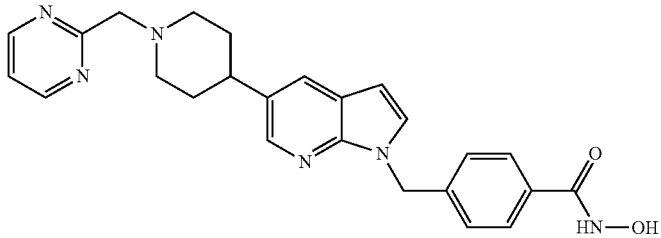 [SMILES: O=C(NO)c1ccc(Cn2ccc3cc(C4CCN(Cc5ncccn5)CC4)cnc32)cc1] |
| 882 | 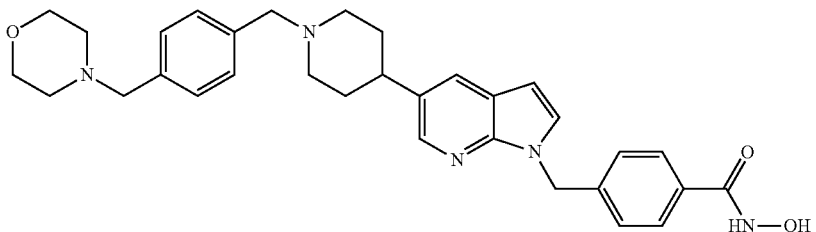 [SMILES: O=C(NO)c1ccc(Cn2ccc3cc(C4CCN(Cc5ccc(CN6CCOCC6)cc5)CC4)cnc32)cc1] |
| 883 | 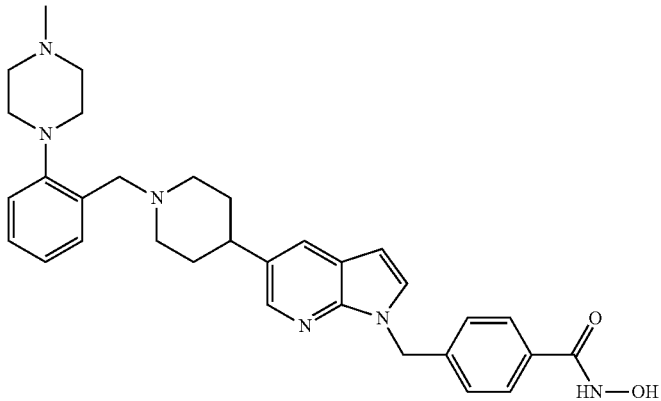 [SMILES: CN1CCN(c2ccccc2CN2CCC(c3cnc4c(ccn4Cc4ccc(C(=O)NO)cc4)c3)CC2)CC1] |
| 957 | 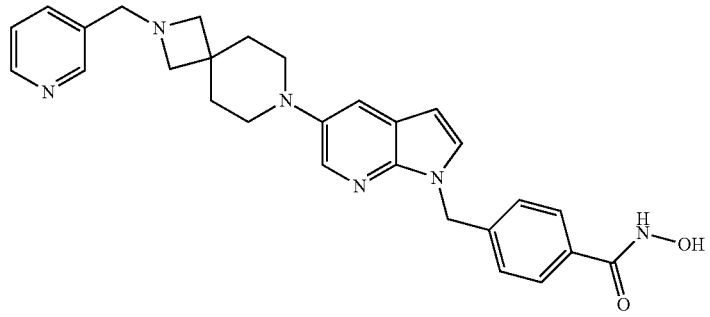 [SMILES: O=C(NO)c1ccc(Cn2ccc3cc(N4CCC5(CC4)CN(Cc4cccnc4)C5)cnc32)cc1] |

TABLE 19
| Compound | Structure |
|---|---|
| 959 | 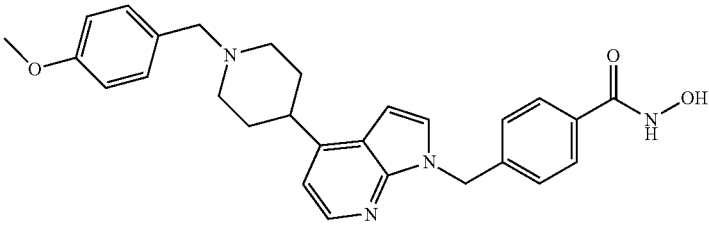 [SMILES: COc1ccc(CN2CCC(c3ccnc4c3ccn4Cc3ccc(C(=O)NO)cc3)CC2)cc1] |
| 984 | 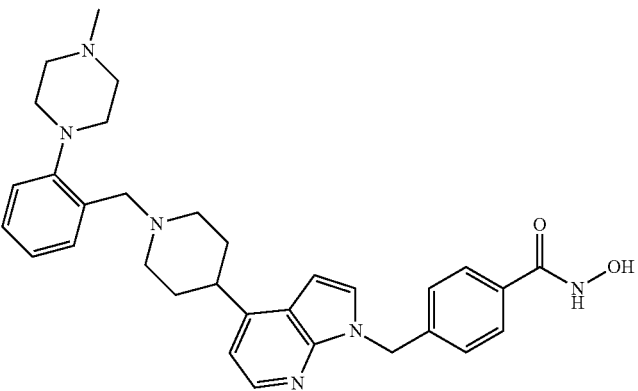 [SMILES: CN1CCN(c2ccccc2CN2CCC(c3ccnc4c3ccn4Cc3ccc(C(=O)NO)cc3)CC2)CC1] |
| 985 | 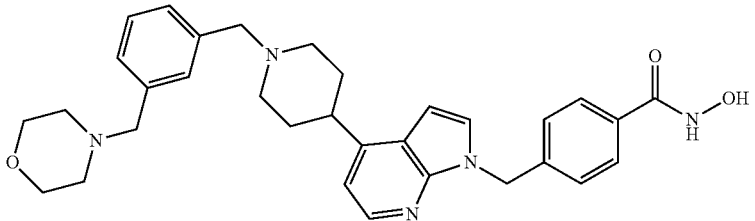 [SMILES: O=C(NO)c1ccc(Cn2ccc3c(C4CCN(Cc5cccc(CN6CCOCC6)c5)CC4)ccnc32)cc1] |
| 986 | 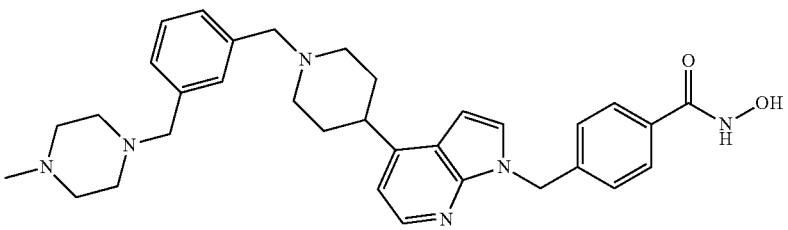 [SMILES: CN1CCN(Cc2cccc(CN3CCC(c4ccnc5c4ccn5Cc4ccc(C(=O)NO)cc4)CC3)c2)CC1] |
| 990 | 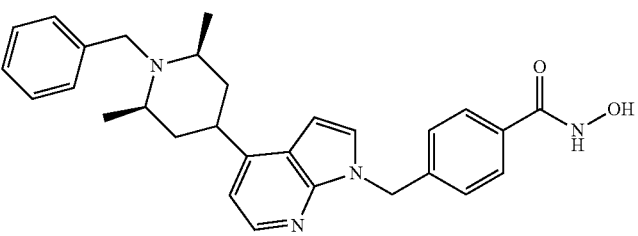 [SMILES: C[C@@H]1CC(c2ccnc3c2ccn3Cc2ccc(C(=O)NO)cc2)C[C@H](C)N1Cc1ccccc1] |

TABLE 19-continued
| Compound | Structure |
|---|---|
| 1017 | 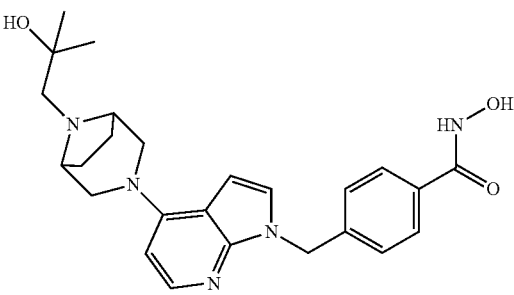 [SMILES: CC(C)(O)CN1C2CCC1CN(c1ccnc3c1ccn3Cc1ccc(C(=O)NO)cc1)C2] |
| 1021 | 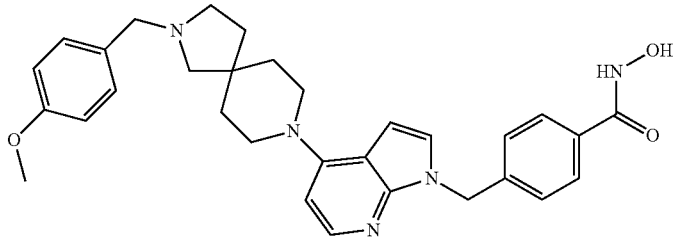 [SMILES: COc1ccc(CN2CCC3(CCN(c4ccnc5c4ccn5Cc4ccc(C(=O)NO)cc4)CC3)C2)cc1] |
| 1023 | 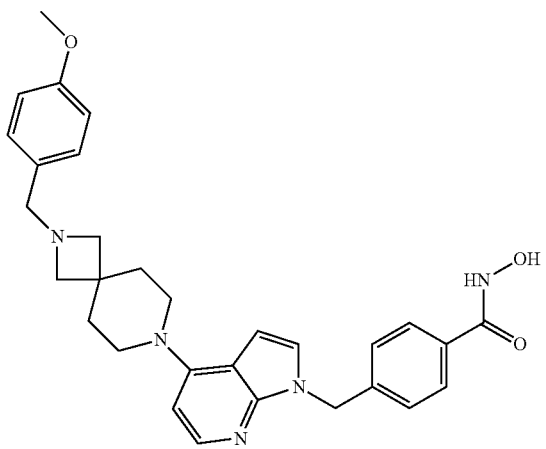 [SMILES: COc1ccc(CN2CC3(CCN(c4ccnc5c4ccn5Cc4ccc(C(=O)NO)cc4)CC3)C2)cc1] |
| 1101 | 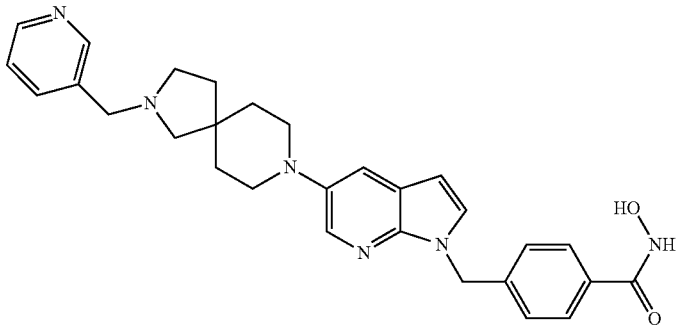 [SMILES: O=C(NO)c1ccc(Cn2ccc3cc(N4CCC5(CCN(Cc6cccnc6)C5)CC4)cnc32)cc1] |
| 1126 | 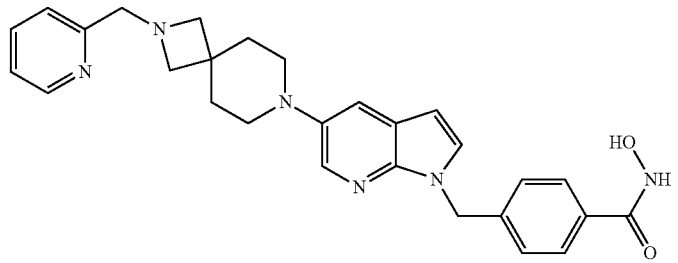 [SMILES: O=C(NO)c1ccc(Cn2ccc3cc(N4CCC5(CC4)CN(Cc4ccccn4)C5)cnc32)cc1] |

In the present invention, the compound of formula I, a pharmaceutically acceptable salt thereof, a solvate thereof, or a hydrate thereof, may be crystalline or amorphous, and the present invention encompasses these crystalline and/or amorphous compounds.

As used herein, the term "pharmaceutically acceptable salt" means salts of inorganic acids, salts of organic acids, or salts of metals, which are generally used in the preparation of medicaments. "Inorganic acids" include hydrochloric acid, hydrobromic acid, sulfuric acid, phosphoric acid and the like. "Organic acids" includes citric acid, acetic acid, lactic acid, tartaric acid, fumaric acid, formic acid, propionic acid, oxalic acid, trifluoroacetic acid, methanesulfonic acid, benzenesulfonic acid, maleic acid, benzoic acid, gluconic acid, glycolic acid, succinic acid, 4-morpholineethanesulfonic acid, camphorsulfonic acid, 4-nitrobenzenesulfonic acid, hydroxy-O-sulfonic acid, 4-toluenesulfonic acid, galacturonic acid, embolic acid, glutamic acid, aspartic acid, adipate salt, camsylate salt, or besylate salt. "Metals" include sodium, potassium, calcium, magnesium and the like.

In the present invention, a solvent "solvate" means any conventional solvent that is used in the preparation of organic compounds. Examples of the solvent include methanol, ethanol, 1-propanol, 2-propanol, 1-butanol, 2-butanol, 1-acetate, acetone, acetic acid, anisole, tetrahydrofuran, methyl acetate, ethyl acetate, propyl acetate, isopropyl acetate, isobutyl acetate, n-butyl acetate, dimethyl sulfoxide, pentane, heptane, and the like, but the solvates of the present invention are not limited these examples.

In the present invention, "hydrate" and "solvate" may be contained in an amount of 0.25-10 moles, for example, 0.5, 1, 1.5, 2, 2.5, 3 or 5 moles, per mole of the compound of formula I, but the scope of the present invention is not limited to these examples.

In the present invention, "isomer" refers to steroisomers, but the scope of the present invention is not limited thereto.

Pharmaceutical Composition Comprising Novel HDAC Inhibitor Compound

The present invention also provides a pharmaceutical composition comprising the compound of formula I, an isomer thereof, a pharmaceutically acceptable salt thereof, a hydrate thereof, or a solvate thereof, together with a pharmaceutically acceptable carrier.

The carrier may be one that is generally in the art. Examples of the carrier include, but are not limited to, sugar, starch, microcrystalline cellulose, lactose (lactose hydrate), glucose, D-mannitol, alginate, an alkaline earth metal salt, clay, polyethylene glycol, anhydrous calcium hydrogen phosphate, and mixtures thereof.

In another embodiment of the present invention, the pharmaceutical composition may contain additives such as a binder, a disintegrant, a lubricant, a pH-adjusting agent or an antioxidant.

Examples of the binder include, but are not limited to, starch, microcrystalline cellulose, highly dispersive silica, mannitol, D-mannitol, sucrose, lactose hydrate, polyethylene glycol, polyvinylpyrrolidone (povidone), a polyvinylpyrrolidone copolymer (copovidone), hypromellose, hydroxypropylcellulose, natural gum, synthetic gum, copovidone, gelatin, and mixtures thereof.

Examples of the disintegrant include, but are not limited to, starches or modified starches such as sodium starch glycolate, corn starch, potato starch, and pregelatinized starch; clays such as bentonite, montmorillonite, and veegum;

celluloses such as microcrystalline cellulose, hydroxypropylcellulose, and carboxymethylcellulose; algins such as sodium alginate, and alginic acid; crosslinked celluloses such as croscarmellose sodium; gums such as guar gum, and xanthan gum; crosslinked polymers such as crosslinked polyvinylpyrrolidone (crospovidone); effervescent agents such as sodium bicarbonate and citric acid; and mixtures thereof.

Examples of the lubricant include, but are not limited to, talc, stearic acid, magnesium stearate, calcium stearate, sodium lauryl sulfate, hydrogenated vegetable oil, sodium benzoate, sodium stearyl fumarate, glyceryl behenate, glyceryl monolaurate, glyceryl monostearate, glyceryl palmitostearate, colloidal silicon dioxide, and mixtures thereof.

Examples of the pH-adjusting agent include, but are not limited to, acidifying agents such as acetic acid, adipic acid, ascorbic acid, sodium ascorbate, sodium etherate, malic acid, succinic acid, tartaric acid, fumaric acid, and citric acid, and basifying agents such as precipitated calcium carbonate, aqueous ammonia, meglumine, sodium carbonate, magnesium oxide, magnesium carbonate, sodium citrate, and tribasic calcium phosphate.

Examples of the antioxidant include, but are not limited to, dibutyl hydroxy toluene, butylated hydroxyanisole, tocopherol acetate, tocopherol, propyl gallate, sodium hydrogen sulfite, and sodium pyrosulfite. Examples of the solubilizer in an immediate-release compartment of the present invention include, but are not limited to, sodium lauryl sulfate, polyoxyethylene sorbitan fatty acid ester (such as polysorbate), docusate sodium, and poloxamer.

The pharmaceutical composition of the present invention exhibits the effect of inhibiting HDAC activity, and may be used for the prevention or treatment of HDAC activity-associated diseases.

The HDAC activity-associated diseases include malignant tumor disease, inflammatory diseases, rheumatoid arthritis, and neurodegenerative diseases.

Method for Preventing or Treating HDAC Activity-Associated Disease

The present invention also provides a method for preventing or treating HDAC activity-associated disease, the method comprising administering to a subject in need thereof a composition comprising the compound of Formula I as an active ingredient.

The composition that is used in the preventing or treating method of the present invention is intended to include the pharmaceutical composition described in the specification.

In addition, the subject in need of the preventing or treating method of the present invention is intended to include mammals, particularly humans.

Method for Preparing Novel HDAC Inhibitor Compound

The compound of formula I according to the present invention may be prepared according to the methods disclosed in various publications (U.S. Pat. No. 8,466,161, and WO2011/011186), but is not limited thereto.

Hereinafter, a method for preparing the compound of formula I will be described in detail with reference to the following reaction schemes.

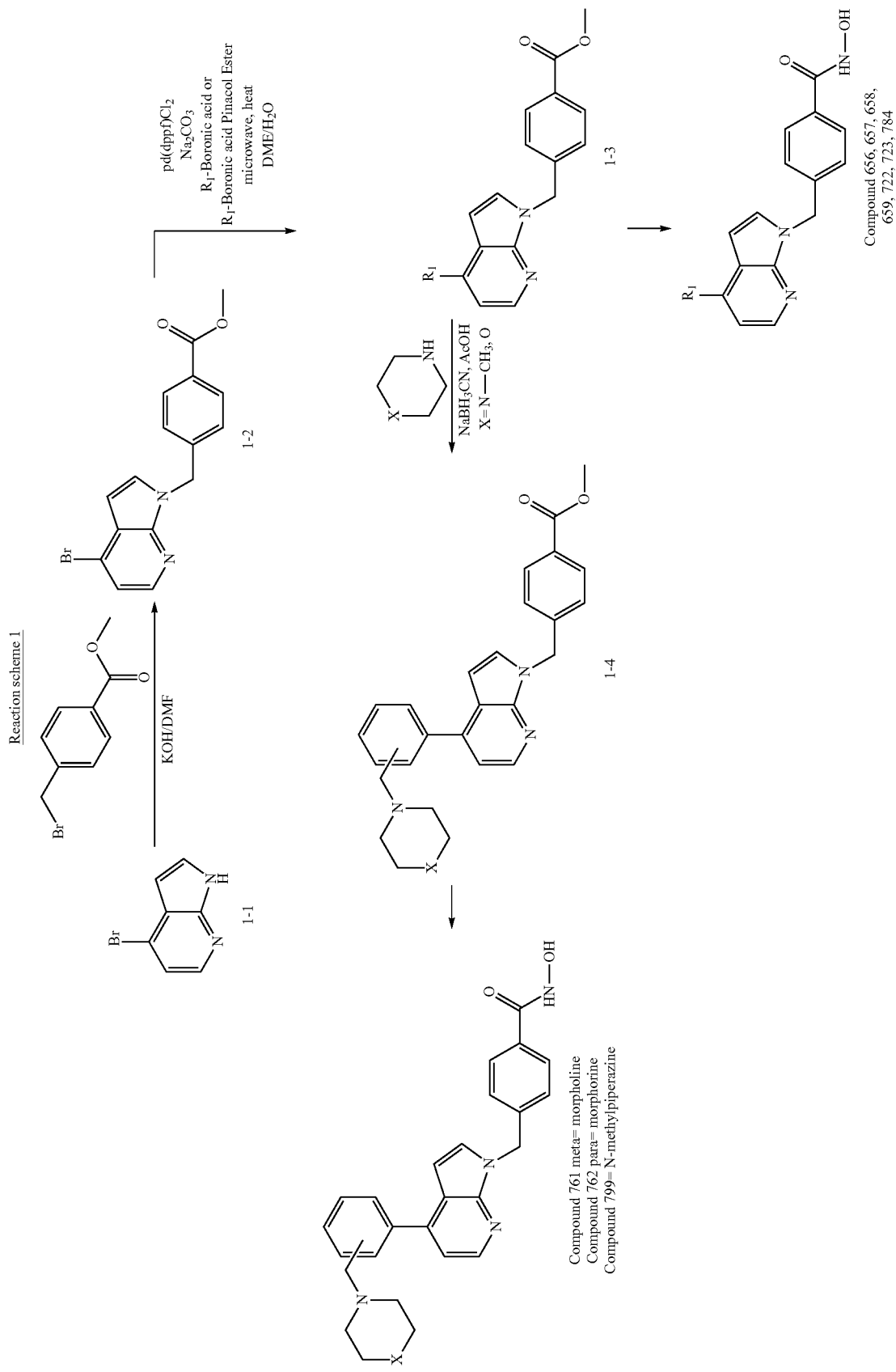

| Compound | R₁ |
|---|---|
| 656 | phenyl |
| 657 | pyridin-4-yl |
| 658 | 2,4-difluorophenyl |
| 659 | pyrimidin-5-yl |
| 722 | 3-aminophenyl |
| 723 | 1-methyl-1,2,3,6-tetrahydropyridin-4-yl |
| 784 | 1-Boc-1,2,3,6-tetrahydropyridin-4-yl |

As shown in reaction scheme 1 above, a compound of formula 1-1 is reacted with methyl 4-(bromomethyl) benzoate at normal temperature to synthesize a compound of formula 1-2, which is then subjected to a Suzuki reaction with boronic acid or boronic acid ester using microwaves, thereby synthesizing a compound of formula 1-3 having substituent R₁ introduced therein. Finally, potassium hydroxide (KOH), methanol and hydroxylamine are added to the compound of formula 1-3, and then reacted at room temperature, thereby synthesizing final compounds 656, 657, 658, 659, 722, 723 and 784.

In addition, the compound of formula 1-3 may be subjected to reductive amination to synthesize a compound of formula 1-4. Finally, potassium hydroxide (KOH), methanol and hydroxylamine are added to the compound of formula 1-4, and then reacted at room temperature, thereby synthesizing final compounds 761, 762 and 799.

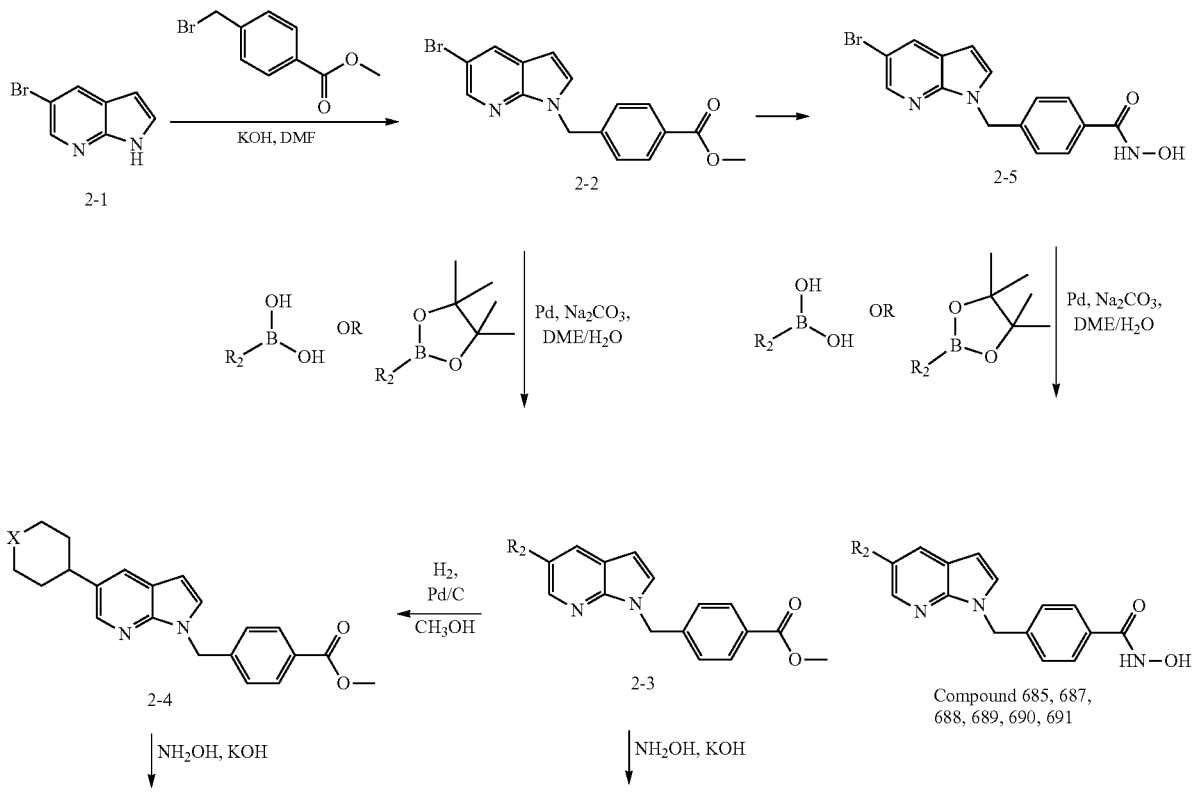

Reaction scheme 2

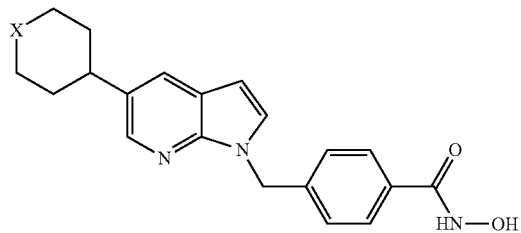
Comopound 635: X = O
Comopound 694: X = N-Boc
Comopound 867: X = N-CH₃
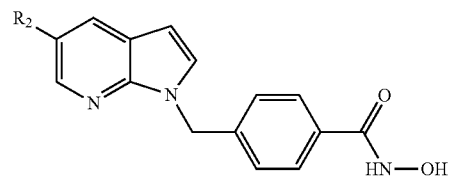
Compound 629, 645, 647, 648, 649, 650, 692, 746, 787, 805, 806, 807, 809, 810
| Compound | R₂ |
|---|---|
| 629 | 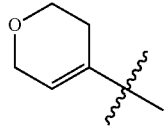 [SMILES: *C1=CCOCC1] |
| 645 | 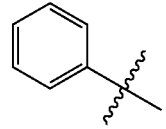 [SMILES: *c1ccccc1] |
| 647 | 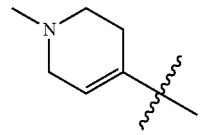 [SMILES: *C1=CCN(C)CC1] |
| 648 | 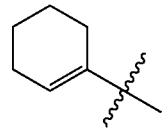 |
| 649 | 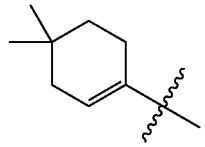 [SMILES: *C1=CCC(C)(C)CC1] |
| 650 | 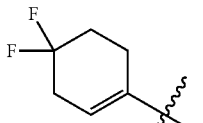 |
| 685 | 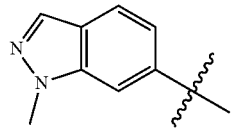 |
| 687 | 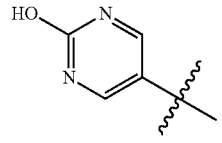 [SMILES: *c1cnc(O)nc1] |
-continued
| Compound | R₂ |
|---|---|
| 688 | 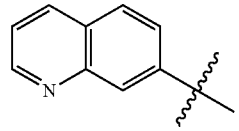 [SMILES: *c1ccc2cccnc2c1] |
| 689 | 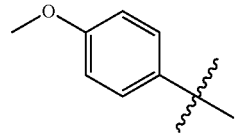 [SMILES: *c1ccc(OC)cc1] |
| 690 | 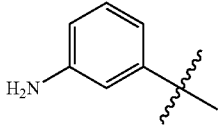 |
| 691 | 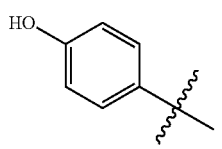 [SMILES: *c1ccc(O)cc1] |
| 692 | 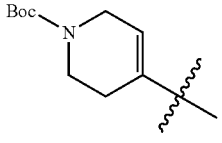 [SMILES: *C1=CCN(C(=O)OC(C)(C)C)CC1] |
| 746 | 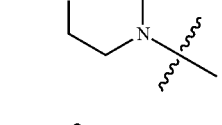 |
| 787 | 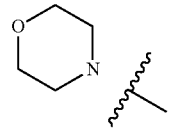 |
| 805 | 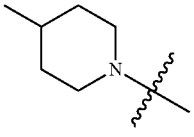 [SMILES: *N1CCC(C)CC1] |

-continued

| Compound | R₂ |
|---|---|
| 806 | Bn-N(piperazine) |
| 807 | 2,6-dimethylmorpholine |
| 809 | BocHN-piperidine |
| 810 | Ph-tetrahydropyridine |

As shown in reaction scheme 2, a compound of formula 2-1 is reacted with methyl 4-(bromomethyl)benzoate at normal temperature to synthesize a compound of formula 2-2. Potassium hydroxide (KOH), methanol and hydroxylamine are added to the compound of formula 2-2, and then reacted at room temperature to synthesize a compound of formula 2-5. Finally, substituent R₂ is introduced into the compound of formula 2-5 by a Suzuki reaction with boronic acid or boronic acid ester using microwaves, thereby synthesizing final compounds 685, 687, 688, 689, 690 and 691.

In addition, substituent R₂ may be introduced into the compound of formula 2-2 by a Suzuki reaction with boronic acid or boronic acid ester using microwaves, thereby synthesizing a compound of formula 2-3. Finally, potassium hydroxide (KOH), methanol and hydroxylamine are added to the compound of formula 2-3, and then reacted at room temperature, thereby synthesizing final compounds 629, 645, 647, 648, 649, 650, 692 and 746.

In addition, substituent R₂ may be introduced into the compound of formula 2-2 by a Buchwald reaction with secondary amine, thereby synthesizing a compound of formula 2-3. Finally, potassium hydroxide (KOH), methanol and hydroxylamine are added to the compound of formula 2-3, and then reacted at room temperature, thereby synthesizing final compounds 787, 805, 806, 807, 809 and 810.

In addition, the compound of formula 2-3 may be hydrogenated in the presence of Pd/C to synthesize a compound of formula 2-4. Finally, potassium hydroxide (KOH), methanol and hydroxylamine are added to the compound of formula 2-4, and then reacted at room temperature, thereby synthesizing final compounds 635, 694 and 867.

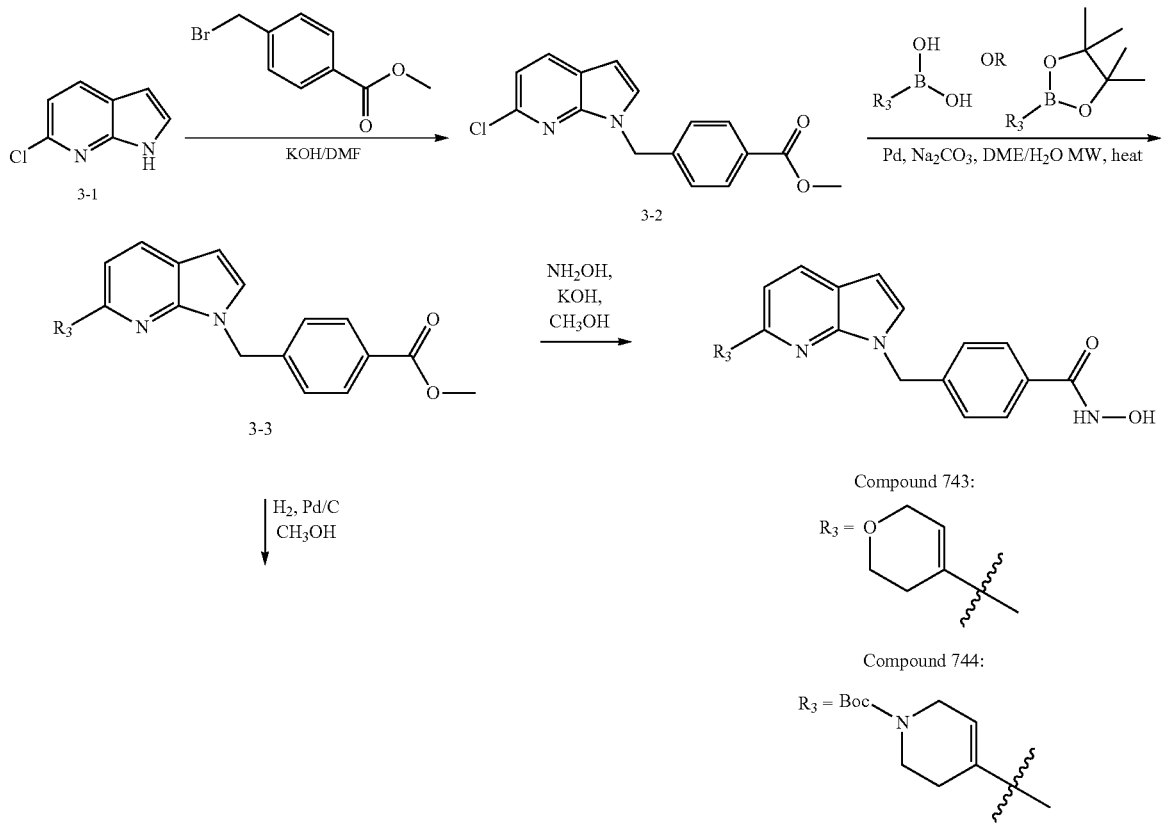

Reaction scheme 3

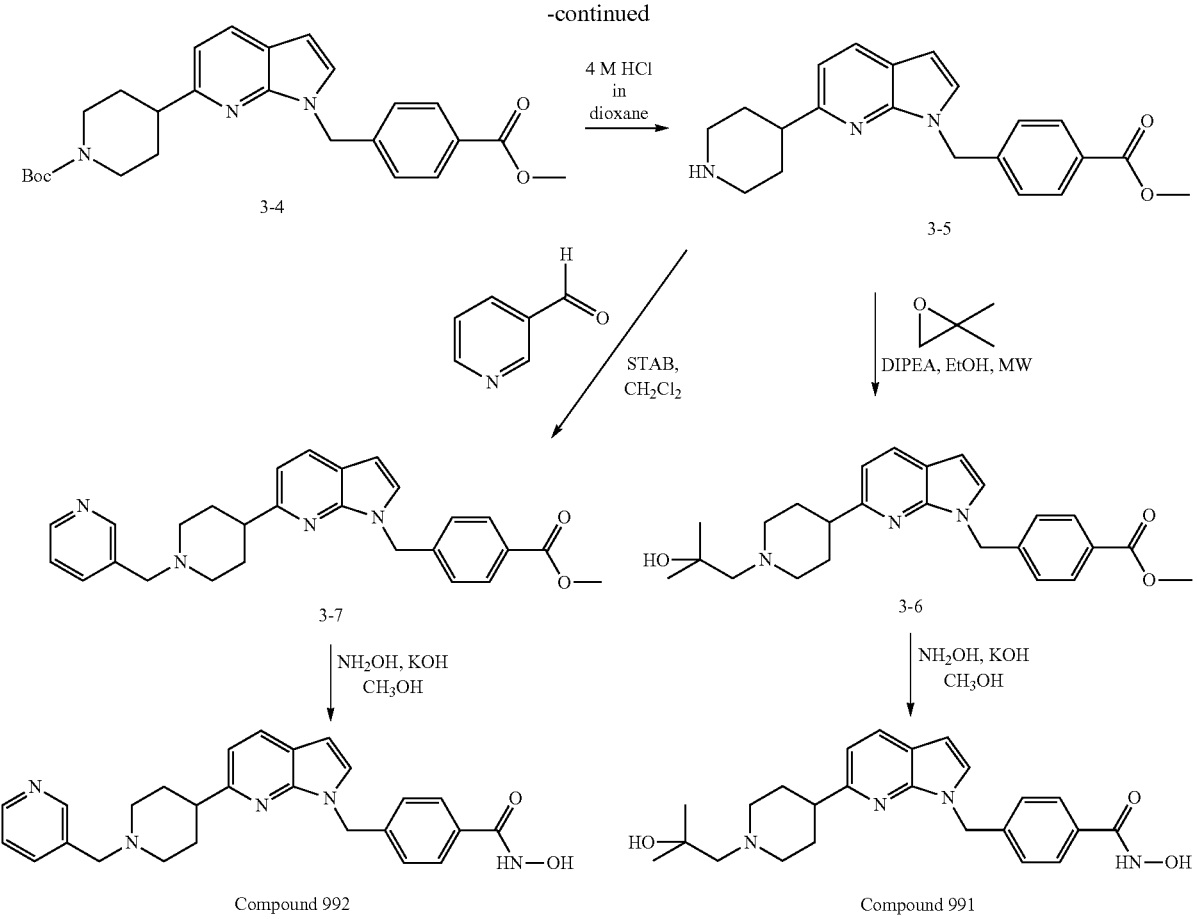

In reaction scheme 3, a compound of formula 3-1 is reacted with 4-(bromomethyl)benzoate at normal temperature to synthesize a compound of formula 3-2. Substituent $R_3$ is introduced into the compound of formula 3-2 by a Suzuki reaction with boronic acid or boronic acid ester using microwaves, thereby synthesizing a compound of formula 3-3. Finally, potassium hydroxide (KOH), methanol and hydroxylamine are added to the compound of formula 3-3, and then reacted at room temperature, thereby synthesizing final compounds 743 and 744.

In addition, a compound of formula 3-3 may be hydrogenated in the presence of Pd/C to synthesize a compound of formula 3-4. The compound of formula 3-4 is reacted with 4 M hydrochloric acid solution to synthesize a compound of formula 3-5, which is then subjected to reductive amination with nicotine aldehyde or reacted with oxirane using microwaves, respectively, thereby synthesizing compounds of formulas 3-7 and 3-6. Finally, Potassium hydroxide (KOH), methanol and hydroxylamine are added to each of the compounds of formulas 3-7 and 3-6, and then reacted at room temperature, thereby synthesizing final compounds 991 and 992.

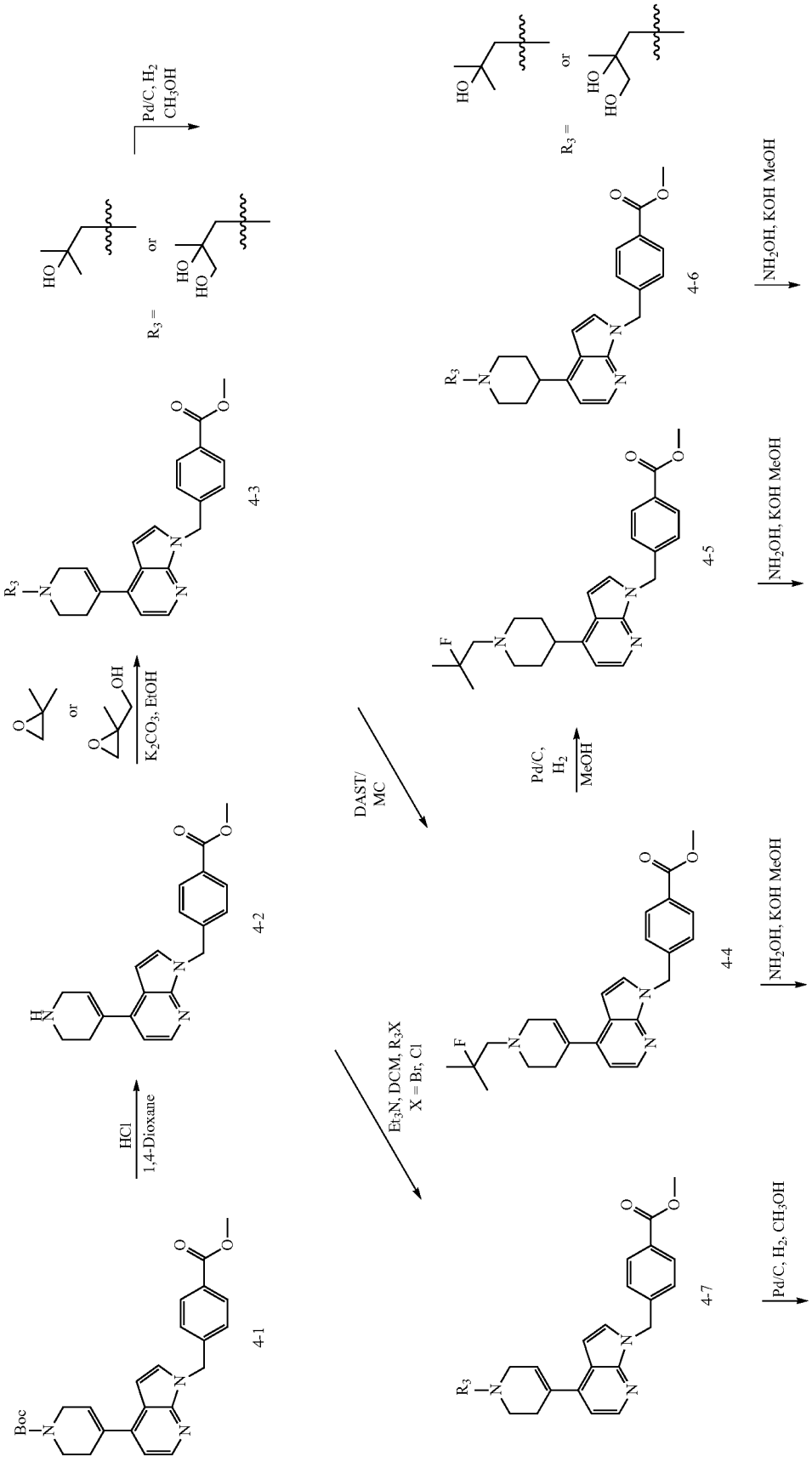

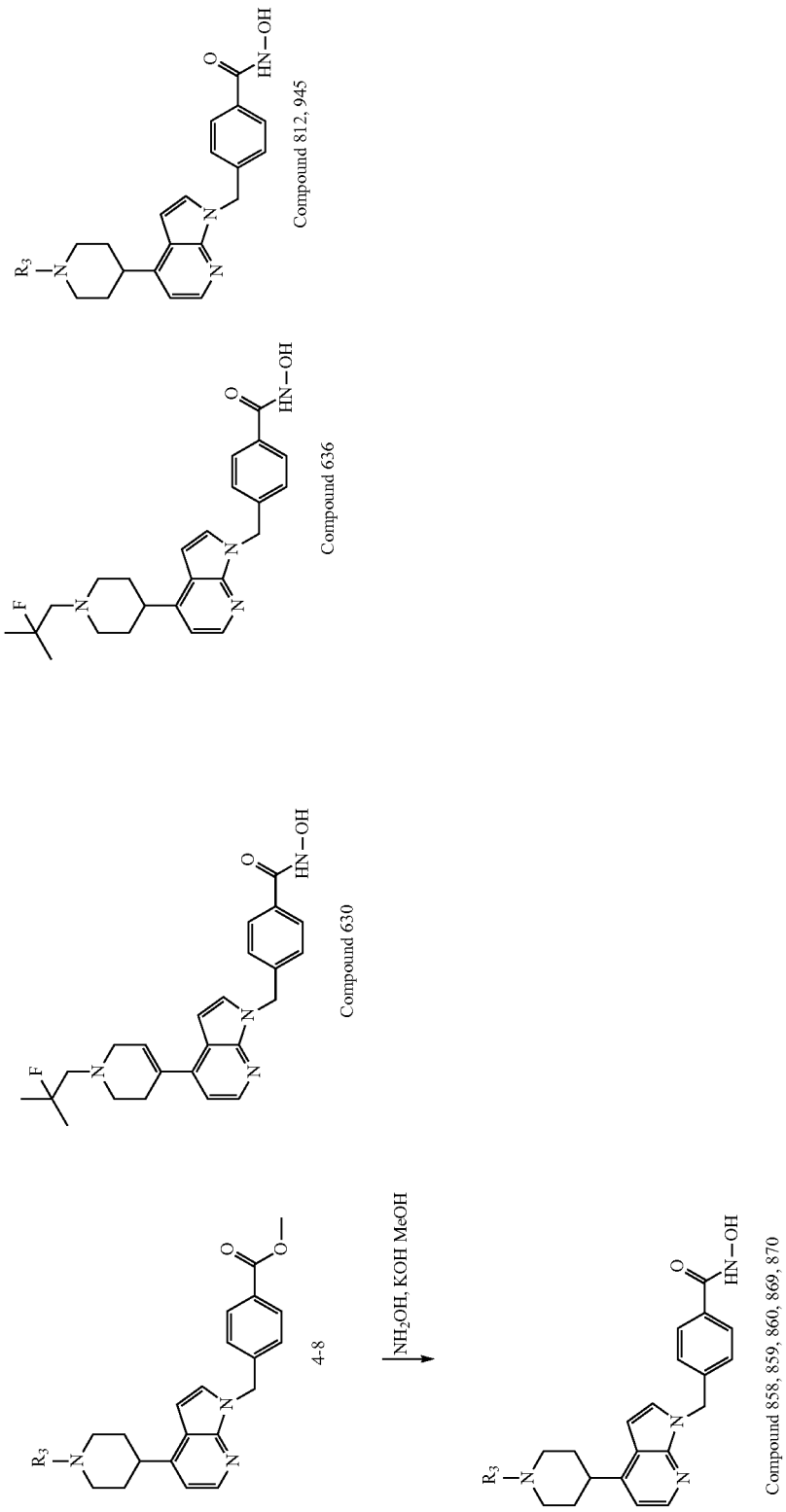

| Compound | R₃ |
|---|---|
| 812 | (HO-C(CH₃)₂-CH₂-) |
| 858 | (F-C(CH₃)₂-C(=O)-) |
| 859 | (3-methoxybenzyl) |
| 860 | (3-fluorobenzoyl) |
| 869 | (2-fluorobenzyl) |
| 870 | (3-fluorobenzyl) |

| Compound | R₃ |
|---|---|
| 945 | (HO-CH₂-C(OH)(CH₃)-CH₂-) |

As shown in reaction scheme 4 above, the amino protective group (Boc) of a compound of formula 4-1 is removed to synthesize a compound of formula 4-2, which is then reacted with an oxirane compound using microwaves, thereby synthesizing a compound of formula 4-3. The hydroxyl group of the compound of formula 4-3 is substituted with fluorine to synthesize a compound of formula 4-4. Finally, potassium hydroxide (KOH), methanol and hydroxylamine hydrochloride are added to the compound of formula 4-4, and then reacted at room temperature, thereby synthesizing final compound 630.

In addition, the compound of 4-4 may be hydrogenated in the presence of Pd/C to synthesize a compound of formula 4-5. Finally, potassium hydroxide (KOH), methanol and hydroxylamine are added to the compound of formula 4-5, and then reacted at room temperature, thereby synthesizing final compound 636.

In addition, the compound of 4-3 may be hydrogenated in the presence of Pd/C to synthesize a compound of formula 4-6. Finally, potassium hydroxide (KOH), methanol and hydroxylamine are added to the compound of formula 4-6, and then reacted at room temperature, thereby synthesizing final compounds 812 and 945.

In addition, the compound of formula 4-2 may be alkylated or acylated to synthesize a compound of formula 4-7, which is then hydrogenated in the presence of Pd/C to synthesize a compound of formula 4-8. Finally, potassium hydroxide (KOH), methanol and hydroxylamine are added to the compound of formula 4-8, and then reacted at room temperature, thereby synthesizing final compounds 858, 859, 860, 869 and 870.

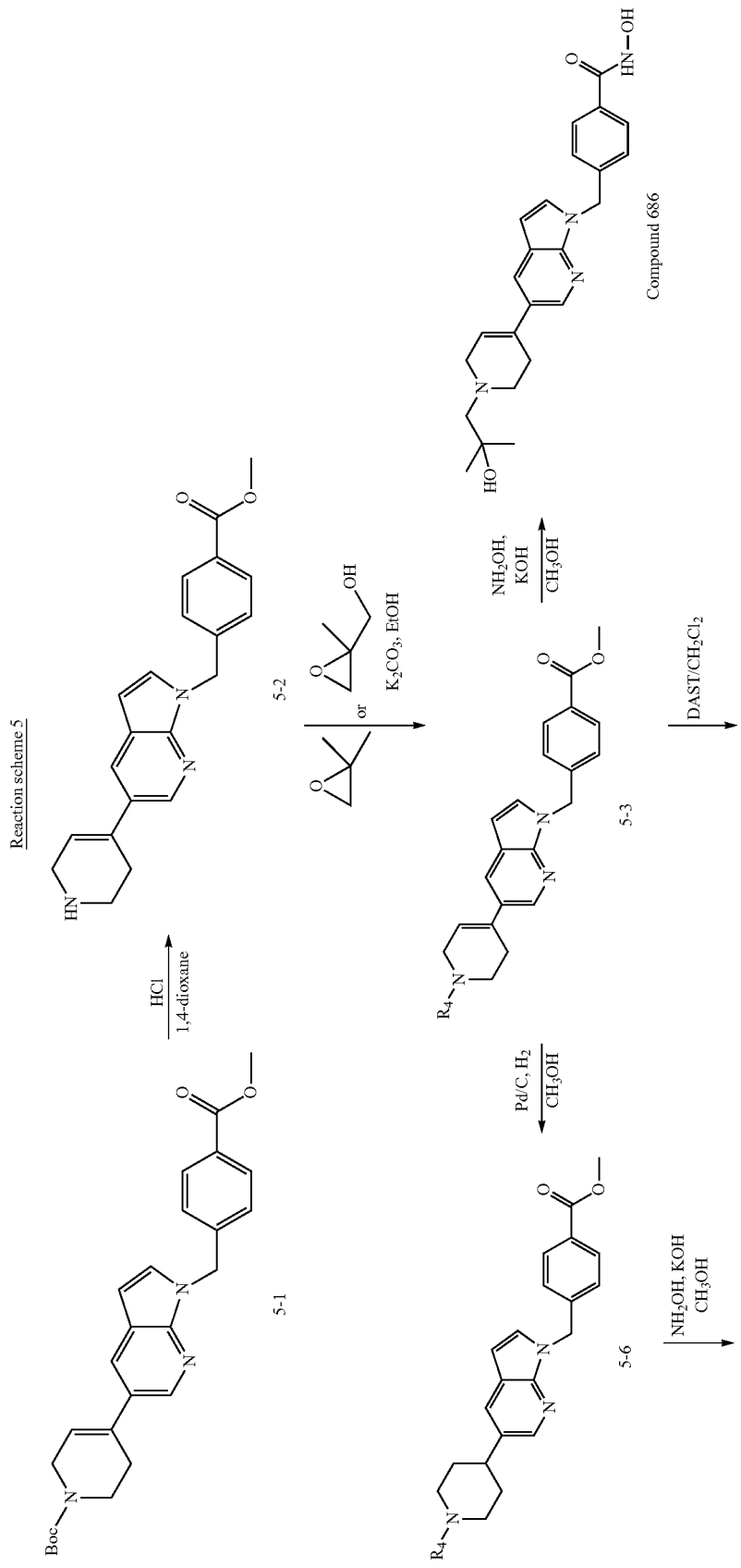

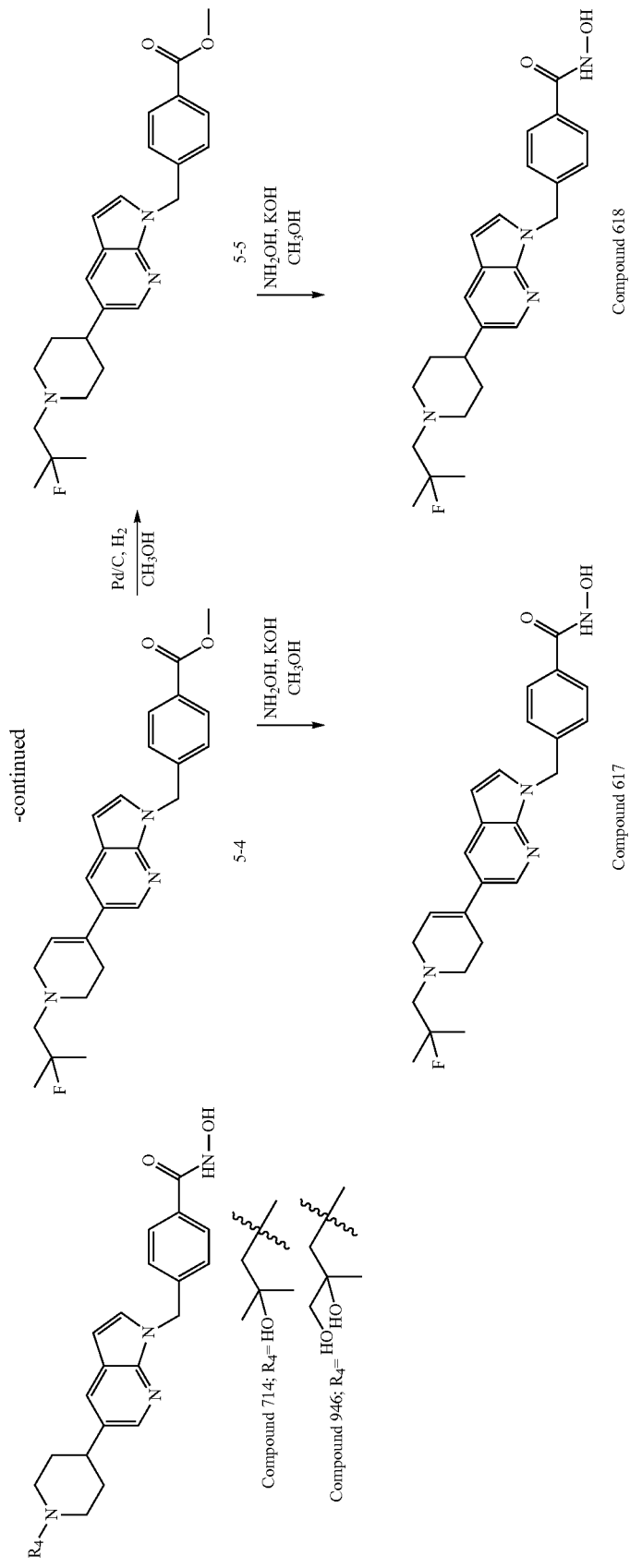

As shown in reaction scheme 5 above, the amino protective group (Boc) of a compound of formula 5-1 is removed to synthesize a compound of formula 5-2, which is then reacted with an oxirane compound using microwaves, thereby synthesizing a compound of formula 5-3. Finally, potassium hydroxide (KOH), methanol and hydroxylamine are added to the compound of formula 5-3, and then reacted at room temperature, thereby synthesizing final compound 686.

In addition, the hydrozyl group of the compound of formula 5-3 may be hydrogenated in the presence of Pd/C to synthesize a compound of formula 5-6. Finally, potassium hydroxide (KOH), methanol and hydroxylamine are added to the compound of formula 5-6, and then reacted at room temperature, thereby synthesizing final compounds 714 and 946.

In addition, the compound of formula 5-3 may be substituted with fluorine to synthesize a compound of formula 5-4. Finally, potassium hydroxide (KOH), methanol and hydroxylamine are added to the compound of formula 5-4, and then reacted at room temperature, thereby synthesizing final compound 617.

In addition, the compound of formula 5-4 may be hydrogenated in the presence of Pd/C to synthesize a compound of formula 5-5. Finally, potassium hydroxide (KOH), methanol and hydroxylamine are added to the compound of formula 5-5, and then reacted at room temperature, thereby synthesizing final compound 618.

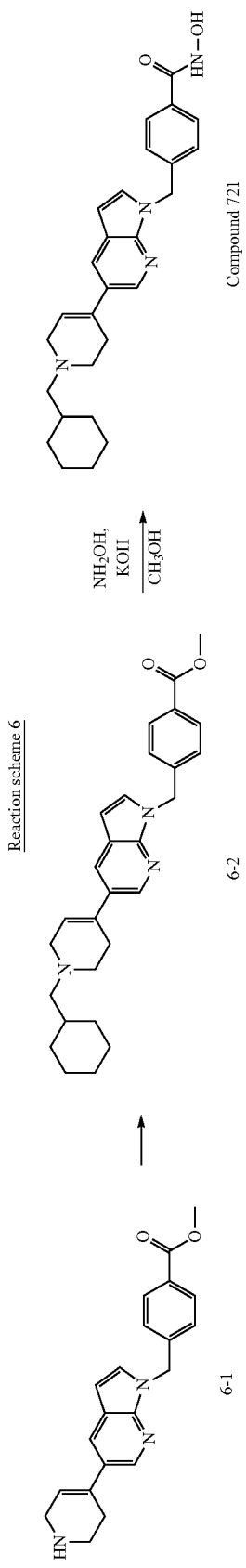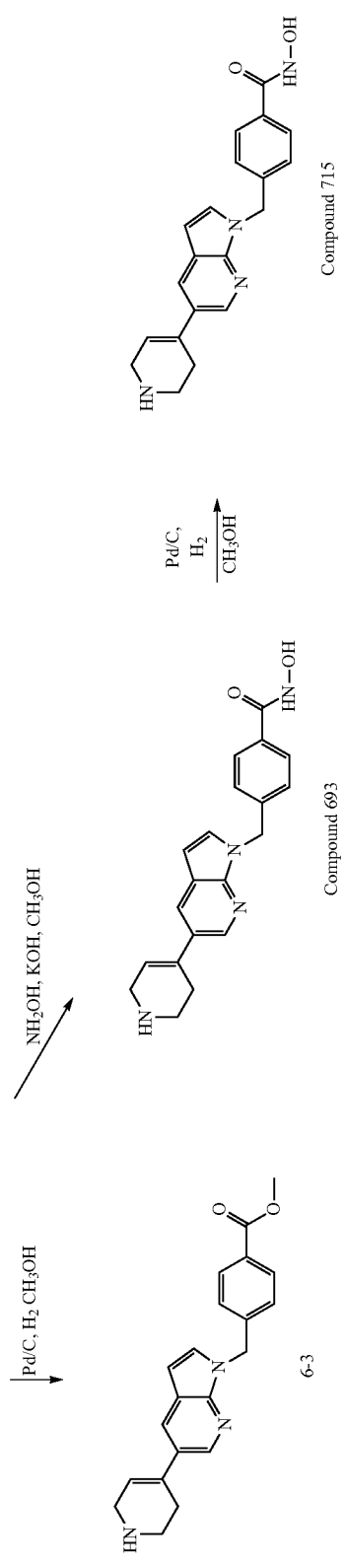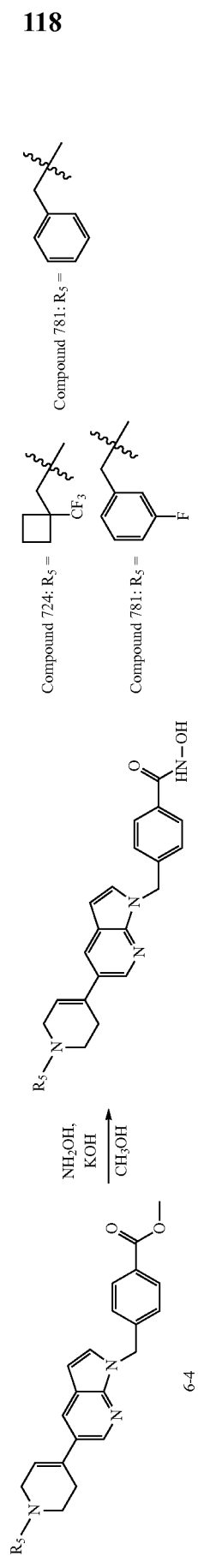

As shown in reaction scheme 6 above, a substituent is introduced into a compound of formula 6-1 to synthesize a compound of formula 6-2. Finally, potassium hydroxide (KOH), methanol and hydroxylamine are added to the compound of formula 6-2, and then reacted at room temperature, thereby synthesizing final compound 721.

In addition, the compound of formula 6-1 may be hydrogenated in the presence of Pd/C to synthesize a compound of formula 6-3, and a substituent is introduced into the compound of formula 6-3 to synthesize a compound of formula 6-4. Finally, potassium hydroxide (KOH), methanol and hydroxylamine are added to the compound of formula 6-4, and then reacted at room temperature, thereby synthesizing final compounds 724, 781 and 804.

In addition, potassium hydroxide (KOH), methanol and hydroxylamine may added to the compound of formula 6-1, and then reacted at room temperature to synthesize compound 693 of formula 6-5. The compound of formula 693 may be hydrogenated in the presence of Pd/C to synthesize a compound of formula 715.

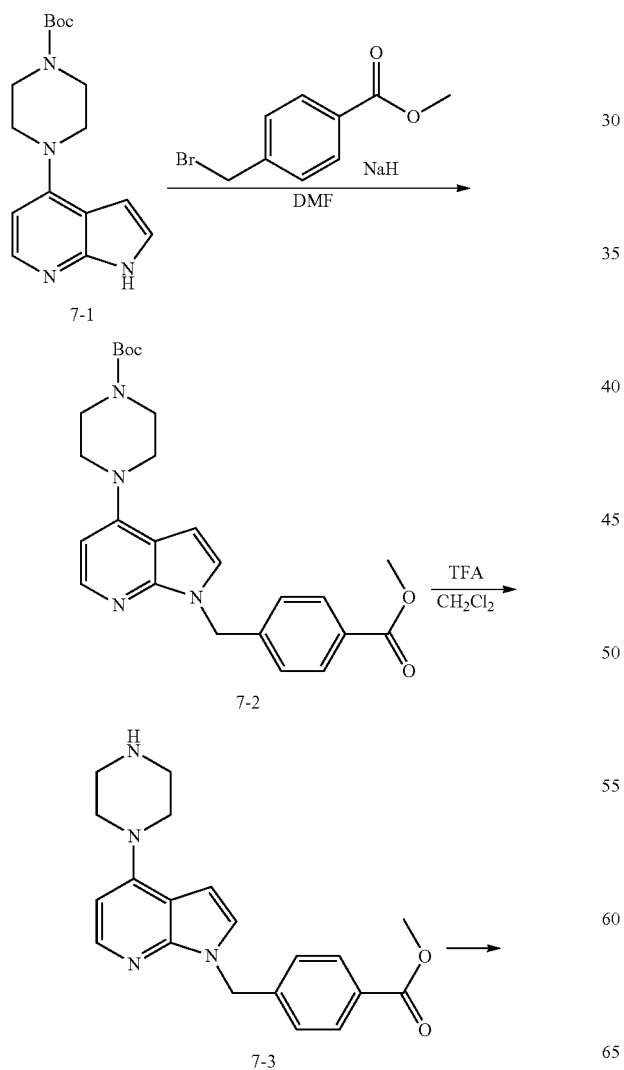

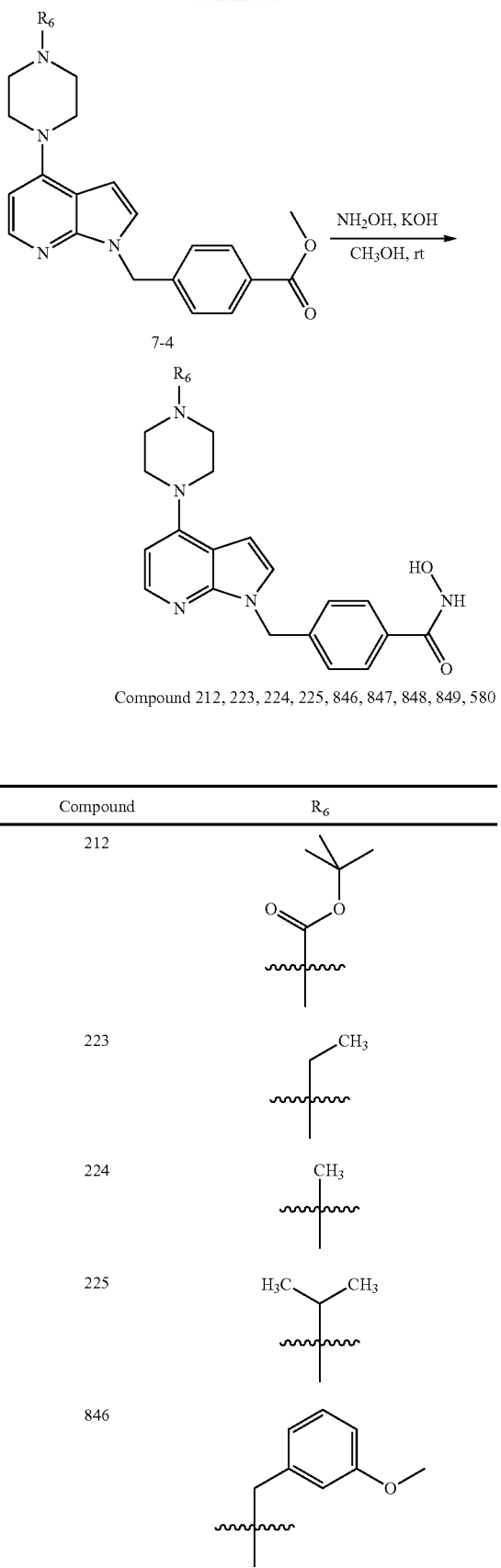

121
-continued

| Compound | R₆ |
|---|---|
| 847 | 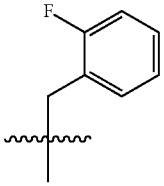 [SMILES: *Cc1ccccc1F] |
| 848 | 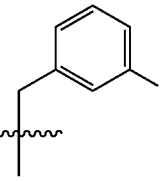 |
| 849 | 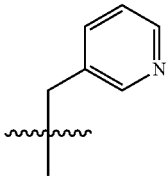 [SMILES: *Cc1cccnc1] |

122
-continued

| Compound | R₆ |
|---|---|
| 850 | 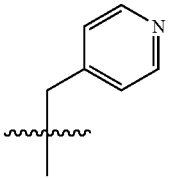 [SMILES: *Cc1ccncc1] |

As shown in reaction scheme 7 above, a compound of formula 7-1 is reacted with methyl 4-(bromomethyl)benzoate at normal temperature to synthesize a compound of formula 7-2, which is then deprotected, thereby synthesizing a compound of formula 7-3. Next, $R_6$ is introduced into the compound of formula 7-3 either by subjecting compound 7-3 to reductive amination at 40-60° C. or normal temperature, or by substitution reaction of compound 7-3 with $R_6$—X, thus obtaining a compound of formula 7-4. Finally, potassium hydroxide (KOH), methanol and hydroxylamine are added to the compound of formula 7-4, and then reacted at room temperature, thereby synthesizing final compounds 212, 223, 224, 225, 846, 847, 848, 849 and 850.

Reaction scheme 8

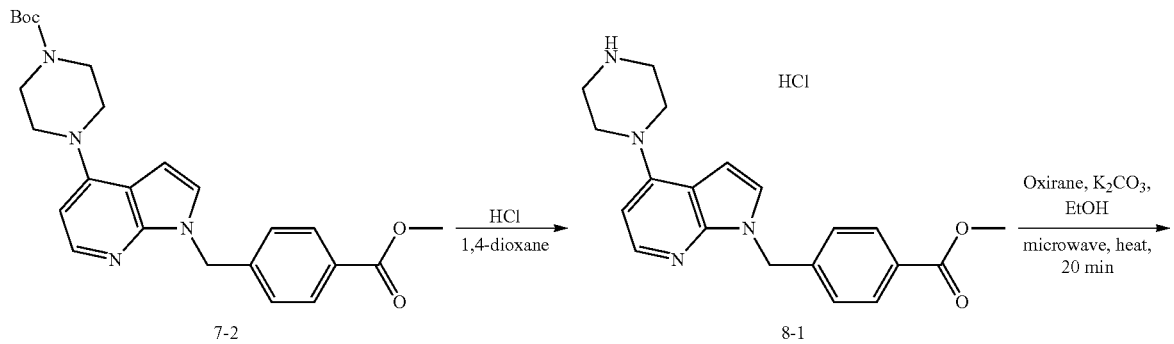

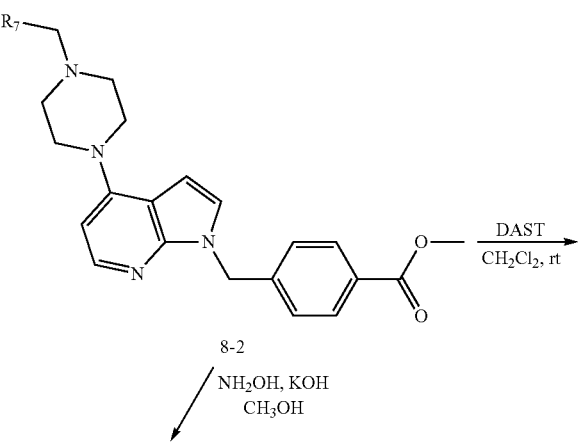

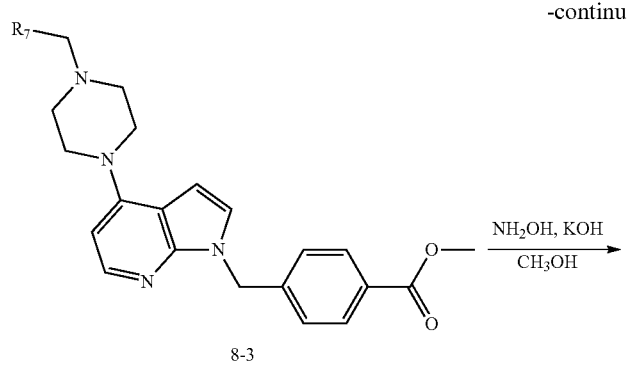

8-3

NH₂OH, KOH / CH₃OH →

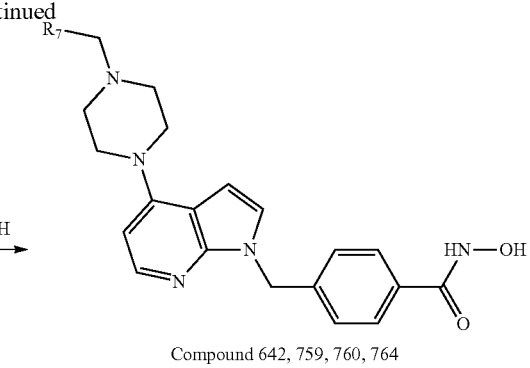

Compound 642, 759, 760, 764

| Compound | R7 |
|---|---|
| 642 | F−C(CH₃)₂− |
| 759 | HO−C(CH₃)₂− |
| 760 | 4-F-1-Boc-piperidin-4-yl |

| Compound | R7 |
|---|---|
| 764 | F−C(CH₃)(CH₂CH₃)− |

As shown in reaction scheme 8 above, the amino protecting group (Boc) of the compound 7-2 obtained by the reaction scheme 7 is removed to obtain a compound of formula 8-1, which is then reacted with an oxirane compound using microwaves, thereby synthesizing a compound of formula 8-2. The compound of formula 8-2 is reacted with potassium hydroxide (KOH), methanol and hydroxylamine to synthesize final compound 759.

In addition, the hydroxyl group of the compound of formula 8-2 may be substituted with fluorine to synthesize a compound of 8-3. Finally, potassium hydroxide (KOH), methanol and hydroxylamine are added to the compound of formula 8-3, and then reacted at room temperature, thereby synthesizing final compounds 642, 760 and 764.

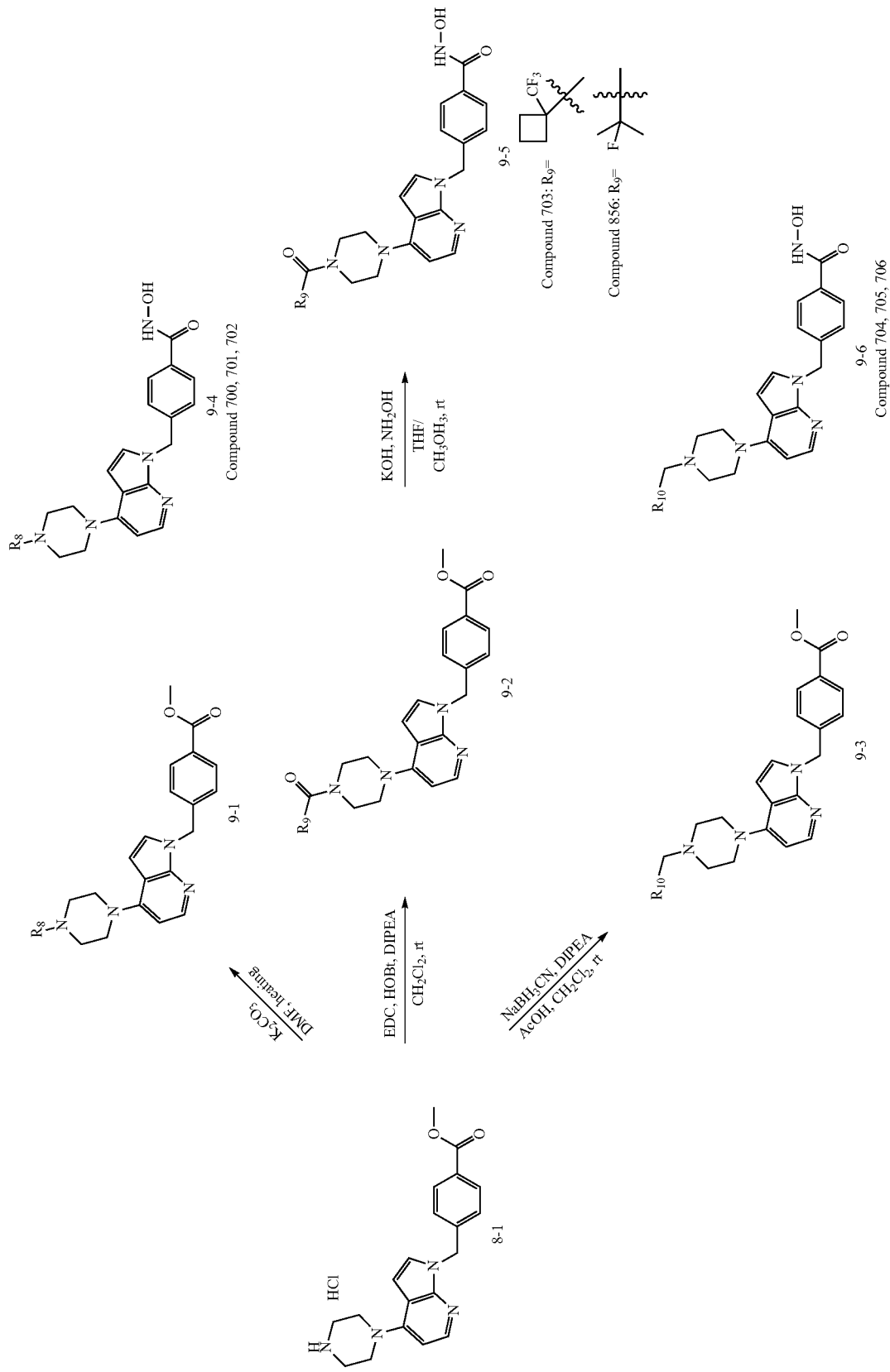

127

| Compound | R8 |
|---|---|
| 700 | 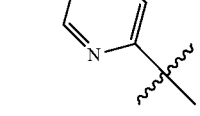 |
| 701 | 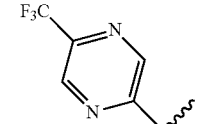 |
| 702 | 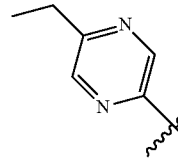 |
| 704 | 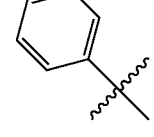 |
| 705 | 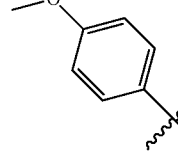 |
| 706 | 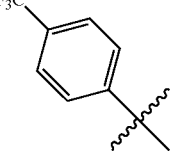 |

As shown in reaction scheme 9 above, the compound of formula 8-1 obtained by the reaction scheme 8 is reacted with $R_8X$ to synthesize a compound of formula 9-1, is subjected to amide coupling with carboxylic acid to synthesize a compound of formula 9-2, or is subjected to reductive amination with aldehyde to synthesize a compound of formula 9-3, respectively. Next, the compounds of formulas 9-1, 9-2 and 9-3 are reacted with potassium hydroxide (KOH), methanol and hydroxylamine to synthesize compounds 700, 701 and 702 of formula 9-4, compounds 703 and 856 of formula 9-5, and compounds 704, 705 and 706 of formula 9-6, respectively.

Reaction scheme 10

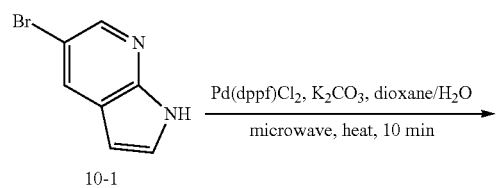

128

-continued

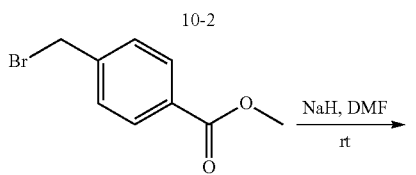

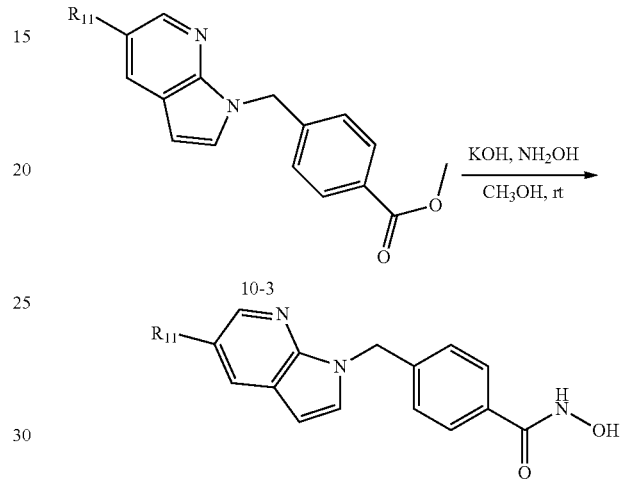

Compound 103, 104, 124, 125

| Compound | R11 |
|---|---|
| 103 | 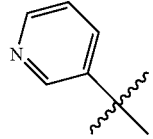 [SMILES: *c1cccnc1] |
| 104 | 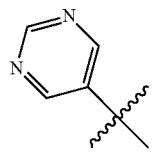 [SMILES: *c1cncnc1] |
| 124 | 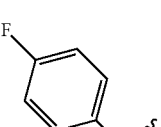 |
| 125 | 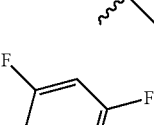 |

As shown in reaction scheme 10 above, a compound of formula 10-1 is subjected to a Suzuki reaction with boronic acid or boronic acid ester using microwaves, thereby synthesizing a compound of formula 10-2 having substituent $R_{11}$ introduced therein. Next, the compound of formula 10-2 is reacted with methyl 4-(bromomethyl)benzoate at normal temperature to synthesize a compound of formula 10-3. Finally, potassium hydroxide (KOH), methanol and hydroxylamine are added to the compound of formula 10-3, and then reacted at room temperature, thereby synthesizing final compounds 103, 104, 124 and 125.

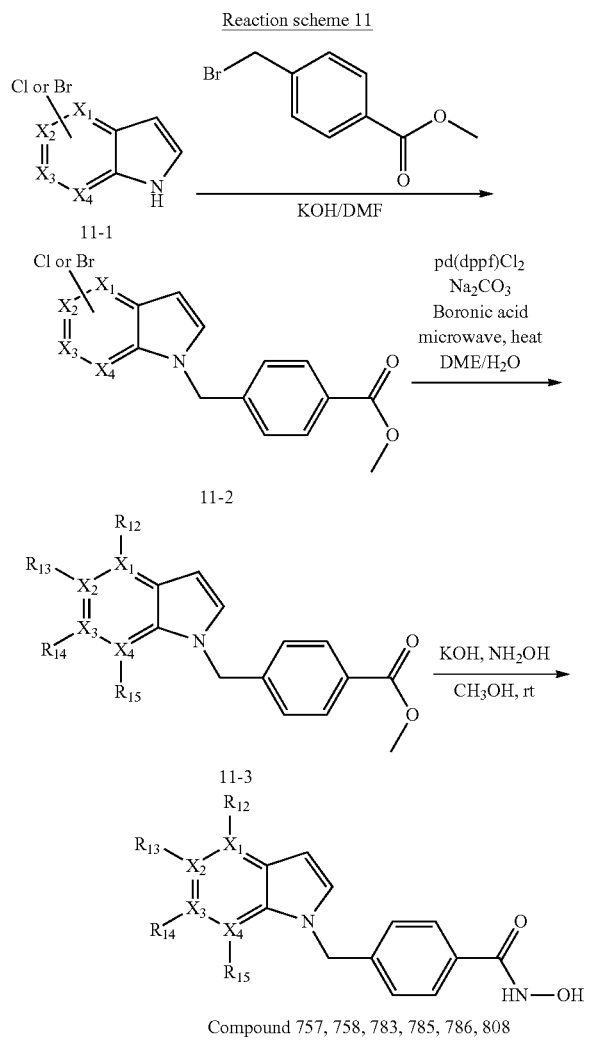

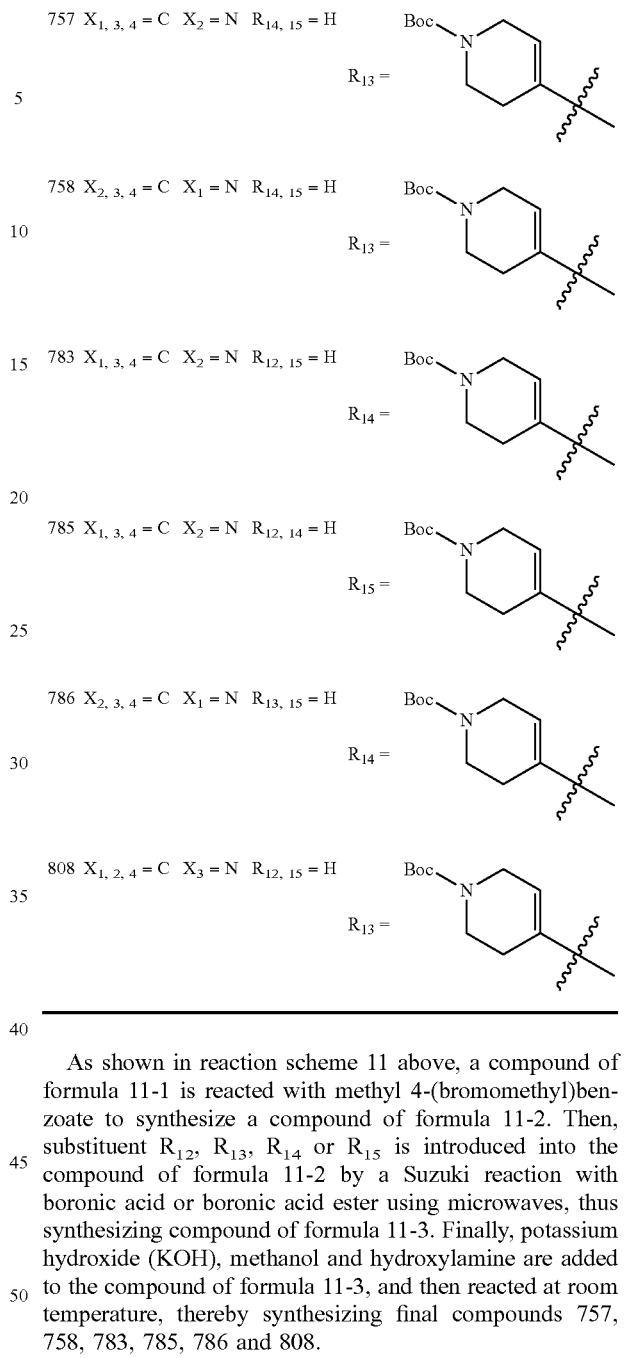

As shown in reaction scheme 11 above, a compound of formula 11-1 is reacted with methyl 4-(bromomethyl)benzoate to synthesize a compound of formula 11-2. Then, substituent $R_{12}$, $R_{13}$, $R_{14}$ or $R_{15}$ is introduced into the compound of formula 11-2 by a Suzuki reaction with boronic acid or boronic acid ester using microwaves, thus synthesizing compound of formula 11-3. Finally, potassium hydroxide (KOH), methanol and hydroxylamine are added to the compound of formula 11-3, and then reacted at room temperature, thereby synthesizing final compounds 757, 758, 783, 785, 786 and 808.

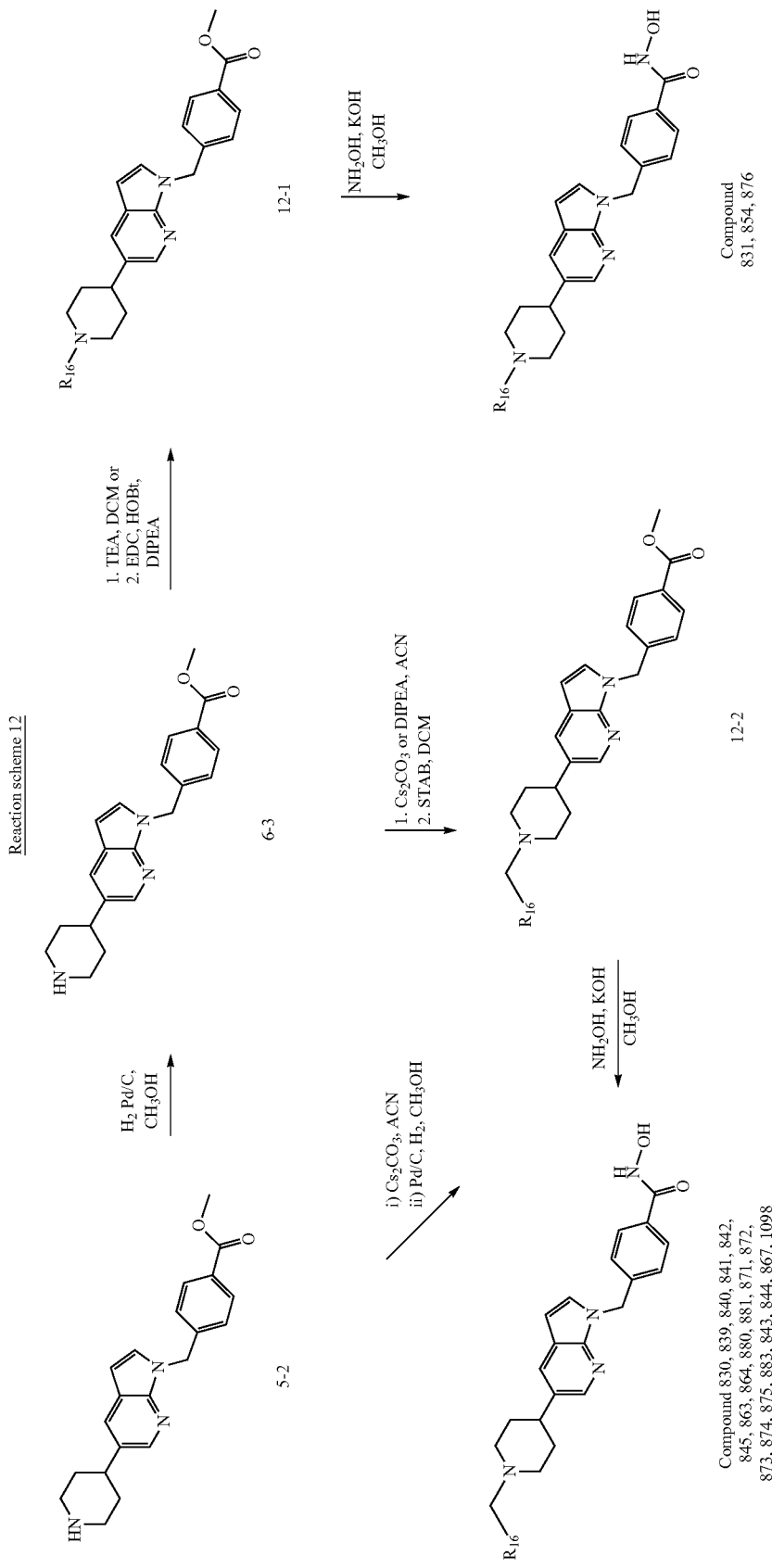

| Compound | R₁₆ |
|---|---|
| 830 | 4-methoxyphenyl |
| 831 | 1-(3-fluorophenyl)-2-methylpropan-1-one-2-yl |
| 839 | 2-fluorophenyl |
| 840 | pyridin-3-yl |
| 841 | pyridin-4-yl |
| 842 | 3-methoxyphenyl |
| 843 | 4-fluorophenyl |
| 844 | pyridin-2-yl |
| 845 | 5-(trifluoromethyl)-1,2,4-oxadiazol-3-yl |
| 854 | 2-fluoro-2-methyl-1-oxopropyl (with methyl) |

| Compound | R₁₆ |
|---|---|
| 863 | isopropyl |
| 864 | neopentyl |
| 871 | 3-(trifluoromethyl)phenyl |
| 872 | 4-(trifluoromethyl)phenyl |
| 873 | 4-(1H-imidazol-1-yl)phenyl |
| 874 | 4-(4H-1,2,4-triazol-4-yl)phenyl |
| 875 | 4-(furan-2-yl)phenyl |
| 876 | phenylsulfonyl |
| 880 | pyrimidin-5-yl |

| Compound | R16 |
|---|---|
| 881 | *pyrimidin-2-yl* |
| 883 | *2-(4-methylpiperazin-1-yl)phenyl* |
| 1098 | *6-methoxypyridin-3-yl* |

As shown in reaction scheme 12 above, a compound of formula 5-2 is hydrogenated in the presence of Pd/C to synthesize a compound of formula 6-3, which is then acylated, sulfonylated and subjected to amide coupling with carboxylic acid, thereby synthesizing a compound of formula 12-1 having $R_{16}$ introduced therein. Finally, potassium hydroxide (KOH), methanol and hydroxylamine are added to the compound of formula 12-1, and then reacted at room temperature, thereby synthesizing final compounds 831, 854 and 876.

In addition, the compound of formula 6-3 may be subjected to reductive amination or reacted with $R_{16}$—$CH_2$—X to obtain a compound of formula 12-2. The compound of formula 12-2 may also be obtained by reacting a compound of 5-2 with $R_{16}$—$CH_2$—X, followed by hydrogenation. Finally, potassium hydroxide (KOH), methanol and hydroxylamine are added to the compound of formula 12-2, and then reacted at room temperature, thereby synthesizing final compounds 830, 839, 840, 841, 842, 843, 844, 845, 863, 864, 871, 872, 873, 874, 875, 880, 881, 883 and 1098.

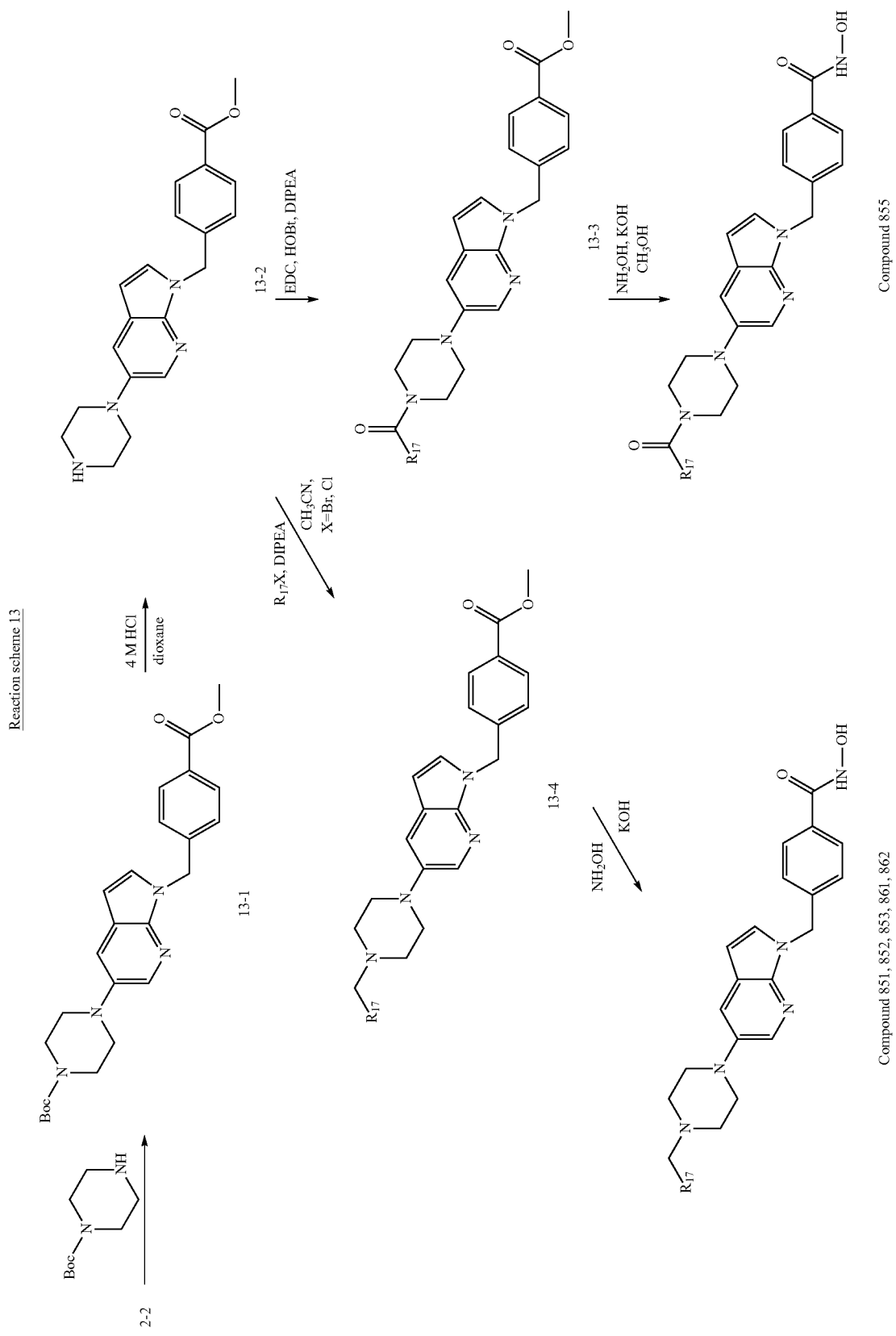

| Compound | R17 |
|---|---|
| 851 | 3-fluorophenyl |
| 852 | 4-fluorophenyl |
| 853 | isopropyl |
| 855 | 2-fluoro-tert-butyl |

| Compound | R17 |
|---|---|
| 861 | 2-fluorophenyl |
| 862 | neopentyl |

As shown in reaction scheme 13 above, the compound of formula 2-2, obtained by the reaction scheme 2 above, is subjected to a Buchwald reaction with secondary amine to obtain a compound of formula 13-1, which is then is treated with hydrochloric acid to remove the amino protecting group (Boc), and is then reacted with $R_{17}$—$CH_2$—X, thereby synthesizing a compound of formula 13-4. Finally, potassium hydroxide (KOH), methanol and hydroxylamine are added to the compound of formula 13-4, and then reacted at room temperature, thereby synthesizing final compounds 851, 852, 853, 861 and 862.

In addition, a compound of formula 13-2 may be subjected to amide coupling with carboxylic acid to synthesize a compound of formula 13-3. Finally, potassium hydroxide (KOH), methanol and hydroxylamine are added to the compound of formula 13-3, and then reacted at room temperature, thereby synthesizing final compound 855.

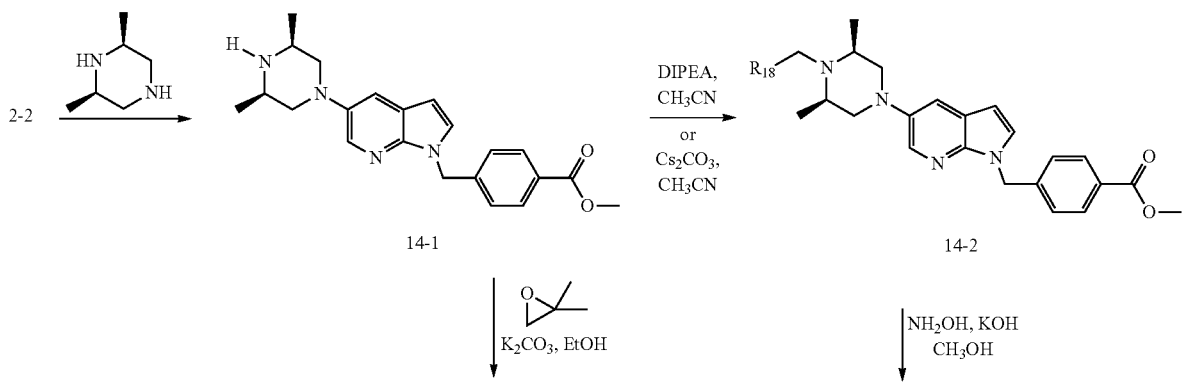

Reaction scheme 14

-continued
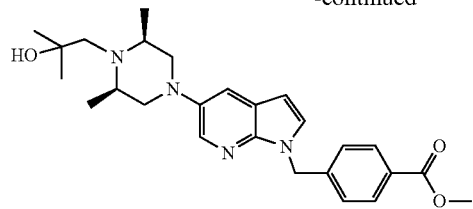
14-3
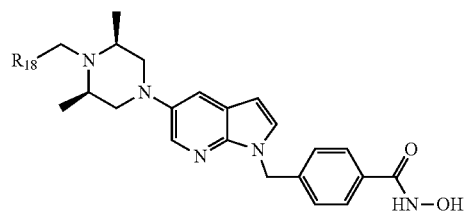
Compound 857, 1003, 1004, 1005
NH₂OH, KOH
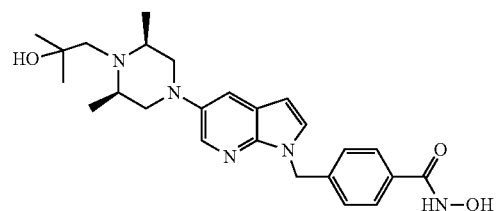
Compound 865
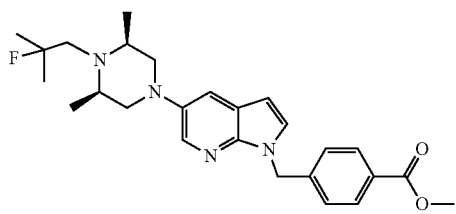
14-4
NH₂OH, KOH, CH₃OH
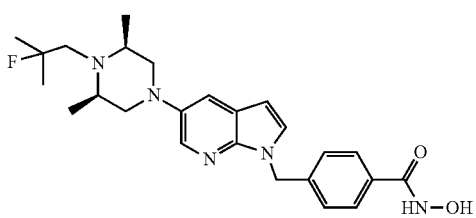
Compound 866
| Compound | R₁₈ |
|---|---|
| 857 | 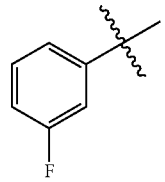 [SMILES: *c1cccc(F)c1] |
| 1003 | 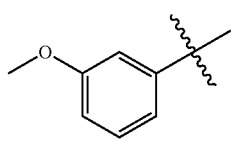 [SMILES: *c1cccc(OC)c1] |
-continued
| Compound | R₁₈ |
|---|---|
| 1004 | 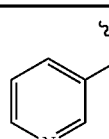 |
| 1005 | 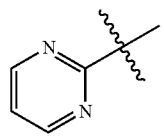 [SMILES: *c1ncccn1] |
As shown in reaction scheme 14 above, the compound of formula 2-2, obtained by the reaction scheme 2 above, is subjected to a Buchwald reaction with a secondary amine to synthesize a compound of formula 14-1, which is then reacted with $R_{18}$—$CH_2$—X to synthesize a compound of formula 14-2. Finally, potassium hydroxide (KOH), methanol and hydroxylamine are added to the compound of formula 14-2, and then reacted at room temperature, thereby synthesizing final compounds 857, 1003, 1004 and 1005.

In addition, the compound of formula 14-1 may be reacted with an oxirane compound using microwaves to synthesize a compound of formula 14-3. Finally, potassium hydroxide (KOH), methanol and hydroxylamine are added to the compound of formula 14-3, and then reacted at room temperature, thereby synthesizing final compound 865.

In addition, the hydroxyl group of the compound of formula 14-3 may be substituted with fluorine to synthesize a compound of formula 14-4. Finally, potassium hydroxide (KOH), methanol and hydroxylamine are added to the compound of formula 14-4, and then reacted at room temperature, thereby synthesizing final compound 866.

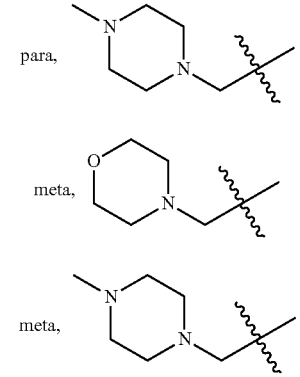

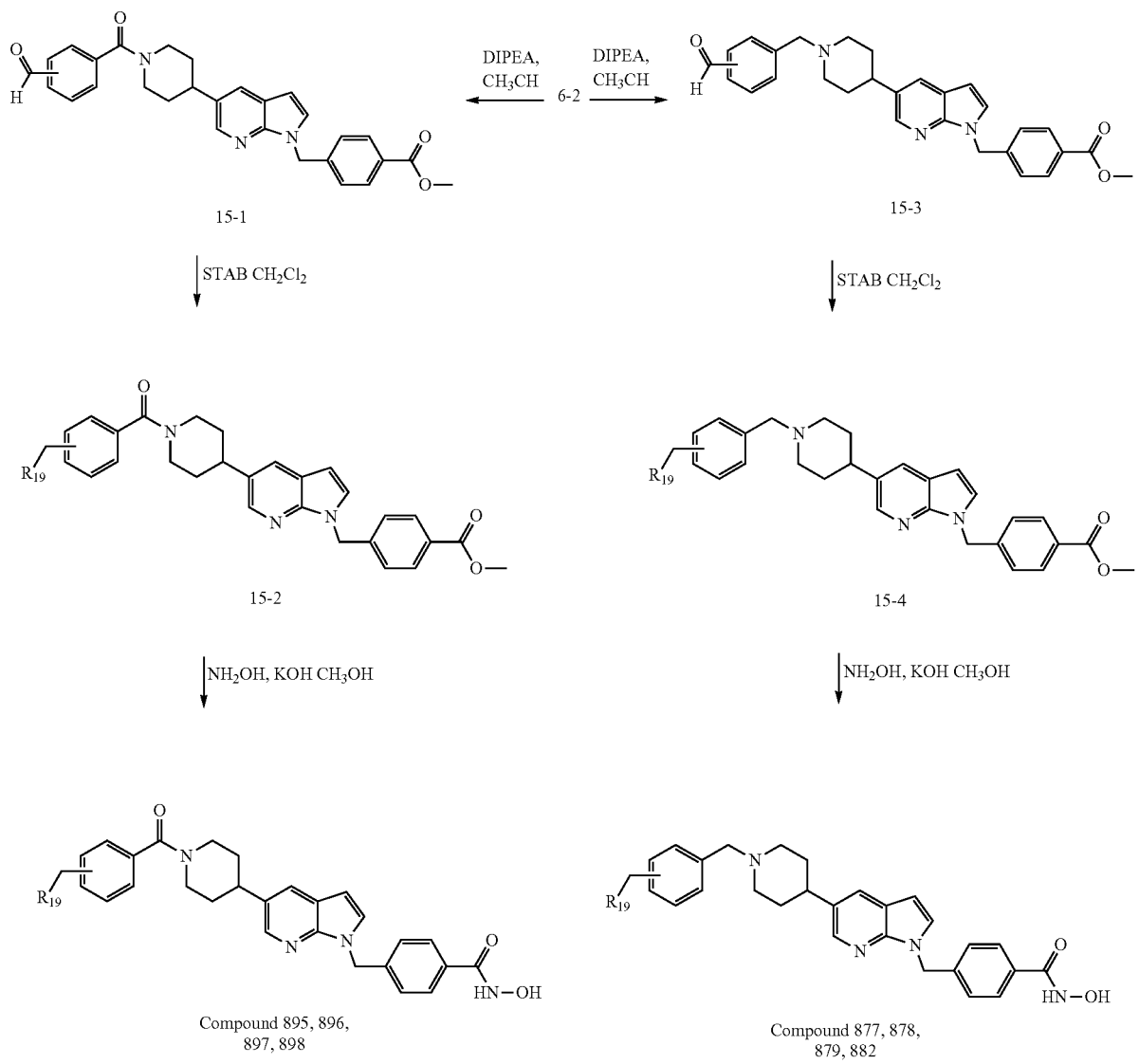

| Compound | R19 |
|---|---|
| 882 | para, 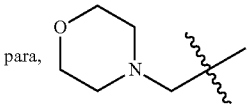 |
| 895 | meta, 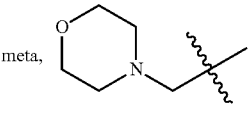 [SMILES: *CN1CCOCC1] |
| 896 | meta, 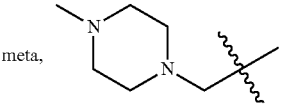 [SMILES: *CN1CCN(C)CC1] |
| 897 | para, 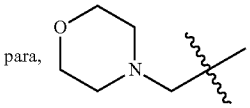 [SMILES: *CN1CCOCC1] |

| Compound | R19 |
|---|---|
| 898 | para, 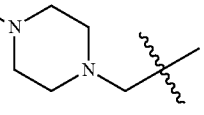 |

As shown in reaction scheme 15 above, the compound of formula 6-2, obtained by the reaction scheme 6 above, is reacted with an aldehyde-substituted compound to obtain a compound of formula 15-3, which is then subjected to reductive amination to synthesize a compound of formula 15-4. Finally, potassium hydroxide (KOH), methanol and hydroxylamine are added to the compound of formula 15-4, and then reacted at room temperature, thereby synthesizing final compounds 877, 878, 879 and 882.

In addition, the compound of formula 6-2 may be subjected to amide coupling with carboxylic acid to synthesize a compound of formula 15-1, which is then subjected to reductive amination, thereby synthesizing a compound of formula 15-2. Finally, potassium hydroxide (KOH), methanol and hydroxylamine are added to the compound of formula 15-2, and then reacted at room temperature, thereby synthesizing final compounds 895, 896, 897 and 898.

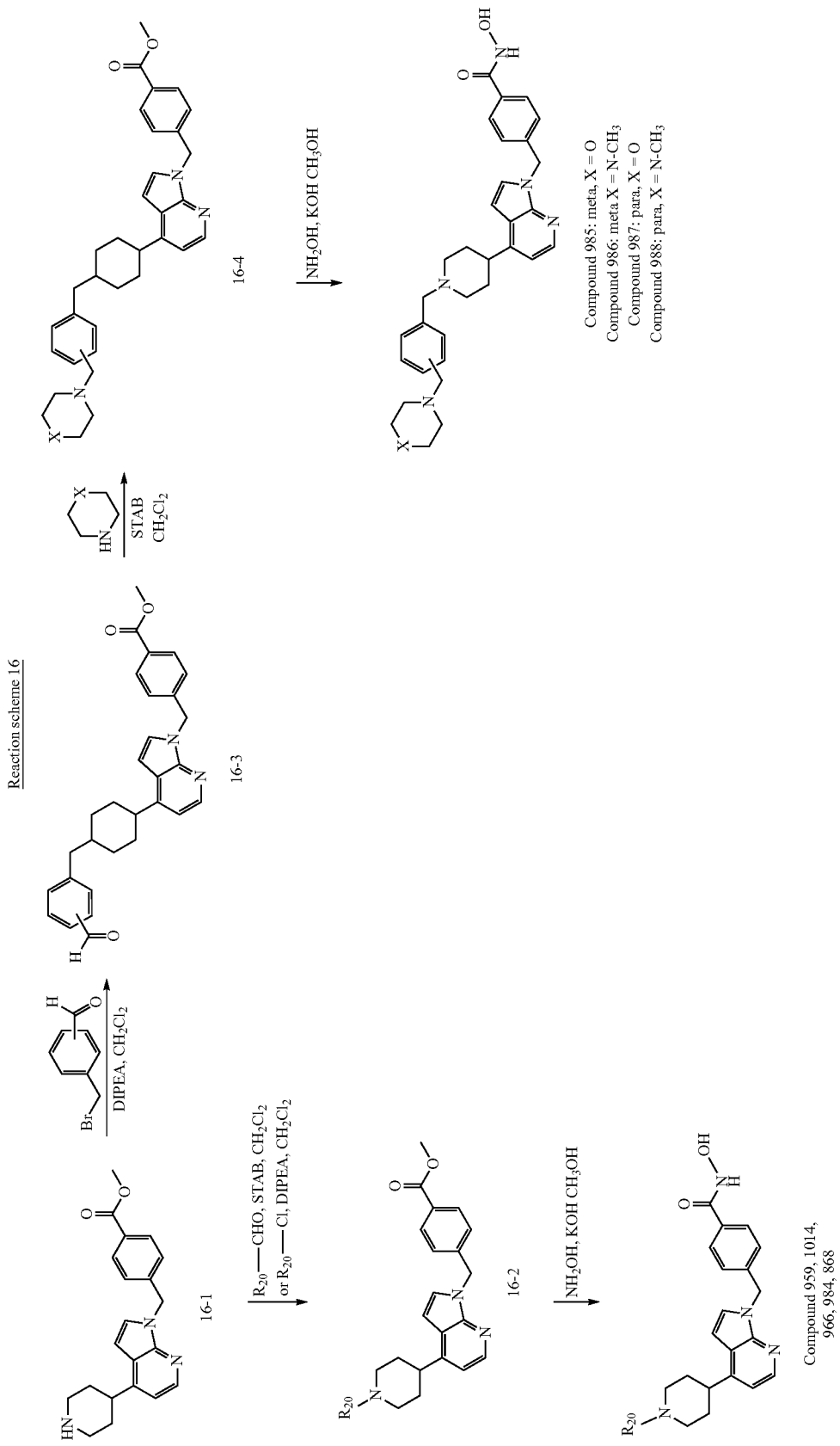

| Compound | R₂₀ |
|---|---|
| 868 | 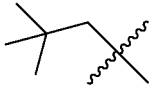 [SMILES: *CC(C)(C)C] |
| 959 | 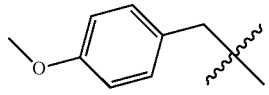 [SMILES: *Cc1ccc(OC)cc1] |
| 966 | 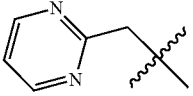 |
| 984 | 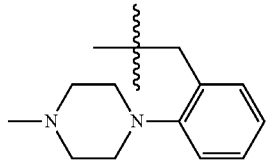 [SMILES: *Cc1ccccc1N1CCN(C)CC1] |

-continued

| Compound | R₂₀ |
|---|---|
| 1014 | 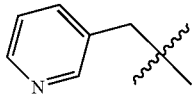 [SMILES: *Cc1cccnc1] |

As shown in reaction scheme 16 above, a compound of formula 16-1 is reacted with an aldehyde-substituted compound to obtain a compound of formula 16-3, which is then subjected to reductive amination to synthesize a compound of formula 16-4. Finally, potassium hydroxide (KOH), methanol and hydroxylamine are added to the compound of formula 16-4, and then reacted at room temperature, thereby synthesizing final compounds 985, 986, 987 and 988.

In addition, the compound of formula 16-1 may be subjected to amide coupling with carboxylic acid or acyl chloride to synthesize a compound of formula 16-2. Finally, potassium hydroxide (KOH), methanol and hydroxylamine are added to the compound of formula 16-2, and then reacted at room temperature, thereby synthesizing final compounds 868, 959, 966, 984 and 1014.

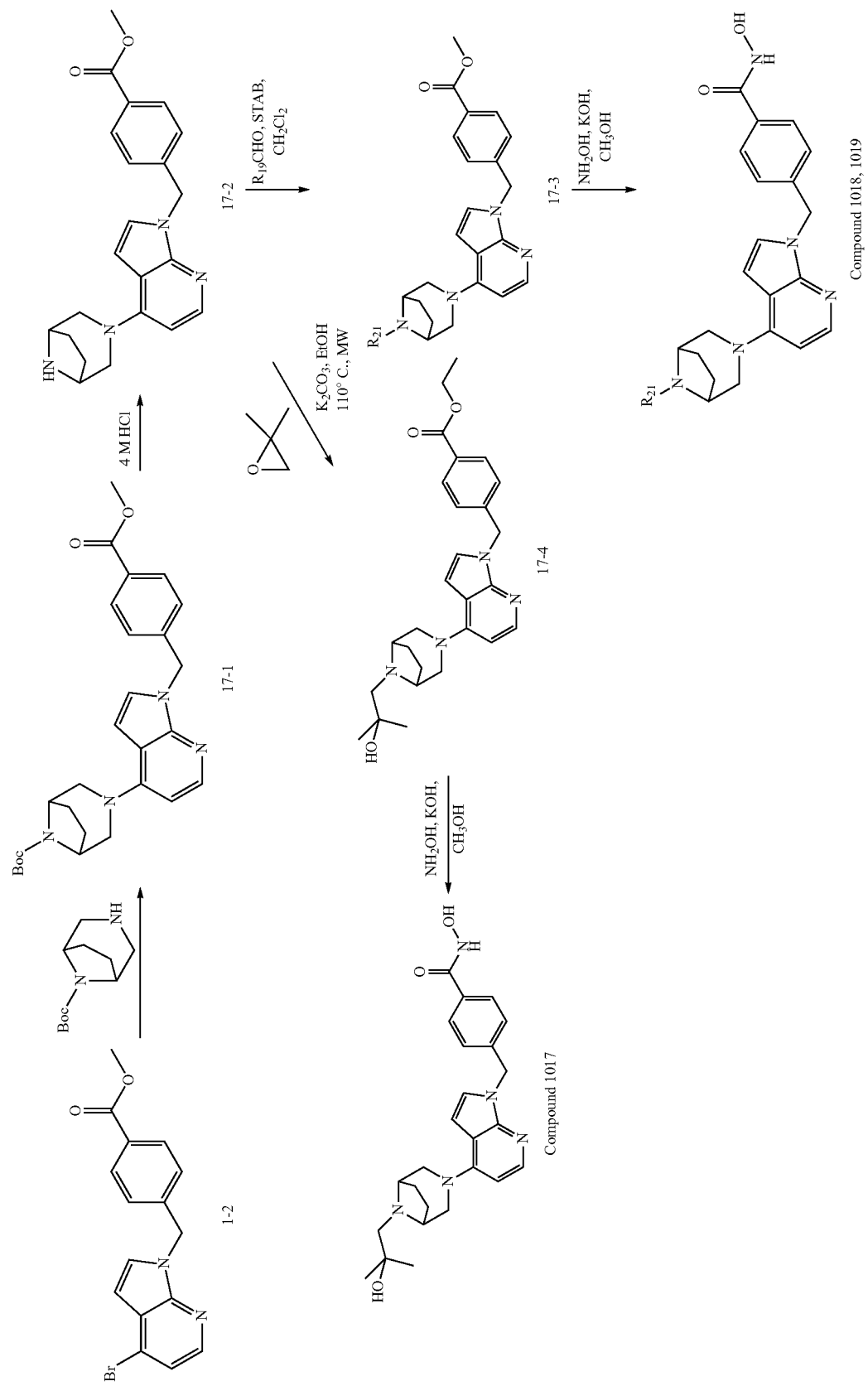

| Compound | R$_{21}$ |
|---|---|
| 1018 | 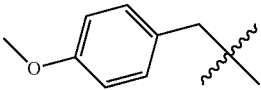 [SMILES: *Cc1ccc(OC)cc1] |
| 1019 | 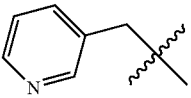 [SMILES: *Cc1cccnc1] |

As shown in reaction scheme 17 above, the compound of formula 1-2, obtained by the reaction scheme 1 above, is subjected to a Buchwald reaction with secondary amine to obtain a compound of formula 17-1, which is then treated with hydrochloric acid to remove the amino protecting group (Boc), and is reacted with an oxirane compound using microwaves, thereby synthesizing a compound of formula 17-4. Finally, potassium hydroxide (KOH), methanol and hydroxylamine are added to the compound of formula 17-4, and then reacted at room temperature, thereby synthesizing final compound 1017.

In addition, the compound of formula 17-2 may be subjected to reductive amination to synthesize a compound of formula 17-3. Finally, potassium hydroxide (KOH), methanol and hydroxylamine are added to the compound of formula 17-3, and then reacted at room temperature, thereby synthesizing final compounds 1018 and 1019.

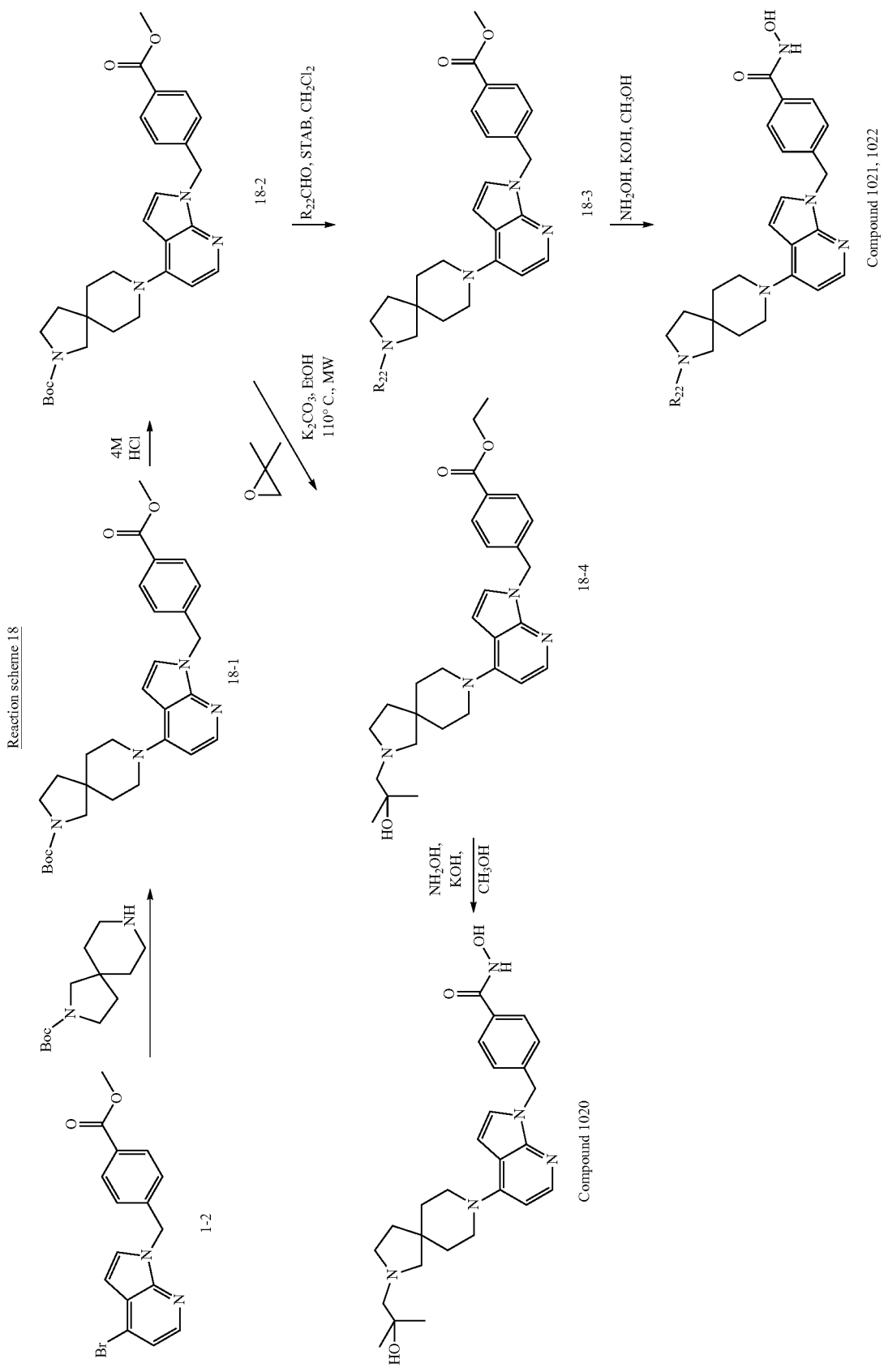

| Compound | R22 |
|---|---|
| 1021 | 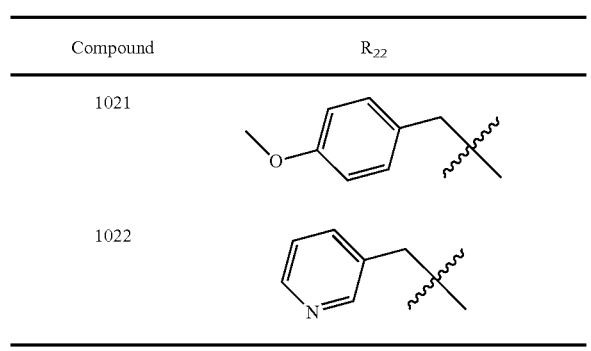 |
| 1022 | |

As shown in reaction scheme 18 above, the compound of formula 1-2, obtained by the reaction scheme 1 above, is subjected to a Buchwald reaction with secondary amine to synthesize a compound of formula 18-1, which is then treated with hydrochloric acid to remove the amino protecting group (Boc), and is reacted with an oxirane compound using microwaves, thereby synthesizing a compound of formula 18-4. Finally, potassium hydroxide (KOH), methanol and hydroxylamine are added to the compound of formula 18-4, and then reacted at room temperature, thereby synthesizing final compound 1020.

In addition, the compound of formula 18-2 may be subjected to reductive amination to synthesize a compound of formula 18-3. Finally, potassium hydroxide (KOH), methanol and hydroxylamine are added to the compound of formula 18-3, and then reacted at room temperature, thereby synthesizing final compounds 1021 and 1022.

Reaction scheme 19

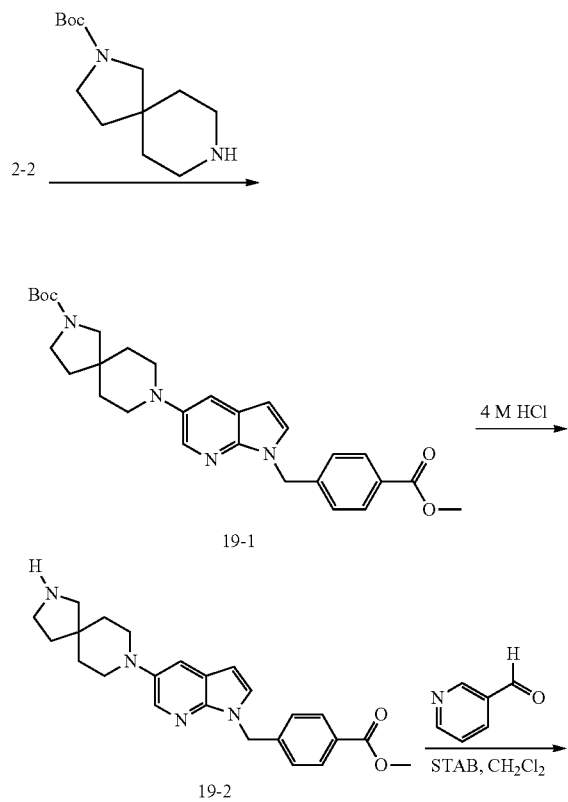

-continued

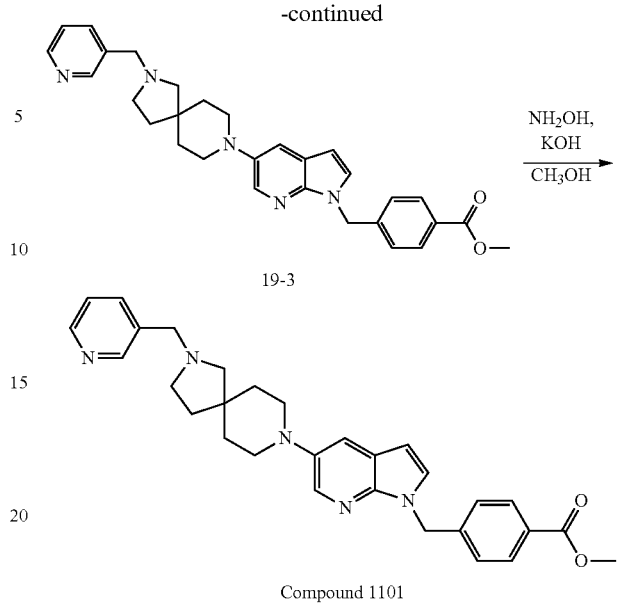

As shown in reaction scheme 19 above, the compound of formula 2-2, obtained by the reaction scheme 2 above, is subjected to a Buchwald reaction with a secondary amine to synthesize a compound of formula 19-1, which is then treated with hydrochloric acid to remove the amino protecting group (Boc), and is subjected to reductive amination to synthesize a compound of formula 19-3. Finally, potassium hydroxide (KOH), methanol and hydroxylamine are added to the compound of formula 19-3, and then reacted at room temperature, thereby synthesizing final compound 1101.

Reaction scheme 20

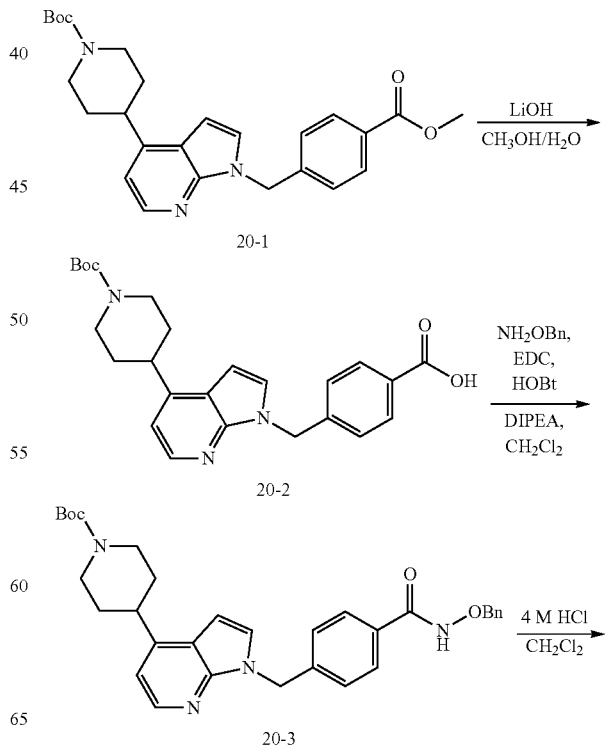

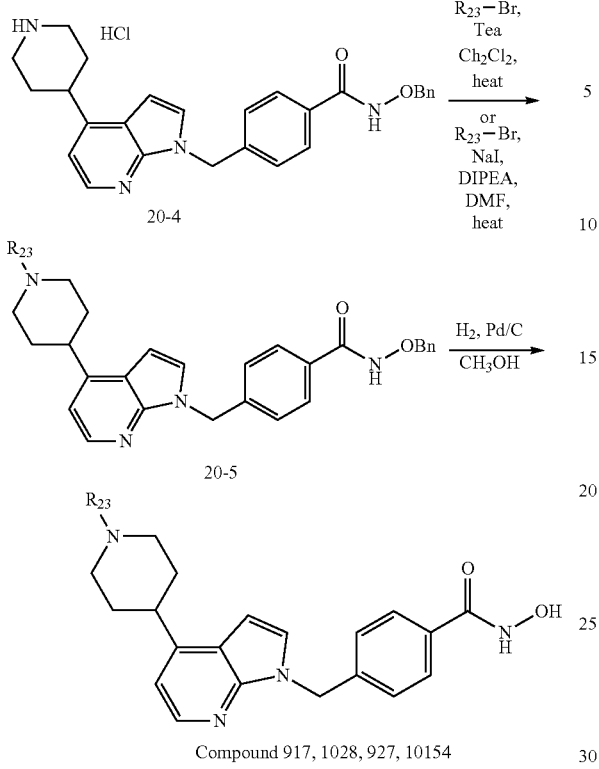

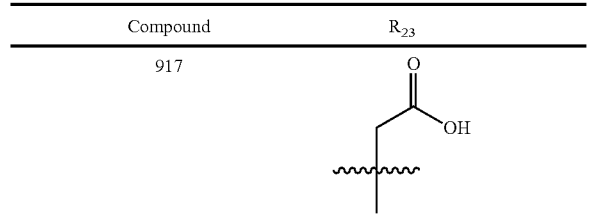

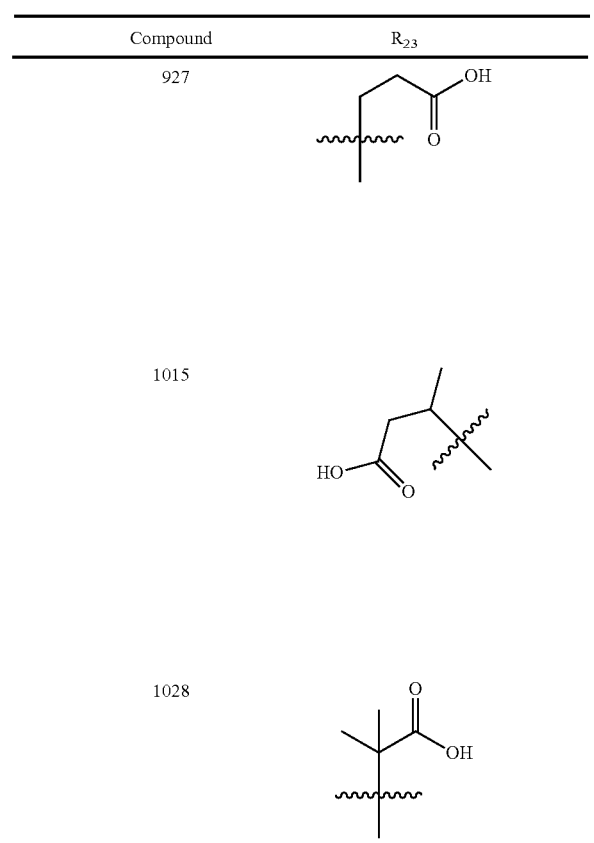

As shown in reaction scheme 20 above, a compound of formula 20-1 is hydrolyzed, and then subjected to amide coupling with a benzyl-protected amine compound to synthesize a compound of formula 20-3, which is then treated with hydrochloric acid to remove the amino protecting group (Boc), and is reacted with $R_{23}$—X to synthesize a compound of formula 20-5. Finally, the compound of formula 20-5 is hydrogenated in the presence of Pd/C, thereby synthesizing final compounds 917, 927, 1015 and 1028.

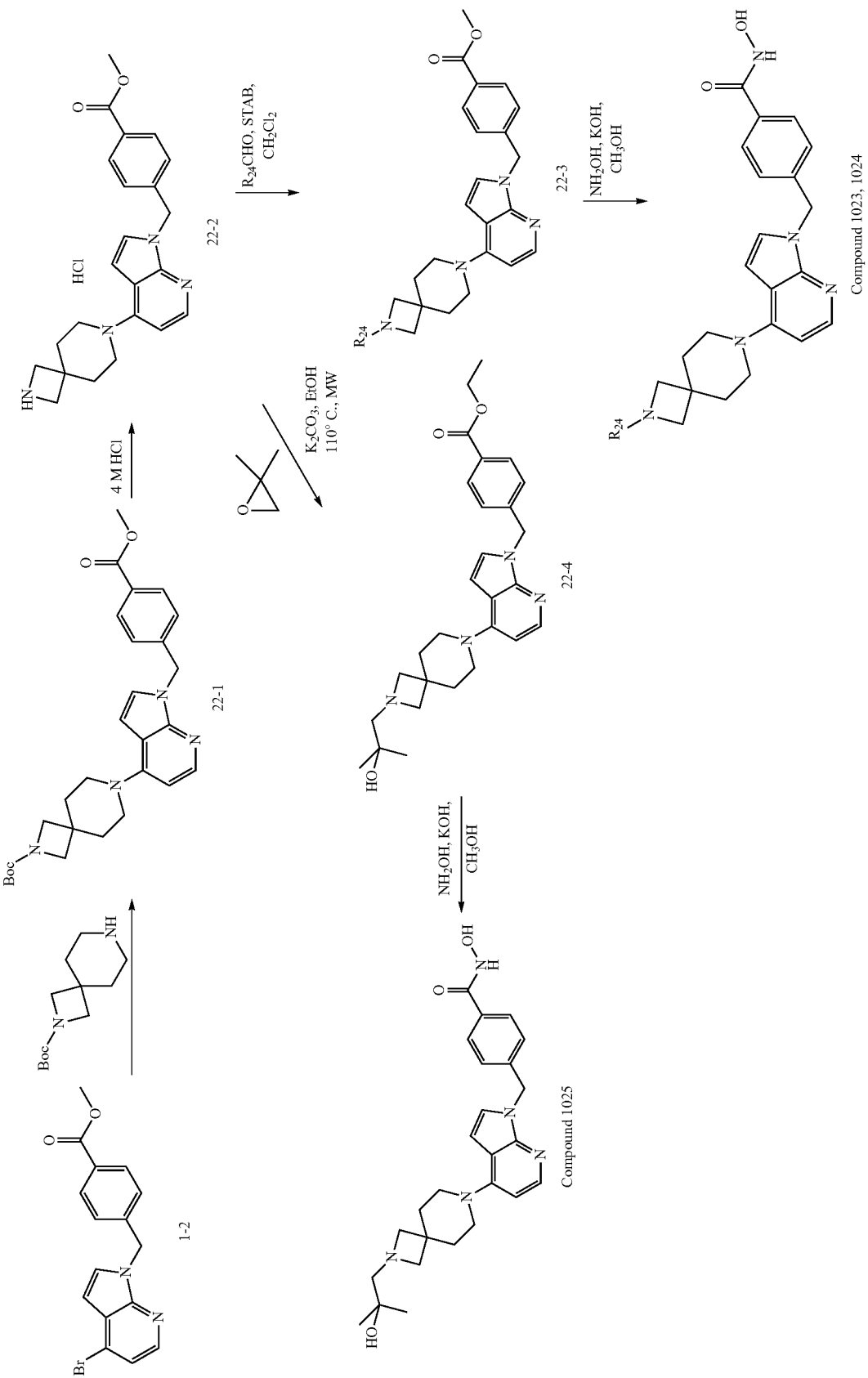
Reaction scheme 22

| Compound | R$_{24}$ | |
|---|---|---|
| 1023 | 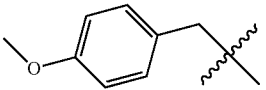 [SMILES: *Cc1ccc(OC)cc1] | 5 |
| 1024 | 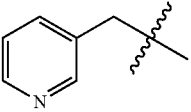 [SMILES: *Cc1cccnc1] | 10 |

As shown in reaction scheme 22 above, the compound of formula 1-2, obtained by the reaction scheme 1 above, is subjected to a Buchwald reaction with secondary amine to synthesize a compound of formula 22-1, which is then treated with hydrochloric acid to remove the amino protecting group (Boc), and is reacted with an oxirane compound using microwaves to synthesize a compound of formula 22-4. Finally, potassium hydroxide (KOH), methanol and hydroxylamine are added to the compound of formula 22-4, and then reacted at room temperature, thereby synthesizing final compound 1025.

In addition, the compound of formula 22-2 may be subjected to reductive amination to synthesize a compound of formula 22-3. Finally, potassium hydroxide (KOH), methanol and hydroxylamine are added to the compound of formula 22-3, and then reacted at room temperature, thereby synthesizing final compounds 1023 and 1024.

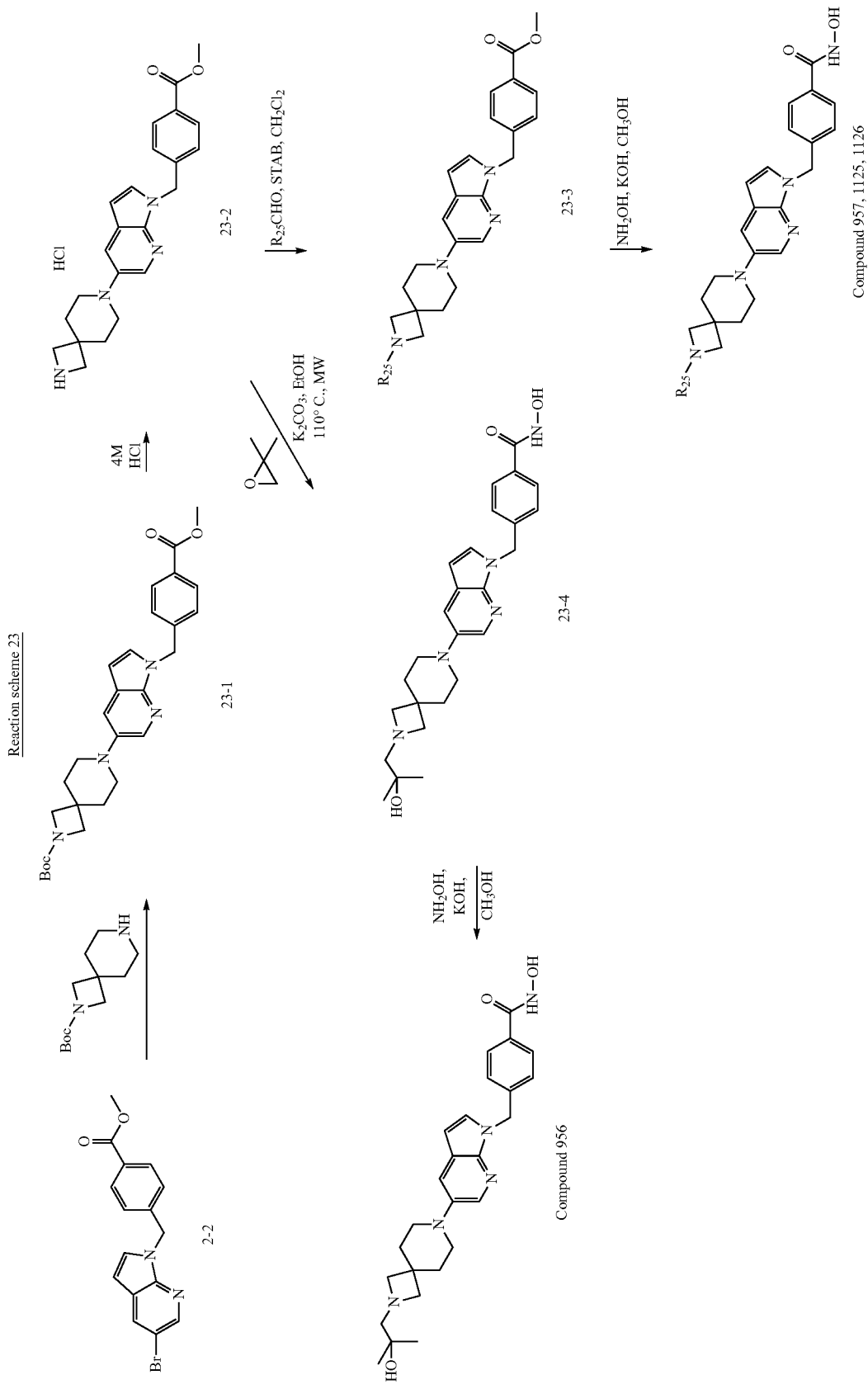

| Compound | R25 |
|---|---|
| 957 | (3-pyridylmethyl) |
| 1125 | (4-methoxybenzyl) |
| 1126 | (2-pyridylmethyl) |

As shown in reaction scheme 23 above, the compound of formula 1-2, obtained by the reaction scheme 1 above, is subjected to a Buchwald reaction with secondary amine to synthesize a compound of formula 23-1, which is then treated with hydrochloric acid to remove the amino protecting group (Boc), and is reacted with an oxirane compound using microwaves to synthesize a compound of formula 23-4. Finally, potassium hydroxide (KOH), methanol and hydroxylamine are added to the compound of formula 23-4, and then reacted at room temperature, thereby synthesizing final compound 956.

In addition, the compound of formula 23-2 may be subjected to reductive amination to synthesize a compound of formula 23-3.

Finally, potassium hydroxide (KOH), methanol and hydroxylamine are added to the compound of formula 23-3, and then reacted at room temperature, thereby synthesizing final compounds 957, 1125 and 1026.

Reaction scheme 24

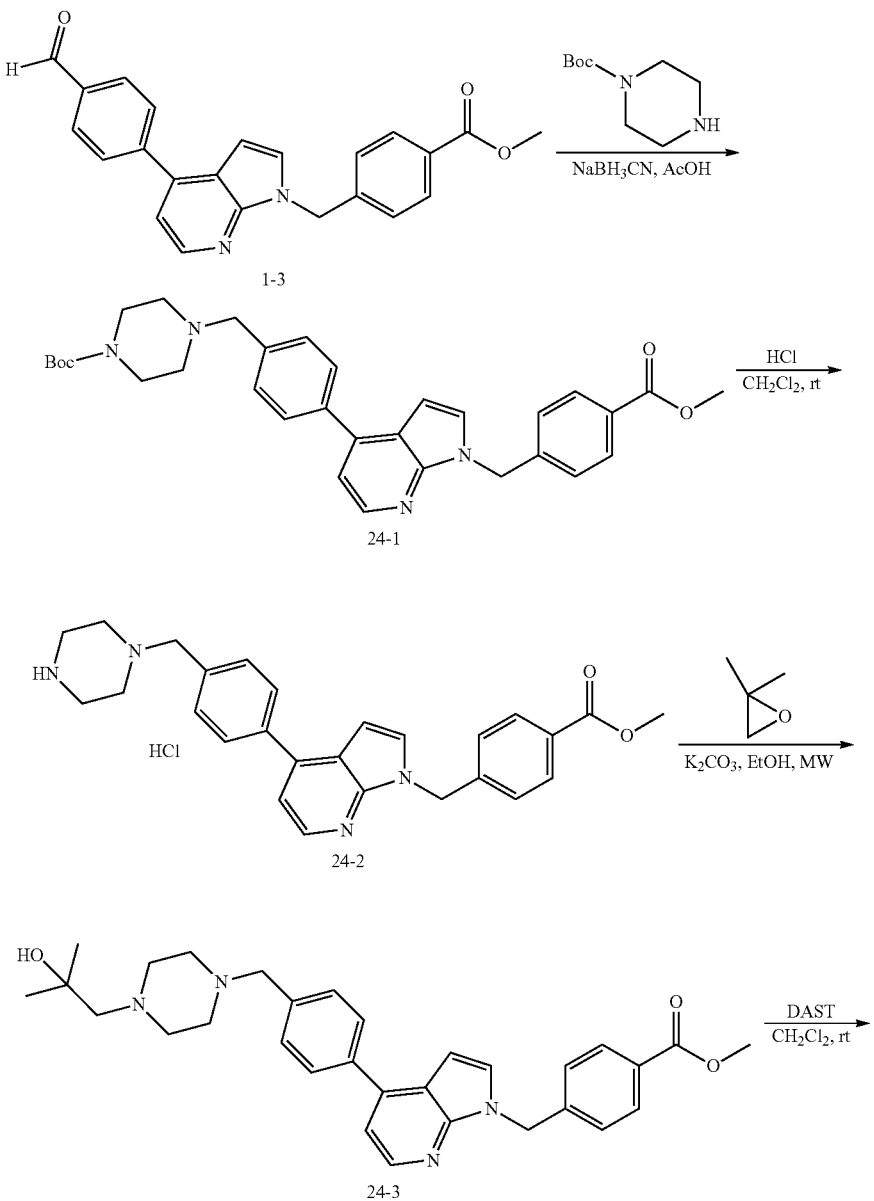

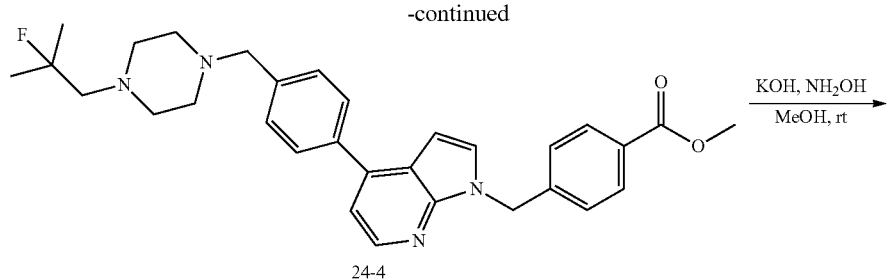

24-4

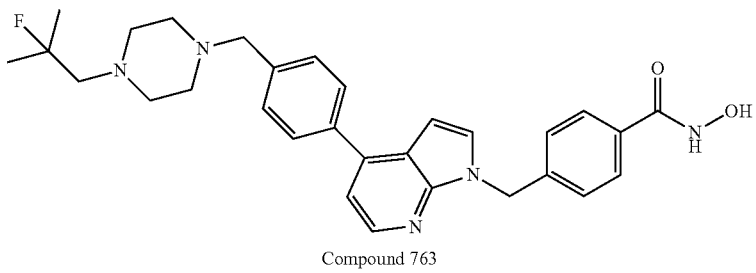

Compound 763

As shown in reaction scheme 24 above, the compound of formula 1-3, obtained by the reaction scheme 1 above, is subjected to reductive amination to synthesize a compound of formula 24-1. The amino protecting group (Boc) of the compound of formula 24-1 is removed, and the deprotected compound is reacted with an oxirane compound using microwaves to synthesize a compound of formula 24-3. The hydroxyl group of the compound of formula 24-3 is substituted with fluorine to synthesize a compound of formula 24-4. Finally, potassium hydroxide (KOH), methanol and hydroxylamine are added to the compound of formula 24-4, and then reacted at room temperature, thereby synthesizing final compound 763.

Reaction scheme 25

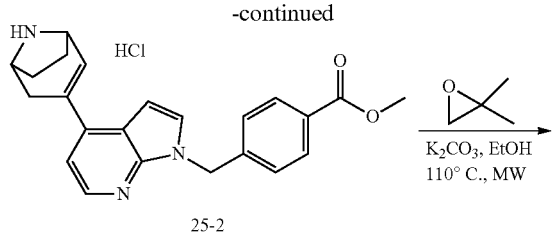

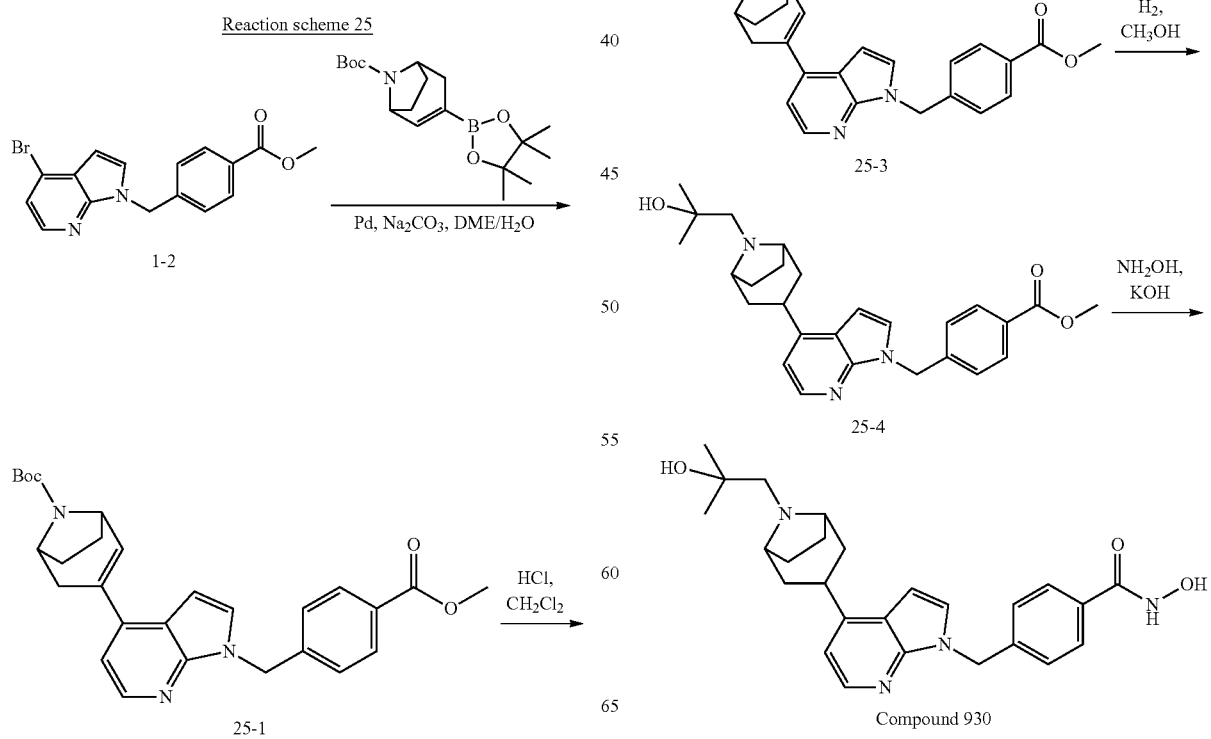

As shown in reaction scheme 25 above, the compound of formula 1-2, obtained by the reaction scheme 1, is subjected to a Suzuki reaction with boronic acid ester using microwaves to synthesize a compound of formula 25-1. The amino protecting group (Boc) of the compound of formula 25-1 is removed, and the deprotected compound is reacted with an oxirane compound using microwaves to synthesize a compound of formula 25-3, which is then hydrogenated to synthesize a compound of formula 25-4. Finally, potassium hydroxide (KOH), methanol and hydroxylamine are added to the compound of formula 25-4, and then reacted at room temperature, thereby synthesizing final compound 930.

Reaction scheme 26
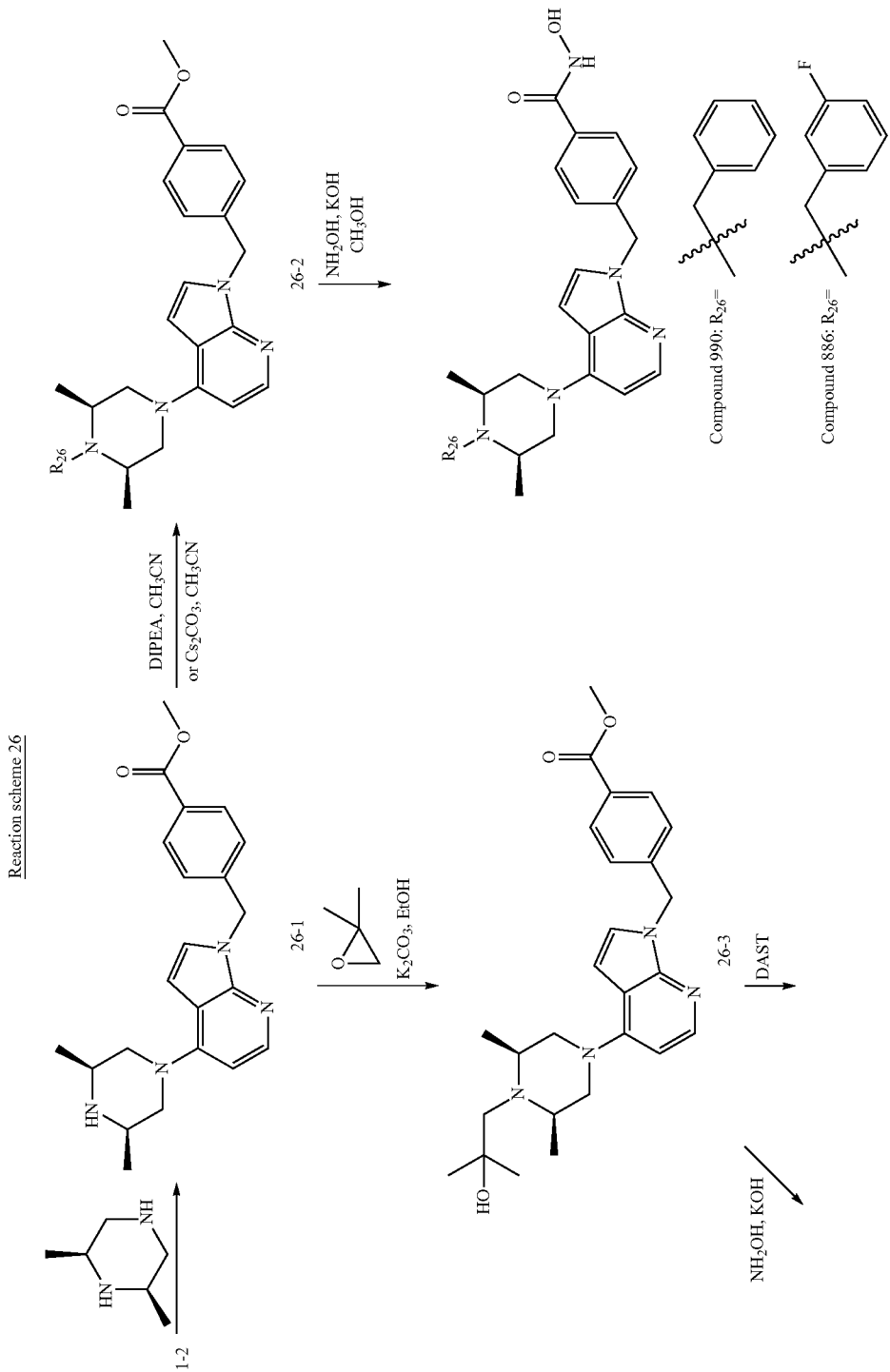

-continued
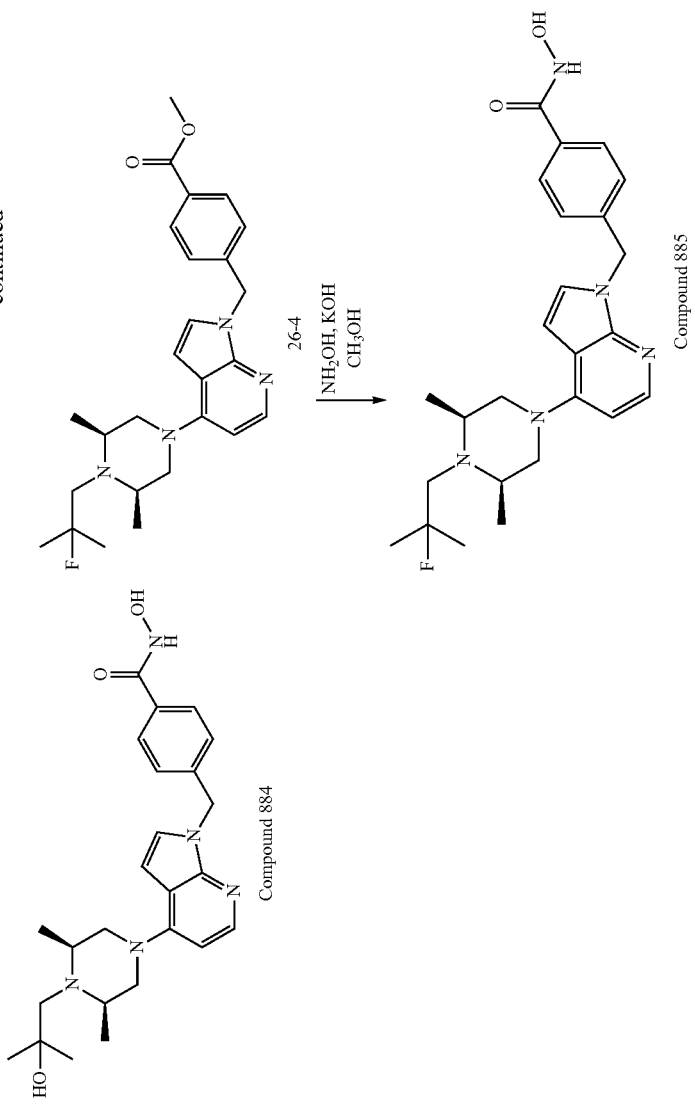

As shown in reaction scheme 26 above, the compound of formula 1-2, obtained by the reaction scheme 1 above, is subjected to a Buchwald reaction with a secondary amine to synthesize a compound of formula 26-1, which is then reacted with $R_{26}$—X to synthesize a compound of formula 26-2. Finally, potassium hydroxide (KOH), methanol and hydroxylamine are added to the compound of formula 26-2, and then reacted at room temperature, thereby synthesizing final compounds 886 and 990.

In addition, the compound of formula 26-1 may be reacted with an oxirane compound using microwaves to synthesize a compound of formula 26-3. Finally, potassium hydroxide (KOH), methanol and hydroxylamine are added to the compound of formula 26-3, and then reacted at room temperature, thereby synthesizing final compound 884.

In addition, the hydroxyl group of the compound of formula 26-3 may be substituted with fluorine to synthesize a compound of formula 26-4. Finally, potassium hydroxide (KOH), methanol and hydroxylamine are added to the compound of formula 26-4, and then reacted at room temperature, thereby synthesizing final compound 885.

Advantageous Effects

Novel HDAC inhibitor compounds according to the present invention, isomers thereof, pharmaceutically acceptable salts thereof, hydrates thereof, or solvates thereof, have less side effects, and exhibit the excellent effect of inhibiting HDAC activity.

Novel HDAC inhibitor compounds according to the present invention, isomers thereof, pharmaceutically acceptable salts thereof, hydrates thereof, or solvates thereof, can be used to prevent or treat HDAC activity-associated diseases. In addition, the novel HDAC inhibitor compounds of the present invention can be prepared by preparation methods according to the present invention.

BEST MODE

Figure 1:
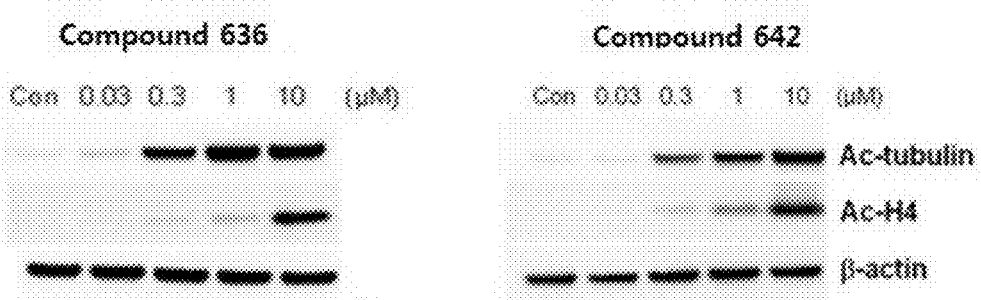
FIG. 1 shows the results of Western blot analysis conducted to examine the degree of tubulin acetylation and histone acetylation caused by compounds of the present invention.

Hereinafter, the present invention will be described in further detail with reference to examples and experimental examples. It is to be understood, however, that these examples are for illustrative purposes only and are not intended to limit the scope of the present invention.

Example 1

Synthesis of Compound 103

Step 1: Synthesis of 5-(pyridin-3-yl)-1H-pyrrolo[2,3-b]pyridine (formula 10-2)

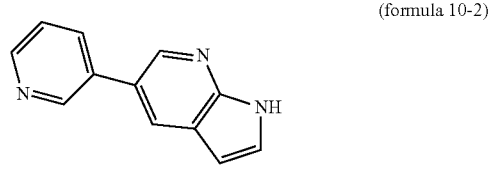 [SMILES: c1cncc(-c2cnc3[nH]ccc3c2)c1]

(formula 10-2)

The compound of formula 10-1 (5-bromo-1H-pyrrolo[2,3-b]pyridine) (0.3 g, 1.52 mmol), pyridine-2-boronic acid (0.22 g, 1.84 mmol), Pd(dppf)Cl$_2$ (0.12 g, 0.15 mmol) and potassium carbonate (0.63 g, 4.57 mmol) were added to 1,4-dioxane (20 mL)/water (10 mL), and heated by microwave irradiation at 120° C. for 10 minutes, and then cooled to room temperature. After completion of the reaction, the reaction mixture was filtered through a celite pad to remove solids, and the filtrate was concentrated under reduced pressure to remove the solvent. The concentrate was purified by column chromatography (SiO$_2$, 12 g cartridge; ethyl acetate/hexane=from 10% to 40%) to afford the desired compound of formula 10-2 (0.21 g, 72%) as a pale brown solid.

Step 2: Synthesis of methyl 4-((5-(pyridin-3-yl)-1H-pyrrolo[2,3-b]pyridin-1-yl)methyl)benzoate (formula 10-3)

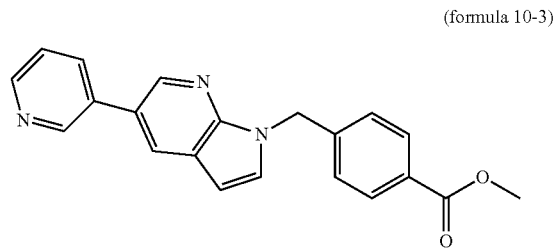 [SMILES: COC(=O)c1ccc(Cn2ccc3cc(-c4cccnc4)cnc32)cc1]

(formula 10-3)

The compound of formula 10-2 (0.30 g, 1.54 mmol), prepared in step 1, was dissolved in N,N-dimethylformamide (10 mL) at room temperature. To the solution, methyl 4-(bromomethyl)benzoate (0.42 g, 1.84 mmol) was added, followed by stirring at the same temperature for 5 minutes. To the reaction mixture, sodium hydride (55.0%, 0.13 g, 3.07 mmol) was added, followed by stirring at the same temperature for 4 hours. Then, a saturated aqueous solution of ammonium chloride was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g Step 3: Synthesis of N-hydroxy-4-((5-pyridin-3-yl)-1H-pyrrolo[2,3-b]pyridin-1-yl)methyl)benzamide (compound 103)

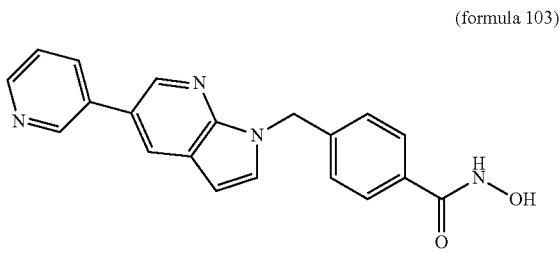 [SMILES: O=C(NO)c1ccc(Cn2ccc3cc(-c4cccnc4)cnc32)cc1]
(formula 103)

The compound of formula 10-3 (0.103 g, 0.30 mmol), prepared in step 2 was dissolved in methanol (10 mL) at room temperature. To the solution, hydroxylamine hydrochloride (0.104 g, 2.12 mmol) and potassium hydroxide (0.168 g, 1.50 mmol) were added, followed by stirring at the same temperature. To the reaction mixture, an aqueous solution of 50 wt % hydroxylamine (2 mL) was added, followed by stirring at the same temperature for 16 hours. Then, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography ($SiO_2$, 12 g cartridge; ethyl acetate/hexane=from 10% to 50%) to afford the desired compound 103 (0.047 g, 46%) as a white solid.

$^1$H NMR (400 MHz, DMSO-$d_6$) δ 11.15 (brs, 1H), 9.02 (brs, $^1$H), 8.60 (d, 1H, J=2.1 Hz), 8.57 (dd, 1H, J=4.7, 1.5 Hz), 8.34 (d, 1H, J=2.2 Hz), 8.13 (dt, 1H, J=8.5, 2.0 Hz), 7.74 (d, 1H, J=3.5 Hz), 7.68 (d, 2H, J=8.3 Hz), 7.50 (q, 1H, J=4.2 Hz), 7.29 (d, 2H, J=8.3 Hz), 6.62 (d, 2H, J=3.5 Hz), 5.57 (s, 2H); MS (ESI) m/z 345 ($M^+$+H)

Example 2

Synthesis of Compound 104

Step 1: Synthesis of 5-(4-fluorophenyl)-1H-pyrrolo[2,3-b]pyridine (formula 10-2)

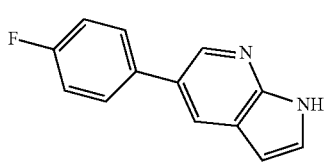
(formula 10-2)

The compound of formula 10-1 (5-bromo-1H-pyrrolo[2,3-b]pyridine) (0.300 g, 1.523 mmol), 4-fluorophenylboronic acid (0.256 g, 1.827 mmol), Pd(dppf)$Cl_2$ (0.124 g, 0.152 mmol) and potassium carbonate (0.631 g, 4.568 mmol) were added to 1,4-dioxane (20 mL)/water (10 mL), and heated by microwave irradiation at 120° C. for 10 minutes, followed by cooling to room temperature. After completion of the reaction, the reaction mixture was filtered through a celite pad to remove solids, and the filtrate was concentrated under reduced pressure to remove the solvent. The concentrate was purified by column chromatography ($SiO_2$, 12 g cartridge; ethyl acetate/hexane=from 20% to 70%) to afford the desired compound of formula 10-2 (0.237 g, 73%) as a yellow solid.

Step 2: Synthesis of methyl 4-((5-(4-fluorophenyl)-1H-pyrrolo[2,3-b]pyridin-1-yl)methyl)benzoate (formula 10-3)

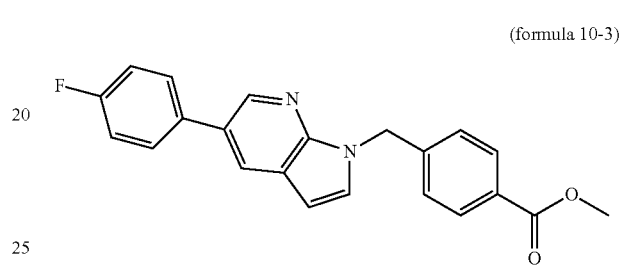
(formula 10-3)

The compound of formula 10-2 (0.108 g, 0.509 mmol), prepared in step 1, was dissolved in N,N-dimethylformamide (10 mL) at room temperature. To the solution, sodium hydride (0.024 g, 1.019 mmol) was added, followed by stirring at the same temperature for 5 hours. To the reaction mixture, methyl 4-(bromomethyl)benzoate (0.140 g, 0.611 mmol) was added, followed by stirring at the same temperature for 4 hours. Then, a saturated aqueous solution of ammonium chloride was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography ($SiO_2$, 12 g cartridge; ethyl acetate/hexane=from 20% to 50%) to afford the desired compound of formula 10-3 (0.13 g, 73%) as a white solid.

Step 3: Synthesis of 4-((5-(4-fluorophenyl)-1H-pyrrolo[2,3-b]pyridin-1-yl)methyl)-N-hydroxybenzamide (compound 104)

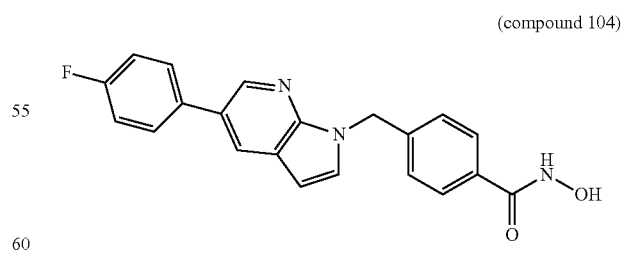
(compound 104)

The compound of formula 10-3 (0.153 g, 0.425 mmol), prepared in step 2, was dissolved in methanol (10 mL) at room temperature. To the solution, hydroxylamine hydrochloride (0.147 g, 2.123 mmol) and potassium hydroxide (0.24 g, 4.25 mmol) were added, followed by stirring at the same temperature. To the reaction mixture, an aqueous solution of 50 wt % hydroxylamine (0.130 mL, 2.123 mmol) was added, followed by stirring at the same temperature for 16 hours. Then, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; ethyl acetate/hexane=from 0% to 30%) to afford the desired compound 104 (0.083 g, 54%) as a white solid.

$^1$H NMR (400 MHz, DMSO-d$_6$) δ 8.52 (d, 1H, J=2.0 Hz), 8.23 (d, 1H, J=2.0 Hz), 7.76-7.66 (m, 5H), 7.33-7.25 (m, 4H), 6.58 (d, 1H, J=0.0 Hz), 5.55 (s, 2H); MS (ESI) m/z 362 (M$^+$+H)

Example 3

Synthesis of Compound 124

Step 1: Synthesis of 5-(pyrimidin-5-yl)-1H-pyrrolo[2,3-b]pyridine (formula 10-2)

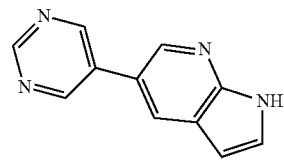
(formula 10-2)

The compound of formula 10-1 (5-bromo-1H-pyrrolo[2,3-b]pyridine) (0.30 g, 1.52 mmol), pyrimidine-5-boronic acid (0.23 g, 1.83 mmol), Pd(dppf)Cl$_2$ (0.12 g, 0.15 mmol), potassium carbonate (0.63 g, 4.57 mmol) and 1,4-dioxane/water (20 mL/10 mL) were added to a microwave vial, and heated by microwave irradiation at 120° C. for 10 minutes. The reaction mixture was filtered through celite and washed with methanol. The filtrate was concentrated under reduced pressure, and the residue was purified by column chromatography (SiO$_2$, 12 g cartridge; ethyl acetate/hexane=from 30% to 50%) to afford the desired compound of formula 10-2 (0.14 g, 47%).

Step 2: Synthesis of methyl 4-((5-(pyridin-5-yl)-1H-pyrrolo[2,3-b]pyridin-1-yl)methyl)benzoate (formula 10-3)

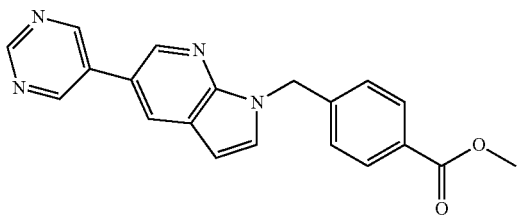
(formula 10-3)

The compound of formula 10-2 (0.14 g, 0.72 mmol), prepared in step 1, methyl 4-(bromomethyl)benzoate (0.19 g, 0.86 mmol), and sodium hydride (0.034 g, 1.43 mmol) were dissolved in N,N-dimethylformamide (20 mL), and stirred at room temperature for 4 hours. After completion of the reaction, the reaction mixture was extracted with ethyl acetate and a saturated aqueous solution of ammonium chloride. The organic layer was washed with saturated brine, dried with anhydrous sodium sulfate, filtered, and concentrated under reduced pressure. The residue was purified by column chromatography (SiO$_2$, 12 g cartridge; ethyl acetate/hexane=from 40% to 60%) to afford the desired compound of formula 10-3 (0.096 g, 39%).

Step 3: Synthesis of N-hydroxy-4-((5-(pyrimidin-5-yl)-1H-pyrrolo[2,3-b]pyridin-1-yl)methyl)benzamide (compound 124)

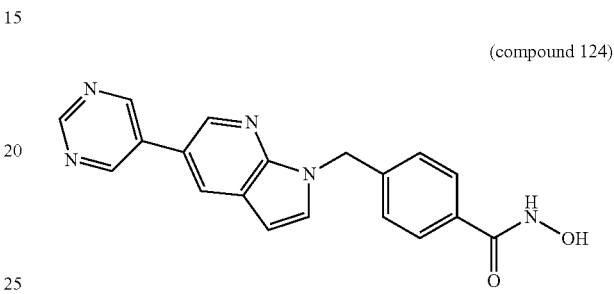
(compound 124)

The compound of formula 10-3 (0.096 g, 0.28 mmol) prepared in step 2, hydroxylamine hydrochloride (0.096 g, 1.39 mmol), potassium hydroxide (0.16 g, 2.77 mmol) and methanol (10 mL) were mixed and stirred for 10 minutes. Then, an aqueous solution of 50 wt % hydroxylamine (4 mL) was added thereto, followed by stirring at room temperature overnight. After completion of the reaction, methanol was removed from the reaction mixture by distillation under reduced pressure, and an aqueous solution of 2M hydrochloric acid was added to the residue to adjust the pH to about 9. The produced white solid was filtered, washed with diethyl ether to remove impurities, and then dried, thereby obtaining compound 124 (0.052 g, 54%) as a white solid.

$^1$H NMR (400 MHz, DMSO-d$_6$) δ 11.16 (brs, 1H), 9.20 (s, 2H), 9.19 (s, 1H), 9.04 (brs, 2H), 8.67 (d, 1H, J=1.8 Hz), 8.44 (d, 1H, J=1.9 Hz), 7.78 (d, 1H, J=3.4 Hz), 7.68 (d, 2H, J=8.1 Hz), 7.28 (d, 2H, J=8.1 Hz), 6.64 (d, 1H, J=3.4 Hz), 5.58 (s, 2H); MS (ESI) m/z 346 (M$^+$+H)

Example 4

Synthesis of Compound 125

Step 1: Synthesis of 5-(2,4-difluorophenyl)-1H-pyrrolo[2,3-b]pyridine (formula 10-2)

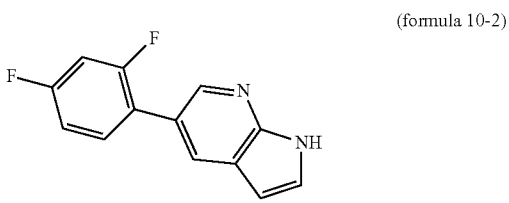 [SMILES: Fc1ccc(-c2cnc3[nH]ccc3c2)c(F)c1]
(formula 10-2)

The compound of formula 10-1 (5-bromo-1H-pyrrolo[2,3-b]pyridine) (0.300 g, 1.52 mmol), 2,4-difluorophenylboronic acid (0.288 g, 1.83 mmol), Pd(dppf)Cl$_2$ (0.124 g, 0.15 mmol), potassium carbonate (0.631 g, 4.57 mmol) and 1,4-dioxane/water (20 mL/10 mL) were added to a microwave vial, and heated by microwave irradiation at 120 r for 10 minutes. The reaction mixture was filtered through celite and washed with methanol. The filtrate was concentrated under reduced pressure, and the residue was purified by column chromatography (SiO$_2$, 12 g cartridge; ethyl acetate/hexane=from 30% to 40%) to afford the desired compound of formula 10-2 (0.24 g, 70%).

Step 2: Synthesis of methyl 4-((5-(2,4-difluorophenyl)-1H-pyrrolo[2,3-b]pyridin-1-yl)methyl)benzoate (formula 10-3)

(formula 10-3)

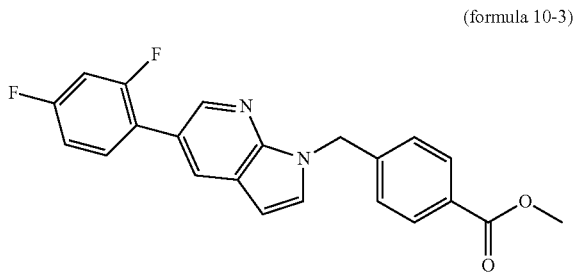 [SMILES: COC(=O)c1ccc(Cn2ccc3cc(-c4ccc(F)cc4F)cnc32)cc1]

The compound of formula 10-2 (0.246 g, 1.07 mmol) prepared in step 1, methyl 4-(bromomethyl)benzoate (0.293 g, 1.28 mmol) and sodium hydride (0.093 g, 2.13 mmol) were dissolved in N,N-dimethylformamide (20 mL), and stirred at room temperature for hours. After completion of the reaction, the reaction mixture was extracted with ethyl acetate and a saturated aqueous solution of ammonium chloride. The organic layer was washed with saturated brine, dried with anhydrous sodium sulfate, filtered, and concentrated under reduced pressure. The residue was purified by column chromatography (SiO$_2$, 12 g cartridge; ethyl acetate/hexane=from 40% to 60%) to afford the desired compound of formula 10-3 (0.23 g, 56%).

Step 3: Synthesis of 4-((5-(2,4-difluorophenyl)-1H-pyrrolo[2,3-b]pyridin-1-yl)methyl)-N-hydroxybenzamide (compound 125)

(compound 125)

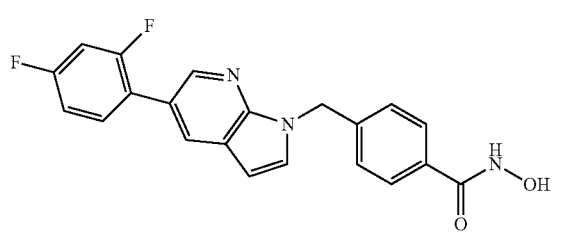

The compound of formula 10-3 (0.227 g, 0.208 mmol) prepared in step 2, hydroxylamine hydrochloride (0.208 g, 3.00 mmol), potassium hydroxide (0.337 g, 5.9 mmol) and methanol (10 mL) were mixed and stirred for 10 minutes. Then, an aqueous solution of 50 wt % hydroxylamine (4 mL) was added thereto, followed by stirring at room temperature overnight. After completion of the reaction, methanol was removed from the reaction mixture by distillation under reduced pressure, and an aqueous solution of 2M hydrochloric acid was added to the residue to adjust the pH to about 9. The produced white solid was filtered, washed with diethyl ether to remove impurities, and then dried, thereby obtaining compound 125 (0.054 g, 24%) as a white solid.

$^1$H NMR (400 MHz, DMSO-d$_6$) δ 11.17 (brs, 1H), 9.05 (brs, $^1$H), 8.38 (s, 1H), 8.14 (s, 1H), 7.74 (d, 1H, J=3.4 Hz), 7.69-7.64 (m, 3H), 7.40 (td, 1H, J=10.1, 2.4 Hz), 7.29 (d, 2H, J=8.2 Hz), 6.61 (d, 1H, J=3.5 Hz), 5.57 (s, 2H); MS (ESI) m/z 380 (M$^+$+H)

Example 5

Synthesis of Compound 212

Step 1: Synthesis of tert-butyl 4-(1-(4-(methoxycarbonyl)benzyl)-1H-pyrrolo[2,3-b]pyridin-4-yl)piperazine-1-carboxylate (formula 7-2)

(formula 7-2)

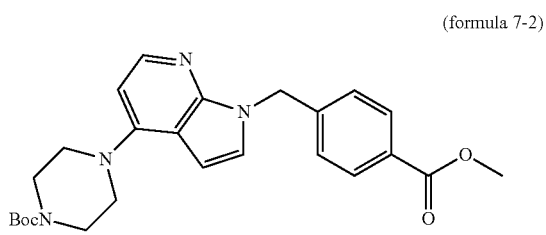 [SMILES: COC(=O)c1ccc(Cn2ccc3c(N4CCN(C(=O)OC(C)(C)C)CC4)ccnc32)cc1]

The compound of formula 7-1 (tert-butyl 4-(1H-pyrrolo[2,3-b]pyridin-4-yl)piperazine-1-carboxylate) (0.30 g, 0.99 mmol) was dissolved in N,N-dimethylformamide (10 mL). To the solution, methyl-4-(bromomethyl)benzoate (0.34 g, 1.49 mmol), sodium hydride (0.04 g, 1.98 mmol) and a small amount of potassium iodide were added. Then, the reaction mixture was stirred at 60° C. for 3 hours, and then cooled to room temperature. After completion of the reaction, water was added to the reaction mixture, followed by extraction with ethyl acetate. The organic layer was washed with a saturated aqueous solution of ammonium chloride, dried with anhydrous sodium sulfate, filtered, and then concentrated under reduced pressure. The concentrate was purified by column chromatography (SiO$_2$, 12 g cartridge; ethyl acetate/hexane=from 0% to 60%) to afford the desired compound of formula 7-2 (0.39 g, 87%) as a white solid.

Step 2: Synthesis of tert-butyl 4-(1-(4-(hydroxycarbamoyl)benzyl-1H-pyrrolo[2,3-b]pyridin-4-yl)piperazine-1-carboxylate (compound 212)

(compound 212)

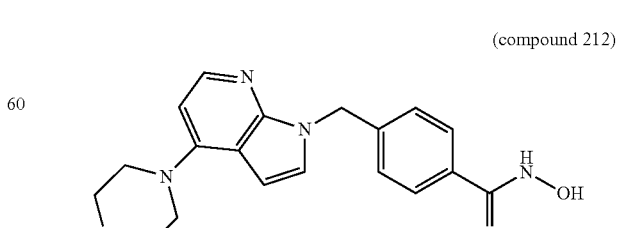

The compound of formula 7-2 (0.08 g, 0.18 mmol) prepared in step 1 was dissolved in methanol (2 mL), and hydroxylamine hydrochloride (0.06 g, 0.89 mmol) was added slowly thereto. Then, potassium hydroxide (0.10 g, 1.78 mmol) was added thereto. The reaction mixture was stirred at room temperature for about 10 minutes, and then an aqueous solution of 50 wt % hydroxylamine (0.21 mL, 3.55 mmol) was added thereto. Then, the solution was stirred at 60° C. for 3 hours, and concentrated under reduced pressure, and neutralized by addition of 2N hydrochloric acid. The produced solid was washed several times with excess water and dried, thereby obtaining compound 212 (0.05 g, 62%) as a white solid.

$^1$H NMR (400 MHz, DMSO-$d_6$) δ 8.00 (d, J=5.7 Hz, 1H), 7.66 (d, J=8.2 Hz, 2H), 7.25 (d, J=3.6 Hz, 1H), 7.19 (d, J=8.4 Hz, 2H), 6.64 (d, J=3.8 Hz, 1H), 6.56 (d, J=6.0 Hz, 1H), 5.51 (s, 2H), 3.64 (brs, 4H), 3.52 (brs, 4H), 1.50 (s, 9H); MS (ESI) m/z 452 (M$^+$+H).

Example 6

Synthesis of Compound 223

Step 1: Synthesis of methyl 4-((4-(piperazin-1-yl)-1H-pyrrolo[2,3-b]pyridin-1-yl)methyl)benzoate (formula 7-3)

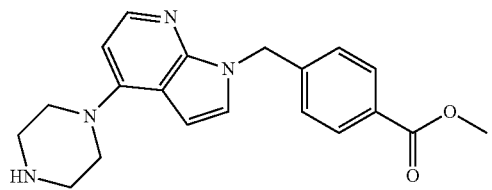

(formula 7-3)

The compound of formula 7-2 (0.05 g, 0.11 mmol) was dissolved in methylene chloride (10 mL), and trifluoroacetic acid (0.28 mL, 3.66 mmol) was added thereto, followed by stirring at room temperature for 2 hours. Water was added to the reaction mixture, neutralized with an aqueous solution of sodium hydrogen carbonate, and then extracted with methylene chloride. The organic layer was washed with a saturated aqueous solution of sodium chloride, dried with anhydrous sodium sulfate, filtered, and then concentrated under reduced pressure. The concentrate was purified by column chromatography (SiO$_2$, 12 g cartridge; methanol/methylene chloride=from 0% to 10%) to afford the desired compound of formula 7-3 (0.23 g, 89%) as a yellow liquid.

Step 2: Synthesis of methyl 4-((4-(4-ethylpiperazin-1-yl)-1H-pyrrolo[2,3-b]pyridin-1-yl)methyl)benzoate (formula 7-4)

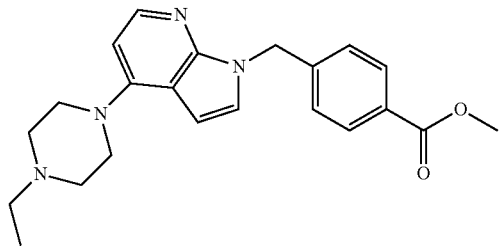

(formula 7-4)

The compound of formula 7-3 (0.10 g, 2.28 mmol) prepared in step 1 was dissolved in acetic acid (2 mL), and acetaldehyde (1.00 g, 22.8 mmol) was added slowly thereto. The solution was stirred at 50° C. for 3 hours, and then NaCNBH$_3$ was added thereto at 0° C., followed by stirring at room temperature for 5 hours. Then, a small amount of water was added to terminate the reaction, and the solvent was removed under reduced pressure. Then, water was added to the residue, followed by extraction with methylene chloride. The organic layer was washed with a saturated aqueous solution of sodium chloride, dried with anhydrous sodium sulfate, filtered, and then concentrated under reduced pressure. The concentrate was purified by column chromatography (SiO$_2$, 12 g cartridge; methanol/methylene chloride=from 0% to 10%) to afford the desired compound of formula 7-4 (0.008 g, 7%) as a transparent liquid.

Step 3: Synthesis of 4-((4-(4-ethylpiperazin-1-yl)-1H-pyrrolo[2,3-b]pyridin-1-yl)methyl)-N-hydroxybenzamide (compound 223)

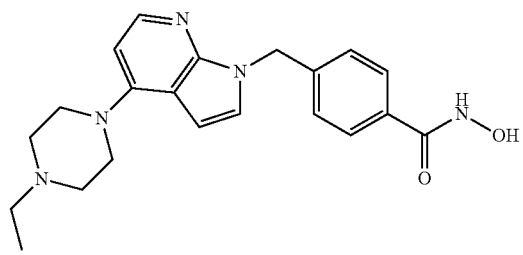

(compound 223)

The compound of formula 7-4 (0.008 g, 0.02 mmol) prepared in step 2 was dissolved in methanol (5 mL), and then hydroxylamine hydrochloride (0.007 g, 0.11 mmol) and potassium hydroxide (0.01 g, 0.21 mmol) were added thereto. The reaction mixture was stirred for 10 minutes, and then an aqueous solution of 50 wt % hydroxylamine (0.02 mL, 0.42 mmol) was added thereto, followed by stirring at room temperature for 12 hours. The organic solvent was removed under reduced pressure, and a small amount of water (5 mL) was added to the residue. Then, the solution was neutralized by addition of 1N aqueous solution of hydrochloric acid, and then extracted with ethyl acetate. The organic layer was washed twice with saturated brine, dried with sodium sulfate, and filtered. The filtrate was concentrated under reduced pressure, thereby obtaining compound 223 (0.007 g, 87%) as a white solid.

$^1$H NMR (400 MHz, CD$_3$OD) δ 7.98 (s, 1H), 7.32-6.76 (m, 5H), 6.52 (s, 1H), 6.41 (s, 1H), 5.45 (s, 2H), 3.55 (brs, 4H), 2.69 (brs, 4H), 2.53 (q, 2H, J=6.4 Hz), 1.17 (t, 3H, J=6.5 Hz); MS (ESI) m/z 380 (M$^+$+H).

Example 7

Synthesis of Compound 224

Step 1: Synthesis of methyl 4-((4-(4-methylpiperazin-1-yl)-1H-pyrrolo[2,3-b]pyridin-1-yl)methyl)benzoate (formula 7-4)

(formula 7-4)

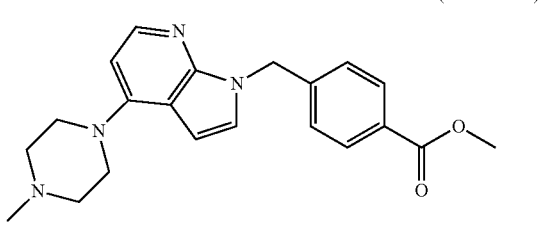

The compound of formula 7-3 (methyl 4-((4-(piperazin-1-yl)-1H-pyrrolo[2,3-b]pyridin-1-yl)methyl)benzoate) (0.05 g, 0.14 mmol) was dissolved in acetic acid (2 mL), and then formaldehyde (0.04 g, 1.43 mmol) was added slowly thereto. The mixture was stirred at 50° C. for 3 hours, and then NaCNBH$_3$ was added thereto at 0° C., followed by stirring at room temperature for 5 hours. Then, a small amount of water was added to terminate the reaction, and the solvent was removed under reduced pressure. Then, water was added to the residue, followed by extraction with methylene chloride. The organic layer was washed with a saturated aqueous solution of sodium chloride, dried with anhydrous sodium sulfate, filtered, and then concentrated under reduced pressure. The concentrate was purified by column chromatography (SiO$_2$, 12 g cartridge; methanol/methylene chloride=from 0% to 10%) to afford the desired compound of formula 7-4 (0.02 g, 38%) as a transparent liquid.

Step 2: Synthesis of N-hydroxy-4-((4-(4-methylpiperazin-1-yl)-1H-pyrrolo[2,3-b]pyridin-1-yl)methyl)benzamide (compound 224)

(compound 224)

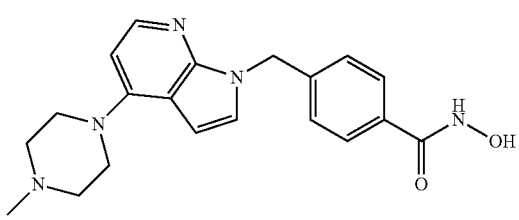

The compound of formula 7-4 (0.02 g, 0.05 mmol) prepared in step 1 was dissolved in methanol (5 mL), and then hydroxylamine hydrochloride (0.01 g, 0.27 mmol) and potassium hydroxide (0.03 g, 0.55 mmol) were added thereto. The reaction mixture was stirred for 10 minutes, and then an aqueous solution of 50 wt % hydroxylamine (0.06 mL, 1.09 mmol) was added thereto, followed by stirring at room temperature for 12 hours. The organic solvent was removed under reduced pressure, and a small amount of water (5 mL) was added to the residue. Then, the solution was neutralized by addition of 1N aqueous solution of hydrochloric acid. The produced solid was filtered, and dried to afford the desired compound 224 (0.01 g, 49%) as a white solid.

$^1$H NMR (400 MHz, CD$_3$OD) δ 7.99 (s, 1H), 7.34 (s, 2H), 7.01 (s, 1H), 6.90 (s, 2H), 6.50 (s, 1H), 6.41 (s, 1H), 5.43 (s, 2H), 3.53 (brs, 4H), 2.63 (brs, 4H), 2.39 (s, 3H); MS (ESI) m/z 366 (M$^+$+H).

Example 8

Synthesis of Compound 225

Step 1: Synthesis of methyl 4-((4-(4-isopropylpiperazin-1-yl)-1H-pyrrolo[2,3-b]pyridin-1-yl)methyl)benzoate (formula 7-4)

(formula 7-4)

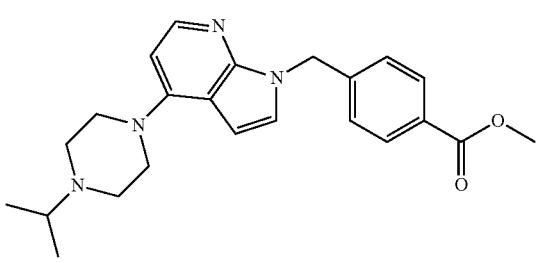

The compound of formula 7-3 (methyl 4-((4-(piperazin-1-yl)-1H-pyrrolo[2,3-b]pyridin-1-yl)methyl)benzoate) (0.10 g, 0.29 mmol) was dissolved in acetonitrile (2 mL), and then potassium carbonate (0.12 g, 0.86 mmol) was added slowly thereto. The solution was stirred at room temperature for 5 minutes, and then 2-iodopropane (0.10 g, 0.57 mmol) was added thereto. The reaction mixture was warmed slowly and stirred at 80° C. for 2 hours. Then, the solvent was removed under reduced pressure, and water was added to the residue, and extracted with methylene chloride. The organic layer was washed with a saturated aqueous solution of sodium chloride, dried with anhydrous sodium sulfate, filtered, and then concentrated under reduced pressure. The concentrate was purified by column chromatography (SiO$_2$, 12 g cartridge; methanol/methylene chloride=from 0% to 20%) to afford the desired compound of formula 7-4 (0.07 g, 62%) as a yellow liquid.

Step 2: Synthesis of N-hydroxy-4-((4-(4-isopropylpiperazin-1-yl)-1H-pyrrolo[2,3-b]pyridin-1-yl)methyl)benzamide (compound 225)

(compound 225)

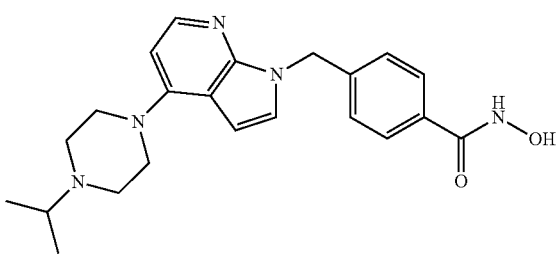

The compound of formula 7-4 (0.06 g, 0.15 mmol) prepared in step 1 was dissolved in methanol (5 mL), and then hydroxylamine hydrochloride (0.05 g, 0.76 mmol) and potassium hydroxide (0.08 g, 1.53 mmol) were added thereto. The mixture was stirred for minutes, and then an aqueous solution of 50 wt % hydroxylamine (0.18 mL, 3.05 mmol) was added thereto, followed by stirring at room temperature for 12 hours. The organic solvent was removed under reduced pressure, and a small amount of water (5 mL) was added to the residue. Then, the solution was neutralized by addition of 1N hydrochloric acid aqueous solution, and then extracted with ethyl acetate. The organic layer was washed twice with a saturated aqueous solution of sodium chloride, dried with sodium sulfate, and filtered. The filtrate was concentrated under reduced pressure to afford the desired compound 225 (0.03 g, 61%) as a white solid.

$^1$H NMR (400 MHz, CD$_3$OD) δ 7.94 (s, 1H), 7.27 (s, 2H), 6.86-6.75 (m, 3H), 6.41 (s, 1H), 6.30 (s, 1H), 5.22 (s, 2H) 3.46 (brs, 4H), 2.70 (brs, 5H), 1.08 (s, 6H); MS (ESI) m/z 394 (H$^+$+H).

Example 9

Synthesis of Compound 617

Step 1: Synthesis of methyl 4-((5-bromo-1H-pyrrolo[2,3-b]pyridin-1-yl)methyl)benzoate (formula 2-2)

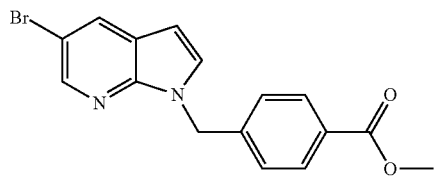

(formula 2-2)

The compound of formula 2-1 (5-bromo-1H-pyrrolo[2,3-b]pyridine) (6.00 g, 30.45 mmol), methyl 4-(bromomethyl)benzoate (7.67 g, 33.49 mmol) and potassium hydroxide (2.05 g, 36.5 mmol) were dissolved in N,N-dimethylformamide (100 mL) at room temperature, and the solution was stirred at the same temperature for 12 hours, after which N,N-dimethylformamide was removed under reduced pressure. Then, the solid was filtered with ethyl acetate, and filtered again with water, thereby obtaining the desired compound of formula 2-2 (10.0 g, 95%) as a yellow solid.

Step 2: Synthesis of tert-butyl 4-(1-(4-(methoxycarbonyl)benzyl)-1H-pyrrolo[2,3-b]pyridin-5-yl)-5,6-dihydropyridine-1(2H)-carboxylate (compound 5-1)

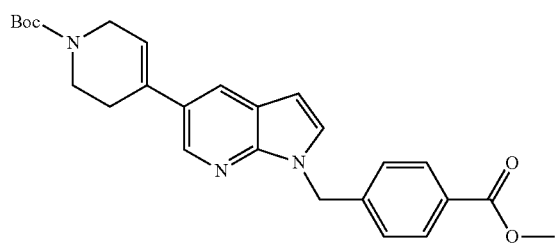

(formula 5-1)

The compound of formula 2-2 (1.00 g, 2.89 mmol) prepared in step 1, 3,6-dihydro-2H-pyridine-1-tert-butoxycarbonyl-4-boronic acid pinacol ester (1.03 g, 3.33 mmol), sodium carbonate (0.614 g, 5.794 mmol) and Pd(dppf)Cl$_2$ (0.24 g, 0.29 mmol) were added to 1,2-dimethoxyethane (2 mL)/water (1 mL), and heated by microwave irradiation 120° C. for 10 minutes, and then cooled to room temperature. Water was added to the reaction mixture, followed by extraction with ethyl acetate. The organic layer was washed with saturated brine, dried with anhydrous magnesium sulfate, and then concentrated under reduced pressure. The concentrate was purified by column chromatography (SiO$_2$, 12 g cartridge; ethyl acetate/hexane=from 0% to 100%) to afford the desired compound of formula 5-1 (0.72 g, 55%) as a yellow solid.

Step 3: Synthesis of methyl 4-((5-(1,2,3,6-tetrahydropyridin-4-yl)-1H-pyrrolo[2,3-b]pyridin-1-yl)methyl)benzoate (formula 5-2)

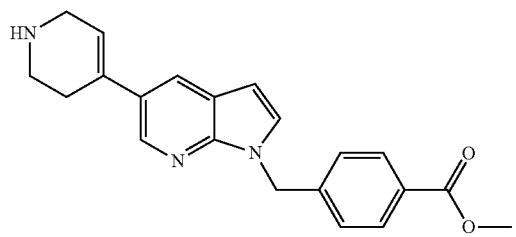

(formula 5-2)

The compound of formula 5-1 (0.72 g, 1.61 mmol) prepared in step 2, and 4M hydrochloric acid solution (4.02 mL, 16.09 mmol) in dioxane, were dissolved in 1,4-dioxane (30 mL) at room temperature. The solution was stirred at the same temperature for 3 hours, and water was added thereto, followed by extraction with ethyl acetate. The aqueous layer was collected, and neutralized by addition of a saturated aqueous solution of sodium hydrogen carbonate thereto, and the produced solid was filtered and dried to afford the desired compound of formula 5-2 (0.25 g, 45%) as a yellow solid.

Step 4: Synthesis of methyl 4-((5-(1-(2-hydroxy-2-methylpropyl)-1,2,3,6-tetrahydropyridin-4-yl)-1H-pyrrolo[2,3-b]pyridin-1-yl)methyl)benzoate (formula 5-3)

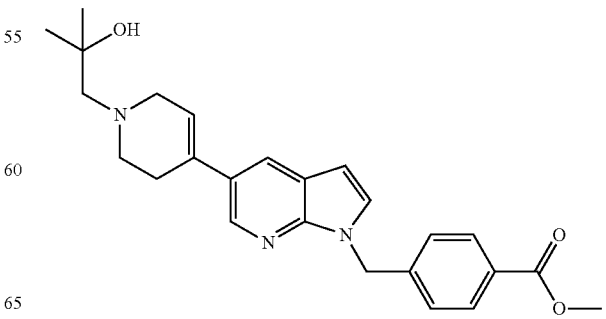

(formula 5-3)

The compound of formula 5-2 (0.390 g, 1.123 mmol) prepared in step 3, isobutylene oxide (1.012 mL, 11.23 mmol) and potassium carbonate (1.55 g, 11.23 mmol) were added to ethanol (5 mL), and heated by microwave irradiation at 110° C. for 10 minutes, followed by cooling to room temperature. Water was added to the reaction mixture, followed by extraction with ethyl acetate. The organic layer was washed with saturated brine, dried with anhydrous magnesium sulfate, and then concentrated under reduced pressure. The concentrate was purified by column chromatography (SiO$_2$, 12 g cartridge; ethyl acetate/hexane=from 20% to 50%) to afford the desired compound of formula 5-3 (0.25 g, 53%) as a yellow solid.

Step 5: Synthesis of methyl 4-((5-(1-(2-fluoro-2-methylpropyl)-1,2,3,6-tetrahydropyridin-4-yl)-1H-pyrrolo[2,3-b]pyridin-1-yl)methyl)benzoate (compound 5-4)

(formula 5-4)

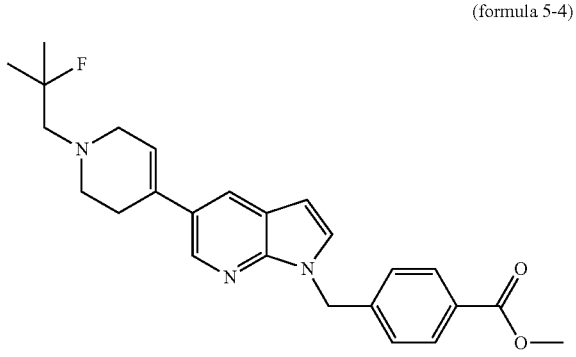 [SMILES: COC(=O)c1ccc(Cn2ccc3cc(C4=CCN(CC(C)(C)F)CC4)cnc32)cc1]

The compound of formula 5-3 (0.130 g, 0.31 mmol) prepared in step 4, and DAST ((diethylamino)sulfur trifluoride) (0.049 mL, 0.37 mmol) were dissolved in dichloromethane (10 mL) at room temperature, and the solution was stirred at the same temperature for 2 hours. Then, water was added to the reaction mixture, followed by extraction with ethyl acetate. The organic layer was washed with saturated brine, dried with anhydrous magnesium sulfate, and then concentrated under reduced pressure. The concentrate was purified by column chromatography (SiO$_2$, 12 g cartridge; ethyl acetate/hexane=from 20% to 30%) to afford the desired compound of formula 5-4 (0.03 g, 23%) as a white solid.

Step 6: Synthesis of 4-((5-(1-(2-fluoro-2-methylpropyl)-1,2,3,6-tetrahydropyridin-4-yl)-1H-pyrrolo[2,3-b]pyridin-1-yl)methyl)-N-hydroxybenzamide (compound 617)

(compound 617)

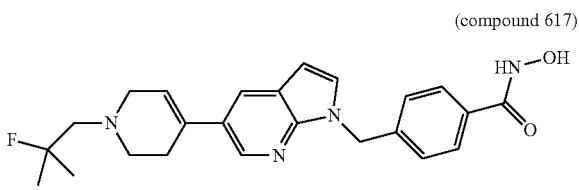 [SMILES: CC(C)(F)CN1CC=C(c2cnc3c(ccn3Cc3ccc(C(=O)NO)cc3)c2)CC1]

The compound of formula 5-4 (0.03 g, 0.071 mmol) prepared in step 5, hydroxylamine hydrochloride (0.025 g, 0.36 mmol), potassium hydroxide (0.04 g, 0.71 mmol) and an aqueous solution of 50 wt % hydroxylamine (0.091 mL, 1.42 mmol) were dissolved in methanol (5 mL) at room temperature, and the mixture was stirred at the same temperature for 3 hours. Then, methanol was removed from the reaction solution under reduced pressure, and a saturated aqueous solution of sodium hydrogen carbonate was added to the residue to produce a solid. The solid was filtered and dried to afford the desired desired compound 617 (0.025 g, 88%) as a white solid.

$^1$H NMR (400 MHz, DMSO-d$_6$) δ 8.40 (d, 1H, J=2.0 Hz), 7.99 (d, 1H, J=2.0 Hz), 7.62 (d, 2H, J=8.2 Hz), 7.60 (d, 1H, J=3.5 Hz), 7.11 (d, 2H, J=8.2 Hz), 6.48 (d, 1H, J=3.5 Hz), 6.14 (s, 1H), 5.43 (s, 2H), 3.36-3.35 (m, 2H), 3.21 (s, 2H), 2.77 (t, 2H, J=5.5 Hz), 2.54-2.51 (m, 2H), 1.38 (s, 3H), 1.32 (s, 3H); MS (ESI) m/z 423.1 (M$^+$+H).

Example 10

Synthesis of Compound 618

Step 1: Synthesis of methyl 4-((5-(1-(2-fluoro-2-methylpropyl)piperidin-4-yl)-1H-pyrrolo[2,3-b]pyridin-1-yl)methyl)benzoate (formula 5-5)

(formula 5-5)

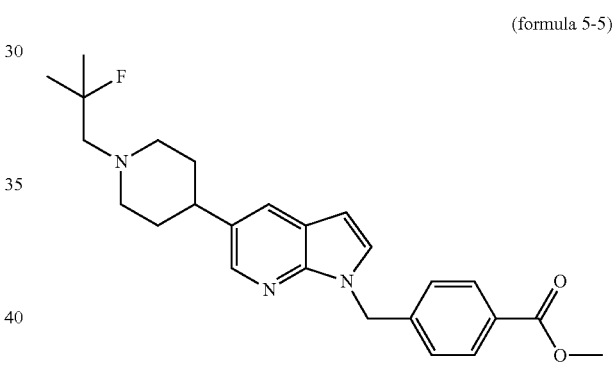

The compound of formula 5-4 (0.06 g, 0.14 mmol) prepared in step 5 of Example 9 was dissolved in methanol (10 mL), and then Pd/C (0.006 g) was added thereto, and a hydrogen balloon was placed over the reaction mixture, followed by stirring at the same temperature for 12 hours. Then, Pd/C was removed by filtration, thus obtaining the desired compound of formula 5-5 (0.040 g, 66%) as a yellow solid.

Step 2: Synthesis of 4-((5-(1-(2-fluoro-2-methylpropyl)piperidin-4-yl)-1H-pyrrolo[2,3-b]pyridin-1-yl)methyl)-N-hydroxybenzamide (compound 618)

(compound 618)

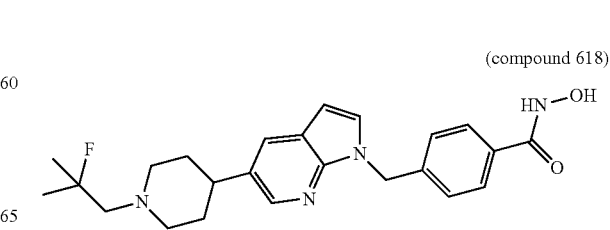

The compound of formula 5-5 (0.04 g, 0.095 mmol) prepared in step 1, hydroxylamine hydrochloride (0.033 g, 0.47 mmol), potassium hydroxide (0.053 g, 0.95 mmol) and an aqueous solution of 50 wt % hydroxylamine (0.12 mL, 1.89 mmol) were dissolved in methanol (5 mL), and the solution was stirred at the same temperature for 3 hours. Then, methanol was removed from the reaction mixture under reduced pressure. Then, a saturated aqueous solution of sodium hydrogen carbonate was added to the residue, and the produced solid was filtered and dried to afford the desired compound 618 (0.023 g, 57%) as a white solid.

$^1$H NMR (400 MHz, DMSO-$d_6$) δ 8.16 (d, 1H, J=2.0 Hz), 7.85 (d, 1H, J=1.9 Hz), 7.69 (d, 2H, J=11.0 Hz), 7.61 (d, 1H, J=3.4 Hz), 7.25 (d, 2H, J=8.2 Hz), 6.46 (d, 1H, J=3.5 Hz), 5.50 (s, 2H), 3.02 (d, 2H, J=11.4 Hz), 2.68-2.57 (m, 2H), 2.24-2.18 (m, 2H), 1.75-1.70 (m, 4H), 1.36 (s, 3H), 1.31 (s, 3H); MS (ESI) m/z 425.2 (M$^+$+H).

Example 11

Synthesis of Compound 629

Step 1: Synthesis of methyl 4-((5-(3,6-dihydro-2H-pyran-4-yl)-1H-pyrrolo[2,3-b]pyridin-1-yl)methyl) benzoate (formula 2-3)

(formula 2-3)

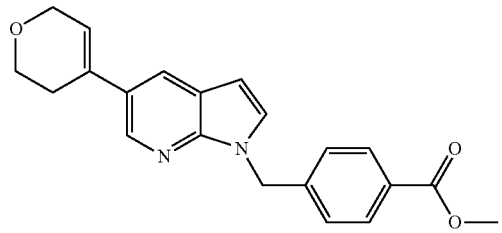

The compound of formula 2-2 (methyl 4-((5-bromo-1H-pyrrolo[2,3-b]pyridin-1-yl)methyl)benzoate, 0.500 g, 1.448 mmol), 3,6-dihydro-2H-pyran-4-boronic acid pinacol ester (0.35 g, 1.67 mmol), sodium carbonate (0.307 g, 2.897 mmol) and Pd(dppf)Cl$_2$ (0.118 g, 0.145 mmol) were added to 1,2-dimethoxyethane (2 mL)/water (1 mL), and heated by microwave irradiation at 120° C. for 10 minutes, and then cooled to room temperature. Then, water was added to the reaction mixture, followed by extraction with ethyl acetate. The organic layer was washed with saturated brine, dried with anhydrous magnesium sulfate, and then concentrated under reduced pressure. The concentrate was purified by column chromatography (SiO$_2$, 12 g cartridge; ethyl acetate/hexane=from 0% to 100%) to afford the desired compound of formula 2-3 (0.4 g, 79%) as a yellow liquid.

Step 2: Synthesis of 4-((5-(3,6-dihydro-2H-pyran-4-yl)-1H-pyrrolo[2,3-b]pyridin-1-yl)methyl)-N-hydroxybenzamide (compound 629)

(compound 629)

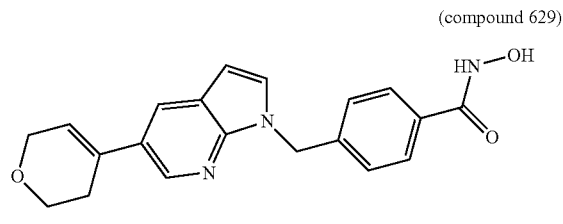 [SMILES: O=C(NO)c1ccc(Cn2ccc3cc(C4=CCOCC4)cnc32)cc1]

The compound of formula 2-3 (0.10 g, 0.29 mmol) prepared in step 1, hydroxylamine hydrochloride (0.10 g, 1.44 mmol), potassium hydroxide (0.16 g, 2.87 mmol) and an aqueous solution of 50 wt % hydroxylamine (0.37 mL, 5.74 mmol) were dissolved in methanol (10 mL) at the same temperature, and the solution was stirred at the same temperature for 3 hours. Then, a saturated aqueous solution of sodium hydrogen carbonate was added to the reaction mixture, and the precipitated solid was filtered and dried to afford the desired compound 629 (0.03 g, 30%) as a white solid.

$^1$H NMR (400 MHz, DMSO-$d_6$) δ 8.41 (d, 1H, J=2.0 Hz), 8.02 (d, 1H, J=2.1 Hz), 7.67 (d, 2H, J=8.4 Hz), 7.65 (d, 1H, J=4.7 Hz), 7.24 (d, 1H, J=8.0 Hz), 6.52 (d, 1H, J=3.4 Hz), 6.25 (s, 1H), 5.51 (s, 2H), 4.24 (d, 2H, J=2.6 Hz), 3.85 (t, 2H, J=5.4 Hz), 2.51-2.50 (m, 2H); MS (ESI) m/z 350.2 (M$^+$+H).

Example 12

Synthesis of Compound 630

Step 1: Synthesis of methyl 4-((4-bromo-1H-pyrrolo[2,3-b]pyridin-1-yl)methyl)benzoate (formula 1-2)

(formula 1-2)

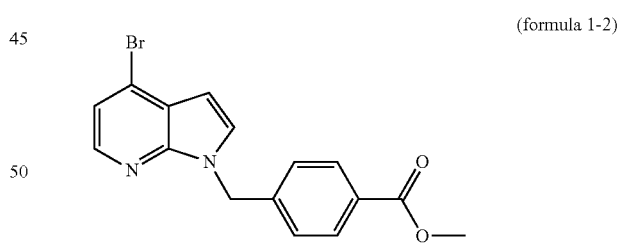

The compound of formula 1-1 (4-bromo-1H-pyrrolo[2,3-b]pyridine) (3.00 g, 15.2 mmol), methyl 4-(bromomethyl)benzoate (3.84 g, 16.75 mmol) and potassium hydroxide (1.03 g, 18.27 mmol) were dissolved in N,N-dimethylformamide (100 mL) at room temperature, and the solution was stirred at the same temperature for 12 hours. Then, water was added to the reaction mixture, followed by extraction with ethyl acetate. The organic layer was washed with saturated brine, dried with anhydrous magnesium sulfate, and then concentrated under reduced pressure. The concentrate was purified by column chromatography (SiO$_2$, 12 g cartridge; ethyl acetate/hexane=from 10% to 15%) to afford the desired compound (3.89 g, 74%) as a white solid.

Step 2: Synthesis of tert-butyl 4-(1-(4-(methoxycarbonyl)benzyl)-1H-pyrrolo[2,3-b]pyridin-4-yl)-5,6-dihydropyridine-1(2H)-carboxylate (formula 4-1)

(formula 4-1)

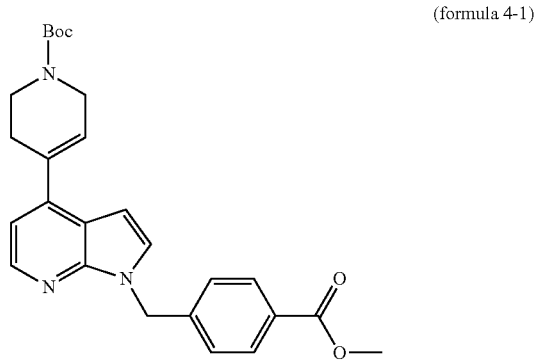 [SMILES: COC(=O)c1ccc(Cn2ccc3c(C4=CCN(C(=O)OC(C)(C)C)CC4)ccnc32)cc1]

The compound of formula 1-2 (0.86 g, 2.49 mmol) prepared in step 1, 3,6-dihydro-2H-pyridine-1-tert-butoxycarbonyl-4-boronic acid pinacol ester (0.89 g, 2.87 mmol), sodium carbonate (0.53 g, 4.98 mmol) and Pd(dppf)Cl₂ (0.21 g, 0.25 mmol) were added to 1,2-dimethoxyethane (2 mL), and heated by microwave irradiation at 120° C. for 20 minutes, followed by cooling to room temperature. Then, water was added to the reaction mixture, followed by extraction with ethyl acetate. The aqueous layer was removed, and the residue was concentrated under reduced pressure. The concentrate was purified by column chromatography (SiO₂, 12 g cartridge; ethyl acetate/hexane=from 20% to 30%) to afford the desired compound of formula 4-1 (0.970 g, 87%) as a yellow liquid.

Step 3: Synthesis of methyl 4-((4-(1,2,3,6-tetrahydropyridin-4-yl)-1H-pyrrolo[2,3-b]pyridin-1-yl)methyl)benzoate (formula 4-2)

(formula 4-2)

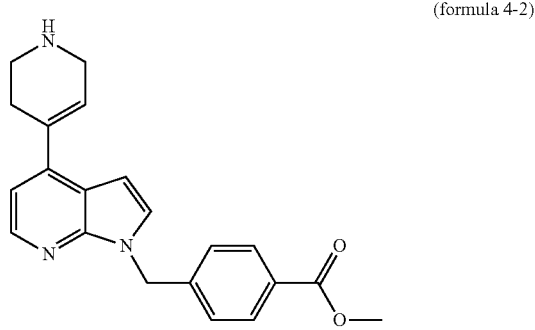 [SMILES: COC(=O)c1ccc(Cn2ccc3c(C4=CCNCC4)ccnc32)cc1]

The compound of formula 4-1 (0.8 g, 1.788 mmol) prepared in step 2, and 4M hydrochloric acid solution (0.447 mL, 1.788 mmol) in dioxane, were dissolved in 1,4-dioxane (10 mL) at room temperature, and the solution was stirred at the same temperature for 12 hours, after which the reaction mixture was concentrated under reduced pressure. Then, the aqueous layer was collected, and saturated sodium hydrogen carbonate was added thereto. The precipitated solid was filtered and dried to afford the desired compound of formula 4-2 (0.62 g, 100%) as a yellow solid.

Step 4: Synthesis of methyl 4-((4-(1-(2-hydroxy-2-methylpropyl)-1,2,3,6-tetrahydropyridin-4-yl)-1H-pyrrolo[2,3-b]pyridin-1-yl)methyl)benzoate (formula 4-3)

(formula 4-3)

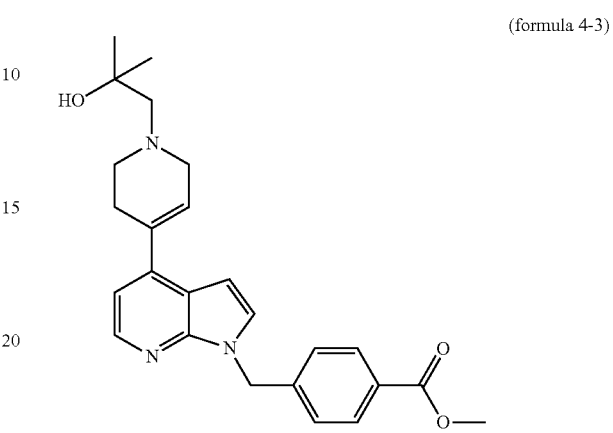

The compound of formula 4-2 (0.21 g, 0.61 mmol) prepared in step 3, isobutylene oxide (0.55 mL, 6.045 mmol) and potassium carbonate (0.84 g, 6.05 mmol) were added to ethanol (2 mL), and heated by microwave irradiation at 110° C. for 10 minutes, and then cooled to room temperature. Then, water was added to the reaction mixture, followed by extraction with ethyl acetate. The organic layer was washed with saturated brine, dried with anhydrous sodium sulfate, and then concentrated under reduced pressure. The concentrate was purified by column chromatography (SiO₂, 12 g cartridge; ethyl acetate/hexane=from 30% to 40%) to afford the desired compound of formula 4-3 (0.25 g, 99%) as a yellow liquid.

Step 5: Synthesis of methyl 4-((4-(1-(2-fluoro-2-methylpropyl)-1,2,3,6-tetrahydropyridin-4-yl)-1H-pyrrolo[2,3-b]pyridin-1-yl)methyl)benzoate (formula 4-4)

(formula 4-4)

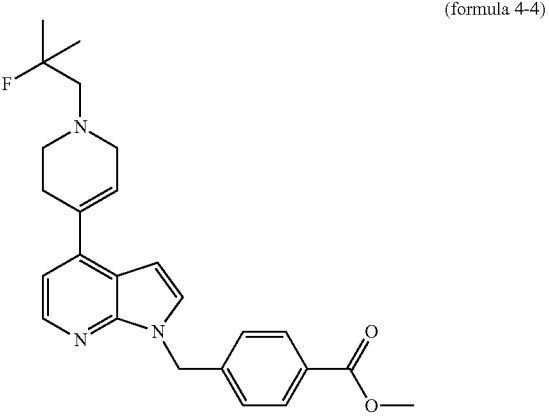 [SMILES: COC(=O)c1ccc(Cn2ccc3c(C4=CCN(CC(C)(C)F)CC4)ccnc32)cc1]

The compound of formula 4-3 (0.25 g, 0.59 mmol) prepared in step 4, and DAST ((diethylamino)sulfur trifluoride) (0.094 mL, 0.72 mmol) were dissolved in dichloromethane (10 mL) at room temperature, and the solution was stirred at the same temperature for 2 hours. Then, water was added to the reaction mixture, followed by extraction with ethyl acetate. The organic layer was washed with saturated brine, dried with anhydrous sodium sulfate, and then concentrated under reduced pressure. The concentrate was purified by column chromatography (SiO$_2$, 4 g cartridge; ethyl acetate/hexane=from 10% to 20%) to afford the desired compound of formula 4-4 (0.04 g, 16%) as a yellow liquid.

Step 6: Synthesis of 4-((4-(1-(2-fluoro-2-methylpropyl)-1,2,3,6-tetrahydropyridin-4-yl)-1H-pyrrolo[2,3-b]pyridin-1-yl)methyl)-N-hydroxybenzamide (compound 630)

(compound 630)

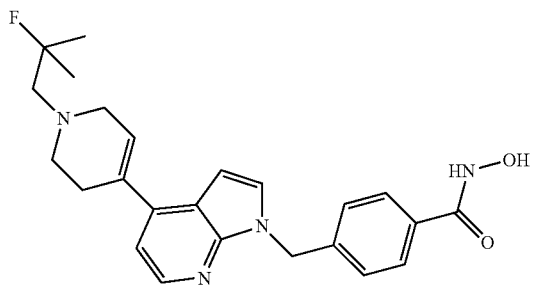

The compound of formula 4-4 (0.04 g, 0.095 mmol) prepared in step 5, hydroxylamine hydrochloride (0.033 g, 0.474 mmol), potassium hydroxide (0.053 g, 0.95 mmol) and an aqueous solution of 50 wt % hydroxylamine (0.122 mL, 1.898 mmol) were dissolved in methanol (10 mL) at room temperature, and the solution was stirred at the same temperature for 3 hours. Then, a saturated aqueous solution of sodium hydrogen carbonate was added to the reaction mixture to produce a solid. The precipitated solid was filtered and dried to afford the desired compound 630 (0.03 g, 75%) as a yellow solid.

$^1$H NMR (400 MHz, DMSO-d$_6$) δ 8.21 (d, 1H, J=5.0 Hz), 7.65 (d, 2H, J=7.9 Hz), 7.63 (d, 1H, J=3.1 Hz), 7.17 (d, 2H, J=8.0 Hz), 7.05 (d, 1H, J=5.0 Hz), 6.70 (d, 1H, J=3.6 Hz), 6.39 (s, 1H), 5.49 (s, 2H), 3.29 (d, 2H, J=2.4 Hz), 2.79 (t, 2H, J=5.4 Hz), 2.63 (s, 2H), 2.60 (t, 2H, J=8.5 Hz), 1.39 (s, 3H), 1.33 (s, 3H); MS (ESI) m/z 423.2 (M$^+$+H).

Example 13

Synthesis of Compound 635

Step 1: Synthesis of methyl 4-((5-(tetrahydro-2H-pyran-4-yl)-1H-pyrrolo[2,3-b]pyridin-1-yl)methyl)benzoate (formula 2-4)

(formula 2-4)

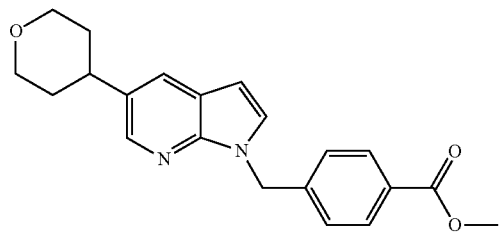

The compound of formula 2-3 (methyl 4-((5-(3,6-dihydro-2H-pyran-4-yl)-1H-pyrrolo[2,3-b]pyridin-1-yl)methyl)benzoate) (0.100 g, 0.29 mmol) was added to methanol (10 mL), and Pd/C (0.005 g) was added thereto. Then, a hydrogen balloon was placed over the mixture, followed by stirring at room temperature for 6 hours. Then, the reaction mixture was filtered through a celite pad to remove a solid, and the filtrate was concentrated under reduced pressure. The concentrate was purified by column chromatography (SiO$_2$, 4 g cartridge; ethyl acetate/hexane=from 20% to 30%) to afford the desired compound of formula 2-4 (0.04 g, 40%) as a colorless liquid.

Step 2: Synthesis of N-hydroxy-4-((5-(tetrahydro-2H-pyran-4-yl)-1H-pyrrolo[2,3-b]pyridin-1-yl)methyl)benzamide (compound 635)

(compound 635)

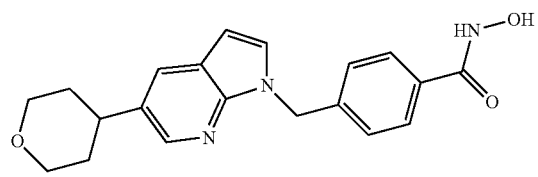

The compound of formula 2-4 (0.04 g, 0.114 mmol) prepared in step 1, hydroxylamine hydrochloride (0.04 g, 0.571 mmol), potassium hydrochloride (0.064 g, 1.142 mmol) and an aqueous solution of 50 wt % hydroxylamine (0.147 mL, 2.283 mmol) were dissolved in methanol (10 mL) at room temperature, and the solution was stirred at the same temperature for 3 hours. The reaction mixture was concentrated under reduced pressure to remove methanol, and then a saturated aqueous solution of sodium hydrogen carbonate was added thereto. The precipitated solid was filtered and dried to afford the desired compound 635 (0.037 g, 92%) as a white solid.

$^1$H NMR (400 MHz, DMSO-d$_6$) δ 8.18 (d, 1H, J=1.8 Hz), 7.86 (d, 1H, J=1.8 Hz), 7.65 (d, 2H, J=8.1 Hz), 7.62 (d, 1H, J=3.4 Hz), 7.22 (d, 2H, J=8.1 Hz), 6.47 (d, 1H, J=3.4 Hz), 5.48 (s, 2H), 3.97 (d, 2H, J=10.7 Hz), 3.46 (t, 2H, J=11.0 Hz), 2.93-2.85 (m, 1H), 1.81-1.70 (m, 4H); MS (ESI) m/z 352.1 (M$^+$+H).

Example 14

Synthesis of Compound 636

Step 1: Synthesis of methyl 4-((5-(tetrahydro-2H-pyran-4-yl)-1H-pyrrolo[2,3-b]pyridin-1-yl)methyl)benzoate (formula 4-5)

(formula 4-5)

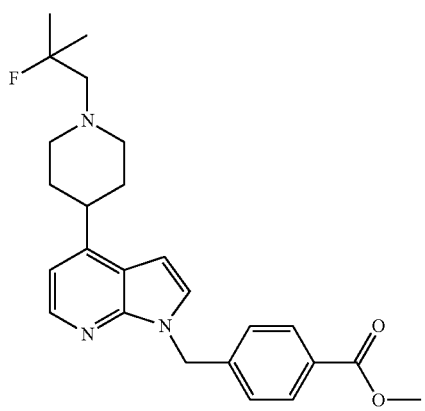

The compound of formula 4-4 (methyl 4-((4-(1-(2-fluoro-2-methylpropyl)-1,2,3,6-tetrahydropyridin-4-yl)-1H-pyrrolo[2,3-b]pyridin-1-yl)methyl)benzoate) (0.040 g, 0.095 mmol) prepared in step 5 of Example 12 was added to methanol (10 mL) at room temperature, Pd/C (0.005 g) was added thereto, and a hydrogen balloon was placed over the mixture, followed by stirring at the same temperature for 12 hours. Then, the reaction mixture was filtered through celite to remove Pd/C. Then, water was added to the reaction mixture, followed by extraction with ethyl acetate. The organic layer was washed with saturated brine, dried with anhydrous sodium sulfate, and then concentrated under reduced pressure. The concentrate was purified by column chromatography (SiO$_2$, 4 g cartridge; ethyl acetate/hexane=from 10% to 20%) to afford the desired compound of formula 4-5 (0.038 g, 95%) as a yellow liquid.

Step 2: Synthesis of 4-((4-(1-(2-fluoro-2-methylpropyl)piperidin-4-yl)-1H-pyrrolo[2,3-b]pyridin-1-yl)methyl)-N-hydroxybenzamide (compound 636)

(compound 636)

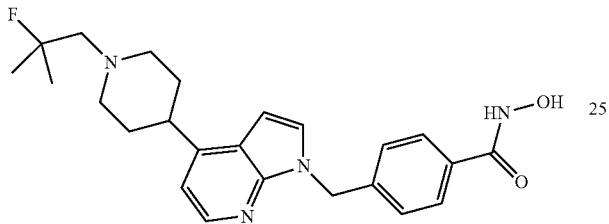

The compound of formula 4-5 (0.038 g, 0.090 mmol) prepared in step 1, hydroxylamine hydrochloride (0.031 g, 0.449 mmol), potassium hydroxide (0.025 g, 0.449 mmol) and an aqueous solution of 50 wt % hydroxylamine (0.115 mL, 1.794 mmol) were dissolved in methanol (5 mL) at room temperature, and the solution was stirred at the same temperature for 3 hours. Then, the reaction mixture was concentrated under reduced pressure to remove methanol, and then a saturated aqueous solution of sodium hydrogen carbonate was added thereto. The precipitated solid was filtered and dried to afford the desired compound 636 (0.037 g, 97%) as a white solid.

$^1$H NMR (400 MHz, DMSO-d$_6$) δ 8.19 (d, 1H, J=4.9 Hz), 7.64 (d, 2H, J=8.2 Hz), 7.57 (d, 1H, J=3.5 Hz), 7.18 (d, 2H, J=8.1 Hz), 6.99 (d, 1H, J=5.0 Hz), 6.61 (d, 1H, J=3.5 Hz), 5.45 (s, 2H), 3.03 (d, 2H, J=11.5 Hz), 2.95-2.89 (m, 1H), 2.33-2.25 (m, 2H), 1.87-1.79 (m, 4H), 1.37 (s, 3H), 1.32 (s, 3H); MS (ESI) m/z 425.2 (M$^+$+H).

Example 15

Synthesis of Compound 642

Step 1: Synthesis of methyl 4-((4-(piperazin-1-yl)-1H-pyrrolo[2,3-b]pyridin-1-yl)methyl)benzoate hydrochloride (formula 8-1)

(formula 8-1)

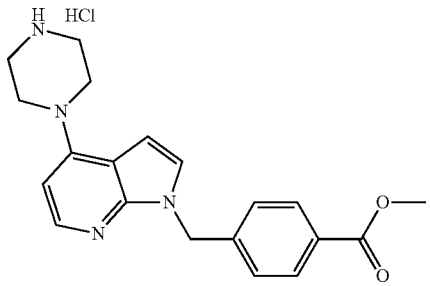

The compound of formula 7-2 (tert-butyl 4-(1-(4-(methoxycarbonyl)benzyl)-1H-pyrrolo[2,3-b]pyridin-4-yl)piperazine-1-carboxylate) (2.1 g, 4.66 mmol) was dissolved in methylene chloride (10 mL) at room temperature, and to the mixture, 4M hydrochloric acid solution (1.39 mL, 5.59 mmol) in dioxane was added, followed by stirring at the same temperature for 3 hours. The precipitated solid was filtered and dried to afford the desired compound of formula 8-1 (1.75 g, 97%) as a white solid.

Step 2: Synthesis of 4-((4-(4-(2-hydroxy-2-methylpropyl)piperazin-1-yl)-1H-pyrrolo[2,3-b]pyridin-1-yl)methyl)benzoate (formula 8-2)

(formula 8-2)

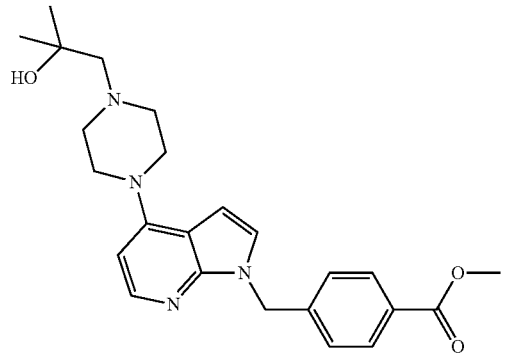

The compound of formula 8-1 (0.80 g, 2.07 mmol) prepared in step 1, 2,2-dimethyloxirane (0.75 g, 10.34 mmol) and potassium carbonate (0.57 g, 4.14 mmol) were added to methanol (8 mL), and heated by microwave irradiation at 120° C. for 20 minutes, followed by cooling to room temperature. The reaction mixture was concentrated under reduced pressure to remove the solvent, and water was added to the concentrate, followed by extraction with ethyl acetate. The organic layer was washed with a saturated aqueous solution of sodium chloride, dried with anhydrous magnesium sulfate, and then concentrated under reduced pressure. The obtained compound of formula 8-2 was used without additional purification (0.85 g, 97%, yellow liquid).

Step 3: Synthesis of methyl 4-((4-(4-(2-fluoro-2-methylpropyl)piperazin-1-yl)-1H-pyrrolo[2,3-b]pyridin-1-yl)methyl)benzoate (formula 8-3)

(formula 8-3)

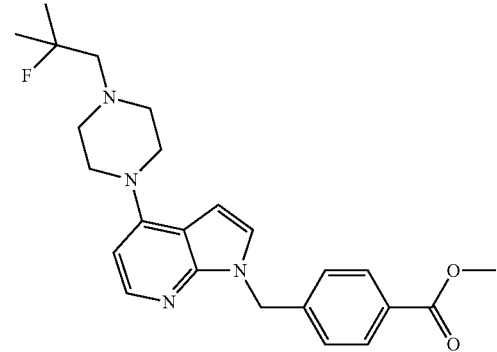

The compound of formula 8-2 (0.54 g, 1.28 mmol) prepared in step 2 was dissolved in methylene chloride (10 mL) at 0° C., and DAST (0.27 g, 1.66 mmol) was added to the solution, followed by stirring at room temperature for 3 hours. Then, a saturated aqueous solution of sodium hydrogen carbonate was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 40 g cartridge; ethyl acetate/hexane=from 20% to 30%) to afford the desired compound of formula 8-3 (0.52 g, 96%) as a yellow liquid.

Step 4: Synthesis of 4-((4-(4-(2-fluoro-2-methylpropyl)piperazin-1-yl)-1H-pyrrolo[2,3-b]pyridin-1-yl)methyl)-N-hydroxybenzamide (compound 642)

(compound 642)

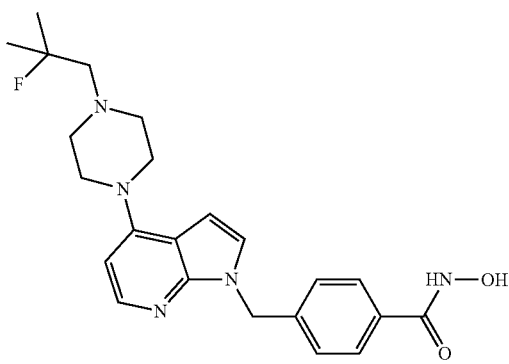

The compound of formula 8-3 (0.75 g, 1.77 mmol) prepared in step 3 was dissolved in tetrahydrofuran (2 mL)/methanol (8 mL) at room temperature. To the solution, potassium hydroxide (0.50 g, 8.83 mmol) and an aqueous solution of 50 wt % hydroxylamine (1.17 g, 17.67 mmol) were added, followed by stirring at the same temperature for 5 hours. The reaction mixture was concentrated under reduced pressure to remove the solvent, and a saturated aqueous solution of sodium hydrogen carbonate was added to the concentrate, followed by extraction with ethyl acetate. The organic layer was washed with a saturated aqueous solution of sodium chloride, dried with anhydrous magnesium sulfate, filtered, and then concentrated under reduced pressure to afford the desired compound 642 (0.65 g, 87%) as a white solid.

$^1$H NMR (400 MHz, DMSO-d$_6$) δ 7.92 (d, 1H, J=5.5 Hz), 7.60 (d, 2H, J=8.2 Hz), 7.35 (d, 1H, J=5.5 Hz), 7.17 (d, 2H, J=8.2 Hz), 6.50 (d, 1H, J=3.6 Hz), 6.40 (d, 1H, J=5.5 Hz), 5.39 (s, 2H), 3.35 (m, 4H), 2.62 (m, 4H), 2.42 (s, 2H), 1.31 (s, 3H), 1.26 (s, 3H); MS (ESI) m/z 426.2 (M$^+$+H).

Example 16

Synthesis of Compound 645

Step 1: Synthesis of methyl 4-((5-phenyl-1H-pyrrolo[2,3-b]pyridin-1-yl)methyl)benzoate (formula 2-3)

(formula 2-3)

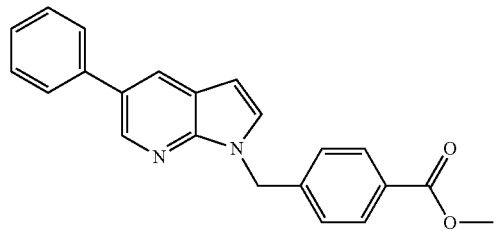

The compound of formula 2-2 (methyl 4-((5-bromo-1H-pyrrolo[2,3-b]pyridin-1-yl)methyl)benzoate) (0.300 g, 0.869 mmol), phenylboronic acid (0.127 g, 1.043 mmol), sodium carbonate (0.184 g, 1.738 mmol) and Pd(dppf)Cl$_2$ (0.071 g, 0.087 mmol) were added to 1,2-dimethoxyethane (2 mL)/water (1 mL), and heated by microwave irradiation at 120° C. for 20 minutes, followed by cooling to room temperature. Then, water was added to the reaction mixture, followed by extraction with ethyl acetate. The organic layer was washed with saturated brine, dried with anhydrous sodium sulfate, and then concentrated under reduced pressure. The concentrate was purified by column chromatography (SiO$_2$, 12 g cartridge; ethyl acetate/hexane=from 10% to 15%) to afford the desired compound of formula 2-3 (0.19 g, 64%) as a white solid.

Step 2: Synthesis of N-hydroxy-4-((5-phenyl-1H-pyrrolo[2,3-b]pyridin-1-yl)methyl)benzamide (compound 645)

(compound 645)

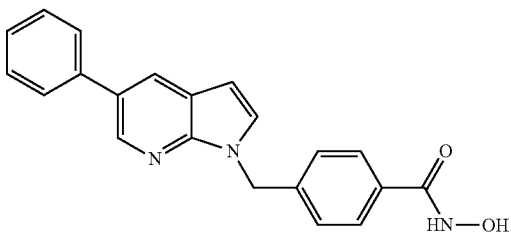

The compound of formula 2-3 (0.050 g, 0.146 mmol) prepared in step 1, hydroxylamine hydrochloride (0.051 g, 0.730 mmol), potassium hydroxide (0.041 g, 0.730 mmol) and an aqueous solution of 50 wt % hydroxylamine (0.188 mL, 2.921 mmol) were dissolved in methanol (5 mL) at room temperature, and the mixture was stirred at the same temperature for 3 hours. Then, the reaction mixture was concentrated under reduced pressure. The concentrate was purified by column chromatography (Waters, C18, acetonitrile/0.1% TFA aqueous solution=from 5% to 70%), and TFA was removed, thereby obtaining the desired compound 645 (0.049 g, 98%) as a white solid.

¹H NMR (400 MHz, DMSO-d₆) δ 8.57 (d, 1H, J=2.1 Hz), 8.28 (d, 1H, J=2.2 Hz), 7.74-7.68 (m, 5H), 7.49 (t, 2H, J=7.7 Hz), 7.37 (t, 1H, J=7.4 Hz), 7.29 (d, 2H, J=8.3 Hz), 6.62 (d, 1H, J=3.5 Hz), 5.58 (s, 2H); MS (ESI) m/z 344.1 (M⁺+H).

Example 17

Synthesis of Compound 647

Step 1: Synthesis of methyl 4-((5-(1-methyl-1,2,3,6-tetrahydropyridin-4-yl)-1H-pyrrolo[2,3-b]pyridin-1-yl)methyl)benzoate (formula 2-3)

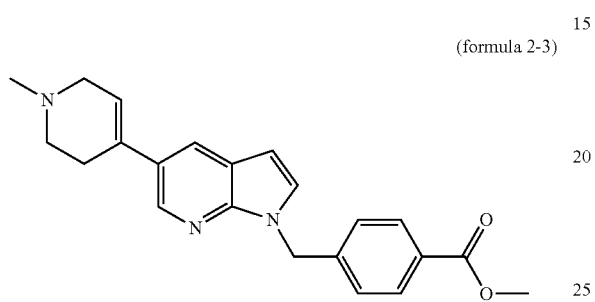

(formula 2-3)

The compound of formula 2-2 (methyl 4-((5-bromo-1H-pyrrolo[2,3-b]pyridin-1-yl)methyl)benzoate) (0.300 g, 0.869 mmol), 1-methyl-1,2,3,6-tetrahydropyridin-4-boronic acid (0.233 g, 1.043 mmol), sodium carbonate (0.184 g, 1.738 mmol) and Pd(dppf)Cl₂ (0.071 g, 0.087 mmol) were added to 1,2-dimethoxyethane (2 mL)/water (1 mL), and heated by microwave irradiation at 120° C. for 20 minutes, followed by cooling to room temperature. Then, water was added to the reaction mixture, followed by extraction with ethyl acetate. The organic layer was washed with saturated brine, dried with anhydrous sodium sulfate, and then concentrated under reduced pressure. The concentrate was purified by column chromatography (SiO₂, 12 g cartridge; methanol/dichloromethane=from 5% to 10%) to afford the desired compound of formula 2-3 (0.153 g, 49%) as a white solid.

Step 2: Synthesis of N-hydroxy-4-((5-(1-methyl-1,2,3,6-tetrahydropyridin-4-yl)-1H-pyrrolo[2,3-b]pyridin-1-yl)methyl)benzamide (compound 647)

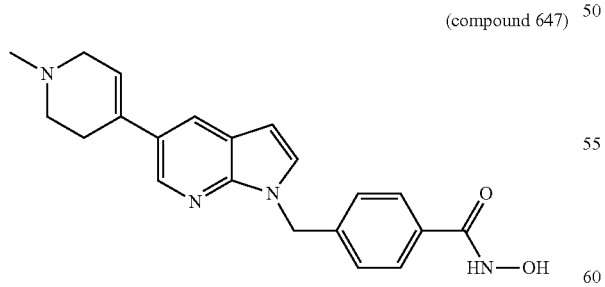

(compound 647)

The compound of formula 2-3 (0.05 g, 0.138 mmol) prepared in step 1, hydroxylamine hydrochloride (0.048 g, 0.692 mmol), potassium hydroxide (0.039 g, 0.692 mmol) and an aqueous solution of 50 wt % hydroxylamine (0.178 mL, 2.767 mmol) were dissolved in methanol (5 mL) at room temperature, and the mixture solution was stirred at the same temperature for 3 hours. Then, the reaction mixture was concentrated under reduced pressure. The concentrate was purified by column chromatography (Waters, C18, acetonitrile/0.1% TFA aqueous solution=from 5% to 70%), and TFA was removed, thereby obtaining the desired compound 647 (0.042 g, 84%) as a white solid.

¹H NMR (400 MHz, DMSO-d₆) δ 11.22 (s, 1H), 8.45 (d, 1H, J=1.9 Hz), 8.25 (d, 1H, J=1.8 Hz), 7.76 (d, 1H, J=3.4 Hz), 7.69 (d, 2H, J=8.2 Hz), 7.29 (d, 2H, J=8.2 Hz), 6.41 (brs, 1H), 6.25 (s, 2H), 5.64 (d, 2H, J=12.0 Hz), 3.96-2.80 (m, 6H), 2.84 (s, 3H); MS (ESI) m/z 363.1 (M⁺+H).

Example 18

Synthesis of Compound 648

Step 1: Synthesis of methyl 4-((5-(cyclohex-1-en-1-yl)-1H-pyrrolo[2,3-b]pyridin-1-yl)methyl)benzoate (formula 2-3)

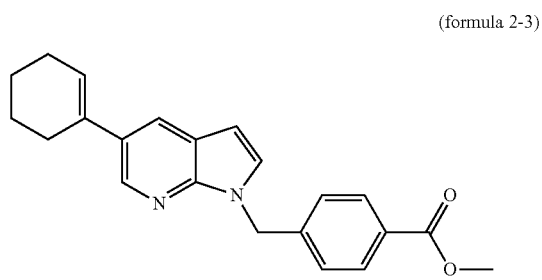 [SMILES: COC(=O)c1ccc(Cn2ccc3cc(C4=CCCCC4)cnc32)cc1]

(formula 2-3)

The compound of formula 2-2 (methyl 4-((5-bromo-1H-pyrrolo[2,3-b]pyridin-1-yl)methyl)benzoate) (0.3 g, 0.869 mmol), cyclohexenylboronic acid (0.217 g, 1.043 mmol), sodium carbonate (0.184 g, 1.74 mmol) and Pd(dppf)Cl₂ (0.071 g, 0.087 mmol) were added to 1,2-dimethoxyethane (2 mL)/water (1 mL), and heated by microwave irradiation at 120° C. for 20 minutes, followed by cooling to room temperature. Then, water was added to the reaction mixture, followed by extraction with ethyl acetate. The organic layer was washed with saturatedbrine, dried with anhydrous sodium sulfate, and then concentrated under reduced pressure. The concentrate was purified by column chromatography (SiO₂, 12 g cartridge; ethyl acetate/hexane=from 5% to 70%) to afford the desired compound of formula 2-3 (0.187 g, 62%) as a white solid.

Step 2: Synthesis of 4-((5-(cyclohex-1-en-1-yl)-1H-pyrrolo[2,3-b]pyridin-1-yl)methyl)-N-hydroxybenzamide (compound 648)

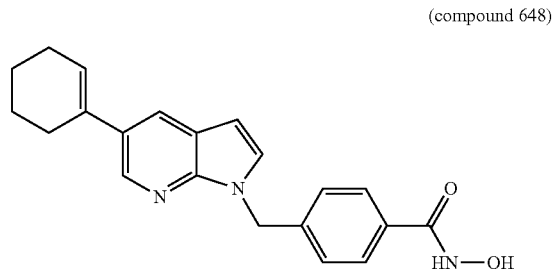 [SMILES: O=C(NO)c1ccc(Cn2ccc3cc(C4=CCCCC4)cnc32)cc1]

(compound 648)

The compound of formula 2-3 (0.050 g, 0.144 mmol) prepared in step 1, hydroxylamine hydrochloride (0.05 g, 0.72 mmol), potassium hydroxide (0.04 g, 0.722 mmol) and an aqueous solution of 50 wt % hydroxylamine (0.19 mL, 2.89 mmol) were dissolved in methanol (5 mL) at room temperature, and the mixture was stirred at the same temperature for 3 hours. Then, the reaction mixture was concentrated under reduced pressure. The concentrate was purified by column chromatography (Waters, C18, acetonitrile/ 0.1% TFA aqueous solution=from 5% to 70%), and TFA was removed, thereby obtaining the desired compound 648 (0.034 g, 68%) as a white solid.

$^{1}$H NMR (400 MHz, DMSO-d$_{6}$) δ 11.22 (s, 1H), 8.35 (d, 1H, J=2.1 Hz), 8.04 (d, 1H, J=2.0 Hz), 7.67 (d, 2H, J=8.4 Hz), 7.65 (s, 1H), 7.26 (d, 2H, J=8.3 Hz), 6.54 (d, 1H, J=3.5 Hz), 6.15 (t, 1H, J=3.9 Hz), 5.54 (s, 2H), 4.43 (brs, 1H), 2.44 (d, 2H, J=1.9 Hz), 2.20 (dd, 2H, J=6.1, 2.3 Hz), 1.77-1.61 (m, 4H); MS (ESI) m/z 348.1 (M$^{+}$+H).

Example 19

Synthesis of Compound 649

Step 1: Synthesis of methyl 4-((5-(4,4-dimethylcyclohex-1-en-1-yl)-1H-pyrrolo[2,3-b]pyridin-1-yl) methyl)benzoate (formula 2-3)

(formula 2-3)

The compound of formula 2-2 (methyl 4-((5-bromo-1H-pyrrolo[2,3-b]pyridin-1-yl)methyl)benzoate) (0.300 g, 0.869 mmol), 4,4-dimethylcyclohex-1-enylboronic acid (0.246 g, 1.043 mmol), sodium carbonate (0.184 g, 1.738 mmol) and Pd(dppf)Cl$_{2}$ (0.071 g, 0.087 mmol) were added to 1,2-dimethoxyethane (2 mL)/water (1 mL), and heated by microwave irradiation at 120° C. for 20 minutes, followed by cooling to room temperature. Then, water was added to the reaction mixture, followed by extraction with ethyl acetate. The organic layer was washed with saturated brine, dried with anhydrous sodium sulfate, and then concentrated under reduced pressure. The concentrate was purified by column chromatography (SiO$_{2}$, 12 g cartridge; ethyl acetate/ hexane=from 10% to 15%) to afford the desired compound of formula 2-3 (0.195 g, 60%) as a white solid.

Step 2: Synthesis of 4-((5-(4,4-dimethylhex-1-en-1-yl)-1H-pyrrolo[2,3-b]pyridin-1-yl)methyl)-N-hydroxybenzamide (compound 649)

(compound 649)

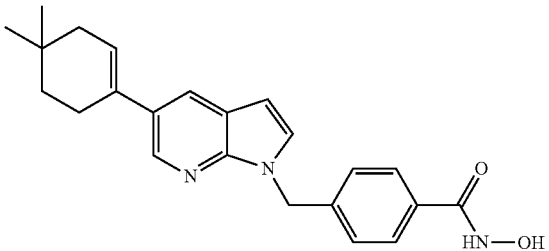

The compound of formula 2-3 (0.050 g, 0.134 mmol) prepared in step 1, hydroxylamine hydrochloride (0.046 g, 0.67 mmol), potassium hydroxide (0.037 g, 0.67 mmol) and an aqueous solution of 50 wt % hydroxylamine (0.17 mL, 2.67 mmol) were dissolved in methanol (5 mL) at room temperature, and the mixture was stirred at the same temperature for 3 hours. Then, the reaction mixture was concentrated under reduced pressure. The concentrate was purified by column chromatography (Waters, C18, acetonitrile/ 0.1% TFA aqueous solution=from 5% to 70%), and TFA was removed, thereby obtaining the desired compound 649 (0.015 g, 30%) as a white solid.

$^{1}$H NMR (400 MHz, DMSO-d$_{6}$) δ 11.22 (s, 1H), 8.37 (d, 1H, J=2.1 Hz), 8.04 (d, J=2.1 Hz), 7.67 (d, 2H, J=8.4 Hz), 7.64 (d, 1H, J=3.5 Hz), 7.25 (d, 2H, J=8.3 Hz), 6.52 (d, 1H, J=3.5 Hz), 6.09 (t, 1H, J=3.9 Hz), 5.53 (s, 2H), 4.03 (brs, 1H), 2.47-2.46 (m, 2H), 2.00 (d, 2H, J=1.9 Hz), 1.51 (t, 2H, J=6.4 Hz), 0.96 (s, 6H); MS (ESI) m/z 376.1 (M$^{+}$+H).

Example 20

Synthesis of Compound 650

Step 1: Synthesis of methyl 4-((5-(4,4-difluorocyclohex-1-en-1-yl)-1H-pyrrolo[2,3-b]pyridin-1-yl) methyl)benzoate (formula 2-3)

(formula 2-3)

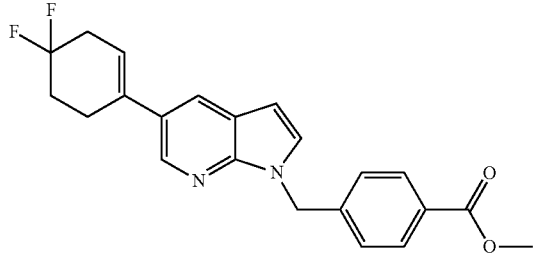

The compound of formula 2-2 (methyl 4-((5-bromo-1H-pyrrolo[2,3-b]pyridin-1-yl)methyl)benzoate) (0.300 g, 0.869 mmol), 4,4-difluorocyclohex-1-enylboronic acid (0.25 g, 1.04 mmol), sodium carbonate (0.184 g, 1.738 mmol) and Pd(dppf)Cl$_{2}$ (0.071 g, 0.087 mmol) were added to 1,2-dimethoxyethane (2 mL)/water (1 mL), and heated by microwave irradiation at 120° C. for 20 minutes, followed by cooling to room temperature. Then, water was added to the reaction mixture, followed by extraction with ethyl acetate. The organic layer was washed with saturated brine, dried with anhydrous sodium sulfate, and then concentrated under reduced pressure. The concentrate was purified by column chromatography (SiO$_2$, 12 g cartridge; ethyl acetate/hexane=from 10% to 15%) to afford the desired compound of formula 2-3 (0.20 g, 60%) as a white solid.

Step 2: Synthesis of 4-((5-(4,4-difluorocyclohex-1-en-1-yl)-1H-pyrrolo[2,3-b]pyridin-1-yl)methyl)-N-hydroxybenzamide (compound 650)

(compound 650)

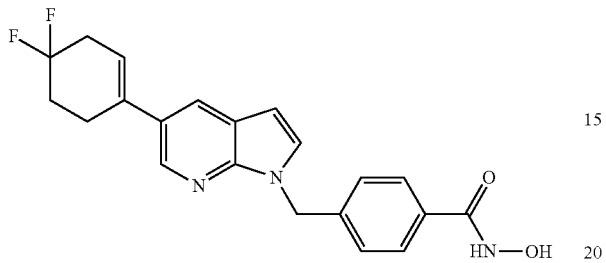

The compound of formula 2-3 (0.050 g, 0.131 mmol) prepared in step 1, hydroxylamine hydrochloride (0.045 g, 0.654 mmol), potassium hydroxide (0.037 g, 0.654 mmol) and an aqueous solution of 50 wt % hydroxylamine (0.168 mL, 2.615 mmol) were dissolved in methanol (5 mL) at room temperature, and the mixture was stirred at the same temperature for 3 hours. Then, the reaction mixture was concentrated under reduced pressure. The concentrate was purified by column chromatography (Waters, C18, acetonitrile/0.1% TFA aqueous solution=from 5% to 70%), and TFA was removed, thereby obtaining the desired compound 650 (0.03 g, 60%) as a white solid.

$^1$H NMR (400 MHz, DMSO-d$_6$) δ 8.40 (d, 1H, J=2.1 Hz), 8.10 (d, 1H, J=2.1 Hz), 7.67 (d, 2H, J=8.6 Hz), 7.67 (d, 1H, J=5.5 Hz), 7.26 (d, 2H, J=8.2 Hz), 6.55 (d, 1H, J=3.5 Hz), 6.02 (s, 1H), 5.55 (s, 2H), 5.00 (brs, 1H), 2.79-2.72 (m, 4H), 2.24-2.17 (m, 2H); MS (ESI) m/z 384.1 (M$^+$+H).

Example 21

Synthesis of Compound 656

Step 1: Synthesis of methyl 4-((4-phenyl-1H-pyrrolo[2,3-b]pyridin-1-yl)methyl)benzoate (formula 1-3)

(formula 1-3)

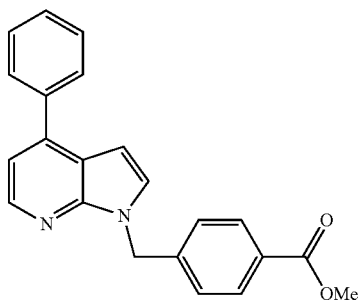

The compound of formula 1-2 (methyl 4-((4-bromo-1H-pyrrolo[2,3-b]pyridin-1-yl)methyl)benzoate) (0.3 g, 0.869 mmol), phenylboronic acid (0.127 g, 1.043 mmol), Pd(dppf)Cl$_2$ (0.057 g, 0.087 mmol) and sodium carbonate (0.184 g, 1.738 mmol) were added to 1,2-dimethoxyethane (8 mL)/water (2 mL), and heated by microwave irradiation at 120° C. for 20 minutes, followed by cooling to room temperature. The reaction mixture was filtered through a celite pad to remove solids. A saturated aqueous solution of ammonium chloride was added to the filtrate, followed by extraction with ethyl acetate. The organic layer was washed with saturated brine, dried with anhydrous magnesium sulfate, and then concentrated under reduced pressure. The concentrate was purified by column chromatography (SiO$_2$, 12 g cartridge; ethyl acetate/hexane=from 0% to 40%) to afford the desired compound of formula 1-3 (0.22 g, 74%) as a white solid.

Step 2: Synthesis of N-hydroxy-4-((4-phenyl-1H-pyrrolo[2,3-b]pyridin-1-yl)methyl)benzamide (compound 656)

(compound 656)

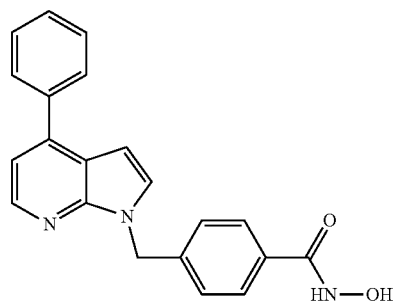

The compound of formula 1-3 (0.22 g, 0.64 mmol) prepared in step 1, potassium hydroxide (0.36 g, 6.42 mmol) and an aqueous solution of 50 wt % hydroxylamine (0.83 mL, 12.85 mmol) were dissolved in methanol (10 mL) at room temperature, and the mixture was stirred at the same temperature for 1 hour. Then, the reaction mixture was concentrated under reduced pressure. A saturated aqueous solution of sodium hydrogen carbonate (20 mL) was added to the concentrate, followed by stirring. The precipitated solid was filtered and dried to afford the desired compound 656 (0.048 g, 22%) as a white solid.

$^1$H NMR (400 MHz, CDCl$_3$) δ 8.34 (d, 1H, J=4.9 Hz), 7.76-7.78 (m, 2H), 7.72 (d, 1H, J=3.5 Hz), 7.67 (d, 2H, J=8.2 Hz), 7.56 (t, 2H, J=7.5 Hz), 7.45-7.49 (m, 1H), 7.22-7.25 (m, 3H), 6.67 (d, 1H, J=3.5 Hz), 5.53 (s, 2H); MS (ESI) m/z 344.1 (M$^+$+H).

Example 22

Synthesis of Compound 657

Step 1: Synthesis of methyl 4-((4-(pyridin-4-yl)-1H-pyrrolo[2,3-b]pyridin-1-yl)methyl)benzoate (formula 1-3)

(formula 1-3)

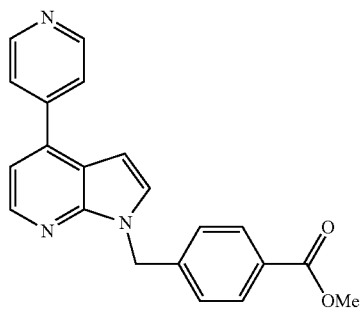

The compound of formula 1-2 (methyl 4-((4-bromo-1H-pyrrolo[2,3-b]pyridin-1-yl)methyl)benzoate) (0.30 g, 0.87 mmol), pyridin-4-ylboronic acid (0.13 g, 1.043 mmol), Pd(dppf)Cl$_2$ (0.057 g, 0.087 mmol) and sodium carbonate (0.18 g, 1.74 mmol) were added to 1,2-dimethoxyethane (8 mL)/water (2 mL), and heated by microwave irradiation at 120° C. for 20 minutes, followed by cooling to room temperature. The reaction mixture was filtered through a celite pad to remove solids, and a saturated aqueous solution of ammonium chloride was added to the filtrate, followed by extraction with ethyl acetate. The organic layer was washed with saturated brine, dried with anhydrous magnesium sulfate, and then concentrated under reduced pressure. The concentrate was purified by column chromatography (SiO$_2$, 12 g cartridge; ethyl acetate/hexane=from 5% to 70%) to afford the desired compound of formula 1-3 (0.24 g, 80%) as a red liquid.

Step 2: Synthesis of N-hydroxy-4-((4-(pyridin-4-yl)-1H-pyrrolo[2,3-b]pyridin-1-yl)methyl)benzamide (compound 657)

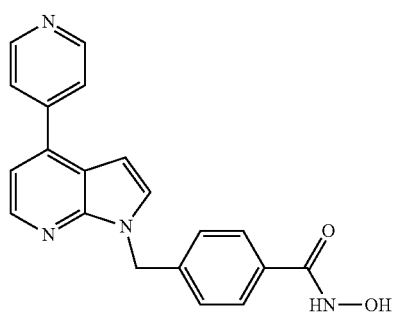

(compound 657)

The compound of formula 1-3 (0.24 g, 0.69 mmol) prepared in step 1, potassium hydroxide (0.39 g, 6.99 mmol) and an aqueous solution of 50 wt % hydroxylamine (0.89 mL, 13.98 mmol) were dissolved in methanol (10 mL) at room temperature, and the mixture was stirred at the same temperature for 2 hours. Then, the reaction mixture was concentrated under reduced pressure. A saturated aqueous solution of sodium hydrogen carbonate (30 mL) was added to the concentrate, followed by stirring. The precipitated solid was filtered and dried to afford the desired compound 657 (0.228 g, 95%) as a yellow solid.

$^1$H NMR (400 MHz, CDCl$_3$) δ 9.04 (s, 1H), 8.75 (d, 2H, J=5.2 Hz), 8.39 (d, 1H, J=4.8 Hz), 7.77-7.83 (m, 3H), 7.69 (d, 2H, J=8.1 Hz), 7.36 (d, 1H, J=4.8 Hz), 7.31 (d, 2H, J=8.1 Hz), 6.76 (d, 1H, J=3.2 Hz), 5.59 (s, 2H); MS (ESI) m/z 345.1 (M$^+$+H).

Example 23

Synthesis of Compound 658

Step 1: Synthesis of methyl 4-((4-(2,4-difluorophenyl)-1H-pyrrolo[2,3-b]pyridin-1-yl)methyl)benzoate (formula 1-3)

(formula 1-3)

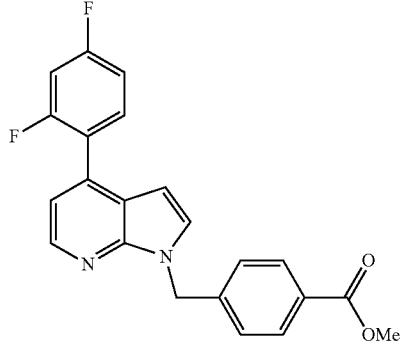

The compound of formula 1-2 (methyl 4-((4-bromo-1H-pyrrolo[2,3-b]pyridin-1-yl)methyl)benzoate) (0.300 g, 0.869 mmol), 2,4-difluoroboronic acid (0.16 g, 1.04 mmol), Pd(dppf)Cl$_2$ (0.057 g, 0.087 mmol) and sodium carbonate (0.18 g, 1.74 mmol) were added to 1,2-dimethoxyethane (4 mL)/water (1 mL), and heated by microwave irradiation at 120° C. for 20 minutes, followed by cooling to room temperature. The reaction mixture was filtered through a celite pad to remove solids, and a saturated aqueous solution of ammonium chloride was added to the filtrate, followed by extraction with ethyl acetate. The organic layer was washed with saturated brine, dried with anhydrous magnesium sulfate, and then concentrated under reduced pressure. The concentrate was purified by column chromatography (SiO$_2$, 12 g cartridge; ethyl acetate/hexane=from 5% to 40%) to afford the desired compound of formula 1-3 (0.31 g, 94%) as a red liquid.

Step 2: Synthesis of 4-((4-(2,4-difluorophenyl)-1H-pyrrolo[2,3-b]pyridin-1-yl)methyl)-N-hydroxybenzamide (compound 658)

(compound 658)

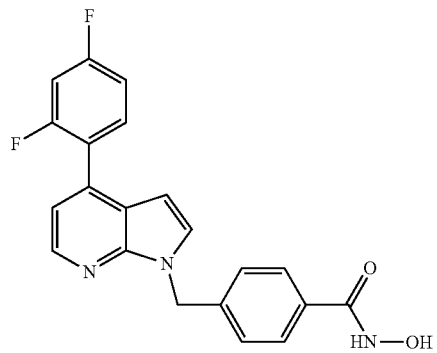

The compound of formula 1-3 (0.30 g, 0.79 mmol) prepared in step 1, potassium hydroxide (0.45 g, 7.93 mmol) and an aqueous solution of 50 wt % hydroxylamine (1.019 mL, 15.857 mmol) were dissolved in methanol (10 mL) at room temperature, and the mixture was stirred at the same temperature for 3 hours. Then, the reaction mixture was concentrated under reduced pressure. A saturated aqueous solution of sodium hydrogen carbonate (30 mL) was added to the concentrate, followed by stirring. The precipitated solid was filtered and dried to afford the desired compound 658 (0.3 g, 100%) as a white solid.

¹H NMR (400 MHz, CDCl₃) δ 8.35 (d, 2H, J=4.9 Hz), 7.67-7.72 (m, 1H), 7.43-7.49 (m, 4H), 7.23-7.29 (m, 3H), 7.10-7.20 (m, 1H), 6.40-6.41 (m, 1H), 5.53 (s, 2H); MS (ESI) m/z 380.1 (M⁺+H).

Example 24

Synthesis of Compound 659

Step 1: Synthesis of methyl 4-((4-(pyrimidin-5-yl)-1H-pyrrolo[2,3-b]pyridine-1-yl)methyl)benzoate (formula 1-3)

(formula 1-3)

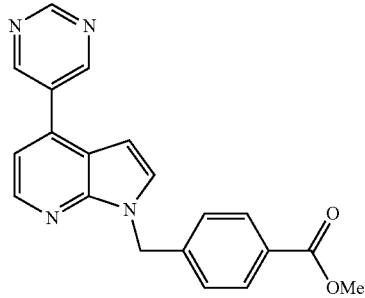

The compound of formula 1-2 (methyl 4-((4-bromo-1H-pyrrolo[2,3-b]pyridin-1-yl)methyl)benzoate) (0.30 g, 0.87 mmol), pyrimidin-5-ylboronic acid (0.13 g, 1.043 mmol), Pd(dppf)Cl₂ (0.057 g, 0.087 mmol) and sodium carbonate (0.18 g, 1.74 mmol) were added to 1,2-dimethoxyethane (4 mL)/water (1 mL), and heated by microwave irradiation at 120° C. for 20 minutes, followed by cooling to room temperature. The reaction mixture was filtered through a celite pad to remove solids, and water was added to the filtrate, followed by extraction with ethyl acetate. The organic layer was washed with saturated brine, dried with anhydrous magnesium sulfate, and then concentrated under reduced pressure. The concentrate was purified by column chromatography (SiO₂, 12 g cartridge; ethyl acetate/hexane=from 5% to 70%) to afford the desired compound of formula 1-3 (0.15 g, 50%) as a red solid.

Step 2: Synthesis of N-hydroxy-4-((4-(pyrimidin-5-yl)-1H-pyrrolo[2,3-b]pyridin-1-yl)methyl)benzamide (compound 659)

(compound 659)

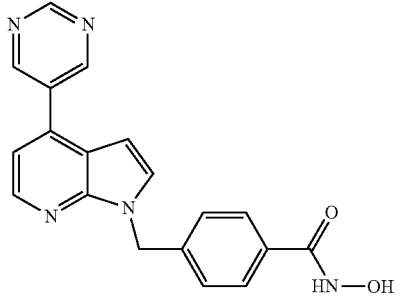

The compound of formula 1-3 (0.15 g, 0.44 mmol) prepared in step 1, potassium hydroxide (0.24 g, 4.36 mmol) and an aqueous solution of 50 wt % hydroxylamine (0.56 mL, 8.712 mmol) were dissolved in methanol (10 mL) at room temperature, and the mixture was stirred at the same temperature for 3 hours. Then, the reaction solution was concentrated under reduced pressure. A saturated aqueous solution of sodium hydrogen carbonate (30 mL) was added to the concentrate, followed by stirring. The precipitated solid was filtered and dried to afford the desired compound 659 (0.13 g, 87%) as a brown solid.

¹H NMR (400 MHz, CDCl₃) δ 9.31 (s, 1H), 9.23 (s, 2H), 9.03 (s, 1H), 8.41 (d, 1H, J=4.7 Hz), 7.83-7.84 (m, 1H), 7.68 (d, 2H, J=8.1 Hz), 7.42 (d, 2H, J=4.7 Hz), 7.31 (d, 2H, J=8.1 Hz), 6.77-6.78 (m, 1H), 5.59 (s, 2H); MS (ESI) m/z 346.1 (H⁺+H).

Example 25

Synthesis of Compound 685

Step 1: Synthesis of 4-((5-bromo-1H-pyrrolo[2,3-b]pyridin-1-yl)methyl)-N-hydroxybenzamide (formula 2-5)

(formula 2-5)

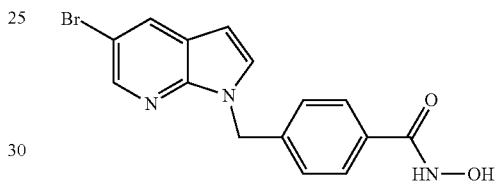

The compound of formula 2-2 (methyl 4-((5-bromo-1H-pyrrolo[2,3-b]pyridin-1-yl)methyl)benzoate) (1.36 g, 3.56 mmol), hydroxylamine hydrochloride (1.23 g, 17.78 mmol), potassium hydroxide (0.99 g, 17.78 mmol) and an aqueous solution of 50 wt % hydroxylamine (4.57 mL, 71.13 mmol) were dissolved in methanol (50 mL) at room temperature, and the mixture stirred at the same temperature for 3 hours. Then, the reaction mixture was concentrated under reduced pressure to remove methanol, a saturated aqueous solution of sodium hydrogen carbonate was added thereto. The precipitated solid was filtered and dried to afford the desired compound of formula 2-5 (1.2 g, 97%) as a white solid.

Step 2: Synthesis of N-hydroxy-4-((5-(1-methyl-1H-indazol-6-yl)-1H-pyrrolo[2,3-b]pyridin-1-yl)methyl)benzamide (compound 685)

(compound 685)

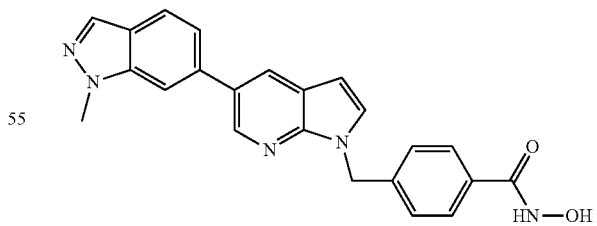

The compound of formula 2-5 (0.100 g, 0.29 mmol) prepared in step 1, 1-methyl-1H-indazole-6-boronic acid (0.061 g, 0.34 mmol), sodium carbonate (0.067 g, 0.64 mmol) and Pd(dppf)Cl₂ (0.024 g, 0.029 mmol) were dissolved in 1,2-dimethoxyethane (2 mL)/water (1 mL) at room temperature, and the mixture was stirred at the same temperature for 3 hours. Then, water was added to the reaction solution, followed by extraction with ethyl acetate. The extract was filtered through a plastic filter to remove the solid residue and the aqueous layer, and then concentrated under reduced pressure. The concentrate was purified by column chromatography (Waters, C18, acetonitrile/0.1% TFA aqueous solution=from 5% to 70%), and TFA was removed, thereby obtaining the desired compound 685 (0.003 g, 3%) as a white solid.

$^{1}$H NMR (400 MHz, CD$_3$OD) δ 8.82 (d, 1H, J=1.5 Hz), 8.76 (d, 1H, J=1.5 Hz), 8.09 (s, 1H), 7.94 (s, 1H), 7.93 (d, 1H, J=8.7 Hz), 7.76 (d, 2H, J=8.2 Hz), 7.71 (d, 1H, J=3.5 Hz), 7.57 (d, 1H, J=8.4 Hz), 7.34 (d, 2H, J=8.2 Hz), 6.92 (d, 1H, J=3.5 Hz), 5.74 (s, 2H), 4.17 (s, 3H); MS (ESI) m/z 398.1 (M$^+$+H).

Example 26

Synthesis of Compound 686 (N-hydroxy-4-((5-(1-(2-hydroxy-2-methylpropyl)-1,2,3,6-tetrahydropyridin-4-yl)-1H-pyrrolo[2,3-b]pyridin-1-yl)methyl)benzamide)

(comound 686)

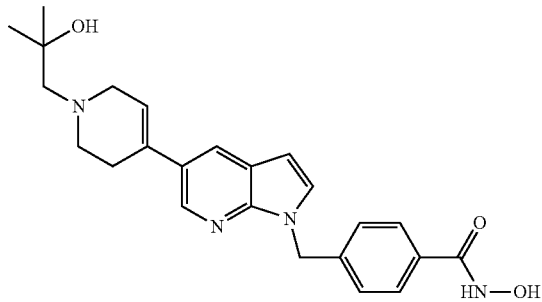

The compound of formula 5-3 (methyl 4-((5-(1-(2-hydroxy-2-methylpropyl)-1,2,3,6-tetrahydropyridin-4-yl)-1H-pyrrolo[2,3-b]pyridin-1-yl)mehyl)benzoate) (0.100 g, 0.238 mmol) prepared in step 4 of Example 9, hydroxylamine hydrochloride (0.083 g, 1.19 mmol), potassium hydroxide (0.067 g, 1.19 mmol) and an aqueous solution of 50 wt % hydroxylamine (0.31 mL, 4.77 mmol) were dissolved in methanol (5 mL) at room temperature, and the mixture was stirred at the same temperature for 3 hours. Then, water was added to the reaction mixture, followed by extraction with ethyl acetate. The organic layer was washed with saturated brine, dried with anhydrous sodium sulfate, and then concentrated under reduced pressure. The concentrate was purified by column chromatography (Waters, C18, acetonitrile/ 0.1% TFA aqueous solution=5% to 70%), and TFA was removed, thereby obtaining the desired compound 686 (0.009 g, 9%) as a yellow liquid.

$^{1}$H NMR (400 MHz, CD$_3$OD) δ 8.67 (d, 1H, J=1.8 Hz), 8.56 (d, 1H, J=1.8 Hz), 7.75 (dd, 1H, J=8.7, 2.1 Hz), 7.72 (d, 1H, J=3.6 Hz), 7.31 (dd, 1H, J=8.3, 2.3 Hz), 6.90 (d, 1H, J=3.6 Hz), 6.32 (s, 1H), 5.72 (s, 1H), 4.24-3.92 (m, 3H), 3.62-3.59 (m, 1H), 3.37 (s, 2H), 3.05-3.03 (m, 1H), 1.42 (s, 6H); MS (ESI) m/z 421.2 (M$^+$+H).

Example 27

Synthesis of Compound 687 (N-hydroxy-4-((5-(2-hydroxypyrimidin-5-yl)-1H-pyrrolo[2,3-b]pyridin-1-yl)methyl)benzamide)

(compound 687)

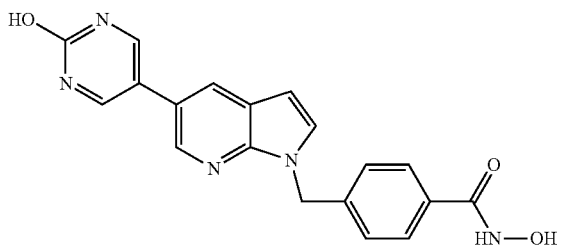

The compound of formula 2-5 (4-((5-bromo-1H-pyrrolo[2,3-b]pyridin-1-yl)methyl)-N-hydroxybenzamide) (0.100 g, 0.29 mmol) prepared in step 1 of Example 25, (2-methoxypyrdin-5-yl)boronic acid (0.053 g, 0.347 mmol), sodium carbonate (0.067 g, 0.64 mmol) and Pd(dppf)Cl$_2$ (0.024 g, 0.029 mmol) were added to 1,2-dimethoxyethane (2 mL)/water (1 mL), and heated by microwave irradiation at 120° C. for 20 minutes, followed by cooling to room temperature. Then, water was added to the reaction mixture, followed by extraction with ethyl acetate. The organic layer was filtered through a plastic filter to remove the solid residue and the aqueous layer, and then concentrated under reduced pressure. The concentrate was purified by column chromatography (Waters, C18, acetonitrile/0.1% TFA aqueous solution=from 5% to 70%), and TFA was removed, thereby obtaining the desired compound 687 (0.015 g, 14%) as a white solid.

$^{1}$H NMR (400 MHz, DMSO-d$_6$) δ 9.13 (s, 2H), 8.57 (d, 1H, J=2.1 Hz), 8.35 (d, 1H, J=2.1 Hz), 7.79 (d, 1H, J=3.5 Hz), 7.69 (d, 2H, J=8.2 Hz), 7.26 (d, 2H, J=8.2 Hz), 6.63 (d, 1H, J=3.5 Hz), 5.58 (s, 2H); MS (ESI) m/z 362.1 (M$^+$+H).

Example 28

Synthesis of Compound 688 (N-hydroxy-4-((5-(quinolin-7-yl)-1H-pyrrolo[2,3-b]pyridin-1-yl)methyl)benzamide)

(compound 688)

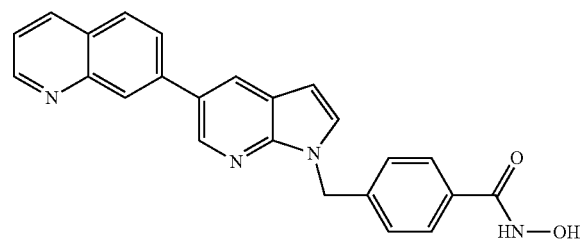

The compound of formula 2-5 (4-((5-bromo-1H-pyrrolo[2,3-b]pyridin-1-yl)methyl)-N-hydroxybenzamide, 0.10 g, 0.29 mmol) prepared in step 1 of Example 25, quinolin-7-ylboronic acid (0.06 g, 0.35 mmol), sodium carbonate (0.067 g, 0.64 mmol) and Pd(dppf)Cl$_2$ (0.024 g, 0.029 mmol) were added to 1,2-dimethoxyethane (2 mL)/water (1 mL), and heated by microwave irradiation at 120° C. for 20 minutes, followed by cooling to room temperature. Then, water was added to the reaction mixture, followed by extraction with ethyl acetate. The extract was filtered through a plastic filter to remove solid residue and the aqueous layer, and then concentrated under reduced pressure. The concentrate was purified by column chromatography (Waters, C18, acetonitrile/0.1% TFA aqueous solution=from 5% to 70%), and TFA was removed, thereby obtaining the desired compound 688 (0.042 g, 37%) as a white solid.

$^1$H NMR (400 MHz, DMSO-$d_6$) δ 9.07 (dd, 1H, J=4.8, 1.4 Hz), 9.02 (d, 1H, J=8.2 Hz), 8.54 (d, 1H, J=1.8 Hz), 8.40 (d, 1H, J=1.8 Hz), 8.31 (d, 1H, J=7.8 Hz), 8.06 (d, 1H, J=7.2 Hz), 7.97-7.87 (m, 2H), 7.74 (d, 1H, J=8.2 Hz), 7.40 (d, 2H, J=8.2 Hz), 6.73 (d, 2H, J=3.4 Hz), 5.69 (s, 2H); MS (ESI) m/z 395.1 (M$^+$+H).

Example 29

Synthesis of Compound 689 (N-hydroxy-4-((5-(4-methoxyphenyl)-1H-pyrrolo[2,3-b]pyridin-1-yl)methyl)benzamide)

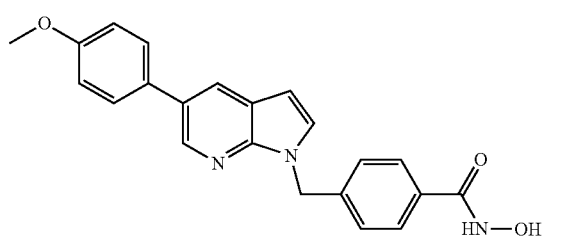

(compound 689)

The compound of formula 2-5 (4-((5-bromo-1H-pyrrolo[2,3-b]pyridin-1-yl)methyl)-N-hydroxybenzamide, 0.100 g, 0.289 mmol) prepared in step 1 of Example 25, 4-methoxyphenylboronic acid (0.053 g, 0.35 mmol), sodium carbonate (0.067 g, 0.64 mmol) and Pd(dppf)Cl$_2$ (0.024 g, 0.029 mmol) were added to 1,2-dimethoxyethane (2 mL)/water (1 mL), and heated by microwave irradiation at 120° C. for 20 minutes, followed by cooling to room temperature. Then, water was added to the reaction mixture, followed by extraction with ethyl acetate. The extract was filtered through a plastic filter to remove solid residue and the aqueous layer, and then concentrated under reduced pressure. The concentrate was purified by column chromatography (Waters, C18, acetonitrile/0.1% TFA aqueous solution=from 5% to 70%), and TFA was removed, thereby obtaining the desired compound 689 (0.051 g, 47%) as a blue solid.

$^1$H NMR (400 MHz, DMSO-$d_6$) δ 8.52 (d, 1H, J=2.0 Hz), 8.22 (d, 1H, J=1.9 Hz), 7.71-7.64 (m, 5H), 7.29 (d, 2H, J=8.2 Hz), 7.05 (d, 2H, J=8.7 Hz), 6.59 (d, 1H, J=3.3 Hz), 5.57 (s, 2H), 3.80 (s, 3H); MS (ESI) m/z 374.1 (M$^+$+H).

Example 30

Synthesis of Compound 690 (4-((5-(3-aminophenyl)-1H-pyrrolo[2,3-b]pyridin-1-yl)methyl)-N-hydroxybenzamide)

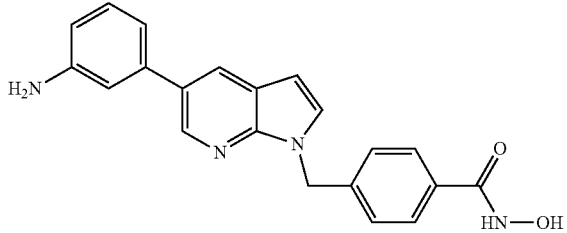

(compound 690)

The compound of formula 2-5 (4-((5-bromo-1H-pyrrolo[2,3-b]pyridin-1-yl)methyl)-N-hydroxybenzamide) (0.100 g, 0.289 mmol) prepared in step 1 of Example 25, 3-aminophenylboronic acid (0.047 g, 0.35 mmol), sodium carbonate (0.067 g, 0.636 mmol) and Pd(dppf)Cl$_2$ (0.024 g, 0.029 mmol) were added to 1,2-diethoxyethane (2 mL)/water (1 mL), and heated by microwave irradiation at 120° C. for 20 minutes, followed by cooling to room temperature. Then, water was added to the reaction mixture, followed by extraction with ethyl acetate. The extract was filtered through a plastic filter to remove solid residue and the aqueous layer, and then concentrated under reduced pressure. The concentrate was purified by column chromatography (Waters, C18, acetonitrile/0.1% TFA aqueous solution=from 5% to 70%), and TFA was removed, thereby obtaining desired compound 690 (0.05 g, 48%) as a white solid.

$^1$H NMR (400 MHz, DMSO-$d_6$) δ 8.55 (s, 1H), 8.27 (s, 1H), 7.79-7.68 (m, 5H), 7.61 (t, 1H, J=7.8 Hz), 7.39 (d, 1H, J=7.4 Hz), 7.30 (d, 2H, J=7.3 Hz), 6.65 (s, 1H), 5.59 (s, 2H); MS (ESI) m/z 359.1 (M$^+$+H).

Example 31

Synthesis of Compound 691 (N-hydroxy-4-((5-(4-hydroxyphenyl)-1H-pyrrolo[2,3-b]pyridin-1-yl)methyl)benzamide)

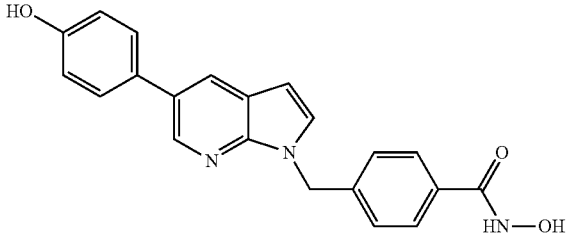

(compound 691)

The compound of formula 2-5 (4-((5-bromo-1H-pyrrolo[2,3-b]pyridin-1-yl)methyl)-N-hydroxybenzamide) (0.10 g, 0.29 mmol) prepared in step 1 of Example 25, 4-hydroxyphenylboronic acid (0.048 g, 0.35 mmol), sodium carbonate (0.067 g, 0.64 mmol) and Pd(dppf)Cl$_{26}$ (0.024 g, 0.029 mmol) were added to 1,2-dimethoxyethane (2 mL)/water (1 mL), and heated by microwave irradiation at 120° C. for 20 minutes, followed by cooling to room temperature. Then, water was added to the reaction mixture, followed by extraction with ethyl acetate. The extract was filtered through a plastic filter to remove solid residue and the aqueous layer, and then concentrated under reduced pressure. The concentrate was purified by column chromatography (Waters, C18, acetonitrile/0.1% TFA aqueous solution=from 5% to 70%), and TFA was removed, thereby obtaining the desired compound 691 (0.02 g, 19%) as a yellow solid.

$^1$H NMR (400 MHz, DMSO-$d_6$) δ 8.48 (d, 1H, J=2.1 Hz), 8.17 (d, 1H, J=2.1 Hz), 7.68 (d, 2H, J=8.6 Hz), 7.68 (d, 1H, J=5.7 Hz), 7.52 (d, 2H, J=8.6 Hz), 7.28 (d, 2H, J=8.3 Hz), 6.88 (d, 2H, J=8.6 Hz), 6.57 (d, 1H, J=3.5 Hz), 5.56 (s, 2H); MS (ESI) m/z 360.1 (M$^+$+H).

Example 32

Synthesis of Compound 692

Step 1: Synthesis of tert-butyl 4-(1-(4-(methoxycarbonyl)benzyl)-1H-pyrrolo[2,3-b]pyridin-5-yl)-5,6-dihydropyridine-1(2H)-carboxylate (formula 2-3)

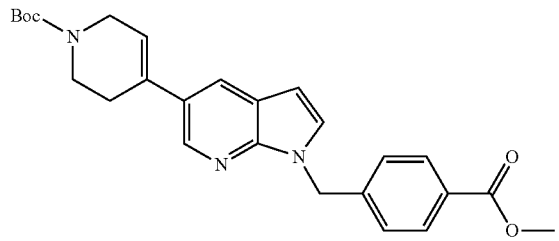

(formula 2-3)

The compound of formula 2-2 (methyl 4-((5-bromo-1H-pyrrolo[2,3-b]pyridin-1-yl)methyl)benzoate) (3.5 g, 10.14 mmol) prepared in step 1 of Example 9, 3,6-dihydro-2H-pyridine-1-tert-butoxycarbonyl-4-boronic acid pinacol ester (3.61 g, 11.660 mmol), sodium carbonate (2.15 g, 20.28 mmol) and Pd(dppf)Cl$_2$ (0.83 g, 1.01 mmol) were added to 1,2-dimethoxyethane (40 mL)/water (10 mL), and heated by microwave irradiation at 120° C. for 20 minutes, followed by cooling to room temperature. Then, water was added to the reaction mixture, followed by extraction with ethyl acetate. The organic layer was washed with saturated brine, dried with anhydrous sodium sulfate, and then concentrated under reduced pressure. The concentrate was purified by column chromatography (SiO$_2$, 40 g cartridge; ethyl acetate/hexane=from 20% to 30%) to afford the desired compound of formula 2-3 (4.04 g, 89%) as a yellow liquid.

Step 2: Synthesis of tert-butyl 4-(1-(4-(hydroxycarbamoyl)benzyl)-1H-pyrrolo[2,3-b]pyridin-5-yl)-5,6-dihydropyridine-1(2H)-carboxylate (compound 692)

(compound 692)

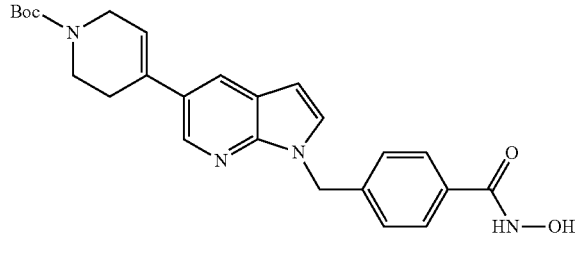

The compound of formula 2-3 (0.500 g, 1.117 mmol) prepared in step 1, hydroxylamine hydrochloride (0.388 g, 5.586 mmol), potassium hydroxide (0.313 g, 5.586 mmol) and an aqueous solution of 50 wt % hydroxylamine (1.436 mL, 22.345 mmol) were dissolved in methanol (20 mL) at room temperature, and the mixture was stirred at the same temperature for 3 hours. Then, the reaction mixture was concentrated under reduced pressure to remove methanol, and an aqueous solution of sodium hydrogen carbonate was added thereto. The precipitated solid was filtered and dried to afford the desired compound 692 (0.44 g, 88%) as a white solid.

$^1$H NMR (400 MHz, DMSO-$d_6$) δ 8.38 (d, 1H, J=2.0 Hz), 8.01 (d, 1H, J=2.1 Hz), 7.66 (d, 2H, J=8.5 Hz), 7.64 (d, 1H, J=4.0 Hz), 7.21 (d, 2H, J=8.2 Hz), 6.51 (d, 1H, J=3.5 Hz), 6.14 (s, 1H), 5.49 (s, 2H), 4.01 (s, 2H), 3.57 (t, 2H, J=5.2 Hz), 2.53 (t, 2H, J=2.4 Hz), 1.44 (s, 9H); MS (ESI) m/z 449.2 (M$^+$+H).

Example 33

Synthesis of Compound 693 (N-hydroxy-4-((5-(1,2,3,6-tetrahydropyridin-4-yl)-1H-pyrrolo[2,3-b]pyridin-1-yl)methyl)benzamide)

(compound 693)

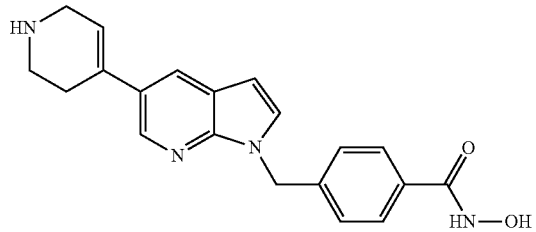

The compound of formula 5-2 (6-1) (methyl 4-((5-(1,2,3,6-tetrahydropyridin-4-yl)-1H-pyrrolo[2,3-b]pyridin-1-yl)methyl)benzoate) (0.200 g, 0.576 mmol) prepared in step 3 of Example 9, hydroxylamine hydrochloride (0.200 g, 2.878 mmol), potassium hydroxide (0.162 g, 2.878 mmol) and an aqueous solution of 50 wt % hydroxylamine (0.740 mL, 11.514 mmol) were dissolved in methanol (10 mL) at room temperature, and the mixture was stirred at the same temperature for 3 hours. Then, the reaction mixture was concentrated under reduced pressure to remove methanol, and an aqueous solution of sodium hydrogen carbonate was added thereto. The precipitated solid was filtered and dried to afford the desired compound 693 (0.17 g, 85%) as a pale orange solid.

$^1$H NMR (400 MHz, DMSO-$d_6$) δ 8.36 (d, 1H, J=2.0 Hz), 7.97 (d, 1H, J=2.0 Hz), 7.66 (d, 2H, J=8.0 Hz), 7.62 (d, 1H, J=3.4 Hz), 7.20 (d, 2H, J=8.0 Hz), 6.50 (d, 1H, J=3.4 Hz), 6.18 (s, 1H), 5.48 (s, 2H), 2.93 (t, 2H, J=2.6 Hz), 2.52-2.51 (m, 2H), 2.41-2.33 (m, 2H); MS (ESI) m/z 349.1 (M$^+$+H).

Example 34

Synthesis of Compound 694 (tert-butyl 4-(1-(4-(hydroxycarbamoyl)benzyl)-1H-pyrrolo[2,3-b]pyridin-5-yl)piperidine-1-carboxylate)

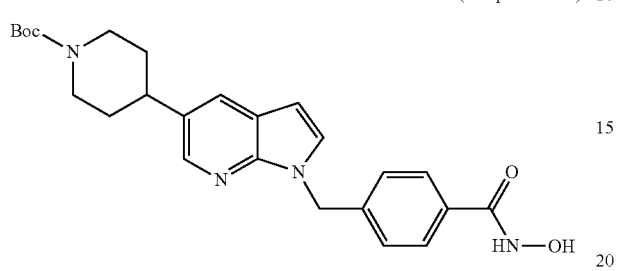
(compound 694)

The compound of formula 5-1 (2-4) (tert-butyl 4-(1-(4-(methoxycarbonyl)benzyl)-1H-pyrrolo[2,3-b]pyridin-5-yl)piperidine-1-carboxylate) (0.100 g, 0.223 mmol) prepared in step 2 of Example 9 was dissolved in methanol (10 mL)/THF (5 mL) at room temperature, and the solution was stirred at the same temperature for 12 hours. Then, water was added to the reaction mixture, followed by extraction with ethyl acetate. The organic layer was washed with saturated brine, dried with anhydrous sodium sulfate, and then concentrated under reduced pressure. The concentrate was purified by column chromatography (SiO$_2$, 4 g cartridge; methanol/dichloromethane=from 5% to 10%), and then freeze-dried, thereby obtaining the desired compound 694 (0.058 g, 58%) as a white solid.

$^1$H NMR (400 MHz, DMSO-d$_6$) δ 8.17 (d, 1H, J=1.6 Hz), 7.85 (d, 1H, J=1.5 Hz), 7.66 (d, 2H, J=8.2 Hz), 7.62 (d, 1H, J=3.4 Hz), 6.46 (d, 2H, J=3.4 Hz), 5.50 (s, 2H), 4.10-4.08 (m, 2H), 2.89-2.73 (m, 2H), 1.80-1.52 (m, 5H), 1.43 (s, 9H); MS (ESI) m/z 451.2 (M$^+$+H).

Example 35

Synthesis of Compound 700

Step 1: Synthesis of methyl 4-((4-(4-(5-(trifluoromethyl)pyridin-2-yl)piperazin-1-yl)-1H-pyrrolo[2,3-b]pyridin-1-yl)methyl)benzoate) (formula 9-1)

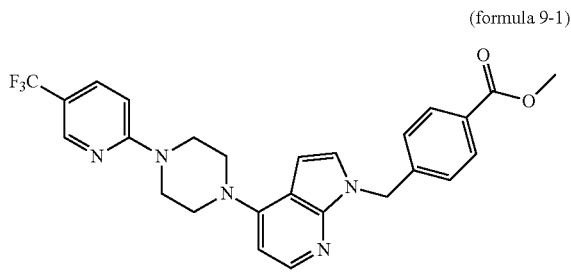 [SMILES: COC(=O)c1ccc(Cn2ccc3c(N4CCN(c5ccc(C(F)(F)F)cn5)CC4)ccnc32)cc1]
(formula 9-1)

The compound of formula 8-1 (methyl 4-((4-(piperazin-1-yl)-1H-pyrrolo[2,3-b]pyridin-1-yl)methyl)benzoate hydrochloride) (0.10 g, 0.26 mmol), 2-chloro-5-(trifluoromethyl)pyridine (0.06 g, 0.31 mmol) and potassium carbonate (0.05 g, 0.34 mmol) were dissolved in N,N-dimethylformamide (2 mL) at 80° C., and the mixture was stirred at the same temperature for 5 hours. Then, a saturated aqueous solution of ammonium chloride was added to the reaction mixture, followed by extraction with ethyl acetate. The organic layer was washed with a saturated aqueous solution of sodium chloride, dried with anhydrous magnesium sulfate, and then concentrated under reduced pressure. The concentrate was purified by column chromatography (SiO$_2$, 4 g cartridge; ethyl acetate/hexane=from 30% to 60%) to afford the desired compound of formula 9-1 (0.08 g, 62%) as a white solid.

Step 2: Synthesis of N-hydroxy-4-((4-(4-(5-(trifluoromethyl)pyridin-2-yl)piperazin-1-yl)-1H-pyrrolo[2,3-b]pyridin-1-yl)methyl)benzamide (compound 700)

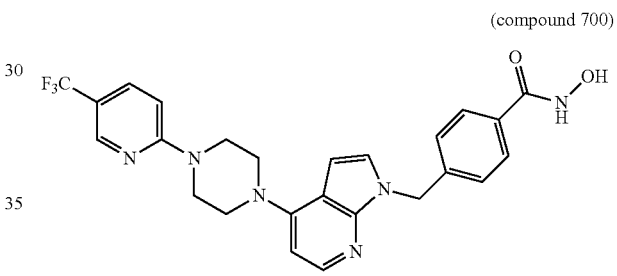
(compound 700)

The compound of formula 9-1 (0.08 g, 0.15 mmol) prepared in step 1 was dissolved in methanol (2 mL)/tetrahydrofuran (1 mL) at room temperature. To the solution, potassium hydroxide (0.04 g, 0.76 mmol) and an aqueous solution of 50 wt % hydroxylamine (0.05 g, 1.51 mmol) were added, followed by stirring at the same temperature for 3 hours. Then, the reaction mixture was concentrated under reduced pressure to remove the solvent, and a saturated aqueous solution of sodium carbonate was added to the concentrate, followed by extraction with ethyl acetate. The organic layer was washed with a saturated aqueous solution of sodium chloride, dried with anhydrous magnesium sulfate, and then concentrated under reduced pressure. Diethyl ether (1 mL) was added to the concentrate, followed by stirring. The precipitated solid was filtered and dried to afford the desired compound 700 (0.02 g, 29%) as a white solid.

$^1$H NMR (400 MHz, DMSO-d$_6$) δ 8.45 (s, 1H), 8.00 (d, 1H, J=5.4 Hz), 7.85 (d, 1H, J=6.8 Hz), 7.66 (d, 2H, J=8.3 Hz), 7.44 (d, 1H, J=3.5 Hz), 7.22 (d, 2H, J=8.0 Hz), 7.00 (d, 1H, J=8.7 Hz), 6.64 (d, 1H, J=5.5 Hz), 6.49 (d, 1H, J=5.5 Hz), 5.46 (s, 2H), 3.86 (m, 4H), 3.64 (m, 4H); MS (ESI) m/z 426.2 (M$^+$+H).

Example 36

Synthesis of Compound 701

Step 1: Synthesis of methyl 4-((4-(4-(5-(trifluoromethyl)pyrazin-2-yl)piperazin-1-yl)-1H-pyrrolo[2,3-b]pyridin-1-yl)methyl)benzoate) (compound 9-1)

(compound 9-1)

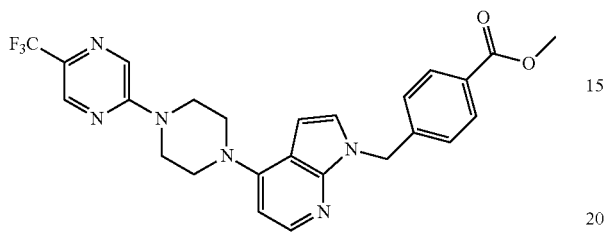

The compound of formula 8-1 (methyl 4-((4-(piperazin-1-yl)-1H-pyrrolo[2,3-b]pyridin-1-yl)methyl)benzoate hydrochloride) (0.10 g, 0.26 mmol), 2-chloro-5-(trifluoromethyl)pyrazine (0.06 g, 0.31 mmol) and potassium carbonate (0.05 g, 0.34 mmol) were dissolved in N,N-dimethylformamide (2 mL) at 80° C., and the solution was stirred at the same temperature for 5 hours. Then, a saturated aqueous solution of ammonium chloride was added to the reaction mixture, followed by extraction with ethyl acetate. The organic layer was washed with a saturated aqueous solution of sodium chloride, dried with anhydrous magnesium sulfate, and then concentrated under reduced pressure. The concentrate was purified by column chromatography (SiO$_2$, 4 g cartridge; ethyl acetate/hexane=from 30% to 60%) to afford the desired compound of formula 9-1 (0.1 g, 74%) as a white solid.

Step 2: Synthesis of N-hydroxy-4-((4-(4-(5-(trifluoromethyl)pyrazin-2-yl)piperazin-1-yl)-1H-pyrrolo[2,3-b]pyridin-1-yl)methyl)benzamide (compound 701)

(compound 701)

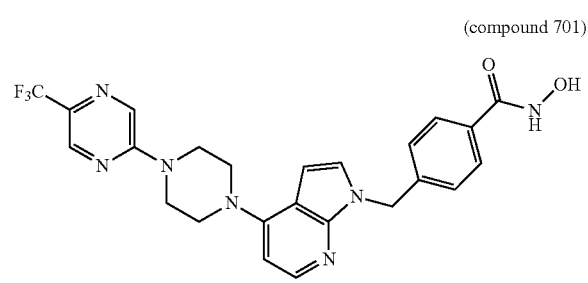 [SMILES: O=C(NO)c1ccc(Cn2ccc3c(N4CCN(c5ccc(C(F)(F)F)cn5)CC4)ccnc32)cc1]

The compound of formula 9-1 (0.09 g, 0.18 mmol) prepared in step 1 was dissolved in methanol (2 mL)/tetrahydrofuran (1 mL) at room temperature. To the solution, potassium hydroxide (0.05 g, 0.91 mmol) and an aqueous solution of 50 wt % hydroxylamine (0.06 g, 1.81 mmol) were added, followed by stirring at the same temperature for 3 hours. Then, the reaction mixture was concentrated under reduced pressure to remove the solvent, and a saturated aqueous solution of sodium carbonate was added to the concentrate, followed by extraction with ethyl acetate. The organic layer was washed with a saturated aqueous solution of sodium chloride, dried with anhydrous magnesium sulfate, and then concentrated under reduced pressure. Diethyl ether (2 mL) was added to the concentrate, followed by stirring. The precipitated solid was filtered and dried to afford the desired compound 701 (0.03 g, 27%) as a white solid.

$^1$H NMR (400 MHz, DMSO-d$_6$) δ 11.15 (s, 1H), 9.01 (s, 1H), 8.67 (s, 1H), 8.48 (s, 1H), 8.01 (d, 1H, J=5.5 Hz), 7.66 (d, 1H, J=7.9 Hz), 7.46 (d, 1H, J=3.4 Hz), 7.20 (m, 2H), 6.65 (d, 1H, J=3.5 Hz), 6.51 (d, 1H, J=5.4 Hz), 5.47 (s, 2H), 3.95 (m, 4H), 3.58 (m, 4H); MS (ESI) m/z 498.1 (M$^+$+H).

Example 37

Synthesis of Compound 702

Step 1: Synthesis of methyl 4-((4-(4-(5-ethylpyrimidin-2-yl)piperazin-1-yl)-1H-pyrrolo[2,3-b]pyridin-1-yl)methyl)benzoate (formula 9-1)

(formula 9-1)

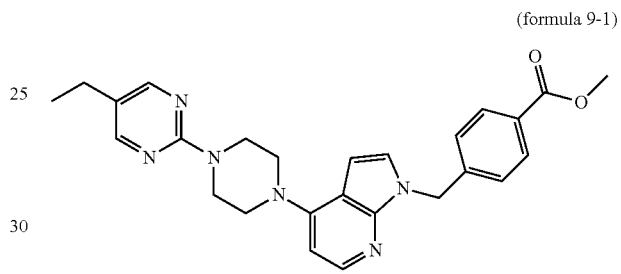

The compound of formula 8-1 (methyl 4-((4-(piperazin-1-yl)-1H-pyrrolo[2,3-b]pyridin-1-yl)methyl)benzoate hydrochloride) (0.10 g, 0.26 mmol), 2-chloro-5-ethylpyrimidine (0.04 g, 0.31 mmol) and potassium carbonate (0.05 g, 0.34 mmol) were dissolved in N,N-dimethylformamide (2 mL) at 80° C., and the mixture was stirred at the same temperature for 5 hours. Then, a saturated aqueous solution of ammonium chloride was added to the reaction mixture, followed by extraction with ethyl acetate. The organic layer was washed with a saturated aqueous solution of sodium chloride, dried with anhydrous magnesium sulfate, and then concentrated under reduced pressure. The concentrate was purified by column chromatography (SiO$_2$, 4 g cartridge; ethyl acetate/hexane=from 30% to 60%) to afford the desired compound of formula 9-1 (0.09 g, 72%) as a white solid.

Step 2: Synthesis of 4-((4-(4-(5-ethylpyrimidin-2-yl)piperazin-1-yl)-1H-pyrrolo[2,3-b]pyridin-1-yl)methyl)-N-hydroxybenzamide (compound 702)

(compound 702)

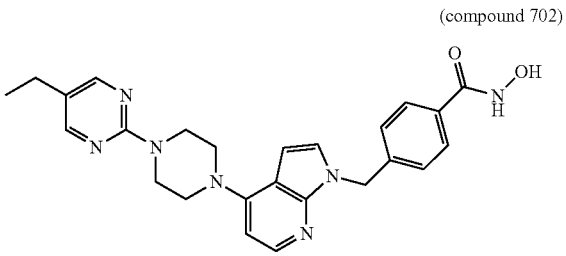 [SMILES: CCc1cnc(N2CCN(c3ccnc4c3ccn4Cc3ccc(C(=O)NO)cc3)CC2)nc1]

The compound of formula 9-1 (0.09 g, 0.19 mmol) prepared in step 1 was dissolved in methanol (2 mL)/tetrahydrofuran (1 mL) at room temperature. To the solution, potassium hydroxide (0.05 g, 0.93 mmol) and an aqueous solution of 50 wt % hydroxylamine (0.06 g, 1.86 mmol) were added, followed by stirring at the same temperature for 3 hours. Then, the reaction mixture was concentrated under reduced pressure to remove the solvent, and a saturated aqueous solution of sodium carbonate was added to the concentrate, followed by extraction with ethyl acetate. The organic layer was washed with a saturated aqueous solution of sodium chloride, dried with anhydrous magnesium sulfate, and then concentrated under reduced pressure. Diethyl ether (2 mL) was added to the concentrate, followed by stirring. The precipitated solid was filtered and dried to afford the desired compound 703 (0.07 g, 82%) as a white solid.

$^1$H NMR (400 MHz, DMSO-d$_6$) δ 9.01 (s, 1H), 8.30 (s, 2H), 8.00 (d, 1H, J=5.4 Hz), 7.66 (d, 2H, J=8.1 Hz), 7.45 (d, 1H, J=3.5 Hz), 7.23 (d, 2H, J=7.8 Hz), 6.64 (d, 1H, J=3.6 Hz), 6.51 (d, 1H, J=5.6 Hz), 5.47 (s, 2H), 3.90 (m, 4H), 3.51 (m, 4H), 2.33 (m, 2H), 1.14 (t, 3H, J=7.6 Hz); MS (ESI) m/z 458.2 (M$^+$+H).

Example 38

Synthesis of Compound 703

Step 1: Synthesis of methyl 4-((4-(4-(1-(trifluoromethyl)cyclobutanecarbonyl)piperazin-1-yl)-1H-pyrrolo[2,3-b]pyridin-1-yl)methyl)benzoate (formula 9-2)

(formula 9-2)

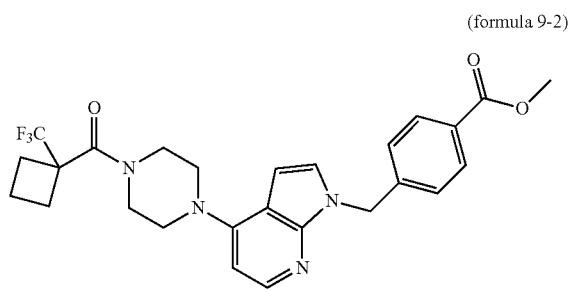 [SMILES: COC(=O)c1ccc(Cn2ccc3c(N4CCN(C(=O)C5(C(F)(F)F)CCC5)CC4)ccnc32)cc1]

1-(trifluoromethyl)cyclobutanecarboxylic acid (0.09 g, 0.52 mmol), EDC (0.10 g, 0.52 mmol), HOBT (0.07 g, 0.52 mmol) and DIPEA (0.10 g, 0.78 mmol) were dissolved in methylene chloride (2 mL) at room temperature. To the solution, the compound of formula 8-1 (methyl 4-((4-(piperazin-1-yl)-1H-pyrrolo[2,3-b]pyridin-1-yl)methyl)benzoate hydrochloride) (0.10 g, 0.26 mmol) was added, followed by stirring at the same temperature for 8 hours. Then, water was added to the reaction mixture, followed by extraction with ethyl acetate. The organic layer was washed with a saturated aqueous solution of sodium chloride, dried with anhydrous magnesium sulfate, and then concentrated under reduced pressure. The concentrate was purified by column chromatography (SiO$_2$, 4 g cartridge; ethyl acetate/hexane=from 30% to 60%) to afford the desired compound of formula 9-2 (0.09 g, 70%) as a white solid.

Step 2: Synthesis of N-hydroxy-4-((4-(4-(1-(trifluoromethyl)cyclobutanecarbonyl)piperazin-1-yl)-1H-pyrrolo[2,3-b]pyridin-1-yl)methyl)benzamide (compound 703)

(compound 703)

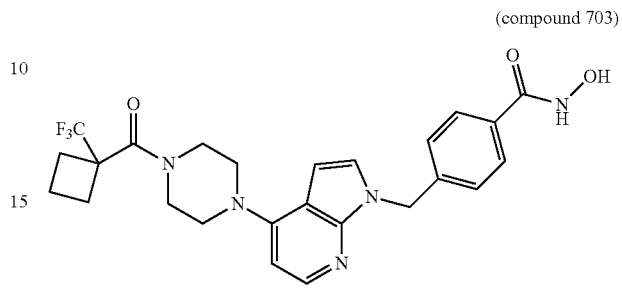

The compound of formula 9-2 (0.08 g, 0.16 mmol) prepared in step 1 was dissolved in methanol (2 mL)/tetrahydrofuran (1 mL) at room temperature. To the solution, potassium hydroxide (0.05 g, 0.80 mmol) and an aqueous solution of 50 wt % hydroxylamine (0.05 g, 1.60 mmol) were added, followed by stirring at the same temperature for 3 hours. Then, the reaction mixture was concentrated under reduced pressure to remove the solvent, and a saturated aqueous solution of sodium carbonate was added to the concentrate, followed by extraction with ethyl acetate. The organic layer was washed with a saturated aqueous solution of sodium chloride, dried with anhydrous magnesium sulfate, and then concentrated under reduced pressure. Diethyl ether (2 mL) was added to the concentrate, followed by stirring. The precipitated solid was filtered and dried to afford the desired compound 703 (0.07 g, 81%) as a white solid.

$^1$H NMR (400 MHz, DMSO-d$_6$) δ 11.14 (s, 1H), 9.01 (s, 1H), 8.01 (d, 1H, J=5.4 Hz), 7.66 (d, 2H, J=8.2 Hz), 7.46 (d, 1H, J=3.6 Hz), 7.23 (d, 2H, J=8.2 Hz), 6.62 (d, 1H, J=3.6 Hz), 6.49 (d, 1H, J=5.5 Hz), 5.47 (s, 2H), 3.72 (m, 2H), 3.49 (m, 2H), 3.34 (m, 4H), 2.71 (m, 2H), 2.50 (m, 2H), 1.99 (m, 1H), 1.78 (m, 1H); MS (ESI) m/z 502.1 (M$^+$+H).

Example 39

Synthesis of Compound 704

Step 1: Synthesis of methyl 4-((4-(4-benzylpiperazin-1-yl)-1H-pyrrolo[2,3-b]pyridin-1-yl)methyl)benzoate (formula 9-3)

The compound of formula 8-1 (methyl 4-((4-(piperazin-1-yl)-1H-pyrrolo[2,3-b]pyridin-1-yl)methyl)benzoate hydrochloride) (0.10 g, 0.26 mmol) and DIPEA (0.07 mL, 0.39 mmol) were dissolved in methylene chloride (4 mL) at room temperature. To the solution, benzaldehyde (0.06 g, 0.52 mmol) and acetic acid (0.03 mL, 0.52 mmol) were added, followed by stirring for 10 minutes. NaBH$_3$CN (0.02 g, 0.31 mmol) was added to the stirred solution, which was then stirred at the same temperature for 8 hours. Then, water was added to the reaction mixture, followed by extraction with ethyl acetate. The organic layer was washed with a saturated aqueous solution of sodium chloride, dried with anhydrous magnesium sulfate, and then concentrated under reduced pressure. The concentrate was purified by column chromatography (SiO$_2$, 4 g cartridge; ethyl acetate/ hexane=from 30% to 60%) to afford the desired compound of formula 9-3 (0.08 g, 70%) as a white solid.

Step 2: Synthesis of 4-((4-(4-benzylpiperazin-1-yl)-1H-pyrrolo[2,3-b]pyridin-1-yl)methyl)-N-hydroxy-benzamide (compound 704)

(compound 704)

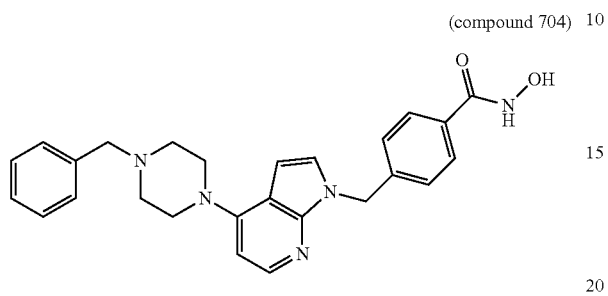

The compound of formula 9-3 (0.07 g, 0.160 mmol) prepared in step 1 was dissolved in methanol (2 mL)/tetrahydrofuran (1 mL) at room temperature. To the solution, potassium hydroxide (0.05 g, 0.79 mmol) and an aqueous solution of 50 wt % hydroxylamine (0.05 g, 1.59 mmol) were added, followed by stirring at the same temperature for 3 hours. Then, the reaction mixture was concentrated under reduced pressure to remove the solvent, and a saturated aqueous solution of sodium carbonate was added to the concentrate, followed by extraction with ethyl acetate. The organic layer was washed with a saturated aqueous solution of sodium chloride, dried with anhydrous magnesium sulfate, and then concentrated under reduced pressure. Diethyl ether (2 mL) was added to the concentrate, followed by stirring. Then, the precipitated solid was filtered and dried to afford the desired compound 704 (0.05 g, 71%) as a white solid.

$^1$H NMR (400 MHz, DMSO-$d_6$) δ 11.14 (s, 1H), 9.01 (s, 1H), 7.97 (d, 1H, J=5.5 Hz), 7.65 (d, 2H, J=8.3 Hz), 7.41 (d, 1H, J=3.6 Hz), 7.35 (d, 4H, J=4.4 Hz), 7.27 (m, 1H), 7.22 (d, 2H, J=8.3 Hz), 6.55 (d, 1H, J=3.6 Hz), 6.46 (d, 1H, J=5.6 Hz), 5.45 (s, 2H), 3.55 (s, 2H), 3.42 (m, 4H), 2.56 (m, 4H); MS (ESI) m/z 442.1 (M$^+$+H).

Example 40

Synthesis of Compound 705

Step 1: Synthesis of methyl 4-((4-(4-(4-methoxybenzyl)piperazin-1-yl)-1H-pyrrolo[2,3-b]pyridin-1-yl)methyl)benzoate (compound 9-3)

(compound 9-3)

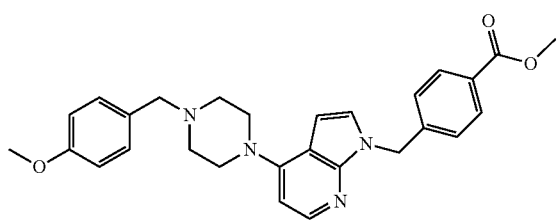

The compound of formula 8-1 (0.06 g, 0.16 mmol) and DIPEA (0.02 g, 0.19 mmol) were dissolved in methylene chloride (4 mL) at room temperature. To the solution, 4-methoxybenzamide (0.04 g, 0.31 mmol) and acetic acid (0.02 g, 0.31 mmol) were added, followed by stirring for 10 minutes. NaCNBH$_3$ (0.01 g, 0.19 mmol) was added to the stirred solution, followed by stirring at the same temperature for 8 hours. Then, water was added to the reaction mixture, followed by extraction with ethyl acetate. The organic layer was washed with a saturated aqueous solution of sodium chloride, dried with anhydrous magnesium sulfate, and then concentrated under reduced pressure. The concentrate was purified by column chromatography (SiO$_2$, 4 g cartridge; ethyl acetate/hexane=from 30% to 60%) to afford the desired compound of formula 9-3 (0.07 g, 89%) as a white solid.

Step 2: Synthesis of N-hydroxy-4-((4-(4-(4-methoxybenzyl)piperazin-1-yl)-1H-pyrrolo[2,3-b]pyridin-1-yl)methyl)-benzamide (compound 705)

(compound 705)

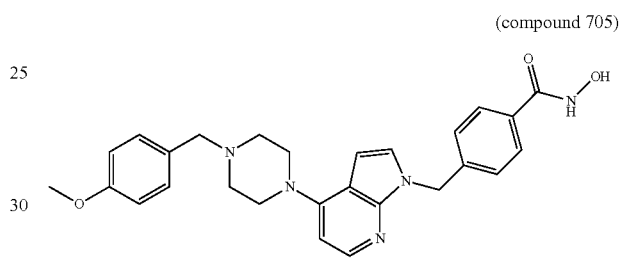

The compound of formula 9-3 (0.06 g, 0.13 mmol) prepared in step 1 was dissolved in methanol (2 mL)/tetrahydrofuran (1 mL) at room temperature. To the solution, potassium hydroxide (0.04 g, 0.64 mmol) and an aqueous solution of 50 wt % hydroxylamine (0.04 g, 1.28 mmol) were added, followed by stirring at the same temperature for 3 hours. Then, the reaction mixture was concentrated under reduced pressure to remove the solvent, and a saturated aqueous solution of sodium carbonate was added to the concentrate, followed by extraction with ethyl acetate. The organic layer was washed with a saturated aqueous solution of sodium chloride, dried with anhydrous magnesium sulfate, and then concentrated under reduced pressure. Diethyl ether (2 mL) was added to the concentrate, followed by stirring. Then, the precipitated solid was filtered and dried to afford the desired compound 705 (0.03 g, 49%) as a white solid.

$^1$H NMR (400 MHz, DMSO-$d_6$) δ 11.14 (s, 1H), 9.02 (s, 1H), 7.97 (d, 1H, J=5.4 Hz), 7.65 (d, 2H, J=8.1 Hz), 7.40 (d, 1H, J=3.5 Hz), 7.24 (m, 4H), 6.90 (d, 2H, J=8.4 Hz), 6.55 (d, 1H, J=3.7 Hz), 6.45 (d, 1H, J=5.5 Hz), 5.45 (s, 2H), 3.74 (s, 3H), 3.47 (s, 2H), 3.34 (m, 4H), 2.52 (m, 4H); MS (ESI) m/z 472.2 (M$^+$+H).

Example 41

Synthesis of Compound 706

Step 1: Synthesis of 4-((4-(4-(4-(trifluoromethyl)benzyl)piperazin-1-yl)-1H-pyrrolo[2,3-b]pyridin-1-yl)methyl)benzoate (formula 9-3)

The compound of formula 8-1 (methyl 4-((4-(piperazin-1-yl)-1H-pyrrolo[2,3-b]pyridin-1-yl)methyl)benzoate hydrochloride) (0.06 g, 0.16 mmol) and DIPEA (0.02 g, 0.19 mmol) were dissolved in methylene chloride (4 mL) at room temperature. To the solution, 4-(trifluoromethyl)benzaldehyde (0.05 g, 0.31 mmol) and acetic acid (0.02 g, 0.31 mmol) were added, followed by stirring for 10 minutes. NaCNBH$_3$ (0.01 g, 0.19 mmol) was added to the stirred solution, followed by stirring at the same temperature for 8 hours. Then, water was added to the reaction mixture, followed by extraction with ethyl acetate. The organic layer was washed with a saturated aqueous solution of sodium chloride, dried with anhydrous magnesium sulfate, and then concentrated under reduced pressure. The concentrate was purified by column chromatography (SiO$_2$, 4 g cartridge; ethyl acetate/hexane=from 30% to 70%) to afford the desired compound of formula 9-3 (0.06 g, 74%) as a white solid.

Step 2: Synthesis of N-hydroxy-4-((4-(4-(4-(trifluoromethyl)benzyl)piperazin-1-yl)-1H-pyrrolo[2,3-b]pyridin-1-yl)methyl)benzamide (compound 706)

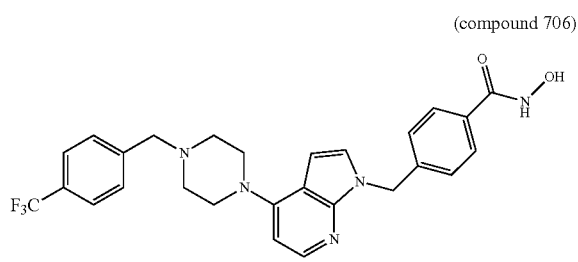 [SMILES: O=C(NO)c1ccc(Cn2ccc3c(N4CCN(Cc5ccc(C(F)(F)F)cc5)CC4)ccnc32)cc1]
(compound 706)

The compound of formula 9-3 (0.05 g, 0.10 mmol) prepared in step 1 was dissolved in methanol (2 mL)/tetrahydrofuran (1 mL) at room temperature. To the solution, potassium hydroxide (0.03 g, 0.49 mmol) and an aqueous solution of 50 wt % hydroxylamine (0.03 g, 0.98 mmol) were added, followed by stirring at the same temperature for 3 hours. Then, the reaction mixture was concentrated under reduced pressure to remove the solvent, and a saturated aqueous solution of sodium carbonate was added to the concentrate, followed by extraction with ethyl acetate. The organic layer was washed with a saturated aqueous solution of sodium chloride, dried with anhydrous magnesium sulfate, and then concentrated under reduced pressure. Diethyl ether (2 mL) was added to the concentrate, followed by stirring. Then, the precipitated solid was filtered and dried to afford the desired compound 706 (0.04 g, 80%) as a white solid.

$^1$H NMR (400 MHz, DMSO-d$_6$) δ 11.14 (s, 1H), 9.01 (s, $^1$H), 7.98 (d, 1H, J=5.5 Hz), 7.72 (d, 2H, J=8.1 Hz), 7.65 (d, 2H, J=8.3 Hz), 7.60 (d, 2H, J=8.0 Hz), 7.41 (d, 1H, J=3.6 Hz), 7.23 (d, 2H, J=8.3 Hz), 6.55 (d, 1H, J=3.6 Hz), 6.47 (d, 1H, J=5.6 Hz), 5.45 (s, 2H), 3.66 (s, 2H), 3.43 (m, 4H), 2.58 (m, 4H); MS (ESI) m/z 510.2 (M$^+$+H).

Example 42

Synthesis of Compound 714

Step 1: Synthesis of methyl 4-((5-(1-(2-hydroxy-2-methylpropyl)piperidin-4-yl)-1H-pyrrolo[2,3-b]pyridin-1-yl)methyl)benzoate (formula 5-6)

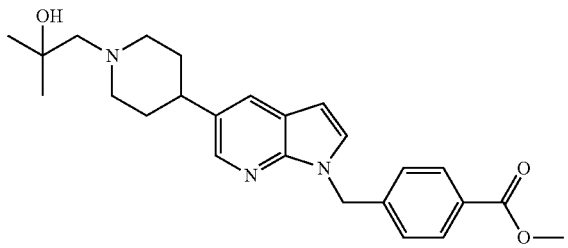
(formula 5-6)

The compound of formula 5-3 (methyl 4-((5-(1-(2-hydroxy-2-methylpropyl)-1,2,3,6-tetrahydropyridin-4-yl)-1H-pyrrolo[2,3-b]pyridin-1-yl)methyl)benzoate) (0.40 g, 0.95 mmol) prepared in step 4 of Example 9 was dissolved in methanol (10 mL) at room temperature. To the solution, Pd/C (0.02 g) was added, and a hydrogen balloon was placed over the solution, followed by stirring at the same temperature for 12 hours. Then, water was added to the reaction mixture, followed by extraction with ethyl acetate. The organic layer was washed with saturated brine, dried with anhydrous sodium sulfate, and then concentrated under reduced pressure. The concentrate was purified by column chromatography (SiO$_2$, 12 g cartridge; ethyl acetate/hexane=from 30% to 50%) to afford the desired compound of formula 5-6 (0.350 g, 87%) as a yellow solid.

Step 2: Synthesis of N-hydroxy-4-((5-(1-(2-hydroxy-2-methylpropyl)piperidin-4-yl)-1H-pyrrolo[2,3-b]pyridin-1-yl)methyl)benzamide (compound 714)

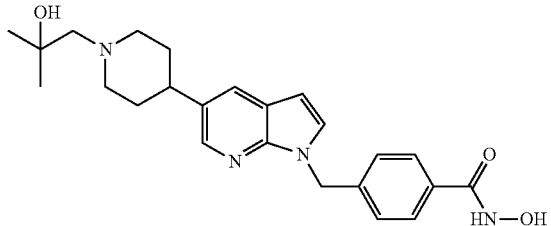
(compound 714)

The compound of formula 5-6 (0.13 g, 0.31 mmol) prepared in step 1, hydroxylamine hydrochloride (0.11 g, 1.54 mmol), potassium hydroxide (0.087 g, 1.54 mmol) and an aqueous solution of 50 wt % hydroxylamine (0.396 mL, 6.17 mmol) were dissolved in methanol (10 mL) at room temperature, and the solution was stirred at the same temperature for 3 hours.

Then, the reaction mixture was concentrated under reduced pressure to remove the solvent. The concentrate was purified by column chromatography (Waters, C18, acetonitrile/0.1% TFA aqueous solution=from 5% to 70%), and TFA was removed, thereby obtaining the desired compound 714 (0.015 g, 12%) as a white solid.

$^1$H NMR (400 MHz, DMSO-d$_6$) δ 11.22 (s, 1H), 9.08 (s, 1H), 8.16 (s, 1H), 7.85 (s, 1H), 7.66 (d, 2H, J=8.2 Hz), 7.61 (s, 1H), 7.25 (d, 2H, J=8.1 Hz), 6.47 (s, 1H), 5.49 (s, 2H), 3.13-3.05 (m, 2H), 2.75 (s, 1H), 2.38-2.24 (m, 4H), 1.89-1.65 (m, 4H), 1.12 (s, 6H); MS (ESI) m/z 423.2 (M$^+$+H).

Example 43

Synthesis of Compound 715 (N-hydroxy-4-((5-(piperidin-4-yl)-1H-pyrrolo[2,3-b]pyridin-1-yl)methyl)benzamide)

(compound 715)

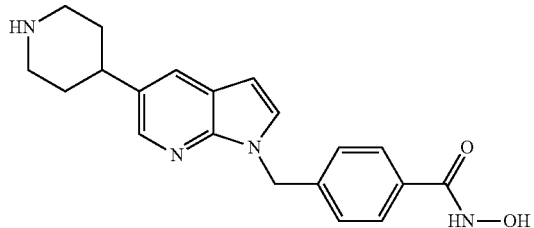

The compound of formula 6-5 (N-hydroxy-4-((5-(1,2,3,6-tetrahydropyridin-4-yl)-1H-pyrrolo[2,3-b]pyridin-1-yl)methyl)benzamide) (0.100 g, 0.287 mmol) prepared in Example 33 was dissolved in methanol (10 mL) at room temperature, and the solution was stirred at the same temperature for 12 hours. Water was added to the reaction mixture, followed by extraction with ethyl acetate. The organic layer was washed with saturated brine, dried with anhydrous magnesium sulfate, and then concentrated under reduced pressure. The concentrate was purified by column chromatography (Waters, C18, acetonitrile/0.1% TFA aqueous solution=from 5% to 70%), and TFA was removed, thereby obtaining the desired compound 715 (0.085 g, 85%) as a white solid.

$^1$H NMR (400 MHz, DMSO-d$_6$) δ 8.15 (d, 1H, J=1.8 Hz), 7.81 (d, 1H, J=1.7 Hz), 7.67 (dd, 2H, J=18.0, 9.7 Hz), 7.61 (d, 1H, J=3.4 Hz), 7.25 (d, 2H, J=8.2 Hz), 6.46 (d, 1H, J=3.5 Hz), 5.49 (s, 2H), 3.06-3.03 (m, 2H), 2.70-2.59 (m, 3H), 1.74-1.55 (m, 4H); MS (ESI) m/z 351.1 (M$^+$+H).

Example 44

Synthesis of Compound 721

Step 1: Synthesis of methyl 4-((5-(1-(cyclohexylmethyl)-1,2,3,6-tetrahydropyridin-4-yl)-1H-pyrrolo[2,3-b]pyridin-1-yl)methyl)benzoate (formula 6-2)

(formula 6-2)

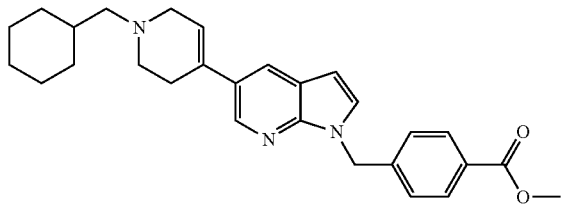

The compound of formula 6-1 (methyl 4-((5-(1,2,3,6-tetrahydropyridin-4-yl)-1H-pyrrolo[2,3-b]pyridin-1-yl)methyl)benzoate) (0.100 mL, 0.288 mmol), (bromomethyl)cyclohexane (0.044 mL, 0.317 mmol) and Cs$_2$CO$_3$ (0.113 g, 0.345 mmol) were dissolved in N,N-dimethylformamide (10 mL) at room temperature, and the mixture was stirred at the same temperature for 12 hours. Then, water was added to the reaction mixture, followed by extraction with ethyl acetate. The organic layer was washed with saturated brine, dried with anhydrous sodium sulfate, and then concentrated under reduced pressure. The concentrate was purified by column chromatography (SiO$_2$, 4 g cartridge; ethyl acetate/hexane=from 20% to 30%) to afford the desired compound of formula 6-2 (0.061 g, 48%) as a yellow liquid.

Step 2: Synthesis of 4-((5-(1-(cyclohexylmethyl)-1,2,3,6-tetrahydropyridin-4-yl)-1H-pyrrolo[2,3-b]pyridin-1-yl)methyl)-N-hydroxybenzamide (compound 721)

(compound 721)

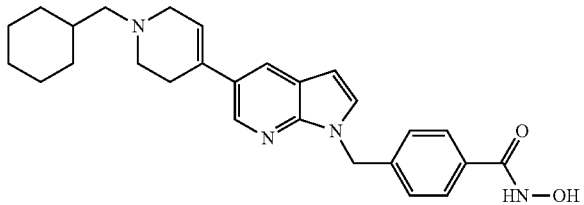

The compound of formula 6-2 (0.050 g, 0.113 mmol) prepared in step 1, hydroxylamine hydrochloride) (0.039 g, 0.56 mmol), potassium hydroxide (0.032 g, 0.564 mmol) and an aqueous solution of 50 wt % hydroxylamine (0.15 mL, 2.25 mmol) were dissolved in methanol (10 mL) at room temperature, and the solution was stirred at the same temperature for 3 hours.

Then, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (Waters, C18, acetonitrile/0.1% TFA aqueous solution=from 5% to 70%), and TFA was removed, thereby obtaining the desired compound 721 (0.012 g, 24%) as a white solid.

$^1$H NMR (400 MHz, DMSO-d$_6$) δ 8.35 (d, 1H, J=2.0 Hz), 8.06 (d, 1H, J=2.0 Hz), 7.68 (d, 2H, J=8.3 Hz), 7.43 (d, 1H, J=3.5 Hz), 7.25 (d, 2H, J=8.2 Hz), 6.57 (d, 1H, J=3.5 Hz), 6.15 (s, 1H), 5.57 (s, 2H), 3.20 (s, 2H), 2.79 (t, 2H, J=5.5 Hz), 2.69 (s, 2H), 2.36 (d, 2H, J=6.9 Hz), 1.90 (d, 2H, J=14.0 Hz), 1.85-1.65 (m, 3H), 1.38-1.22 (m, 4H), 1.03-1.00 (m, 2H); MS (ESI) m/z 445.2 (M$^+$+H).

Example 45

Synthesis of Compound 722

Step 1: Synthesis of methyl 4-((4-(3-aminophenyl)-1H-pyrrolo[2,3-b]pyridin-1-yl)methyl)benzoate (formula 1-3)

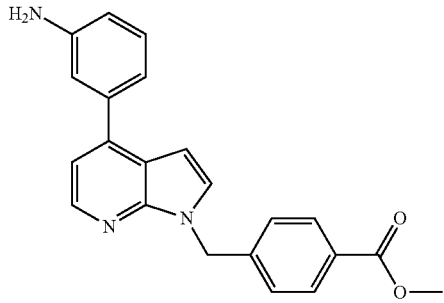

(formula 1-3)

The compound of formula 1-2 (0.200 g, 0.523 mmol), 3-aminophenylboronic acid (0.086 g, 0.628 mmol), sodium carbonate (0.122 g, 1.151 mmol) and Pd(dppf)Cl$_2$ (0.043 g, 0.052 mmol) were added to 1,2-dimethoxyethane (2 mL)/water (1 mL), and heated by microwave irradiation for 10 minutes, followed by cooling to room temperature. Then, water was added to the reaction mixture, followed by extraction with ethyl acetate. The organic layer was washed with saturated brine, dried with anhydrous magnesium sulfate, and then concentrated under reduced pressure. The concentrate was purified by column chromatography (SiO$_2$, 12 g cartridge; ethyl acetate/hexane=from 20% to 30%) to afford the desired compound of formula 1-3 (0.12 g, 64%) as a yellow liquid.

Step 2: Synthesis of 4-((4-(3-aminophenyl)-1H-pyrrolo[2,3-b]pyridin-1-yl)methyl)-N-hydroxybenzamide (compound 722)

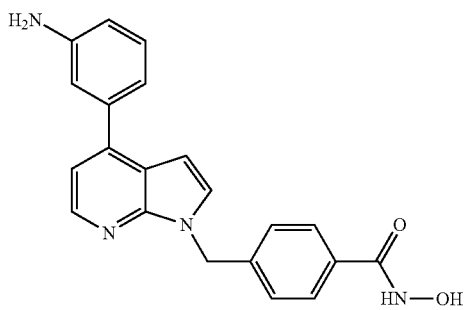

(compound 722)

The compound of formula 1-3 (0.12 g, 0.336 mmol) prepared in step 1, hydroxylamine hydrochloride (0.117 g, 1.679 mmol), potassium hydroxide (0.094 g, 1.679 mmol) and an aqueous solution of 50 wt % hydroxylamine (0.432 mL, 6.715 mmol) were dissolved in methanol (10 mL) at room temperature, and the solution was stirred at the same temperature for 3 hours. Then, water was added to the reaction mixture, followed by extraction with ethyl acetate. The organic layer was washed with a saturated aqueous solution of sodium hydrogen carbonate, dried with anhydrous magnesium sulfate, filtered, and then concentrated under reduced pressure. The concentrate was stirred, and the precipitated solid was filtered and dried to afford the desired compound 722 (0.110 g, 91%) as a brown solid.

$^1$H NMR (400 MHz, DMSO-d$_6$) δ 8.29 (d, 1H, J=4.9 Hz), 7.79-7.66 (m, 3H), 7.24 (d, 2H, J=8.1 Hz), 7.20-7.15 (m, 2H), 7.00 (s, 1H), 6.88 (d, 1H, J=7.6 Hz), 6.67 (d, 2H, J=3.5 Hz), 5.54 (s, 2H), 5.28 (s, 2H); MS (ESI) m/z 359.1 (M$^+$+H).

Example 46

Synthesis of Compound 723

Step 1: Synthesis of methyl 4-((4-(1-methyl-1,2,3,6-tetrahydropyridin-4-yl)-1H-pyrrolo[2,3-b]pyridin-1-yl)methyl)benzoate (formula 1-3)

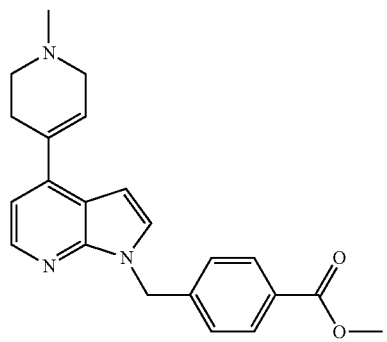

(formula 1-3)

The compound of formula 1-2 (methyl 4-((4-bromo-1H-pyrrolo[2,3-b]pyridin-1-yl)methyl)benzoate) (0.2 g, 0.523 mmol), 1-methyl-1,2,3,6-tetrahydropyridine-4-boronic acid pinacol ester (0.140 g, 0.63 mmol), sodium carbonate (0.122 g, 1.151 mmol) and Pd(dppf)Cl$_2$ (0.043 g, 0.052 mmol) were added to 1,2-dimethoxyethane (2 mL)/water (1 mL), and heated by microwave irradiation for 10 minutes, followed by cooling to room temperature. Then, water was added to the reaction mixture, followed by extraction with ethyl acetate. The organic layer was washed with saturated brine, dried with anhydrous magnesium sulfate, and then concentrated under reduced pressure. The concentrate was purified by column chromatography (SiO$_2$, 12 g cartridge; methanol/dichloromethane=from 5% to 10%) to afford the desired compound of formula 1-3 (0.1 g, 53%) as a brown solid.

Step 2: Synthesis of N-hydroxy-4-((4-(1-methyl-1,2,3,6-tetrahydropyridin-4-yl)-1H-pyrrolo[2,3-b]pyridin-1-yl)methyl)benzamide (compound 723)

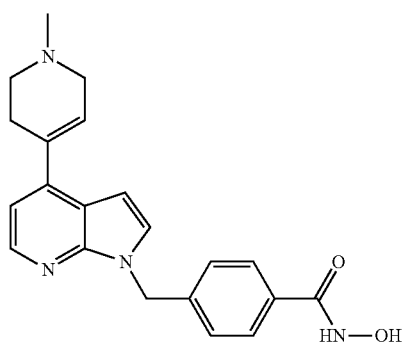

(compound 723)

The compound of formula 1-3 (0.10 g, 0.28 mmol) prepared in step 1, hydroxylamine hydrochloride (0.096 g, 1.38 mmol), potassium hydroxide (0.078 g, 1.38 mmol) and an aqueous solution of 50 wt % hydroxylamine (0.36 mL, 5.53 mmol) were dissolved in methanol (10 mL) at room temperature, and the solution was stirred at the same temperature for 3 hours. Then, water was added to the reaction mixture, followed by extraction. The organic layer was washed with a saturated aqueous solution of sodium hydrogen carbonate, dried with anhydrous magnesium sulfate, filtered, and then concentrated under reduced pressure. The precipitated solid was filtered and dried to afford the desired compound 723 (0.021 g, 21%) as a yellow solid.

$^1$H NMR (400 MHz, DMSO-$d_6$) δ 8.21 (d, 1H, J=5.0 Hz), 7.68-7.64 (m, 3H), 7.21 (d, 2H, J=8.1 Hz), 7.04 (d, 1H, J=5.0 Hz), 6.69 (d, 1H, J=3.6 Hz), 6.38 (s, 1H), 5.50 (s, 2H), 3.09 (s, 3H), 2.61-2.31 (m, 7H); MS (ESI) m/z 363.1 (M$^+$+H).

Example 47

Synthesis of Compound 724

Step 1: Synthesis of methyl 4-((5-(piperidin-4-yl)-1H-pyrrolo[2,3-b]pyridin-1-yl)methyl)benzoate (formula 6-3)

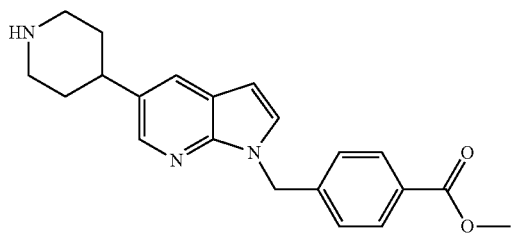

(formula 6-3)

The compound of formula 6-1 (methyl 4-((5-(1,2,3,6-tetrahydropyridin-4-yl)-1H-pyrrolo[2,3-b]pyridin-1-yl)methyl)benzoate) (1.85 g, 5.33 mmol) was dissolved in methanol (50 mL) at room temperature. To the solution, Pd/C (0.02 g) was added, and a hydrogen balloon was placed over the solution, followed by stirring at the same temperature for 12 hours. After completion of the reaction, the reaction mixture was filtered through a celite pad to remove Pd/C, and the residue was dried to afford the desired compound of formula 6-3 (1.5 g, 81%) as a yellow liquid.

Step 2: Synthesis of methyl 4-((5-(1-((1-(trifluoromethyl)cyclobutyl)methyl)piperidin-4-yl)-1H-pyrrolo[2,3-b]pyridin-1-yl)methyl)benzoate (formula 6-4)

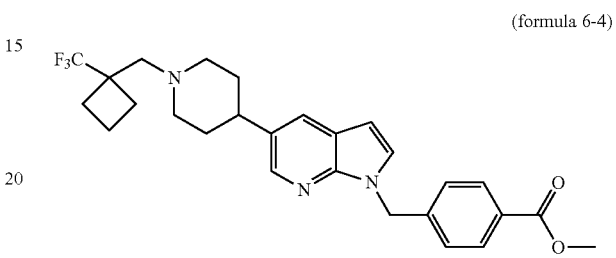

(formula 6-4)

The compound of formula 6-3 (0.2 g, 0.57 mmol) prepared in step 1, (1-(trifluoromethyl)cyclobutyl)methyl 4-methylbenzene sulfonate (0.212 g, 0.69 mmol) and cesium carbonate (0.205 g, 0.63 mmol) were added to N,N-dimethylformamide (10 mL), and heated by microwave irradiation at 120° C. for 24 hours, followed by cooling to room temperature. After completion of the reaction, water was added to the reaction mixture, followed by extraction with ethyl acetate. The organic layer was washed with a saturated aqueous solution of sodium chloride, dried with anhydrous sodium sulfate, filtered, and then concentrated under reduced pressure. The concentrate was purified by column chromatography (SiO$_2$, 12 g cartridge; ethyl acetate/hexane=from 10% to 30%) to afford the desired compound of formula 6-4 (0.021 g, 8%) as a yellow liquid.

Step 3: Synthesis of N-hydroxy-4-((5-(1-((1-(trifluoromethyl)cyclobutyl)methyl)piperidin-4-yl)-1H-pyrrolo[2,3-b]pyridin-1-yl)methyl)benzamide (compound 724)

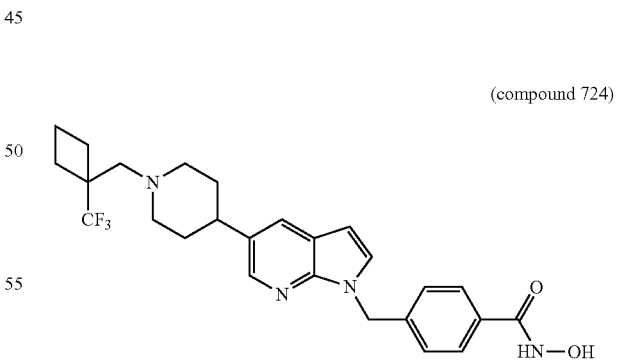

(compound 724)

The compound of formula 6-4 (0.02 g, 0.041 mmol) prepared in step 2, hydroxylamine hydrochloride (0.014 g, 0.21 mmol), potassium hydroxide (0.012 g, 0.21 mmol) and an aqueous solution of 50 wt % hydroxylamine (0.053 mL, 0.82 mmol) were dissolved in methanol (10 mL) at room temperature, and the solution was stirred at the same temperature for 3 hours. The reaction mixture was concentrated under reduced pressure to remove the solvent. Then, the precipitated solid was filtered, washed with sodium hydrogen carbonate, and dried, thereby obtaining the desired compound 724 (0.005 g, 25%) as a white solid.

$^1$H NMR (400 MHz, DMSO-$d_6$) δ 8.15 (d, 1H, J=1.9 Hz), 7.92 (d, 1H, J=1.9 Hz), 7.69 (d, 2H, J=8.2 Hz), 7.40 (d, 1H, J=3.5 Hz), 7.18 (d, 2H, J=8.1 Hz), 6.53 (d, 1H, J=3.5 Hz), 5.53 (s, 2H), 3.03 (d, 2H, J=11.5 Hz), 2.65-2.63 (m, 1H), 2.64 (s, 2H), 2.40-2.18 (m, 6H), 2.04-1.87 (m, 6H); MS (ESI) m/z 487.2 (M$^+$+H).

Example 48

Synthesis of Compound 743

Step 1: Synthesis of methyl 4-((6-chloro-1H-pyrrolo[2,3-b]pyridin-1-yl)methyl)benzoate (formula 3-2)

(formula 3-2)

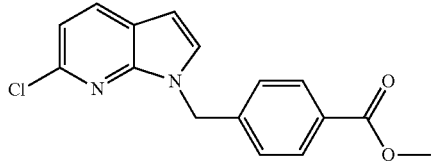

The compound of formula 3-1 (6-chloro-1H-pyrrolo[2,3-b]pyridine) (1.0 g, 6.55 mmol), methyl 4-(bromomethyl)benzoate (1.65 g, 7.21 mmol) and sodium hydride (60.00%, 0.315 g, 7.87 mmol) were dissolved in N,N-dimethylformamide (50 mL) at room temperature, and the solution was stirred at the same temperature for 12 hours. Then, water was added to the reaction mixture, followed by extraction with ethyl acetate. The organic layer was washed with saturated brine, dried with anhydrous sodium sulfate, and then concentrated under reduced pressure. The concentrate was purified by column chromatography (SiO$_2$, 40 g cartridge; ethyl acetate/hexane=from 5% to 10%) to afford the desired compound of formula 3-2 (1.25 g, 63%) as a white solid.

Step 2: Synthesis of methyl 4-((6-(3,6-dihydro-2H-pyran-4-yl)-1H-pyrrolo[2,3-b]pyridin-1-yl)methyl)benzoate (formula 3-3)

(formula 3-3)

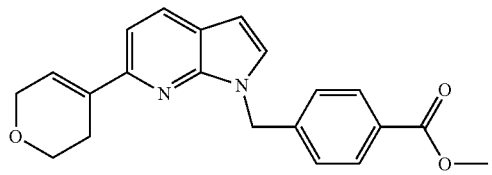

The compound of formula 3-2 (0.5 g, 1.66 mmol) prepared in step 1, 2-(3,6-dihydro-2H-pyran-4-yl)-4,4,5,5-tetramethyl-1,3,2-dioxaborane (0.402 g, 1.91 mmol), sodium carbonate (0.35 g, 3.33 mmol) and Pd(dppf)Cl$_2$ (0.14 g, 0.16 mmol) were added to 1,2-dimethoxyethane (10 mL)/water (5 mL), and heated by microwave irradiation at 120° C. for 20 minutes, followed by cooling to room temperature. After completion of the reaction, water was added to the reaction mixture, followed by extraction with ethyl acetate. The organic layer was washed with a saturated aqueous solution of sodium chloride, dried with anhydrous sodium sulfate, filtered, and then concentrated under reduced pressure. The concentrate was purified by column chromatography (SiO$_2$, 12 g cartridge; ethyl acetate/hexane=from 10% to 20%) to afford the desired compound of formula 3-3 (0.46 g, 79%) as a white solid.

Step 3: Synthesis of 4-((6-(3,6-dihydro-2H-pyran-4-yl)-1H-pyrrolo[2,3-b]pyridin-1-yl)methyl)-N-hydroxybenzamide (compound 743)

(compound 743)

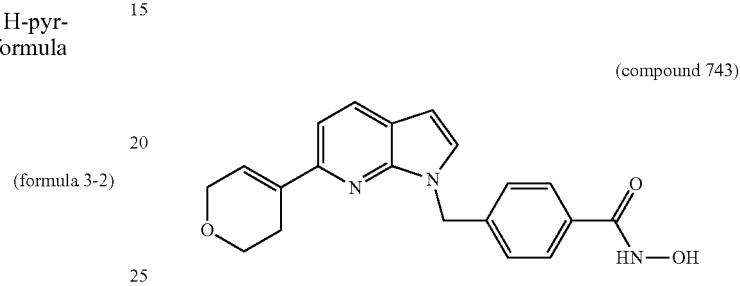

The compound of formula 3-3 (0.150 g, 0.431 mmol) prepared in step 2, hydroxylamine hydrochloride (0.15 g, 2.15 mmol), potassium hydroxide (0.12 g, 2.153 mmol) and an aqueous solution of 50 wt % hydroxylamine (0.55 mL, 8.61 mmol) were dissolved in methanol (10 mL) at room temperature, and the solution was stirred at the same temperature for 3 hours. Then, the reaction mixture was concentrated under reduced pressure to remove the solvent, and water (20 mL) and sodium hydrogen carbonate (10 mL) were added to the concentrate, followed by stirring. Then, the precipitated solid was filtered and dried to afford the desired compound 743 (0.03 g, 20%) as a white solid.

$^1$H NMR (400 MHz, DMSO-$d_6$) δ 7.95 (d, 1H, J=8.2 Hz), 7.67 (d, 2H, J=8.2 Hz), 7.63 (d, 1H, J=3.5 Hz), 7.36 (d, 2H, J=8.2 Hz), 7.34 (d, 1H, J=7.7 Hz), 6.74 (s, 1H), 6.49 (d, 1H, J=3.4 Hz), 5.50 (s, 2H), 4.28 (d, 2H, J=2.6 Hz), 3.85 (t, 2H, J=5.4 Hz), 2.64 (s, 2H); MS (ESI) m/z 350.1 (M$^+$+H).

Example 49

Synthesis of Compound 744

Step 1: Synthesis of tert-butyl 4-(1-(4-(methoxycarbonyl)benzyl)-1H-pyrrolo[2,3-b]pyridin-6-yl)-5,6-dihydropyridine-1(2H)-carboxylate (formula 3-3)

(formula 3-3)

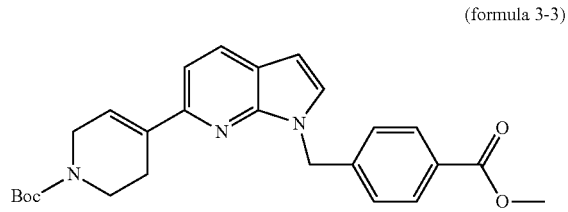 [SMILES: COC(=O)c1ccc(Cn2ccc3ccc(C4=CCN(C(=O)OC(C)(C)C)CC4)nc32)cc1]

The compound of formula 3-2 (methyl 4-((6-chloro-1H-pyrrolo[2,3-b]pyridin-1-yl)methyl)benzoate) (0.50 g, 1.66 mmol), 3,6-dihydro-2H-pyridin-1-tert-butoxycarbonyl-4-boronic acid pinacol ester (0.59 g, 1.91 mmol), sodium carbonate (0.352 g, 3.32 mmol) and Pd(dppf)Cl$_2$ (0.136 g, 0.166 mmol) were added to 1,2-dimethoxyethane (10 mL)/water (5 mL), and heated by microwave irradiation at 120° C. for 20 minutes, followed by cooling to room temperature. After completion of the reaction, water was added to the reaction mixture, followed by extraction with ethyl acetate. The organic layer was washed with a saturated aqueous solution of sodium chloride, dried with anhydrous sodium sulfate, filtered and then concentrated under reduced pressure. The concentrate was purified by column chromatography (SiO$_2$, 12 g cartridge; ethyl acetate/hexane=from 10% to 20%) to afford the desired compound of formula 3-3 (0.55 g, 74%) as a yellow liquid.

Step 2: Synthesis of tert-butyl 4-(1-(4-(hydroxycarbamoyl)benzyl)-1H-pyrrolo[2,3-b]pyridin-6-yl)-5,6-dihydropyridine-1(2H)-carboxylate (compound 744)

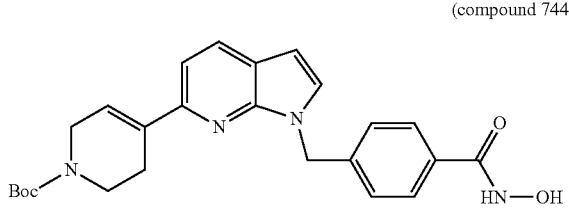 [SMILES: CC(C)(C)OC(=O)N1CC=C(c2ccc3ccn(Cc4ccc(C(=O)NO)cc4)c3n2)CC1]

(compound 744)

The compound of formula 3-3 (0.100 g, 0.223 mmol) prepared in step 1, hydroxylamine hydrochloride (0.078 g, 1.117 mmol), potassium hydroxide (0.063 g, 1.117 mmol) and an aqueous solution of 50 wt % hydroxylamine (0.29 mL, 4.47 mmol) were dissolved in methanol (10 mL) at room temperature, and the solution was stirred at the same temperature for 3 hours. Then, the reaction mixture was concentrated under reduced pressure to remove the solvent, and sodium hydrogen carbonate (20 mL) and water (10 mL) were added to the concentrate, followed by stirring. Then, the precipitated solid was filtered and dried to afford the desired compound 744 (0.088 g, 88%) as a white solid.

$^1$H NMR (400 MHz, DMSO-d$_6$) δ 7.94 (d, 1H, J=8.2 Hz), 7.66 (d, 2H, J=8.2 Hz), 7.61 (d, 1H, J=3.4 Hz), 7.35 (d, 1H, J=8.2 Hz), 7.28 (d, 2H, J=8.2 Hz), 6.67 (s, 1H), 6.48 (d, 1H, J=3.5 Hz), 5.48 (s, 2H), 4.07 (s, 2H), 3.57-3.56 (m, 2H), 2.68 (s, 2H), 1.44 (s, 9H); MS (ESI) m/z 449.1 (M$^+$+H).

Example 50

Synthesis of Compound 746

Step 1: Synthesis of tert-butyl 4-(1-(4-(methoxycarbonyl)benzyl)-1H-pyrrolo[2,3-b]pyridin-5-yl)piperazine-1-carboxylate (formula 2-3)

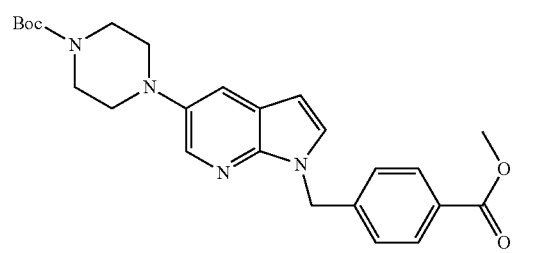

(formula 2-3)

The compound of formula 2-2 (methyl 4-((5-bromo-1H-pyrrolo[2,3-b]pyridin-1-yl)methyl)benzoate) (0.50 g, 1.45 mmol), 1-(tert-butoxycarbonyl)piperazine (0.325 g, 1.74 mmol), Pd(dppf)Cl$_2$([1,1-bis(diphenylphosphino)ferrocene]dichloropalladium (II) (0.074 g, 0.15 mmol) and sodium tert-butoxide (0.17 g, 1.74 mmol) were dissolved in toluene (10 mL) at 120° C., and the solution was stirred at the same temperature for 2 hours, followed by cooling to room temperature. After completion of the reaction, water was added to the reaction mixture, followed by extraction with ethyl acetate. The organic layer was washed with a saturated aqueous solution of sodium chloride, dried with anhydrous magnesium sulfate, filtered and then concentrated under reduced pressure. The concentrate was purified by column chromatography (SiO$_2$, 12 g cartridge; ethyl acetate/hexane=from 20% to 30%) to afford the desired compound of formula 2-3 (0.28 g, 43%) as a white solid.

Step 2: Synthesis of tert-butyl 4-(1-(4-(hydroxycarbamoyl)benzyl)-1H-pyrrolo[2,3-b]pyridine-5-yl)piperazine-1-carboxylate (compound 746)

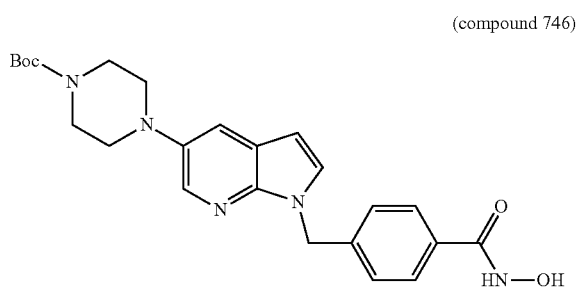 [SMILES: CC(C)(C)OC(=O)N1CCN(c2cnc3c(ccn3Cc3ccc(C(=O)NO)cc3)c2)CC1]

(compound 746)

The compound of formula 2-3 (0.100 g, 0.22 mmol) prepared in step 1, hydroxylamine hydrochloride (0.077 g, 1.11 mmol), potassium hydroxide (0.062 g, 1.110 mmol) and an aqueous solution of 50 wt % hydroxylamine (0.285 mL, 4.44 mmol) were dissolved in methanol (10 mL) at room temperature, and the solution was stirred at the same temperature for 3 hours. Then, the reaction mixture was concentrated under reduced pressure to remove the solvent, and water (20 mL) and sodium hydrogen carbonate (10 mL) were added to the concentrate, followed by stirring. Then, the precipitated solid was filtered, washed with hexane, and dried, thereby obtaining the desired compound 746 (0.084 g, 84%) as a white solid.

$^1$H NMR (400 MHz, DMSO-d$_6$) δ 8.12 (d, 1H, J=2.5 Hz), 7.66 (d, 2H, J=8.2 Hz), 7.58-7.55 (m, 2H), 7.22 (d, 2H, J=8.1 Hz), 6.41 (d, 1H, J=3.4 Hz), 5.46 (s, 2H), 3.50 (s, 4H), 3.03 (t, 4H, J=4.8 Hz), 1.43 (s, 9H); MS (ESI) m/z 452.2 (M$^+$+H).

Example 51

Synthesis of Compound 757

Step 1: Synthesis of methyl 4-((4-chloro-1H-pyrrolo[3,2-c]pyridin-1-yl)methyl)benzoate (formula 11-2)

The compound of formula 11-1 (4-chloro-1H-pyrrolo[3,2-c]pyridine) (0.300 g, 1.966 mmol), methyl 4-(bromoethyl)benzoate (0.495 g, 2.163 mmol) and potassium hydroxide (0.132 g, 2.359 mmol) were dissolved in N,N-dimethylformamide (10 mL) at room temperature, and the solution was stirred at the same temperature for 12 hours. Then, the reaction mixture was concentrated under reduced pressure to remove the solvent, and water (20 mL) was added to the concentrate, followed by stirring. Then, the precipitated solid was filtered, washed with water, and dried, thereby obtaining the desired compound of formula 11-2 (0.497 g, 84.2%) as a white solid.

Step 2: Synthesis of tert-butyl 4-(1-(4-(methoxycarbonyl)benzyl)-1H-pyrrolo[3,2-c]pyridin-4-yl)-5,6-dihydropyridine-1(2H)-carboxylate (formula 11-3)

The compound of formula 11-2 (0.100 g, 0.333 mmol) prepared in step 1, 3,6-dihydro-2H-pyridine-1-tert-butoxycarbonyl-4-boronic acid pinacol ester (0.118 g, 0.382 mmol), $Na_2CO_3$ (0.070 g, 0.665 mmol) and $Pd(dppf)Cl_2$ (0.027 g, 0.033 mmol) were added to 1,2-dimethoxyethane (2 mL)/water (1 mL), and heated by microwave irradiation at 120° C. for 10 minutes, followed by cooling to room temperature. After completion of the reaction, water was added to the reaction mixture, followed by extraction with ethyl acetate. The organic layer was washed with a saturated aqueous solution of sodium chloride, dried with anhydrous sodium sulfate, filtered, and then concentrated under reduced pressure. The concentrate was purified by column chromatography ($SiO_2$, 12 g cartridge; ethyl acetate/hexane=from 20% to 30%) to afford the desired compound of formula 11-3 (0.050 g, 33.6%) as a brown oil.

Step 3: Synthesis of tert-butyl 4-(1-(4-(hydroxycarbamoyl)benzyl)-1H-pyrrolo[3,2-c]pyridin-4-yl)-5,6-dihydropyridine-1(2H)-carboxylate (compound 757)

(compound 757)

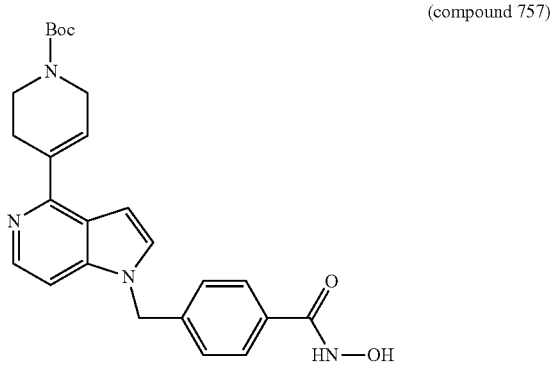 [SMILES: CC(C)(C)OC(=O)N1CC=C(c2nccc3c2ccn3Cc2ccc(C(=O)NO)cc2)CC1]

The compound of formula 11-3 (0.050 g, 0.112 mmol) prepared in step 2, $NH_2OH$ (0.039 g, 0.559 mmol), potassium hydroxide (0.031 g, 0.559 mmol), and an aqueous solution of 50 wt % hydroxylamine (0.144 mL, 2.234 mmol) were dissolved in methanol (5 mL) at room temperature, and the solution was stirred at the same temperature for 3 hours. Then, the reaction mixture was concentrated under reduced pressure to remove the solvent, and sodium hydrogen carbonate (20 mL) and water (10 mL) were added to the concentrate, followed by stirring. Then, the precipitated solid was filtered and dried to afford the desired compound 757 (0.004 g, 8.0%) as a brown solid.

$^1$H NMR (400 MHz, DMSO-$d_6$) δ 8.15 (d, 1H, J=5.7 Hz), 7.68 (d, 2H, J=8.0 Hz), 7.64 (d, 1H, J=3.1 Hz), 7.41 (d, 1H, J=5.7 Hz), 7.23 (d, 2H, J=8.0 Hz), 6.85 (d, 1H, J=3.0 Hz), 6.54 (m, 1H), 5.50 (s, 2H), 4.11 (m, 2H), 3.58-3.56 (m, 2H), 2.72 (m, 2H), 1.45 (s, 9H); MS (ESI) m/z 449.2 (M$^+$+H).

Example 52

Synthesis of Compound 758

Step 1: Synthesis of methyl 4-((5-chloro-1H-pyrrolo[3,2-b]pyridin-1-yl)methyl)benzoate (formula 11-2)

The compound of formula 11-1 (5-chloro-1H-pyrrolo[3,2-b]pyridine) (0.300 g, 1.966 mmol), methyl 4-(bromomethyl)benzoate (0.495 g, 2.163 mmol) and potassium hydroxide (0.132 g, 2.359 mmol) were dissolved in N,N-dimethylformamide (10 mL) at room temperature, and the solution was stirred at the same temperature for 12 hours. Then, the reaction mixture was concentrated under reduced pressure to remove the solvent, and water (20 mL) was added to the concentrate, followed by stirring. Then, the precipitated solid was filtered, washed with water, and dried to afford the desired compound (0.488 g, 82.7%) as a white solid.

Step 2: Synthesis of tert-butyl 4-(1-(4-(methoxycarbonyl)benzyl)-1H-pyrrolo[3,2-b]pyridin-5-yl)-5,6-dihydropyridine-1(2H)-carboxylate (formula 11-3)

The compound of formula 11-2 (0.100 g, 0.333 mmol) prepared in step 1, 3, 6-dihydro-2H-pyridine-1-tert-butoxycarbonyl-4-boronic acid pinacol ester (0.118 g, 0.382 mmol), $Na_2CO_3$ (0.070 g, 0.665 mmol) and $Pd(dppf)Cl_2$ (0.027 g, 0.033 mmol) were added to 1,2-dimethoxyethane (2 mL)/water (1 mL), and heated by microwave irradiation at 120° C. for 10 minutes, followed by cooling to room temperature. After completion of the reaction, water was added to the reaction mixture, followed by extraction with ethyl acetate. The organic layer was washed with a saturated aqueous solution of sodium chloride, dried with anhydrous sodium sulfate, filtered, and then concentrated under reduced pressure. The concentrate was purified by column chromatography ($SiO_2$, 12 g cartridge; ethyl acetate/hexane=from 20% to 30%) to afford the desired compound of formula 11-3 (0.050 g, 33.6%) as a white solid.

Step 3: Synthesis of tert-butyl 4-(1-(4-(hydroxycarbamoyl)benzyl)-1H-pyrrolo[3,2-b]pyridin-5-yl)-5,6-dihydropyridine-1(2H)-carboxylate (compound 758)

(compound 758)

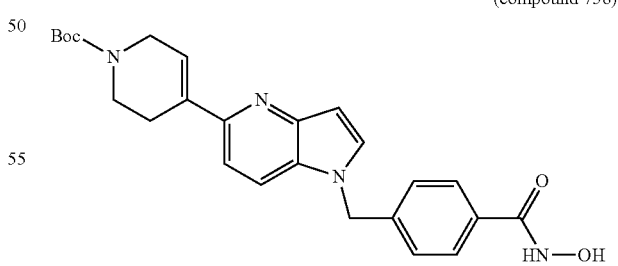

The compound of formula 11-3 (0.050 g, 0.112 mmol) prepared in step 2, $NH_2OH$ (0.039 g, 0.559 mmol), potassium hydroxide (0.031 g, 0.559 mmol), and an aqueous solution of 50 wt % hydroxylamine (0.144 mL, 2.234 mmol) were dissolved in methanol (5 mL) at room temperature, and the solution was stirred at the same temperature for 3 hours. Then, the reaction mixture was concentrated under reduced pressure to remove the solvent, and sodium hydrogen carbonate (20 mL) and water (10 mL) were added to the concentrate, followed by stirring. Then, the precipitated solid was filtered and dried to afford the desired compound 758 (0.021 g, 41.9%) as a white solid.

$^1$H NMR (400 MHz, DMSO-$d_6$) δ 7.84 (d, 1H, J=8.7 Hz), 7.78 (d, 1H, J=3.2 Hz), 7.67 (d, 2H, J=8.0 Hz), 7.37 (d, 1H, J=8.7 Hz), 7.19 (d, 1H, J=7.9 Hz), 6.59 (d, 1H, J=3.1 Hz), 6.52 (m, 1H), 5.46 (s, 2H), 4.03 (m, 2H), 3.56-3.53 (m, 2H), 2.65 (m, 2H), 1.43 (s, 9H); MS (ESI) m/z 449.1 (M$^+$+H).

Example 53

Synthesis of Compound 759 (N-hydroxy-4-((4-(4-(2-hydroxy-2-methylpropyl)piperazin-1-yl)-1H-pyrrolo[2,3-b]pyridin-1-yl)methyl)benzamide)

(compound 759)

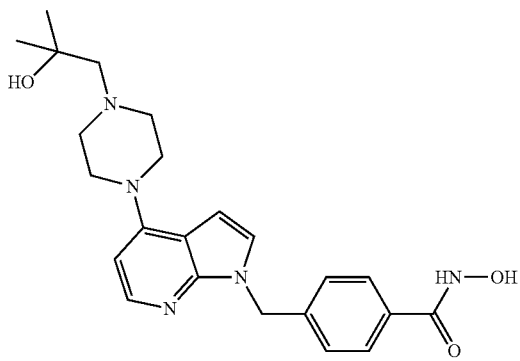

The compound of formula 8-2 (methyl 4-((4-(4-(2-hydroxy-2-methylpropyl)piperazin-1-yl)-1H-pyrrolo[2,3-b]pyridin-1-yl)methyl)benzoate) (0.10 g, 0.24 mmol) was dissolved in methanol (2 mL)/tetrahydrofuran (1 mL) at room temperature. To the solution, potassium hydroxide (0.07 g, 1.18 mmol) and an aqueous solution of 50 wt % hydroxylamine (0.08 g, 2.36 mmol) were added, followed by stirring at the same temperature for 3 hours. Then, the reaction mixture was concentrated under reduced pressure to remove the solvent, and a saturated aqueous solution of sodium carbonate was added to the concentrate, followed by extraction with ethyl acetate. The organic layer was washed with a saturated aqueous solution of sodium chloride, dried with anhydrous magnesium sulfate, and then concentrated under reduced pressure. Diethyl ether (1 mL) was added to the concentrate, followed by stirring. Then, the precipitated solid was filtered and dried to afford the desired compound 759 (0.07 g, 69%) as a white solid.

$^1$H NMR (400 MHz, CH$_3$OD) δ 7.93 (d, 1H, J=5.7 Hz), 7.61 (d, 1H, J=8.2 Hz), 7.15 (m, 3H), 6.55 (d, 1H, J=3.6 Hz), 6.48 (d, 1H, J=5.7 Hz), 5.44 (s, 2H), 3.51 (m, 4H), 2.84 (m, 4H), 2.44 (s, 2H), 1.81 (s, 6H), 1.20 (s, 6H); MS (ESI) m/z 424.2 (M$^+$+H).

Example 54

Synthesis of Compound 760

Step 1: Synthesis of tert-butyl 4-hydroxy-4-((4-(1-(4-(methoxycarbonyl)benzyl)-1H-pyrrolo[2,3-b]pyridin-4-yl)piperazin-1-yl)methyl)piperidine-1-carboxylate (formula 8-2)

(formula 8-2)

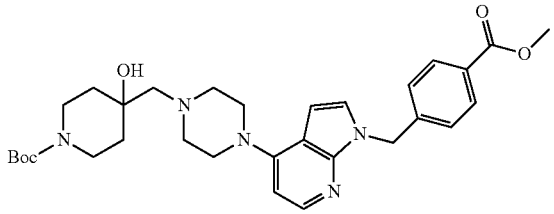

The compound of formula 8-1 (methyl 4-((4-(piperazin-1-yl)-1H-pyrrolo[2,3-b]pyridin-1-yl)methyl)benzoate hydrochloride) (0.12 g, 0.31 mmol), tert-butyl 1-oxa-6-azaspiro[2,5]octane-6-carboxylate (0.20 g, 0.93 mmol) and potassium carbonate (0.09 g, 0.62 mmol) were added to ethanol (6 mL), and heated by microwave irradiation at 120° C. for 20 minutes, followed by cooling to room temperature. Then, the reaction mixture was concentrated under reduced pressure to remove the solvent, and water was added to the concentrate, followed by extraction with ethyl acetate. The organic layer was washed with a saturated aqueous solution of sodium chloride, dried with anhydrous magnesium sulfate, and then concentrated under reduced pressure. The product was used without additional purification (0.17 g, 97%, yellow oil).

Step 2: Synthesis of tert-butyl 4-fluoro-4-((4-(1-(4-(methoxycarbonyl)benzyl)-1H-pyrrolo[2,3-b]pyridin-4-yl)piperazin-1-yl)methyl)piperidine-1-carboxylate (formula 8-3)

(formula 8-3)

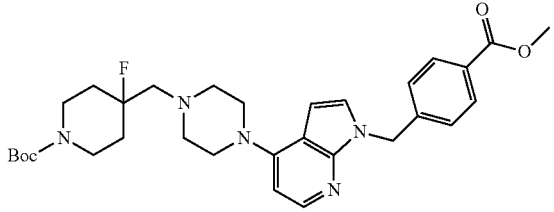

The compound of formula 8-2 (0.16 g, 0.28 mmol) prepared in step 1 was dissolved in dichloromethane (6 mL) at 0° C. To the solution, (diethylamino)sulfur trifluoride (0.06 g, 0.37 mmol) was added, followed by stirring at room temperature for 5 hours. Then, a saturated aqueous solution of sodium carbonate was added to the reaction mixture, followed by extraction with ethyl acetate. The organic layer was washed with a saturated aqueous solution of sodium chloride, dried with anhydrous magnesium sulfate, and then concentrated under reduced pressure. The product was used without additional purification (0.15 g, 93%, yellow oil).

Step 3: Synthesis of tert-butyl 4-fluoro-4-((4-(1-(4-(hydroxycarbamoyl)benzyl)-1H-pyrrolo[2,3-b]pyridin-4-yl)piperazin-1-yl)methyl)piperidine-1-carboxylate (compound 760)

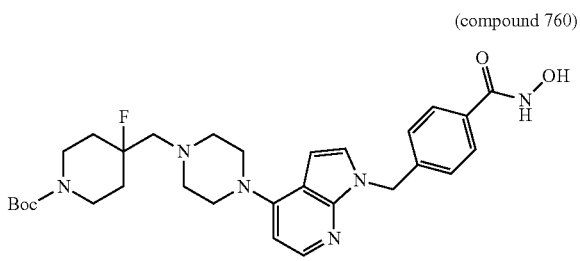 [SMILES: CC(C)(C)OC(=O)N1CCC(F)(CN2CCN(c3ccnc4c3ccn4Cc3ccc(C(=O)NO)cc3)CC2)CC1]

(compound 760)

The compound of formula 8-3 (0.14 g, 0.25 mmol) prepared in step 2 was dissolved in methanol (2 mL)/tetrahydrofuran (1 mL) at room temperature. To the solution, potassium hydroxide (0.07 g, 1.24 mmol) and an aqueous solution of 50 wt % hydroxylamine (0.08 g, 2.47 mmol) were added, followed by stirring at the same temperature for 3 hours. Then, a saturated aqueous solution of sodium carbonate was added to the reaction mixture, followed by extraction with ethyl acetate. The organic layer was washed with a saturated aqueous solution of sodium chloride, dried with anhydrous magnesium sulfate, and then concentrated under reduced pressure. Diethyl ether (1 mL) was added to the concentrate, followed by stirring. Then, the precipitated solid was filtered and dried to afford the desired compound 760 (0.11 g, 78%) as a white solid.

$^1$H NMR (400 MHz, CH$_3$OD) δ 7.96 (d, 1H, J=5.7 Hz), 7.65 (d, 1H, J=8.2 Hz), 7.19 (m, 3H), 6.59 (d, 1H, J=3.6 Hz), 6.51 (d, 1H, J=5.8 Hz), 5.47 (s, 2H), 3.89-3.85 (m, 2H), 3.50 (m, 4H), 3.08 (m, 2H), 2.75 (m, 4H), 2.62 (s, 1H), 2.56 (s, 1H), 1.90 (m, 2H), 1.68 (m, 2H), 1.27 (s, 9H); MS (ESI) m/z 567.2 (M$^+$+H).

Example 55

Synthesis of Compound 761

Step 1: Synthesis of methyl 4-((4-(3-formylphenyl)-1H-pyrrolo[2,3-b]pyridin-1-yl)methyl)benzoate (formula 1-3)

(formula 1-3)

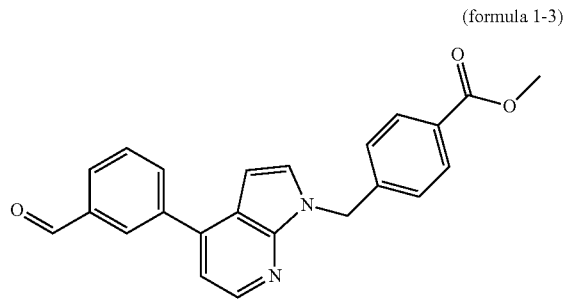 [SMILES: COC(=O)c1ccc(Cn2ccc3c(-c4cccc(C=O)c4)ccnc32)cc1]

The compound of formula 1-2 (0.30 g, 0.87 mmol), 3-formylphenylboronic acid (0.15 g, 1.04 mmol), Pd(dppf)Cl$_2$ (0.07 g, 0.09 mmol) and sodium carbonate (0.18 g, 1.74 mmol) were added to dimethoxyethane (9 mL)/water (3 mL), and heated by microwave irradiation 120° C. for 15 minutes, followed by cooling to room temperature. The reaction mixture was filtered through a celite pad to remove solids, and a saturated aqueous solution of sodium carbonate was added to the filtrate, followed by extraction with ethyl acetate. The organic layer was washed with a saturated aqueous solution of sodium chloride, dried with anhydrous magnesium sulfate, and then concentrated under reduced pressure. The concentrate was purified by column chromatography (SiO$_2$, 12 g cartridge; ethyl acetate/hexane=from 10% to 30%) to afford the desired compound (0.25 g, 77%) as a white solid.

Step 2: Synthesis of methyl 4-((4-(3-(morpholinomethyl)phenyl)-1H-pyrrolo[2,3-b]pyridin-1-yl)methyl)benzoate (formula 1-4)

(formula 1-4)

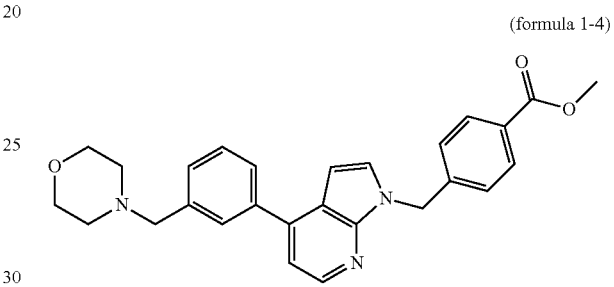

The compound of formula 1-3 (0.07 g, 0.19 mmol) prepared in step 1, and morpholine (0.02 g, 0.19 mmol) were dissolved in dichloromethane (2 mL) at room temperature, and acetic acid (0.02 g, 0.38 mmol) was added thereto, followed by stirring for 10 minutes. NaBH$_3$CN (0.01 g, 0.23 mmol) was added to the stirred solution, followed by stirring at the same temperature for 8 hours. Then, water added to the reaction mixture, followed by extraction with ethyl acetate. The organic layer was washed with a saturated aqueous solution of sodium chloride, dried with anhydrous magnesium sulfate, and then concentrated under reduced pressure. The concentrate was purified by column chromatography (SiO$_2$, 4 g cartridge; ethyl acetate/hexane=from 20% to 40%) to afford the desired compound (0.05 g, 65%) as a white solid.

Step 3: Synthesis of N-hydroxy-4-((4-(3-(morpholinomethyl)phenyl)-1H-pyrrolo[2,3-b]pyridin-1-yl)methyl)benzamide (compound 761)

(compound 761)

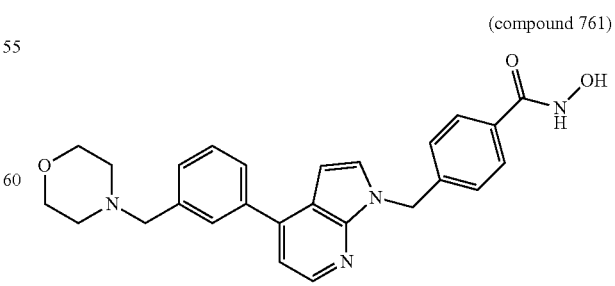

The compound of formula 1-4 (0.05 g, 0.11 mmol) prepared in step 2 was dissolved in methanol (2 mL)/ tetrahydrofuran (1 mL) at room temperature. To the solution, potassium hydroxide (0.03 g, 0.56 mmol) and an aqueous solution of 50 wt % hydroxylamine (0.04 g, 1.13 mmol) were added, followed by stirring at the same temperature for 3 hours. Then, the reaction mixture was concentrated under reduced pressure to remove the solvent, and a saturated aqueous solution of sodium carbonate was added to the concentrate, followed by extraction with ethyl acetate. The organic layer was washed with a saturated aqueous solution of sodium chloride, dried with anhydrous magnesium sulfate, and then concentrated under reduced pressure. Diethyl ether (1 mL) was added to the concentrate, followed by stirring. Then, the precipitated solid was filtered and dried to afford the desired compound 761 (0.04 g, 89%) as a white solid.

$^1$H NMR (400 MHz, CH$_3$OD) δ 8.31 (d, 1H, J=5.0 Hz), 7.77 (d, 2H, J=8.2 Hz), 7.69 (d, 2H, J=8.4 Hz), 7.54 (d, 2H, J=8.2 Hz), 7.50 (d, 1H, J=3.6 Hz), 7.28 (d, 2H, J=8.5 Hz), 6.75 (d, 1H, J=3.6 Hz), 5.61 (s, 2H), 3.73 (t, 4H, J=4.7 Hz), 3.63 (s, 2H), 2.53 (m, 4H); MS (ESI) m/z 443.1 (M$^+$+H).

Example 56

Synthesis of Compound 762

Step 1: Synthesis of methyl 4-((4-(4-formylphenyl)-1H-pyrrolo[2,3-b]pyridin-1-yl)methyl)benzoate (formula 1-3)

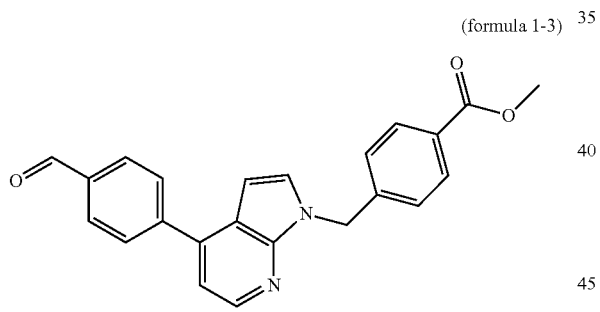

(formula 1-3)

The compound of formula 1-2 (methyl 4-((4-bromo-1H-pyrrolo[2,3-b]pyridin-1-yl)methyl)benzoate) (0.30 g, 0.87 mmol), 4-formylphenylboronic acid (0.15 g, 1.04 mmol), Pd(dppf)Cl$_2$ (0.07 g, 0.09 mmol) and sodium carbonate (0.18 g, 1.74 mmol) were added to dimethoxyethane (9 mL)/water (3 mL), and heated by microwave irradiation at 120° C. for 15 minutes, followed by cooling to room temperature. The reaction mixture was filtered through a celite pad to remove solids, and a saturated aqueous solution of sodium hydrogen carbonate was added to the filtrate, followed by extraction with ethyl acetate. The organic layer was washed with a saturated aqueous solution of sodium chloride, dried with anhydrous magnesium sulfate, and then concentrated under reduced pressure. The concentrate was purified by column chromatography (SiO$_2$, 12 g cartridge; ethyl acetate/hexane=from 10% to 30%) to afford the desired compound of formula 1-3 (0.23 g, 71%) as a white solid.

Step 2: Synthesis of 4-((4-(4-(morpholinomethyl)phenyl)-1H-pyrrolo[2,3-b]pyridin-1-yl)methyl)benzoate (formula 1-4)

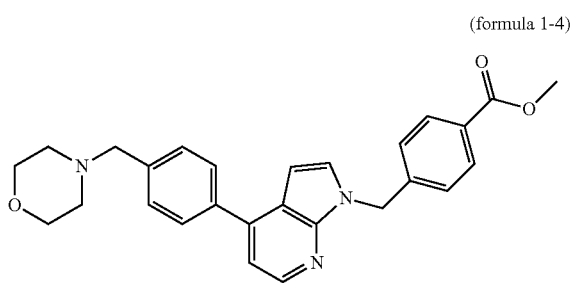 [SMILES: COC(=O)c1ccc(Cn2ccc3c(-c4ccc(CN5CCOCC5)cc4)ccnc32)cc1]

(formula 1-4)

The compound of formula 1-3 (0.07 g, 0.19 mmol) prepared in step 1, and morpholine (0.02 g, 0.19 mmol) were dissolved in dichloromethane (2 mL) at room temperature, and acetic acid (0.02 g, 0.38 mmol) was added thereto, followed by stirring for 10 minutes. NaBH$_3$CN (0.01 g, 0.23 mmol) was added to the stirred solution, followed by stirring at the same temperature for 8 hours. Then, water added to the reaction mixture, followed by extraction with ethyl acetate. The organic layer was washed with a saturated aqueous solution of sodium chloride, dried with anhydrous magnesium sulfate, and then concentrated under reduced pressure. The concentrate was purified by column chromatography (SiO$_2$, 4 g cartridge; ethyl acetate/hexane=from 20% to 40%) to afford the desired compound of formula 1-4 (0.04 g, 47%) as a white solid.

Step 3: Synthesis of N-hydroxy-4-((4-(4-(morpholinomethyl)phenyl)-1H-pyrrolo[2,3-b]pyridin-1-yl)methyl)benzamide (compound 762)

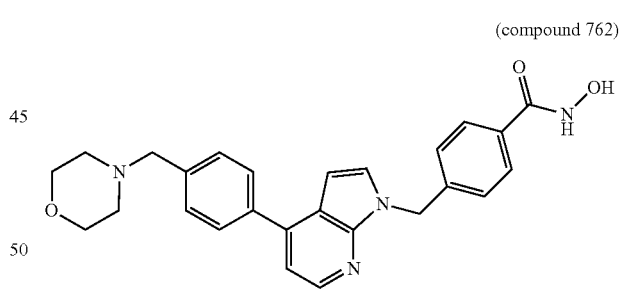

(compound 762)

The compound of formula 1-4 (0.05 g, 0.11 mmol) prepared in step 2 was dissolved in methanol (2 mL)/tetrahydrofuran (1 mL) at room temperature. To the solution, potassium hydroxide (0.03 g, 0.45 mmol) and an aqueous solution of 50 wt % hydroxylamine (0.03 g, 0.91 mmol) were added, followed by stirring at the same temperature for 3 hours. Then, the reaction mixture was concentrated under reduced pressure to remove the solvent, and a saturated aqueous solution of sodium carbonate was added to the concentrate, followed by extraction with ethyl acetate. The organic layer was washed with a saturated aqueous solution of sodium chloride, dried with anhydrous magnesium sulfate, and then concentrated under reduced pressure. Diethyl ether (1 mL) was added to the concentrate, followed by stirring. Then, the precipitated solid was filtered and dried to afford the desired compound 762 (0.03 g, 79%) as a white solid.

$^1$H NMR (400 MHz, CH$_3$OD) δ 8.32 (d, 1H, J=5.0 Hz), 7.79 (s, 1H), 7.70 (m, 3H), 7.52 (m, 3H), 7.28 (m, 3H), 6.76 (d, 1H, J=3.6 Hz), 5.63 (s, 2H), 3.73 (t, 4H, J=4.6 Hz), 3.66 (s, 2H), 2.55 (m, 4H); MS (ESI) m/z 443.1 (M$^+$+H).

Example 57

Synthesis of Compound 763

Step 1: Synthesis of tert-butyl 4-(3-(1-(4-(methoxycarbonyl)benzyl)-1H-pyrrolo[2,3-b]pyridin-4-yl)benzyl)piperazine-1-carboxylate (formula 24-1)

(formula 24-1)

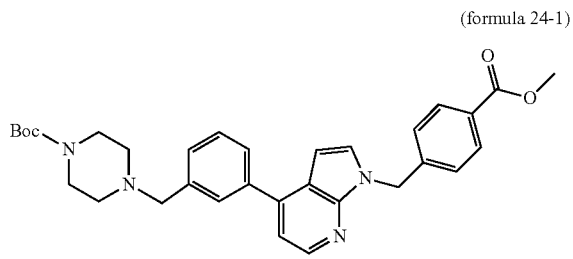 [SMILES: COC(=O)c1ccc(Cn2ccc3c(-c4cccc(CN5CCN(C(=O)OC(C)(C)C)CC5)c4)ccnc32)cc1]

The compound of formula 1-3 (4-((4-(4-formylphenyl)-1H-pyrrolo[2,3-b]pyridin-1-yl)methyl)benzoate) (0.15 g, 0.41 mmol) and tert-butyl piperazine-1-carboxylate (0.08 g, 0.41 mmol) were dissolved in dichloromethane (6 mL) at room temperature, and acetic acid (0.05 g, 0.81 mmol) was added thereto, followed by stirring for 10 minutes. NaBH$_3$CN (0.03 g, 0.49 mmol) was added to the stirred solution, followed by stirring at the same temperature for 8 hours. Then, water added to the reaction mixture, followed by extraction with ethyl acetate. The organic layer was washed with a saturated aqueous solution of sodium chloride, dried with anhydrous magnesium sulfate, and then concentrated under reduced pressure. The concentrate was purified by column chromatography (SiO$_2$, 12 g cartridge; ethyl acetate/hexane=from 20% to 40%) to afford the desired compound of formula 24-1 (0.11 g, 50%) as a white solid.

Step 2: Synthesis of methyl 4-((4-(4-(piperazin-1-ylmethyl)phenyl)-1H-pyrrolo[2,3-b]pyridin-1-yl)methyl)benzoate hydrochloride (formula 24-2)

(formula 24-2)

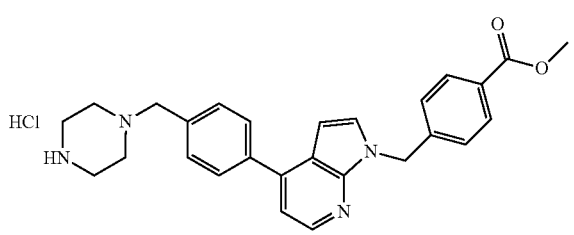

The compound of formula 24-1 (0.08 g, 0.15 mmol) prepared in step 1 was dissolved in dichloromethane (2 mL) at room temperature, and hydrochloric acid (4.00 M solution in 1,4-dioxane, 0.04 mL, 0.18 mmol) was added thereto, followed by stirring at the same temperature for 2 hours. Then, the precipitated solid was filtered and dried to afford the desired compound of formula 24-2 (0.07 g, 99%) as a white solid.

Step 3: Synthesis of methyl 4-((4-(4-((4-(2-hydroxy-2-methylpropyl)piperazin-1-yl)methyl)phenyl)-1H-pyrrolo[2,3-b]pyridin-1-yl)methyl)benzoate (formula 24-3)

(formula 24-3)

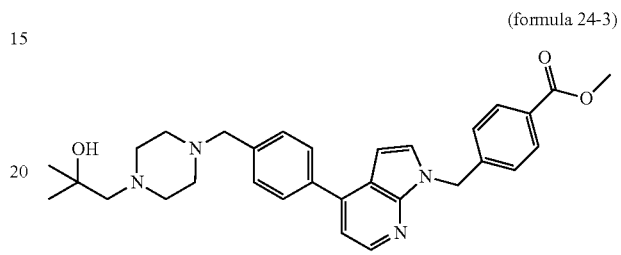

The compound of formula 24-2 (0.09 g, 0.20 mmol) prepared in step 2, 2,2-dimethyloxirane (0.07 g, 0.99 mmol), and potassium carbonate (0.05 g, 0.40 mmol) were added to ethanol (8 mL), and heated by microwave irradiation at 120° C. for 20 minutes, followed by cooling to room temperature. After completion of the reaction, the reaction mixture was concentrated under reduced pressure to remove the solvent, and water was added to the concentrate, followed by extraction with ethyl acetate. The organic layer was washed with a saturated aqueous solution of sodium chloride, dried with anhydrous magnesium sulfate, filtered, and then concentrated under reduced pressure. The product was used without additional purification (0.10 g, 97%, colorless oil).

Step 4: Synthesis of methyl 4-((4-(4-((4-(2-fluoro-2-methylpropyl)piperazin-1-yl)methyl)phenyl)-1H-pyrrolo[2,3-b]pyridin-1-yl)methyl)benzoate (formula 24-4)

(formula 24-4)

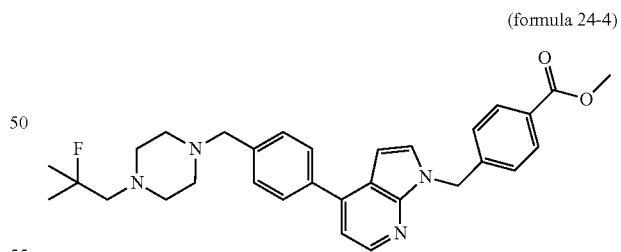

The compound of formula 24-3 (0.10 g, 0.19 mmol) prepared in step 3 was dissolved in methylene chloride (4 mL) at 0° C., and DAST (0.04 g, 0.25 mmol) was added thereto, followed by stirring at room temperature for 5 hours. Then, a saturated aqueous solution of sodium hydrogen carbonate was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO2, 12 g cartridge; ethyl acetate/hexane=from 20% to 40%) to afford the desired compound of formula 24-4 (0.06 g, 64%) as a white solid.

Step 5: Synthesis of 4-((4-(4-((4-(2-fluoro-2-methylpropyl)piperazin-1-yl)methyl)phenyl)-1H-pyrrolo[2,3-b]pyridin-1-yl)methyl)-N-hydroxybenzamide (compound 763)

(compound 763)

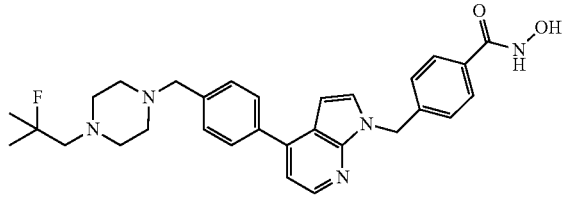

The compound of formula 24-4 (0.06 g, 0.12 mmol) was dissolved in tetrahydrofuran (1 mL)/methanol (3 mL) at room temperature. To the solution, potassium hydroxide (0.03 g, 0.63 mmol) and an aqueous solution of hydroxylamine (50.00%, 0.04 g, 1.26 mmol) were added, followed by stirring at the same temperature for 5 hours. Then, a saturated aqueous solution of sodium hydrogen carbonate was added to the reaction mixture, followed by extraction with ethyl acetate. The organic layer was washed with a saturated aqueous solution of sodium chloride, dried with anhydrous magnesium sulfate, filtered, and then concentrated under reduced pressure to obtain the desired compound 763 (0.05 g, 76%, white solid). The obtained compound was used without additional purification.

$^1$H NMR (400 MHz, CH$_3$OD) δ 8.30 (m, 1H), 7.75 (d, 1H, J=8.3 Hz), 7.71 (d, 1H, J=8.3 Hz), 7.59 (m, 1H), 7.47-7.41 (m, 6H), 7.12 (t, 1H, J=4.9 Hz), 6.24 (m, 1H), 5.62 (d, 2H, J=10.6 Hz), 3.50 (d, 2H, J=13.7 Hz), 2.36-2.31 (m, 6H), 2.22 (m, 4H), 1.30-1.22 (m, 6H); MS (ESI) m/z 516.2 (M$^+$+H).

Example 58

Synthesis of Compound 764

Step 1: Synthesis of methyl 4-((4-(4-(2-ethyl-2-hydroxybutyl)piperazin-1-yl)-1H-pyrrolo[2,3-b]pyridin-1-yl)methyl)benzoate (formula 8-2)

(formula 8-2)

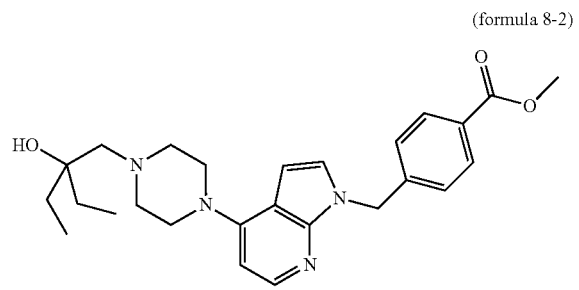 [SMILES: CCC(O)(CC)CN1CCN(c2ccnc3c2ccn3Cc2ccc(C(=O)OC)cc2)CC1]

The compound of formula 8-1 (methyl 4-((4-(piperazin-1-yl)-1H-pyrrolo[2,3-b]pyridin-1-yl)methyl)benzoate hydrochloride) (0.28 g, 0.724 mmol), 2,2-diethyloxirane (0.36 g, 3.62 mmol), and potassium carbonate (0.20 g, 1.44 mmol) were added to ethanol (8 mL), and heated by microwave irradiation at 120° C. for 20 minutes, followed by cooling to room temperature. After completion of the reaction, the reaction mixture was concentrated under reduced pressure to remove the solvent, and water was added to the concentrate, followed by extraction with ethyl acetate. The organic layer was washed with a saturated aqueous solution of sodium chloride, dried with anhydrous magnesium sulfate, filtered, and then concentrated under reduced pressure. The product was used without additional purification (0.27 g, 84%, yellow oil).

Step 2: Synthesis of methyl 4-((4-(4-(2-ethyl-2-fluorobutyl)piperazin-1-yl)-1H-pyrrolo[2,3-b]pyridin-1-yl)methyl)benzoate (formula 8-3)

(formula 8-3)

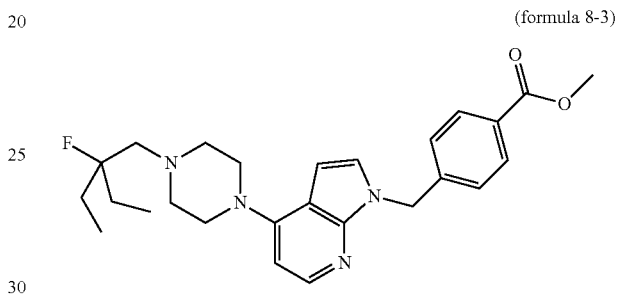

The compound of formula 8-2 (0.25 g, 0.55 mmol) prepared in step 1 was dissolved in methylene chloride (10 mL) at 0° C., and DAST (0.11 g, 0.72 mmol) was added thereto, followed by stirring at room temperature for 5 hours. Then, a saturated aqueous solution of sodium hydrogen carbonate was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; ethyl acetate/hexane=from 20% to 40%) to afford the desired compound (0.11 g, 43%) as a white solid.

Step 3: Synthesis of 4-((4-(4-(2-ethyl-2-fluorobutyl)piperazin-1-yl)-1H-pyrrolo[2,3-b]pyridin-1-yl)methyl)-N-hydroxybenzamide (compound 764)

(compound 764)

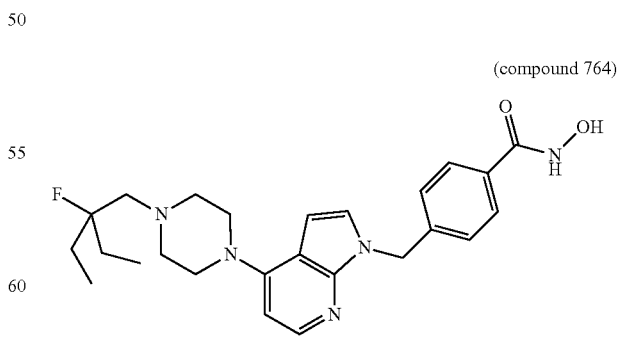

The compound of formula 8-3 (0.11 g, 0.24 mmol) prepared in step 2 was dissolved in tetrahydrofuran (1 mL)/methanol (4 mL) at room temperature, and potassium hydroxide (0.07 g, 1.21 mmol) and an aqueous solution of 50 wt % hydroxylamine (0.16 g, 2.43 mmol) were added thereto, followed by stirring at the same temperature for 5 hours. Then, the reaction solution was concentrated under reduced pressure to remove the solvent, and a saturated aqueous solution of sodium hydrogen carbonate was added to the concentrate, followed by extraction with ethyl acetate. The organic layer was washed with a saturated aqueous solution of sodium chloride, dried with anhydrous magnesium sulfate, filtered, and then concentrated under reduced pressure to obtain the desired compound 764 (0.07 g, 61%, white solid). The obtained compound was used without additional purification.

$^1$H NMR (400 MHz, CH$_3$OD) δ 7.98 (m, 1H), 7.74-7.66 (m, 2H), 7.23-7.19 (m, 3H), 6.62 (d, 1H, J=3.7 Hz), 6.54 (d, 1H, J=5.7 Hz), 5.50 (d, 2H, J=10.7 Hz), 3.54 (t, 4H, J=4.8 Hz), 2.77 (t, 4H, J=4.8 Hz), 2.60 (s, 1H), 2.54 (s, 1H), 1.80-1.73 (m, 4H), 0.94 (t, 6H, J=7.5 Hz); MS (ESI) m/z 516.2 (M$^+$+H).

Example 59

Synthesis of Compound 781

Step 1: Synthesis of methyl 4-((5-(1-(3-fluorobenzyl)piperidin-4-yl)-1H-pyrrolo[2,3-b]pyridin-1-yl)methyl)benzoate (formula 6-4)

(formula 6-4)

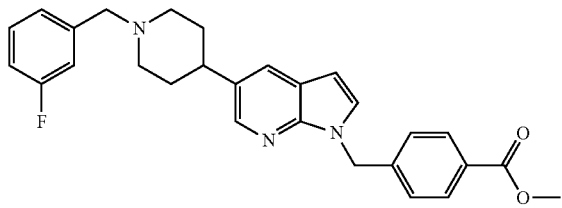

The compound of formula 6-3 (methyl 4-((5-(piperidin-4-yl)-1H-pyrrolo[2,3-b]pyridin-1-yl)methyl)benzoate) (0.100 g, 0.286 mmol) prepared in step 1 of Example 47, 1-(bromomethyl)-3-fluorobenzene (0.039 mL, 0.315 mmol) and cesium carbonate (0.112 g, 0.343 mmol) were dissolved in acetonitrile (10 mL) at room temperature, and the solution was stirred at room temperature for 12 hours. After completion of the reaction, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO2, 12 g cartridge; ethyl acetate/hexane=from 20% to 30%) to afford the desired compound of formula 6-4 (0.053 g, 40.5%) as a white solid.

Step 2: Synthesis of 4-((5-(1-(3-fluorobenzyl)piperidin-4-yl)-1H-pyrrolo[2,3-b]pyridin-1-yl)methyl)-N-hydroxybenzamide (compound 781)

(compound 781)

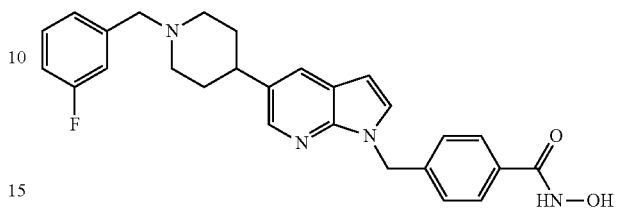

The compound of formula 6-4 (0.050 g, 0.109 mmol) prepared in step 1, hydroxylamine hydrochloride (0.038 g, 0.546 mmol), potassium hydroxide (0.031 g, 0.546 mmol) and an aqueous solution of 50 wt % hydroxylamine (0.140 mL, 2.186 mmol) were dissolved in methanol (30 mL) at room temperature, and the solution was stirred at the same temperature for 3 hours. Then, the reaction mixture was concentrated under reduced pressure to remove the solvent, and sodium hydrogen carbonate (20 mL) and water (10 mL) were added to the concentrate, followed by stirring. Then, the precipitated solid was filtered, washed with water, and dried, thereby obtaining the desired compound 781 (0.025 g, 49.1%) as a white solid.

$^1$H NMR (400 MHz, DMSO-d$_6$) δ 8.17 (d, 1H, J=2.0 Hz), 7.86 (d, 1H, J=2.0 Hz), 7.65 (d, 2H, J=8.3 Hz), 7.60 (d, 1H, J=3.4 Hz), 7.39-7.37 (m, 1H), 7.23-7.15 (m, 5H), 6.45 (d, 1H, J=3.4 Hz), 5.48 (s, 2H), 3.54 (s, 2H), 2.93 (d, 2H, J=11.4 Hz), 2.56-2.53 (m, 2H), 1.79-1.76 (m, 3H); MS (ESI) m/z 459.1 (H$^+$+H)

Example 60

Synthesis of Compound 783

Step 1: Synthesis of tert-butyl 4-(1-(4-(hydroxycarbamoyl)benzyl)-1H-pyrrolo[3,2-c]pyridin-6-yl)-5,6-dihydropyridine-1(2H)-carboxylate (formula 11-3)

(formula 11-3)

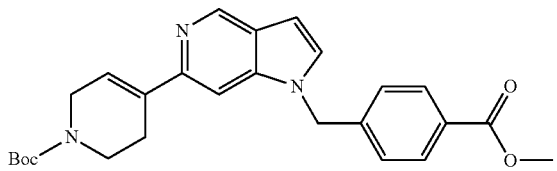

The compound of formula 11-2 (methyl 4-((6-chloro-1H-pyrrolo[3,2-c]pyridin-1-yl)methyl)benzoate) (0.100 g, 0.333 mmol), 3,6-dihydro-2H-pyridine-1-tert-butoxycarbonyl-4-boronic acid pinacol ester (0.118 g, 0.382 mmol), Na$_2$CO$_3$ (0.070 g, 0.665 mmol) and Pd(dppf)Cl$_2$ (0.027 g, 0.033 mmol) were added to 1,2-dimethoxyethane (2 mL)/water (1 mL), and heated by microwave irradiation at 120° C. for 10 minutes, followed by cooling to room temperature. After completion of the reaction, the reaction mixture was concentrated under reduced pressure to remove the solvent, and water was added to the concentrate, followed by extraction Step 2: Synthesis of tert-butyl 4-(1-(4-(hydroxycarbamoyl)benzyl)-1H-pyrrolo[3,2-c]pyridin-6-yl)-5,6-dihydropyridine-1(2H)-carboxylate (compound 783)

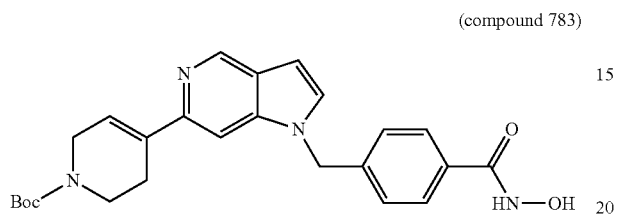

(compound 783)

The compound of formula 11-3 (0.050 g, 0.112 mmol) prepared in step 1, NH₂OH (0.039 g, 0.559 mmol), potassium hydroxide (0.031 g, 0.559 mmol), and an aqueous solution of 50 wt % hydroxylamine solution in water (0.144 mL, 2.234 mmol), were dissolved in methanol (30 mL) at room temperature, and the solution was stirred at the same temperature for 3 hours. Then, the reaction mixture was concentrated under reduced pressure to remove the solvent, and sodium hydrogen carbonate (20 mL) and water (10 mL) were added to the concentrate, followed by stirring. Then, the precipitated solid was filtered, washed with water, and dried to afford the desired compound 783 (0.010 g, 20.0%) as a white solid.

$^1$H NMR (400 MHz, MeOD-d$_4$) δ 8.80 (s, 1H), 7.71 (d, 1H, J=7.8 Hz), 7.47-7.44 (m, 2H), 7.24 (d, 2H, J=8.0 Hz), 6.71 (s, 1H), 6.44-6.38 (m, 1H), 5.53 (s, 2H), 4.11-4.07 (m, 2H), 3.66 (m, 2H), 2.62 (m, 2H), 1.51 (s, 9H); MS (ESI) m/z 449.1 (M$^+$+H)

Example 61

Synthesis of Compound 784

Step 1: Synthesis of methyl 4-((4-bromo-1H-pyrrolo[2,3-b]pyridin-1-yl)methyl)benzoate (formula 1-2)

(formula 1-2)

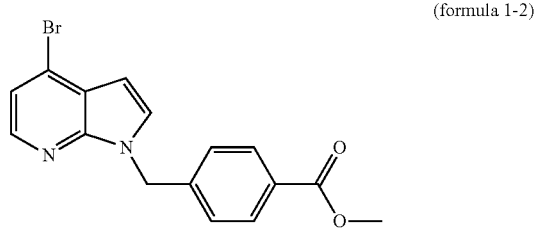 [SMILES: COC(=O)c1ccc(Cn2ccc3c(Br)ccnc32)cc1]

4-bromo-1H-pyrrolo[2,3-b]pyridine (10.000 g, 50.751 mmol), methyl 4-(bromomethyl)benzoate (12.788 g, 55.826 mmol) and potassium hydroxide (3.417 g, 60.901 mmol) were dissolved in N,N-dimethylformamide (150 mL) at room temperature, and the solution was stirred at the same temperature for 12 hours. Then, the reaction mixture was concentrated under reduced pressure to remove the solvent, and water was added to the concentrate, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO₂, 40 g cartridge; methylene chloride/hexane=from 30% to 50%) to afford the compound of formula 1-2 (11.000 g, 62.8%) as a white solid.

Step 2: Synthesis of tert-butyl 4-(1-(4-(methoxycarbonyl)benzyl)-1H-pyrrolo[2,3-b]pyridin-4-yl)-3,6-dihydropyridine-1(2H)-carboxylate (formula 1-3)

(formula 1-3)

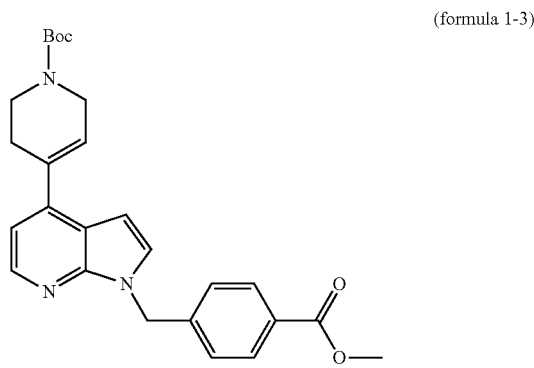 [SMILES: COC(=O)c1ccc(Cn2ccc3c(C4=CCN(C(=O)OC(C)(C)C)CC4)ccnc32)cc1]

The compound of formula 1-2 (10.500 g, 30.418 mmol) prepared in step 1, 3,6-dihydro-2H-pyridine-1-tert-butoxycarbonyl-4-boronic acid pinacol ester (10.816 g, 34.981 mmol), sodium carbonate (6.448 g, 60.836 mmol), and Pd(dppf)Cl₂ (2.484 g, 3.042 mmol) were added to 1,2-dimethoxyethane (50 mL)/water (25 mL), and heated by microwave irradiation at 120° C. for 20 minutes, followed by cooling to room temperature. After completion of the reaction, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO₂, 12 g cartridge; ethyl acetate/hexane=from 10% to 20%) to afford the desired compound of formula 1-3 (11.000 g, 80.8%) as yellow oil.

Step 3: Synthesis of tert-butyl 4-(1-(4-(hydroxycarbamoyl)benzyl)-1H-pyrrolo[3,2-b]pyridin-4-yl)-5,6-dihydropyridine-1(2H)-carboxylate (compound 784)

(compound 784)

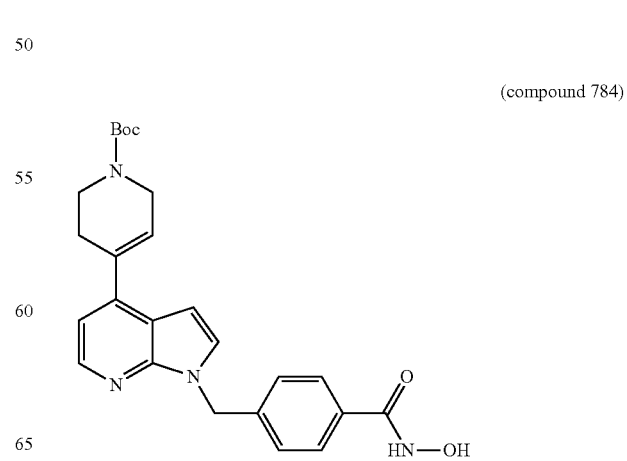

The compound of formula 1-3 (0.150 g, 0.335 mmol) prepared in step 2, potassium hydroxide (0.094 g, 1.676 mmol), and an aqueous solution of 50 wt % hydroxylamine (0.465 g, 6.703 mmol), were dissolved in methanol (30 mL) at room temperature, and the solution was stirred at the same temperature for 3 hours. Then, the reaction mixture was concentrated under reduced pressure to remove the solvent, and sodium hydrogen carbonate (20 mL) and water (10 mL) were added to the concentrate, followed by stirring. The precipitated solid was filtered, washed with water, and dried to afford the desired compound 784 (0.140 g, 93.1%) as a white solid.

$^1$H NMR (400 MHz, DMSO-$d_6$) δ 8.23 (d, 1H, J=5.0 Hz), 7.66-7.64 (m, 3H), 7.20 (d, 2H, J=8.1 Hz), 7.05 (d, 1H, J=5.0 Hz), 6.71 (d, 1H, J=3.6 Hz), 6.38 (m, 1H), 5.50 (s, 2H), 4.09 (m, 2H), 3.59 (m, 2H), 2.60 (m, 2H), 1.45 (s, 9H); MS (ESI) m/z 449.1 (M$^+$+H)

Example 62

Synthesis of Compound 785

Step 1: Synthesis of methyl 4-((7-bromo-1H-pyrrolo[2,3-c]pyridin-1-yl)methyl)benzoate (formula 11-2)

(formula 11-2)

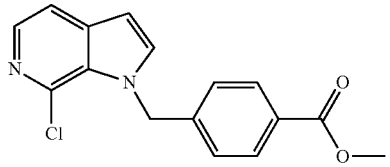

The compound of formula 11-1 (7-bromo-1H-pyrrolo[2,3-c]pyridine) (0.300 g, 1.523 mmol), methyl 4-(bromomethyl)benzoate (0.384 g, 1.675 mmol), and potassium hydroxide (0.103 g, 1.827 mmol) were dissolved in N,N-dimethylformamide (10 mL) at room temperature, and the solution was stirred at the same temperature for 12 hours. Then, the reaction mixture was concentrated under reduced pressure to remove the solvent, and water (10 mL) was added to the concentrate, followed by stirring. The precipitated solid was filtered, washed with water, and dried to afford the desired compound of formula 11-2 (0.432 g, 82.2%) as a yellow solid.

Step 2: Synthesis of tert-butyl 4-(1-(4-(methoxycarbonyl)benzyl)-1H-pyrrolo[2,3-c]pyridin-7-yl)-5,6-dihydropyridine-1(2H)-carboxylate (formula 11-3)

(formula 11-3)

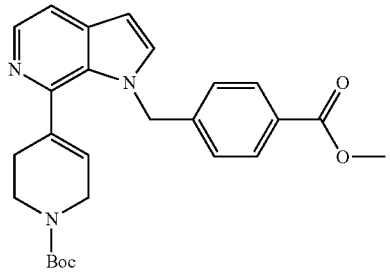

The compound of formula 11-2 (0.100 g, 0.290 mmol) prepared in step 1, 3,6-dihydro-2H-pyridine-1-tert-butoxycarbonyl-4-boronic acid pinacol ester (0.103 g, 0.333 mmol), sodium carbonate (0.061 g, 0.579 mmol), and Pd(dppf)Cl$_2$ (0.024 g, 0.029 mmol) were added to 1,2-dimethoxyethane (2 mL)/water (1 mL), and heated by microwave irradiation at 120° C. for 10 minutes, followed by cooling to room temperature. After completion of the reaction, was added to the concentrate, followed by extraction with ethyl acetate. The organic layer was washed with a saturated aqueous solution of sodium chloride, dried with anhydrous sodium sulfate, filtered, and then concentrated under reduced pressure. The concentrate was purified by column chromatography (SiO$_2$, 12 g cartridge; ethyl acetate/hexane=from 20% to 30%) to afford the desired compound of formula 11-3 (0.070 g, 54.0%) as brown oil.

Step 3: Synthesis of tert-butyl 4-(1-(4-(hydroxycarbamoyl)benzyl)-1H-pyrrolo[3,2-c]pyridin-7-yl)-5,6-dihydropyridine-1(2H)-carboxylate (compound 785)

(compound 785)

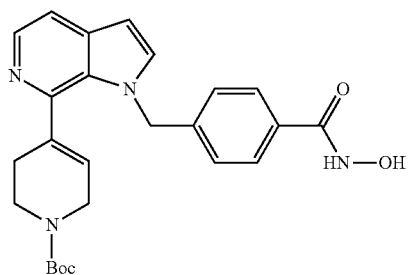

The compound of formula 11-3 (0.070 g, 0.156 mmol) prepared in step 2, NH$_2$OH (0.054 g, 0.782 mmol), potassium hydroxide (0.044 g, 0.782 mmol), and an aqueous solution of 50 wt % hydroxylamine solution in water (0.201 mL, 3.128 mmol), were dissolved in methanol (5 mL) at room temperature, and the solution was stirred at the same temperature for 3 hours. Then, the reaction mixture was concentrated under reduced pressure to remove the solvent, and sodium hydrogen carbonate (20 mL) and water (10 mL) were added to the concentrate, followed by stirring. The precipitated solid was filtered and dried to afford the desired compound 785 (0.067 g, 95.5%) as a brown solid.

$^1$H NMR (400 MHz, DMSO-$d_6$) δ 8.08 (d, 1H, J=5.3 Hz), 7.81 (d, 1H, J=3.0 Hz), 7.58 (d, 2H, J=8.2 Hz), 7.51 (d, 1H, J=5.3 Hz), 6.67 (d, 1H, J=3.0 Hz), 6.65 (m, 2H), 5.57 (m, 3H), 4.01 (m, 2H), 3.34 (m, 2H), 2.51 (m, 2H), 1.49 (s, 9H); MS (ESI) m/z 449.2 (M$^+$+H)

Example 63

Synthesis of Compound 786

Step 1: Synthesis of methyl 4-((6-bromo-1H-pyrrolo[3,2-b]pyridin-1-yl)methyl)benzoate (formula 11-2)

(formula 11-2)

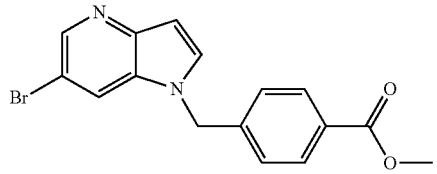

The compound of formula 11-1 (6-bromo-1H-pyrrolo[3,2-b]pyridine) (0.300 g, 1.523 mmol), methyl 4-(bromomethyl)benzoate (0.384 g, 1.675 mmol) and potassium hydroxide (0.103 g, 1.827 mmol) were dissolved in N,N-dimethylformamide (10 mL) at room temperature, and the solution was stirred at the same temperature for 12 hours. Then, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; ethyl acetate/hexane=from 20% to 30%) to afford the desired compound (0.300 g, 57.1%) as yellow oil.

Step 2: Synthesis of tert-butyl 4-(1-(4-(methoxycarbonyl)benzyl)-1H-pyrrolo[3,2-b]pyridin-6-yl)-5,6-dihydropyridine-1(2H)-carboxylate (formula 11-3)

(formula 11-3)

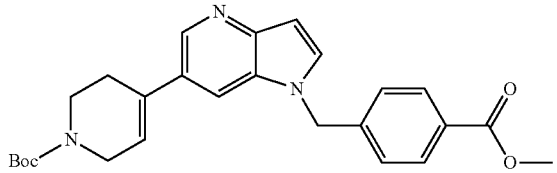

The compound of formula 11-2 (0.100 g, 0.290 mmol) prepared in step 1, 3,6-dihydro-2H-pyridine-1-tert-butoxycarbonyl-4-boronic acid pinacol ester (0.103 g, 0.333 mmol), sodium carbonate (0.061 g, 0.579 mmol), and Pd(dppf)Cl$_2$ (0.024 g, 0.029 mmol) were added to 1,2-dimethoxyethane (2 mL)/water (1 mL), and heated by microwave irradiation at 120° C. for 10 minutes, followed by cooling to room temperature. After completion of the reaction, water was added to the reaction mixture, followed by extraction with ethyl acetate. The organic layer was washed with a saturated aqueous solution of sodium chloride, dried with anhydrous sodium sulfate, filtered, and then concentrated under reduced pressure. The concentrate was purified by column chromatography (SiO$_2$, 12 g cartridge; ethyl acetate/hexane=from 20% to 30%) to afford the desired compound of formula 11-3 (0.050 g, 38.6%) as brown oil.

Step 3: Synthesis of tert-butyl 4-(1-(4-(hydroxycarbamoyl)benzyl)-1H-pyrrolo[3,2-b]pyridin-6-yl)-5,6-dihydropyridine-1(2H)-carboxylate (compound 786)

(compound 786)

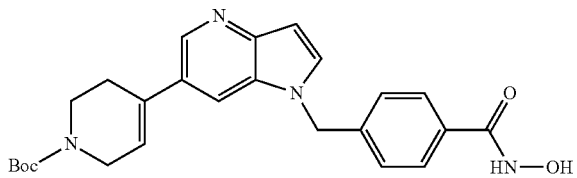

The compound of formula 11-3 (0.050 g, 0.112 mmol) prepared in step 2, NH$_2$OH (0.039 g, 0.559 mmol), potassium hydroxide (0.031 g, 0.559 mmol), and an aqueous solution of 50 wt % hydroxylamine (0.144 mL, 2.234 mmol), were dissolved in methanol (5 mL) at room temperature, and the solution was stirred at the same temperature for 3 hours. Then, the reaction mixture was concentrated under reduced pressure to remove the solvent, and sodium hydrogen carbonate (20 mL) and water (10 mL) were added to the concentrate, followed by stirring. The precipitated solid was filtered and dried to afford the desired compound 786 (0.019 g, 37.9%) as a white solid.

$^1$H NMR (400 MHz, DMSO-d$_6$) δ 8.47 (d, 1H, J=1.8 Hz), 7.95 (s, 1H), 7.79 (d, 1H, J=3.2 Hz), 7.68 (d, 2H, J=8.1 Hz), 7.24 (d, 2H, J=7.2 Hz), 6.60 (d, 1H, J=3.2 Hz), 6.19 (m, 1H), 5.50 (s, 2H), 4.02 (m, 2H), 3.58-3.55 (m, 2H), 2.53 (m, 2H), 1.43 (s, 9H); MS (ESI) m/z 449.1 (M$^+$+H).

Example 64

Synthesis of Compound 787

Step 1: Synthesis of methyl 4-((5-morpholino-1H-pyrrolo[2,3-b]pyridin-1-yl)methyl)benzoate (formula 2-3)

(formula 2-3)

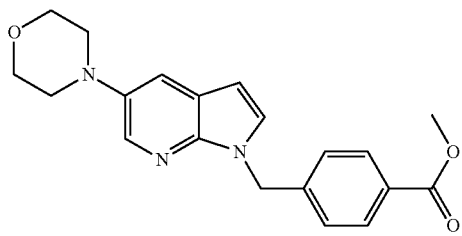

The compound of formula 2-2 (4-((5-bromo-1H-pyrrolo[2,3-b]pyridin-1-yl)methyl)benzoate) (1.000 g, 2.897 mmol), morpholine (0.304 mL, 3.476 mmol), bis(tri-tert-butylphosphine)palladium(0) (0.148 g, 0.290 mmol), and sodium tert-butoxide (0.334 g, 3.476 mmol) were dissolved in toluene (30 mL) at 120° C., and the solution was stirred at the same temperature for 2 hours, followed by cooling to room temperature. After completion of the reaction, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; ethyl acetate/hexane=from 20% to 30%) to afford the desired compound of formula 2-3 (0.260 g, 25.5%) as a white solid.

Step 2: Synthesis of N-hydroxy-4-((5-morpholino-1H-pyrrolo[2,3-b]pyridin-1-yl)methyl)benzamide (compound 787)

(compound 787)

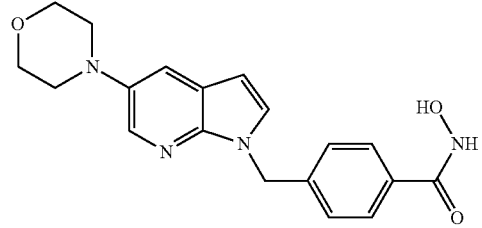

The compound of formula 2-3 (0.200 g, 0.569 mmol) prepared in step 1, NH$_2$OH (0.198 g, 2.846 mmol), potassium hydroxide (0.160 g, 2.846 mmol), and an aqueous solution of 50 wt % hydroxylamine (0.732 mL, 11.383 mmol), were dissolved in methanol (20 mL) at room temperature, and the solution was stirred at the same temperature for 3 hours. Then, the reaction mixture was concentrated under reduced pressure to remove the solvent, and sodium hydrogen carbonate (20 mL) and water (10 mL) were added to the concentrate, followed by stirring. The precipitated solid was filtered, washed with hexane, and dried to afford the desired compound 787(0.162 g, 80.8%) as a light brown solid.

$^1$H NMR (400 MHz, DMSO-$d_6$) δ 8.11 (d, 1H, J=2.6 Hz), 7.66 (d, 2H, J=8.2 Hz), 7.57 (d, 1H, J=3.4 Hz), 7.53 (d, 1H, J=2.6 Hz), 7.22 (d, 2H, J=8.2 Hz), 6.40 (d, 1H, J=3.4 Hz), 5.46 (s, 2H), 3.77 (t, 4H, J=4.5 Hz), 3.07 (t, 4H, J=4.7 Hz); MS (ESI) m/z 353.2 (M$^+$+H).

Example 65

Synthesis of Compound 799

Step 1: Synthesis of methyl 4-((4-(3-((4-methylpiperazin-1-yl)methyl)phenyl)-1H-pyrrolo[2,3-b]pyridin-1-yl)methyl)benzoate (formula 1-4)

(formula 1-4)

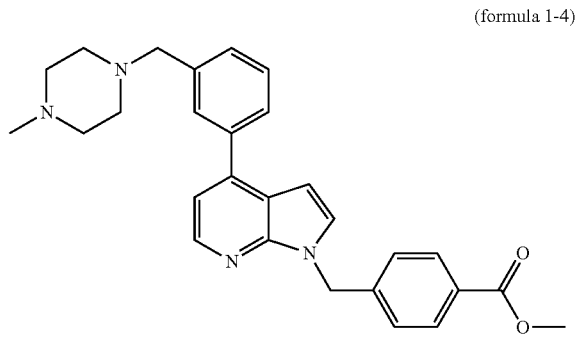

The compound of formula 1-3 (methyl 4-((4-(3-formylphenyl)-1H-pyrrolo[2,3-b]pyridin-1-yl)methyl)benzoate) (0.1 g, 0.27 mmol), N-methylpiperazine (0.032 g, 0.324 mmol), and acetic acid (0.0016 g, 0.027 mmol) were dissolved in tetrahydrofuran (2 ml) at room temperature, and the solution was stirred at the same temperature for 2 hours. To the reaction mixture, sodium cyanoborohydride (0.021 g, 0.324 mmol) was added, followed by stirring at the same temperature for 14 hours. The organic layer was washed with a saturated aqueous solution of sodium chloride, dried with anhydrous magnesium sulfate, filtered, and then concentrated under reduced pressure. The concentrate was purified by column chromatography (SiO$_2$, 80 g cartridge; ethyl acetate/hexane=from 0% to 30%) to afford the desired compound of formula 1-4 (0.053 g, 43.2%) as a white solid.

Step 2: Synthesis of N-hydroxy-4-((4-(3-((4-methylpiperazin-1-yl)methyl)phenyl)-1H-pyrrolo[2,3-b]pyridin-1-yl)methyl)benzamide (compound 799)

(compound 799)

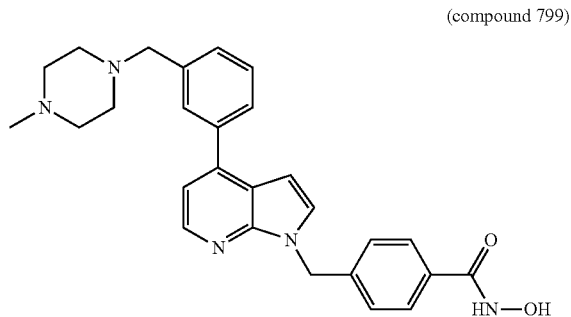 [SMILES: CN1CCN(Cc2cccc(-c3ccnc4c3ccn4Cc3ccc(C(=O)NO)cc3)c2)CC1]

The compound of formula 1-4 (0.03 g, 0.066 mmol) prepared in step 1, an aqueous solution of 50 wt % hydroxylamine (0.081 mL, 1.32 mmol) and potassium hydroxide (0.037 g, 0.66 mmol) were dissolved in methanol (1 mL)/tetrahydrofuran (1 mL) at room temperature, and the solution was stirred at the same temperature for 1 hours. The reaction mixture was concentrated under reduced pressure to remove the solvent, thereby obtaining the desired compound 799 (0.014 g, 46.6%) as a light yellow solid.

MS (ESI) m/z 456.17 (M$^+$+1).

Example 66

Synthesis of Compound 804

Step 1: Synthesis of methyl 4-((5-(1-benzylpiperidin-4-yl)-1H-pyrrolo[2,3-b]pyridin-1-yl)methyl)benzoate (formula 6-4)

(formula 6-4)

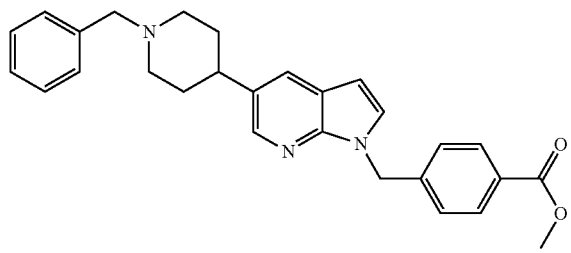

The compound of formula 1-4 (methyl 4-((5-(1-benzylpiperidin-4-yl)-1H-pyrrolo[2,3-b]pyridin-1-yl)methyl)benzoate) (0.100 g, 0.286 mmol), benzyl bromide (0.037 mL, 0.315 mmol), and Cs$_2$CO$_3$ (0.112 g, 0.343 mmol) were dissolved in acetonitrile (10 mL) at room temperature, and the solution was stirred at the same temperature for 12 hours. Then, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; ethyl acetate/hexane=from 20% to 30%) to afford the desired compound of formula 6-4 (0.019 g, 15.2%) as colorless oil.

Step 2: Synthesis of 4-((5-(1-benzylpiperidin-4-yl)-1H-pyrrolo[2,3-b]pyridin-1-yl)methyl)-N-hydroxybenzamide (compound 804)

(compound 804)

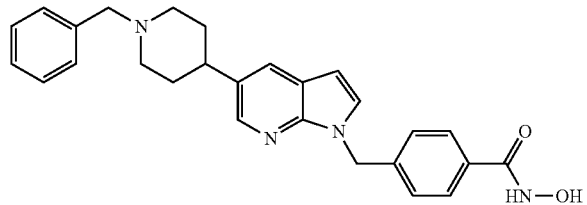

The compound of formula 6-4 (0.020 g, 0.046 mmol) prepared in step 1, NH$_2$OH (0.016 g, 0.228 mmol), potassium hydroxide (0.013 g, 0.228 mmol), and an aqueous solution of 50 wt % hydroxylamine (0.058 mL, 0.910 mmol), were dissolved in methanol (30 mL) at room temperature, and the solution was stirred at the same temperature for 3 hours. Then, the reaction mixture was concentrated under reduced pressure to remove the solvent, and sodium hydrogen carbonate (20 mL) and water (10 mL) were added to the concentrate, followed by stirring. The precipitated solid was filtered, washed with water, and dried to afford the desired compound 804 (0.006 g, 28.4%) as a white solid.

$^1$H NMR (400 MHz, DMSO-$d_6$) δ 8.14 (d, 1H, J=1.8 Hz), 7.91 (d, 1H, J=1.9 Hz), 7.68 (d, 2H, J=8.1 Hz), 7.40-7.28 (m, 6H), 7.20 (d, 2H, J=8.2 Hz), 6.52 (d, 1H, J=3.5 Hz), 5.53 (s, 2H), 3.61 (s, 2H), 3.09-3.06 (m, 2H), 2.73-2.67 (m, 1H), 2.25-2.18 (m, 2H), 1.89-1.87 (m, 4H); MS (ESI) m/z 441.1 (H$^+$+H).

Example 67

Synthesis of Compound 805

Step 1: Synthesis of methyl 4-((5-(4-methylpiperidin-1-yl)-1H-pyrrolo[2,3-b]pyridin-1-yl)methyl)benzoate (formula 2-3)

(formula 2-3)

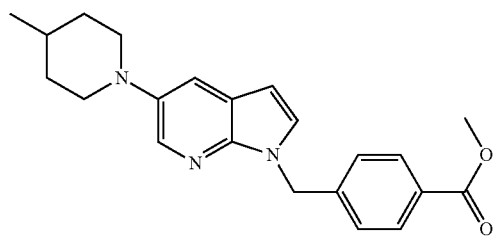

The compound of formula 2-2 (0.500 g, 1.448 mmol), 4-methyl piperidine (0.205 mL, 1.738 mmol), bis(tri-tert-butylphosphine)palladium(0) (0.074 g, 0.145 mmol), and sodium t-butoxide (0.167 g, 1.738 mmol) were dissolved in toluene (30 mL) at 120° C., and the solution was stirred at the same temperature for 2 hours, followed by cooling to room temperature. After completion of the reaction, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; ethyl acetate/hexane=from 20% to 30%) to afford the desired compound of formula 2-3 (0.080 g, 15.2%) as a white solid.

Step 2: Synthesis of N-hydroxy-4-((5-(4-methylpiperidin-1-yl)-1H-pyrrolo[2,3-b]pyridin-1-yl)methyl)benzamide (compound 805)

(compound 805)

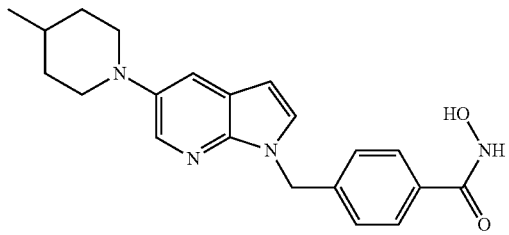

The compound of formula 2-3 (0.080 g, 0.220 mmol) prepared in step 1 was dissolved in methanol (30 mL) at room temperature, and potassium hydroxide (0.062 g, 1.101 mmol) and an aqueous solution of 50 wt % hydroxylamine (0.283 mL, 4.402 mmol) were added thereto, followed by stirring at the same temperature for 3 hours. Then, the reaction mixture was concentrated under reduced pressure to remove the solvent, and sodium hydrogen carbonate (20 mL) and water (10 mL) were added to the concentrate, followed by stirring. The precipitated solid was filtered and dried to afford the desired compound 805 (0.018 g, 22.4%) as a white solid.

$^1$H NMR (400 MHz, DMSO-$d_6$) δ 8.08 (d, 1H, J=2.5 Hz), 7.66 (d, 2H, J=8.2 Hz), 7.53 (d, 1H, J=3.4 Hz), 7.51 (d, 1H, J=2.6 Hz), 7.23 (d, 2H, J=8.2 Hz), 6.38 (d, 1H, J=3.4 Hz), 5.45 (s, 2H), 3.50-3.47 (m, 2H), 2.67-2.61 (m, 2H), 1.73-1.70 (m, 2H), 1.36-1.30 (m, 1H), 1.78 (m, 2H), 0.96 (d, 3H, J=6.4 Hz); MS (ESI) m/z 365.1 (M$^+$+H).

Example 68

Synthesis of Compound 806

Step 1: Synthesis of methyl 4-((5-(4-benzylpiperazin-1-yl)-1H-pyrrolo[2,3-b]pyridin-1-yl)methyl)benzoate (formula 2-3)

(formula 2-3)

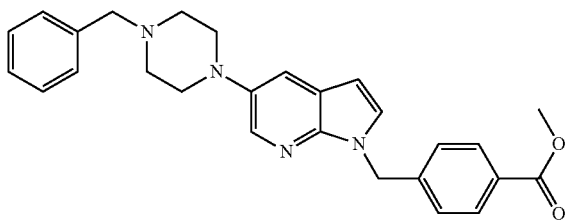

The compound of formula 2-2 (0.500 g, 1.448 mmol), 1-benzylpiperazine (0.297 mL, 1.738 mmol), bis(tri-tert-butylphosphine)palladium(0) (0.074 g, 0.145 mmol), and sodium tert-butoxide (0.167 g, 1.738 mmol) were dissolved in toluene (30 mL) at 120° C., and the solution was stirred at the same temperature for 2 hours, followed by cooling to room temperature. After completion of the reaction, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; ethyl acetate/hexane=from 20% to 30%) to afford the desired compound of formula 2-3 (0.089 g, 13.9%) as a white solid.

Step 2: Synthesis of 4-((5-(4-benzylpiperazin-1-yl)-1H-pyrrolo[2,3-b]pyridin-1-yl)methyl)-N-hydroxybenzamide (compound 806)

(compound 806)

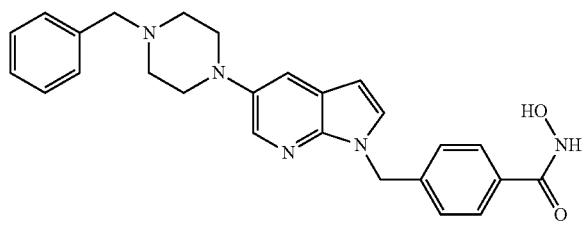

The compound of formula 2-3 (0.089 g, 0.202 mmol) prepared in step 1 was dissolved in methanol (30 mL) at room temperature, and potassium hydroxide (0.062 g, 1.101 mmol) and an aqueous solution of 50 wt % hydroxylamine (0.283 mL, 4.402 mmol) were added thereto, followed by stirring at the same temperature for 3 hours. Then, the reaction mixture was concentrated under reduced pressure to remove the solvent, and sodium hydrogen carbonate (20 mL) and water (10 mL) were added to the concentrate, followed by stirring. The precipitated solid was filtered and dried to afford the desired compound 806 (0.049 g, 54.9%) as a white solid.

$^1$H NMR (400 MHz, DMSO-$d_6$) δ 8.10 (d, 1H, J=2.5 Hz), 7.64 (d, 2H, J=8.2 Hz), 7.53 (d, 1H, J=3.4 Hz), 7.50 (d, 1H, J=2.6 Hz), 7.35 (d, 4H, J=4.4 Hz), 7.29-7.26 (m, 1H), 7.17 (d, 2H, J=8.2 Hz), 6.37 (d, 1H, J=6.4 Hz), 5.42 (s, 2H), 3.54 (s, 2H), 3.09 (t, 4H, J=4.2 Hz), 2.55 (t, 4H, J=4.4 Hz); MS (ESI) m/z 442.2 (M$^+$+H).

Example 69

Synthesis of Compound 807

Step 1: Synthesis of methyl 4-((5-(2,6-dimethyl-morpholino)-1H-pyrrolo[2,3-b]pyridin-1-yl)methyl)benzoate (formula 2-3)

(formula 2-3)

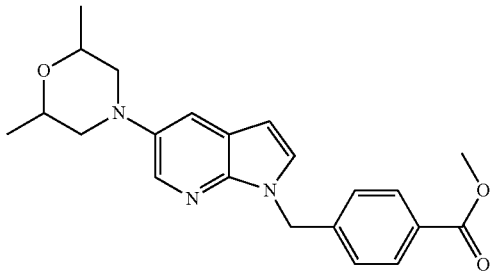

The compound of formula 2-2 (0.500 g, 1.448 mmol), 2,6-dimethylmorpholine (0.213 mL, 1.738 mmol), bis(tri-tert-butylphosphine)palladium(0) (0.074 g, 0.145 mmol), and sodium tert-butoxide (0.167 g, 1.738 mmol) were dissolved in toluene (30 mL) at 120° C., and the solution was stirred at the same temperature for 2 hours, and then cooled to room temperature. After completion of the reaction, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; ethyl acetate/hexane=from 20% to 30%) to afford the compound of formula 2-3 (0.050 g, 9.1%) as a white solid.

Step 2: Synthesis of 4-((5-(2,6-dimethylmor-pholino)-1H-pyrrolo[2,3-b]pyridin-1-yl)methyl)-N-hydroxybenzamide (compound 807)

(compound 807)

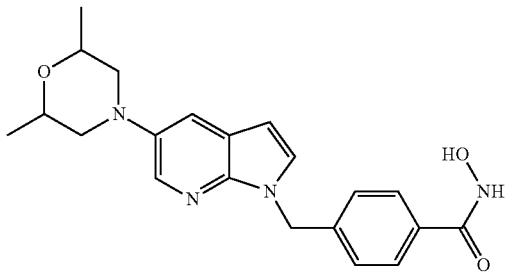

The compound of formula 2-3 (0.05 g, 0.13 mmol) was dissolved in methanol (30 mL) at room temperature, and the solution was stirred at the same temperature for 3 hours. Then, the reaction solution was concentrated under reduced pressure to remove the solvent, and sodium hydrogen carbonate (20 mL) and water (10 mL) were added to the concentrate, followed by stirring. The precipitated solid was filtered and dried to yield desired compound 807 (0.031 g, 61.8%) as a gray solid.

$^1$H NMR (400 MHz, DMSO-$d_6$) δ 8.11 (s, 1H), 7.65 (d, 2H, J=7.8 Hz), 7.55-7.51 (m, 2H), 7.21 (d, 2H, J=7.7 Hz), 6.39 (d, 1H, J=2.8 Hz), 5.45 (s, 2H), 3.76 (m, 2H), 3.47 (m, 2H), 2.29 (t, 2H, J=11.1 Hz), 1.15 (d, 6H, J=6.0 Hz); MS (ESI) m/z 379.1 (M$^+$–H)

Example 70

Synthesis of Compound 808

Step 1: Synthesis of methyl 4-((5-chloro-1H-pyr-rolo[2,3-c]pyridin-1-yl)methyl)benzoate (compound 11-2)

(compound 11-2)

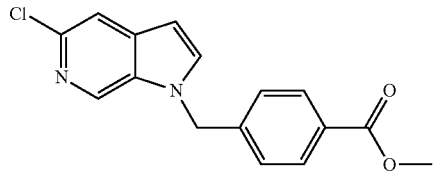

The compound of formula 11-1 (5-chloro-1H-pyrrolo[2,3-c]pyridine) (0.300 g, 1.966 mmol), methyl 4-(bromomethyl)benzoate (0.495 g, 2.163 mmol), and potassium hydroxide (0.132 g, 2.359 mmol) were dissolved in N,N-dimethylformamide (10 mL) at room temperature, and the solution was stirred at the same temperature for 12 hours. Then, the reaction mixture was concentrated under reduced pressure to remove the solvent, and water (20 mL) was added to the concentrate, followed by stirring. The precipitated solid was filtered, washed with water, and dried to afford the desired compound of formula 11-2 (0.488 g, 82.7%) as a yellow solid.

Step 2: Synthesis of tert-butyl 4-(1-(4-(methoxycarbonyl)benzyl)-1H-pyrrolo[2,3-c]pyridin-5-yl)-5,6-dihydropyridine-1(2H)-carboxylate (formula 11-3)

(formula 11-3)

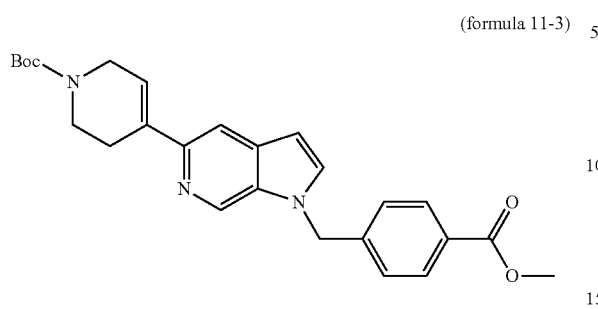

The compound of formula 11-2 (0.100 g, 0.333 mmol) prepared in step 1, 3,6-dihydro-2H-pyridine-1-tert-butoxycarbonyl-4-bornic acid pinacol ester (0.118 g, 0.382 mmol), sodium carbonate (0.070 g, 0.665 mmol), and Pd(dppf)Cl$_2$ (0.027 g, 0.033 mmol) were added to 1,2-dimethoxyethane (2 mL)/water (1 mL), and heated by microwave irradiation at 120° C. for 10 minutes, followed by cooling to room temperature. After completion of the reaction, the reaction mixture was concentrated under reduced pressure to remove the solvent, and water was added to the concentrate, followed by extraction with ethyl acetate. The organic layer was washed with a saturated aqueous solution of sodium chloride, dried with anhydrous sodium sulfate, filtered, and then concentrated under reduced pressure. The concentrate was purified by column chromatography (SiO$_2$, 12 g cartridge; ethyl acetate/hexane=from 20% to 30%) to afford the desired compound of formula 11-3 (0.010 g, 6.7%) as colorless oil.

Step 3: Synthesis of tert-butyl 4-(1-(4-(hydroxycarbamoyl)benzyl)-1H-pyrrolo[2,3-c]pyridin-5-yl)-5,6-dihydropyridine-1(2H)-carboxylate (compound 808)

(compound 808)

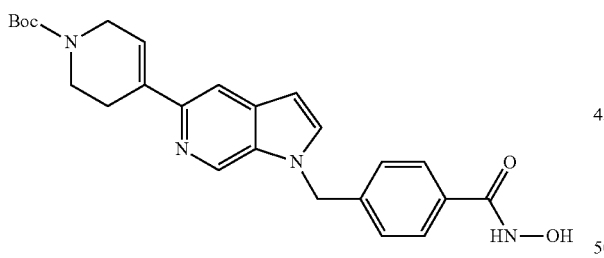

The compound of formula 11-3 (0.020 g, 0.045 mmol) prepared in step 2, potassium hydroxide (0.013 g, 0.223 mmol), and an aqueous solution of 50 wt % hydroxylamine (0.057 mL, 0.894 mmol), were dissolved in methanol (30 mL) at room temperature, and the solution was stirred at the same temperature for 3 hours. Then, the reaction mixture was concentrated under reduced pressure to remove the solvent, and sodium hydrogen carbonate (20 mL) and water (10 mL) were added to the concentrate, followed by stirring. The precipitated solid was filtered, washed with water, and dried to afford the desired compound 808 (0.001 g, 6.0%) as an orange solid.
$^1$H NMR (400 MHz, DMSO-d$_6$) δ 8.57 (s, 1H), 7.75-7.55 (m, 4H), 7.25 (m, 2H), 6.62 (m, 2H), 6.41 (m, 1H), 5.59 (s, 2H), 4.12 (m, 2H), 3.68 (m, 2H), 2.66 (m, 2H), 1.54 (s, 9H); MS (ESI) m/z 449.1 (M$^+$+H).

Example 71

Synthesis of Compound 809

Step 1: Synthesis of methyl 4-((5-(4-((tert-butoxycarbonyl)amino)piperidin-1-yl)-1H-pyrrolo[2,3-b]pyridin-1-yl)methyl)benzoate (formula 2-3)

(formula 2-3)

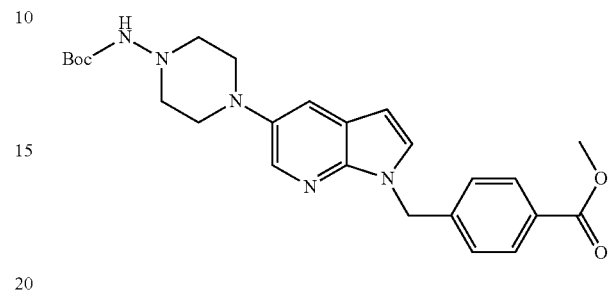

The compound of formula 2-2 (0.500 g, 1.448 mmol), tert-butyl piperidin-4-ylcarbamate (0.348 g, 1.738 mmol), bis(tri-tert-butylphosphine)palladium(0) (0.074 g, 0.145 mmol), and sodium tert-butoxide (0.167 g, 1.738 mmol) were dissolved in toluene (30 mL) at 120° C., and the solution was stirred at the same temperature for 2 hours, and then cooled to room temperature. After completion of the reaction, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; ethyl acetate/hexane=from 20% to 30%) to afford the desired compound of formula 2-3 (0.054 g, 8.0%) as a white solid.

Step 2: Synthesis of tert-butyl (1-(1-(4-(hydroxycarbamoyl)benzyl)-1H-pyrrolo[2,3-b]pyridin-5-yl)piperidin-4-yl)carbamate (compound 809)

(compound 809)

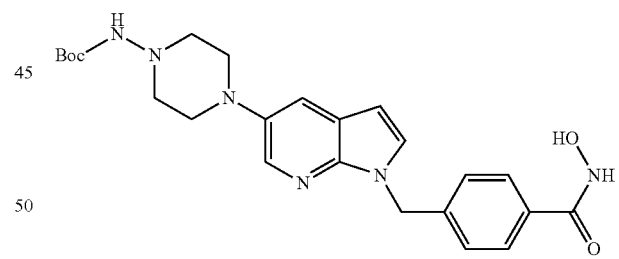

The compound of formula 2-3 (0.054 g, 0.12 mmol) prepared in step 1 was dissolved in methanol (30 mL) at room temperature, and potassium hydroxide (0.013 g, 0.223 mmol) and an aqueous solution of 50 wt % hydroxylamine (0.057 mL, 0.894 mmol) were added thereto, followed by stirring at the same temperature for 3 hours. Then, the reaction solution was concentrated under reduced pressure to remove the solvent, and sodium hydrogen carbonate (20 mL) and water (10 mL) were added to the concentrate, followed by stirring. The precipitated solid was filtered and dried to yield desired compound 809 (0.014 g, 25.9%) as a gray solid.
$^1$H NMR (400 MHz, DMSO-d$_6$) δ 8.09 (d, 1H, J=2.3 Hz), 7.64 (d, 2H, J=8.1 Hz), 7.52-7.51 (m, 2H), 7.13 (d, 2H, J=8.1

Hz), 6.89 (d, 1H, J=7.6 Hz), 5.40 (s, 2H), 3.48-3.45 (m, 2H), 2.74-2.68 (m, 2H), 1.84-1.81 (m, 2H), 1.60-1.51 (m, 2H), 1.40 (s, 9H); MS (ESI) m/z 464.1 (M$^+$–H).

Example 72

Synthesis of Compound 810

Step 1: Synthesis of methyl 4-((5-(4-phenyl-5,6-dihydropyridin-1(2H)-yl)-1H-pyrrolo[2,3-b]pyridin-1-yl)methyl)benzoate (formula 2-3)

(formula 2-3)

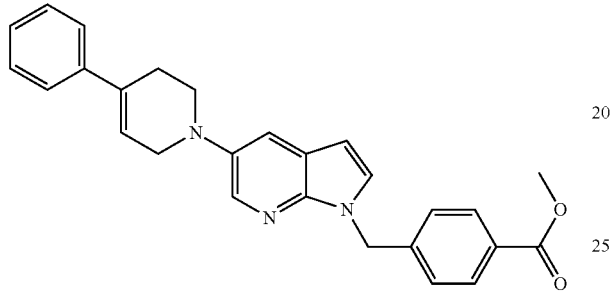

The compound of formula 2-2 (0.500 g, 1.448 mmol), 4-phenyl-1,2,3,6-tetrahydropyridine (0.340 g, 1.738 mmol), bis(tri-tert-butylphosphine)palladium(0) (0.074 g, 0.145 mmol), and sodium tert-butoxide (0.167 g, 1.738 mmol) were dissolved in toluene (30 mL) at 120° C., and the solution was stirred at the same temperature for 2 hours, and then cooled to room temperature. After completion of the reaction, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; ethyl acetate/hexane=from 20% to 30%) to afford the desired compound of formula 2-3 (0.023 g, 3.7%) as a white solid.

Step 2: Synthesis of N-hydroxy-4-((5-(4-phenyl-5,6-dihydropyridin-1(2H)-yl)-1H-pyrrolo[2,3-b]pyridin-1-yl)methyl)benzamide (compound 810)

(compound 810)

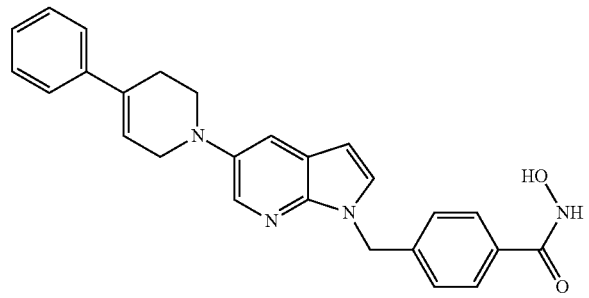

The compound of formula 2-3 (0.023 g, 0.054 mmol) prepared in step 1 was dissolved in methanol (30 mL) at room temperature, and potassium hydroxide (0.013 g, 0.223 mmol) and an aqueous solution of 50 wt % hydroxylamine (0.057 mL, 0.894 mmol) were added thereto, followed by stirring at the same temperature for 3 hours. Then, the reaction mixture was concentrated under reduced pressure to remove the solvent, and sodium hydrogen carbonate (20 mL) and water (10 mL) were added to the concentrate, followed by stirring. The precipitated solid was filtered and dried to afford the desired compound 810 (0.002 g, 8.7%) as a gray solid.

$^1$H NMR (400 MHz, DMSO-d$_6$) δ 8.20 (d, 1H, J=2.4 Hz), 7.64 (d, 2H, J=7.9 Hz), 7.59 (d, 1H, J=2.5 Hz), 7.54 (d, 1H, J=3.3 Hz), 7.51 (d, 2H, J=8.3 Hz), 7.32 (t, 2H, J=7.3 Hz), 7.27 (m, 1H), 7.14 (d, 2H, J=8.0 Hz), 6.39 (d, 1H, J=3.4 Hz), 6.32 (m, 1H), 3.45 (m, 2H), 2.67 (m, 2H), 1.25 (m, 2H); MS (ESI) m/z 423.1 (M$^+$–H).

Example 73

Synthesis of Compound 812

Step 1: Synthesis of methyl 4-((4-(1-(2-hydroxy-2-methylpropyl)piperidin-4-yl)-1H-pyrrolo[2,3-b]pyridin-1-yl)methyl)benzoate (formula 4-6)

(formula 4-6)

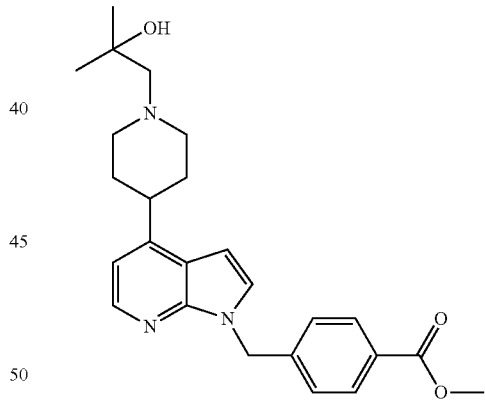

The compound of formula 4-3 (methyl 4-((4-bromo-1H-pyrrolo[2,3-b]pyridin-1-yl)methyl)benzoate) (0.400 g, 0.953 mmol) was dissolved in methanol (50 mL) at room temperature, and Pd/C (30 mg) was added slowly thereto, and a hydrogen balloon was placed over the solution, followed by stirring at the same temperature for 12 hours. The reaction mixture was concentrated under reduced pressure to remove the solvent, and the concentrate was purified by column chromatography (SiO$_2$, 12 g cartridge; methanol/methylene chloride=from 5% to 10%) to afford the desired compound of formula 4-6 (0.310 g, 77.1%) as yellow oil.

Step 2: Synthesis of N-hydroxy-4-((4-(1-(2-hydroxy-2-methylpropyl)piperidin-4-yl)-1H-pyrrolo[2,3-b]pyridin-1-yl)methyl)benzamide (compound 812)

(compound 812)

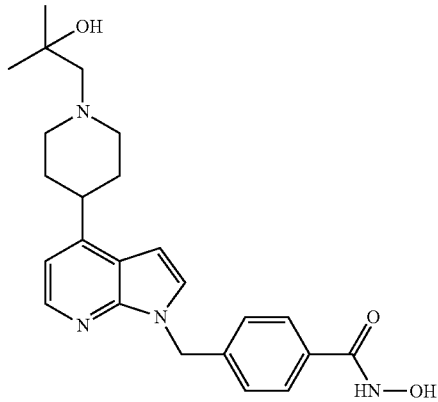

The compound of formula 4-6 (0.310 g, 0.735 mmol) prepared in step 1 was dissolved in (10 mL) at room temperature. To the solution, potassium hydroxide (0.206 g, 3.677 mmol) and an aqueous solution of 50 wt % hydroxylamine (0.945 mL, 14.708 mmol) were added, followed by stirring at the same temperature for 3 hours. Then, the reaction mixture was concentrated under reduced pressure to remove the solvent, and sodium hydrogen carbonate (20 mL) and water (10 mL) were added to the concentrate, followed by stirring. The precipitated solid was filtered, washed with water, and dried to afford the desired compound 812 (0.210 g, 67.6%) as a white solid.

$^1$H NMR (400 MHz, DMSO-$d_6$) δ 8.18 (d, 1H, J=4.9 Hz), 7.64 (d, 2H, J=8.2 Hz), 7.58 (d, 1H, J=3.6 Hz), 7.19 (d, 2H, J=8.2 Hz), 6.98 (d, 1H, J=4.9 Hz), 6.61 (d, 1H, J=3.6 Hz), 5.46 (s, 2H), 4.10 (s, 1H), 3.09-3.06 (m, 2H), 2.92-2.86 (m, 1H), 2.32-2.29 (m, 2H), 2.25 (s, 2H), 1.88-1.75 (m, 4H), 1.11 (s, 6H); MS (ESI) m/z 423.3 (M$^+$+H).

Example 74

Synthesis of Compound 830

Step 1: Synthesis of methyl 4-((5-(1-(4-methoxybenzyl)piperidin-4-yl)-1H-pyrrolo[2,3-b]pyridin-1-yl)methyl)benzoate (formula 12-2)

(formula 12-2)

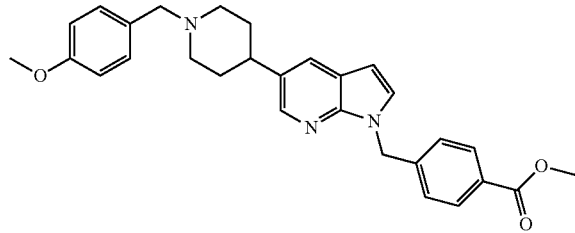

The compound of formula 6-3 (methyl 4-((5-(piperidin-4-yl)-1H-pyrrolo[2,3-b]pyridin-1-yl)methyl)benzoate) (0.100 g, 0.286 mmol), 4-methoxybenzylchloride (0.067 g, 0.429 mmol), and cesium carbonate (0.186 g, 0.572 mmol) were dissolved in acetonitrile (5 mL) at room temperature, and the solution was stirred at the same temperature for 16 hours. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; ethyl acetate/hexane=from 0% to 50%) to afford the desired compound of formula 12-2 (0.049 g, 36.5%) as colorless liquid.

Step 2: Synthesis of N-hydroxy-4-((5-(1-(4-methoxybenzyl)piperidin-4-yl)-1H-pyrrolo[2,3-b]pyridin-1-yl)methyl)benzamide (compound 830)

(compound 830)

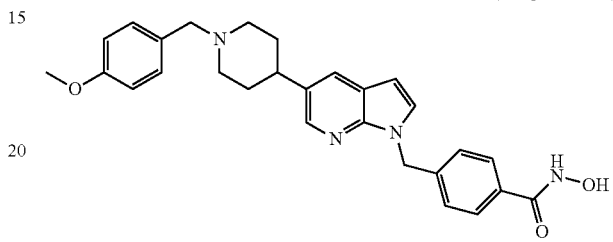

The compound of formula 12-2 (0.049 g, 0.104 mmol) prepared in step 1, hydroxylamine (50.00 wt % aqueous solution, 0.064 mL, 1.044 mmol), and potassium hydroxide (0.059 g, 1.044 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to afford the desired compound 830 (0.039 g, 79.4%) as a white solid.

$^1$H-NMR (400 MHz, CD$_3$OD) δ 8.14 (d, 1H, J=2.1 Hz), 7.92 (d, 1H, J=2.0 Hz), 7.68 (d, 2H, J=8.3 Hz), 7.41 (d, 1H, J=3.5 Hz), 7.30 (d, 2H, J=8.6 Hz), 7.20 (d, 2H, J=8.5 Hz), 6.92 (d, 2H, J=8.7 Hz), 6.52 (d, 1H, J=3.5 Hz), 5.54 (s, 2H), 3.81 (s, 3H), 3.56 (s, 2H), 3.08 (d, 2H, J=11.9 Hz), 2.76-2.68 (m, 1H), 2.23-2.17 (m, 2H), 1.91-1.86 (m, 4H); MS (ESI) m/z 471.3 (H$^+$+1).

Example 75

Synthesis of Compound 831

Step 1: Synthesis of methyl 4-((5-(1-(3-fluorobenzoyl)piperidin-4-yl)-1H-pyrrolo[2,3-b]pyridin-1-yl)methyl)benzoate (formula 12-1)

(formula 12-1)

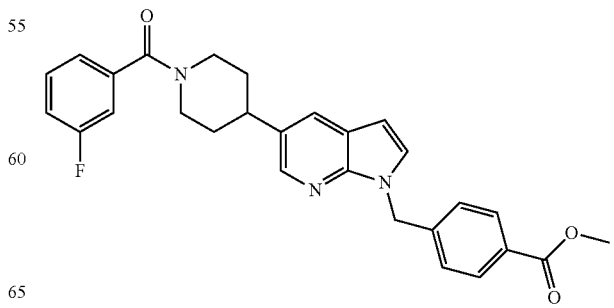

The compound of formula 6-3 (methyl 4-((5-(piperidin-4-yl)-1H-pyrrolo[2,3-b]pyridin-1-yl)methyl)benzoate) (0.100 g, 0.286 mmol), 3-fluorobenzoyl chloride (0.054 g, 0.343 mmol), and triethylamine (0.080 mL, 0.572 mmol) were dissolved in methylene chloride (5 mL) at room temperature, and the solution was stirred at the same temperature for 16 hours. Then, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; ethyl acetate/hexane=from 0% to 50%) to afford the desired compound of formula 12-1 (0.056 g, 41.5%) as colorless liquid.

Step 2: Synthesis of 4-((5-(1-(3-fluorobenzoyl)piperidin-4-yl)-1H-pyrrolo[2,3-b]pyridin-1-yl)methyl)-N-hydroxybenzamide (compound 831)

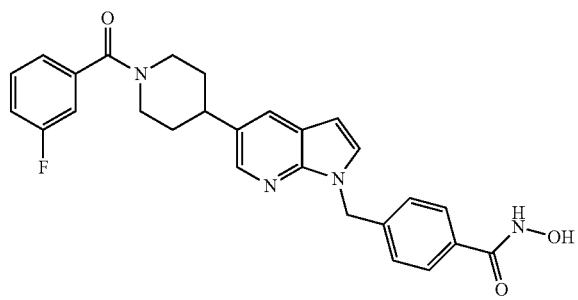

(compound 831)

The compound of formula 12-1 (0.056 g, 0.119 mmol) prepared in step 1, hydroxylamine (50.00 wt % aqueous solution, 0.073 mL, 1.188 mmol), and potassium hydroxide (0.067 g, 1.188 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to afford the desired compound 831 (0.039 g, 69.5%) as a white solid.

$^1$H-NMR (400 MHz, CD$_3$OD) δ 8.19 (d, 1H, J=1.9 Hz), 7.98 (d, 1H, J=2.0 Hz), 7.69 (d, 2H, J=8.2 Hz), 7.52 (q, 1H, J=4.5 Hz), 7.42 (d, 1H, J=3.6 Hz), 7.31 (d, 1H, J=7.7 Hz), 7.27 (d, 2H, J=8.9 Hz), 7.19 (d, 2H, J=8.1 Hz), 6.54 (d, 1H, J=3.5 Hz), 5.54 (s, 2H), 3.85 (d, 2H, J=13.2 Hz), 3.04 (d, 2H, J=11.8 Hz), 2.12-1.97 (m, 2H), 1.96-1.69 (m, 4H), 1.35-1.31 (m, 1H); MS (ESI) m/z 473.2 (M$^+$+1).

Example 76

Synthesis of Compound 839

Step 1: Synthesis of methyl 4-((5-(1-(2-fluorobenzyl)piperidin-4-yl)-1H-pyrrolo[2,3-b]pyridin-1-yl)methyl)benzoate (formula 12-2)

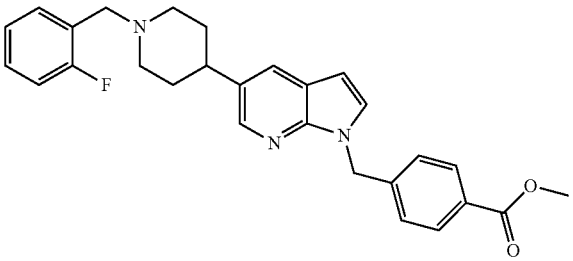

(formula 12-2)

The compound of formula 6-3 (methyl 4-((5-(piperidin-4-yl)-1H-pyrrolo[2,3-b]pyridin-1-yl)methyl)benzoate) (0.100 g, 0.286 mmol), 2-fluorobenzyl chloride (0.050 g, 0.343 mmol), and cesium carbonate (0.186 g, 0.572 mmol) were dissolved in acetonitrile (5 mL) at room temperature, and the solution was stirred at the same temperature for 1 hour. Then, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; ethyl acetate/hexane=from 0% to 50%) to afford the desired compound of formula 2-2 (0.044 g, 33.8%) as colorless liquid.

Step 2: Synthesis of 4-((5-(1-(2-fluorobenzyl)piperidin-4-yl)-1H-pyrrolo[2,3-b]pyridin-1-yl)methyl)-N-hydroxybenzamide (compound 839)

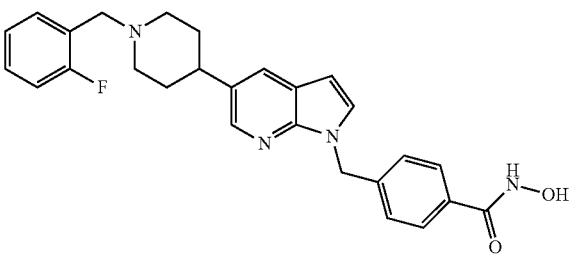

(compound 839)

The compound of formula 12-2 (0.044 g, 0.096 mmol) prepared in step 1, hydroxylamine (50.00 wt % aqueous solution, 0.059 mL, 0.962 mmol), and potassium hydroxide (0.054 g, 0.962 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to afford the desired compound 839 (0.014 g, 31.7%) as a white solid.

$^1$H-NMR (400 MHz, CD$_3$OD) δ 8.19 (d, 1H, J=2.0 Hz), 7.93 (d, 1H, J=2.0 Hz), 7.71 (d, 2H, J=8.3 Hz), 7.53-7.49 (m, 1H), 7.47 (d, 1H, J=3.4 Hz), 7.40-7.35 (m, 1H), 7.26 (d, 2H,

J=8.2 Hz), 7.23-7.18 (m, 1H), 7.18-7.14 (m, 1H), 6.54 (d, 1H, J=3.5 Hz), 5.56 (s, 2H), 3.71 (d, 2H, J=1.2 Hz), 3.11 (d, 2H, J=11.8 Hz), 2.74-2.70 (m, 1H), 2.32-2.25 (m, 2H), 1.93-1.87 (m, 4H); MS (ESI) m/z 459.2 (M$^+$+1).

Example 77

Synthesis of Compound 840

Step 1: Synthesis of methyl 4-((5-(1-(pyridin-3-ylmethyl)piperidin-4-yl)-1H-pyrrolo[2,3-b]pyridin-1-yl)methyl)benzoate (formula 12-2)

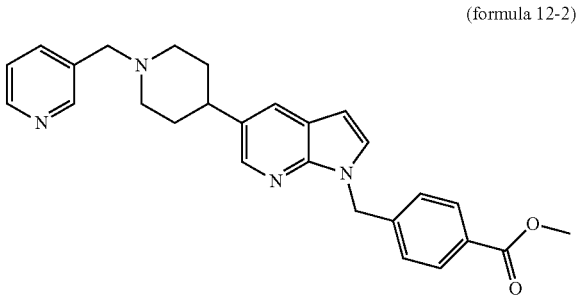 [SMILES: COC(=O)c1ccc(Cn2ccc3cc(C4CCN(Cc5cccnc5)CC4)cnc32)cc1]

(formula 12-2)

The compound of formula 6-3 (0.100 g, 0.286 mmol), 3-(chloromethyl)pyridine (0.055 g, 0.429 mmol), and cesium carbonate (0.186 g, 0.572 mmol) were dissolved in acetonitrile (5 mL) at room temperature, and the solution was stirred at the same temperature for 16 hours. Then, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; methanol/methylene chloride=from 0% to 20%) to afford the desired compound of formula 12-2 (0.044 g, 34.9%) as yellow liquid.

Step 2: Synthesis of N-hydroxy-4-((5-(1-(pyridin-3-ylmethyl)piperidin-4-yl)-1H-pyrrolo[2,3-b]pyridin-1-yl)methyl)benzamide (compound 840)

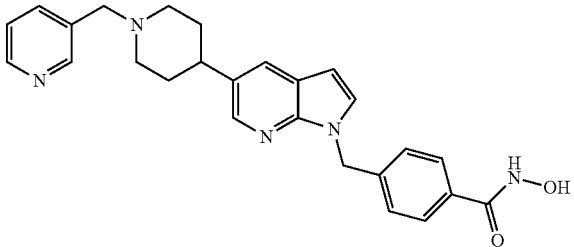

(compound 840)

The compound of formula 12-2 (0.044 g, 0.100 mmol) prepared in step 1, hydroxylamine (50.00 wt % aqueous solution, 0.061 mL, 0.999 mmol), and potassium hydroxide (0.056 g, 0.999 mmol) were dissolved in methanol (1 mL)/tetrahydrofuran (1 mL) at room temperature, and the solution was stirred at the same temperature for 1 hour. Then, the reaction solution was concentrated under reduced pressure to remove the solvent, and a saturated aqueous solution of sodium hydrogen carbonate (20 mL) was added to the concentrate, followed by stirring. The precipitated solid was filtered and dried to afford the desired compound 840 (0.030 g, 67.6%) as an ivory solid.

$^1$H-NMR (400 MHz, CD$_3$OD) δ 8.59 (s, 1H), 8.51 (d, 1H, J=3.6 Hz), 8.20 (s, 1H), 7.94 (d, 2H, J=1.6 Hz), 7.71 (d, 2H, J=8.1 Hz), 7.50-7.47 (m, 2H), 7.30-7.26 (m, 2H), 6.55 (d, 1H, J=3.4 Hz), 5.57 (s, 2H), 3.68 (s, 2H), 3.07 (d, 2H, J=11.2 Hz), 2.78-2.71 (m, 1H), 2.30-2.18 (m, 2H), 1.93-1.87 (m, 4H); MS (ESI) m/z 442.3 (M$^+$+1)

Example 78

Synthesis of Compound 841

Step 1: Synthesis of methyl 4-((5-(1-(pyridin-4-ylmethyl)piperidin-4-yl)-1H-pyrrolo[2,3-b]pyridin-1-yl)methyl)benzoate (formula 12-2)

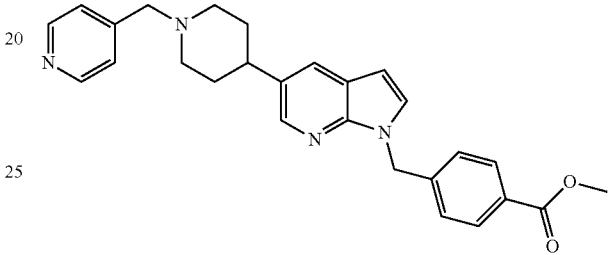

(formula 12-2)

The compound of formula 6-3 (methyl 4-((5-(piperidin-4-yl)-1H-pyrrolo[2,3-b]pyridin-1-yl)methyl)benzoate) (0.100 g, 0.286 mmol), 4-(chloromethyl)pyridine (0.055 g, 0.429 mmol), and cesium carbonate (0.186 g, 0.572 mmol) were dissolved in acetonitrile (5 mL) at room temperature, and the solution was stirred at the same temperature for 16 hours. Then, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; methanol/methylene chloride=from 0% to 20%) to afford the desired compound of formula 12-2 (0.044 g, 34.9%) as yellow liquid.

Step 2: Synthesis of N-hydroxy-4-((5-(1-(pyridin-4-ylmethyl)piperidin-4-yl)-1H-pyrrolo[2,3-b]pyridin-1-yl)methyl)benzamide (compound 841)

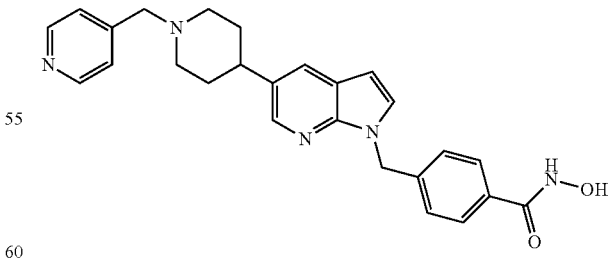

(compound 841)

The compound of formula 12-2 (0.044 g, 0.100 mmol) prepared in step 1, hydroxylamine (50.00 wt % aqueous solution, 0.061 mL, 0.999 mmol), and potassium hydroxide (0.056 g, 0.999 mmol) were dissolved in methanol (1 mL)/tetrahydrofuran (1 mL) at room temperature, and the solution was stirred at the same temperature for 1 hour.

Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to yield desired compound 841 (0.024 g, 54.4%) as an ivory solid.

$^1$H-NMR (400 MHz, CD$_3$OD) δ 8.54 (d, 2H, J=6.0 Hz), 8.19 (d, 1H, J=2.0 Hz), 7.94 (d, 1H, J=2.0 Hz), 7.70 (d, 2H, J=8.4 Hz), 7.52 (d, 2H, J=6.0 Hz), 7.46 (d, 1H, J=7.7 Hz), 7.26 (d, 2H, J=8.3 Hz), 6.55 (d, 1H, J=3.5 Hz), 5.57 (s, 2H), 3.68 (s, 2H), 3.05 (d, 2H, J=11.6 Hz), 2.79-2.71 (m, 1H), 2.31-2.24 (m, 2H), 1.98-1.90 (m, 4H); MS (ESI) m/z 442.2 (M$^+$+1).

Example 79

Synthesis of Compound 842

Step 1: Synthesis of methyl 4-((5-(1-(3-methoxybenzyl)piperidin-4-yl)-1H-pyrrolo[2,3-b]pyridin-1-yl)methyl)benzoate (formula 12-2)

(formula 12-2)

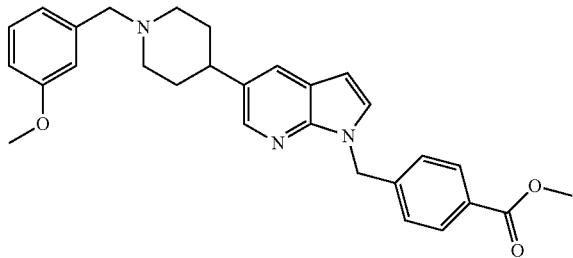

The compound of formula 6-3 (methyl 4-((5-(piperidin-4-yl)-1H-pyrrolo[2,3-b]pyridin-1-yl)methyl)benzoate) (0.100 g, 0.286 mmol), 3-methoxybenzyl chloride (0.067 g, 0.429 mmol), and cesium carbonate (0.186 g, 0.572 mmol) were dissolved in acetonitrile (5 mL), and the solution was stirred at the same temperature for 16 hours. Then, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; ethyl acetate/hexane=from 0% to 50%) to afford the desired compound of formula 12-2 (0.044 g, 32.9%) as colorless liquid.

Step 2: Synthesis of N-hydroxy-4-((5-(1-(3-methoxybenzyl)piperidin-4-yl)-1H-pyrrolo[2,3-b]pyridin-1-yl)methyl)benzamide (compound 842)

(compound 842)

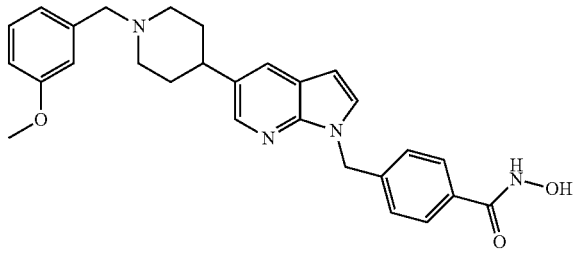

The compound of formula 12-2 (0.044 g, 0.094 mmol) prepared in step 1, hydroxylamine (50.00 wt % aqueous solution, 0.057 mL, 0.937 mmol), and potassium hydroxide (0.053 g, 0.937 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to afford the desired compound 842 (0.023 g, 52.2%) as a white solid.

$^1$H-NMR (400 MHz, CD$_3$OD) δ 8.19 (d, 1H, J=2.0 Hz), 7.93 (d, 1H, J=2.0 Hz), 7.71 (d, 2H, J=8.3 Hz), 7.47 (d, 1H, J=3.5 Hz), 7.32-7.24 (m, 3H), 7.32-6.97 (m, 2H), 6.94-6.88 (m, 1H), 6.54 (d, 1H, J=3.5 Hz), 5.55 (s, 2H), 3.84 (s, 3H), 3.08 (d, 2H, J=11.7 Hz), 2.74-2.69 (m, 1H), 2.25-2.19 (m, 2H), 1.92-1.87 (m, 4H); MS (ESI) m/z 471.3 (M$^+$+1).

Example 80

Synthesis of Compound 843

Step 1: Synthesis of methyl 4-((5-(1-(4-fluorobenzyl)-1,2,3,6-tetrahydropyridin-4-yl)-1H-pyrrolo[2,3-b]pyridin-1-yl)methyl)benzoate (formula 12-2)

(formula 12-2)

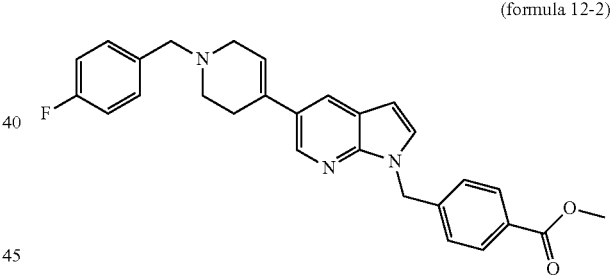

The compound of formula 6-3 (methyl 4-((5-(1,2,3,6-tetrahydropyridin-4-yl)-1H-pyrrolo[2,3-b]pyridin-1-yl)methyl)benzoate) (0.100 g, 0.288 mmol), 1-(bromomethyl)-4-fluorobenzene (0.072 mL, 0.576 mmol), and cesium carbonate (0.188 g, 0.576 mmol) were dissolved in acetonitrile (2 mL), and the solution was stirred at the same temperature for 1 hour. Then, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; ethyl acetate/hexane=from 0% to 20%) to afford the desired compound of formula 12-2 (0.070 g, 53.6%) as colorless liquid.

Step 2: Synthesis of 4-((5-(1-(4-fluorobenzyl)piperidin-4-yl)-1H-pyrrolo[2,3-b]pyridin-1-yl)methyl)-N-hydroxybenzamide (compound 843)

(compound 843)

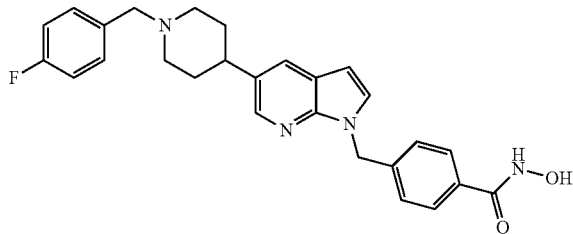

The compound of formula 12-2 (0.058 g, 0.127 mmol) prepared in step 1, hydroxylamine (50.00 wt % aqueous solution, 0.078 mL, 1.268 mmol), and potassium hydroxide (0.071 g, 1.268 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (10 mL) was added to the concentrate, followed by stirring. The precipitated solid was filtered and dried to afford the desired compound 843 (0.044 g, 75.7%) as a pink solid.

$^1$H-NMR (400 MHz, CDCl$_3$) δ 8.16 (d, 1H, J=1.9 Hz), 7.83 (d, 1H, J=1.9 Hz), 7.64 (d, 2H, J=8.0 Hz), 7.58 (d, 1H, J=3.4 Hz), 7.38-7.35 (m, 2H), 7.17-7.13 (m, 4H), 6.44 (d, 1H, J=3.5 Hz), 5.44 (s, 2H), 3.48 (s, 2H), 2.91 (d, 2H, J=11.3 Hz), 2.64-2.57 (m, 1H), 2.08-2.03 (m, 2H), 1.75-1.67 (m, 4H); MS (ESI) m/z 459.3 (M$^+$+1).

Example 81

Synthesis of Compound 844

Step 1: Synthesis of methyl 4-((5-(1-(pyridin-2-ylmethyl)-1,2,3,6-tetrahydropyridin-4-yl)-1H-pyrrolo[2,3-b]pyridin-1-yl)methyl)benzoate (formula 12-2)

(formula 12-2)

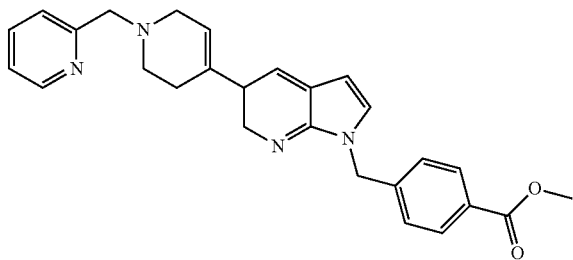

The compound of formula 6-3 (methyl 4-((5-(1,2,3,6-tetrahydropyridin-4-yl)-1H-pyrrolo[2,3-b]pyridin-1-yl)methyl)benzoate) (0.100 g, 0.288 mmol), 2-(bromomethyl)pyridine bromide (0.146 g, 0.576 mmol), and cesium carbonate (0.188 g, 0.576 mmol) were dissolved in acetonitrile (2 mL), and the solution was stirred at the same temperature for 1 hour. Then, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; methanol/methylene chloride=from 0% to 10%) to afford the desired compound of formula 12-2 (0.062 g, 49.2%) as colorless liquid.

Step 2: Synthesis of N-hydroxy-4-((5-(1-(pyridin-4-ylmethyl)piperidin-4-yl)-1H-pyrrolo[2,3-b]pyridin-1-yl)methyl)benzamide (compound 844)

(compound 844)

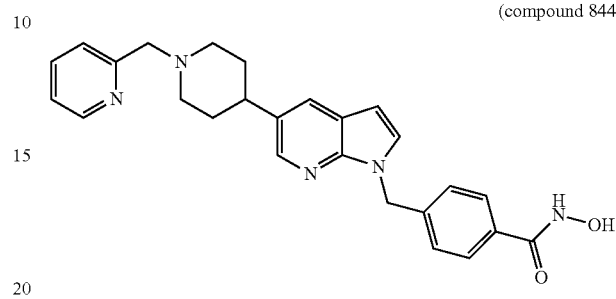

The compound of formula 12-2 (0.058 g, 0.132 mmol) prepared in step 1, hydroxylamine (50.00 wt % aqueous solution, 0.081 mL, 1.317 mmol), and potassium hydroxide (0.074 g, 1.317 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (10 mL) was added to the concentrate, followed by stirring. The precipitated solid was filtered and dried to afford the desired compound 844 (0.018 g, 31.0%) as a pink solid.

$^1$H-NMR (400 MHz, DMSO-d$_6$) δ 8.50 (d, 1H, J=4.0 Hz), 8.17 (s, 1H), 7.84 (s, 1H), 7.78 (t, 1H, J=7.5 Hz), 7.63 (d, 2H, J=8.0 Hz), 7.58 (d, 1H, J=3.4 Hz), 7.49 (d, 1H, J=7.8 Hz), 7.28-7.25 (m, 1H), 7.15 (d, 2H, J=8.0 Hz), 6.45 (d, 1H, J=3.4 Hz), 5.44 (s, 2H), 3.63 (s, 2H), 2.95 (d, 2H, J=10.8 Hz), 2.68-2.61 (m, 1H), 2.16-2.14 (m, 2H), 1.77-1.76 (m, 4H); MS (ESI) m/z 442.3 (M$^+$+1).

Example 82

Synthesis of Compound 845

Step 1: Synthesis of methyl 4-((5-(1-((5-(trifluoromethyl)-1,2,4-oxadiazol-3-yl)methyl)piperidin-4-yl)-1H-pyrrolo[2,3-b]pyridin-1-yl)methyl)benzoate (formula 12-2)

(formula 12-2)

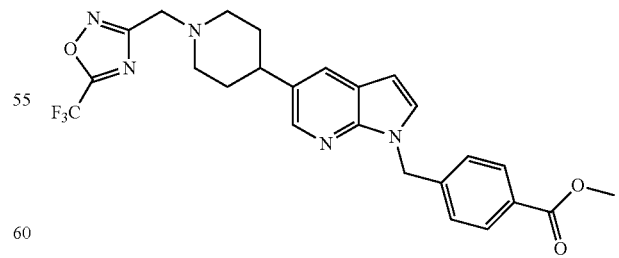

The compound of formula 6-3 (methyl 4-((5-(piperidin-4-yl)-1H-pyrrolo[2,3-b]pyridin-1-yl)methyl)benzoate) (0.100 g, 0.286 mmol), 3-(chloromethyl)-5-(trifluoromethyl)-1,2,4-oxadiazole (0.107 g, 0.572 mmol), and cesium carbonate (0.186 g, 0.572 mmol) were dissolved in acetonitrile (2 mL), and the solution was stirred at the same temperature for 1 hour. Then, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; ethyl acetate/hexane=from 0% to 20%) to afford the desired compound of formula 12-2 (0.051 g, 35.7%) as a colorless liquid.

Step 2: N-hydroxy-4-((5-(1-((5-(trifluoromethyl)-1,2,4-oxadiazol-3-yl)methyl)piperidin-4-yl)-1H-pyrrolo[2,3-b]pyridin-1-yl)methyl)benzamide (compound 845)

(compound 845)

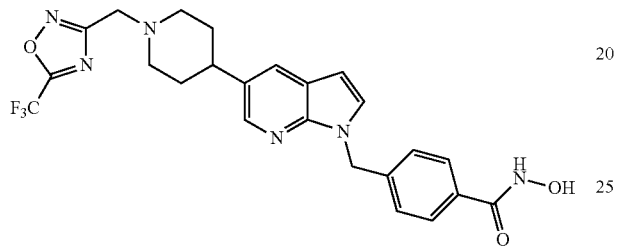

The compound of formula 12-2 (0.051 g, 0.102 mmol) prepared in step 1, hydroxylamine (50.00 wt % aqueous solution, 0.062 mL, 1.019 mmol), and potassium hydroxide (0.057 g, 1.019 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (10 mL) was added to the concentrate, followed by stirring. The precipitated solid was filtered and dried to afford the desired compound 845 (0.034 g, 66.1%) as a white solid.

$^1$H-NMR (400 MHz, DMSO-d$_6$) δ 8.17 (d, 1H, J=2.0 Hz), 7.83 (d, 1H, J=1.9 Hz), 7.63 (d, 2H, J=8.2 Hz), 7.58 (d, 1H, J=3.5 Hz), 7.14 (d, 2H, J=8.2 Hz), 6.45 (d, 1H, J=3.5 Hz), 5.43 (s, 2H), 5.26 (s, 2H), 2.92 (d, 2H, J=11.0 Hz), 2.61-2.57 (m, 1H), 2.08-2.03 (m, 2H), 1.78-1.69 (m, 4H).

Example 83

Synthesis of Compound 846

Step 1: Synthesis of methyl 4-((4-(4-(3-methoxybenzyl)piperazin-1-yl)-1H-pyrrolo[2,3-b]pyridin-1-yl)methyl)benzoate (formula 7-4)

(formula 7-4)

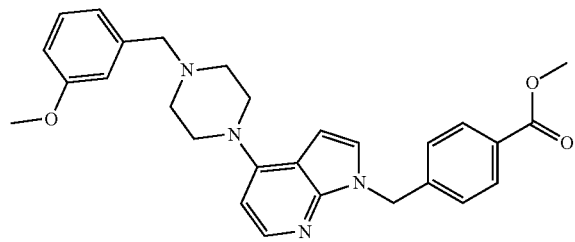

The compound of formula 7-3 (methyl 4-((4-(piperazin-1-yl)-1H-pyrrolo[2,3-b]pyridin-1-yl)methyl)benzoate hydrochloride) (0.150 g, 0.388 mmol), 1-(chloromethyl)-3-methoxybenzene (0.121 g, 0.775 mmol), and TEA (0.109 mL, 0.775 mmol) were dissolved in methylene chloride (3 mL), and the solution was stirred at the same temperature for 12 hours. Then, water was added to the reaction mixture, followed by extraction with ethyl acetate. The organic layer was washed with a saturated aqueous solution of ammonium chloride, dried with anhydrous magnesium sulfate, filtered, and then concentrated under reduced pressure. The concentrate was purified by column chromatography (SiO$_2$, 4 g cartridge; methanol/methylene chloride=from 0% to 10%) to afford the desired compound of formula 7-3 (0.090 g, 49.3%) as a yellow oil.

Step 2: Synthesis of N-hydroxy-4-((4-(4-(3-methoxybenzyl)piperazin-1-yl)-1H-pyrrolo[2,3-b]pyridin-1-yl)methyl)benzamide (compound 846)

(compound 846)

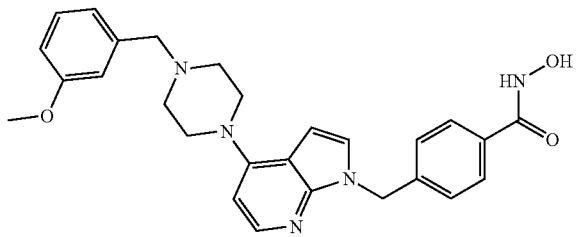

The compound of formula 7-4 (0.090 g, 0.191 mmol) prepared in step 1, potassium hydroxide (0.107 g, 1.913 mmol), and an aqueous solution of 50 wt % NH$_2$OH (0.246 mL, 3.825 mmol) were dissolved in methanol (3 mL) at room temperature, and the solution was stirred at the same temperature for 2 hours. Then, the reaction mixture was concentrated under reduced pressure to remove the solvent, and a saturated aqueous solution of sodium hydrogen carbonate (2 mL) was added to the concentrate, followed by stirring. The precipitated solid was filtered, washed with water, and dried to afford the desired compound 846 (0.036 g, 39.9%) as a yellow solid.

$^1$H-NMR (400 MHz, DMSO-d$_6$) δ 7.93 (d, 1H, J=5.5 Hz), 7.61 (d, 2H, J=8.3 Hz), 7.35 (d, 1H, J=3.6 Hz), 7.23-7.20 (m, 1H), 7.19 (d, 2H, J=8.3 Hz), 6.91-6.89 (m, 2H), 6.83-6.80 (m, 1H), 6.54 (d, 1H, J=3.6 Hz), 6.45-6.40 (m, 1H), 5.40 (s, 2H), 3.73 (s, 3H), 3.62 (s, 2H), 3.49-3.40 (m, 8H); MS (ESI) m/z 472.3 (M$^+$+1).

Example 84

Synthesis of Compound 847

Step 1: Synthesis of methyl 4-((4-(4-(2-fluorobenzyl)piperazin-1-yl)-1H-pyrrolo[2,3-b]pyridin-1-yl)methyl)benzoate (formula 7-4)

(formula 7-4)

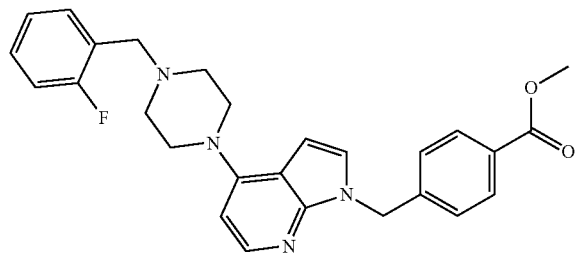

The compound of formula 7-3 (methyl 4-((4-(piperazin-1-yl)-1H-pyrrolo[2,3-b]pyridin-1-yl)methyl)benzoate hydrochloride) (0.150 g, 0.388 mmol), 1-(bromomethyl)-2-fluorobenzene (0.147 g, 0.775 mmol), and TEA (0.109 mL, 0.775 mmol) were dissolved in methylene chloride (3 mL) at room temperature, and the solution was stirred at the same temperature for 12 hours. Then, water was added to the reaction mixture, followed by extraction with ethyl acetate. The organic layer was washed with a saturated aqueous solution of ammonium chloride, dried with anhydrous magnesium sulfate, filtered, and then concentrated under reduced pressure. The concentrate was purified by column chromatography (SiO$_2$, 4 g cartridge; methanol/methylene chloride=from 0% to 10%) to afford the desired compound of formula 7-4 (0.095 g, 53.4%) as a yellow oil.

Step 2: Synthesis of 4-((4-(4-(2-fluorobenzyl)piperazin-1-yl)-1H-pyrrolo[2,3-b]pyridin-1-yl)methyl)-N-hydroxybenzamide (compound 847)

(compound 847)

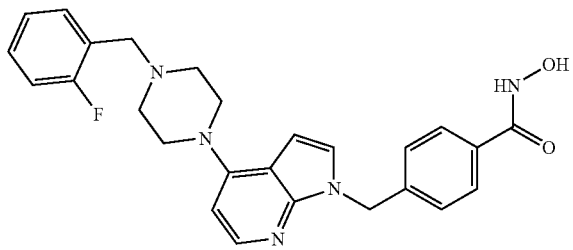

The compound of formula 7-4 (0.095 g, 0.207 mmol) prepared in step 1, potassium hydroxide (0.116 g, 2.072 mmol), and an aqueous solution of 50 wt % NH$_2$OH (0.266 mL, 4.144 mmol) were dissolved in methanol (3 mL) at room temperature, and the solution was stirred at the same temperature for 2 hours. Then, the reaction mixture was concentrated under reduced pressure to remove the solvent, and the concentrate was purified by column chromatography (SiO$_2$, 12 g cartridge; methanol/methylene chloride=from 0% to 30%) to afford the desired compound 847 (0.061 g, 64.1%) as a white solid.

$^1$H-NMR (400 MHz, DMSO-d6) δ 7.93 (d, 1H, J=5.6 Hz), 7.60 (d, 2H, J=8.3 Hz), 7.42-7.40 (m, 2H), 7.35-7.34 (m, 2H), 7.19-7.14 (m, 3H), 6.53 (d, 1H, J=3.6 Hz), 6.46 (d, 1H, J=5.6 Hz), 5.39 (s, 2H), 3.93 (s, 2H), 3.74 (s, 2H), 3.58 (s, 2H), 3.39 (s, 2H), 2.55 (s, 2H); MS (ESI) m/z 460.3 (M$^+$+1).

Example 85

Synthesis of Compound 848

Step 1: Synthesis of methyl 4-((4-(4-(3-fluorobenzyl)piperazin-1-yl)-1H-pyrrolo[2,3-b]pyridin-1-yl)methyl)benzoate (formula 7-4)

(formula 7-4)

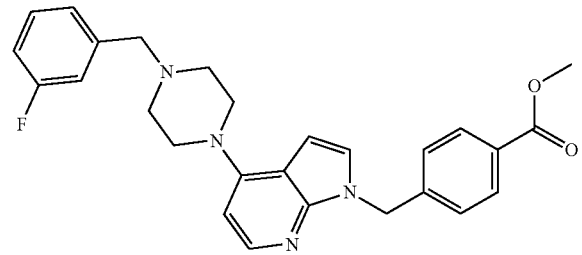

The compound of formula 7-3 (methyl 4-((4-(piperazin-1-yl)-1H-pyrrolo[2,3-b]pyridin-1-yl)methyl)benzoate) (0.150 g, 0.388 mmol), 1-(bromomethyl)-3-fluorobenzene (0.147 g, 0.775 mmol), and TEA (0.109 mL, 0.775 mmol) were dissolved in methylene chloride (3 mL) at room temperature, and the solution was stirred at the same temperature for 12 hours. Then, water was added to the reaction mixture, followed by extraction with ethyl acetate. The organic layer was washed with a saturated aqueous solution of ammonium chloride, dried with anhydrous magnesium sulfate, filtered, and then concentrated under reduced pressure. The concentrate was purified by column chromatography (SiO$_2$, 4 g cartridge; methanol/methylene chloride=from 0% to 10%) to afford the desired compound of formula 7-4 (0.100 g, 56.2%) as a yellow oil.

Step 2: Synthesis of 4-((4-(4-(3-fluorobenzyl)piperazin-1-yl)-1H-pyrrolo[2,3-b]pyridin-1-yl)methyl)-N-hydroxybenzamide (compound 848)

(compound 848)

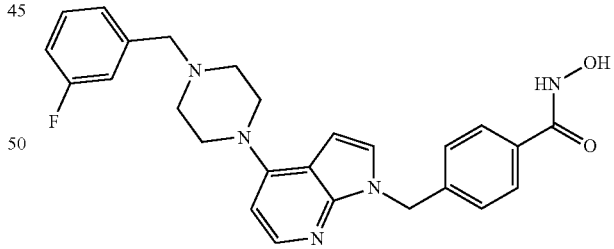

The compound of formula 7-4 (0.100 g, 0.218 mmol) prepared in step 1, potassium hydroxide (0.122 g, 2.181 mmol), and an aqueous solution of 50 wt % NH$_2$OH (0.280 mL, 4.362 mmol) were dissolved in methanol (3 mL) at room temperature, the solution was stirred at the same temperature for 2 hours. Then, the reaction mixture was concentrated under reduced pressure to remove the solvent, and a saturated aqueous solution of sodium hydrogen carbonate (10 mL) was added to the concentrate, followed by stirring. The precipitated solid was filtered, washed with water, and dried to afford the desired compound 848 (0.071 g, 70.8%) as a white solid.

$^1$H-NMR (400 MHz, DMSO-d$_6$) δ 7.94 (d, 1H, J=5.6 Hz), 7.60 (d, 2H, J=8.2 Hz), 7.37-7.33 (m, 2H), 7.18-7.13 (m, 4H), 7.09-7.07 (m, 1H), 6.53 (d, 1H, J=3.6 Hz), 6.46 (d, 1H, J=5.6 Hz), 5.38 (s, 2H), 3.90 (s, 2H), 3.40 (s, 4H), 2.53 (s, 4H); MS (ESI) m/z 460.3 (M$^+$+1).

Example 86

Synthesis of Compound 849

Step 1: Synthesis of methyl 4-((4-(4-(pyridin-3-ylmethyl)piperazin-1-yl)-1H-pyrrolo[2,3-b]pyridin-1-yl)methyl)benzoate (formula 7-4)

(formula 7-4)

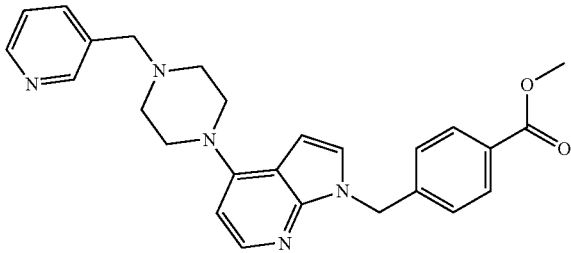

The compound of formula 7-3 (methyl 4-((4-(piperazin-1-yl)-1H-pyrrolo[2,3-b]pyridin-1-yl)methyl)benzoate hydrochloride) (0.150 g, 0.388 mmol), 3-(chloromethyl)pyridine hydrochloride (0.127 g, 0.775 mmol), and TEA (0.109 mL, 0.775 mmol) were dissolved in methylene chloride (3 mL) at room temperature, and the solution was stirred at the same temperature for 12 hours. Then, water was added to the reaction mixture, followed by extraction with ethyl acetate. The organic layer was washed with a saturated aqueous solution of ammonium chloride, dried with anhydrous magnesium sulfate, filtered, and then concentrated under reduced pressure. The concentrate was purified by column chromatography (SiO$_2$, 4 g cartridge; methanol/methylene chloride=from 0% to 10%) to afford the desired compound of formula 7-4 (0.110 g, 64.3%) as a yellow oil.

Step 2: Synthesis of N-hydroxy-4-((4-(4-(pyridin-3-ylmethyl)piperazin-1-yl)-1H-pyrrolo[2,3-b]pyridin-1-yl)methyl)benzamide (compound 849)

(compound 849)

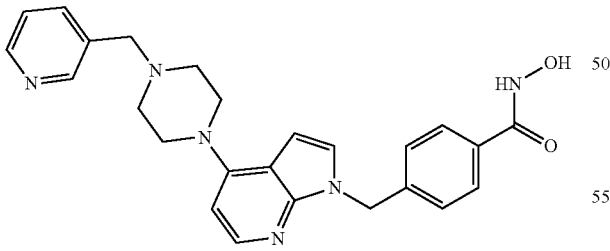

The compound of formula 7-4 (0.110 g, 0.249 mmol) prepared in step 1, potassium hydroxide (0.140 g, 2.491 mmol), and an aqueous solution of 50 wt % NH$_2$OH (0.320 mL, 4.983 mmol) were dissolved in methanol (3 mL) at room temperature, the solution was stirred at the same temperature for 2 hours. Then, the reaction mixture was concentrated under reduced pressure to remove the solvent, and a saturated aqueous solution of sodium hydrogen carbonate (2 mL) was added to the concentrate, followed by stirring. The precipitated solid was filtered, washed with water, and dried to afford the desired compound 849 (0.081 g, 73.5%) as a white solid.

$^1$H-NMR (400 MHz, DMSO-d$_6$) δ 8.49 (s, 1H), 8.45 (d, 1H, J=4.8 Hz), 7.94 (d, 1H, J=5.5 Hz), 7.81-7.68 (m, 1H), 7.61 (d, 2H, J=8.2 Hz), 7.36-7.35 (m, 2H), 7.19 (d, 2H, J=8.3 Hz), 6.54 (d, 1H, J=3.6 Hz), 6.46 (d, 1H, J=5.6 Hz), 5.40 (s, 2H), 3.90 (s, 2H), 3.40 (s, 4H), 2.54 (s, 4H); MS (ESI) m/z 443.3 (M$^+$+1).

Example 87

Synthesis of Compound 850

Step 1: Synthesis of methyl 4-((4-(4-(pyridin-4-ylmethyl)piperazin-1-yl)-1H-pyrrolo[2,3-b]pyridin-1-yl)methyl)benzoate (formula 7-4)

(formula 7-4)

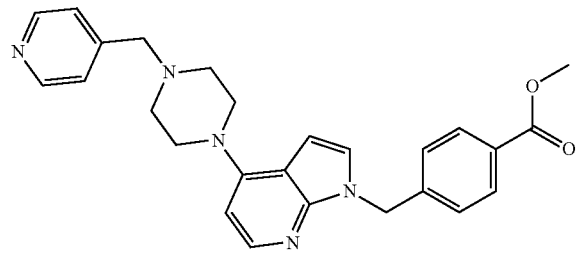

The compound of formula 7-3 (methyl 4-((4-(piperazin-1-yl)-1H-pyrrolo[2,3-b]pyridin-1-yl)methyl)benzoate hydrochloride) (0.150 g, 0.388 mmol), 4-(chloromethyl)pyridine hydrochloride (0.127 g, 0.775 mmol), and TEA (0.109 mL, 0.775 mmol) were dissolved in methylene chloride (3 mL) at room temperature, and the solution was stirred at the same temperature for 12 hours. Then, water was added to the reaction mixture, followed by extraction with ethyl acetate. The organic layer was washed with a saturated aqueous solution of ammonium chloride, dried with anhydrous magnesium sulfate, filtered, and then concentrated under reduced pressure. The concentrate was purified by column chromatography (SiO$_2$, 4 g cartridge; methanol/methylene chloride=from 0% to 10%) to afford the desired compound of formula 7-4 (0.120 g, 70.1%) as a yellow oil.

Step 2: Synthesis of N-hydroxy-4-((4-(4-(pyridin-4-ylmethyl)piperazin-1-yl)-1H-pyrrolo[2,3-b]pyridin-1-yl)methyl)benzamide (compound 850)

(compound 850)

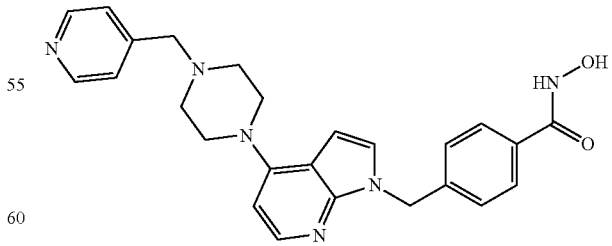

The compound of formula 7-4 (0.120 g, 0.272 mmol) prepared in step 1, potassium hydroxide (0.153 g, 2.718 mmol), and an aqueous solution of 50 wt % NH$_2$OH (0.349 mL, 5.436 mmol) were dissolved in methanol (3 mL) at room temperature, the solution was stirred at the same temperature for 2 hours. Then, the reaction mixture was concentrated under reduced pressure to remove the solvent, and a saturated aqueous solution of sodium hydrogen carbonate (3 mL) was added to the concentrate, followed by stirring. The precipitated solid was filtered, washed with water, and dried to afford the desired compound 850 (0.077 g, 64.0%) as a white solid.

$^1$H-NMR (400 MHz, DMSO-$d_6$) δ 8.49 (d, 2H, J=5.8 Hz), 7.94 (d, 1H, J=5.5 Hz), 7.61 (d, 2H, J=8.2 Hz), 7.39-7.35 (m, 3H), 7.20 (d, 2H, J=8.2 Hz), 6.54 (d, 1H, J=3.6 Hz), 6.47 (d, 1H, J=5.6 Hz), 5.41 (s, 2H), 3.90 (s, 2H), 3.42 (s, 4H), 2.55 (s, 4H); MS (ESI) m/z 443.3 (M$^+$+1).

Example 88

Synthesis of Compound 851

Step 1: Synthesis of tert-butyl 4-(1-(4-(methoxycarbonyl)benzyl)-1H-pyrrolo[2,3-b]pyridin-5-yl)piperazine-1-carboxylate (formula 13-1)

(formula 13-1)

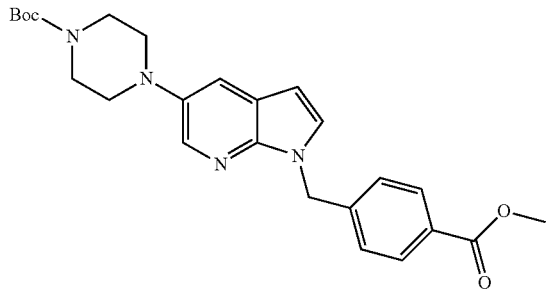

The compound of formula 2-2 (methyl 4-((5-bromo-1H-pyrrolo[2,3-b]pyridin-1-yl)methylbenzoate) (3.000 g, 8.691 mmol), tert-butyl piperazine-1-carboxylate (1.942 g, 10.429 mmol), bis(tri-tert-butylphosphino)palladium(0) (0.444 g, 0.869 mmol), and sodium tert-butoxide (1.002 g, 10.429 mmol) were dissolved in toluene (100 mL) at 120° C., and the solution was stirred at the same temperature for 2 hours, and then cooled to room temperature. After completion of the reaction, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 40 g cartridge; ethyl acetate/hexane=from 0% to 20%) to afford the desired compound of formula 13-1 (2.105 g, 53.8%) as an ivory solid.

Step 2: Synthesis of methyl 4-((5-(piperazin-1-yl)-1H-pyrrolo[2,3-b]pyridin-1-yl)methyl)benzoate (formula 13-2)

(formula 13-2)

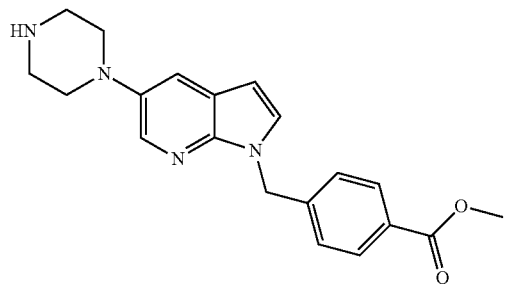

The compound of formula 13-1 (2.105 g, 4.672 mmol) prepared in step 1 and hydrochloric acid (4.00 M, 1,4-dioxane solution, 5.840 mL, 23.361 mmol) were dissolved in 1,4-dioxane (10 mL) at room temperature, and the solution was stirred at the same temperature for 3 hours. Then, the reaction mixture was concentrated under reduced pressure to remove the solvent, and diethyl ether (100 mL) was added to the concentrate, followed by stirring. The precipitated solid was filtered and dried to afford the desired compound of formula 13-2 (1.512 g, 92.4%) as an ivory solid.

Step 3: Synthesis of methyl 4-((5-(4-(3-fluorobenzyl)piperazin-1-yl)-1H-pyrrolo[2,3-b]pyridin-1-yl)methyl)benzoate (formula 13-4)

(formula 13-4)

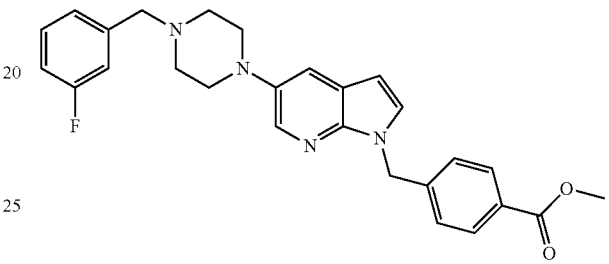

The compound of formula 13-2 (0.100 g, 0.285 mmol) prepared in step 2, 1-(bromomethyl)-3-fluorobenzene (0.108 g, 0.571 mmol), and N,N-diisopropylethylamine (0.102 mL, 0.571 mmol) were dissolved in acetonitrile (2 mL) at room temperature, and the solution was stirred at the same temperature for 1 hour. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; ethyl acetate/hexane=from 0% to 50%) to afford the desired compound of formula 13-4 (0.062 g, 47.4%) as a colorless liquid.

Step 4: Synthesis of 4-((5-(4-(3-fluorobenzyl)piperazin-1-yl)-1H-pyrrolo[2,3-b]pyridin-1-yl)methyl)-N-hydroxybenzamide (compound 851)

(compound 851)

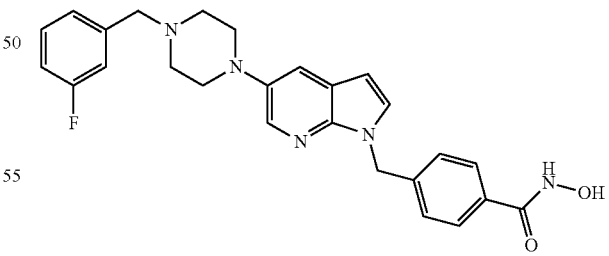

The compound of formula 13-4 (0.062 g, 0.135 mmol) prepared in step 3, hydroxylamine (50.00 wt % aqueous solution, 0.083 mL, 1.352 mmol), and potassium hydroxide (0.076 g, 1.352 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (10 mL) was added to the concentrate, followed by stirring. The precipitated solid was filtered and dried to afford the desired compound 851 (0.020 g, 31.5%) as a white solid.

$^1$H-NMR (400 MHz, DMSO-$d_6$) δ 8.10 (d, 1H, J=2.6 Hz), 7.64 (d, 2H, J=8.1 Hz), 7.54 (d, 1H, J=3.4 Hz), 7.51 (d, 1H, J=2.4 Hz), 7.42-7.36 (m, 1H), 7.20-7.16 (m, 4H), 7.10 (td, 1H, J=8.6, 2.7 Hz), 6.38 (d, 1H, J=3.4 Hz), 5.39 (s, 2H), 3.57 (s, 2H), 3.10 (m, 4H), 2.57-2.55 (m, 4H); MS (ESI) m/z 460.3 (M$^+$+1)

Example 89

Synthesis of Compound 852

Step 1: Synthesis of methyl 4-((5-(4-(4-fluorobenzyl)piperazin-1-yl)-1H-pyrrolo[2,3-b]pyridin-1-yl)methyl)benzoate (formula 13-4)

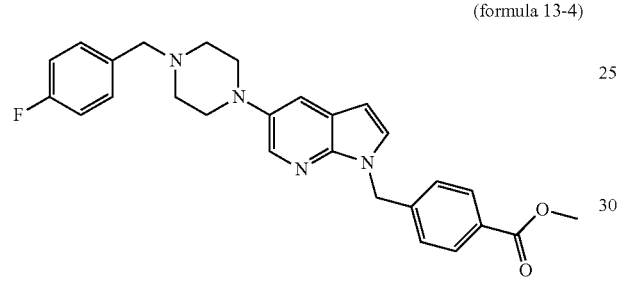

(formula 13-4)

The compound of formula 13-2 (0.100 g, 0.285 mmol), 1-(bromomethyl)-4-fluorobenzene (0.108 g, 0.571 mmol), and N,N-diisopropylethylamine (0.102 mL, 0.571 mmol) were dissolved in acetonitrile (2 mL) at room temperature, and the solution was stirred at the same temperature for 1 hour. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; ethyl acetate/hexane=from 0% to 50%) to afford the desired compound of formula 13-4 (0.106 g, 81.0%) as a colorless liquid.

Step 2: Synthesis of 4-((5-(4-(4-fluorobenzyl)piperazin-1-yl)-1H-pyrrolo[2,3-b]pyridin-1-yl)methyl)-N-hydroxybenzamide (compound 852)

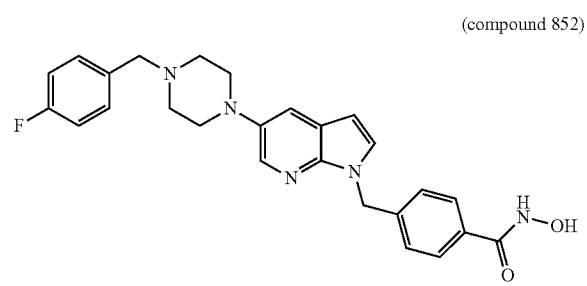 [SMILES: O=C(NO)c1ccc(Cn2ccc3cc(N4CCN(Cc5ccc(F)cc5)CC4)cnc32)cc1]

(compound 852)

The compound of formula 13-4 (0.106 g, 0.231 mmol) prepared in step 1, hydroxylamine (50.00 wt % aqueous solution, 0.141 mL, 2.312 mmol), and potassium hydroxide (0.130 g, 2.312 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (10 mL) was added to the concentrate, followed by stirring. The precipitated solid was filtered and dried to afford the desired compound 852 (0.080 g, 75.4%) as white solid.

$^1$H-NMR (400 MHz, DMSO-$d_6$) δ 8.10 (d, 1H, J=2.0 Hz), 7.63 (d, 2H, J=8.0 Hz), 7.51 (d, 2H, J=8.6 Hz), 7.38-7.36 (m, 2H), 7.19-7.13 (m, 4H), 6.37 (d, 1H, J=2.9 Hz), 5.41 (s, 2H), 3.52 (s, 2H), 3.09 (m, 4H), 2.55 (m, 4H); MS (ESI) m/z 460.3 (M$^+$+1).

Example 90

Synthesis of Compound 853

Step 1: Synthesis of methyl 4-((5-(4-isobutylpiperazin-1-yl)-1H-pyrrolo[2,3-b]pyridin-1-yl)methyl)benzoate (formula 13-4)

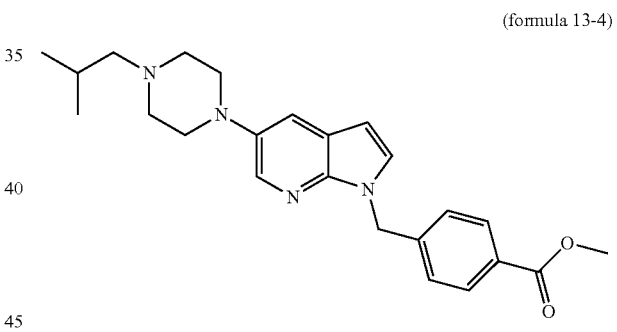

(formula 13-4)

The compound of formula 13-2 (methyl 4-((5-(piperazin-1-yl)-1H-pyrrolo[2,3-b]pyridin-1-yl)methyl)benzoate) (0.100 g, 0.285 mmol), isobutyl 4-methylbenzene sulfonate (0.078 g, 0.342 mmol), and N,N-diisopropylethylamine (0.101 mL, 0.571 mmol) were dissolved in acetonitrile (2 mL) at room temperature, and the solution was stirred at the same temperature for 1 hour. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; methanol/methylene chloride=from 0% to 10%) to afford the desired compound of formula 13-4 (0.018 g, 15.3%) as a colorless liquid.

Step 2: Synthesis of N-hydroxy-4-((5-(4-isobutylpiperazin-1-yl)-1H-pyrrolo[2,3-b]pyridin-1-yl)methyl)benzamide (compound 853)

(compound 853)

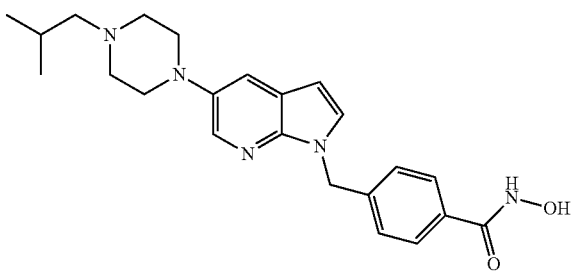

The compound of formula 13-4 (0.018 g, 0.044 mmol) prepared in step 1, hydroxylamine (50.00 wt % aqueous solution, 0.027 mL, 0.443 mmol), and potassium hydroxide (0.025 g, 0.443 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to afford the desired compound 853 (0.012 g, 68.2%) as a white solid.
$^1$H-NMR (400 MHz, DMSO-$d_6$) δ 8.11 (d, 1H, J=2.6 Hz), 7.62 (d, 2H, J=8.2 Hz), 7.52 (d, 1H, J=3.5 Hz), 7.50 (d, 1H, J=2.6 Hz), 7.11 (d, 2H, J=8.0 Hz), 6.37 (d, 1H, J=3.4 Hz), 5.39 (s, 2H), 3.08-3.07 (m, 4H), 2.54 (m, 4H), 1.41-1.37 (m, 2H), 1.26-1.24 (m, 1H), 0.91 (s, 6H); MS (ESI) m/z 408.2 (M$^+$+1).

Example 91

Synthesis of Compound 854

Step 1: Synthesis of methyl 4-((5-(1-(2-fluoro-2-methylpropanoyl)piperidin-4-yl)-1H-pyrrolo[2,3-b]pyridin-1-yl)methyl)benzoate (formula 12-1)

(formula 12-1)

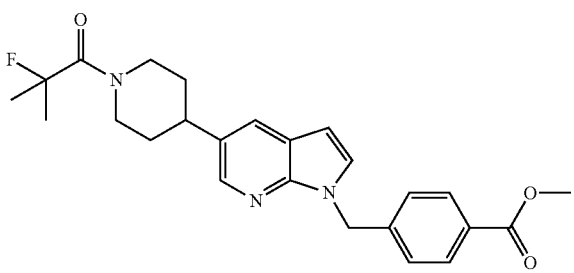

The compound of formula 6-3 (methyl 4-((5-(piperidin-4-yl)-1H-pyrrolo[2,3-b]pyridin-1-yl)methyl)benzoate) (0.100 g, 0.259 mmol), 2-fluoro-2-methylpropanoic acid (0.055 g, 0.518 mmol), 1-ethyl-3-[3-dimethylaminopropyl] carbodiimide hydrochloride (0.099 g, 0.518 mmol), 1-hydroxybenzotriazole hydrate (0.070 g, 0.518 mmol), and N,N-diisopropylethylamine (0.229 mL, 1.296 mmol) were dissolved in N,N-dimethylformamide (2 mL) at 40° C., and the solution was stirred at the same temperature for 16 hours, and then cooled to room temperature. After completion of the reaction, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; ethyl acetate/hexane=from 0% to 50%) to afford the desired compound of formula 12-1 (0.089 g, 78.3%) as a colorless liquid.

Step 2: Synthesis of 4-((5-(1-(2-fluoro-2-methylpropanoyl)piperidin-4-yl)-1H-pyrrolo[2,3-b]pyridin-1-yl)methyl)-N-hydroxybenzamide (compound 854)

(compound 854)

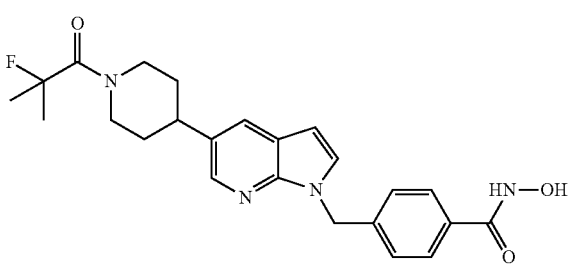

The compound of formula 12-1 (0.089 g, 0.203 mmol) prepared in step 1, hydroxylamine (50.00 wt % aqueous solution, 0.124 mL, 2.034 mmol), and potassium hydroxide (0.114 g, 2.034 mmol) were dissolved in methanol (1 mL)/tetrahydrofuran (1 mL) at room temperature, and the solution was dissolved at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to afford the desired compound 854 (0.081 g, 90.8%) as a white solid.
$^1$H-NMR (400 MHz, DMSO-$d_6$) δ 8.18 (d, 1H, J=2.0 Hz), 7.86 (d, 1H, J=2.0 Hz), 7.64 (d, 2H, J=8.3 Hz), 7.60 (d, 1H, J=3.5 Hz), 7.16 (d, 2H, J=8.3 Hz), 6.45 (d, 1H, J=3.5 Hz), 5.45 (s, 2H), 4.51-4.45 (m, 2H), 3.21-3.17 (m, 2H), 2.68-2.61 (m, 1H), 1.90-1.87 (m, 2H), 1.71-1.64 (m, 2H), 1.61 (s, 3H), 1.55 (s, 3H); MS (ESI) m/z 439.2 (M$^+$+1).

Example 92

Synthesis of Compound 855

Step 1: Synthesis of methyl 4-((5-(4-(2-fluoro-2-methylpropanoyl)piperazin-1-yl)-1H-pyrrolo[2,3-b]pyridin-1-yl)methyl)benzoate (formula 13-3)

(formula 13-3)

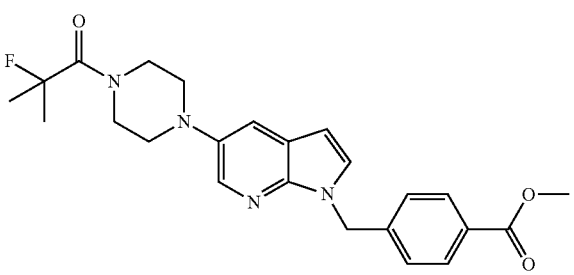

The compound of formula 13-2 (methyl 4-((5-(piperazin-1-yl)-1H-pyrrolo[2,3-b]pyridin-1-yl)methyl)benzoate) (0.100 g, 0.258 mmol), 2-fluoro-2-methylpropanoic acid (0.055 g, 0.517 mmol), 1-ethyl-3-[3-dimethylaminopropyl] carbodiimide hydrochloride (0.099 g, 0.517 mmol), 1-hydroxybenzotriazole hydrate (0.070 g, 0.517 mmol), and N,N-diisopropylethylamine (0.229 mL, 1.292 mmol) were dissolved in N,N-dimethylformamide (2 mL) at 40° C., and the solution was stirred at the same temperature for 16 hours, and then cooled to room temperature. After completion of the reaction, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; ethyl acetate/hexane=from 0% to 50%) to afford the desired compound of formula 13-3 (0.026 g, 23.0%) as a colorless liquid.

Step 2: Synthesis of 4-((5-(4-(2-fluoro-2-methylpropanoyl)piperazin-1-yl)-1H-pyrrolo[2,3-b]pyridin-1-yl)methyl)-N-hydroxybenzamide (compound 855)

(compound 855)

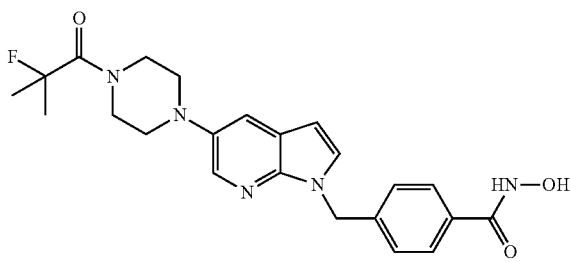

The compound of formula 13-3 (0.026 g, 0.059 mmol) prepared in step 1, hydroxylamine (50.00 wt % aqueous solution, 0.036 mL, 0.593 mmol), and potassium hydroxide (0.033 g, 0.593 mmol) were dissolved in methanol (1 mL)/tetrahydrofuran (1 mL) at room temperature, and the solution was dissolved at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to afford the desired compound 855 (0.020 g, 76.7%) as a white solid.

$^1$H-NMR (400 MHz, DMSO-d$_6$) δ 8.14 (d, 1H, J=2.6 Hz), 7.65 (d, 2H, J=8.2 Hz), 7.57 (d, 2H, J=2.5 Hz), 7.18 (d, 2H, J=8.2 Hz), 6.40 (d, 1H, J=3.4 Hz), 5.44 (s, 2H), 3.88-3.69 (m, 4H), 3.11 (m, 4H), 1.61 (s, 3H), 1.55 (s, 3H); MS (ESI) m/z 440.3 (M$^+$+1).

Example 93

Synthesis of Compound 856

Step 1: Synthesis of methyl 4-((4-(4-(2-fluoro-2-methylpropanoyl)piperazin-1-yl)-1H-pyrrolo[2,3-b]pyridin-1-yl)methyl)benzoate (formula 9-2)

(formula 9-2)

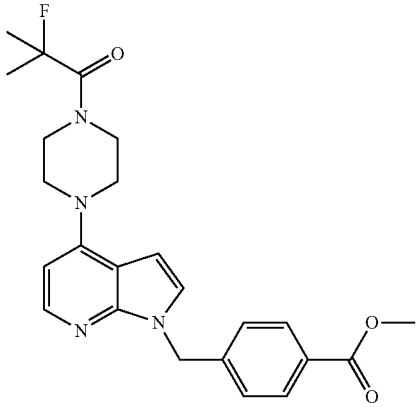

The compound of formula 8-1 (methyl 4-((4-(piperazin-1-yl)-1H-pyrrolo[2,3-b]pyridin-1-yl)methyl)benzoate) (0.100 g, 0.258 mmol), 2-fluoro-2-methylpropanoic acid (0.055 g, 0.517 mmol), 1-ethyl-3-[3-dimethylaminopropyl] carbodiimide hydrochloride (0.099 g, 0.517 mmol), 1-hydroxybenzotriazole hydrate (0.070 g, 0.517 mmol), and N,N-diisopropylethylamine (0.167 g, 1.292 mmol) were dissolved in N,N-dimethylformamide (2 mL) at 40° C., and the solution was stirred at the same temperature for 16 hours, and then cooled to room temperature. After completion of the reaction, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; ethyl acetate/hexane=from 0% to 50%) to afford the desired compound of formula 9-2 (0.066 g, 58.2%) as a colorless liquid.

Step 2: Synthesis of 4-((4-(4-(2-fluoro-2-methylpropanoyl)piperazin-1-yl)-1H-pyrrolo[2,3-b]pyridin-1-yl)methyl)-N-hydroxybenzamide (compound 856)

(compound 856)

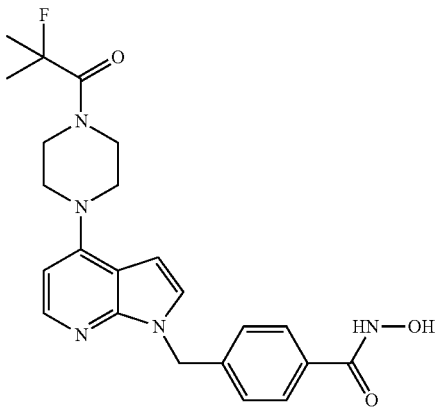

The compound of formula 9-2 (0.066 g, 0.151 mmol) prepared in step 1, hydroxylamine (50.00 wt % aqueous solution, 0.092 mL, 1.505 mmol), and potassium hydroxide (0.084 g, 1.505 mmol) were dissolved in methanol (1 mL)/tetrahydrofuran (1 mL) at room temperature, and the solution was dissolved at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to afford the desired compound 856 (0.035 g, 52.9%) as a yellow solid.

$^1$H-NMR (400 MHz, DMSO-$d_6$) δ 8.00 (d, 1H, J=5.4 Hz), 7.64 (d, 2H, J=8.2 Hz), 7.43 (d, 1H, J=3.6 Hz), 7.18 (d, 2H, J=7.9 Hz), 6.62 (d, 1H, J=3.6 Hz), 6.48 (d, 1H, J=5.4 Hz), 5.44 (s, 2H), 3.93-3.71 (m, 4H), 3.52-3.47 (m, 4H), 1.61 (s, 3H), 1.55 (s, 3H); MS (ESI) m/z 440.3 (M$^+$+1).

Example 94

Synthesis of Compound 857

Step 1: Synthesis of methyl 4-((5-((3S,5R)-3,5-dimethylpiperazin-1-yl)-1H-pyrrolo[2,3-b]pyridin-1-yl)methyl)benzoate (formula 14-1)

(formula 14-1)

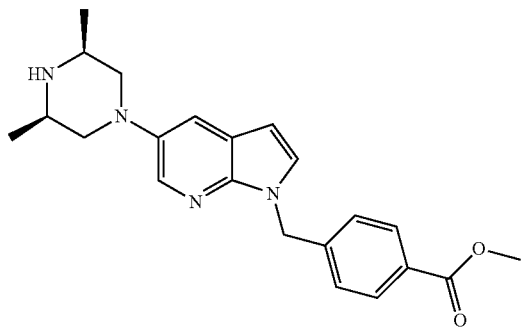

The compound of formula 2-2 (methyl 4-((5-bromo-1H-pyrrolo[2,3-b]pyridin-1-yl)methyl)benzoate) (3.000 g, 8.691 mmol), (2R,6S)-2,6-dimethylpiperazine (2.235 g, 10.429 mmol), bis(tri-tert-butylphosphino)palladium(0) (0.444 g, 0.869 mmol), and sodium tert-butoxide (1.002 g, 10.429 mmol) were dissolved in toluene (100 mL) at 120° C., and the solution was stirred at the same temperature for 16 hours, and then cooled to room temperature. After completion of the reaction, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 40 g cartridge; methanol/methylene chloride=from 0% to 10%) to afford the desired compound of formula 14-1 (1.124 g, 27.0%) as a yellow liquid.

Step 2: Synthesis of methyl 4-((5-((3S,5R)-4-(3-fluorobenzyl)-3,5-dimethylpiperazin-1-yl)-1H-pyrrolo[2,3-b]pyridin-1-yl)methyl)benzoate (formula 14-2)

(formula 14-2)

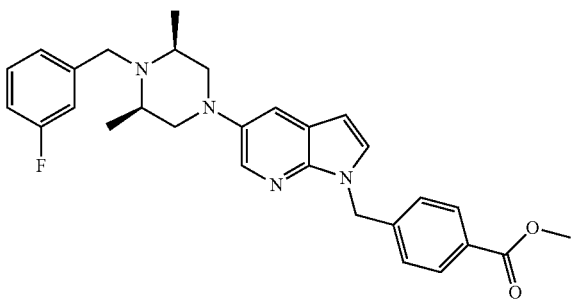

The compound of formula 14-1 (0.100 g, 0.264 mmol) prepared in step 1, 1-(bromomethyl)-3-fluorobenzene (0.100 g, 0.528 mmol), and N,N-diisopropylethylamine (0.090 mL, 0.528 mmol) were dissolved in acetonitrile (2 mL) at room temperature, and the solution was stirred at the same temperature for 3 hours. Water was added to the reaction solution, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; ethyl acetate/hexane=from 0% to 50%) to afford the desired compound of formula 14-2 (0.040 g, 31.1%) as a yellow liquid.

Step 3: Synthesis of 4-((5-((3S,5R)-4-(3-fluorobenzyl)-3,5-dimethylpiperazin-1-yl)-1H-pyrrolo[2,3-b]pyridin-1-yl)methyl)-N-hydroxybenzamide (compound 857)

(compound 857)

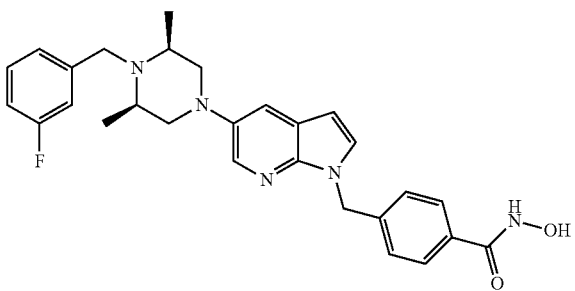

The compound of formula 14-2 (0.040 g, 0.082 mmol) prepared in step 2, hydroxylamine (50.00 wt % aqueous solution, 0.050 mL, 0.822 mmol), and potassium hydroxide (0.046 g, 0.822 mmol) were dissolved in methanol (1 mL)/tetrahydrofuran (1 mL) at room temperature, and the solution was dissolved at the same temperature for 1 hour.

Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to afford the desired compound 857 (0.007 g, 16.2%) as a white solid.

$^1$H-NMR (400 MHz, CDCl$_3$) δ 8.12 (d, 1H, J=2.6 Hz), 7.62 (d, 2H, J=8.0 Hz), 7.52-7.51 (m, 2H), 7.35 (q, 1H, J=7.5 Hz), 7.25-7.22 (m, 2H), 7.10 (d, 2H, J=8.3 Hz), 7.02 (t, 1H, J=7.2 Hz), 6.37 (d, 1H, J=3.4 Hz), 5.39 (s, 2H), 3.81 (s, 2H), 3.51-3.44 (m, 2H), 2.81-2.77 (m, 2H), 2.68 (m, 2H), 1.01 (s, 3H), 1.00 (s, 3H); MS (ESI) m/z 488.3 (M$^+$+1).

Example 95

Synthesis of Compound 858

Step 1: Synthesis of methyl 4-((4-(1-(2-fluoro-2-methylpropanoyl)-1,2,3,6-tetrahydropyridin-4-yl)-1H-pyrrolo[2,3-b]pyridin-1-yl)methyl)benzoate (formula 4-7)

(formula 4-7)

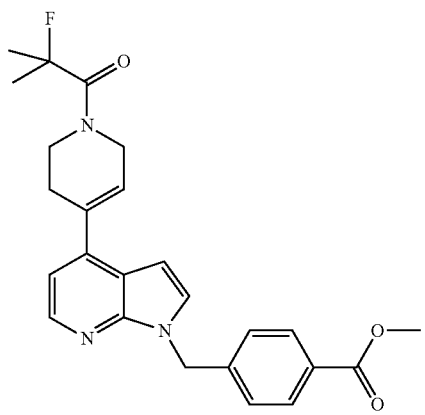

The compound of formula 4-2 (0.100 g, 0.261 mmol), 2-fluoro-2-methylpropanoic acid (0.055 g, 0.521 mmol), 1-ethyl-3-[3-dimethylaminopropyl]carbodiimide hydrochloride (0.100 g, 0.521 mmol), 1-hydroxybenzotriazole hydrate (0.070 g, 0.521 mmol), and N,N-diisopropylethylamine (0.168 g, 1.303 mmol) were dissolved in N,N-dimethylformamide (2 mL) at 40° C., and the solution was stirred at the same temperature for 16 hours, and then cooled to room temperature. After completion of the reaction, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; ethyl acetate/hexane=from 0% to 50%) to afford the desired compound of formula 4-7 (0.044 g, 38.8%) as a colorless liquid.

Step 2: Synthesis of methyl 4-((4-(1-(2-fluoro-2-methylpropanoyl)piperidin-4-yl)-1H-pyrrolo[2,3-b]pyridin-1-yl)methyl)benzoate (formula 4-8)

(formula 4-8)

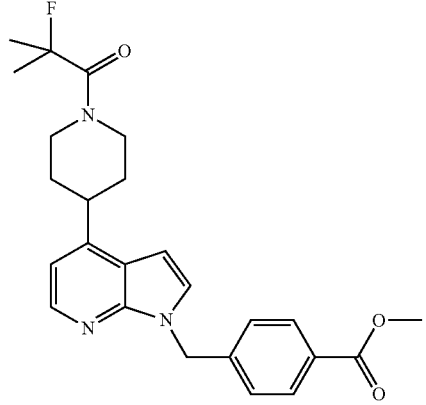

The compound of formula 4-7 (0.044 g, 0.101 mmol) prepared in step 1 was dissolved in methanol (10 mL) at room temperature, and Pd/C (10 mg) was added slowly thereto, and a hydrogen balloon was placed over the solution, which was then stirred at the same temperature for 16 hours. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; ethyl acetate/hexane=from 0% to 50%) to afford the desired compound of 4-8 (0.044 g, 99.5%) as a colorless liquid.

Step 3: Synthesis of 4-((4-(1-(2-fluoro-2-methylpropanoyl)piperidin-4-yl)-1H-pyrrolo[2,3-b]pyridin-1-yl)methyl)-N-hydroxybenzamide (compound 858)

(compound 858)

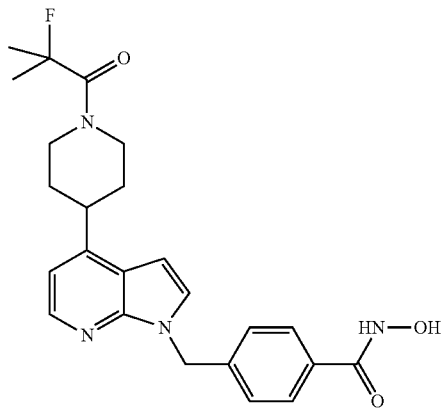

The compound of formula 4-8 (0.044 g, 0.101 mmol) prepared in step 2, hydroxylamine (50.00 wt % aqueous solution, 0.062 mL, 1.006 mmol), and potassium hydroxide (0.056 g, 1.006 mmol) were dissolved in methanol (1 mL)/tetrahydrofuran (1 mL) at room temperature, and the solution was dissolved at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to afford the desired compound 858 (0.019 g, 42.2%) as an ivory solid.

$^1$H-NMR (400 MHz, DMSO-$d_6$) δ 8.19 (d, 1H, J=4.9 Hz), 7.65 (d, 2H, J=8.2 Hz), 7.62 (d, 1H, J=3.6 Hz), 7.23 (d, 2H, J=8.0 Hz), 6.99 (d, 1H, J=5.0 Hz), 6.65 (d, 1H, J=3.6 Hz), 5.48 (s, 2H), 4.52-4.44 (m, 2H), 3.31-3.27 (m, 2H), 2.91-2.77 (m, 1H), 1.95-1.91 (m, 2H), 1.72-1.65 (m, 2H), 1.61 (s, 3H), 1.56 (s, 3H); MS (ESI) m/z 439.3 (M$^+$+1).

Example 96

Synthesis of Compound 859

Step 1: Synthesis of methyl 4-((4-(1-(3-methoxybenzyl)piperidin-4-yl)-1H-pyrrolo[2,3-b]pyridin-1-yl)methyl)benzoate (formula 4-8)

(formula 4-8)

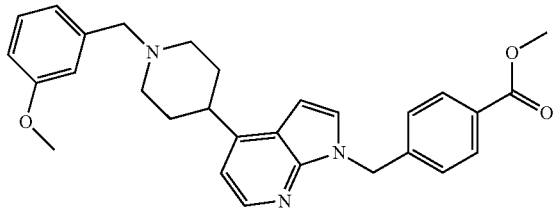

The compound of formula 4-7 (methyl 4-((4-(1-(3-methoxybenzyl)-1,2,3,6-tetrahydropyridin-4-yl)-1H-pyrrolo[2,3-b]pyridin-1-yl)methyl)benzoate) (0.098 g, 0.210 mmol), and Pd/C (30 mg) were dissolved in methanol (5 mL) at room temperature, and the solution was stirred at the same temperature under hydrogen gas for 12 hours. The reaction mixture was filtered through a celite pad to remove solids, and water was added to the filtrate, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; ethyl acetate/hexane=from 0% to 80%) to afford the desired compound of formula 4-8 (0.036 g, 36.6%) as a yellow oil.

Step 2: Synthesis of N-hydroxy-4-((4-(1-(3-methoxybenzyl)piperidin-4-yl)-1H-pyrrolo[2,3-b]pyridin-1-yl)methyl)benzamide (compound 859)

(compound 859)

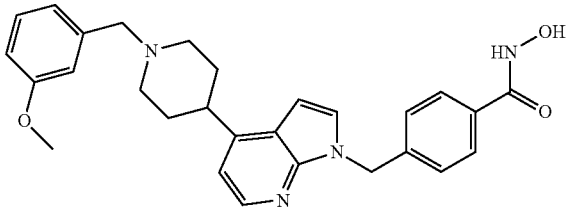

The compound of formula 4-8 (0.036 g, 0.077 mmol) prepared in step 1, potassium hydroxide (0.043 g, 0.767 mmol), and an aqueous solution of 50 wt % NH$_2$OH (0.099 mL, 1.533 mmol) were dissolved in methanol (3 mL) at room temperature, and the solution was dissolved at the same temperature for 2 hours. Then, the reaction mixture was concentrated under reduced pressure to remove the solvent, and a saturated aqueous solution of sodium hydrogen carbonate (2 mL) was added to the concentrate, followed by stirring. The precipitated solid was filtered, washed with hexane, and dried to afford the desired compound 859 (0.031 g, 85.9%) as a white solid.

$^1$H-NMR (400 MHz, CD$_3$OD) δ 8.15 (d, 1H, J=5.0 Hz), 7.66 (d, 2H, J=8.4 Hz), 7.37 (d, 1H, J=3.6 Hz), 7.26-7.18 (m, 3H), 7.03-7.01 (m, 1H), 6.97-6.95 (m, 2H), 6.93-6.83 (m, 1H), 6.71-6.69 (m, 1H), 5.52 (s, 2H), 3.80 (s, 3H), 3.58 (s, 2H), 3.09-3.03 (m, 3H), 2.27-2.21 (m, 2H), 2.02-1.90 (m, 4H); MS (ESI) m/z 471.3 (M$^+$+1).

Example 97

Synthesis of Compound 860

Step 1: Synthesis of methyl 4-((4-(1-(3-fluorobenzoyl)-1,2,3,6-tetrahydropyridin-4-yl)-1H-pyrrolo[2,3-b]pyridin-1-yl)methyl)benzoate (formula 4-7)

(formula 4-7)

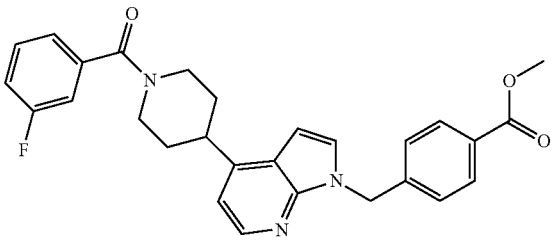

The compound of formula 4-2 (methyl 4-((4-(1,2,3,6-tetrahydropyridin-4-yl)-1H-pyrrolo[2,3-b]pyridin-1-yl)methyl)benzoate hydrochloride) (0.200 g, 0.521 mmol), 3-fluorobenzoyl chloride (0.165 g, 1.042 mmol), and TEA (0.146 mL, 1.042 mmol) were dissolved in methylene chloride (3 mL) at room temperature, and the solution was stirred at the same temperature for 12 hours. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; ethyl acetate/hexane=from 0% to 60%) to afford the desired compound of formula 4-7 (0.084 g, 34.3%) as a yellow oil.

Step 2: Synthesis of methyl 4-((4-(1-(3-fluorobenzyl)piperidin-4-yl)-1H-pyrrolo[2,3-b]pyridin-1-yl)methyl)benzoate (formula 4-8)

(formula 4-8)

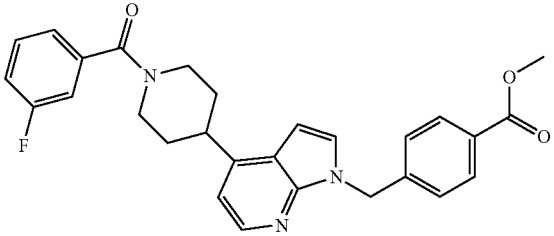

The compound of formula 4-7 (0.084 g, 0.179 mmol) prepared in step 1 and Pd/C (30 mg) were dissolved in methanol (5 mL) at room temperature, and the solution was stirred at the same temperature under hydrogen gas for 12 hours. The reaction mixture was filtered through a celite pad to remove solids, and water was added to the filtrate, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO₂, 4 g cartridge; ethyl acetate/hexane=from 0% to 80%) to afford the desired compound of formula 4-8 (0.039 g, 46.2%) as a yellow oil.

Step 3: Synthesis of 4-((4-(1-(3-fluorobenzoyl)piperidin-4-yl)-1H-pyrrolo[2,3-b]pyridin-1-yl)methyl)-N-hydroxybenzamide (compound 860)

(compound 860)

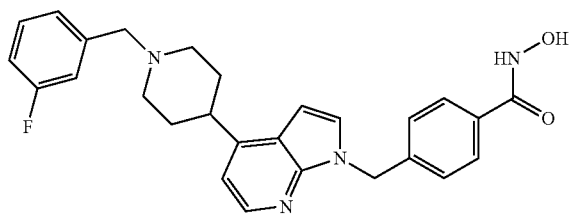

The compound of formula 4-8 (0.039 g, 0.083 mmol) prepared in step 2, potassium hydroxide (0.046 g, 0.827 mmol), and an aqueous solution of 50 wt % NH₂OH (0.106 mL, 1.654 mmol) were dissolved in methanol (3 mL) at room temperature, and the solution was stirred at the same temperature for 2 hours. Then, the reaction mixture was concentrated under reduced pressure to remove the solvent, and a saturated aqueous solution of sodium hydrogen carbonate (2 mL) was added to the concentrate, followed by stirring. The precipitated solid was filtered, washed with water, and dried to afford the desired compound 860 (0.025 g, 64.0%) as a white solid.

¹H-NMR (400 MHz, DMSO-d₆) δ 8.20 (d, 1H, J=4.9 Hz), 7.66 (d, 2H, J=8.2 Hz), 7.61 (d, 1H, J=3.6 Hz), 7.54-7.49 (m, 1H), 7.34-7.27 (m, 3H), 7.25 (d, 2H, J=8.1 Hz), 7.05 (d, 1H, J=5.0 Hz), 6.70 (d, 1H, J=3.5 Hz), 5.49 (s, 2H), 3.33 (s, 4H), 2.95 (brs, 1H), 2.51 (s, 4H); MS (ESI) m/z 473.5 (M⁺+1).

Example 98

Synthesis of Compound 861

Step 1: Synthesis of methyl 4-((5-(4-(2-fluorobenzyl)piperazin-1-yl)-1H-pyrrolo[2,3-b]pyridin-1-yl)methyl)benzoate (formula 13-4)

(formula 13-4)

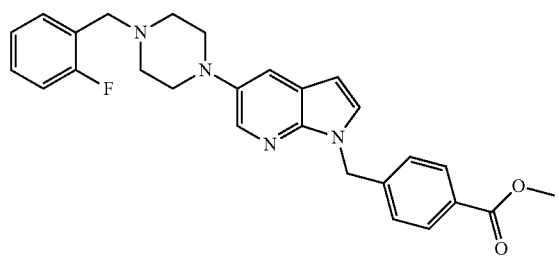

The compound of formula 13-2 (methyl 4-((5-(piperazin-1-yl)-1H-pyrrolo[2,3-b]pyridin-1-yl)methyl)benzoate) (0.100 g, 0.285 mmol), 1-(bromomethyl)-2-fluorobenzene (0.108 g, 0.571 mmol), and N,N-diisopropylethylamine (0.102 mL, 0.571 mmol) were dissolved in acetonitrile (2 mL) at room temperature, and the solution was stirred at the same temperature for 1 hour. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO₂, 4 g cartridge; ethyl acetate/hexane=from 0% to 50%) to afford the desired compound of formula 13-4 (0.040 g, 30.6%) as colorless liquid.

Step 2: Synthesis of 4-((5-(4-(2-fluorobenzyl)piperazin-1-yl)-1H-pyrrolo[2,3-b]pyridin-1-yl)methyl)-N-hydroxybenzamide (compound 861)

(compound 861)

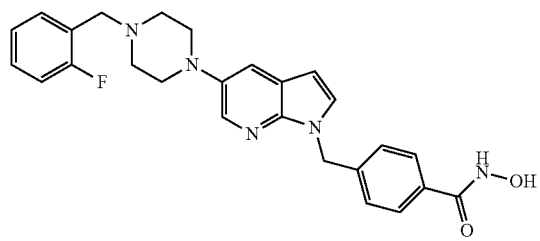

The compound of formula 13-4 (0.040 g, 0.087 mmol) prepared in step 1, hydroxylamine (50.00 wt % aqueous solution, 0.053 mL, 0.872 mmol), and potassium hydroxide (0.049 g, 0.872 mmol) were dissolved in methanol (1 mL)/tetrahydrofuran (1 mL) at room temperature, and the solution was stirred at the same temperature for 1 hours. Then, the reaction mixture was concentrated under reduced pressure to remove the solvent, and a saturated aqueous solution of sodium hydrogen carbonate (10 mL) was added to the concentrate, followed by stirring. The precipitated solid was filtered and dried to afford the desired compound 861 (0.018 g, 44.7%) as a white solid.

¹H-NMR (400 MHz, DMSO-d₆) δ 8.10 (d, 1H, J=2.5 Hz), 7.63 (d, 2H, J=8.2 Hz), 7.53 (d, 1H, J=3.4 Hz), 7.50 (d, 1H, J=2.5 Hz), 7.47-7.44 (m, 1H), 7.37-7.32 (m, 1H), 7.22-7.17 (m, 2H), 7.14 (d, 2H, J=8.1 Hz), 6.37 (d, 1H, J=3.4 Hz), 5.41 (s, 2H), 3.61 (s, 2H), 3.09 (m, 4H), 2.60 (m, 4H); MS (ESI) m/z 460.3 (M⁺+1).

Example 99

Synthesis of Compound 862

Step 1: Synthesis of methyl 4-((5-(4-(3,3-dimethylbutyl)piperazin-1-yl)-1H-pyrrolo[2,3-b]pyridin-1-yl)methyl)benzoate (formula 13-4)

(formula 13-4)

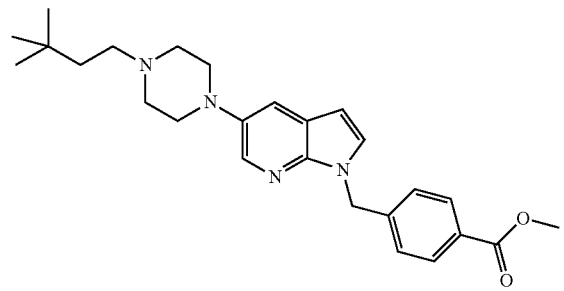

The compound of formula 13-2 (methyl 4-((5-(piperazin-1-yl)-1H-pyrrolo[2,3-b]pyridin-1-yl)methyl)benzoate) (0.100 g, 0.285 mmol), 3,3-dimethylbutyl 4-methylbenzene sulfonate (0.088 g, 0.342 mmol), and N,N-diisopropylethylamine (0.101 mL, 0.571 mmol) were dissolved in acetonitrile (2 mL) at room temperature, and the solution was stirred at the same temperature for 1 hour. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; methanol/methylene chloride=from 0% to 10%) to afford the desired compound of formula 13-4 (0.021 g, 16.5%) as a colorless liquid.

Step 2: Synthesis of 4-((5-(4-(3,3-dimethylbutyl)piperazin-1-yl)-1H-pyrrolo[2,3-b]pyridin-1-yl)methyl)-N-hydroxybenzamide (compound 862)

(compound 862)

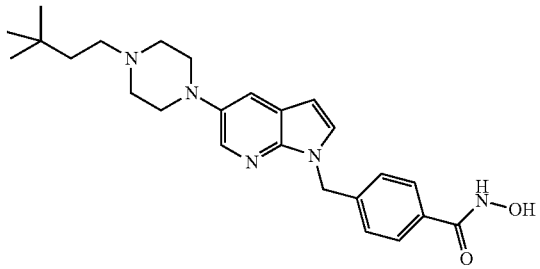

The compound of formula 13-4 (0.021 g, 0.047 mmol) prepared in step 1, hydroxylamine (50.00 wt % aqueous solution, 0.029 mL, 0.472 mmol), and potassium hydroxide (0.026 g, 0.472 mmol) were dissolved in methanol (1 mL)/tetrahydrofuran (1 mL) at room temperature, and the solution was stirred at the same temperature for 1 hour. Then, the reaction solution was concentrated under reduced pressure to remove the solvent, and a saturated aqueous solution of sodium hydrogen carbonate (20 mL) was added to the concentrate, followed by stirring. The precipitated solid was filtered and dried to afford the desired compound 862 (0.015 g, 72.0%) as a white solid.

$^1$H-NMR (400 MHz, DMSO-d$_6$) δ 8.11 (s, 1H), 7.63 (d, 2H, J=6.8 Hz), 7.52-7.51 (m, 2H), 7.13 (d, 2H, J=6.3 Hz), 6.37 (s, 1H), 5.40 (s, 2H), 3.09 (m, 4H), 2.51 (m, 4H), 1.81-1.74 (m, 2H), 1.24 (m, 2H), 0.89 (s, 9H); MS (ESI) m/z 436.3 (M$^+$+1).

Example 100

Synthesis of Compound 863

Step 1: Synthesis of methyl 4-((5-(1-isobutylpiperidin-4-yl)-1H-pyrrolo[2,3-b]pyridin-1-yl)methyl)benzoate (formula 12-2)

(formula 12-2)

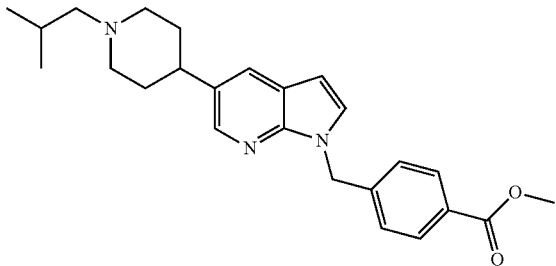

The compound of formula 6-3 (methyl 4-((5-(piperidin-4-yl)-1H-pyrrolo[2,3-b]pyridin-1-yl)methyl)benzoate) (0.100 g, 0.286 mmol), isobutyl 4-methylbenzene sulfonate (0.078 g, 0.343 mmol), and N,N-diisopropylethylamine (0.074 g, 0.572 mmol) were dissolved in acetonitrile (2 mL) at room temperature, and the solution was stirred at the same temperature for 1 hour. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; ethyl acetate/hexane=from 0% to 50%) to afford the desired compound of formula 12-2 (0.055 g, 47.0%) as a colorless liquid.

Step 2: Synthesis of N-hydroxy-4-((5-(1-isobutylpiperidin-4-yl)-1H-pyrrolo[2,3-b]pyridin-1-yl)methyl)benzamide (compound 863)

(compound 863)

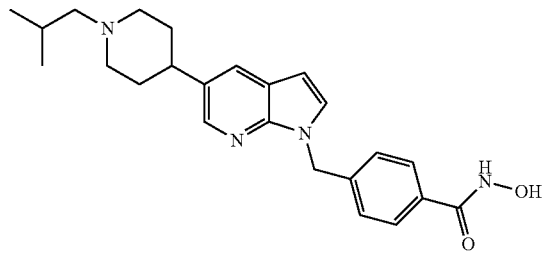

The compound of formula 12-2 (0.055 g, 0.136 mmol) prepared in step 1, hydroxylamine (50.00 wt % aqueous solution, 0.083 mL, 1.356 mmol), and potassium hydroxide (0.076 g, 1.356 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to afford the desired compound 863 (0.055 g, 99.8%) as an ivory solid.

$^1$H-NMR (400 MHz, DMSO-d$_6$) δ 8.17 (d, 1H, J=2.0 Hz), 7.84 (d, 1H, J=2.0 Hz), 7.63 (d, 2H, J=8.1 Hz), 7.58 (d, 1H, J=3.5 Hz), 7.12 (d, 2H, J=8.2 Hz), 6.43 (d, 1H, J=3.4 Hz), 5.42 (s, 2H), 2.94 (d, 2H, J=11.4 Hz), 2.63-2.56 (m, 1H), 2.06 (d, 2H, J=7.4 Hz), 1.97 (td, 1H, J=11.3, 2.8 Hz), 1.83-1.67 (m, 5H), 0.89 (s, 3H), 0.87 (s, 3H); MS (ESI) m/z 407.3 (M$^+$+1).

Example 101

Synthesis of Compound 864

Step 1: Synthesis of methyl 4-((5-(1-(3,3-dimethylbutyl)piperidin-4-yl)-1H-pyrrolo[2,3-b]pyridin-1-yl)methyl)benzoate (formula 12-2)

(formula 12-2)

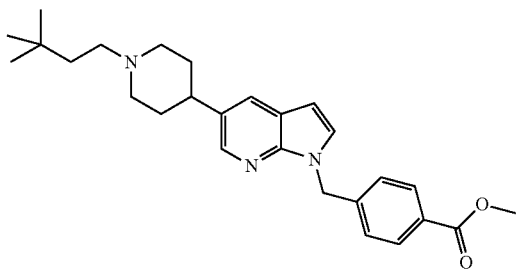

The compound of formula 6-3 (methyl 4-((5-(piperidin-4-yl)-1H-pyrrolo[2,3-b]pyridin-1-yl)methyl)benzoate) (0.100 g, 0.286 mmol), 3,3-dimethylbutyl 4-methylbenzenesulfonate (0.088 g, 0.343 mmol), and N,N-diisopropylethylamine (0.074 g, 0.572 mmol) were dissolved in acetonitrile (2 mL) at room temperature, and the solution was stirred at the same temperature for 1 hour. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; ethyl acetate/hexane=from 0% to 50%) to afford the desired compound of formula 12-2 (0.088 g, 70.7%) as a colorless liquid.

Step 2: Synthesis of 4-((5-(1-(3,3-dimethylbutyl)piperidin-4-yl)-1H-pyrrolo[2,3-b]pyridin-1-yl)methyl)-N-hydroxybenzamide (compound 864)

(compound 864)

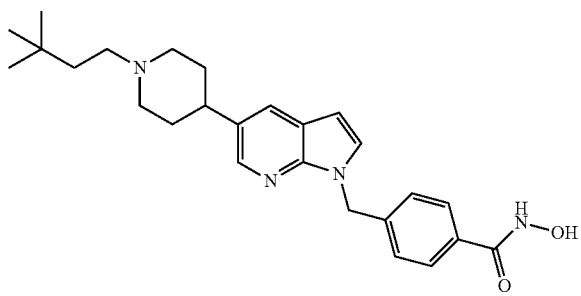

The compound of formula 12-2 (0.088 g, 0.203 mmol) prepared in step 1, hydroxylamine (50.00 wt % aqueous solution, 0.124 mL, 2.030 mmol), and potassium hydroxide (0.114 g, 2.030 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to afford the desired compound 864 (0.062 g, 70.7%) as an ivory solid.

$^1$H-NMR (400 MHz, DMSO-d$_6$) δ 8.17 (d, 1H, J=1.8 Hz), 7.82 (d, 1H, J=1.7 Hz), 7.63 (d, 2H, J=8.0 Hz), 7.58 (d, 1H, J=3.4 Hz), 7.12 (d, 2H, J=8.0 Hz), 6.43 (d, 1H, J=3.4 Hz), 5.42 (s, 2H), 2.99 (d, 2H, J=11.1 Hz), 2.63-2.56 (m, 1H), 2.32-2.28 (m, 2H), 1.98 (t, 2H, J=10.3 Hz), 1.78-1.69 (m, 4H), 1.40-1.36 (m, 2H), 0.90 (s, 9H); MS (ESI) m/z 435.3 (M$^+$+1).

Example 102

Synthesis of Compound 865

Step 1: Synthesis of methyl 4-((5-((3S,5R)-4-(2-hydroxy-2-methylpropyl)-3,5-dimethylpiperazin-1-yl)-1H-pyrrolo[2,3-b]pyridin-1-yl)methyl)benzoate (formula 14-3)

(formula 14-3)

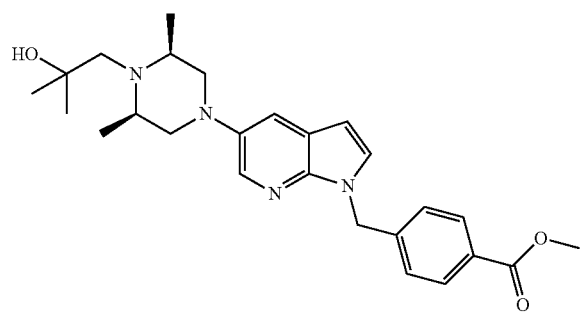

The compound of formula 14-1 (0.200 g, 0.528 mmol), 2,2-dimethyloxirane (0.191 g, 2.642 mmol), and potassium carbonate (0.365 g, 2.642 mmol) were added to ethanol (3 mL), and heated by microwave irradiation at 120° C., followed by cooling to room temperature. After completion of the reaction, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; ethyl acetate/hexane=from 0% to 80%) to afford the desired compound of formula 14-3 (0.124 g, 50.5%) as a colorless liquid.

Step 2: Synthesis of N-hydroxy-4-((5-((3S,5R)-4-(2-hydroxy-2-methylpropyl)-3,5-dimethylpiperazin-1-yl)-1H-pyrrolo[2,3-b]pyridin-1-yl)methyl)benzamide (compound 865)

(compound 865)

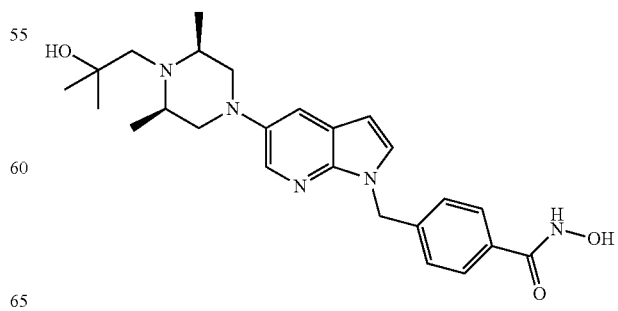

The compound of formula 14-3 (0.040 g, 0.089 mmol) prepared in step 1, hydroxylamine (50.00 wt % aqueous solution, 0.054 mL, 0.888 mmol), and potassium hydroxide (0.050 g, 0.888 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to afford the desired compound 865 (0.009 g, 21.2%) as an ivory solid.

$^1$H-NMR (400 MHz, DMSO-$d_6$) δ 8.07 (d, 1H, J=2.4 Hz), 7.64 (d, 2H, J=8.2 Hz), 7.53 (d, 1H, J=3.4 Hz), 7.47 (d, 1H, J=2.4 Hz), 7.19 (d, 2H, J=8.0 Hz), 6.38 (d, 1H, J=3.4 Hz), 5.43 (s, 2H), 4.01 (brs, 1H), 3.22-3.20 (m, 2H), 2.89 (m, 2H), 2.74-2.70 (m, 2H), 2.47 (s, 2H), 1.14 (s, 3H), 1.12 (s, 3H), 1.10 (s, 6H); MS (ESI) m/z 452.3 ($M^+$+1).

Example 103

Synthesis of Compound 866

Step 1: Synthesis of methyl 4-((5-((3S,5R)-4-(2-fluoro-2-methylpropyl)-3,5-dimethylpiperazin-1-yl)-1H-pyrrolo[2,3-b]pyridin-1-yl)methyl)benzoate (formula 14-4)

(formula 14-4)

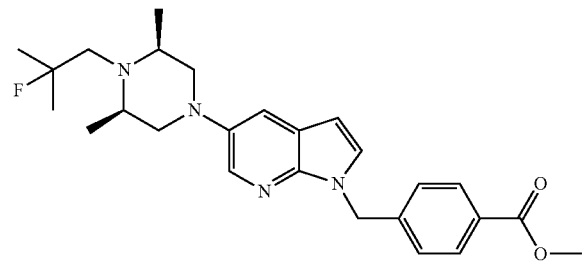

The compound of formula 14-3 (methyl 4-((5-((3S,5R)-4-(2-hydroxy-2-methylpropyl)-3,5-dimethylpiperazin-1-yl)-1H-pyrrolo[2,3-b]pyridin-1-yl)methyl)benzoate) (0.080 g, 0.178 mmol) and diethylaminosulfur trifluoride (0.043 g, 0.266 mmol) were dissolved in methylene chloride (10 mL) at room temperature, and the solution was stirred at the same temperature for 3 hours. Water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; ethyl acetate/hexane=from 0% to 30%) to afford the desired compound (0.051 g, 61.6%) as a colorless liquid.

Step 2: Synthesis of 4-((5-((3S,5R)-4-(2-fluoro-2-methylpropyl)-3,5-dimethylpiperazin-1-yl)-1H-pyrrolo[2,3-b]pyridin-1-yl)methyl)-N-hydroxybenzamide (compound 866)

(compound 866)

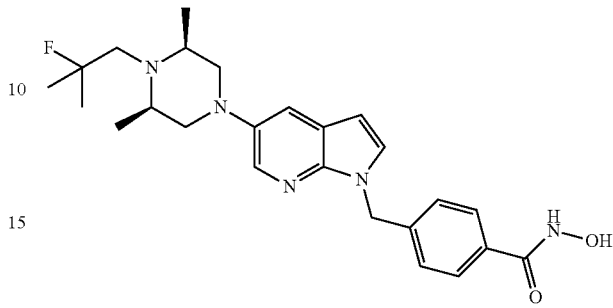

The compound of formula 14-4 (0.051 g, 0.109 mmol) prepared in step 1, hydroxylamine (50.00 wt % aqueous solution, 0.067 mL, 1.093 mmol), and potassium hydroxide (0.061 g, 1.093 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to afford the desired compound 866 (0.027 g, 55.1%) as a white solid.

$^1$H-NMR (400 MHz, DMSO-$d_6$) δ 8.09 (d, 1H, J=2.6 Hz), 7.64 (d, 2H, J=8.3 Hz), 7.53 (d, 1H, J=3.4 Hz), 7.49 (d, 1H, J=2.5 Hz), 7.19 (d, 2H, J=9.4 Hz), 6.38 (d, 1H, J=3.4 Hz), 5.43 (s, 2H), 3.31 (d, 2H, J=10.0 Hz), 2.79-2.78 (m, 2H), 2.72-2.66 (m, 2H), 2.59-2.54 (m, 2H), 1.33 (s, 3H), 1.28 (s, 3H), 1.09 (s, 3H), 1.07 (s, 3H); MS (ESI) m/z 454.3 ($M^+$+1).

Example 104

Synthesis of Compound 867

Step 1: Synthesis of methyl 4-((5-(1-methyl-piperidin-4-yl)-1H-pyrrolo[2,3-b]pyridin-1-yl)methyl)benzoate (formula 2-4)

(formula 2-4)

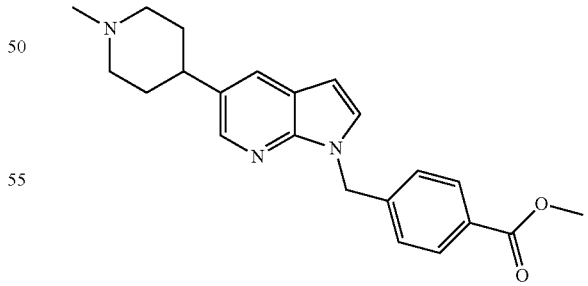

The compound of formula 2-3 (methyl 4-((5-(1-methyl-1,2,3,6-tetrahydropyridin-4-yl)-1H-pyrrolo[2,3-b]pyridin-1-yl)methyl)benzoate) (0.429 g, 1.187 mmol) was dissolved in methanol (30 mL) at room temperature, and the solution was stirred at the same temperature under hydrogen gas for 48 hours. The reaction mixture was filtered through a celite pad to remove solids, and water was added to the filtrate, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; methanol/methylene chloride=from 0% to 10%) to afford the desired compound of formula 2-4 (0.254 g, 59.0%) as a brown liquid.

Step 2: Synthesis of N-hydroxy-4-((5-(1-methylpiperidin-4-yl)-1H-pyrrolo[2,3-b]pyridin-1-yl)methyl)benzamide (compound 867)

(compound 867)

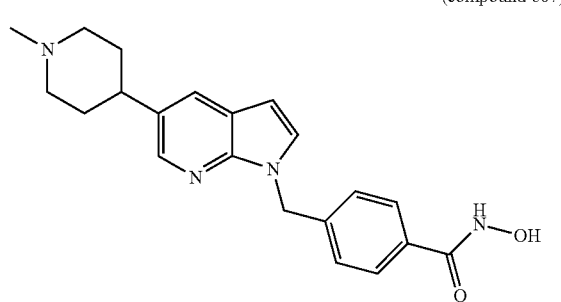

The compound of formula 2-4 (0.254 g, 0.699 mmol) prepared in step 1, hydroxylamine (50.00 wt % aqueous solution, 0.427 mL, 6.989 mmol), and potassium hydroxide (0.392 g, 6.989 mmol) were dissolved in methanol (3 mL) at room temperature, and the solution was stirred at the same temperature for 3 hours. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to afford the desired compound 867 (0.149 g, 58.3%) as a brown solid.

$^1$H-NMR (400 MHz, DMSO-d$_6$) δ 8.16 (s, 1H), 7.83 (s, 1H), 7.66 (d, 2H, J=6.8 Hz), 7.61 (s, 1H), 7.25 (d, 2H, J=7.1 Hz), 6.46 (s, 1H), 5.49 (s, 2H), 2.87 (d, 2H, J=10.4 Hz), 2.57 (m, 1H), 2.19 (s, 3H), 1.97 (m, 2H), 1.74 (m, 4H); MS (ESI) m/z 365.2 (M$^+$+1).

Example 105

Synthesis of Compound 868

Step 1: Synthesis of methyl 4-((4-(1-nepentylpiperidin-4-yl)-1H-pyrrolo[2,3-b]pyridin-1-yl)methyl)benzoate (formula 16-2)

The compound of formula 16-1 (methyl 4-((4-(piperidin-4-yl)-1H-pyrrolo[2,3-b]pyridin-1-yl)methyl)benzoate hydrochloride) (0.080 g, 0.207 mmol) was dissolved in methanol (10 mL) at room temperature, and DIPEA (0.073 mL, 0.415 mmol) was added thereto, followed by stirring at the same temperature for 10 minutes. To the reaction mixture, pivalaldehyde (0.089 g, 1.037 mmol) and NaBH(OAc)$_3$ (0.132 g, 0.622 mmol) were added, followed by stirring for 12 hours. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; ethyl acetate/hexane=from 0% to 50%) to afford the desired compound of formula 16-2 (0.046 g, 52.9%) as a white solid.

Step 2: Synthesis of N-hydroxy-4-((4-(1-neopentylpiperidin-4-yl)-1H-pyrrolo[2,3-b]pyridin-1-yl)methyl)benzamide (compound 868)

(compound 868)

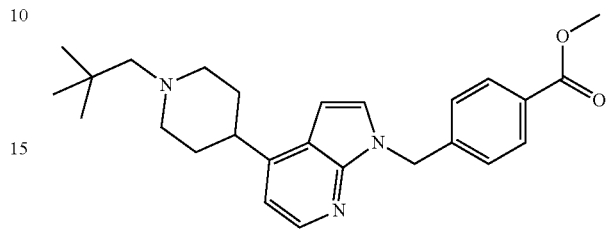

The compound of formula 16-2 (0.046 g, 0.110 mmol) prepared in step 1, potassium hydroxide (0.062 g, 1.096 mmol) and an aqueous solution of 50 wt % NH$_2$OH (0.141 mL, 2.193 mmol) were dissolved in methanol (3 mL) at room temperature, and the solution was stirred at the same temperature for 2 hours. Then, the reaction mixture was concentrated under reduced pressure to remove the solvent, and a saturated aqueous solution of sodium hydrogen carbonate (2 mL) was added to the concentrate, followed by stirring. The precipitated solid was filtered, washed with water and dried to afford the desired compound 868 (0.021 g, 45.5%) as a white solid. $^1$H-NMR (400 MHz, DMSO-d$_6$) δ 9.00 (s, 1H), 8.19 (s, $^1$H), 7.67 (d, 2H, J=8.3 Hz), 7.61 (s, 1H), 7.28 (d, 2H, J=8.2 Hz), 6.99-6.98 (m, 1H), 5.50 (s, 2H), 2.94-2.88 (brs, 1H), 2.55 (s, 4H), 2.19 (s, 2H), 1.80 (s, 4H), 0.92 (s, 9H); MS (ESI) m/z 421.6 (M$^+$+1).

Example 106

Synthesis of Compound 869

Step 1: Synthesis of methyl 4-((4-(1-(2-fluorobenzyl)-1,2,3,6-tetrahydropyridin-4-yl)-1H-pyrrolo[2,3-b]pyridin-1-yl)methyl)benzoate (formula 4-7)

(formula 4-7)

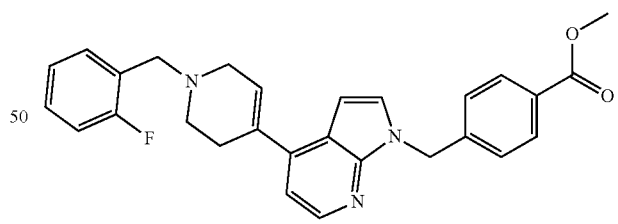

The compound of formula 4-2 (methyl 4-((4-(1,2,3,6-tetrahydropyridin-4-yl)-1H-pyrrolo[2,3-b]pyridin-1-yl)methyl)benzoate hydrochloride) (0.300 g, 0.782 mmol), 1-(bromomethyl)-2-fluorobenzene (0.189 mL, 1.563 mmol), and TEA (0.219 mL, 1.563 mmol) were dissolved in methylene chloride (5 mL) at room temperature, and the solution was dissolved at the same temperature for 12 hours. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified Step 2: Synthesis of methyl 4-((4-(1-(2-fluorobenzyl)piperidin-4-yl)-1H-pyrrolo[2,3-b]pyridin-1-yl)methyl)benzoate (formula 4-8)

(formula 4-8)

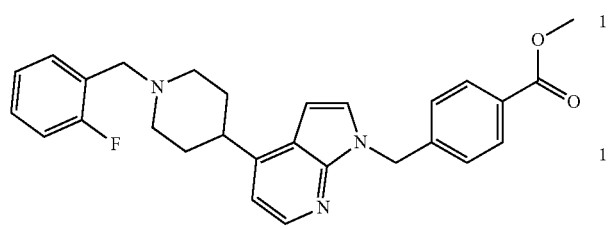

The compound of formula 4-7 (0.120 g, 0.263 mmol) prepared in step 1 and Pd/C (50 mg) were dissolved in methanol (10 mL), and the solution was stirred under hydrogen gas for 12 hours. The reaction mixture was filtered through a celite pad to remove solids, and water was added to the filtrate, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; ethyl acetate/hexane=from 0% to 60%) to afford the desired compound of formula 4-8 (0.081 g, 67.2%) as a yellow oil.

Step 3: Synthesis of 4-((4-(1-(2-fluorobenzyl)piperidin-4-yl)-1H-pyrrolo[2,3-b]pyridin-1-yl)methyl)-N-hydroxybenzamide (compound 869)

(compound 869)

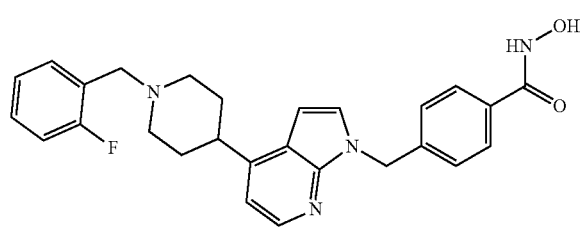

The compound of formula 4-8 (0.081 g, 0.177 mmol) prepared in step 2, potassium hydroxide (0.099 g, 1.770 mmol), and an aqueous solution of 50 wt % NH$_2$OH (0.228 mL, 3.541 mmol) were dissolved in methanol (5 mL) at room temperature, and the solution was stirred at the same temperature for 2 hours. Then, the reaction mixture was concentrated under reduced pressure to remove the solvent, and a saturated aqueous solution of sodium hydrogen carbonate (2 mL) was added to the concentrate, followed by stirring. The precipitated solid was filtered, washed with water, and dried to afford the desired compound 869 (0.051 g, 62.8%) as a white solid.

$^1$H-NMR (400 MHz, DMSO-d$_6$) δ 8.18 (d, 1H, J=4.9 Hz), 7.65 (d, 2H, J=8.2 Hz), 7.56 (d, 1H, J=3.6 Hz), 7.47-7.44 (m, 1H), 7.35-7.30 (m, 1H), 7.21-7.12 (m, 4H), 6.98 (d, 1H, J=5.0 Hz), 6.61 (d, 1H, J=3.5 Hz), 5.45 (s, 2H), 3.59 (s, 2H), 2.98-2.91 (m, 3H), 2.22-2.15 (m, 2H), 1.83-1.76 (m, 4H); MS (ESI) m/z 459.5 (M$^+$+1).

Example 107

Synthesis of Compound 870

Step 1: Synthesis of methyl 4-((4-(1-(3-fluorobenzyl)-1,2,3,6-tetrahydropyridin-4-yl)-1H-pyrrolo[2,3-b]pyridin-1-yl)methyl)benzoate (formula 4-7)

(formula 4-7)

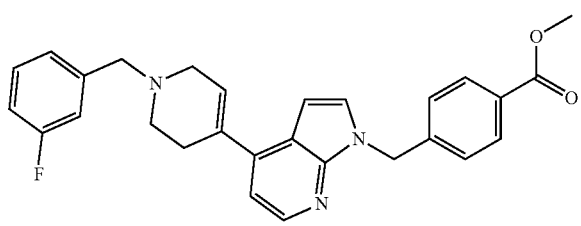

The compound of formula 4-2 (methyl 4-((4-(1,2,3,6-tetrahydropyridin-4-yl)-1H-pyrrolo[2,3-b]pyridin-1-yl)methyl)benzoate hydrochloride) (0.300 g, 0.782 mmol), 1-(bromomethyl)-3-fluorobenzene (0.194 mL, 1.563 mmol), and TEA (0.219 mL, 1.563 mmol) were methylene chloride (5 mL) at room temperature, and the solution was stirred at the same temperature for 12 hours. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; ethyl acetate/hexane=from 0% to 70%) to afford the desired compound of formula 4-2 (0.150 g, 42.1%) as a yellow oil.

Step 2: Synthesis of methyl 4-((4-(1-(3-fluorobenzyl)piperidin-4-yl)-1H-pyrrolo[2,3-b]pyridin-1-yl)methyl)benzoate (formula 4-8)

The compound of formula 4-7 (0.150 g, 0.329 mmol) prepared in step 1 and Pd/C (50 mg) were dissolved in methanol (10 mL), and the solution was stirred under hydrogen gas for 12 hours. The reaction mixture was filtered through a celite pad to remove solids, and water was added to the filtrate, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; ethyl acetate/hexane=from 0% to 65%) to afford the desired compound of formula 4-8 (0.096 g, 63.7%) as a yellow oil.

Step 3: Synthesis of 4-((4-(1-(3-fluorobenzyl)piperidin-4-yl)-1H-pyrrolo[2,3-b]pyridin-1-yl)methyl)-N-hydroxybenzamide (compound 870)

(compound 870)

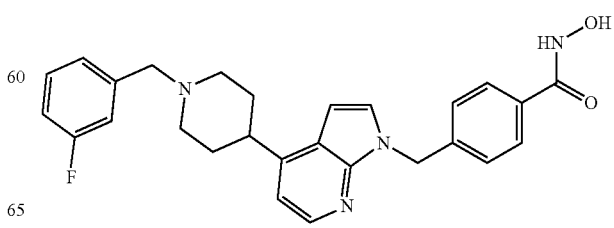

The compound of formula 4-8 (0.096 g, 0.210 mmol) prepared in step 2, potassium hydroxide (0.118 g, 2.098 mmol), and an aqueous solution of 50 wt % NH$_2$OH (0.270 mL, 4.196 mmol) were dissolved in methanol (3 mL) at room temperature, and the solution was stirred at the same temperature for 2 hours. Then, the reaction mixture was concentrated under reduced pressure to remove the solvent, and a saturated aqueous solution of sodium hydrogen carbonate (2 mL) was added to the concentrate, followed by stirring. The precipitated solid was filtered, washed with water, and dried to afford the desired compound 870 (0.050 g, 52.0%) as a white solid.

$^1$H-NMR (400 MHz, DMSO-d$_6$) δ 8.19 (d, 1H, J=4.8 Hz), 7.66 (d, 2H, J=7.9 Hz), 7.57 (d, 1H, J=3.3 Hz), 7.40-7.35 (m, 1H), 7.21-7.15 (m, 4H), 7.10-7.06 (m, 1H), 6.99 (d, 1H, J=4.8 Hz), 6.62 (d, 1H, J=3.2 Hz), 5.46 (s, 2H), 3.55 (s, 2H), 2.95-2.93 (m, 3H), 2.19-2.12 (m, 2H), 1.99-1.83 (m, 4H); MS (ESI) m/z 459.5 (M$^+$+1).

Example 108

Synthesis of Compound 871

Step 1: Synthesis of methyl 4-((5-(1-(3-(trifluoromethyl)benzyl)piperidin-4-yl)-1H-pyrrolo[2,3-b]pyridin-1-yl)methyl)benzoate (formula 12-2)

(formula 12-2)

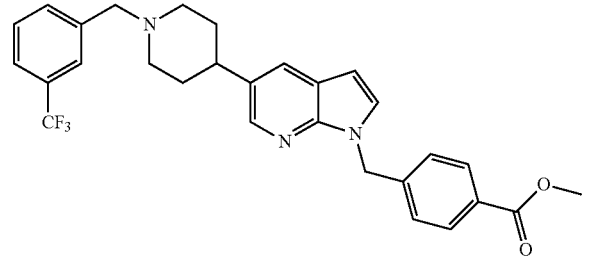

The compound of formula 6-3 (methyl 4-((5-(piperidin-4-yl)-1H-pyrrolo[2,3-b]pyridin-1-yl)methyl)benzoate) (0.100 g, 0.286 mmol), 3-(trifluoromethyl)benzaldehyde (0.055 g, 0.315 mmol), and sodium triacetoxyborohydride (0.091 g, 0.429 mmol) were dissolved in methylene chloride (3 mL) at room temperature, and the solution was stirred at the same temperature for 3 hours. Water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; methanol/methylene chloride=from 0% to 10%) to afford the desired compound of formula 12-2 (0.059 g, 42.1%) as a yellow solid.

Step 2: Synthesis of N-hydroxy-4-((5-(1-(3-(trifluoromethyl)benzyl)piperidin-4-yl)-1H-pyrrolo[2,3-b]pyridin-1-yl)methyl)benzamide (compound 871)

(compound 871)

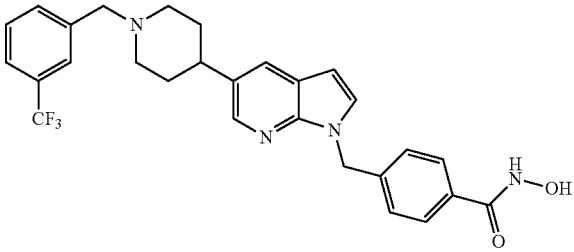

The compound of formula 12-2 (0.059 g, 0.116 mmol) prepared in step 1, hydroxylamine (50.00 wt % aqueous solution, 0.071 mL, 1.162 mmol), and potassium hydroxide (0.065 g, 1.162 mmol) were dissolved in methanol (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to afford the desired compound 871 (0.046 g, 77.0%) as a bright yellow solid.

$^1$H-NMR (400 MHz, CDCl$_3$) δ 8.15 (d, 1H, J=2.0 Hz), 7.92 (d, 1H, J=2.0 Hz), 7.73 (s, 1H), 7.71-7.66 (m, 3H), 7.61-7.55 (m, 2H), 7.39 (d, 1H, J=3.5 Hz), 7.15 (d, 2H, J=8.3 Hz), 6.51 (d, 1H, J=3.5 Hz), 5.51 (s, 2H), 3.69 (s, 2H), 3.06 (d, 2H, J=11.6 Hz), 2.75-2.72 (m, 1H), 2.29-2.22 (m, 2H), 1.92-1.90 (m, 4H); MS (ESI) m/z 509.3 (M$^+$+1).

Example 109

Synthesis of Compound 872

Step 1: Synthesis of methyl 4-((5-(1-(4-(trifluoromethyl)benzyl)piperidin-4-yl)-1H-pyrrolo[2,3-b]pyridin-1-yl)methyl)benzoate (formula 12-2)

(formula 12-2)

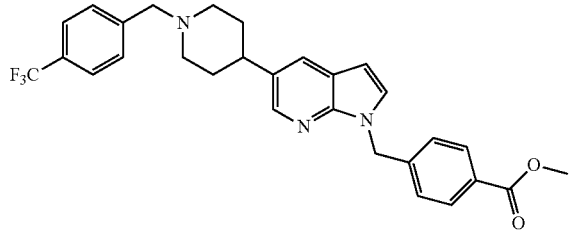

The compound of formula 6-3 (methyl 4-((5-(piperidin-4-yl)-1H-pyrrolo[2,3-b]pyridin-1-yl)methyl)benzoate) (0.100 g, 0.286 mmol), 4-(trifluoromethyl)benzaldehyde (0.075 g, 0.429 mmol), and sodium triacetoxyborohydride (0.091 g, 0.429 mmol) were dissolved in methylene chloride (3 mL) at room temperature, and the solution was stirred at the same temperature for 3 hours. Water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; methanol/methylene chloride=from 0% to 10%) to afford the desired compound of formula 12-2 (0.046 g, 31.4%) as a yellow liquid.

Step 2: Synthesis of N-hydroxy-4-((5-(1-(4-(trifluoromethyl)benzyl)piperidin-4-yl)-1H-pyrrolo[2,3-b]pyridin-1-yl)methyl)benzamide (compound 872)

(compound 872)

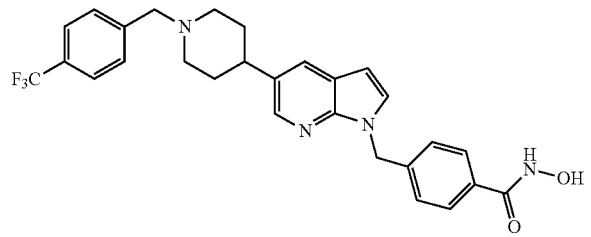

The compound of formula 12-2 (0.046 g, 0.090 mmol) prepared in step 1, hydroxylamine (50.00 wt % aqueous solution, 0.055 mL, 0.898 mmol), and potassium hydroxide (0.050 g, 0.898 mmol) were dissolved in methanol (1 mL) at room temperature, and the solution was stirred at the same temperature for 1 hour. Then, the reaction mixture was concentrated under reduced pressure to remove the solvent. The concentrate was purified by column chromatography (SiO$_2$, 12 g cartridge; saturated aqueous solution of sodium hydrogen carbonate) to afford the desired compound 872 (0.042 g, 91.9%) as a bright yellow solid.

$^1$H-NMR (400 MHz, CD$_3$OD) δ 8.15 (d, 1H, J=1.8 Hz), 7.92 (d, 1H, J=1.8 Hz), 7.70-7.66 (m, 4H), 7.62-7.60 (m, 2H), 7.39 (d, 1H, J=3.5 Hz), 7.16 (d, 2H, J=8.2 Hz), 6.51 (d, 1H, J=3.5 Hz), 5.51 (s, 2H), 3.69 (s, 2H), 3.07 (d, 2H, J=11.6 Hz), 2.78-2.69 (m, 1H), 2.29-2.22 (m, 2H), 1.92-1.90 (m, 4H); MS (ESI) m/z 509.3 (M$^+$+1).

Example 110

Synthesis of Compound 873

Step 1: Synthesis of methyl 4-((5-(1-(4-(1H-imidazol-1-yl)benzyl)piperidin-4-yl)-1H-pyrrolo[2,3-b]pyridin-1-yl)methyl)benzoate (formula 12-2)

(formula 12-2)

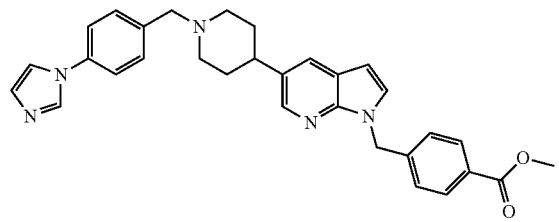

The compound of formula 6-3 (methyl 4-((5-(piperidin-4-yl)-1H-pyrrolo[2,3-b]pyridin-1-yl)methyl)benzoate) (0.100 g, 0.286 mmol), 4-(1H-imidazol-1-yl)benzaldehyde (0.074 g, 0.429 mmol), and sodium triacetoxyborohydride (0.091 g, 0.429 mmol) were dissolved in methylene chloride (3 mL) at room temperature, and the solution was stirred at the same temperature for 3 hours. Water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; methanol/methylene chloride=from 0% to 10%) to afford the desired compound of formula 12-2 (0.077 g, 52.9%) as a yellow liquid.

Step 2: Synthesis of 4-((5-(1-(4-(1H-imidazol-1-yl)benzyl)piperidin-4-yl)-1H-pyrrolo[2,3-b]pyridin-1-yl)methyl)-N-hydroxybenzamide (compound 873)

(compound 873)

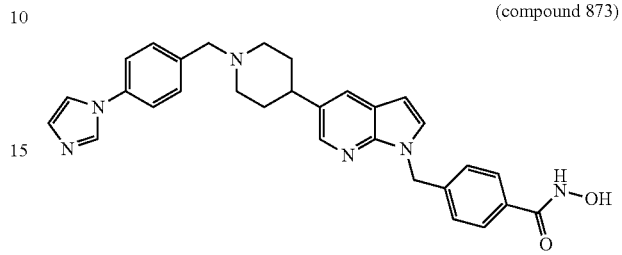

The compound of formula 12-2 (0.077 g, 0.151 mmol) prepared in step 1, hydroxylamine (50.00 wt % aqueous solution, 0.093 mL, 1.513 mmol), and potassium hydroxide (0.085 g, 1.513 mmol) were dissolved in methanol (1 mL) at room temperature, and the solution was stirred at the same temperature for 1 hour. Then, the reaction solution was concentrated under reduced pressure to remove the solvent, and a saturated aqueous solution of sodium hydrogen carbonate (20 mL) was added to the concentrate, followed by stirring. The precipitated solid was filtered and dried to afford the desired compound 873 (0.071 g, 93.2%) as a bright yellow solid.

$^1$H-NMR (400 MHz, CD$_3$OD) δ 8.18 (t, 1H, J=1.1 Hz), 8.15 (d, 1H, J=2.0 Hz), 7.92 (d, 1H, J=2.0 Hz), 7.69 (d, 2H, J=8.4 Hz), 7.61 (t, 1H, J=1.4 Hz), 7.60-7.56 (m, 4H), 7.39 (d, 1H, J=3.5 Hz), 7.18-7.17 (m, 2H), 7.15 (s, 1H), 6.52 (d, 1H, J=3.6 Hz), 5.51 (s, 2H), 3.67 (s, 2H), 3.10 (d, 2H, J=11.7 Hz), 2.78-2.70 (m, 1H), 2.29-2.22 (m, 2H), 1.93-1.85 (m, 4H); MS (ESI) m/z 507.3 (M$^+$+1).

Example 111

Synthesis of Compound 874

Step 1: Synthesis of methyl 4-((5-(1-(4-(4H-1,2,4-triazol-4-yl)benzyl)piperidin-4-yl)-1H-pyrrolo[2,3-b]pyridin-1-yl)methyl)benzoate (formula 12-2)

(formula 12-2)

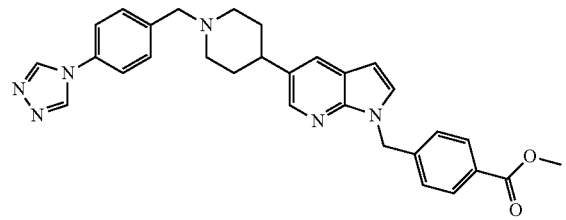

The compound of formula 6-3 (methyl 4-((5-(piperidin-4-yl)-1H-pyrrolo[2,3-b]pyridin-1-yl)methyl)benzoate) (0.100 g, 0.286 mmol), 4-(4H-1,2,4-triazol-4-yl)benzaldehyde (0.074 g, 0.429 mmol), and sodium triacetoxyborohydride (0.091 g, 0.429 mmol) were dissolved in methylene chloride (3 mL) at room temperature, and the solution was stirred at the same temperature for 3 hours. Water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; methanol/methylene chloride=from 0% to 10%) to afford the desired compound of formula 12-2 (0.068 g, 46.6%) as a yellow liquid.

Step 2: Synthesis of 4-((5-(1-(4-(4H-1,2,4-triazol-4-yl)benzyl)piperidin-4-yl)-1H-pyrrolo[2,3-b]pyridin-1-yl)methyl)-N-hydroxybenzamide (compound 874)

(compound 874)

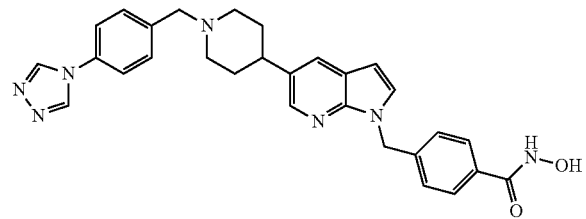

The compound of formula 12-2 (0.068 g, 0.133 mmol) prepared in step 1, hydroxylamine (50.00 wt % aqueous solution, 0.082 mL, 1.334 mmol), and potassium hydroxide (0.075 g, 1.334 mmol) were dissolved in methanol (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to afford the desired compound 874 (0.064 g, 94.6%) as a bright yellow solid.

$^1$H-NMR (400 MHz, CD$_3$OD+DMSO-d$_6$) δ 9.22 (s, 1H), 8.26 (s, 1H), 8.25 (d, 1H, J=2.0 Hz), 7.95 (d, 1H, J=2.0 Hz), 7.90 (d, 1H, J=8.6 Hz), 7.74 (d, 2H, J=8.4 Hz), 7.65 (d, 2H, J=8.6 Hz), 7.52 (d, 1H, J=3.5 Hz), 7.23 (d, 2H, J=8.4 Hz), 6.55 (d, 1H, J=3.5 Hz), 5.54 (s, 2H), 3.71 (s, 2H), 3.11 (d, 2H, J=11.6 Hz), 2.84-2.74 (m, 1H), 2.31-2.24 (m, 2H), 1.96-1.90 (m, 4H); MS (ESI) m/z 508.3 (M$^+$+1).

Example 112

Synthesis of Compound 875

Step 1: Synthesis of methyl 4-((5-(1-(4-(furan-2-yl)benzyl)piperidin-4-yl)-1H-pyrrolo[2,3-b]pyridin-1-yl)methyl)benzoate (formula 12-2)

(formula 12-2)

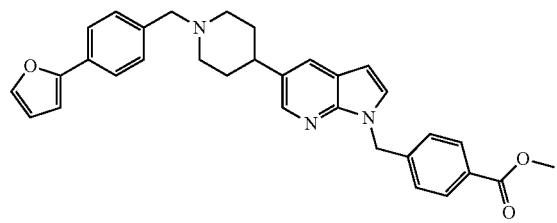

The compound of formula 6-3 (methyl 4-((5-(piperidin-4-yl)-1H-pyrrolo[2,3-b]pyridin-1-yl)methyl)benzoate) (0.100 g, 0.286 mmol), 4-(furan-2-yl)benzaldehyde (0.074 g, 0.429 mmol), and sodium triacetoxyborohydride (0.091 g, 0.429 mmol) were dissolved in methylene chloride (3 mL) at room temperature, and the solution was stirred at the same temperature for 3 hours. Water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; methanol/methylene chloride=from 0% to 10%) to afford the desired compound of formula 12-2 (0.095 g, 65.4%) as a yellow liquid.

Step 2: Synthesis of 4-((5-(1-(4-(furan-2-yl)benzyl)piperidin-4-yl)-1H-pyrrolo[2,3-b]pyridin-1-yl)methyl)-N-hydroxybenzamide (compound 875)

(compound 875)

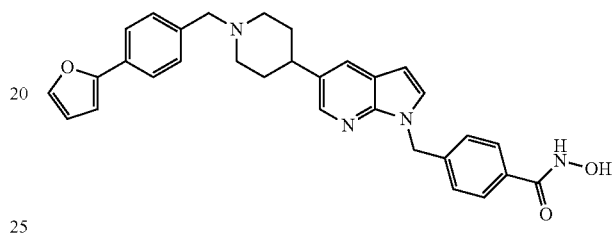

The compound of formula 12-2 (0.095 g, 0.187 mmol) prepared in step 1, hydroxylamine (50.00 wt % aqueous solution, 0.115 mL, 1.873 mmol), and potassium hydroxide (0.105 g, 1.873 mmol) were dissolved in methanol (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to afford the desired compound 875 (0.058 g, 60.9%) as a bright yellow solid.

$^1$H-NMR (400 MHz, CD$_3$OD+DMSO-d$_6$) δ 8.23 (d, 1H, J=1.9 Hz), 7.94 (d, 1H, J=2.0 Hz), 7.76-7.73 (m, 4H), 7.67 (d, 1H, J=1.2 Hz), 7.51-7.47 (m, 3H), 7.22 (d, 2H, J=8.3 Hz), 6.88 (d, 1H, J=2.8 Hz), 6.61 (dd, 1H, J=3.3, 1.8 Hz), 6.55 (d, 1H, J=3.5 Hz), 5.54 (s, 2H), 3.65 (s, 2H), 3.11 (d, 2H, J=11.4 Hz), 2.83-2.72 (m, 1H), 2.28-2.22 (m, 2H), 1.95-1.89 (m, 4H); MS (ESI) m/z 507.3 (M$^+$+1).

Example 113

Synthesis of Compound 876

Step 1: Synthesis of methyl 4-((5-(1-(phenylsufonyl)piperidin-4-yl)-1H-pyrrolo[2,3-b]pyridin-1-yl)methyl)benzoate (formula 12-1)

(formula 12-1)

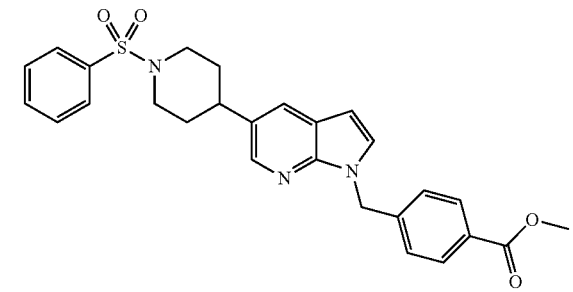

The compound of formula 6-3 (methyl 4-((5-(piperidin-4-yl)-1H-pyrrolo[2,3-b]pyridin-1-yl)methyl)benzoate) (0.100 g, 0.286 mmol), benzenesulfonyl chloride (0.076 g, 0.429 mmol), and triethylamine (0.058 g, 0.572 mmol) were dissolved in methylene chloride (3 mL) at room temperature, and the solution was stirred at the same temperature for 1 hour. Water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; ethyl acetate/hexane=from 0% to 50%) to afford the desired compound of formula 12-1 (0.107 g, 84.3%) as a colorless liquid.

Step 2: Synthesis of N-hydroxy-4-((5-(1-(phenylsulfonyl)piperidin-4-yl)-1H-pyrrolo[2,3-b]pyridin-1-yl)methyl)benzamide (compound 876)

(compound 876)

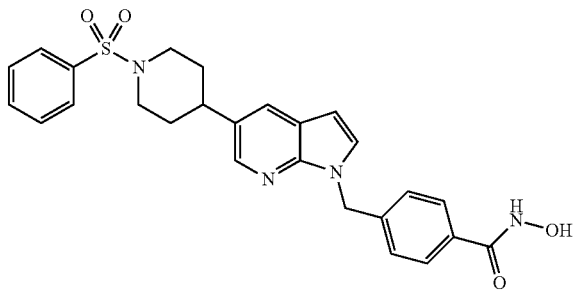

The compound of formula 12-1 (0.107 g, 0.219 mmol) prepared in step 1, hydroxylamine (50.00 wt % aqueous solution, 0.134 mL, 2.186 mmol), and potassium hydroxide (0.123 g, 2.186 mmol) were dissolved in methanol (1 mL)/tetrahydrofuran (1 mL) at room temperature, and the solution was stirred at the room temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to afford the desired compound 876 (0.099 g, 92.3%) as a white solid.

$^1$H-NMR (400 MHz, CD$_3$OD+DMSO-d$_6$) δ 8.14 (d, 1H, J=2.0 Hz), 7.90-7.86 (m, 3H), 7.76-7.68 (m, 5H), 7.46 (d, 1H, J=3.5 Hz), 7.17 (d, 2H, J=8.2 Hz), 6.52 (d, 1H, J=3.5 Hz), 5.51 (s, 2H), 3.96 (d, 2H, J=11.7 Hz), 2.70-2.68 (m, 1H), 2.50-2.44 (m, 2H), 1.99-1.83 (m, 4H); MS (ESI) m/z 491.2 (M$^+$+1).

Example 114

Synthesis of Compound 877

Step 1: Synthesis of methyl 4-((5-(1-(3-formylbenzyl)piperidin-4-yl)-1H-pyrrolo[2,3-b]pyridin-1-yl)methyl)benzoate (formula 15-3)

(formula 15-3)

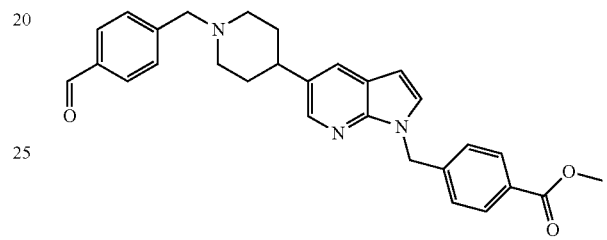

The compound of formula 6-2 (methyl 4-((5-(piperidin-4-yl)-1H-pyrrolo[2,3-b]pyridin-1-yl)methyl)benzoate) (1.000 g, 2.862 mmol), 4-(bromomethyl)benzaldehyde (0.684 g, 3.434 mmol), and N,N-diisopropylethylamine (1.013 mL, 5.724 mmol) were dissolved in acetonitrile (5 mL) at room temperature, and the solution was stirred at the same temperature for 3 hours. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; ethyl acetate/hexane=from 0% to 50%) to afford the desired compound of formula 15-3 (0.586 g, 43.8%) as a white solid.

Step 2: Synthesis of methyl 4-((5-(1-(4-((4-methylpiperazin-1-yl)methyl)benzyl)piperidin-4-yl)-1H-pyrrolo[2,3-b]pyridin-1-yl)methyl)benzoate (formula 15-4)

(formula 15-4)

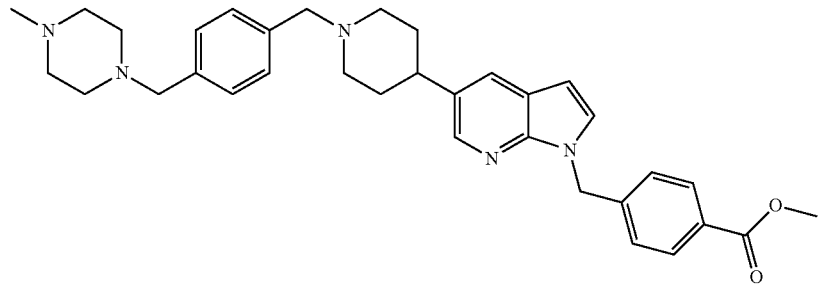

The compound of formula 15-3 (0.200 g, 0.428 mmol) prepared in step 1, 1-methylpiperazine (0.086 mL, 0.856 mmol), and sodium triacetoxyborohydride (0.181 g, 0.856 mmol) were dissolved in methylene chloride (3 mL) at room temperature, and the solution was stirred at the same temperature for 3 hours. Water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; methanol/methylene chloride=from 0% to 10%) to afford the desired compound of formula 15-4 (0.230 g, 97.5%) as a yellow liquid.

Step 3: Synthesis of N-hydroxy-4-((5-(1-(4-((4-methylpiperazin-1-yl)methyl)benzyl)piperidin-4-yl)-1H-pyrrolo[2,3-b]pyridin-1-yl)methyl)benzamide (compound 877)

The compound of formula 6-2 (methyl 4-((5-(piperidin-4-yl)-1H-pyrrolo[2,3-b]pyridin-1-yl)methyl)benzoate) (1.000 g, 2.862 mmol), 4-(bromomethyl)benzaldehyde (0.684 g, 3.434 mmol), and N,N-diisopropylethylamine (1.013 mL, 5.724 mmol) were dissolved in acetonitrile (5 mL) at room temperature, and the solution was stirred at the same temperature for 3 hours. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; ethyl acetate/hexane=from 0% to 50%) to afford the desired compound of formula 15-3 (0.586 g, 43.8%) as a white solid.

(compound 877)

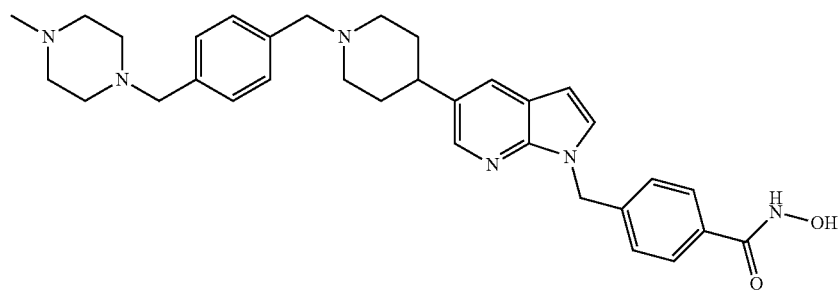

The compound of formula 15-4 (0.230 g, 0.417 mmol) prepared in step 2, hydroxylamine (50.0 wt % aqueous solution, 0.255 mL, 4.172 mmol), and potassium hydroxide (0.234 g, 4.172 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to afford the desired compound 877 (0.156 g, 67.6%) as a yellow solid.

2$^1$H-NMR (400 MHz, CD$_3$OD) δ 8.14 (d, 1H, J=2.0 Hz), 7.91 (d, 1H, J=2.0 Hz), 7.67 (d, 2H, J=8.4 Hz), 7.40-7.27 (m, 5H), 7.23-7.19 (m, 2H), 6.52 (d, 1H, J=3.5 Hz), 5.53 (s, 2H), 3.61 (s, 2H), 3.57 (s, 2H), 3.07 (d, 2H, J=11.6 Hz), 2.81-2.28 (m, 1H), 2.70-2.67 (m, 4H), 2.62-2.34 (m, 4H), 2.29 (s, 3H), 2.24-2.18 (m, 2H), 1.91-1.86 (m, 4H); MS (ESI) m/z 553.4 (M$^+$+1).

Example 115

Synthesis of Compound 878

Step 1: Synthesis of methyl 4-((5-(1-(3-formylbenzyl)piperidin-4-yl)-1H-pyrrolo[2,3-b]pyridin-1-yl)methyl)benzoate (formula 15-3)

(formula 15-3)

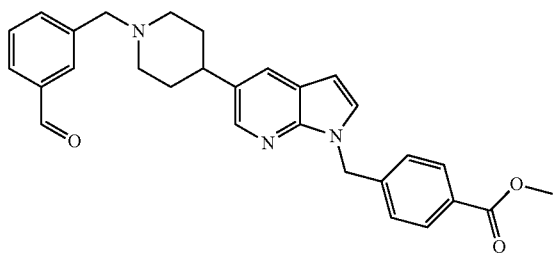

Step 2: Synthesis of methyl 4-((5-(1-(3-(morpholinomethyl)benzyl)piperidin-4-yl)-1H-pyrrolo[2,3-b]pyridin-1-yl)methyl)benzoate (formula 15-4)

(formula 15-4)

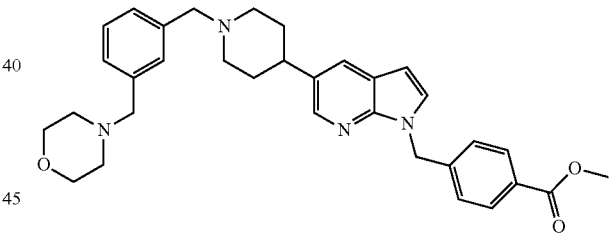

The compound of formula 15-3 (0.200 g, 0.428 mmol) prepared in step 1, morpholine (0.075 g, 0.856 mmol), and sodium triacetoxyborohydride (0.181 g, 0.856 mmol) were dissolved in methylene chloride (3 mL) at room temperature, and the solution was stirred at the same temperature for 3 hours. Water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; methanol/methylene chloride=from 0% to 10%) to afford the desired compound of formula 15-4 (0.124 g, 53.6%) as a yellow liquid.

Step 3: Synthesis of N-hydroxy-4-((5-(1-(3-(morpholinomethyl)benzyl)piperidin-4-yl)-1H-pyrrolo[2,3-b]pyridin-1-yl)methyl)benzamide (compound 878)

(compound 878)

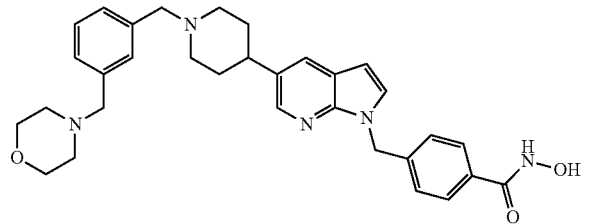

The compound of formula 15-4 (0.124 g, 0.229 mmol) prepared in step 2, hydroxylamine (50.00 wt % aqueous solution, 0.140 mL, 2.294 mmol), and potassium hydroxide (0.129 g, 2.294 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to afford the desired compound 878 (0.117 g, 94.2%) as a yellow solid.

$^1$H-NMR (400 MHz, CD$_3$OD) δ 8.14 (d, 1H, J=2.0 Hz), 7.91 (d, 1H, J=2.0 Hz), 7.69 (d, 2H, J=8.4 Hz), 7.39 (d, 1H, J=3.5 Hz), 7.37-7.36 (m, 4H), 7.15 (d, 2H, J=8.4 Hz), 6.51 (d, 1H, J=3.5 Hz), 5.50 (s, 2H), 3.71-3.69 (m, 4H), 3.61 (s, 2H), 3.54 (s, 2H), 3.07 (d, 2H, J=11.8 Hz), 2.76-2.68 (m, 1H), 2.48 (m, 4H), 2.25-2.18 (m, 2H), 1.91-1.88 (m, 4H); MS (ESI) m/z 540.3 (M$^+$+1).

Example 116

Synthesis of Compound 879

Step 1: Synthesis of methyl 4-((5-(1-(3-((4-methylpiperazin-1-yl)methyl)benzyl)piperidin-4-yl)-1H-pyrrolo[2,3-b]pyridin-1-yl)methyl)benzoate (formula 15-4)

(formula 15-4)

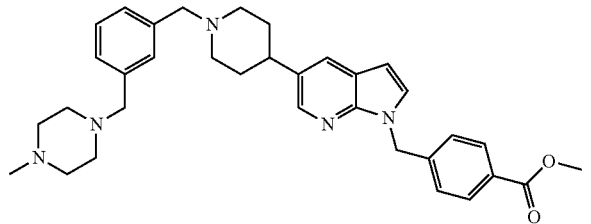

The compound of formula 15-3 (methyl 4-((5-(1-(3-formylbenzyl)piperidin-4-yl)-1H-pyrrolo[2,3-b]pyridin-1-yl)methyl)benzoate) (0.100 g, 0.214 mmol), 1-methylpiperizine (0.043 g, 0.428 mmol), and sodium triacetoxyborohydride (0.091 g, 0.428 mmol) were dissolved in methylene chloride (3 mL) at room temperature, and the solution was stirred at the same temperature for 3 hours. Water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; methanol/methylene chloride=from 0% to 10%) to afford the desired compound of formula 15-4 (0.075 g, 63.6%) as a yellow liquid.

Step 2: Synthesis of N-hydroxy-4-((5-(1-(3-((4-methylpiperazin-1-yl)methyl)benzyl)piperidin-4-yl)-1H-pyrrolo[2,3-b]pyridin-1-yl)methyl)benzamide (compound 879)

(compound 879)

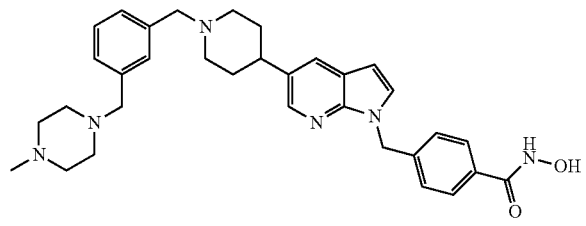

The compound of formula 15-4 (0.075 g, 0.136 mmol) prepared in step 1, hydroxylamine (50.00 wt % aqueous solution, 0.083 mL, 1.359 mmol), and potassium hydroxide (0.076 g, 1.359 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to afford the desired compound 879 (0.055 g, 73.2%) as a yellow solid.

$^1$H-NMR (400 MHz, CD$_3$OD) δ 8.15 (d, 1H, J=2.0 Hz), 7.91 (d, 1H, J=2.0 Hz), 7.69 (d, 2H, J=8.4 Hz), 7.41-7.31 (m, 5H), 7.14 (d, 2H, J=8.4 Hz), 6.51 (d, 1H, J=3.5 Hz), 5.50 (s, 2H), 3.61 (s, 2H), 3.56 (s, 2H), 3.08 (d, 2H, J=12.4 Hz), 2.81-2.80 (m, 1H), 2.74-2.66 (m, 4H), 2.63-2.35 (m, 4H), 2.29 (s, 3H), 2.25-2.19 (m, 2H), 1.91-1.86 (m, 4H); MS (ESI) m/z 553.4 (M$^+$+1).

Example 117

Synthesis of Compound 880

Step 1: Synthesis of methyl 4-((5-(1-(pyrimidin-5-ylmethyl)piperidin-4-yl)-1H-pyrrolo[2,3-b]pyridin-1-yl)methyl)benzoate (formula 12-2)

(formula 12-2)

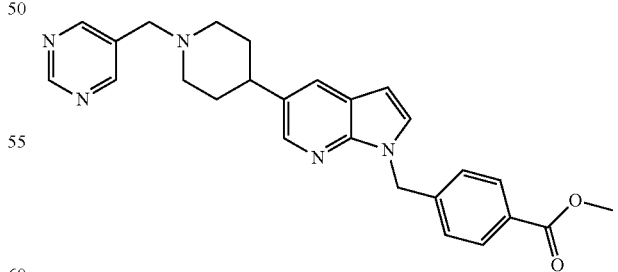

The compound of formula 6-3 (methyl 4-((5-(piperidin-4-yl)-1H-pyrrolo[2,3-b]pyridin-1-yl)methyl)benzoate) (0.100 g, 0.286 mmol), 5-(chloromethyl)pyrimidine (0.044 g, 0.343 mmol), and N,N-diisopropylethylamine (0.101 mL, 0.572 mmol) were dissolved in acetonitrile (3 mL) at room temperature, and the solution was stirred at the same temperature for 3 hours. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO₂, 4 g cartridge; methanol/methylene chloride=from 0% to 10%) to afford the desired compound of formula 12-2 (0.054 g, 42.7%) as a yellow liquid.

Step 2: Synthesis of N-hydroxy-4-((5-(1-(pyrimidin-5-ylmethyl)piperidin-4-yl)-1H-pyrrolo[2,3-b]pyridin-1-yl)methyl)benzamide (compound 880)

(compound 880)

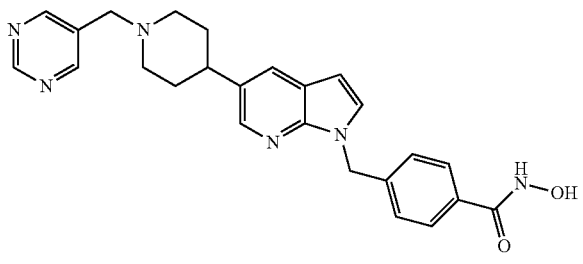

The compound of formula 12-2 (0.054 g, 0.122 mmol) prepared in step 1, hydroxylamine (50.00 wt % aqueous solution, 0.075 mL, 1.223 mmol), and potassium hydroxide (0.069 g, 1.223 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to afford the desired compound 880 (0.042 g, 77.4%) as a white solid.

¹H-NMR (400 MHz, CD₃OD) δ 9.11 (s, 1H), 8.84 (s, 2H), 8.15 (d, 1H, J=2.0 Hz), 7.93 (d, 1H, J=2.0 Hz), 7.67 (d, 2H, J=8.4 Hz), 7.42 (d, 1H, J=3.5 Hz), 7.22 (d, 2H, J=8.4 Hz), 6.53 (d, 1H, J=3.6 Hz), 5.55 (s, 2H), 3.68 (s, 2H), 3.05 (d, 2H, J=11.7 Hz), 2.76-2.69 (m, 1H), 2.32-2.25 (m, 2H), 1.92-1.86 (m, 4H); MS (ESI) m/z 443.3 (M⁺+1).

Example 118

Synthesis of Compound 881

Step 1: Synthesis of methyl 4-((5-(1-(pyrimidin-2-ylmethyl)piperidin-4-yl)-1H-pyrrolo[2,3-b]pyridin-1-yl)methyl)benzoate (formula 12-2)

(formula 12-2)

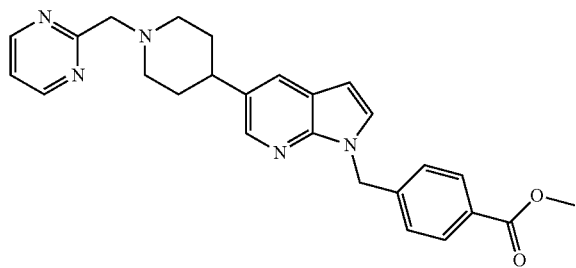

The compound of formula 6-3 (methyl 4-((5-(piperidin-4-yl)-1H-pyrrolo[2,3-b]pyridin-1-yl)methyl)benzoate) (0.100 g, 0.286 mmol), 2-(chloromethyl)pyrimidine (0.044 g, 0.343 mmol), and N,N-diisopropylethylamine (0.101 mL, 0.572 mmol) were dissolved in acetonitrile (3 mL) at room temperature, and the solution was stirred at the same time for 3 hours. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO₂, 4 g cartridge; methanol/methylene chloride=from 0% to 10%) to afford the desired compound of formula 12-2 (0.064 g, 50.7%) as a yellow liquid.

Step 2: Synthesis of N-hydroxy-4-((5-(1-(pyrimidin-2-ylmethyl)piperidin-4-yl)-1H-pyrrolo[2,3-b]pyridine-1-yl)methyl)benzamide (compound 881)

(compound 881)

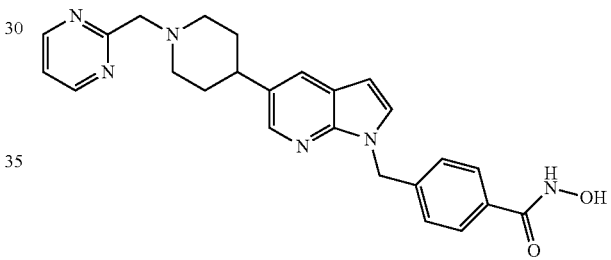

The compound of formula 12-2 (0.064 g, 0.145 mmol) prepared in step 1, hydroxylamine (50.00 wt % aqueous solution, 0.089 mL, 1.450 mmol), and potassium hydroxide (0.081 g, 1.450 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to afford the desired compound 881 (0.041 g, 63.9%) as a white solid.

¹H-NMR (400 MHz, CD₃OD) δ 8.84 (s, 2H), 8.16 (s, 1H), 7.94 (s, 1H), 7.67 (d, 2H, J=5.9 Hz), 7.43 (d, 2H, J=4.2 Hz), 7.24 (m, 2H), 6.54 (s, 1H), 5.56 (s, 2H), 3.90 (s, 2H), 3.17 (d, 2H, J=9.6 Hz), 2.72 (m, 1H), 2.43-2.38 (m, 2H), 1.99-1.87 (m, 4H); MS (ESI) m/z 443.3 (M⁺+1).

Example 119

Synthesis of Compound 882

Step 1: Synthesis of methyl 4-((5-(1-(4-(morpholinomethyl)benzyl)piperidin-4-yl)-1H-pyrrolo[2,3-b]pyridin-1-yl)methyl)benzoate (formula 15-4)

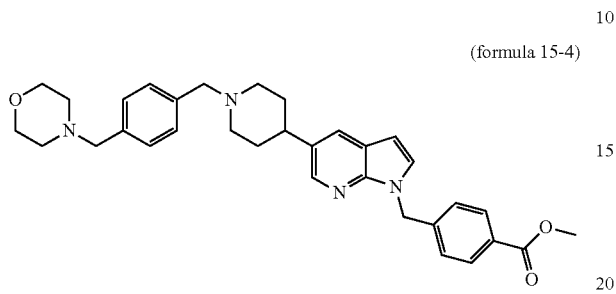

(formula 15-4)

The compound of formula 15-3 (methyl 4-((5-(1-(4-formylbenzyl)piperidin-4-yl)-1H-pyrrolo[2,3-b]pyridin-1-yl)methyl)benzoate) (0.100 g, 0.214 mmol), morpholine (0.037 g, 0.428 mmol), and sodium triacetoxyborohydride (0.091 g, 0.428 mmol) were dissolved in methylene chloride (3 mL) at room temperature, and the solution was stirred at the same temperature for 3 hours. Water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography ($SiO_2$, 12 g cartridge; methanol/methylene chloride=from 0% to 10%) to afford the desired compound of formula 15-4 (0.065 g, 56.2%) as a yellow liquid.

Step 2: Synthesis of N-hydroxy-4-((5-(1-(4-(morpholinomethyl)benzyl)piperidin-4-yl)-1H-pyrrolo[2,3-b]pyridin-1-yl)methyl)benzamide (compound 882)

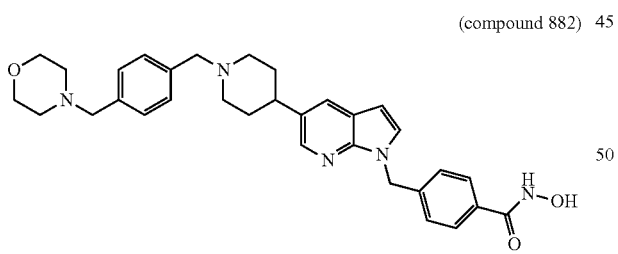

(compound 882)

The compound of formula 15-4 (0.065 g, 0.120 mmol) prepared in step 1, hydroxylamine (50.0 wt % aqueous solution, 0.074 mL, 1.203 mmol), and potassium hydroxide (0.067 g, 1.203 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to yield desired compound 882 (0.059 g, 91.0%) as an ivory solid.

$^1$H-NMR (400 MHz, $CD_3OD$) δ 8.14 (d, 1H, J=2.0 Hz), 7.92 (d, 1H, J=2.0 Hz), 7.67 (d, 2H, J=8.4 Hz), 7.41 (d, 1H, J=3.5 Hz), 7.38 (s, 1H), 7.35-7.29 (m, 3H), 7.21 (d, 2H, J=8.4 Hz), 6.52 (d, 1H, J=3.5 Hz), 5.54 (s, 2H), 3.72-3.70 (m, 4H), 3.61 (s, 2H), 3.56 (s, 2H), 3.07 (d, 2H, J=11.8 Hz), 2.75-2.68 (m, 1H), 2.49 (m, 4H), 2.25-2.19 (m, 2H), 1.90-1.86 (m, 4H); MS (ESI) m/z 540.3 ($M^+$+1).

Example 120

Synthesis of Compound 883

Step 1: Synthesis of methyl 4-((5-(1-(2-(4-methylpiperazin-1-yl)benzyl)piperidin-4-yl)-1H-pyrrolo[2,3-b]pyridin-1-yl)methyl)benzoate (formula 12-2)

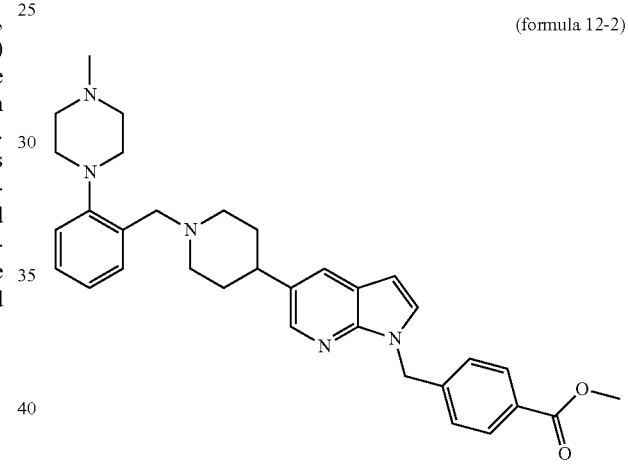

(formula 12-2)

The compound of formula 6-3 (methyl 4-((5-(piperidin-4-yl)-1H-pyrrolo[2,3-b]pyridin-1-yl)methyl)benzoate) (0.100 g, 0.286 mmol), 2-(4-methylpiperazin-1-yl)benzaldehyde (0.088 g, 0.429 mmol), and sodium triacetoxyborohydride (0.091 g, 0.429 mmol) were dissolved in methylene chloride (3 mL) at room temperature, and the solution was stirred at the same time for 1 hour. Then, water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography ($SiO_2$, 12 g cartridge; methanol/methylene chloride=from 0% to 10%) to afford the desired compound of formula 12-2 (0.038 g, 24.7%) as a colorless liquid.

Step 2: Synthesis of N-hydroxy-4-((5-(1-(2-(4-methylpiperzin-1-yl)benzyl)piperidin-4-yl)-1H-pyrrolo[2,3-b]pyridin-1-yl)methyl)benzamide (compound 883)

(compound 883)

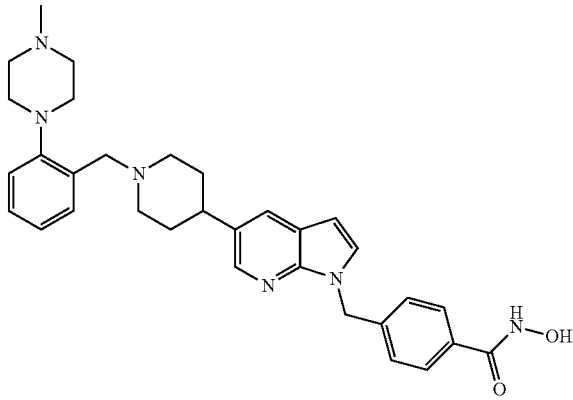

The compound of formula 12-2 (0.100 g, 0.186 mmol) prepared in step 1, hydroxylamine (50.00 wt % aqueous solution, 0.114 mL, 1.860 mmol), and potassium hydroxide (0.104 g, 1.860 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to afford the desired compound 883 (0.043 g, 42.9%) as an ivory solid.

$^1$H-NMR (400 MHz, CD$_3$OD) δ 8.15 (d, 1H, J=1.9 Hz), 7.91 (d, 1H, J=2.0 Hz), 7.69 (d, 2H, J=8.4 Hz), 7.48 (dd, 1H, J=7.6, 1.5 Hz), 7.38 (d, 2H, J=3.5 Hz), 7.28 (td, 1H, J=7.6, 1.6 Hz), 7.20 (dd, 1H, J=8.1, 1.2 Hz), 7.15-7.10 (m, 3H), 6.51 (d, 1H, J=3.5 Hz), 5.50 (s, 2H), 3.70 (s, 2H), 3.11 (d, 2H, J=11.6 Hz), 3.03 (m, 4H), 2.77-2.65 (m, 5H), 2.40 (s, 3H), 2.30-2.23 (m, 2H), 1.90-1.84 (m, 4H); MS (ESI) m/z 539.3 (M$^+$+1).

Example 121

Synthesis of Compound 884

Step 1: Synthesis of methyl 4-((4-((3S,5R)-3,5-dimethylpiperazin-1-yl)-1H-pyrrolo[2,3-b]pyridin-1-yl)methy)benzoate (formula 26-1)

(formula 26-1)

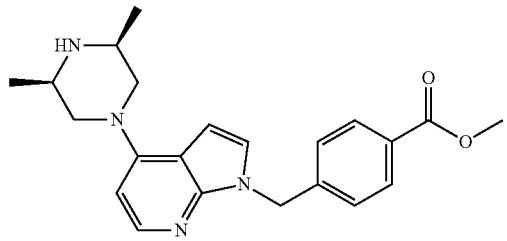

The compound of formula 1-2 (methyl 4-((4-bromo-1H-pyrrolo[2,3-b]pyridin-1-yl)methy)benzoate) (2.000 g, 5.794 mmol), (2R,6S)-2,6-dimethylpiperazine (0.794 g, 6.953 mmol), bis(tri-tert-butylphosphine)palladium(0) (0.296 g, 0.579 mmol) and sodium tert-butoxide (0.668 g, 6.953 mmol) were dissolved in toluene (50 mL) at 120° C., and the solution was stirred at the same temperature for 12 hours, and then cooled to room temperature. After completion of the reaction, water was added to the reaction mixture, followed by extraction with ethyl acetate. The organic layer was washed with a saturated aqueous solution of sodium chloride, dried with anhydrous magnesium sulfate, and then concentrated under reduced pressure. The concentrate was purified by column chromatography (SiO$_2$, 40 g cartridge; methanol/methylene chloride=from 0% to 10%) to afford the desired compound of formula 26-1 (0.910 g, 41.5%) as yellow oil.

Step 2: Synthesis of methyl 4-((4-((3S,5R)-4-(2-hydroxy-2-methylpropyl)-3,5-dimethylpiperazin-1-yl)-1H-pyrrolo[2,3-b]pyridin-1-yl)methy)benzoate (formula 26-3)

(formula 26-3)

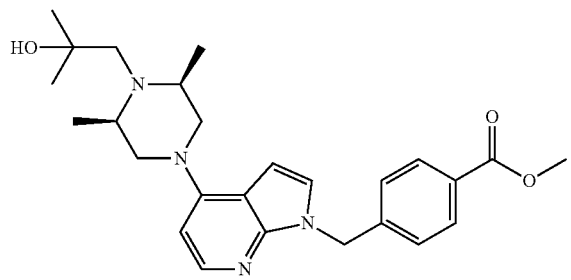

The compound of formula 26-1 (0.910 g, 2.404 mmol) prepared in step 1, dimethyloxirane (2.167 mL, 24.044 mmol) and DIPEA (0.851 mL, 4.809 mmol) were dissolved in ethanol (10 mL), and heated by microwave irradiation 110 r for 3 hours, and then cooled to room temperature. After completion of the reaction, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; methanol/methylene chloride=from 0% to 10%) to afford the desired compound of formula 26-3 (0.100 g, 9.2%) as brown oil.

Step 3: Synthesis of N-hydroxy-4-((4-((3S,5R)-4-(2-hydroxy-2-methylpropyl)-3,5-dimethylpiperazin-1-yl)-1H-pyrrolo[2,3-b]pyridin-1-yl)methy)benzamide (compound 884)

(compound 884)

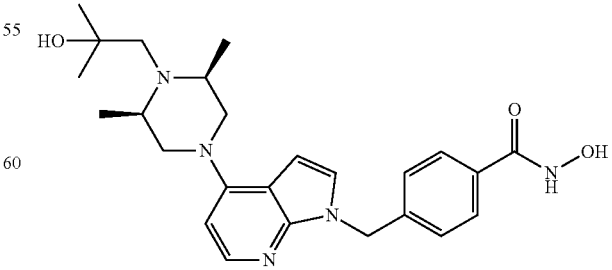

The compound of formula 26-3 (0.050 g, 0.111 mmol) prepared in step 2, potassium hydroxide (0.062 g, 1.110 mmol) and an aqueous solution of 50.00 wt % NH$_2$OH (0.143 mL, 2.219 mmol) were dissolved in methanol (5 mL) at room temperature, and the solution was stirred at the same temperature for 2 hour. Then, the reaction mixture was concentrated under reduced pressure to remove the solvent, and a saturated aqueous solution of sodium hydrogen carbonate (3 mL) was added to the concentrate, followed by stirring. The precipitated solid was filtered and dried to afford the desired compound 884 (0.015 g, 29.9%) as a white solid.

$^1$H-NMR (400 MHz, DMSO-d$_6$) δ 7.93 (d, 1H, J=5.5 Hz), 7.65 (d, 2H, J=8.0 Hz), 7.34 (d, 1H, J=3.5 Hz), 7.18 (d, 2H, J=8.1 Hz), 6.56 (d, 1H, J=3.5 Hz), 6.34 (d, 1H, J=5.6 Hz), 5.41 (s, 2H), 4.03 (s, 1H), 3.55-3.52 (m, 2H), 3.01-3.00 (m, 2H), 2.46 (s, 2H), 1.51 (s, 1H), 1.12 (s, 12H); MS (ESI) m/z 452.3 (M$^+$+1).

Example 122

Synthesis of Compound 885

Step 1: Synthesis of methyl 4-((4-((3S,5R)-4-(2-fluoro-2-methylpropyl)-3,5-dimethylpiperazin-1-yl)-1H-pyrrolo[2,3-b]pyridin-1-yl)methy)benzoate (formula 26-4)

(formula 26-4)

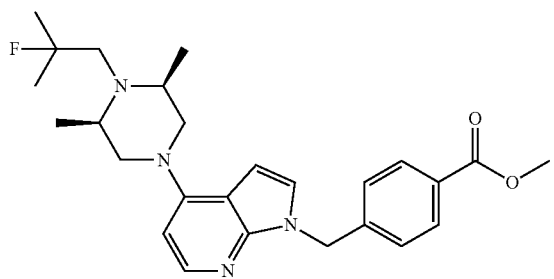

The compound of formula 26-3 (methyl 4-((4-((3S,5R)-4-(2-hydroxy-2-methylpropyl)-3,5-dimethylpiperazin-1-yl)-1H-pyrrolo[2,3-b]pyridin-1-yl)methy)benzoate) (0.050 g, 0.111 mmol) were dissolved in methylene chloride (5 mL). The solution was stirred at the same temperature for 5 minutes, and trifluoride (0.021 g, 0.133 mmol) was added thereto at 0 followed by stirring at room temperature for 1 hour. Water was added to the reaction mixture, followed by extraction with ethyl acetate. The organic layer was washed with a saturated aqueous solution of sodium hydrogen carbonate, dried with anhydrous magnesium sulfate, filtered, and then concentrated under reduced pressure. The concentrate was purified by column chromatography (SiO$_2$, 12 g cartridge; ethyl acetate/hexane=from 0% to 30%) to afford the desired compound of formula 26-4 (0.021 g, 41.8%) as a white solid.

Step 2: Synthesis of 4-((4-((3S,5R)-4-(2-fluoro-2-methylpropyl)-3,5-dimethylpiperazin-1-yl)-1H-pyrrolo[2,3-b]pyridin-1-yl)methy)-N-hydroxybenzamide (compound 885)

(compound 885)

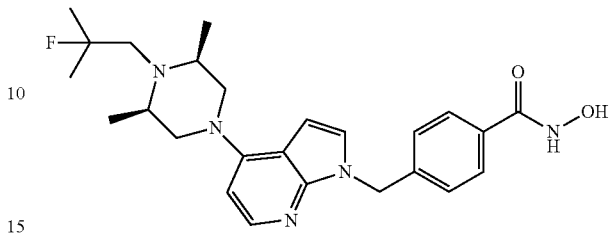

The compound of formula 26-4 (0.021 g, 0.046 mmol) prepared in step 1, potassium hydroxide (0.026 g, 0.464 mmol) and an aqueous solution of 50 wt % NH$_2$OH (0.060 mL, 0.928 mmol) were dissolved in methanol (10 mL) at room temperature, and the solution was stirred at the same temperature for 2 hours. Then, the reaction mixture was concentrated under reduced pressure to remove the solvent, and a saturated aqueous solution of sodium hydrogen carbonate (3 ml) was added to the concentrate, followed by stirring. The precipitated solid was filtered, washed with water, and dried to afford the desired compound 885 (0.010 g, 47.5%) as a yellow solid.

$^1$H-NMR (400 MHz, DMSO-d$_6$) δ 7.95 (d, 1H, J=5.5 Hz), 7.65 (d, 2H, J=8.0 Hz), 7.36 (d, 1H, J=3.4 Hz), 7.17 (d, 2H, J=7.8 Hz), 6.56 (d, 1H, J=3.5 Hz), 6.37 (d, 1H, J=5.4 Hz), 5.41 (s, 2H), 3.65-3.62 (m, 2H), 3.16-3.11 (m, 2H), 2.93-2.81 (m, 2H), 2.78-2.66 (m, 2H), 1.35 (s, 3H), 1.30 (s, 3H), 1.10 (s, 3H), 1.09 (s, 3H); MS (ESI) m/z 454.5 (M$^+$+1).

Example 123

Synthesis of Compound 886

Step 1: Synthesis of methyl 4-((4-((3S,5R)-4-(3-fluorobenzyl)-3,5-dimethylpiperazin-1-yl)-1H-pyrrolo[2,3-b]pyridin-1-yl)methy)benzoate (formula 26-2)

(formula 26-2)

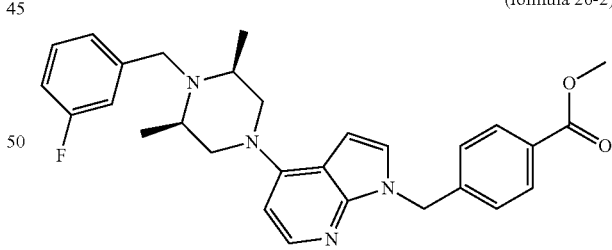

The compound of formula 26-1 (methyl 4-((4-((3S,5R)-3,5-dimethylpiperazin-1-yl)-1H-pyrrolo[2,3-b]pyridin-1-yl)methy)benzoate) (0.100 g, 0.264 mmol), 1-(bromomethyl)-3-fluorobenzene (0.100 g, 0.528 mmol) and DIPEA (0.094 mL, 0.528 mmol) were dissolved in methylene chloride (5 mL) at room temperature, and the solution was stirred at the same temperature for 12 hours. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; methanol/methylene chloride=from 0% to 10%) to afford the desired compound of formula 26-2 (0.036 g, 28.0%) as yellow oil.

Step 2: Synthesis of 4-((4-((3S,5R)-4-(3-fluorobenzyl)-3,5-dimethylpiperazin-1-yl)-1H-pyrrolo[2,3-b]pyridin-1-yl)methy)-N-hydroxybenzamide (compound 886)

(compound 886)

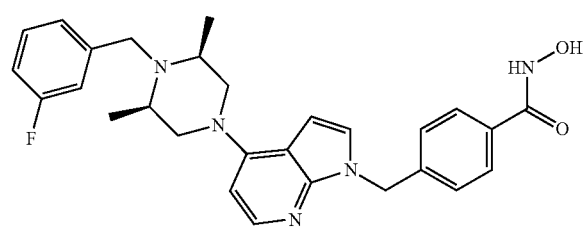

The compound of formula 26-2 (0.036 g, 0.074 mmol) prepared in step 1, potassium hydroxide (0.042 g, 0.740 mmol) and an aqueous solution of 50 wt % NH$_2$OH (0.095 mL, 1.480 mmol) were dissolved in methanol (3 mL) at room temperature, and the solution was stirred at the same temperature for 2 hours. Then, the reaction mixture was concentrated under reduced pressure to remove the solvent, and a saturated aqueous solution of sodium hydrogen carbonate (3 ml) was added to the concentrate, followed by stirring. The precipitated solid was filtered, washed with water, and dried to afford the desired compound 886 (0.011 g, 30.5%) as a white solid.

$^1$H-NMR (400 MHz, DMSO-d$_6$) δ 7.98 (d, 1H, J=5.5 Hz), 7.64 (d, 2H, J=8.1 Hz), 7.39-7.32 (m, 2H), 7.24-7.22 (m, 2H), 7.16 (d, 2H, J=8.1 Hz), 7.03-6.99 (m, 1H), 6.55 (d, 1H, J=3.5 Hz), 6.46 (d, 1H, J=5.5 Hz), 5.41 (s, 2H), 3.85-3.80 (m, 4H), 2.83-2.78 (m, 4H), 1.03 (s, 3H), 1.01 (s, 3H); MS (ESI) m/z 488.6 (M$^+$+1).

Example 124

Synthesis of Compound 895

Step 1: Synthesis of methyl 4-((5-(1-(3-formylbenzoyl)piperidin-4-yl)-1H-pyrrolo[2,3-b]pyridin-1-yl)methyl)benzoate (formula 15-1)

(formula 15-1)

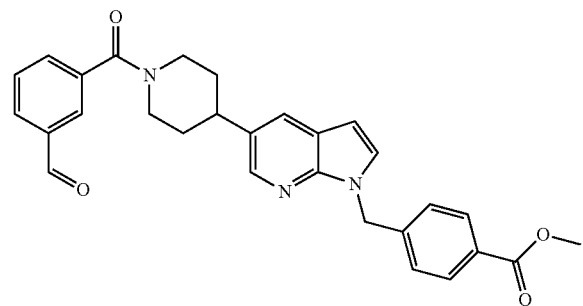

The compound of formula 6-2 (methyl 4-((5-(piperidin-4-yl)-1H-pyrrolo[2,3-b]pyridin-1-yl)methyl)benzoate) (1.000 g, 2.862 mmol), 3-formylbenzoic acid (0.859 g, 5.724 mmol), 1-ethyl-3-[3-dimethylaminopropyl]carbodiimide hydrochloride (1.097 g, 5.724 mmol), 1-hydroxybenzotriazole hydrate (0.773 g, 5.724 mmol), and N,N-diisopropylethylamine (1.013 mL, 5.724 mmol) were dissolved in N,N-dimethylformamide (10 mL) at 40° C., and the solution was stirred at the same temperature for 6 hours, and then cooled to room temperature. After completion of the reaction, water was added to the reaction mixture, followed by extraction with ethyl acetate. The organic layer was washed with a saturated aqueous solution of sodium chloride, dried with anhydrous magnesium sulfate, and then concentrated under reduced pressure. The concentrate was purified by column chromatography (SiO$_2$, 40 g cartridge; methanol/methylene chloride=from 0% to 10%) to afford the desired compound of formula 15-1 (1.051 g, 76.3%) as a yellow liquid.

Step 2: Synthesis of methyl 4-((5-(1-(3-(morpholinomethyl)benzoyl)piperidin-4-yl)-1H-pyrrolo[2,3-b]pyridin-1-yl)methyl)benzoate (formula 15-2)

(formula 15-2)

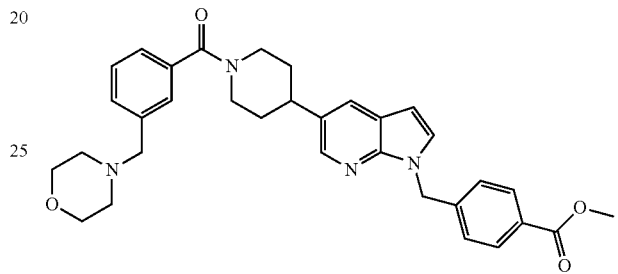

The compound of formula 15-1 (0.100 g, 0.208 mmol) prepared in step 1, morpholine (0.036 g, 0.415 mmol) and sodium triacetoxyborohydride (0.088 g, 0.415 mmol) were dissolved in methylene chloride (3 mL) at room temperature, and the solution was stirred at the same temperature for 3 hours. Then, water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; methanol/methylene chloride=from 0% to 10%) to afford the desired compound of formula 15-2 (0.100 g, 86.9%) as a colorless liquid.

Step 3: Synthesis of N-hydroxy-4-((5-(1-(3-(morpholinomethyl)benzoyl)piperidin-4-yl)-1H-pyrrolo[2,3-b]pyridin-1-yl)methyl)benzamide (compound 895)

(compound 895)

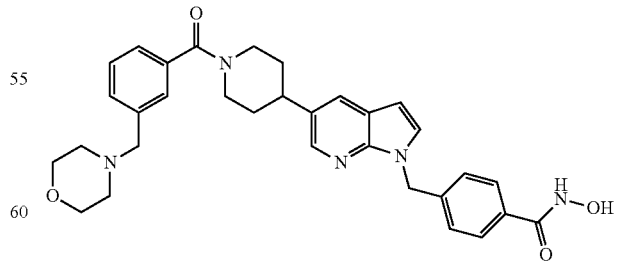

The compound of formula 15-2 (0.100 g, 0.181 mmol) prepared in step 2, hydroxylamine (50.00 wt % aqueous solution, 0.111 mL, 1.809 mmol) and potassium hydroxide (0.102 g, 1.809 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to afford the desired compound 895 (0.067 g, 67.3%) as a white solid.

$^1$H-NMR (400 MHz, CD$_3$OD) δ 8.19 (d, 1H, J=2.0 Hz), 7.97 (d, 1H, J=2.0 Hz), 7.68 (d, 2H, J=8.4 Hz), 7.49-7.39 (m, 5H), 7.21 (d, 2H, J=8.5 Hz), 6.54 (d, 1H, J=3.5 Hz), 5.55 (s, 2H), 3.72-3.69 (m, 4H), 3.60 (s, 2H), 3.08-2.98 (m, 2H), 2.79-2.77 (m, 1H), 2.49 (m, 4H), 2.06-2.04 (m, 2H), 1.91-1.77 (m, 4H); MS (ESI) m/z 554.0 (M$^+$+1).

Example 125

Synthesis of Compound 896

Step 1: Synthesis of methyl 4-((5-(1-(3-((4-methyl-piperazin-1-yl)methyl)benzoyl)piperidin-4-yl)-1H-pyrrolo[2,3-b]pyridin-1-yl)methyl)benzoate (formula 15-2)

(formula 15-2)

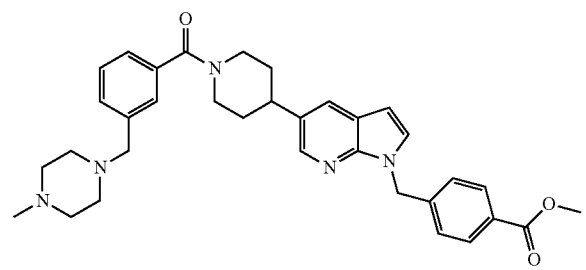

The compound of formula 15-1 (methyl 4-((5-(1-(3-formylbenzoyl)piperidin-4-yl)-1H-pyrrolo[2,3-b]pyridin-1-yl)methyl)benzoate) (0.100 g, 0.208 mmol), 1-methylpiperazine (0.042 g, 0.415 mmol) and sodium triacetoxyborohydride (0.088 g, 0.415 mmol) were dissolved in methylene chloride (3 mL) at room temperature, and the solution was stirred at the same temperature for 3 hours. Then, water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; methanol/methylene chloride=from 0% to 10%) to afford the desired compound of formula 15-2 (0.110 g, 93.6%) as a colorless liquid.

Step 2: Synthesis of N-hydroxy-4-((5-(1-(3-((4-methylpiperazin-1-yl)methyl)benzoyl)piperidin-4-yl)-1H-pyrrolo[2,3-b]pyridin-1-yl)methyl)benzamide (compound 896)

(compound 896)

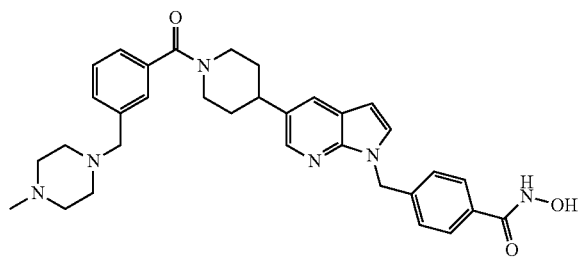

The compound of formula 15-2 (0.110 g, 0.194 mmol) prepared in step 1, hydroxylamine (50.00 wt % aqueous solution, 0.119 mL, 1.944 mmol) and potassium hydroxide (0.109 g, 1.944 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to afford the desired compound 896 (0.107 g, 96.9%) as an ivory solid.

$^1$H-NMR (400 MHz, CD$_3$OD) δ 8.19 (d, 1H, J=2.0 Hz), 7.98 (d, 1H, J=2.0 Hz), 7.68 (d, 2H, J=8.4 Hz), 7.49-7.39 (m, 5H), 7.22 (d, 2H, J=8.5 Hz), 6.55 (d, 1H, J=3.5 Hz), 5.55 (s, 2H), 3.62 (s, 2H), 3.08-2.98 (m, 2H), 2.66-2.35 (m, 9H), 2.27 (s, 3H), 2.10-2.03 (m, 2H), 1.91-1.77 (m, 4H); MS (ESI) m/z 567.0 (H$^+$+1).

Example 126

Synthesis of Compound 897

Step 1: Synthesis of methyl 4-((5-(1-(4-(morpholinomethyl)benzoyl)piperidin-4-yl)-1H-pyrrolo[2,3-b]pyridin-1-yl)methyl)benzoate (formula 15-2)

(formula 15-2)

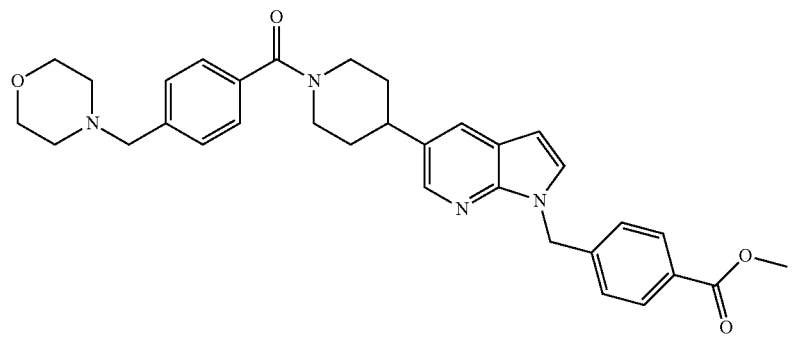

The compound of formula 15-1 (methyl 4-((5-(1-(4-form-ylbenzoyl)piperidin-4-yl)-1H-pyrrolo[2,3-b]pyridin-1-yl)methyl)benzoate) (0.100 g, 0.208 mmol), morpholine (0.036 g, 0.415 mmol) and sodium triacetoxyborohydride (0.088 g, 0.415 mmol) were dissolved in methylene chloride (3 mL) at room temperature, and the solution was stirred at the same temperature for 3 hours. Then, water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; methanol/methylene chloride=from 0% to 10%) to afford the desired compound of formula 15-2 (0.104 g, 90.7%) as a colorless liquid.

Step 2: Synthesis of N-hydroxy-4-((5-(1-(4-(morpholinomethyl)benzoyl)piperidin-4-yl)-1H-pyrrolo[2,3-b]pyridin-1-yl)methyl)benzamide (compound 897)

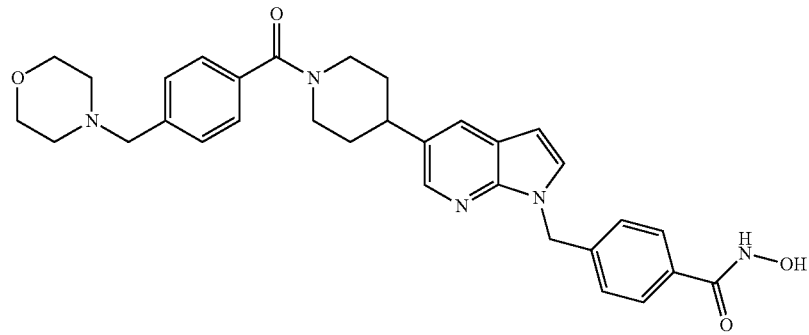

(compound 897)

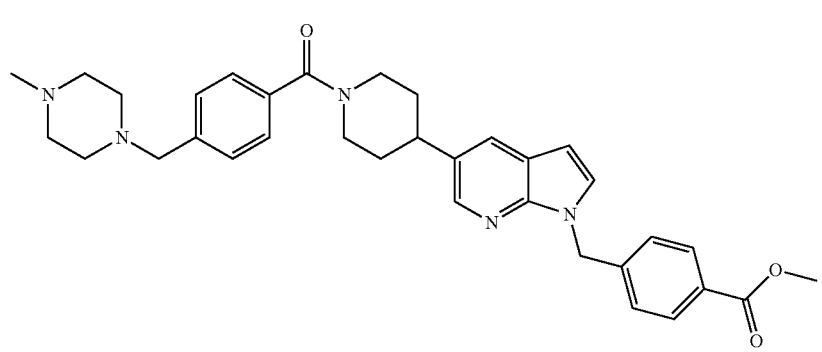

(formula 15-2)

The compound of formula 15-2 (0.104 g, 0.188 mmol) prepared in step 1, hydroxylamine (50.00 wt % aqueous solution, 0.115 mL, 1.882 mmol) and potassium hydroxide (0.106 g, 1.882 mmol) were dissolved in methanol (1 mL)/tetrahydrofuran (1 mL) at room temperature, and the solution was dissolved at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to afford the desired compound 897 (0.054 g, 51.8%) as an ivory solid.

$^1$H-NMR (400 MHz, CD$_3$OD) δ 8.19 (d, 1H, J=2.0 Hz), 7.97 (d, 1H, J=2.0 Hz), 7.68 (d, 2H, J=8.4 Hz), 7.51-7.42 (m, 5H), 7.21 (d, 2H, J=8.4 Hz), 6.54 (d, 1H, J=3.5 Hz), 5.55 (s, 2H), 3.72-3.70 (m, 4H), 3.59 (s, 2H), 3.07-3.01 (m, 2H), 2.77-2.70 (m, 1H), 2.49 (m, 4H), 2.06-2.03 (m, 2H), 1.88-1.76 (m, 4H); MS (ESI) m/z 554.0 (M$^+$+1).

Step 127: Synthesis of compound 898

Step 1: Synthesis of methyl 4-((5-(1-(4-((4-methylpiperazin-1-yl)methyl)benzoyl)piperidin-4-yl)-1H-pyrrolo[2,3-b]pyridin-1-yl)methyl)benzoate (formula 15-2)

The compound of formula 15-1 (methyl 4-((5-(1-(4-formylbenzoyl)piperidin-4-yl)-1H-pyrrolo[2,3-b]pyridin-1-yl)methyl)benzoate) (0.100 g, 0.208 mmol), 1-methylpiperazine (0.042 g, 0.415 mmol) and sodium triacetoxyborohydride (0.088 g, 0.415 mmol) were dissolved in methylene chloride (3 mL) at room temperature, and the solution was stirred at the same temperature for 3 hours. Then, water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO₂, 4 g cartridge; methanol/methylene chloride=from 0% to 10%) to afford the desired compound of formula 15-2 (0.079 g, 67.2%) as a colorless liquid.

Step 2: Synthesis of N-hydroxy-4-((5-(1-(4-((4-methylpiperazin-1-yl)methyl)benzoyl)piperidin-4-yl)-1H-pyrrolo[2,3-b]pyridin-1-yl)methyl)benzamide (compound 898)

(compound 898)

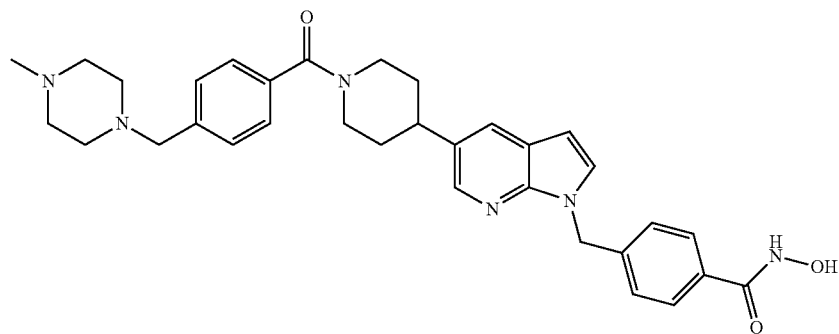

The compound of formula 15-2 (0.079 g, 0.140 mmol) prepared in step 2, hydroxylamine (50.00 wt % aqueous solution, 0.085 mL, 1.396 mmol) and potassium hydroxide (0.078 g, 1.396 mmol) were dissolved in methanol (1 mL)/tetrahydrofuran (1 mL) at room temperature, and the solution was stirred at the same temperature for 1 hour. Then, the reaction mixture was concentrated under reduced pressure to remove the solvent, and a saturated aqueous solution of sodium hydrogen carbonate (20 mL) was added to the concentrate, followed by stirring. The precipitated solid was filtered and dried to afford the desired compound 898(0.054 g, 68.4%) as an ivory solid.

¹H-NMR (400 MHz, CD₃OD) δ 8.19 (d, 1H, J=2.0 Hz), 7.97 (d, 1H, J=2.0 Hz), 7.68 (d, 2H, J=8.3 Hz), 7.49-7.43 (m, 5H), 7.22 (d, 2H, J=8.2 Hz), 6.55 (d, 1H, J=3.5 Hz), 5.55 (s, 2H), 3.60 (s, 2H), 3.07-2.98 (m, 2H), 2.77-2.39 (m, 9H), 2.29 (s, 3H), 2.60-2.03 (m, 2H), 1.88-1.77 (m, 4H); MS (ESI) m/z 567.0 (H⁺+1).

Example 128

Synthesis of Compound 917

Step 1: Synthesis of 4-((4-(1-(tert-butoxycarbonyl)piperidin-4-yl)-1H-pyrrolo[2,3-b]pyridin-1-yl)methyl)benzoic acid (formula 20-2)

(formula 20-2)

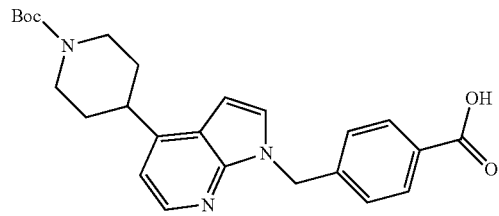

The compound of formula 20-1 (tert-butyl 4-(1-(4-methoxycarbonyl)benzyl-1H-pyrrolo[2,3-b]pyridin-4-yl)piperidine-1-carboxxylate) (0.900 g, 2.002 mmol), and LiOH (0.096 g, 4.004 mmol) were dissolved in methanol (10 mL)/water (5 mL) at room temperature, and the solution was stirred at 60° C. for 4 hours, and then cooled to room temperature. After completion of the reaction, the reaction mixture was concentrated under reduced pressure to remove the solvent. The precipitated solid was filtered, washed with water, and dried to afford the desired compound of formula 20-2 (0.900 g, 103.2%) as a gray solid.

Step 2: Synthesis of tert-butyl 4-(1-(4-((benzyloxy)carbamoyl)benzyl)-1H-pyrrolo[2,3-b]pyridin-4-yl)piperidine-1-carboxylate (formula 20-3)

(formula 20-3)

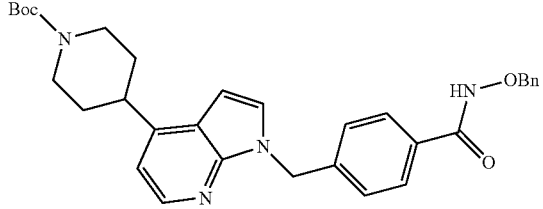

The compound of formula 20-2 (0.900 g, 2.066 mmol) prepared in step 1, o-benzylhydroxylamine (0.509 g, 4.133 mmol), EDC (0.792 g, 4.133 mmol), HOBt (0.558 g, 4.133 mmol) and DIPEA (1.335 g, 10.332 mmol) were dissolved in methylene chloride (30 mL) at room temperature, and the solution was stirred at the same temperature for 1 hour. A saturated aqueous solution of sodium hydrogen carbonate was added to the reaction mixture, followed by extraction with methylene chloride. The extract was filtered through a plastic filter to remove solid residue and the aqueous layer, and then concentrated under reduced pressure. The concentrate was purified by column chromatography (SiO₂, 12 g cartridge; ethyl acetate/hexane=from 5% to 60%) to afford the desired compound of formula 20-3 (0.759 g, 67.9%) as a pale yellow solid.

Step 3: Synthesis of N-(benzyloxy)-4-((4-(piperidin-4-yl)-1H-pyrrolo[2,3-b]pyridin-1-yl)methyl)benzamide hydrochloride (formula 20-4)

(formula 20-4)

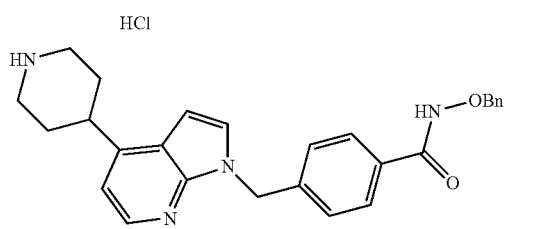

The compound of formula 20-3 (0.759 g, 1.404 mmol) prepared in step 2 was dissolved in methylene chloride (5 mL) at room temperature, and HCl (4.0 M solution, 2.457 mL, 9.827 mmol) was added thereto, followed by stirring at the same temperature for 17 hours. The precipitated solid was filtered, washed with methylene chloride, and dried to afford the desired compound of 20-4 (0.629 g, 93.9%) as a yellow solid.

Step 4: Synthesis of benzyl 2-(4-(1-(4-((benzyloxy)carbamoyl)benzyl)-1H-pyrrolo[2,3-b]pyridin-4-yl)piperidin-1-yl)acetate (formula 20-5)

(formula 20-5)

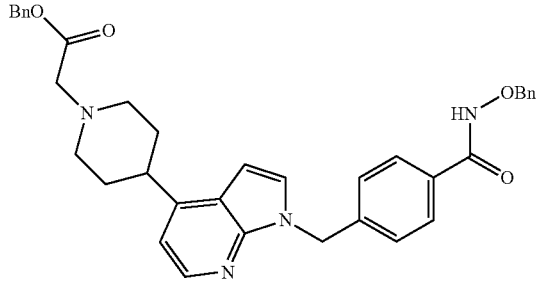

The compound of formula 20-4 (0.200 g, 0.419 mmol) prepared in step 3, and TEA (0.292 mL, 2.096 mmol) were dissolved in methylene chloride (4 mL) at room temperature, and benzyl 2-bromoacetate (0.192 g, 0.839 mmol) was added thereto, followed by stirring at the same temperature for 2 hours. Then, water was added to the reaction mixture, followed by extraction with methylene chloride. The extract was filtered through a plastic filter to remove solid residue and the aqueous layer, and then concentrated under reduced pressure. The concentrate was purified by column chromatography (SiO$_2$, 4 g cartridge; ethyl acetate/hexane=from 5% to 20%) to afford the desired compound of formula 20-5 (0.163 g, 66.0%) as a white solid.

Step 5: Synthesis of 2-(4-(1-(4-(hydroxycarbamoyl)benzyl)-1H-pyrrolo[2,3-b]pyridin-4-yl)piperidin-1-yl)acetic acid (compound 917)

(compound 917)

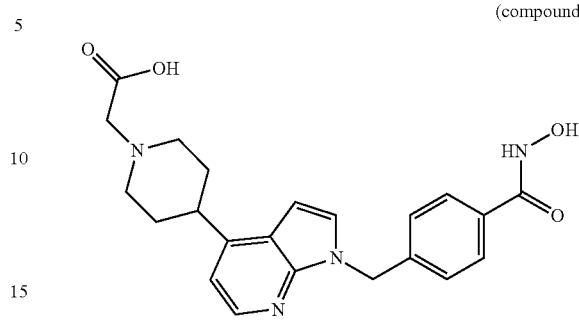

The compound of formula 20-5 (0.163 g, 0.277 mmol) prepared in step 4 was dissolved in methanol (5 mL) at room temperature, and Pd/C (20 mg) was added slowly thereto. Then, the solution was stirred under a hydrogen balloon for 1 hour. The reaction mixture was filtered through a celite pad to remove solids, and the filtrate was concentrated under reduced pressure to remove the solvent. Diethyl ether (5 mL) was added to the concentrate, followed by stirring. The precipitated solid was filtered, washed with diethyl ether, and dried to afford the desired compound 917 (0.068 g, 60.1%) as a white solid.

$^1$H NMR (400 MHz, DMSO-d$_6$) δ 11.18 (brs, 1H), 8.20 (d, 1H, J=4.9 Hz), 7.67 (d, 2H, J=8.3 Hz), 7.64 (d, 1H, J=3.5 Hz), 7.28 (d, 2H, J=8.4 Hz), 6.99 (d, 1H, J=5.0 Hz), 6.72 (d, 1H, J=3.6 Hz), 5.51 (s, 2H), 3.37-3.31 (m, 4H), 3.17-3.14 (m, 1H), 2.78 (t, 2H, J=11.0 Hz), 2.09-2.05 (m, 2H), 1.89 (d, 2H, J=12.1 Hz); MS (ESI) m/z 409.3 (M$^+$+H).

Example 129

Synthesis of Compound 927

Step 1: Synthesis of benzyl 3-(4-(1-(4-((benzyloxy)carbamoyl)benzyl)-1H-pyrrolo[2,3-b]pyridin-4-yl)piperidin-1-yl)propanoate (formula 20-5)

(formula 20-5)

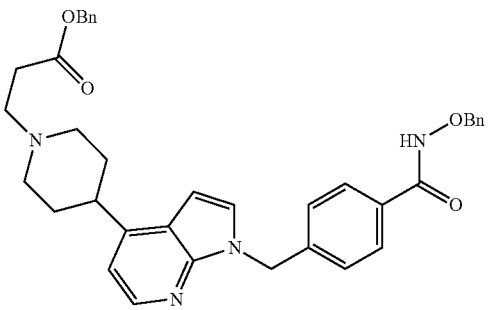

The compound of formula 20-4 (N-(benzyloxy)-4-((4-piperidin-4-yl)-1H-pyrrolo[2,3-b]pyridin-4-yl)methyl)benzamide hydrochloride) (0.100 g, 0.210 mmol), and TEA (0.146 mL, 1.048 mmol) were dissolved in methylene chloride (5 mL). The solution was stirred at room temperature for 10 minutes, and benzyl acrylate (0.041 g, 0.252 mmol) was added thereto, followed by stirring at the same temperature for 2 hours. Water was added to the reaction mixture, followed by extraction with methylene chloride. The extract was filtered through a plastic filter to remove solid residue and the aqueous layer, and then concentrated under reduced pressure. The concentrate was purified by column chromatography (SiO$_2$, 12 g cartridge; ethyl acetate/hexane=from 50% to 80%) to afford the desired compound of formula 20-5 (0.066 g, 52.2%) as a white solid.

Step 2: Synthesis of 3-(4-(1-(4-(hydroxycarbamoyl) benzyl)-1H-pyrrolo[2,3-b]pyridin-4-yl)piperidin-1-yl)propionic acid (compound 927)

(compound 927)

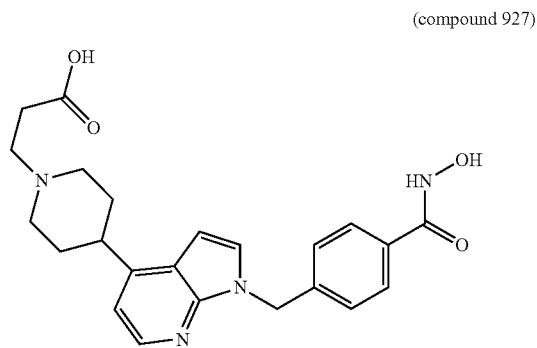 [SMILES: O=C(O)CCN1CCC(c2ccnc3c2ccn3Cc2ccc(C(=O)NO)cc2)CC1]

The compound of formula 20-5 (0.066 g, 0.110 mmol) prepared in step 1 was dissolved in methanol (5 mL) at room temperature, and Pd/C (10 mg) was added slowly thereto. Then, the solution was stirred under a hydrogen balloon for 2 hours. The reaction mixture was filtered through a celite pad to remove solids, and the filtrate was concentrated under reduced pressure to remove the solvent. Methanol (1 mL) and diethyl ether (10 mL) were added to the concentrate, followed by stirring. The precipitated solid was filtered, washed with diethyl ether, and dried to afford the desired compound 927 (0.018 g, 38.9%) as a pale purple solid.

$^1$H NMR (400 MHz, DMSO-d$_6$) δ 11.18 (brs, 1H), 8.18 (d, 1H, J=4.9 Hz), 7.67 (d, 2H, J=8.0 Hz), 7.61 (d, 1H, J=3.5 Hz), 7.28 (d, 2H, J=8.1 Hz), 6.99 (d, 1H, J=4.9 Hz), 6.63 (d, 1H, J=3.5 Hz), 3.06 (d, 2H, J=11.5 Hz), 3.01-2.95 (m, 1H), 2.67 (t, 2H, J=6.9 Hz), 2.41 (t, 2H, J=6.9 Hz), 2.43-2.40 (m, 2H), 1.87-1.77 (m, 4H).

Example 130

Synthesis of Compound 930

Step 1: Synthesis of methyl 4-((4-(8-aza-bicyclo [3.2.1]oct-2-en-3-yl)-1H-pyrrolo[2,3-b]pyridin-1-yl) methyl)benzoate hydrochloride (formula 25-2)

(formula 25-2)

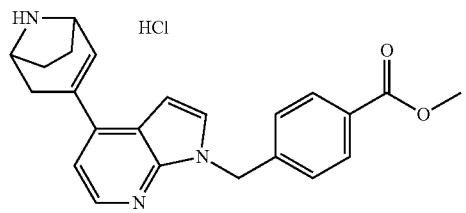

The compound of formula 25-1 (0.550 g, 1.156 mmol), and 4 M HCl (4.0 M solution, 1.446 mL, 5.782 mmol) were dissolved in methylene chloride (10 mL) at room temperature, and the solution was stirred at the same temperature for 12 hours. The reaction mixture was concentrated under reduced pressure, thereby obtaining the desired compound of formula 25-2 (0.470 g, 99.1%) as a white foam solid. The product was used without additional purification.

Step 2: Synthesis of methyl 4-((4-(8-(2-hydroxy-2-methylpropyl)-8-aza-bicyclo[3.2.1]oct-2-en-3-yl)-1H-pyrrolo[2,3-b]pyridin-1-yl)methyl)benzoate (formula 25-3)

(formula 25-3)

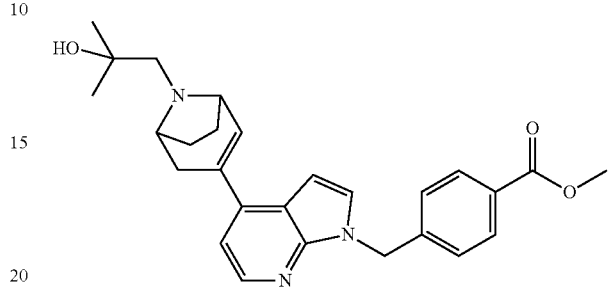

The compound of formula 25-2 (0.200 g, 0.488 mmol) prepared in step 1, 2,2-dimethyloxirane (0.220 mL, 2.440 mmol) and sodium carbonate (0.337 g, 2.440 mmol) were dissolved in ethanol (10 mL), and heated by microwave irradiation at 120° C. for 30 hours, and then cooled to room temperature. After completion of the reaction, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; methanol/methylene chloride=from 5% to 30%) to afford the desired compound of formula 25-3 (0.063 g, 29.0%) as a colorless oil.

Step 3: Synthesis of methyl 4-((4-(8-(2-hydroxy-2-methylpropyl)-8-aza-bicyclo[3.2.1]octan-3-yl)-1H-pyrrolo[2,3-b]pyridin-1-yl)methyl)benzoate (formula 25-4)

(formula 25-4)

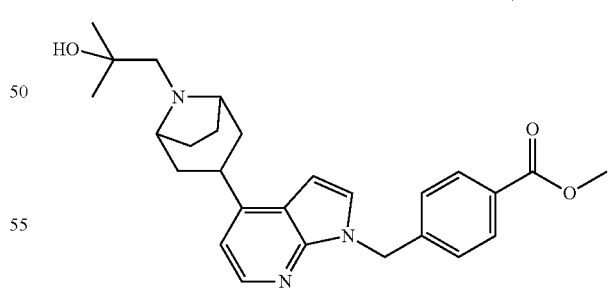

The compound of formula 25-3 (0.240 g, 0.539 mmol) prepared in step 2 was dissolved in methanol (3 mL) at room temperature, Pd/C (10 mg) was added slowly thereto. Then, the solution was stirred under a hydrogen balloon for 12 hours. The reaction solution was concentrated under reduced pressure to remove the solvent, thereby obtaining the desired compound of formula 25-4 (0.200 g, 83.0%) as a colorless oil. The product was used without additional purification.

Step 4: Synthesis of N-hydroxy-4-((4-(8-(2-hydroxy-2-methylpropyl)-8-aza-bicyclo[3.2.1]octan-3-yl)-1H-pyrrolo[2,3-b]pyridin-1-yl)methyl)benzamide (compound 930)

(compound 930)

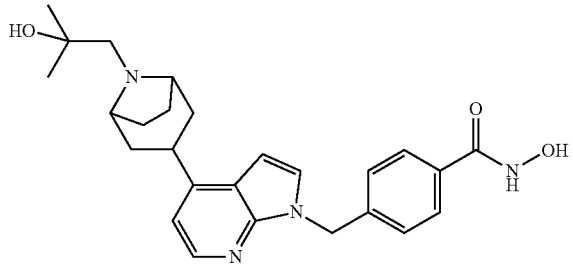

The compound of formula 25-4 (0.096 g, 0.214 mmol) prepared in step 3, NH₂OH (50.0% solution, 0.131 mL, 2.145 mmol) and potassium hydroxide (0.120 g, 2.145 mmol) were dissolved in methanol (3 mL) at room temperature, and the solution was stirred at the same temperature for 1 hour. Then, the reaction solution was concentrated under reduced pressure to remove the solvent, and ethyl acetate (20 mL) and hexane (10 mL) were added to the concentrate, followed by stirring. The precipitated solid was filtered, washed with hexane, and dried to afford the desired compound 930 (0.045 g, 46.8%) as a white solid.

$^1$H NMR (400 MHz, DMSO-$d_6$) δ 8.14 (t, 1H, J=5.3 Hz), 7.64 (m, 2H), 7.38 (t, 1H, J=4.6 Hz), 7.20 (m, 2H), 7.08 (dd, 1H, J=6.8, 5.2 Hz), 6.67 (m, 1H), 5.55 (s, 2H), 3.59 (m, 1H), 3.32 (m, 2H), 2.54 (m, 1H), 2.16 (m, 1H), 2.06-1.99 (m, 2H), 1.86 (m, 1H), 1.74-1.69 (m, 2H), 1.56 (m, 1H); MS (ESI) m/z 449.0 (M⁺+H).

Example 131

Synthesis of Compound 945

Step 1: Synthesis of methyl 4-((4-(1-(2,3-dihydroxy-2-methylpropyl)piperidin-4-yl)-1H-pyrrolo[2,3-b]pyridin-1-yl)methyl)benzoate (formula 4-6)

(formula 4-6)

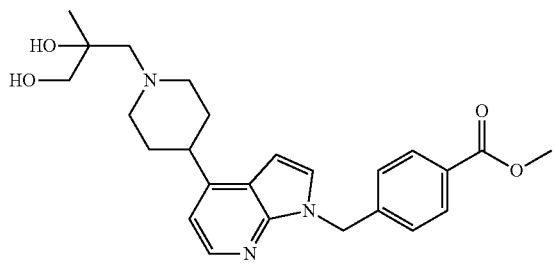

methyl 4((4-(1,2,3,6-tetrahydropyridin-4-yl)-1H-pyrrolo[2,3-b]pyridin-1-yl)methyl)benzoate (0.300 g, 0.777 mmol) as a starting material, (2-methyloxiran-2-yl)methanol (0.205 g, 2.332 mmol) and sodium carbonate (0.322 g, 2.332 mmol) were dissolved in ethanol (3 mL), and heated by microwave irradiation at 120° C. for 20 minutes, and then cooled to room temperature. After completion of the reaction, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO₂, 12 g cartridge; ethyl acetate/hexane=from 0% to 30%) to afford the desired compound of formula 4-6 (0.150 g, 44.1%) as a colorless oil.

Step 2: Synthesis of 4-((4-(1-(2,3-dihydroxy-2-methylpropyl)piperidin-4-yl)-1H-pyrrolo[2,3-b]pyridin-1-yl)methyl)-N-hydroxybenzamide (compound 945)

(compound 945)

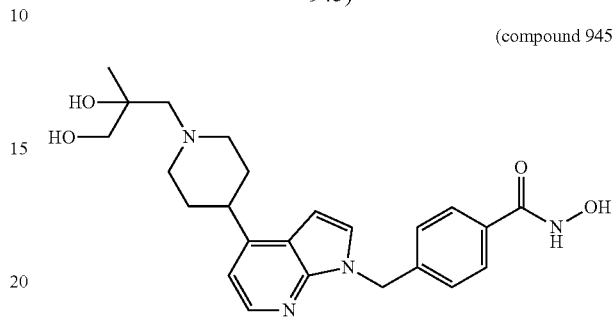

The compound of formula 4-6 (0.160 g, 0.354 mmol) prepared in step 1, and NH₂OH (50.0% solution, 0.217 mL, 3.543 mmol) were dissolved in methanol (3 mL) at room temperature. To the solution, potassium hydroxide (0.199 g, 3.543 mmol) was added, followed by stirring at the same temperature for 1 hour. Then, a saturated aqueous solution of sodium hydrogen carbonate (20 mL) was added to the reaction solution at 0° C., followed by stirring for 10 minutes. After completion of the reaction, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO₂, 12 g cartridge; ethyl acetate/hexane=from 0% to 30%) to afford desired compound 945 (0.085 g, 54.7%) as a white solid.

$^1$H NMR (400 MHz, CD₃OD) δ 8.15 (m, 1H), 7.67 (m, 2H), 7.34 (m, 1H), 7.15 (m, 2H), 7.01 (m, 1H), 6.65 (m, 1H), 5.50 (s, 2H), 3.55-3.49 (m, 2H), 3.33 (m, 1H), 3.13 (m, 1H), 2.99 (m, 1H), 2.59-2.37 (m, 4H), 1.99-1.90 (m, 4H), 1.15 (s, 3H); MS (ESI) m/z 438.9 (M⁺+H).

Example 132

Synthesis of Compound 946

Step 1: Synthesis of methyl 4-((5-(1-(2,3-dihydorxy-2-methylpropyl)piperidin-4-yl)-1H-pyrrolo[2,3-b]pyridin-1-yl)methyl)benzoate (formula 5-6)

(formula 5-6)

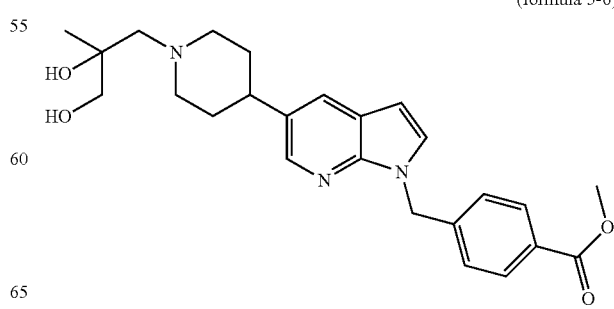

Methyl 4-((5-(piperidin-4-yl)-1H-pyrrolo[2,3-b]pyridin-1-yl)methyl)benzoate (0.300 g, 0.859 mmol) as a starting material, (2-methyloxiran-2-yl)methanol (0.227 g, 2.576 mmol) and sodium carbonate (0.356 g, 2.576 mmol) were dissolved in ethanol (3 mL), and heated by microwave irradiation at 120° C. for minutes, and then cooled to room temperature. After completion of the reaction, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; ethyl acetate/hexane=from 0% to 30%) to afford the desired compound of formula 5-6 (0.200 g, 53.2%) as a colorless oil.

Step 2: Synthesis of 4-((5-(1-(2,3-dihydroxy-2-methylpropyl)piperidin-4-yl)-1H-pyrrolo[2,3-b]pyridin-1-yl)methyl)-N-hydroxybenzamide (compound 946)

(compound 946)

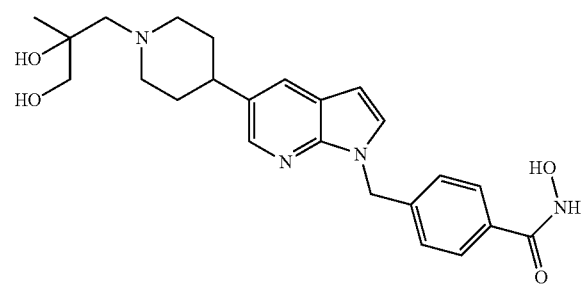

The compound of formula 5-6 (0.230 g, 0.509 mmol) prepared in step 1, and NH$_2$OH (50.0% solution, 0.312 mL, 5.093 mmol) were dissolved in methanol (3 mL) at room temperature. To the solution, potassium hydroxide (0.286 g, 5.093 mmol) was added, followed by stirring at the same temperature for 1 hour. Then, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; ethyl acetate/hexane=from 0% to 30%) to afford the desired compound 946 (0.035 g, 15.7%) as a white solid.

$^1$H NMR (400 MHz, DMSO-d$_6$) δ 8.14 (d, 1H, J=2.04 Hz), 7.33 (d, 1H, J=2.0 Hz), 7.65 (m, 2H), 7.59 (d, 1H, J=3.48 Hz), 7.23 (m, 2H), 6.45 (d, 1H, J=3.40 Hz), 5.48 (s, 2H), 4.70 (brs, 1H), 4.02 (s, 1H), 3.25 (m, 2H), 3.08 (m, 2H), 2.54 (m, 1H), 2.37-2.08 (m, 4H), 1.73 (m, 4H), 1.04 (s, 3H); MS (ESI) m/z 438.9 (M$^+$+H).

Example 133

Synthesis of Compound 956

Step 1: Synthesis of tert-butyl 7-(1-(4-(methoxycarbonyl)benzyl)-1H-pyrrolo[2,3-b]pyridin-5-yl)-2,7-diazaspiro[3.5]nonane-2-carboxylate (formula 23-1)

(formula 23-1)

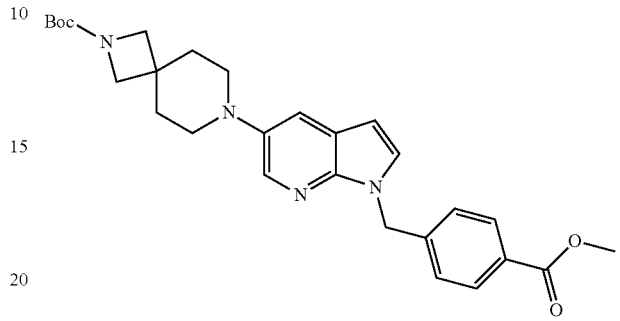

The compound of formula 2-2 (2.000 g, 5.794 mmol), tert-butyl 2,7-diazaspiro[3.5]nonane-2-carboxylate (1.574 g, 6.953 mmol), bis(tri-tert-butylphosphine)Palladium(0) (0.296 g, 0.579 mmol) and sodium tert-butoxide (0.668 g, 6.953 mmol) were dissolved in toluene (30 mL) at 120° C., and the solution was stirred at the same temperature for 5 hours, and then cooled to room temperature. After completion of the reaction, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; ethyl acetate/hexane=from 0% to 30%) to afford the desired compound of formula 23-1 (0.690 g, 24.3%) as a yellow solid.

Step 2: Synthesis of methyl 4-((5-(2,7-diazaspiro[3.5]nonan-7-yl)-1H-pyrrolo[2,3-b]pyridin-1-yl)methyl)benzoate hydrochloride (formula 23-2)

(formula 23-2)

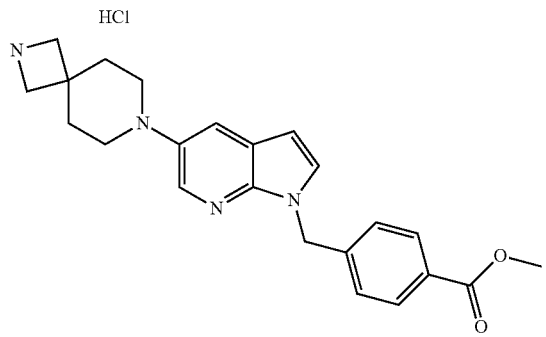

The compound of formula 23-1 (0.690 g, 1.406 mmol) prepared in step 1, and 4M HCl (4.00 M solution in dioxane, 1.406 mL, 5.626 mmol) were dissolved in methylene chloride (10 mL) at room temperature, and the solution was stirred at the same temperature for 5 hours. The reaction mixture was concentrated under reduced pressure to remove the solvent, and the product was used without additional purification (0.450 g, 74.9%, yellow oil).

Step 3: Synthesis of methyl 4-((5-(2-(2-hydroxy-2-methylpropyl)-2,7-diazaspiro[3.5]nonan-7-yl)-1H-pyrrolo[2,3-b]pyridin-1-yl)methyl)benzoate (formula 23-4)

(formula 23-4)

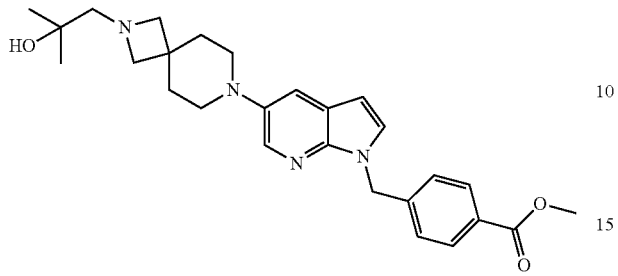

The compound of formula 23-2 (0.150 g, 0.351 mmol) prepared in step 2, 2,2-dimethyloxirane (0.038 mL, 0.422 mmol) and DIPEA (0.123 mL, 0.703 mmol) were dissolved in ethanol (3 mL), and heated by microwave irradiation 110° C. for 20 minutes, and then cooled to room temperature. After completion of the reaction, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; ethyl acetate/hexane=from 0% to 40%) to afford the desired compound of formula 23-4 (0.047 g, 31.4%) as a colorless oil.

Step 4: Synthesis of N-hydroxy-4-((5-(2-(2-hydroxy-2-methylpropyl)-2,7-diazaspiro[3.5]nanan-7-yl)-1H-pyrrolo[2,3-b]pyridin-1-yl)methyl)benzamide (compound 956)

(compound 956)

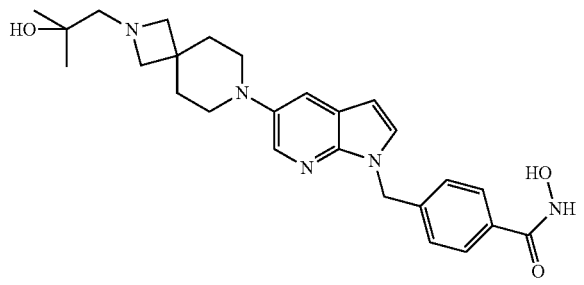

The compound of formula 23-4 (0.024 g, 0.052 mmol) prepared in step 3, hydroxylamine (50.00% solution in H$_2$O, 0.064 mL, 1.042 mmol) and potassium hydroxide (0.029 g, 0.521 mmol) were dissolved in methanol (3 mL) at 0° C., and the solution was stirred at the same temperature for 2 hours. Then, the reaction mixture was concentrated under reduced pressure to remove the solvent, and a saturated aqueous solution of sodium hydrogen carbonate was added to the concentrate, followed by extraction with ethyl acetate. The organic layer was washed with a saturated aqueous solution of sodium chloride, dried with anhydrous magnesium sulfate, filtered, and then concentrated under reduced pressure, thereby obtaining the desired compound 956 (0.014 g, 58.0%) as a white foam solid without additional purification.

$^1$H NMR (400 MHz, CD$_3$OD) δ 8.09 (d, 1H, J=2.5 Hz), 7.69-7.66 (m, 3H), 7.38 (d, 1H, J=3.4 Hz), 7.22 (d, 2H, J=8.4 Hz), 6.49-6.47 (m, 1H), 5.52-5.51 (m, 2H), 3.43-3.42 (m, 4H), 3.08-3.06 (m, 4H), 2.69 (s, 2H), 2.03-2.01 (m, 4H), 1.24 (s, 6H); MS (ESI) m/z 464.0 (M$^+$+H).

Example 134

Synthesis of Compound 957

Step 1: Synthesis of methyl 4-((5-(2-(pyridin-3-ylmethyl)-2,7-diazaspiro[3.5]nonan-7-yl)-1H-pyrrolo[2,3-b]pyridin-1-yl)methyl)benzoate (formula 23-3)

(formula 23-3)

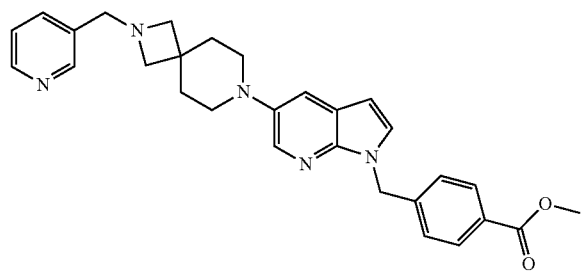

The compound of formula 23-2 (0.150 g, 0.351 mmol), nicotinaldehyde (0.036 mL, 0.386 mmol) and NaBH(OAc)$_3$ (0.149 g, 0.703 mmol) were dissolved in methylene chloride (5 mL) at room temperature, and the solution was stirred at the same temperature for 1 hour. Then, water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; methanol/methylene chloride=from 0% to 10%) to afford the desired compound of formula 23-3 (0.100 g, 59.1%) as a colorless oil.

Step 2: Synthesis of N-hydroxy-4-((5-(2-(pyridin-3-ylmethyl)-2,7-diazaspiro[3.5]nonan-7-yl)-1H-pyrrolo[2,3-b]pyridin-1-yl)methyl)benzamide (compound 957)

(compound 957)

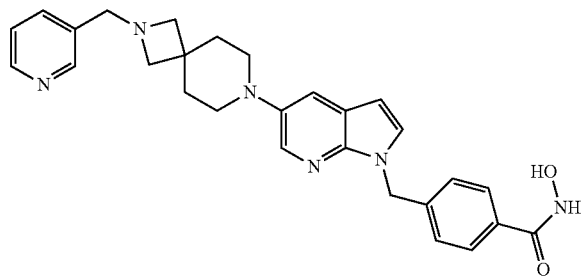

The compound of formula 23-3 (0.100 g, 0.208 mmol) prepared in step 1, hydroxylamine (50.0% solution in H$_2$O, 0.254 mL, 4.153 mmol) and potassium hydroxide (0.117 g, 2.076 mmol) were dissolved in methanol (3 mL), and the solution was stirred at 0° C. for 30 minutes, and then stirred at room temperature for 2 hours. Then, the reaction mixture was concentrated under reduced pressure to remove the solvent, and a saturated aqueous solution of sodium hydrogen carbonate was added to the concentrate, followed by extraction with ethyl acetate. The organic layer was washed with a saturated aqueous solution of sodium chloride, dried with anhydrous magnesium sulfate, filtered, and then concentrated under reduced pressure, thereby obtaining the desired compound 957 (0.040 g, 39.9%) as a white foam solid without additional purification.

$^1$H NMR (400 MHz, CD$_3$OD) δ 8.52 (s, 1H), 8.47 (d, 1H, J=4.6 Hz), 8.07 (s, 1H), 7.83 (d, 1H, J=7.7 Hz), 7.66-7.65 (m, 3H), 7.43 (dd, 1H, J=7.7, 4.8 Hz), 7.36 (d, 1H, J=3.1 Hz), 7.21 (d, 2H, J=7.9 Hz), 6.46 (d, 1H, J=3.1 Hz), 5.51-5.50 (m, 2H), 3.75 (s, 2H), 3.37 (s, 4H), 3.04 (s, 4H), 1.97 (s, 4H); MS (ESI) m/z 483.0 (M$^+$+H).

Example 135

Synthesis of Compound 959

Step 1: Synthesis of methyl 4-((4-(1-(4-methoxybenzyl)piperidin-4-yl)-1H-pyrrolo[2,3-b]pyridin-1-yl)methyl)benzoate (formula 16-2)

(formula 16-2)

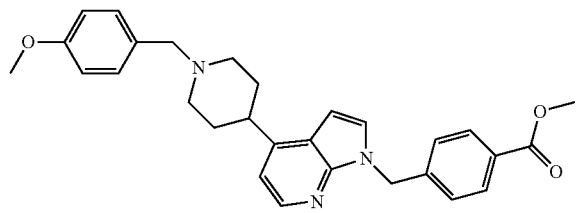

The compound of formula 16-1 (methyl 4-((4-(piperidin-4-yl)-1H-pyrrolo[2,3-b]pyridin-1-yl)methyl)benzoate) (0.300 g, 0.859 mmol), and p-anisaldehyde (0.175 g, 1.288 mmol) were dissolved in methylene chloride (5 mL). The solution was dissolved at room temperature for 10 minutes, and Na(OAc)$_3$BH (0.364 g, 1.717 mmol) was added thereto, followed by stirring at the same temperature for 17 hours. Then, a saturated aqueous solution of sodium hydrogen carbonate was added to the reaction mixture, followed by extraction with methylene chloride. The extract was filtered through a plastic filter to remove solid residue and the aqueous layer, and then concentrated under reduced pressure. The concentrate was purified by column chromatography (SiO$_2$, 12 g cartridge; methanol/methylene chloride=from 0% to 50%) to afford the desired compound of formula 16-2 (0.280 g, 69.5%) as a white solid.

Step 2: Synthesis of N-hydroxy-4-((4-(1-(4-methoxybenzyl)piperidin-4-yl)-1H-pyrrolo[2,3-b]pyridin-1-yl)methyl)benzamide (compound 959)

(compound 959)

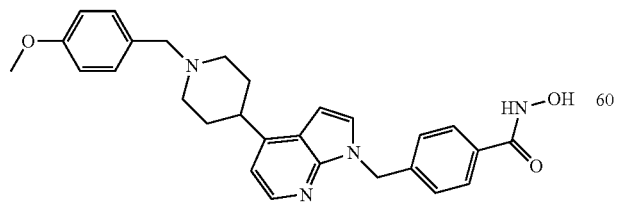

The compound of formula 16-2 (0.100 g, 0.213 mmol) prepared in step 1, hydroxylamine (50.00% solution in water, 0.261 mL, 4.259 mmol), and potassium hydroxide (0.119 g, 2.130 mmol) were dissolved in methanol (2 mL)/tetrahydrofuran (0.5 mL) at room temperature, and the solution was stirred at the same temperature for 30 minutes. Then, the reaction mixture was concentrated under reduced pressure to remove the solvent, and a saturated aqueous solution of sodium hydrogen carbonate (50 mL) was added to the concentrate, followed by stirring. The precipitated solid was filtered, washed with water, and dried to afford the desired compound 959 (0.084 g, 83.8%) as a white solid.

$^1$H NMR (400 MHz, DMSO-d$_6$) δ 8.17 (d, 1H, J=5.0 Hz), 7.66 (d, 2H, J=8.2 Hz), 7.59 (d, 1H, J=3.6 Hz), 7.27-7.23 (m, 4H), 6.99 (d, 1H, J=5.0 Hz), 6.90 (d, 2H, J=8.6 Hz), 6.62 (d, 1H, J=3.6 Hz), 5.49 (s, 2H), 3.74 (s, 3H), 3.45 (s, 2H), 2.94 (d, 3H, J=11.2 Hz), 2.12-2.07 (m, 2H), 1.81-1.77 (m, 4H); MS (ESI) m/z 471.0 (M$^+$+H).

Example 136

Synthesis of Compound 966

Step 1: Synthesis of methyl 4-((4-(1-(pyrimidin-2-ylmethyl)piperidin-4-yl)-1H-pyrrolo[2,3-b]pyridin-1-yl)methyl)benzoate (formula 16-2)

(formula 16-2)

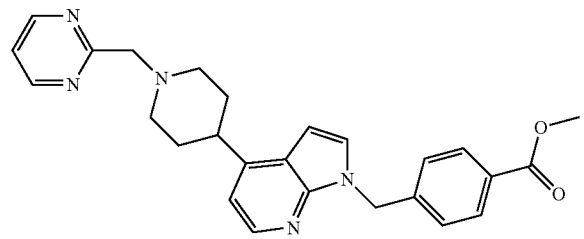

The compound of formula 16-1 (methyl 4-((4-(piperidin-4-yl)-1H-pyrrolo[2,3-b]pyridin-1-yl)methyl)benzoate) (0.500 g, 1.431 mmol), 2-(chloromethyl)pyrimidine hydrochloride (0.260 g, 1.574 mmol), and DIPEA (0.555 g, 4.293 mmol) were dissolved in acetonitrile (10 mL) at room temperature, and the solution was stirred at the same temperature for 17 hours. Then, the reaction mixture was concentrated under reduced pressure to remove the solvent, and the concentrate was purified by column chromatography (SiO$_2$, 12 g cartridge; methanol/methylene chloride=from 0% to 10%) to afford the desired compound of formula 16-2 (0.365 g, 57.8%) as a brown oil.

Step 2: Synthesis of N-hydroxy-4-((4-(1-(pyrimidin-2-ylmethyl)piperidin-4-yl)-1H-pyrrolo[2,3-b]pyridin-1-yl)methyl)benzamide (compound 966)

(compound 966)

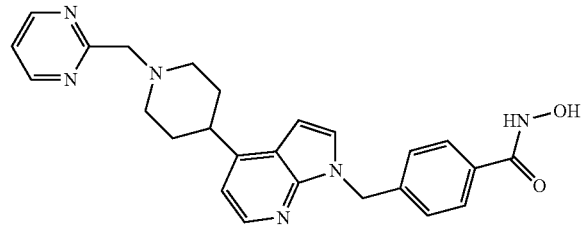

The compound of formula 16-2 (0.100 g, 0.226 mmol) prepared in step 1, hydroxylamine (50.00% solution in water, 0.277 mL, 4.530 mmol) and potassium hydroxide (0.127 g, 2.265 mmol) were dissolved in methanol (2 mL) at room temperature, and the solution was stirred at the same temperature for 30 minutes. Then, the reaction mixture was concentrated under reduced pressure to remove the solvent, and a saturated aqueous solution of sodium hydrogen carbonate was added to the concentrate, followed by extraction with methylene chloride. The extract was filtered through a plastic filter to remove solid residue and the aqueous layer, and then concentrated under reduced pressure, thereby obtaining the desired compound 966 (0.039 g, 38.9%) as a pale orange solid without additional purification.

$^1$H NMR (400 MHz, DMSO-$d_6$) δ 8.77 (d, 2H, J=4.8 Hz), 8.16 (d, 1H, J=5.0 Hz), 7.64 (d, 2H, J=8.0 Hz), 7.52 (d, 1H, J=3.5 Hz), 7.37 (t, 1H, J=5.0 Hz), 7.22 (d, 2H, J=8.0 Hz), 6.95 (d, 1H, J=4.9 Hz), 6.62 (d, 1H, J=3.5 Hz), 3.77 (s, 2H), 3.03 (d, 2H, J=11.3 Hz), 2.93-2.89 (m, 1H), 2.31 (t, 2H, J=10.1 Hz), 1.88-1.73 (m, 4H); MS (ESI) m/z 443.0 (M$^+$+H).

Example 137

Synthesis of Compound 984

Step 1: Synthesis of methyl 4-((4-(1-(2-(4-methylpiperazin-1-yl)benzyl)piperidin-4-yl)-1H-pyrrolo[2,3-b]pyridin-1-yl)methyl)benzoate (formula 16-4)

(formula 16-4)

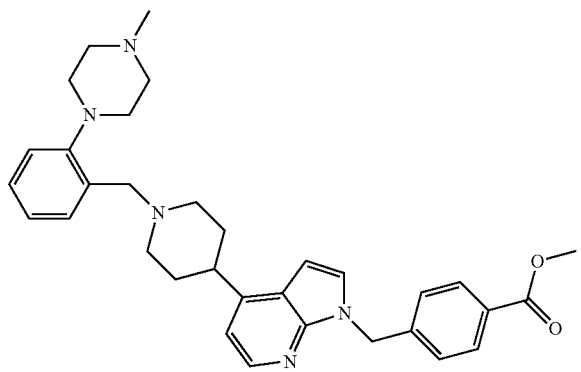

The compound of formula 16-3 (methyl 4-((4-piperidin-4-yl)-1H-pyrrolo[2,3-b]pyridin-1-yl)methyl)benzoate) (0.250 g, 0.715 mmol), and 2-(4-methylpiperazin-1-yl)benzaldehyde (0.219 g, 1.073 mmol) were dissolved in methylene chloride (5 mL). The solution was stirred at room temperature for 10 minutes, and Na(OAc)$_3$BH (0.303 g, 1.431 mmol) was added thereto, followed by stirring at the same temperature for 17 hours. Then, a saturated aqueous solution of sodium hydrogen carbonate was added to the reaction mixture, followed by extraction with methylene chloride. The extract was filtered through a plastic filter to remove solid residue and the aqueous layer, and then concentrated under reduced pressure. The concentrate was purified by column chromatography (SiO$_2$, 12 g cartridge; methanol/methylene chloride=from 0% to 10%) to afford the desired compound of formula 16-4 (0.280 g, 72.8%) as a pale yellow solid.

Step 2: Synthesis of N-hydroxy-4-((4-(1-(2-(4-methylpiperazin-1-yl)benzyl)piperidin-4-yl)-1H-pyrrolo[2,3-b]pyridin-1-yl)methyl)benzamide (compound 984)

(compound 984)

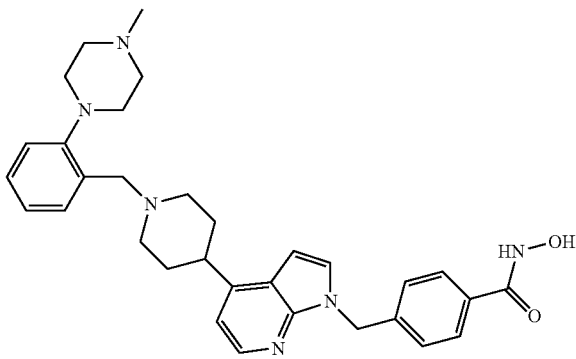

The compound of formula 16-4 (0.140 g, 0.260 mmol) prepared in step 1, hydroxylamine (50.00% solution in water, 0.319 mL, 5.207 mmol) and potassium hydroxide (0.146 g, 2.604 mmol) were dissolved in methanol (3 mL) at room temperature, and the solution was stirred at the same temperature for 30 minutes. Then, the reaction mixture was concentrated under reduced pressure to remove the solvent, and a saturated aqueous solution of sodium hydrogen carbonate (50 mL) was added to the concentrate, followed by stirring. The precipitated solid was filtered, washed with water, and dried to afford the desired compound 984 (0.071 g, 50.6%) as a white solid.

$^1$H NMR (400 MHz, CD$_3$OD) δ 8.16 (d, 1H, J=5.1 Hz), 7.67 (d, 2H, J=8.3 Hz), 7.47 (dd, 1H, J=7.6, 1.4 Hz), 7.39 (d, 1H, J=3.6 Hz), 7.29-7.24 (m, 1H), 7.23-7.18 (m, 3H), 7.11 (td, 1H, J=7.4, 1.3 Hz), 7.03 (d, 1H, J=5.1 Hz), 6.70 (d, 1H, J=3.6 Hz), 5.54 (s, 2H), 3.71 (s, 2H), 3.12 (d, 1H, J=11.8 Hz), 3.03-3.01 (m, 5H), 2.67 (brs, 4H), 2.38 (s, 3H), 2.33-2.30 (m, 2H), 1.97-1.87 (m, 4H); MS (ESI) m/z 539.0 (M$^+$+H).

Example 138

Synthesis of Compound 985

Step 1: Synthesis of methyl 4-((4-(1-(3-formylbenzyl)piperidin-4-yl)-1H-pyrrolo[2,3-b]pyridin-1-yl)methyl)benzoate (formula 16-3)

(formula 16-3)

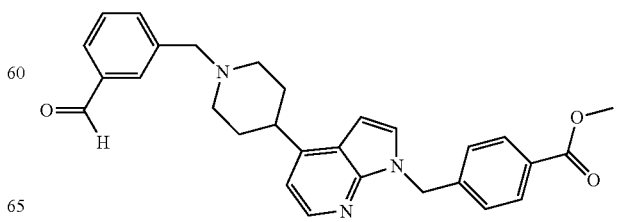

The compound of formula 16-1 (methyl 4-((4-(piperdin-4-yl)-1H-pyrrolo[2,3-b]pyridin-1-yl)methyl)benzoate) (0.500 g, 1.296 mmol), 3-(bromomethyl)benzaldehyde (0.284 g, 1.425 mmol) and DIPEA (0.502 g, 3.887 mmol) were dissolved in acetonitrile (8 mL) at room temperature, and the solution was stirred at the same temperature for 17 hours. Then, the reaction mixture was concentrated under reduced pressure to remove the solvent, and the concentrate was purified by column chromatography (SiO$_2$, 24 g cartridge; ethyl acetate/hexane=from 40% to 90%) to afford the desired compound of formula 16-3 (0.391 g, 64.5%) as a yellow oil.

Step 2: Synthesis of methyl 4-((4-(1-(3-(morpholinomethyl)benzyl)piperidin-4-yl)-1H-pyrrolo[2,3-b]pyridin-1-yl)methyl)benzoate (formula 16-4)

(formula 16-4)

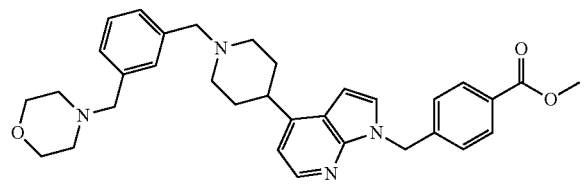

The compound of formula 16-3 (0.200 g, 0.428 mmol) prepared in step 1, and morpholine (0.056 mL, 0.642 mmol) were dissolved in methylene chloride (8 mL). The solution was stirred at room temperature for 10 minutes, and Na(OAc)$_3$BH (0.181 g, 0.856 mmol) was added thereto, followed by stirred at the same temperature for 17 hours. Then, a saturated aqueous solution of sodium hydrogen carbonate was added to the reaction mixture, followed by extraction with methylene chloride. The extract was filtered through a plastic filter to remove solid residue and the aqueous layer, and then concentrated under reduced pressure. The concentrate was purified by column chromatography (SiO$_2$, 4 g cartridge; methanol/methylene chloride=from 0% to 5%) to afford the desired compound of formula 16-4 (0.167 g, 72.5%) as a light yellow oil.

Step 3: Synthesis of N-hydroxy-4-((4-(1-(3-(morpholinomethyl)benzyl)piperidin-4-yl)-1H-pyrrolo[2,3-b]pyridin-1-yl)methyl)benzamide (compound 985)

(compound 985)

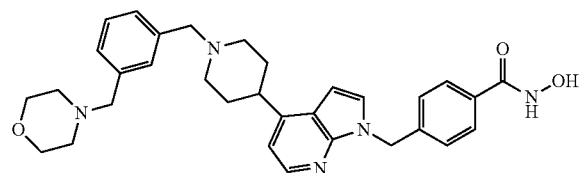

The compound of formula 16-4 (0.070 g, 0.130 mmol) prepared in step 2, hydroxylamine (50.0% solution in water, 0.159 mL, 2.599 mmol) and potassium hydroxide (0.073 g, 1.299 mmol) were dissolved in methanol (3 mL) at room temperature, and the solution was stirred at the same temperature for 30 minutes. Then, the reaction mixture was concentrated under reduced pressure to remove the solvent, and a saturated aqueous solution of sodium hydrogen carbonate was added to the concentrate, followed by extraction with methylene chloride. The extract was filtered through a plastic filter to remove solid residue and the aqueous layer, and then concentrated under reduced pressure. The concentrate was crystallized from diethyl ether (10 mL) at room temperature and filtered, and the obtained solid was washed with diethyl ether and dried to afford the desired compound 985 (0.052 g, 74.1%) as a white solid.

$^1$H NMR (400 MHz, DMSO-d$_6$) δ 11.11 (brs, 1H), 9.00 (brs, 1H), 8.18 (d, 1H, J=5.0 Hz), 7.66 (d, 2H, J=8.3 Hz), 7.60 (d, 1H, J=3.6 Hz), 7.31-7.18 (m, 6H), 7.00 (d, 1H, J=5.0 Hz), 6.62 (d, 1H, J=3.5 Hz), 5.49 (s, 2H), 3.57 (t, 4H, J=4.5 Hz), 3.52 (s, 2H), 3.46 (s, 2H), 2.95 (d, 3H, J=11.4 Hz), 2.34 (brs, 4H), 2.14-2.10 (m, 2H), 1.83-1.78 (m, 4H); MS (ESI) m/z 540.0 (M$^+$+H).

Example 139

Synthesis of Compound 986

Step 1: Synthesis of methyl 4-((4-(1-(3-((4-methylpiperazin-1-yl)methyl)benzyl)piperidin-4-yl)-1H-pyrrolo[2,3-b]pyridin-1-yl)methyl)benzoate (formula 16-4)

(formula 16-4)

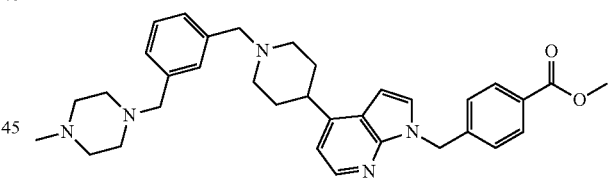

The compound of formula 16-3 (methyl 4-((4-(1-(3-formylbenzyl)piperidin-4-yl)-1H-pyrrolo[2,3-b]pyridin-1-yl)methyl)benzoate) (0.200 g, 0.428 mmol), and N-methylpiperazine (0.071 mL, 0.642 mmol) were dissolved in methylene chloride (8 mL). The solution was stirred at room temperature for 10 minutes, and Na(OAc)$_3$BH (0.181 g, 0.856 mmol) was added thereto, followed by stirring at the same temperature for 17 hours. Then, a saturated aqueous solution of sodium hydrogen carbonate was added to the reaction mixture, followed by extraction with methylene chloride. The extract was filtered through a plastic filter to remove solid residue and the aqueous layer, and then concentrated under reduced pressure. The concentrate was purified by column chromatography (SiO$_2$, 4 g cartridge; methanol/methylene chloride=from 0% to 10%) to afford the desired compound of formula 16-4 (0.230 g, 97.5%) as a pale yellow oil.

Step 2: Synthesis of N-hydroxy-4-((4-(1-(3-((4-methylpiperazin-1-yl)methyl)benzyl)piperidin-4-yl)-1H-pyrrolo[2,3-b]pyridin-1-yl)methyl)benzamide (compound 986)

(compound 986)

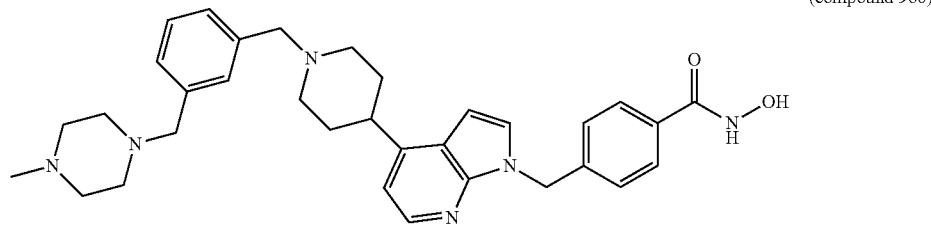

The compound of formula 16-4 (0.135 g, 0.264 mmol) prepared in step 1, hydroxylamine (50.00% solution in water, 0.323 mL, 5.276 mmol) and potassium hydroxide (0.148 g, 2.638 mmol) were dissolved in methanol (3 mL) at room temperature, and the solution was stirred at the same temperature for 30 minutes. Then, the reaction mixture was concentrated under reduced pressure to remove the solvent, and a saturated aqueous solution of sodium hydrogen carbonate was added to the concentrate, followed by extraction with methylene chloride. The extract was filtered through a plastic filter to remove solid residue and the aqueous layer, and then concentrated under reduced pressure. The concentrate was crystallized from diethyl ether (10 mL) at room temperature and filtered, and the obtained solid was washed with diethyl ether and dried to afford the desired compound 986 (0.022 g, 16.3%) as a pale orange solid.

$^1$H NMR (400 MHz, DMSO-$d_6$) δ 8.15 (d, 1H, J=5.0 Hz), 7.64 (d, 2H, J=8.2 Hz), 7.50 (d, 1H, J=3.6 Hz), 7.27-7.19 (m, 5H), 7.16 (d, 1H, J=7.3 Hz), 6.96 (d, 1H, J=5.0 Hz), 6.61 (d, 1H, J=3.6 Hz), 5.47 (s, 2H), 3.51 (s, 2H), 3.44 (s, 2H), 2.95 (d, 3H, J=11.9 Hz), 2.33 (brs, 8H), 2.14-2.12 (m, 5H), 1.85-1.83 (m, 4H); MS (ESI) m/z 553.0 (M$^+$+H).

Example 140

Synthesis of Compound 987

Step 1: Synthesis of methyl 4-((4-(1-(4-formylbenzyl)piperidin-4-yl)-1H-pyrrolo[2,3-b]pyridin-1-yl)methyl)benzoate (formula 16-3)

(formula 16-3)

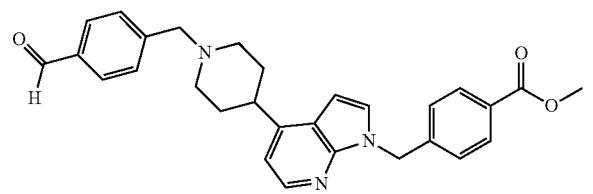

The compound of formula 16-1 (methyl 4-((4-(piperidin-4-yl)-1H-pyrrolo[2,3-b]pyridin-1-yl)methyl)benzoate) (0.500 g, 1.296 mmol), 4-(bromomethyl)benzaldehyde (0.284 g, 1.425 mmol) and DIPEA (0.502 g, 3.887 mmol) were dissolved in acetonitrile (8 mL) at room temperature, and the solution was stirred at the same temperature for 17 hours. Then, the reaction mixture was concentrated under reduced pressure to remove the solvent, and the concentrate was purified by column chromatography (SiO$_2$, 24 g cartridge; ethyl acetate/hexane=from 30% to 70%) to afford the desired compound of formula 16-3 (0.448 g, 73.9%) as a yellow oil.

Step 2: Synthesis of methyl 4-((4-(1-(4-(morpholinomethyl)benzyl)piperidin-4-yl)-1H-pyrrolo[2,3-b]pyridin-1-yl)methyl)benzoate (formula 16-4)

(formula 16-4)

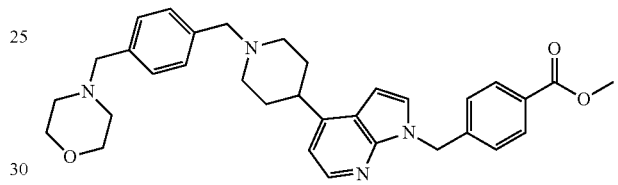

The compound of formula 16-3 (0.200 g, 0.428 mmol) prepared in step 1, and morpholine (0.056 mL, 0.642 mmol) were dissolved in methylene chloride (8 mL). The solution was stirred at room temperature for 10 minutes, and Na(OAc)$_3$BH (0.181 g, 0.856 mmol) was added thereto, followed by stirring at the same temperature for 17 hours. Then, a saturated aqueous solution of sodium hydrogen carbonate was added to the reaction mixture, followed by extraction with methylene chloride. The extract was filtered through a plastic filter to remove solid residue and the aqueous layer, and then concentrated under reduced pressure. The concentrate was purified by column chromatography (SiO$_2$, 4 g cartridge; methanol/methylene chloride=from 0% to 5%) to afford the desired compound of formula 16-4 (0.189 g, 82.0%) as a pale yellow oil.

Step 3: Synthesis of N-hydroxy-4-((4-(1-(4-(morpholinomethyl)benzyl)piperidin-4-yl)-1H-pyrrolo[2,3-b]pyridin-1-yl)methyl)benzamide (compound 987)

(compound 987)

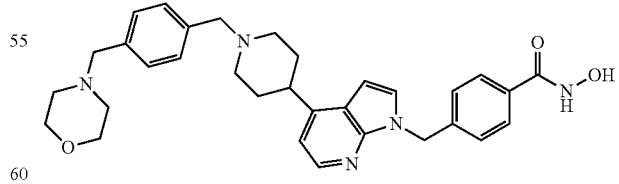

The compound of formula 16-4 (0.080 g, 0.149 mmol) prepared in step 2, hydroxylamine (50.0% solution in water, 0.182 mL, 2.970 mmol) and potassium hydroxide (0.083 g, 1.485 mmol) were dissolved in methanol (3 mL) at room temperature, and the solution was stirred at the same temperature for 30 minutes. Then, the reaction mixture was concentrated under reduced pressure to remove the solvent, and a saturated aqueous solution of sodium hydrogen carbonate (15 mL) was added to the concentrate, followed by stirring. The precipitated solid was filtered, washed with water, and dried to afford the desired compound 987 (0.047 g, 58.6%) as a white solid.

$^1$H NMR (400 MHz, DMSO-$d_6$) δ 11.16 (brs, 1H), 8.97 (brs, 1H), 8.18 (d, 1H, J=4.9 Hz), 7.66 (d, 2H, J=8.2 Hz), 7.60 (d, 1H, J=3.6 Hz), 7.31-7.25 (m, 6H), 6.99 (d, 1H, J=5.0 Hz), 6.62 (d, 1H, J=3.6 Hz), 5.49 (s, 2H), 3.57 (t, 4H, J=4.5 Hz), 3.51 (s, 2H), 3.44 (s, 2H), 2.95 (d, 3H, J=10.6 Hz), 2.34-2.33 (m, 4H), 2.13-2.09 (m, 2H), 1.82-1.81 (m, 4H); MS (ESI) m/z 540.0 (M$^+$+H).

Example 141

Synthesis of Compound 988

Step 1: Synthesis of methyl 4-((4-(1-(4-((4-methyl-piperazin-1-yl)methyl)benzyl)piperidin-4-yl)-1H-pyrrolo[2,3-b]pyridin-1-yl)methyl)benzoate (formula 16-4)

(formula 16-4)

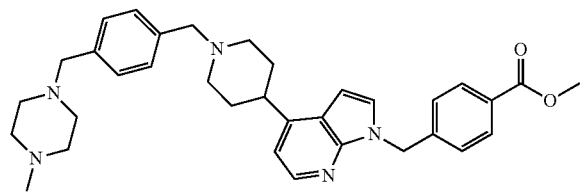

The compound of formula 16-3 (methyl 4-((4-(1-(4-formylbenzyl)piperidin-4-yl)-1H-pyrrolo[2,3-b]pyridin-1-yl) methyl)benzoate) (0.200 g, 0.428 mmol), and N-methylpiperazine (0.064 g, 0.642 mmol) were dissolved in methylene chloride (8 mL). The solution was stirred at room temperature for 10 minutes, and Na(OAc)$_3$BH (0.181 g, 0.856 mmol) was added thereto, followed by stirring at the same temperature for 17 hours. Then, a saturated aqueous solution of sodium hydrogen carbonate was added to the reaction mixture, followed by extraction with methylene chloride. The extract was filtered through a plastic filter to remove solid residue and the aqueous layer, and then concentrated under reduced pressure. The concentrate was purified by column chromatography (SiO$_2$, 4 g cartridge; methanol/methylene chloride=from 0% to 5%) to afford the desired compound of formula 16-4 (0.192 g, 81.4%) as a pale yellow oil.

Step 2: Synthesis of N-hydroxy-4-((4-(1-(4-((4-methylpiperazin-1-yl)methyl)benzyl)piperidin-4-yl)-1H-pyrrolo[2,3-b]pyridin-1-yl)methyl)benzamide (compound 988)

(compound 988)

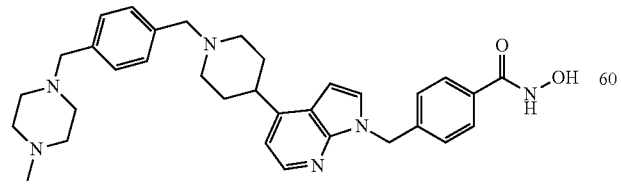

The compound of formula 16-4 (0.090 g, 0.163 mmol) prepared in step 1, hydroxylamine (50.00% solution in water, 0.200 mL, 3.263 mmol) and potassium hydroxide (0.092 g, 1.631 mmol) were dissolved in methanol (3 mL) at room temperature, and the solution was stirred at the same temperature for 30 minutes. Then, the reaction mixture was concentrated under reduced pressure to remove the solvent, and a saturated aqueous solution of sodium hydrogen carbonate (15 mL) was added to the concentrate, followed by stirring. The precipitated solid was filtered, washed with water, and dried to yield desired compound 988 (0.070 g, 77.6%) as a white solid.

$^1$H NMR (400 MHz, DMSO-$d_6$) δ 11.15 (brs, 1H), 9.05 (brs, $^1$H), 8.17 (d, 1H, J=5.0 Hz), 7.66 (d, 2H, J=8.3 Hz), 7.60 (d, 1H, J=3.6 Hz), 7.29-7.23 (m, 6H), 6.99 (d, 1H, J=5.0 Hz), 6.63 (d, 1H, J=3.5 Hz), 5.50 (s, 2H), 3.50 (s, 2H), 3.42 (s, 2H), 2.95 (d, 3H, J=11.2 Hz), 2.34-2.33 (m, 8H), 2.14-2.12 (m, 5H), 1.82-1.81 (m, 4H); MS (ESI) m/z 553.0 (M$^+$+H).

Example 142

Synthesis of Compound 990

Step 1: Synthesis of methyl 4-((4-((3S,5R)-4-benzyl-3,5-dimethylpiperazin-1-yl)-1H-pyrrolo[2,3-b]pyridin-1-yl)methyl)benzoate (formula 26-2)

(formula 26-2)

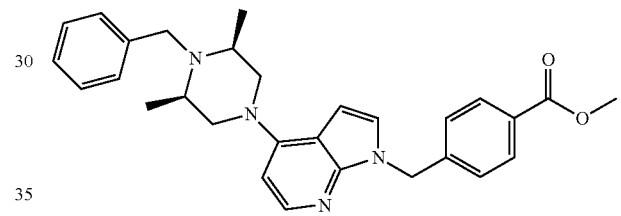

The compound of formula 26-1 (0.236 g, 0.624 mmol), benzyl bromide (0.082 mL, 0.686 mmol) and cesium carbonate (0.305 g, 0.935 mmol) were dissolved in acetonitrile (20 mL) at room temperature, and the solution was stirred at the same temperature for 12 hours. Then, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; methanol/methylene chloride=from 0% to 10%) to afford the desired compound of formula 26-2 (0.120 g, 41.1%) as a colorless oil.

Step 2: Synthesis of 4-((4-((3S,5R)-4-benzyl-3,5-dimethylpiperazin-1-yl)-1H-pyrrolo[2,3-b]pyridin-1-yl)methyl)-N-hydroxybenzamide (compound 990)

(compound 990)

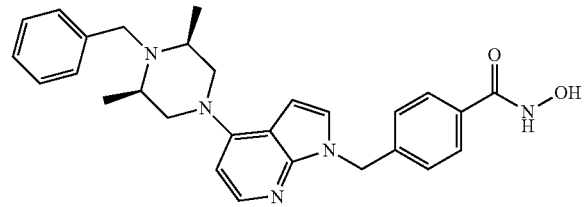

The compound of formula 26-2 (0.054 g, 0.115 mmol) prepared in step 1, hydroxylamine (50.00% solution in H$_2$O, 0.141 mL, 2.305 mmol) and potassium hydroxide (0.065 g, 1.152 mmol) were dissolved in methanol (2 mL), and the solution was stirred at 0° C. for 30 minutes, and then stirred at room temperature for 2 hours. Then, the reaction mixture was concentrated under reduced pressure to remove the solvent, and a saturated aqueous solution of sodium hydrogen carbonate was added to the concentrate, followed by extraction with ethyl acetate. The organic layer was washed with a saturated aqueous solution of sodium chloride, dried with anhydrous magnesium sulfate, filtered, and then concentrated under reduced pressure, thereby obtaining the desired compound 990 (0.028 g, 51.7%) as a colorless oil without additional purification.

$^1$H NMR (400 MHz, CD$_3$OD) δ 7.97 (d, 1H, J=5.4 Hz), 7.63 (d, 2H, J=8.2 Hz), 7.41-7.37 (m, 3H), 7.31 (t, 2H, J=7.6 Hz), 7.20 (t, 1H, J=7.2 Hz), 7.12 (d, 2H, J=8.1 Hz), 6.53 (d, 1H, J=3.6 Hz), 6.45 (d, 1H, J=5.5 Hz), 5.40 (s, 2H), 3.81 (s, 2H), 2.83-2.74 (m, 4H), 1.05 (d, 6H, J=5.4 Hz); MS (ESI) m/z 470.0 (M$^+$+H).

Example 143

Synthesis of Compound 991

Step 1: Synthesis of methyl 4-((6-(1-(2-hydroxy-2-methylpropyl)piperidin-4-yl)-1H-pyrrolo[2,3-b]pyridin-1-yl)methyl)benzoate (formula 3-6)

(formula 3-6)

The compound of formula 3-5 (0.170 g, 0.487 mmol), 2,2-dimethyloxirane (0.053 mL, 0.584 mmol) and DIPEA (0.169 mL, 0.973 mmol) were dissolved in ethanol (2 mL), and heated by microwave irradiation at 120° C. for 20 minutes, and then cooled to room temperature. After completion of the reaction, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; methanol/methylene chloride=from 0% to 10%) to afford the desired compound of formula 3-6 (0.119 g, 58.0%) as a colorless oil.

Step 2: Synthesis of N-hydroxy-4-((6-(1-(2-hydroxy-2-methylpropyl)piperidin-4-yl)-1H-pyrrolo[2,3-b]pyridin-1-yl)methyl)benzamide (compound 991)

(compound 991)

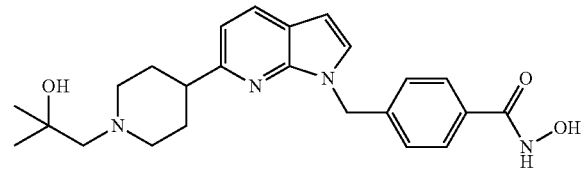

The compound of formula 3-6 (0.119 g, 0.282 mmol) prepared in step 1, hydroxylamine (50.0% solution in H$_2$O, 0.345 mL, 5.646 mmol) and potassium hydroxide (0.158 g, 2.823 mmol) were dissolved in methanol (5 mL), and the solution was stirred at 0° C. for 30 minutes, and then stirred at room temperature for 2 hours. Then, the reaction mixture was concentrated under reduced pressure to remove the solvent, and a saturated aqueous solution of sodium hydrogen carbonate was added to the concentrate, followed by extraction with ethyl acetate. The organic layer was washed with a saturated aqueous solution of sodium chloride, dried with anhydrous magnesium sulfate, filtered, and then concentrated under reduced pressure, thereby obtaining the desired compound 991 (0.080 g, 67.1%) as a colorless oil without additional purification.

$^1$H NMR (400 MHz, CD$_3$OD) δ 7.87 (d, 1H, J=8.0 Hz), 7.67 (d, 2H, J=8.1 Hz), 7.30-7.27 (m, 3H), 7.03 (d, 1H, J=8.0 Hz), 6.46 (d, 1H, J=3.4 Hz), 5.54 (s, 2H), 3.13 (d, 2H, J=11.4 Hz), 2.75-2.74 (m, 1H), 2.42-2.37 (m, 4H), 2.04-2.01 (m, 2H), 1.88-1.85 (m, 2H), 1.23 (s, 6H); MS (ESI) m/z 423.15 (H$^+$+H).

Example 144

Synthesis of Compound 992

Step 1: Synthesis of methyl 4-((6-(1-(pyridin-3-ylmethyl)piperidin-4-yl)-1H-pyrrolo[2,3-b]pyridin-1-yl)methyl)benzoate (formula 3-7)

(formula 3-7)

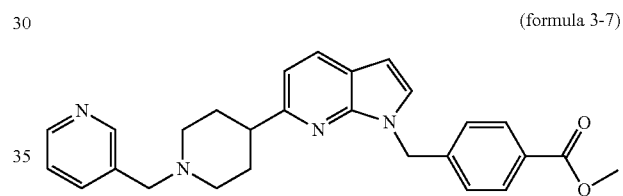

The compound of formula 3-5 (0.190 g, 0.544 mmol), nicotinaldehyde (0.056 mL, 0.598 mmol) and NaBH(OAc)$_3$ (0.230 g, 1.087 mmol) were dissolved in methylene chloride (10 mL) at room temperature, and the solution was stirred at the same temperature for 12 hours. Then, water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; methanol/methylene chloride=from 0% to 10%) to afford the desired compound of formula 3-7 (0.149 g, 62.2%) as a colorless oil.

Step 2: Synthesis of N-hydroxy-4-((6-(1-(pyridin-3-ylmethyl)piperidin-4-yl)-1H-pyrrolo[2,3-b]pyridin-1-yl)methyl)benzamide (compound 992)

(compound 992)

The compound of formula 3-7 (0.149 g, 0.338 mmol) prepared in step 1, hydroxylamine (50.0% solution in H₂O, 0.414 mL, 6.764 mmol) and potassium hydroxide (0.190 g, 3.382 mmol) were dissolved in methanol (2 mL), and the solution was stirred at 0° C. for 30 minutes, and then stirred at room temperature for 2 hours. Then, the reaction mixture was concentrated under reduced pressure to remove the solvent, and a saturated aqueous solution of sodium hydrogen carbonate was added to the concentrate, followed by extraction with ethyl acetate. The organic layer was washed with a saturated aqueous solution of sodium chloride, dried with anhydrous magnesium sulfate, filtered, and then concentrated under reduced pressure, thereby obtaining the desired compound 992 (0.098 g, 65.6%) as a colorless oil without additional purification.

¹H NMR (400 MHz, CD₃OD) δ 8.54 (s, 1H), 8.47 (dd, 1H, J=4.3, 1.9 Hz), 7.90-7.86 (m, 2H), 7.66 (d, 2H, J=8.2 Hz), 7.44 (dd, 1H, J=7.7, 4.9 Hz), 7.32-7.28 (m, 3H), 7.01 (d, 1H, J=8.0 Hz), 6.46 (d, 1H, J=3.5 Hz), 5.53 (s, 2H), 3.62 (s, 2H), 3.00 (d, 2H, J=11.4 Hz), 2.85-2.75 (m, 1H), 2.23-2.18 (m, 2H), 2.00-1.89 (m, 4H); MS (ESI) m/z 441.97 (M⁺+H).

Example 145

Synthesis of Compound 1003

Step 1: Synthesis of methyl 4-((5-((3S,5R)-4-(3-methoxybenzyl)-3,5-dimethylpiperazin-1-yl)-1H-pyrrolo[2,3-b]pyridin-1-yl)methyl)benzoate (formula 14-2)

(formula 14-2)

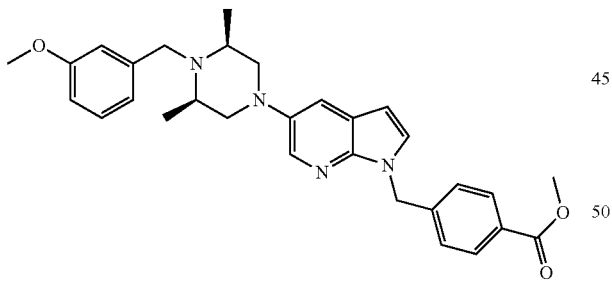

The compound of formula 14-1 (0.200 g, 0.528 mmol), 3-methoxybenzyl bromide (0.081 mL, 0.581 mmol) and cesium carbonate (0.517 g, 1.585 mmol) were dissolved in acetonitrile (5 mL) at room temperature, and the solution was stirred at the same temperature for 16 hours. Then, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO₂, 24 g cartridge; ethyl acetate/hexane=from 0% to 3%) to afford the desired compound of formula 14-2 (0.109 g, 41.4%) as a yellow oil.

Step 2: Synthesis of N-hydroxy-4-((5-((3S,5R)-4-(3-methoxybenzyl)-3,5-dimethylpiperazin-1-yl-1H-pyrrolo[2,3-b]methyl)benzamide (compound 1003)

(compound 1003)

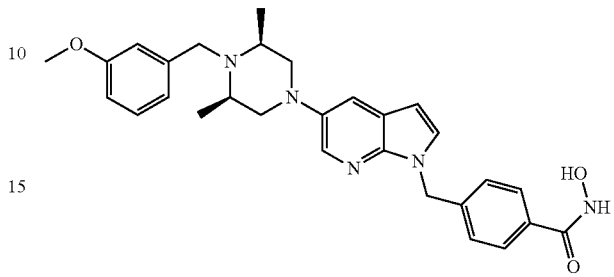

The compound of formula 14-2 (0.101 g, 0.203 mmol) prepared in step 1, and hydroxylamine (50.00% solution in water, 0.124 mL, 2.026 mmol) were dissolved in methanol (2 mL) at 0° C., and potassium hydroxide (0.114 g, 2.026 mmol) was added thereto, followed by stirring at room temperature for 16 hours. Then, a saturated aqueous solution of 1N sodium hydrogen carbonate was added to the reaction mixture, followed by extraction with ethyl acetate. The organic layer was washed with a saturated aqueous solution of sodium hydrogen carbonate, dried with anhydrous magnesium sulfate, filtered, and then concentrated under reduced pressure. The concentrate was purified by column chromatography (Waters, C18; acetonitrile/formic acid (methanoic acid)=from 5% to 50%) to afford the desired compound 1003 (0.042 g, 41.5%) as a white solid.

¹H NMR (400 MHz, CDCl₃) δ 7.96-7.95 (m, 1H), 7.47-7.46 (m, 1H), 7.36-7.34 (m, 2H), 7.24-7.22 (m, 1H), 7.09-7.08 (m, 1H), 6.96-6.90 (m, 4H), 6.80-6.78 (m, 1H), 6.38 (d, 1H, J=3.3 Hz), 5.37 (s, 2H), 3.94-3.93 (m, 2H), 3.80 (s, 3H), 3.25-3.22 (m, 2H), 2.91-2.90 (m, 2H), 2.72-2.69 (m, 2H), 1.18-1.17 (m, 6H); MS (ESI) m/z 500.0 (M⁺+H).

Example 146

Synthesis of Compound 1004

Step 1: Synthesis of methyl 4-((5-((3S,5R)-3,5-dimethyl-4-(pyridin-3-ylmethyl)piperazin-1-yl)-1H-pyrrolo[2,3-b]pyridin-1-yl)benzoate (formula 14-2)

(formula 14-2)

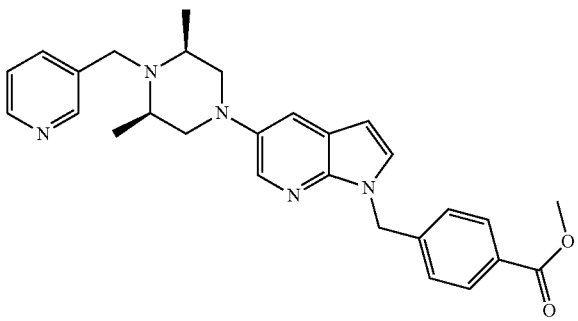

The compound of formula 14-1 (0.200 g, 0.528 mmol), 3-pyridinecarboxaldehyde (0.055 mL, 0.581 mmol) and sodium triacetoxyborohydride (0.224 g, 1.057 mmol) were dissolved in methylene chloride (5 mL) at room temperature, and the solution was stirred at the same temperature for 16 hours. Then, water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO$_2$, 24 g cartridge; methanol/methylene chloride=from 0% to 3%) to afford the desired compound of formula 14-2 (0.191 g, 77.0%) as a yellow oil.

Step 2: Synthesis of 4-((5-((3S,5R)-3,5-dimethyl-4-(pyridin-3-ylmethyl)piperazin-1-yl)-1H-pyrrolo[2,3-b]pyridin-1-yl)methyl)-N-hydroxybenzamide (compound 1004)

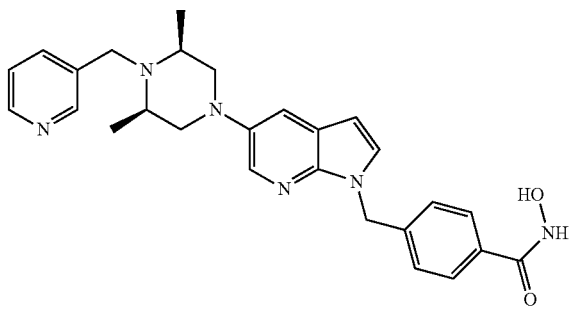

(compound 1004)

The compound of formula 14-2 (0.183 g, 0.390 mmol) prepared in step 1, and hydroxylamine (50.00% solution in water, 0.238 mL, 3.897 mmol) were dissolved in methanol (2 mL). The solution was stirred at 0° C. for 20 minutes, and potassium hydroxide (0.219 g, 3.897 mmol) was added thereto, followed by stirring at room temperature for 16 hours. Then, a saturated aqueous solution of 1N sodium hydrogen carbonate was added to the reaction mixture, followed by extraction with ethyl acetate. The organic layer was washed with a saturated aqueous solution of sodium hydrogen carbonate, dried with anhydrous magnesium sulfate, filtered, and then concentrated under reduced pressure. The concentrate was purified by column chromatography (Waters, C18; acetonitrile/formic acid (methanoic acid)= from 5% to 50%) to afford the desired compound 1004 (0.079 g, 43.0%) as a white solid.

$^1$H NMR (400 MHz, CDCl$_3$) δ 8.64-8.63 (m, 1H), 8.49-8.48 (m, 1H), 8.03-8.02 (m, 1H), 7.76-7.74 (m, 1H), 7.49 (d, 1H, J=2.3 Hz), 7.44 (d, 2H, J=8.0 Hz), 7.28-7.27 (m, 1H), 7.11 (d, 1H, J=3.4 Hz), 6.99 (d, 2H, J=7.9 Hz), 6.40 (d, 1H, J=3.4 Hz), 5.40 (s, 2H), 3.93 (s, 2H), 3.29-3.27 (m, 2H), 2.88-2.87 (m, 2H), 2.67-2.66 (m, 2H), 1.13-1.12 (m, 6H); MS (ESI) m/z 471.0 (M$^+$+H).

Example 147

Synthesis of Compound 1005

Step 1: Synthesis of methyl 4-((5-((3S,5R)-3,5-dimethyl-4-(pyrimidin-2-ylmethyl)piperazin-1-yl)-1H-pyrrolo[2,3-b]pyridin-1-yl)methyl)benzoate (formula 14-2)

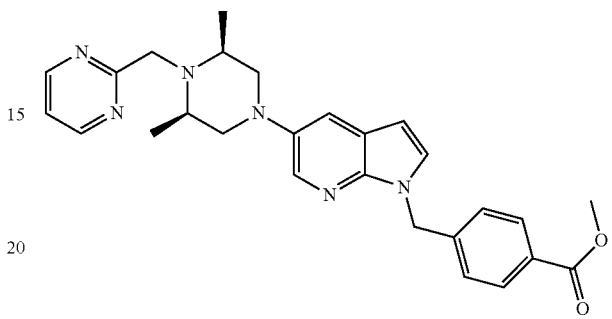

(formula 14-2)

The compound of formula 14-1 (0.200 g, 0.528 mmol), 2-(chloromethyl)pyrimidine hydrochloride (0.096 g, 0.581 mmol) and cesium carbonate (0.517 g, 1.585 mmol) were dissolved in acetonitrile (5 mL), and heated by microwave irradiation at 150° C. for 1.5 hours, and then cooled to room temperature. After completion of the reaction, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 24 g cartridge; methanol/methylene chloride=from 0% to 3%) to afford the desired compound of formula 14-2 (0.099 g, 39.8%) as a yellow oil.

Step 2: Synthesis of 4-((5-((3S,5R)-3,5-dimethyl-4-(pyrimidin-2-ylmethyl)-1-yl)-1H-pyrrolo[2,3-b]pyridin-1-yl)methyl)-N-hydroxybenzamide (compound 1005)

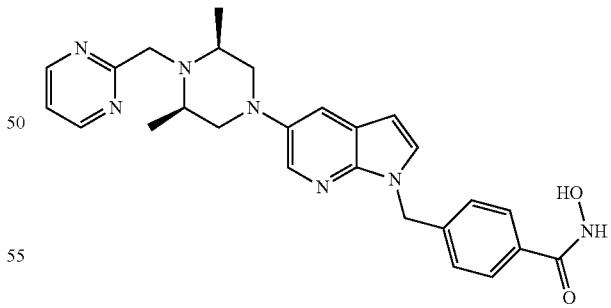

(compound 1005)

The compound of formula 14-2 (0.093 g, 0.198 mmol) prepared in step 1, and hydroxylamine (50.00% solution in water, 0.121 mL, 1.976 mmol) were dissolved in methanol (2 mL). The solution was stirred at 0° C. for 20 minutes, and potassium hydroxide (0.111 g, 1.976 mmol) was added thereto, followed by stirring at room temperature for 16 hours. Then, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (Waters, C18; acetonitrile/formic acid (methanoic acid)=from 5% to 50%) to afford the desired compound 1005 (0.033 g, 35.4%) as an ivory solid.

$^1$H NMR (400 MHz, CDCl$_3$) δ 8.73 (d, 1H, J=4.9 Hz), 7.90-7.89 (m, 1H), 7.49 (d, 1H, J=2.5 Hz), 7.29-7.28 (m, 2H), 7.20 (t, 1H, J=5.0 Hz), 7.14 (d, 1H, J=3.4 Hz), 6.93 (d, 2H, J=8.2 Hz), 6.41 (d, 1H, J=3.4 Hz), 5.42 (s, 2H), 4.32 (s, 2H), 3.26-3.23 (m, 2H), 3.18-3.16 (m, 2H), 2.72-2.70 (m, 2H), 1.31-1.30 (m, 6H); MS (ESI) m/z 472.0 (M$^+$+H).

Example 148

Synthesis of Compound 1014

Step 1: Synthesis of methyl 4-((4-(1-(pyridin-3-ylmethyl)piperidin-4-yl)-1H-pyrrolo[2,3-b]pyridin-1-yl)methyl)benzoate (formula 16-2)

(formula 16-2)

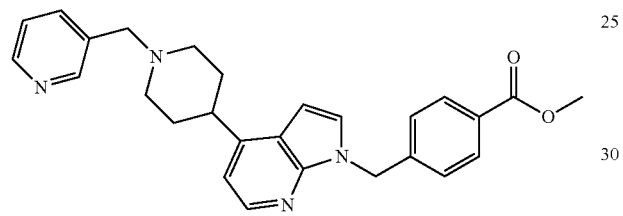

The compound of formula 16-1 (methyl 4-((4-(piperidin-4-yl)-1H-pyrrolo[2,3-b]pyridin-1-yl)methyl)benzoate) (0.250 g, 0.715 mmol), and nicotinaldehyde (0.115 g, 1.073 mmol) were dissolved in methylene chloride (5 mL). The solution was stirred at room temperature for 10 minutes, and Na(OAc)$_3$BH (0.303 g, 1.431 mmol) was added thereto, followed by stirring at the same temperature for 17 hours. Then, a saturated aqueous solution of sodium hydrogen carbonate was added to the reaction mixture, followed by extraction with methylene chloride. The extract was filtered through a plastic filter to remove solid residue and the aqueous solution, and then concentrated under reduced pressure. The concentrate was purified by column chromatography (SiO$_2$, 12 g cartridge; methanol/methylene chloride=from 2.5% to 5%) to afford the desired compound of formula 16-2 (0.116 g, 36.8%) as a pale yellow solid.

Step 2: Synthesis of N-hydroxy-4-((4-(1-(pyridin-3-ylmethyl)piperidin-4-yl)-1H-pyrrolo[2,3-b]pyridin-1-yl)methyl)benzamide (compound 1014)

(compound 1014)

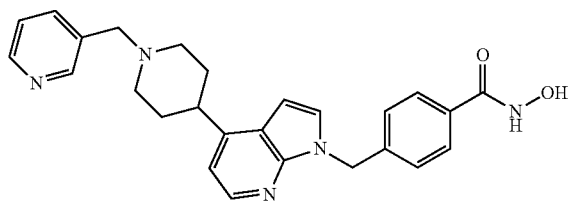

The compound of formula 16-2 (0.060 g, 0.136 mmol) prepared in step 1, hydroxylamine (50.00% solution in water, 0.167 mL, 2.724 mmol) and potassium hydroxide (0.076 g, 1.362 mmol) were dissolved in methanol (3 mL) at room temperature, and the solution was stirred at the same temperature for 30 minutes. Then, the reaction mixture was concentrated under reduced pressure to remove the solvent, and a saturated aqueous solution of sodium hydrogen carbonate was added to the concentrate, followed by extraction with methylene chloride. The extract was filtered through a plastic filter to remove solid residue and the aqueous solution, and then concentrated under reduced pressure, thereby obtaining the desired compound 1014 (0.026 g, 43.2%) as a pale orange solid without additional purification.

$^1$H NMR (400 MHz, DMSO-d$_6$) δ 8.51 (d, 1H, J=1.5 Hz), 8.45 (dd, 1H, J=4.7, 1.6 Hz), 8.16 (d, 1H, J=4.9 Hz), 7.75 (dt, 1H, J=7.9, 1.9 Hz), 7.64 (d, 2H, J=8.3 Hz), 7.52 (d, 1H, J=3.6 Hz), 7.36 (dd, 1H, J=7.8, 4.8 Hz), 7.24 (d, 2H, J=8.3 Hz), 6.96 (d, 1H, J=5.0 Hz), 6.61 (d, 1H, J=3.6 Hz), 5.48 (s, 2H), 3.56 (s, 2H), 2.96-2.93 (m, 3H), 2.20-2.14 (m, 2H), 1.86-1.81 (m, 4H); MS (ESI) m/z 442.0 (M$^+$+H).

Example 149

Synthesis of Compound 1015

Step 1: Synthesis of benzyl 3-(4-(1-(4-((benzyloxy)carbamoyl)benzyl)-1H-pyrrolo[2,3-b]pyridin-4-yl)piperidin-1-yl)butanoate (formula 20-5)

(formula 20-5)

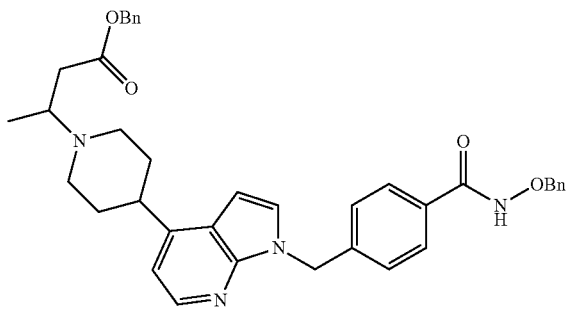

The compound of formula 20-4 (N-(benzyloxy)-4-((4-piperidin-4-yl)-1H-pyrrolo[2,3-b]pyridin-1-yl)benzamide hydrochloride) (0.300 g, 0.629 mmol), (E)-benzyl 2-butanoate (0.133 g, 0.755 mmol) and TEA (0.438 mL, 3.145 mmol) were dissolved in methylene chloride (4 mL). The solution was stirred at room temperature for 8 hours, and further stirred at 50° C. for 17 hours, and then cooled to room temperature. After completion of the reaction, the reaction mixture was concentrated under reduced pressure to remove the solvent. The concentrate was purified by column chromatography (SiO$_2$, 12 g cartridge; methanol/methylene chloride=from 0% to 10%) to afford the desired compound of formula 20-5 (0.056 g, 14.4%) as a colorless oil.

Step 2: Synthesis of 3-(4-(1-(4-(hydroxycarbamoyl)benzyl)-1H-pyrrolo[2,3-b]pyridin-4-yl)piperidin-1-yl)butanoic acid (compound 1015)

(compound 1015)

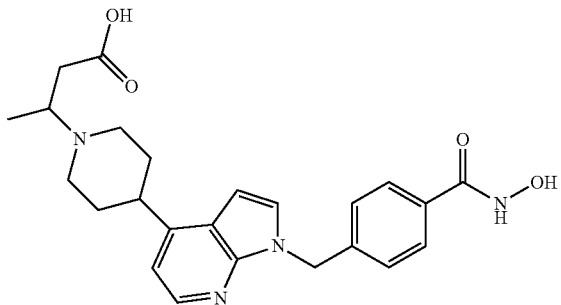

The compound of formula 20-5 (0.056 g, 0.091 mmol) prepared in step 1 was dissolved in methanol (3 mL) at room temperature.

10% Pd/C (10 mg) was added slowly to the solution, which was then stirred under a hydrogen balloon for 1 hour. The reaction mixture was filtered through a celite pad to remove solids, and the filtrate was concentrated under reduced pressure to remove the solvent. The concentrate was crystallized from methanol (0.5 mL) and diethyl ether (10 mL) at room temperature, and the obtained solid was washed with ethyl ether, and dried to afford the desired compound 1015 (0.006 g, 15.1%) as a white solid.

$^1$H NMR (400 MHz, DMSO-$d_6$) δ 8.20 (d, 1H, J=5.0 Hz), 7.67 (d, 2H, J=8.2 Hz), 7.63 (d, 1H, J=3.5 Hz), 7.28 (d, 2H, J=8.1 Hz), 6.98 (d, 1H, J=5.0 Hz), 6.64 (d, 1H, J=3.4 Hz), 3.22-3.17 (m, 2H), 3.08-3.07 (m, 2H), 2.79 (t, 1H, J=11.0 Hz), 2.16 (dd, 1H, J=15.9, 6.0 Hz), 1.97 (d, 2H, J=12.4 Hz), 1.85-1.75 (m, 3H), 1.06 (d, 3H, J=6.6 Hz); MS (ESI) m/z 437.5 (M$^+$+H).

Example 150

Synthesis of Compound 1017

Step 1: Synthesis of methyl 4-((4-((1R,5S)-3,8-diazabicyclo[3.2.1]octan-3-yl)-1H-pyrrolo[2,3-b]pyridin-1-yl)methyl)benzoate (formula 17-2)

(formula 17-2)

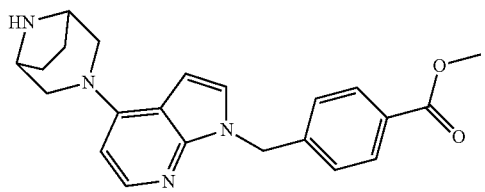

The compound of formula 17-1 ((1R,5S)-tert-butyl 3-(1-(4-methoxycarbonyl)benzyl-1H-pyrrolo[2,3-b]pyridin-4-yl)-3,8-diazabicyclo[3.2.1]octan-8-carboxylate) (0.479 g, 1.005 mmol) was dissolved in methylene chloride (10 mL) at room temperature. To the solution, hydrochloric acid (4.0 M solution 1,4-dioxane, 1.256 mL, 5.025 mmol) was added, followed by stirring at the same temperature for 3 hours. Then, a saturated aqueous solution of sodium hydrogen carbonate was added to the reaction mixture, followed by extraction with methylene chloride. The extract was filtered through a plastic filter to remove solid residue and the aqueous solution, and then concentrated under reduced pressure, thereby obtaining the desired compound 17-2 (0.375 g, 99.1%) as an orange oil without addition purification.

Step 2: Synthesis of ethyl 4-((4-((1R,5S)-8-(2-hydroxy-2-methylpropyl)-3,8-diazabicyclo[3.2.1]octan-3-yl)-1H-pyrrolo[2,3-b]pyridin-1-yl)methyl)benzoate (formula 17-4)

(formula 17-4)

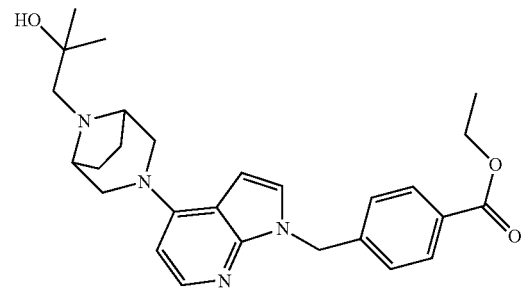

The compound of formula 17-2 (0.100 g, 0.266 mmol) prepared in step 1, 2,2-dimethyloxirane (0.239 mL, 2.656 mmol) and potassium carbonate (0.367 g, 2.656 mmol) were dissolved in ethanol (5 mL), and heated by microwave irradiation at 110° C. for 30 minutes, and then cooled to room temperature. After completion of the reaction, a saturated aqueous solution of sodium hydrogen carbonate was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; methanol/chloroform=from 0% to 5%) to afford the desired compound of formula 17-4 (0.031 g, 25.2%) as a yellow oil.

Step 3: Synthesis of N-hydroxy-4-((4-(8-(2-hydroxy-2-methylpropyl)-3,8-diazabicyclo[3.2.1]octan-3-yl)-1H-pyrrolo[2,3-b]pyridin-1-yl)methyl)benzamide (compound 1017)

(compound 1017)

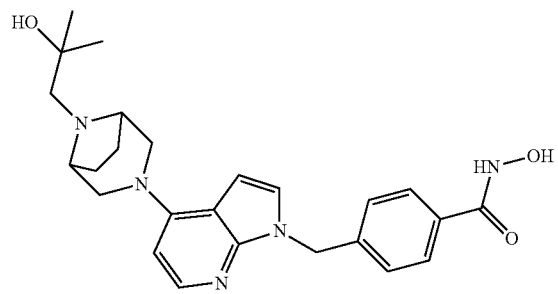

The compound of formula 17-4 (0.031 g, 0.067 mmol) prepared in step 2, hydroxylamine (50.0% solution in water, 0.082 mL, 1.340 mmol) and potassium hydroxide (0.038 g, 0.670 mmol) were dissolved in methanol (3 mL) at room temperature, and the solution was stirred at the same temperature for 1 hour. Then, the reaction mixture was concentrated under reduced pressure to remove the solvent, and a saturated aqueous solution of sodium hydrogen carbonate (30 mL) was added to the concentrate, followed by stirring.

The precipitated solid was filtered, washed with water, and dried to afford the desired compound 1017 (0.013 g, 43.2%) as a white solid.

¹H NMR (400 MHz, DMSO-d₆) δ 11.15 (brs, 1H), 9.02 (brs, 1H), 7.90 (d, 1H, J=5.6 Hz), 7.65 (d, 2H, J=8.1 Hz), 7.35 (d, 1H, J=3.5 Hz), 7.22 (d, 2H, J=8.2 Hz), 6.60 (d, 1H, J=3.6 Hz), 6.35 (d, 1H, J=5.6 Hz), 5.47 (s, 2H), 4.07 (s, 1H), 3.69 (d, 2H, J=10.1 Hz), 3.19 (d, 2H, J=10.2 Hz), 2.22 (s, 2H), 1.87-1.85 (m, 2H), 1.75 (d, 2H, J=13.8 Hz), 1.69-1.68 (m, 2H), 1.13 (s, 6H); MS (ESI) m/z 450.0 (M⁺+H).

Example 151

Synthesis of Compound 1018

Step 1: Synthesis of methyl 4-((4-((1R,5S)-8-(4-methoxybenzyl)-3,8-diazabicyclo[3.2.1]octan-3-yl)-1H-pyrrolo[2,3-b]pyridin-1-yl)methyl)benzoate (formula 17-3)

(formula 17-3)

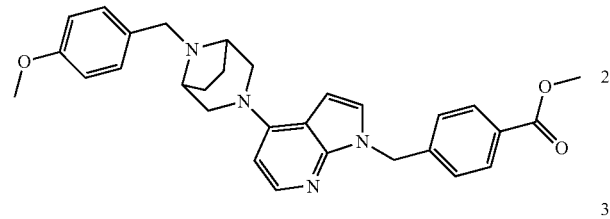

The compound of formula 17-2 (methyl 4-((4-((1R,5S)-3,8-diazabicyclo[3.2.1]octan-3-yl)-1H-pyrrolo[2,3-b]pyridin-1-yl)methyl)benzoate) (0.100 g, 0.266 mmol), p-anisaldehyde (0.048 mL, 0.398 mmol) and Na(OAc)₃BH (0.113 g, 0.531 mmol) were dissolved in methylene chloride (4 mL) at room temperature, and the solution was stirred at the same temperature for 10 minutes. Then, a saturated aqueous solution of sodium hydrogen carbonate was added to the reaction mixture, followed by extraction with methylene chloride. The extract was filtered through a plastic filter to remove solid residue and the aqueous solution, and then concentrated under reduced pressure. The concentrate was purified by column chromatography (SiO₂, 4 g cartridge; ethyl acetate/hexane=from 0% to 30%) to afford the desired compound of formula 17-3 (0.079 g, 59.9%) as colorless oil.

Step 2: Synthesis of N-hydroxy-4-((4-(8-(4-methoxybenzyl)-3,8-diazabicyclo[3.2.1]octan-3-yl)-1H-pyrrolo[2,3-b]pyridin-1-yl)methyl)benzamide (compound 1018)

(compound 1018)

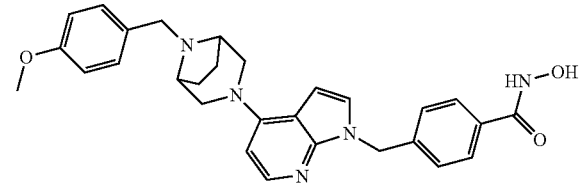

The compound of formula 17-3 (0.079 g, 0.159 mmol) prepared in step 1, hydroxylamine (50.0% solution in water, 0.195 mL, 3.182 mmol) and potassium hydroxide (0.089 g, 1.591 mmol) were dissolved in methanol (4 mL) at room temperature, and the solution was stirred at the same temperature for 1 hour. Then, the reaction mixture was concentrated under reduced pressure to remove the solvent, and a saturated aqueous solution of sodium hydrogen carbonate was added to the concentrate, followed by extraction with methylene chloride. The extract was filtered through a plastic filter to remove solid residue and the aqueous layer, and then concentrated under reduced pressure. Diethyl ether (10 mL) was added to the concentrate, followed by stirring. The precipitated solid was filtered, washed with diethyl ether, and dried to afford the desired compound 1018 (0.013 g, 16.4%) as a white solid.

¹H NMR (400 MHz, DMSO-d₆) δ 7.92 (d, 1H, J=5.5 Hz), 7.61 (d, 2H, J=8.1 Hz), 7.33-7.30 (m, 3H), 7.08 (d, 2H, J=7.8 Hz), 6.90 (d, 2H, J=9.0 Hz), 6.57 (d, 1H, J=3.6 Hz), 6.34 (d, 1H, J=5.7 Hz), 5.36 (s, 2H), 3.75 (s, 3H), 3.71 (d, 2H, J=9.3 Hz), 3.49 (s, 2H), 3.27 (s, 2H), 3.13 (d, 2H, J=9.8 Hz), 2.03-2.01 (m, 2H), 1.74 (d, 2H, J=7.7 Hz); MS (ESI) m/z 499.0 (M⁺+H).

Example 152

Synthesis of Compound 1019

Step 1: Synthesis of methyl 4-((4-((1R,5S)-8-(pyridin-3-ylmethyl)-3,8-diazabicyclo[3.2.1]octan-3-yl)-1H-pyrrolo[2,3-b]pyridin-1-yl)methyl)benzoate (formula 17-3)

(formula 17-3)

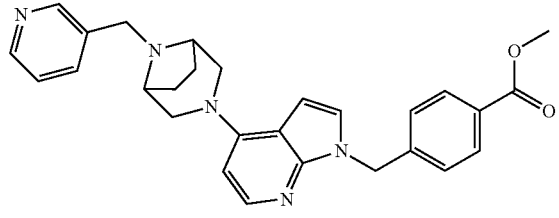

The compound of formula 17-2 (methyl 4-((4-((1R,5S)-3,8-diazabicyclo[3.2.1]octan-3-yl)-1H-pyrrolo[2,3-b]pyridin-1-yl)methyl)benzoate) (0.100 g, 0.266 mmol), nicotinaldehyde (0.043 g, 0.398 mmol) and Na(OAc)₃BH (0.113 g, 0.531 mmol) were dissolved in methylene chloride (4 mL) at room temperature, and the solution was stirred at the same temperature for 10 minutes. Then, a saturated aqueous solution of sodium hydrogen carbonate was added to the reaction mixture, followed by extraction with methylene chloride. The extract was filtered through a plastic filter to remove solid residue and the aqueous solution, and then concentrated under reduced pressure. The concentrate was purified by column chromatography (SiO₂, 4 g cartridge; methanol/methylene chloride=from 0% to 5%) to afford the desired compound of formula 17-3 (0.067 g, 53.9%) as a colorless oil.

Step 2: Synthesis of N-hydroxy-4-((4-(8-(pyridin-3-ylmethyl)-3,8-diazabicyclo[3.2.1]octan-3-yl)-1H-pyrrolo[2,3-b]pyridin-1-yl)methyl)benzamide (compound 1019)

(compound 1019)

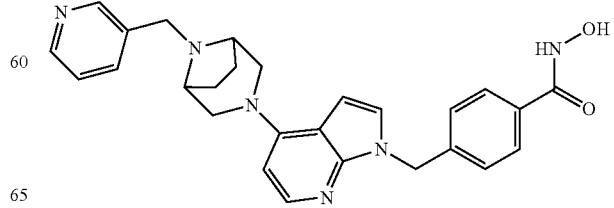

The compound of formula 17-3 (0.067 g, 0.143 mmol) prepared in step 1, hydroxylamine (50.0% solution in water, 0.175 mL, 2.866 mmol) and potassium hydroxide (0.080 g, 1.433 mmol) were dissolved in methanol (3 mL) at room temperature, and the solution was stirred at the same temperature for 1 hour. Then, the reaction mixture was concentrated under reduced pressure to remove the solvent, and a saturated aqueous solution of sodium hydrogen carbonate (30 mL) was added to the concentrate, followed by stirring. The precipitated solid was filtered, washed with water, and dried to afford the desired compound 1019 (0.060 g, 89.4%) as a white solid.

$^1$H NMR (400 MHz, DMSO-d$_6$) δ 8.59 (s, 1H), 8.48 (d, 1H, J=3.4 Hz), 7.91 (d, 1H, J=5.6 Hz), 7.84 (d, 1H, J=8.1 Hz), 7.65 (d, 2H, J=8.1 Hz), 7.38 (dd, 1H, J=7.6, 4.7 Hz), 7.34 (d, 1H, J=3.6 Hz), 7.18 (d, 2H, J=8.0 Hz), 6.60 (d, 1H, J=3.6 Hz), 6.36 (d, 1H, J=5.6 Hz), 5.42 (s, 2H), 3.72 (d, 2H, J=10.3 Hz), 3.61 (s, 2H), 3.29 (s, 2H), 3.16 (d, 2H, J=10.4 Hz), 2.06-2.04 (m, 2H), 1.77-1.75 (m, 2H); MS (ESI) m/z 469.0 (M$^+$+H).

Example 153

Synthesis of Compound 1020

Step 1: Synthesis of tert-butyl 8-(1-(4-(methoxycarbonyl)benzyl)-1H-pyrrolo[2,3-b]pyridin-4-yl)-2,8-diazabicyclo[4.5]decane-2-carboxylate (formula 18-1)

(formula 18-1)

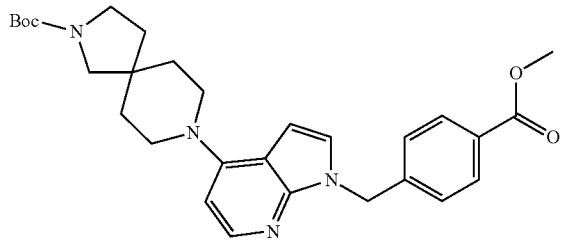

The compound of formula 1-2 (methyl 4-((4-bromo-1H-pyrrolo[2,3-b]pyridin-1-yl)methyl)benzoate) (0.700 g, 2.028 mmol), tert-butyl 2,8-diazabicyclo[4.5]decane-2-carboxylate (0.585 g, 2.433 mmol), Pd(t-Bu$_3$P)$_2$Cl$_2$ (0.104 g, 0.203 mmol) and sodium tert-butoxide (0.234 g, 2.433 mmol) were dissolved in toluene (4 mL) at room temperature, and the solution was stirred at 120° C. for 17 hours, and then cooled to room temperature. After completion of the reaction, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; ethyl acetate/hexane=from 0% to 30%) to afford the desired compound of formula 18-1 (0.464 g, 45.3%) as a colorless oil.

Step 2: Synthesis of methyl 4-((4-(2,8-diazaspiro[4.5]decan-8-yl)-1H-pyrrolo[2,3-b]pyridin-1-yl)methyl)benzoate (formula 18-2)

(formula 18-2)

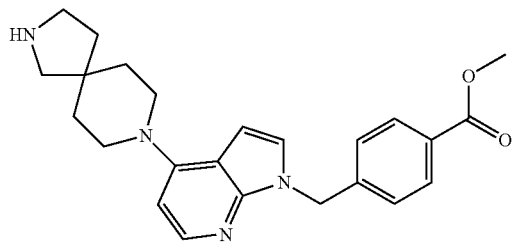

The compound of formula 18-1 (0.464 g, 0.919 mmol) prepared in step 1 was dissolved in methylene chloride (10 mL) at room temperature. To the solution, HCl (4.0 M solution in 1,4-dioxane, 1.149 mL, 4.597 mmol) was added, followed by stirring at the same temperature for 3 hours. Then, a saturated aqueous solution of sodium hydrogen carbonate was added to the reaction mixture, followed by extraction with methylene chloride. The extract was filtered through a plastic filter to remove solid residue and the aqueous solution, and then concentrated under reduced pressure, thereby obtaining the desired compound 18-2 (0.365 g, 98.1%) as a pale orange solid.

Step 3: Synthesis of ethyl 4-((4-((1R,5S)-8-(2-hydroxy-2-methylpropyl)-3,8-diazabicyclo[3.2.1]octane-3-yl)-1H-pyrrolo[2,3-b]pyridin-1-yl)methyl)benzoate (formula 18-4)

(formula 18-4)

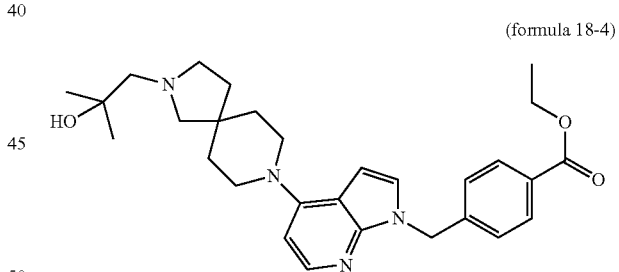

The compound of formula 18-2 (0.100 g, 0.247 mmol) prepared in step 2, 2,2-dimethyloxirane (0.223 mL, 2.472 mmol) and K$_2$CO$_3$ (0.342 g, 2.472 mmol) were dissolved in ethanol (5 mL), and heated by microwave irradiation at 110° C. for 30 minutes, and then cooled to room temperature. After completion of the reaction, a saturated aqueous solution of ammonium chloride was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; methanol/methylene chloride=from 0% to 5%) to afford the compound of formula 18-4 (0.058 g, 47.8%) as a colorless oil.

Step 4: Synthesis of N-hydroxy-4-((4-(2-(2-hydroxy-2-methylpropyl)-2,8-diazaspiro[4.5]decan-8-yl)-1H-pyrrolo[2,3-b]pyridin-1-yl)methyl)benzamide (compound 1020)

(compound 1020)

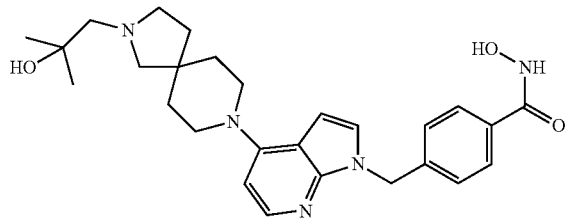

The compound of formula 18-4 (0.031 g, 0.067 mmol) prepared in step 2, hydroxylamine (50.0% solution in water, 0.082 mL, 1.340 mmol) and potassium hydroxide (0.038 g, 0.670 mmol) were dissolved in methanol (3 mL) at room temperature, and the solution was stirred at the same temperature for 1 hour. Then, the reaction mixture was concentrated under reduced pressure to remove the solvent, and a saturated aqueous solution of sodium hydrogen carbonate (30 mL) was added to the concentrate, followed by stirring. The precipitated solid was filtered, washed with water, and dried to afford the desired compound 1020 (0.013 g, 43.2%) as a white solid.

$^1$H NMR (400 MHz, DMSO-$d_6$) δ 7.95 (d, 1H, J=5.4 Hz), 7.66 (d, 2H, J=8.0 Hz), 7.39 (d, 1H, J=3.4 Hz), 7.21 (d, 2H, J=7.9 Hz), 6.51 (d, 1H, J=3.5 Hz), 6.46 (d, 1H, J=5.6 Hz), 5.44 (s, 2H), 4.04 (s, 1H), 3.45-3.37 (m, 4H), 2.66 (t, 2H, J=6.7 Hz), 2.32 (s, 2H), 1.74-7.66 (m, 4H), 1.62-1.58 (m, 2H), 1.09 (s, 6H); MS (ESI) m/z 478.1 (M$^+$+H).

Example 154

Synthesis of Compound 1021

Step 1: Synthesis of methyl 4-((4-(2-(4-methoxybenzyl)-2,8-diazaspiro[4.5]decan-8-yl)-1H-pyrrolo[2,3-b]pyridin-1-yl)methyl)benzoate (formula 18-3)

(formula 18-3)

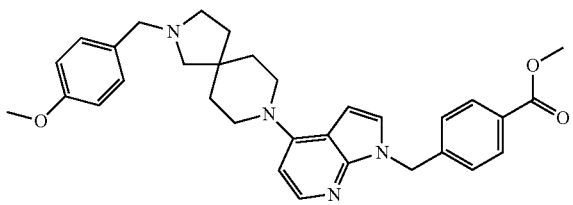

The compound of formula 18-2 (methyl 4-((4-(2,8-diazaspiro[4.5]decan-8-yl)-1H-pyrrolo[2,3-b]pyridin-1-yl)methyl)benzoate) (0.100 g, 0.247 mmol), and p-anisaldehyde (0.045 mL, 0.371 mmol) were dissolved in methylene chloride (4 mL). The solution was stirred at room temperature for 10 minutes, and Na(OAc)$_3$BH (0.105 g, 0.494 mmol) was added thereto, followed by stirring at the same temperature for 17 hours. Then, a saturated aqueous solution of sodium hydrogen carbonate was added to the reaction mixture, followed by extraction with methylene chloride. The extract was filtered through a plastic filter to remove solid residue and the aqueous solution, and then concentrated under reduced pressure. The concentrate was purified by column chromatography (SiO$_2$, 4 g cartridge; methanol/methylene chloride=from 0% to 5%) to afford the desired compound of 18-3 (0.102 g, 78.6%) as a yellow oil.

Step 2: Synthesis of N-hydroxy-4-((4-(2-(4-methoxybenzyl)-2,8-diazaspiro[4.5]decan-8-yl)-1H-pyrrolo[2,3-b]pyridin-1-yl)methyl)benzamide (compound 1021)

(compound 1021)

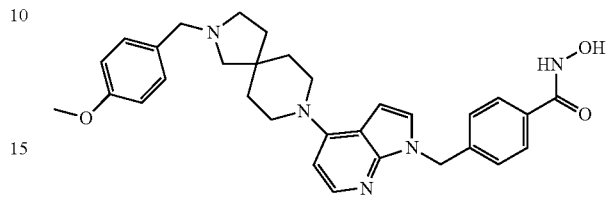

The compound of formula 18-3 (0.102 g, 0.194 mmol) prepared in step 1, hydroxylamine (50.00% solution in water, 0.238 mL, 3.888 mmol) and potassium hydroxide (0.109 g, 1.944 mmol) were dissolved in methanol (3 mL) at room temperature, and the solution was stirred at the same temperature for 1 hour. Then, the reaction mixture was concentrated under reduced pressure to remove the solvent, and a saturated aqueous solution of sodium hydrogen carbonate (30 mL) was added to the concentrate, followed by stirring. The precipitated solid was filtered, washed with water, and dried to afford the desired compound 1021 (0.098 g, 95.9%) as a white solid.

$^1$H NMR (400 MHz, DMSO-$d_6$) δ 9.75 (brs, 2H), 7.95 (d, 1H, J=5.4 Hz), 7.64 (d, 2H, J=8.1 Hz), 7.37 (d, 1H, J=3.5 Hz), 7.22 (d, 2H, J=8.5 Hz), 7.16 (d, 2H, J=8.1 Hz), 6.87 (d, 2H, J=8.5 Hz), 6.49 (d, 1H, J=3.6 Hz), 5.41 (s, 2H), 3.73 (s, 3H), 3.48 (s, 2H), 3.42-3.35 (m, 6H), 2.37 (s, 2H), 1.65-1.61 (m, 6H); MS (ESI) m/z 526.0 (M$^+$+H).

Example 155

Synthesis of Compound 1022

Step 1: Synthesis of methyl 4-((4-(2-(pyridin-3-ylmethyl)-2,8-diazaspiro[4.5]decan-8-yl)-1H-pyrrolo[2,3-b]pyridin-1-yl)methyl)benzoate (formula 18-3)

(formula 18-3)

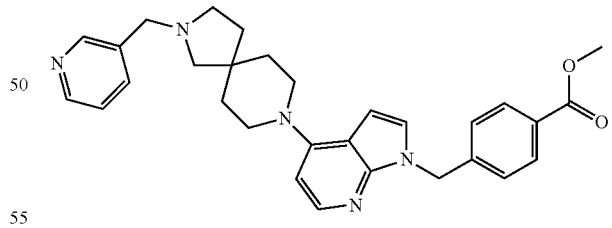

The compound of formula 18-2 (methyl 4-((4-2,8-diazaspiro[4.5]decan-8-yl)-1H-pyrrolo[2,3-b]pyridin-1-yl)methyl)benzoate) (0.100 g, 0.247 mmol), and nicotinaldehyde (0.040 g, 0.371 mmol) were dissolved in methylene chloride (4 mL). The solution was stirred at room temperature for 10 minutes, and Na(OAc)$_3$BH (0.105 g, 0.494 mmol) was added thereto, followed by stirring at the same temperature for 17 hours. Then, a saturated aqueous solution of sodium hydrogen carbonate was added to the reaction mixture, followed by extraction with methylene chloride. The extract was filtered through a plastic filter to remove solid residue and the aqueous solution, and then concentrated under reduced pressure. The concentrate was purified by column chromatography (SiO$_2$, 4 g cartridge; methanol/methylene chloride=from 0% to 5%) to afford the desired compound of 18-3 (0.080 g, 65.3%) as a colorless oil.

Step 2: Synthesis of N-hydroxy-4-((4-(2-(pyridin-3-ylmethyl)-2,8-diazaspiro[4.5]decan-8-yl)-1H-pyrrolo[2,3-b]pyridin-1-yl)methyl)benzamide (compound 1022)

(compound 1022)

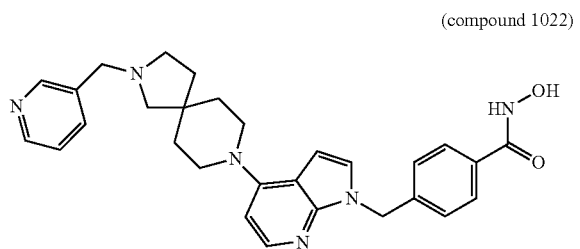 [SMILES: O=C(NO)c1ccc(Cn2ccc3c(N4CCC5(CCN(Cc6cccnc6)C5)CC4)ccnc32)cc1]

The compound of formula 18-3 (0.080 g, 0.161 mmol) prepared in step 1, hydroxylamine (50.00% solution in water, 0.197 mL, 3.228 mmol) and potassium hydroxide (0.091 g, 1.614 mmol) were dissolved in methanol (3 mL) at room temperature, and the solution was stirred at the same temperature for 1 hour. Then, the reaction mixture was concentrated under reduced pressure to remove the solvent, and a saturated aqueous solution of sodium hydrogen carbonate (50 mL) was added to the concentrate, followed by stirring. The precipitated solid was filtered, washed with water, and dried to afford the desired compound 1022 (0.079 g, 98.6%) as a white solid.

$^1$H NMR (400 MHz, DMSO-d$_6$) δ 11.17 (brs, 1H), 9.00 (brs, 1H), 8.51 (s, 1H), 8.46 (d, 1H, J=3.9 Hz), 7.95 (d, 1H, J=5.4 Hz), 7.72 (d, 1H, J=7.9 Hz), 7.65 (d, 2H, J=8.1 Hz), 7.39-7.34 (m, 2H), 7.21 (d, 2H, J=8.0 Hz), 5.44 (s, 2H), 3.60 (s, 2H), 3.43-3.38 (m, 3H), 2.55-2.50 (m, 3H), 2.41 (s, 2H), 1.68-1.64 (m, 6H); MS (ESI) m/z 497.0 (M$^+$+H).

Example 156

Synthesis of Compound 1023

Step 1: Synthesis of tert-butyl 7-(1-(4-(methoxycarbonyl)benzyl)-1H-pyrrolo[2,3-b]pyridin-4-yl)-2,7-diazaspiro[3.5]nonane-2-carboxylate (formula 22-1)

(formula 22-1)

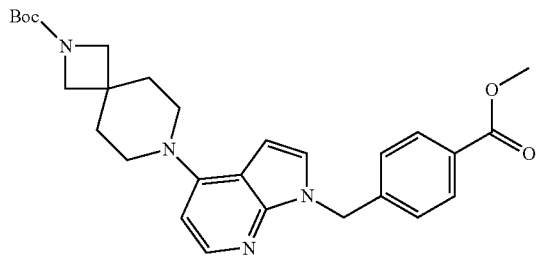

The compound of formula 1-2 (1.500 g, 4.345 mmol), tert-butyl 2,7-diazaspiro[3.5]nonane-2-carboxylate (1.180 g, 5.215 mmol), bis (tri-t-butylphosphine)palladium(0) (0.222 g, 0.435 mmol) and sodium tert-butoxide (0.501 g, 5.215 mmol) were dissolved in toluene (50 mL) at 120° C., and the solution was stirred at the same temperature for 5 hours, and then cooled to room temperature. After completion of the reaction, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; ethyl acetate/hexane=from 0% to 30%) to afford the compound of formula 22-1 (0.900 g, 42.2%) as a white solid.

Step 2: Synthesis of methyl 4-((4-(2,7-diazaspiro[3.5]nonan-7-yl)-1H-pyrrolo[2,3-b]pyridin-1-yl)methyl)benzoate hydrochloride (formula 22-2)

(formula 22-2)

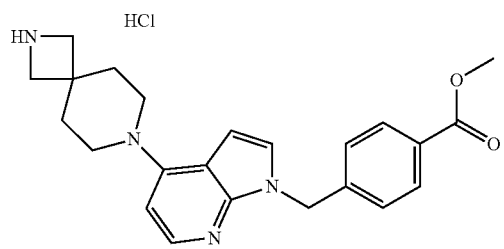

The compound of formula 22-1 (0.900 g, 1.835 mmol) prepared in step 1, and 4M hydrochloric acid (4.0 M solution in dioxane, 1.835 mL, 7.338 mmol) were dissolved in methylene chloride (10 mL) at room temperature, and the solution was stirred at the same temperature for 12 hours. The formed solid was filtered, washed with hexane, and dried to afford the desired compound 22-2 (0.650 g, 90.7%) as a white solid.

Step 3: Synthesis of methyl 4-((4-(2-(2-hydroxy-2-methylpropyl)-2,7-diazaspiro[3.5]nonan-7-yl)-1H-pyrrolo[2,3-b]pyridin-1-yl)methyl)benzoate (formula 22-3)

(formula 22-3)

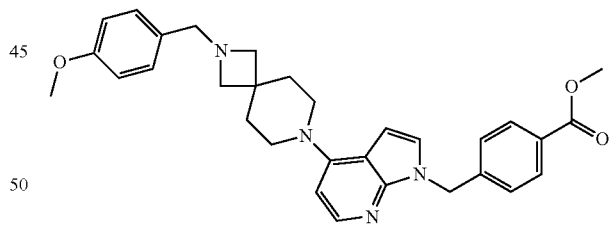

The compound of formula 22-2 (0.190 g, 0.487 mmol) prepared in step 2, 4-methoxybenzaldehyde (0.070 mL, 0.584 mmol) and NaBH(OAc)$_3$ (0.206 g, 0.973 mmol) were dissolved in methylene chloride (10 mL) at room temperature, and the solution was stirred at the same temperature for 12 hours. Then, water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; methanol/methylene chloride=from 0% to 10%) to afford the desired compound of formula 22-3 (0.120 g, 48.3%) as a white foam solid.

Step 4: Synthesis of N-hydroxy-4-((4-(2-(4-methoxybenzyl)-2,7-diazaspiro[3.5]nonan-7-yl)-1H-pyrrolo[2,3-b]pyridin-1-yl)methyl)benzamide (compound 1023)

(compound 1023)

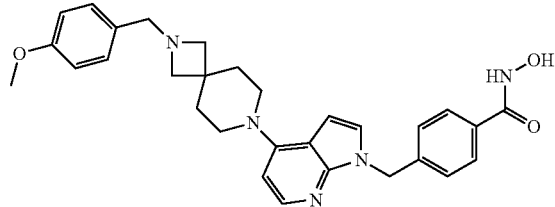

The compound of formula 22-3 (0.119 g, 0.233 mmol) prepared in step 3, and hydroxylamine (0.143 mL, 4.661 mmol) were dissolved in methanol (5 mL). Potassium hydroxide (0.131 g, 2.330 mmol) was added to the solution at 0° C., and the solution was stirred at the same temperature for 30 minutes, and then stirred at room temperature for 2 hours. Then, the reaction mixture was concentrated under reduced pressure to remove the solvent, and a saturated aqueous solution of sodium hydrogen carbonate was added to the concentrate, followed by extraction with ethyl acetate. The organic layer was washed with a saturated aqueous solution of sodium chloride, dried with anhydrous magnesium sulfate, filtered, and then concentrated under reduced pressure, thereby obtaining the desired compound 1023 (0.080 g, 67.1%) as a white foam solid without additional purification.

$^1$H NMR (400 MHz, CD$_3$OD) δ 7.81 (d, 1H, J=125.7 Hz), 7.69 (dd, 2H, J=6.6, 1.7 Hz), 7.25 (dd, 2H, J=6.6, 2.1 Hz), 7.18 (d, 1H, J=3.6 Hz), 7.13 (d, 2H, J=8.4 Hz), 6.91-6.88 (m, 2H), 6.56 (d, 1H, J=3.7 Hz), 6.52 (d, 1H, J=5.8 Hz), 5.45 (s, 2H), 3.79 (s, 3H), 3.65 (s, 2H), 3.47-3.44 (m, 4H), 3.19 (s, 4H), 1.96-1.91 (m, 4H); MS (ESI) m/z 512.0 (M$^+$+H).

Example 157

Synthesis of Compound 1024

Step 1: Synthesis of methyl 4-((4-(2-(pyridin-3-ylmethyl)-2,7-diazaspiro[3.5]nonan-7-yl)-1H-pyrrolo[2,3-b]pyridin-1-yl)methyl)benzoate (formula 22-3)

(formula 22-3)

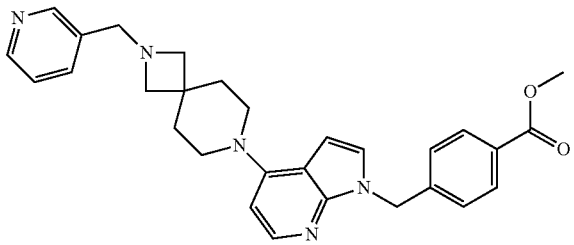

The compound of formula 22-2 (0.253 g, 0.648 mmol), nicotinaldehyde (0.067 mL, 0.713 mmol) and NaBH(OAc)$_3$ (0.275 g, 1.296 mmol) were dissolved in methylene chloride (10 mL) at room temperature, and the solution was stirred at the same temperature for 12 hours. Then, water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; methanol/methylene chloride=from 0% to 10%) to afford the desired compound of formula 22-3 (0.150 g, 48.1%) as a white foam solid.

Step 2: Synthesis of N-hydroxy-4-((4-(2-(pyridin-3-ylmethyl)-2,7-diazaspiro[3.5]nonan-7-yl)-1H-pyrrolo[2,3-b]pyridin-1-yl)methyl)benzamide (compound 1024)

(compound 1024)

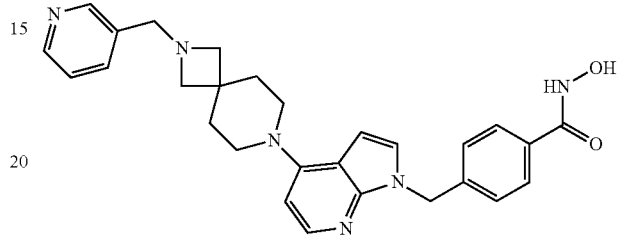

The compound of formula 22-3 (0.110 g, 0.228 mmol) prepared in step 1, and hydroxylamine (0.140 mL, 4.568 mmol) were dissolved in methanol, and potassium hydroxide (0.128 g, 2.284 mmol) was added thereto at 0° C. Then, the solution was stirred at the same temperature for 30 minutes, and then stirred at room temperature for 2 hours. Then, the reaction mixture was concentrated under reduced pressure to remove the solvent, and a saturated aqueous solution of sodium hydrogen carbonate was added to the concentrate, followed by extraction with ethyl acetate. The organic layer was washed with a saturated aqueous solution of sodium chloride, dried with anhydrous magnesium sulfate, filtered, and then concentrated under reduced pressure, thereby obtaining the desired compound 1024 (0.069 g, 62.6%) as a white foam solid without additional purification.

$^1$H NMR (400 MHz, CD$_3$OD) δ 8.53 (s, 1H), 8.48 (dd, 1H, J=4.9, 1.6 Hz), 7.96 (d, 1H, J=5.7 Hz), 7.86 (d, 1H, J=8.4 Hz), 7.67 (d, 2H, J=8.4 Hz), 7.45 (dd, 1H, J=7.8, 4.9 Hz), 7.23-7.19 (m, 3H), 6.60 (d, 1H, J=3.7 Hz), 6.54 (d, 1H, J=5.8 Hz), 5.50 (s, 2H), 3.79 (s, 2H), 3.50-3.48 (m, 4H), 3.26 (s, 4H), 2.00-1.97 (m, 4H); MS (ESI) m/z 483.0 (M$^+$+H).

Example 158

Synthesis of Compound 1025

Step 1: Synthesis of methyl 4-((4-(2-(2-hydroxy-2-methylpropyl)-2,7-diazaspiro[3.5]nonan-7-yl)-1H-pyrrolo[2,3-b]pyridin-1-yl)methyl)benzoate (formula 22-4)

(formula 22-4)

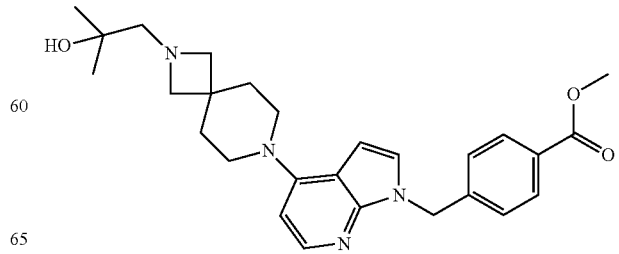

The compound of formula 22-2 (0.220 g, 0.563 mmol), 2,2-dimethyloxirane (0.056 mL, 0.620 mmol) and DIPEA (0.196 mL, 1.127 mmol) were dissolved in ethanol (10 ml), and heated by microwave irradiation at 120° C. for 20 minutes, and then cooled to room temperature. After completion of the reaction, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; methanol/chloroform=from 0% to 10%) to afford the desired compound of formula 22-4 (0.125 g, 48.0%) as a white foam solid.

Step 2: Synthesis of N-hydroxy-4-((4-(2-(2-hydroxy-2-methylpropyl)-2,7-diazaspiro[3.5]nonan-7-yl)-1H-pyrrolo[2,3-b]pyridin-1-yl)methyl)benzamide (compound 1025)

(compound 1025)

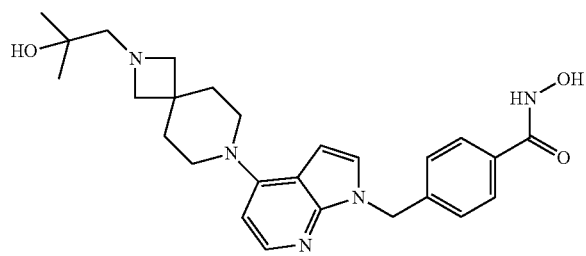

The compound of formula 22-4 (0.125 g, 0.284 mmol) prepared in step 1, and hydroxylamine (0.174 mL, 5.675 mmol) were dissolved in methanol (5 mL), and potassium hydroxide (0.159 g, 2.838 mmol) was added thereto at 0° C. Then, the solution was stirred at the same temperature, and then stirred at room temperature for 2 hours. Then, the reaction mixture was concentrated under reduced pressure to remove the solvent, and a saturated aqueous solution of sodium hydrogen carbonate was added to the concentrate, followed by extraction with ethyl acetate. The organic layer was washed with a saturated aqueous solution of sodium chloride, dried with anhydrous magnesium sulfate, filtered, and then concentrated under reduced pressure, thereby obtaining the desired compound 1025 (0.070 g, 53.2%) as a white foam solid without additional purification.

$^1$H NMR (400 MHz, DMSO-d$_6$) δ 7.96 (d, 1H, J=5.4 Hz), 7.62 (d, 2H, J=8.2 Hz), 7.36 (d, 1H, J=3.6 Hz), 7.09 (d, 2H, J=8.2 Hz), 6.48 (d, 1H, J=3.6 Hz), 6.44 (d, 1H, J=5.6 Hz), 5.37 (s, 2H), 4.02 (s, 1H), 3.06 (s, 4H), 2.33 (s, 2H), 1.83-1.80 (m, 4H), 1.04 (s, 6H); MS (ESI) m/z 464.0 (M$^+$+H).

Example 159

Synthesis of Compound 1028

Step 1: Synthesis of benzyl 2-(4-(1-(4-((benzyloxy)carbamoyl)benzyl)-1H-pyrrolo[2,3-b]pyridin-4-yl)piperidin-1-yl)-2-methylpropanoate (formula 20-5)

(formula 20-5)

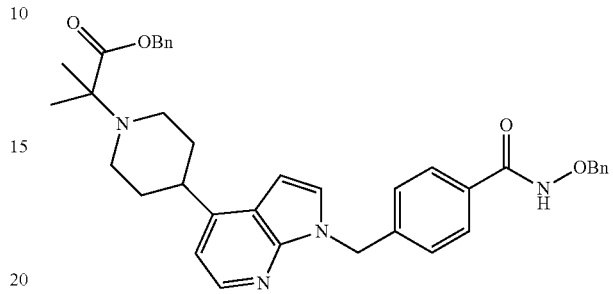

The compound of formula 20-4 (N-(benzyloxy)-4-((4-piperidin-4-yl)-1H-pyrrolo[2,3-b]pyridin-1-yl)benzamide hydrochloride) (0.300 g, 0.629 mmol), benzyl 2-bromo-2-methylpropanoate (0.194 g, 0.755 mmol), DIPEA (0.549 mL, 3.145 mmol) and NaI (0.009 g, 0.063 mmol) were dissolved in N,N-dimethylformamide (4 mL), and the solution was stirred at room temperature for 17 hours, and then stirred at 100° C. for 17 hours, followed by cooling to room temperature. After completion of the reaction, water was added to the reaction mixture, followed by extraction with ethyl acetate. The extract was filtered through a plastic filter to remove solid residue and the aqueous layer, and then concentrated under reduced pressure. The concentrate was purified by column chromatography (SiO$_2$, 12 g cartridge; ethyl acetate/hexane=from 10% to 70%) to afford the desired compound of formula 20-5 (0.034 g, 8.8%) as a yellow oil.

Step 2: Synthesis of 2-(4-(1-(4-(hydroxycarbamoyl)benzyl)-1H-pyrrolo[2,3-b]pyridin-4-yl)piperidin-1-yl)-2-methylpropionic acid (compound 1028)

(compound 1028)

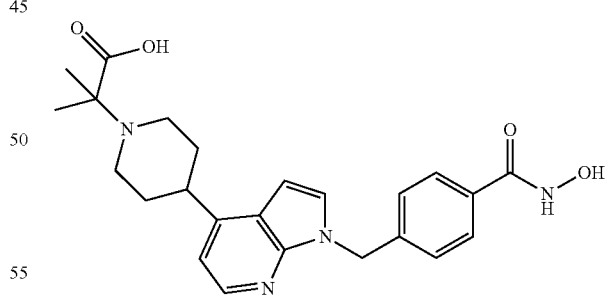

The compound of formula 20-5 (0.036 g, 0.058 mmol) prepared in step 1 was dissolved in methanol (2 mL) at room temperature, and 10% Pd/C (5 mg) was added slowly thereto, after which the solution was stirred at the same temperature under a hydrogen balloon at 8 hours. Then, the reaction mixture was filtered through a celite pad to remove solids, and the filtrate was concentrated under reduced pressure to remove the solvent. The concentrate was crystallized from diethyl ether (10 mL) and methanol (0.5 mL) at room temperature, and the obtained solid was washed with diethyl ether and dried to yield desired compound 1028 (0.016 g, 62.8%) as a yellow solid.

$^1$H NMR (400 MHz, DMSO-$d_6$) δ 8.22 (d, 1H, J=4.9 Hz), 7.68-7.65 (m, 3H), 7.29 (d, 2H, J=8.2 Hz), 6.97 (d, 1H, J=5.1 Hz), 6.76 (d, 1H, J=3.4 Hz), 5.51 (s, 2H), 3.23-3.17 (m, 2H), 2.90 (t, 2H, J=11.8 Hz), 2.67 (d, 1H, J=7.9 Hz), 2.22-2.16 (m, 2H), 1.96 (d, 2H, J=13.9 Hz), 1.29 (s, 6H); MS (ESI) m/z 435.2 (M$^+$+H).

Example 160

Synthesis of Compound 1098

Step 1: Synthesis of methyl 4-((5-(1-((6-methoxypyridin-3-yl)methyl)piperidin-4-yl)-1H-pyrrolo[2,3-b]pyridin-1-yl)methyl)benzoate (formula 12-2)

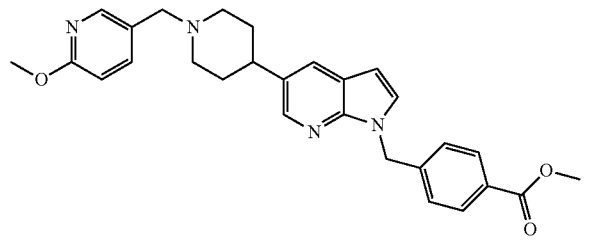

(formula 12-2)

The compound of formula 6-3 (0.200 g, 0.572 mmol), 6-methoxynicotinaldehyde (0.082 g, 0.601 mmol) and sodium triacetoxyborohydride (0.243 g, 1.145 mmol) were dissolved in methylene chloride (10 mL) at room temperature, and the solution was stirred at the same temperature for 16 hours. The reaction mixture was filtered through a plastic filter to remove solids, and the filtrate was purified by column chromatography (SiO$_2$, 4 g cartridge; methanol/methylene chloride=from 0% to 3%) to afford the desired compound of formula 12-2 (0.053 g, 19.6%) as a colorless oil.

Step 2: Synthesis of N-hydroxy-4-((5-(1-((6-methoxypyridin-3-yl)methyl)piperidin-4-yl)-1H-pyrrolo[2,3-b]pyridin-1-yl)methyl)benzamide (compound 1098)

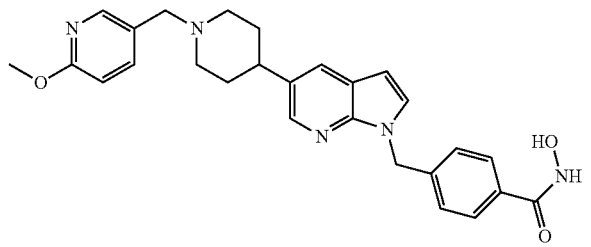

(compound 1098)

The compound of formula 12-2 (0.172 g, 0.366 mmol) prepared in step 1, and NH$_2$OH (50.00% solution in water, 0.224 mL, 3.655 mmol) were dissolved in methanol (5 mL). The solution was stirred at 0° C. for 20 minutes, and potassium hydroxide (0.205 g, 3.655 mmol) was added thereto, followed by stirring at room temperature for 2 hours. Then, the reaction mixture was concentrated under reduced pressure to remove the solvent, and a saturated aqueous solution of sodium hydrogen carbonate was added to the concentrate, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (Waters, C18; acetonitrile/formic acid (methanoic acid)=from 5% to 50%) to afford the desired compound 1098 (0.065 g, 37.7%) as a white solid.

$^1$H NMR (400 MHz, DMSO-$d_6$) δ 8.15 (d, 1H, J=1.8 Hz), 8.07 (d, 1H, J=2.2 Hz), 7.83 (d, 1H, 1.9 Hz), 7.66-7.64 (m, 3H), 7.60 (d, 1H, J=3.4 Hz), 7.24 (d, 2H, J=8.2 Hz), 6.79 (d, 1H, J=6.2 Hz), 6.45 (d, 1H, J=3.3 Hz), 5.48 (s, 2H), 3.83 (s, 3H), 3.44 (s, 2H), 2.91-2.89 (m, 2H), 2.60-2.59 (m, 1H), 2.07-2.02 (m, 2H), 1.77-1.68 (m, 4H); MS (ESI) m/z 472.54 (M$^+$+H).

Example 161

Synthesis of Compound 1101

Step 1: Synthesis of tert-butyl 8-(1-(4-(methoxycarbonyl)benzyl)-1H-pyrrolo[2,3-b]pyridin-5-yl)-2,8-diazaspiro[4.5]decane-2-carboxylate (formula 19-1)

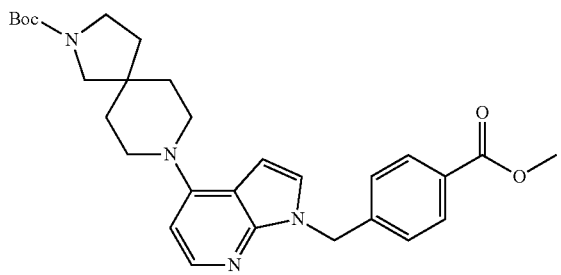

(formula 19-1)

The compound of formula 2-2 (methyl 4-((bromo-1H-pyrrolo[2,3-b]pyridin-5-yl)methyl)benzoate) (2.000 g, 5.794 mmol), tert-butyl 2,8-diazaspiro[4.5]decane-2-carboxylate (1.671 g, 6.953 mmol), Pd(t-Bu$_3$)$_2$Cl$_2$ (0.296 g, 0.579 mmol) and sodium tert-butoxide (0.668 g, 6.953 mmol) were dissolved in toluene (30 mL) at room temperature, and the solution was stirred at 120° C. for 17 hours, and then cooled to room temperature. After completion of the reaction, the reaction mixture was concentrated under reduced pressure to remove the solvent, and a saturated aqueous solution of sodium hydrogen carbonate was added to the concentrate, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 40 g cartridge; ethyl acetate/hexane=from 5% to 70%) to afford the desired compound of formula 19-1 (0.430 g, 14.7%) as a pale yellow oil.

Step 2: Synthesis of methyl 4-((5-(2,8-diazaspiro[4.5]decan-8-yl)-1H-pyrrolo[2,3-b]pyridin-1-yl)methyl)benzoate (formula 19-2)

(formula 19-2)

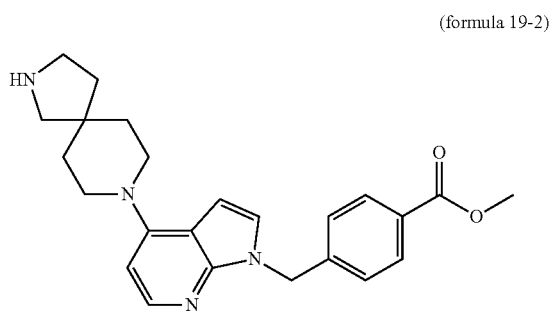 [SMILES: COC(=O)c1ccc(Cn2ccc3c(N4CCC5(CCNC5)CC4)ccnc32)cc1]

The compound of formula 19-1 (0.430 g, 0.852 mmol) prepared in step 1 was dissolved in methylene chloride (10 mL) at room temperature, and HCl (4.0 M solution in 1,4-dioxane, 1.065 mL, 4.261 mmol) was added thereto, followed by stirring at the same temperature for 17 hours. Then, a saturated aqueous solution of sodium hydrogen carbonate was added to the reaction mixture, followed by extraction with methylene chloride. The organic layer was washed with a saturated aqueous solution of sodium chloride, dried with anhydrous magnesium sulfate, filtered, and then concentrated under reduced pressure, thereby obtaining the desired compound 19-2 (0.231 g, 67.0%) as an orange oil without additional purification.

Step 3: Synthesis of methyl 4-((5-(2-(pyridin-3-ylmethyl)-2,8-diazaspiro[4.5]decan-8-yl)-1H-pyrrolo[2,3-b]pyridin-1-yl)methyl)benzoate (formula 19-3)

(formula 19-3)

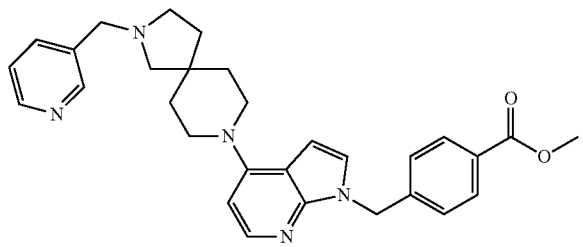

The compound of formula 19-2 (0.110 g, 0.272 mmol) prepared in step 2, and nicotinaldehyde (0.310 mL, 0.408 mmol) were dissolved in methylene chloride (3 mL). The solution was stirred at room temperature for 10 minutes, and Na(OAc)₃BH (0.115 g, 0.544 mmol) was added thereto, followed by stirring at the same temperature for 17 hours. Then, a saturated aqueous solution of sodium hydrogen carbonate was added to the reaction mixture, followed by extraction with methylene chloride. The extract was filtered through a plastic filter to remove solid residue and the aqueous layer, and then concentrated under reduced pressure. The concentrate was purified by column chromatography (SiO₂, 4 g cartridge; methanol/methylene chloride=from 0% to 10%) to afford the desired compound of formula 19-3 (0.092 g, 68.3%) as a yellow oil.

Step 4: Synthesis of N-hydroxy-4-((5-(2-(pyridin-3-ylmethyl)-2,8-diazaspiro[4.5]decan-8-yl)-1H-pyrrolo[2,3-b]pyridin-1-yl)methyl)benzamide (compound 1101)

(compound 1101)

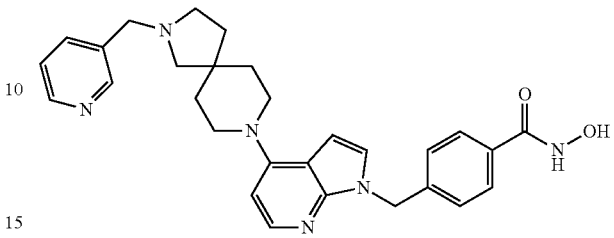

The compound of formula 19-3 (0.092 g, 0.186 mmol) prepared in step 3, hydroxylamine (50.0% solution in water, 0.227 mL, 3.713 mmol) and potassium hydroxide (0.104 g, 1.856 mmol) were dissolved in methanol (3 mL) at room temperature, and the solution was stirred at the same temperature for 30 minutes. Then, the reaction solution was concentrated under reduced pressure to remove the solvent, and a saturated aqueous solution of sodium hydrogen carbonate was added to the concentrate, followed by extraction with methylene chloride. The organic layer was washed with a saturated aqueous solution of sodium chloride, dried with anhydrous magnesium sulfate, filtered, and then concentrated under reduced pressure, thereby obtaining the desired compound 1101 (0.050 g, 54.2%) as an orange solid without additional purification.

$^1$H NMR (400 MHz, DMSO-d$_6$) δ 8.51 (s, 1H), 8.46 (d, 1H, J=3.6 Hz), 8.08 (d, 1H, J=2.4 Hz), 7.72 (d, 1H, J=7.8 Hz), 7.65 (d, 2H, J=8.1 Hz), 7.53-7.51 (m, 2H), 7.35 (dd, 1H, J=7.6, 4.8 Hz), 7.21 (d, 2H, J=8.1 Hz), 6.37 (d, 1H, J=3.4 Hz), 5.44 (s, 2H), 3.59 (s, 2H), 3.01-3.00 (m, 4H), 2.56-2.55 (m, 2H), 2.38 (s, 2H), 1.69-1.60 (m, 6H); MS (ESI) m/z 497.6 (M$^+$+H).

Example 162

Synthesis of Compound 1125

Step 1: Synthesis of methyl 4-((5-(2-(4-methoxybenzyl)-2,7-diazaspiro[3.5]nonan-7-yl)-1H-pyrrrolo[2,3-b]pyridin-1-yl)methyl)benzoate (formula 23-3)

(formula 23-3)

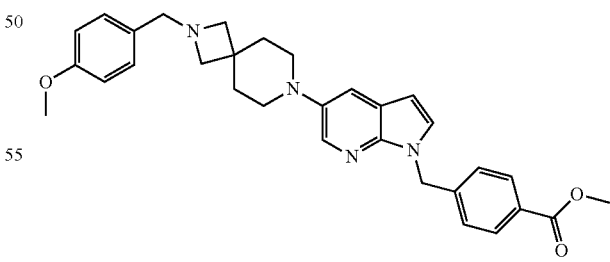

The compound of formula 23-2 (0.164 g, 0.384 mmol), 4-methoxybenzaldehyde (0.068 mL, 0.576 mmol), NaBH(OAc)₃ (0.163 g, 0.768 mmol) and DIPEA (0.067 mL, 0.384 mmol) were dissolved in methylene chloride (10 mL) at room temperature, and the solution was stirred at the same temperature for 5 hours. Then, water was added to the reaction mixture, followed by extraction with methylene chloride. The organic layer was washed with a saturated aqueous solution of sodium chloride, dried with anhydrous magnesium sulfate, and then concentrated under reduced pressure. The concentrate was purified by column chromatography (SiO$_2$, 12 g cartridge; methanol/methylene chloride=from 0% to 10%) to afford the desired compound of formula 23-3 (0.133 g, 67.8%) as a colorless oil.

Step 2: Synthesis of N-hydroxy-4-((5-(2-(4-methoxybenzyl)-2,7-diazaspiro[3.5]nonan-7-yl)-1H-pyrrolo[2,3-b]pyridin-1-yl)methyl)benzamide (compound 1125)

(compound 1125)

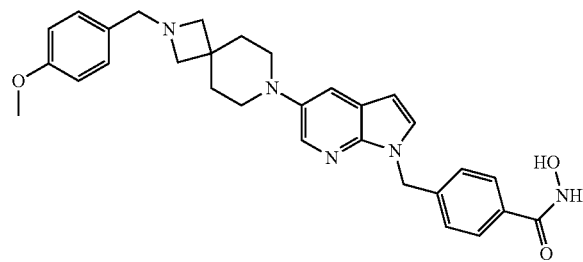

The compound of formula 23-3 (0.133 g, 0.260 mmol) prepared in step 1 was dissolved in methanol (10 mL), and hydroxylamine (50.00% solution in H$_2$O, 0.319 mL, 5.209 mmol) and potassium hydroxide (0.146 g, 2.605 mmol) were added thereto at 0° C. The solution was stirred at the same temperature, and then stirred at room temperature for 2 hours. Then, the reaction mixture was concentrated under reduced pressure to remove the solvent, and a saturated aqueous solution of sodium hydrogen carbonate was added to the concentrate, followed by extraction with ethyl acetate. The organic layer was washed with a saturated aqueous solution of sodium chloride, dried with anhydrous magnesium sulfate, filtered, and then concentrated under reduced pressure, thereby obtaining the desired compound 1125 (0.100 g, 75.0%) as a colorless oil without additional purification.

$^1$H NMR (400 MHz, DMSO-d$_6$) δ 8.04 (d, 1H, J=2.4 Hz), 7.59 (d, 2H, J=8.4 Hz), 7.47-7.45 (m, 2H), 7.16-7.11 (m, 4H), 6.82 (d, 2H, J=8.4 Hz), 6.32 (d, 1H, J=3.2 Hz), 5.37 (s, 2H), 3.69 (s, 3H), 3.46 (s, 2H), 2.95-2.91 (m, 4H), 2.91 (s, 4H), 1.78-1.77 (m, 4H); MS (ESI) m/z 512.36 (M$^+$+H).

Example 163

Synthesis of Compound 1126

Step 1: Synthesis of methyl 4-((5-(2-(pyridin-2-ylmethyl)-2,7-diazaspiro[3.5]nonan-7-yl)-1H-pyrrolo[2,3-b]pyridin-1-yl)methyl)benzoate (formula 23-3)

(formula 23-3)

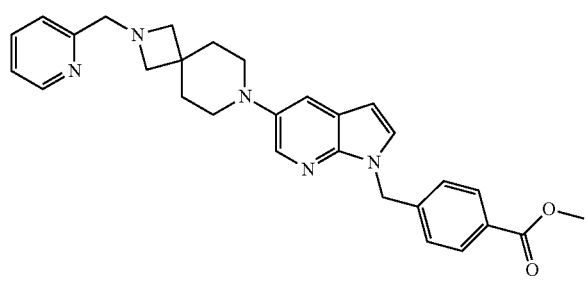

The compound of formula 23-2 (0.134 g, 0.314 mmol) was dissolved in methylene chloride (10 mL) at room temperature. To the solution, DIPEA (0.055 mL, 0.314 mmol) was added, followed by stirring at the same temperature for 30 minutes. To the reaction mixture, picolinaldehyde (0.045 mL, 0.471 mmol) and NaBH(OAc)$_3$ (0.133 g, 0.628 mmol) were added, followed by stirring at the same temperature for 5 hours. Then, water was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; methanol/methylene chloride=from 0% to 10%) to afford the desired compound of formula 23-3 (0.104 g, 68.8%) as a colorless oil.

Step 2: Synthesis of N-hydroxy-4-((5-(2-(pyridin-2-ylmethyl)-2,7-diazaspiro[3.5]nonan-7-yl)-1H-pyrrolo[2,3-b]pyridin-1-yl)methyl)benzamide (compound 1126)

(compound 1126)

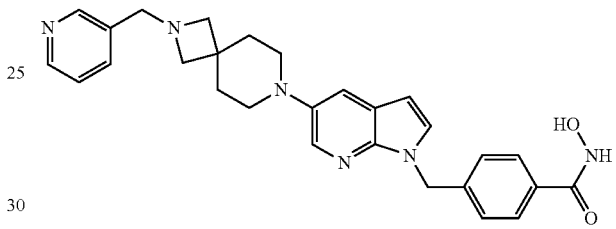

The compound of formula 23-3 (0.104 g, 0.216 mmol) prepared in step 1 was dissolved in methanol (10 mL), and hydroxylamine (50.00% solution in H$_2$O, 0.264 mL, 4.320 mmol) and potassium hydroxide (0.121 g, 2.160 mmol) were added thereto at 0° C. The solution was stirred at the same temperature for 30 minutes, and then stirred at room temperature for 2 hours. Then, the reaction mixture was concentrated under reduced pressure to remove the solvent, and a saturated aqueous solution of sodium hydrogen carbonate was added to the concentrate, followed by extraction with ethyl acetate. The organic layer was washed with a saturated aqueous solution of sodium chloride, dried with anhydrous magnesium sulfate, filtered, and then concentrated under reduced pressure, thereby obtaining the desired compound 1126 (0.080 g, 76.8%) as a colorless oil without additional purification.

$^1$H NMR (400 MHz, DMSO-d$_6$) δ 8.44-8.43 (m, 1H), 8.04 (d, 1H, J=2.4 Hz), 7.73-7.69 (m, 1H), 7.63-7.61 (m, 2H), 7.49-7.47 (m, 2H), 7.32 (d, 1H, J=7.6 Hz), 7.21-7.18 (m, 3H), 6.34 (d, 1H, J=3.6 Hz), 5.41 (s, 2H), 3.68 (s, 2H), 3.03 (s, 4H), 2.98-2.95 (m, 4H), 1.83-1.80 (m, 4H); MS (ESI) m/z 483.56 (H$^+$+H).

Experimental Examples

Measurement of Activities of Compounds According to the Present Invention—Experimental Protocol Experimental Example 1

Experiment on Inhibition of HDAC Activities (HDAC1 and HDAC6)

Assays were performed using a HDAC1 fluorimetric drug discovery assay kit (Enzolifesciences: BML-AK511) and a HDAC6 human recombinant (Calbiochem: 382180). The assay mixture of the kit was treated with a test compound at concentrations of 100, 1000 and 10000 nM for HDAC1 assay and concentrations of 0.1, 1, 10, 100 and 1000 nM for HDAC6 assay. The treated assay mixture was allowed to react at 37° C. for 60 minutes, and then was treated with a developer and allowed to stand at 37° C. for 30 minutes, followed by quantification of the fluorescence. The results of the experiment are shown in Table 20 to Table 23 below.

TABLE 20

| Compound | HDAC6 (μM) | HDAC1 (μM) |
| --- | --- | --- |
| 103 | 0.00026 | 0.382 |
| 104 | 0.0007 | 1.67 |
| 124 | 0.12 | 0.54 |
| 125 | 0.052 | 1.61 |
| 212 | 0.014 | 0.89 |
| 223 | 0.007 | 0.38 |
| 224 | 0.002 | 0.18 |
| 225 | 0.003 | 0.41 |
| 617 | 0.009 | 4.22 |
| 618 | 0.016 | 1.30 |
| 629 | 0.004 | 1.05 |
| 630 | 0.008 | 1.09 |
| 635 | 0.011 | 1.17 |
| 636 | 0.008 | 0.93 |
| 642 | 0.009 | 4.31 |
| 645 | 0.017 | 3.05 |
| 647 | 0.015 | 1.17 |
| 648 | 0.018 | 3.55 |
| 649 | 0.093 | 7.05 |
| 650 | 0.014 | 2.30 |
| 656 | 0.016 | 1.35 |
| 657 | 0.009 | 0.47 |
| 658 | 0.021 | 1.95 |
| 659 | 0.004 | 0.90 |
| 685 | 0.006 | 0.79 |
| 686 | 0.039 | 2.74 |
| 687 | 0.061 | 3.23 |
| 688 | 0.022 | 4.61 |
| 689 | 0.083 | 3.17 |
| 690 | 0.012 | 2.31 |
| 691 | 0.005 | 2.31 |
| 692 | 0.008 | 3.43 |
| 693 | 0.003 | 0.52 |
| 694 | 0.028 | 5.17 |
| 700 | 0.041 | 4.24 |
| 701 | 0.023 | 1.53 |
| 702 | 0.016 | 1.04 |
| 703 | 0.006 | 0.72 |
| 704 | 0.009 | 0.62 |
| 705 | 0.011 | 1.12 |
| 706 | 0.030 | 2.33 |
| 714 | 0.012 | 1.20 |
| 715 | 0.008 | 0.54 |
| 721 | 0.019 | 1.32 |
| 722 | 0.003 | 0.27 |
| 723 | 0.005 | 0.31 |
| 724 | 0.147 | 9.82 |
| 743 | 0.025 | 0.19 |
| 744 | 0.062 | 1.89 |
| 746 | 0.022 | 1.96 |

TABLE 21

| Compound | HDAC6 (μM) | HDAC1 (μM) |
| --- | --- | --- |
| 757 | 0.017 | 1.12 |
| 758 | 0.008 | 1.63 |
| 760 | 0.037 | 3.21 |
| 761 | 0.009 | 0.43 |
| 762 | 0.01 | 0.78 |
| 763 | 0.3 | 4.20 |
| 764 | 0.091 | 3.22 |
| 781 | 0.018 | 2.44 |

TABLE 21-continued

| Compound | HDAC6 (μM) | HDAC1 (μM) |
| --- | --- | --- |
| 783 | 0.012 | 0.45 |
| 784 | 0.016 | 0.93 |
| 785 | 0.499 | 13.59 |
| 786 | 0.0057 | 0.62 |
| 787 | 0.0249 | 2.78 |
| 799 | 0.0038 | 0.57 |
| 804 | 0.058 | 1.98 |
| 805 | 0.038 | 1.61 |
| 806 | 0.0067 | 0.68 |
| 807 | 0.0104 | 0.39 |
| 809 | 0.03 | 3.72 |
| 811 | 0.017 | 2.34 |
| 812 | 0.005 | 0.15 |
| 830 | 0.013 | 1.92 |
| 831 | 0.007 | 1.22 |
| 839 | 0.0175 | 1.91 |
| 840 | 0.0041 | 0.61 |
| 841 | 0.0069 | 0.54 |
| 842 | 0.014 | 1.79 |
| 843 | 0.014 | 0.77 |
| 844 | 0.0034 | 0.55 |
| 845 | 0.0012 | 0.30 |
| 846 | 0.0057 | 1.41 |
| 847 | 0.0056 | 0.60 |
| 848 | 0.0091 | 0.85 |
| 849 | 0.0117 | 0.29 |
| 850 | 0.0044 | 0.22 |
| 851 | 0.0127 | 1.93 |
| 852 | 0.0115 | 2.21 |
| 853 | 0.024 | 3.51 |
| 854 | 0.005 | 0.35 |
| 855 | 0.0035 | 0.25 |
| 856 | 0.0023 | 0.08 |
| 857 | 0.0248 | 2.14 |
| 858 | 0.0036 | 0.06 |
| 859 | 0.006 | 0.33 |
| 860 | 0.0025 | 0.12 |
| 861 | 0.0112 | 1.88 |
| 862 | 0.0121 | 1.43 |
| 863 | 0.0115 | 1.12 |
| 864 | 0.018 | 1.74 |
| 865 | 0.012 | 0.68 |

TABLE 22

| Compound | HDAC6 (μM) | HDAC1 (μM) |
| --- | --- | --- |
| 866 | 0.012 | 1.63 |
| 867 | 0.0078 | 0.62 |
| 868 | 0.0156 | 0.93 |
| 869 | 0.0263 | 0.35 |
| 870 | 0.0206 | 0.33 |
| 871 | 0.0927 | 3.24 |
| 872 | 0.165 | 6.34 |
| 873 | 0.0165 | 0.76 |
| 874 | 0.0185 | 0.69 |
| 875 | 0.0324 | 2.32 |
| 876 | 0.042 | 2.8 |
| 877 | 0.0087 | 0.77 |
| 878 | 0.0064 | 1.12 |
| 879 | 0.0076 | 1.05 |
| 880 | 0.006 | 0.77 |
| 881 | 0.0053 | 0.85 |
| 882 | 0.0075 | 1.14 |
| 883 | 0.0021 | 2.09 |
| 895 | 0.0076 | 1.06 |
| 896 | 0.0086 | 0.80 |
| 897 | 0.0074 | 1.09 |
| 898 | 0.0062 | 0.78 |
| 917 | 0.0058 | 0.78 |
| 927 | 0.0045 | 0.83 |
| 930 | 0.0017 | 0.25 |
| 945 | 0.0037 | 0.20 |
| 946 | 0.002 | 0.49 |
| 956 | 0.0037 | 0.83 |

TABLE 22-continued

| Compound | HDAC6 (μM) | HDAC1 (μM) |
|---|---|---|
| 957 | 0.0016 | 0.65 |
| 959 | 0.012 | 0.90 |
| 966 | 0.0038 | 0.28 |
| 984 | 0.0076 | 0.53 |
| 985 | 0.0023 | 0.51 |
| 986 | 0.0115 | 0.42 |
| 987 | 0.0057 | 0.32 |
| 988 | 0.0059 | 0.29 |
| 990 | 0.0046 | 1.36 |
| 991 | 0.032 | 0.88 |
| 992 | 0.034 | 0.86 |
| 1003 | 0.0077 | 2.68 |
| 1004 | 0.0032 | 0.61 |
| 1005 | 0.0055 | 0.75 |
| 1014 | 0.0085 | 0.67 |
| 1015 | 0.0085 | 0.67 |
| 1017 | 0.006 | 0.22 |
| 1019 | 0.0068 | 0.26 |
| 1021 | 0.014 | 0.24 |
| 1022 | 0.0058 | 0.07 |
| 1023 | 0.0033 | 0.56 |
| 1024 | 0.0018 | 0.19 |

TABLE 23

| Compound | HDAC6 (μM) | HDAC1 (μM) |
|---|---|---|
| 1025 | 0.0011 | 0.17 |
| 1028 | 0.0014 | 0.42 |
| 1098 | 5.23 | ND |
| 1101 | 0.001 | 0.50 |
| 1125 | 0.0018 | ND |
| 1126 | 0.00124 | 0.64 |

Experimental Example 2

Analysis of the Degrees of Acetylation of Tubulin, Histone H3 and Histone H4 in Cells The degrees of acetylation of Histone H3 and H4 (substrates of HDAC class 1) and tubulin (representative substrate of HDAC6) were examined by Western blot analysis in order to confirm the ability of the test compound to selectively inhibit HDAC6 in cells.

Specifically, RPMI8226 cells were seeded into a six-well plate at a density of $1.0 \times 10^6$ cells/well, and then treated with varying concentrations of each of compounds 636 and 642. After 24 hours, protein was extracted from the cells using RIPA buffer and quantified by the Bradford method. 25 μg of the protein was dissolved to sample buffer and electrophoresed on 4-12% gradient gel, and the gel was transferred to a nitrocellulose membrane for 50 minutes. The membrane was blocked in 5% skim milk solution for 1 hour. Anti-acetyl H3 antibody (1:2,000), anti-acetyl H4 antibody (1:5,000), anti-acetyl tubulin antibody (1:5,000) and anti-β-actin antibody (1:10,000) were added to 5% skim milk, and the membrane was immersed in the skim milk and allowed to react at 4° C. for 16 hours, after which it was washed three times with 1×TBS-T for 10 minutes each washing. IgG-HRP antibody (1:5,000) was added to 5% skim milk, and the membrane was immersed in the skim milk and allowed to react at room temperature for 40 minutes, after which it was washed three times with 1×TBS-T for 10 minutes each washing. Detection was performed by LAS 3000 using ECL solution. The results are shown in FIG. 1.

As can be seen in FIG. 1, in the case of both compounds 636 and 642, tubulin acetylation (HDAC6) appeared at a compound concentration as low as about 300 nM, suggesting that the compounds have high activity even at low concentrations. However, histone acetylation (HDAC1) appeared at a compound concentration of at least 10 IIM for compounds 636 and 642, suggesting that the compounds have little or no activity against HDAC1 at low concentrations. From this difference in concentration of the compounds between the expressions of tubulin and histone in cells, it can be seen that the compounds according to the present invention have high cell selectivity.

Experimental Example 3

CTLA4 Assay

In order to evaluate the effect of the compounds of the present invention on the expression of CTLA4, FOXP3+ induced regulatory T cells were induced from effector T cells (CD4+CD25−) isolated from the spleen of C57BL/6 mouse. Specifically, 6-week-old C57BL/6 mouse were purchased, and spleens were isolated therefrom, and separated into single cells by treatment with collagenase D. Effector T cells (CD4+CD25−, Teff) were separated from the mouse spleen cells using a CD4+CD25 regulatory T cell isolation kit (Miltenyi Biotec). Teff were plated on a 48-well plate at a density of $5 \times 10^5$ cells/well, and activated by adding a CD6εCD28 mAb-conjugated magnetic bead (T cell Activation/Expansion kit, Miltenyi Biotec) thereto. The activated cells were treated with TGF-β2 and each compound, and after 6 days, the cells were subjected to cell surface staining with CD4-PECy7 and CD25-APC (eBioscience) and to intracellular staining with FOXP3-Alexafluor488 and CTLA4-PE (eBioscience). Then, a change in the expression of CTLA4 in the induced regulatory T cells (iTreg) was analyzed by FACS Canto II (BD bioscience). The results of the analysis are shown in FIGS. 2a and 2b.

Figure 2A:
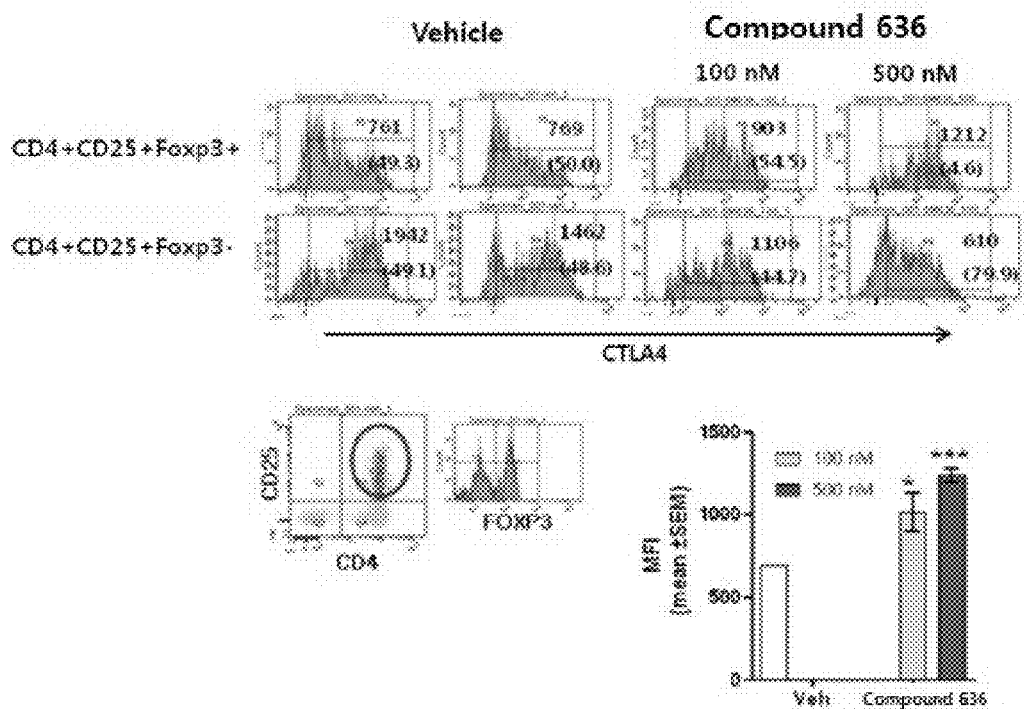
FIGS. 2a and 2b show the results of analyzing the change in expression of CTLA4 in iTreg cells by a compound of the present invention.
Figure 2B:
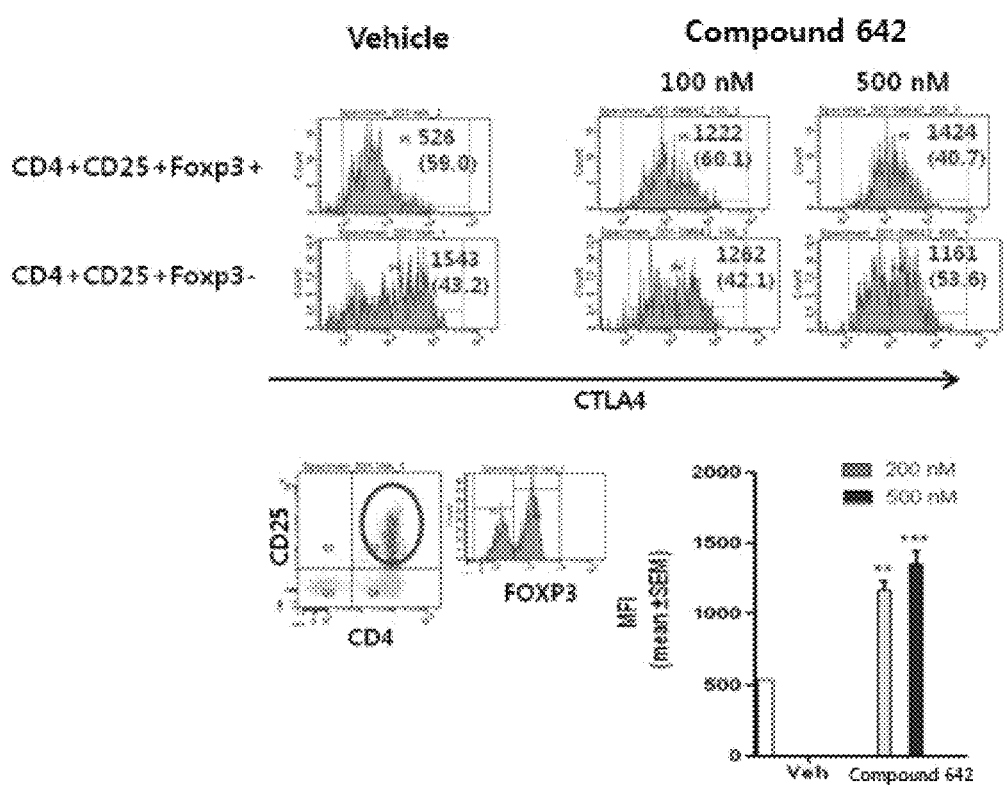

As shown in FIGS. 2a and 2b, when the change in the expression of CTLA4 was observed after the Teff were incubated with each compound for 6 days to induce iTreg cells, it could be seen that compound 636 increased the expression of CTLA4 in the iTreg (CD4+CD25+Foxp3+) population by 1.5-2 times when used at concentrations of 100 and 500 nM, and compound 642 increased the expression of CTLA4 in the iTreg cells by 2 times or more.

Experimental Example 4

Analysis of the Function of Suppressing Regulatory T Cells

The effect of compound 636 on the proliferation of effector T cells in the co-culture condition of the regulatory T cells (Treg) and effector T cells (Teff) isolated from the spleen of C57BL/6 mouse was evaluated.

Specifically, 6-week-old C57BL/6 mouse were purchased, and spleens were isolated therefrom, and separated into single cells by treatment with collagenase D. Teff (CD4$^+$CD25$^-$) and Treg (CD4$^+$CD25$^{high}$) were isolated from the mouse spleen cells using a CD4$^+$CD25$^{high}$ regulatory T cell isolation kit (Miltenyi Biotec). The Teff were stained with 5 μM Cell Proliferation Dye eFluor® 670 (eBioscience) at 37° C. under a light-shielded condition for 10 minutes, and incubated in cold complete media on ice for 5 minutes to stop the staining reaction, and then washed three times with complete media. The eFluor-stained effector T cells and the Treg were co-cultured on a U-bottom plate at a ratio of 2:1, and activated by adding a CD3εCD28 mAb-conjugated magnetic bead (T cell Activation/Expansion kit, Miltenyi Biotec) thereto. The activated cells were treated with compound 636, and after 3 days, the proliferation of the Teff was evaluated by analyzing the dilution pattern of eFluor® 670 with FACS Canto II (BD bioscience). The results of the analysis are shown in FIGS. 3 and 4.

Figure 3:
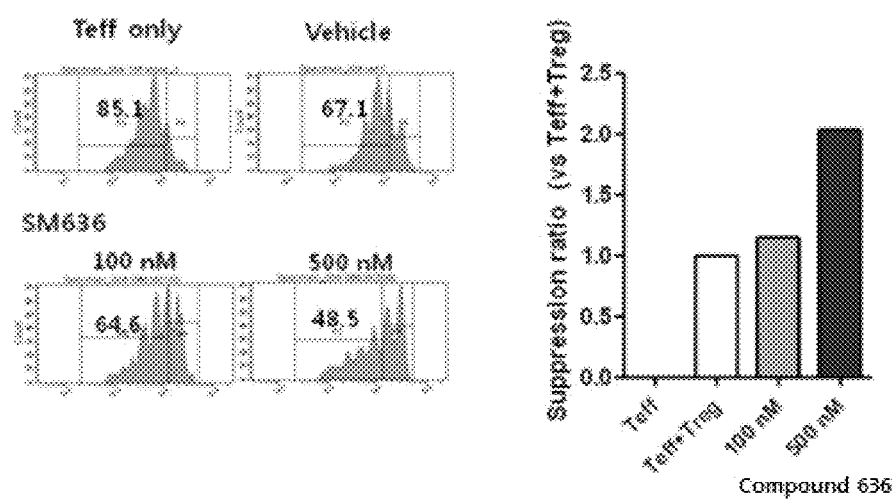
FIG. 3 shows the results of analyzing the effect of a compound of the present invention on the functionary improvement of Treg cells.
Figure 4:
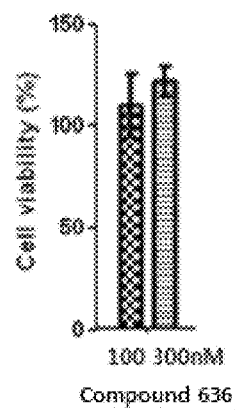
FIG. 4 shows the results of analyzing the effect of a compound of the present invention on the death of Teff cells.

As shown in FIGS. 3 and 4, the viability of the Teff treated with compound 636 for 24 hours did not differ from that of the non-drug-treated group. In the vehicle group including the Treg not treated with the compound, the differentiation of Teff was suppressed by 27%. However, the suppression ratio of Teff in the group treated with compound 636 was 2 times higher than that in the vehicle group. This suggests that compound 636 enhances the function of Treg to inhibit the differentiation of Teff.

Experimental Example 5

TNFa Assay

The effect of the compounds of the present invention on the secretion of TNFa from macrophages was evaluated using THP-1 cell strain.

Specifically, THP-1 cells were seeded into a 24-well plate at a density of $1.0 \times 10^5$ cells/well, and then allowed to differentiate into macrophages using PMA (phorbol 12-myristate 13-acetate) for 24 hours. Then, the cells were pretreated with the compounds of the present invention for 24 hours. Next, the cells were washed, and stimulated by treated with 100 ng/mL LPS (*E. coli*, O55:B5, Sigma) for 4 hours. Then, the supernatant was collected, and the amount of TNFa in the collected supernatant was measured using a TNFa ELISA kit (eBioscience). The results of the measurement are shown in FIG. 5.

Figure 5:
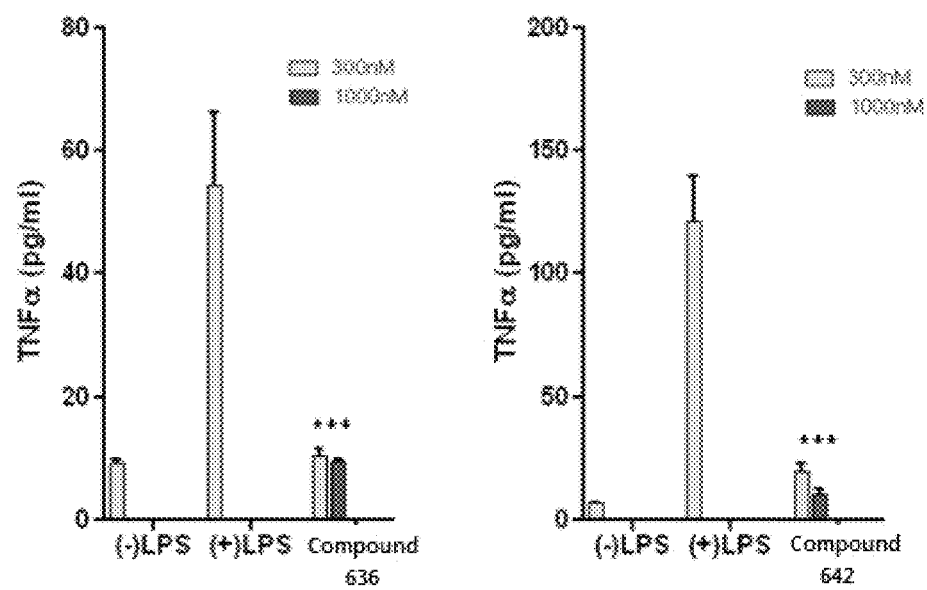
FIG. 5 shows the results of analyzing the effect of a compound of the present invention on the inhibition of TNFa secretion.

As shown in FIG. 5, when the cells were treated with 300 and 1000 nM of compounds 636 and 642, the secretion of TNFa from the cells was significantly inhibited by 80% or more.

The invention claimed is:

1. A compound of the following formula I, an isomer thereof, or a pharmaceutically acceptable salt thereof:

Formula I

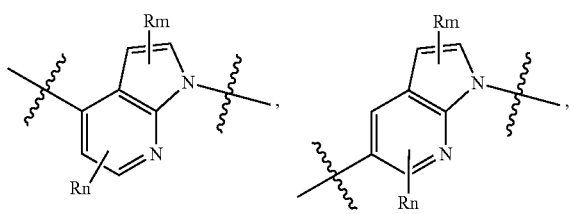

wherein
X is C or N;
Rh is hydrogen, halogen, —CF$_3$, or —C$_{1-5}$ alkyl;
A is selected from the group consisting of

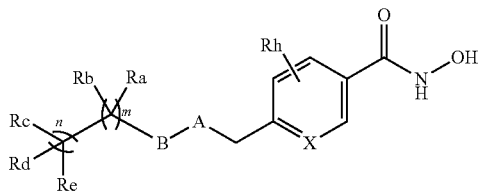

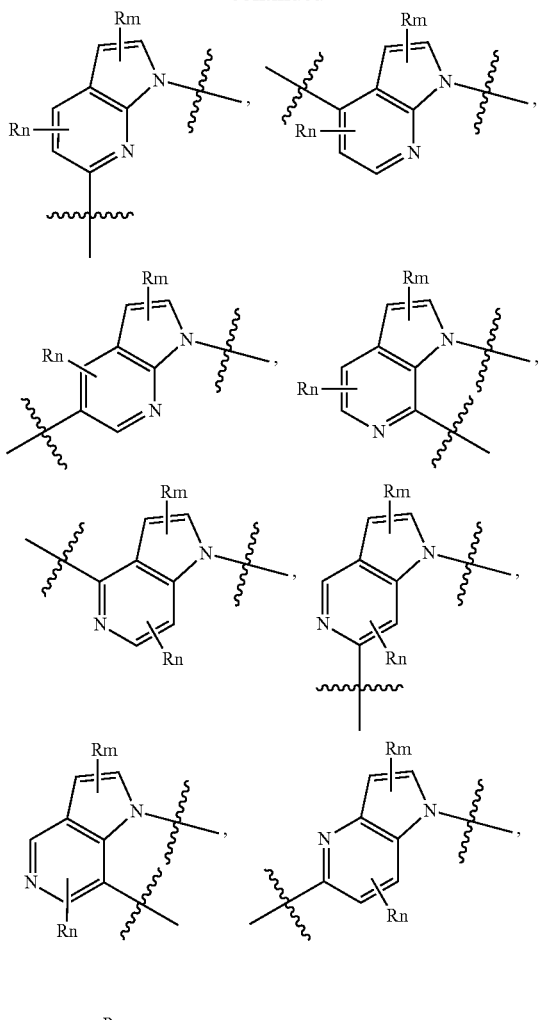

Rm and Rn are each independently hydrogen, halogen, C$_{1-5}$ alkyl, or C$_{3-12}$ cycloalkyl, wherein the C$_{1-5}$ alkyl and C$_{3-12}$ cycloalkyl may each independently be unsubstituted or substituted with halogen, —CN, —OC$_{1-5}$ alkyl or —C$_{1-5}$ alkyl at one or more hydrogen atoms thereof;

B is selected from the group consisting of

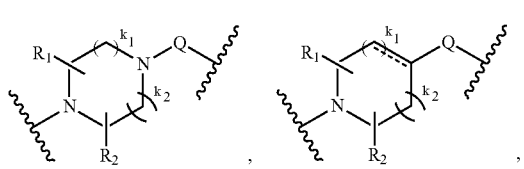

-continued

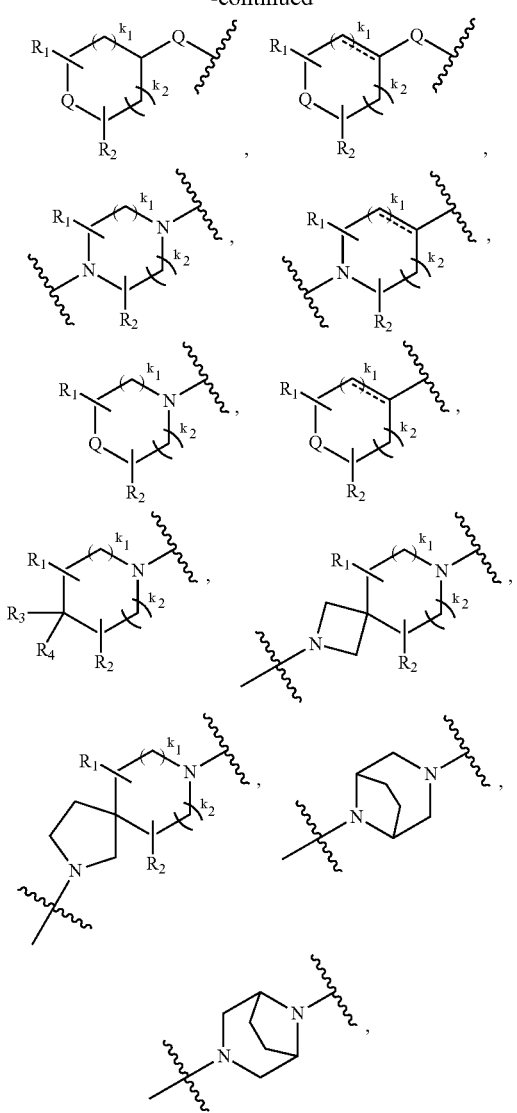

aryl, heteroaryl, $C_{3-12}$ cycloalkyl, and $C_{3-12}$ cycloalkenyl, wherein the aryl, heteroaryl, $C_{3-12}$ cycloalkyl and $C_{3-12}$ cycloalkenyl may each independently be unsubstituted or substituted with halogen, —$C_{1-5}$ alkyl, —$NH_2$, —OH, —$OC_{1-5}$ alkyl or —$CF_3$ at one or more hydrogen atoms thereof, and the dotted line denotes a single or double bond;

Q is aryl, heteroaryl, —$C_{1-5}$ alkyl-aryl, —O-aryl, —$NR_5$-aryl, —$C_{1-5}$ alkyl-heteroaryl, —O-heteroaryl or —$NR_5$-heteroaryl, wherein the aryl and heteroaryl may each independently be unsubstituted or substituted with halogen, —$C_{1-5}$ alkyl, —$NH_2$, —OH, —$OC_{1-5}$ alkyl, —$CF_3$, —$NHC_{1-5}$ alkyl, —$N(C_{1-5}$ alkyl) or —$NHSO_2C_{1-5}$ alkyl at one or more carbon atoms thereof;

$R_1$ and $R_2$ are each independently hydrogen, halogen, —$C_{1-5}$ alkyl, —$NH_2$, —OH, —$OC_{1-5}$ alkyl or —$CF_3$;

$R_3$ and $R_4$ are each independently hydrogen, halogen, —$CF_3$, —$C_{1-5}$ alkyl, or —$NHCO(O)C_{1-5}$ alkyl;

$R_5$ is hydrogen or —$C_{1-5}$ alkyl;

$k_1$ and $k_2$ are each independently 0, 1 or 2;

Ra and Rb are each independently hydrogen, halogen, —$C_{1-5}$ alkyl, —$OC_{1-5}$ alkyl, —$C_{3-12}$ cycloalkyl, =O, or —$SO_2$, provided that if any one of Ra and Rb is =O or —$SO_2$, the other one is null, wherein the —$C_{1-5}$ alkyl and —$C_{3-12}$ cycloalkyl may each independently be unsubstituted or substituted with halogen, —CN, —$OC_{1-5}$ alkyl or —$C_{1-5}$ alkyl at one or more hydrogen atoms thereof;

m is 0, 1 or 2;

Rc and Rd are each independently hydrogen, halogen, =O, —$C_{1-5}$ alkyl, —$C_{3-12}$ cycloalkyl, —$CO(O)C_{1-5}$ alkyl, —$C_{1-5}$ alkyl-OH, aryl or heteroaryl, or are linked together to form —$C_{3-12}$ cycloalkyl, provided that if any one of Rc and Rd is =O, the other one is null, wherein the aryl, heteroaryl and $C_{3-12}$ cycloalkyl may each independently be unsubstituted or substituted with halogen, —$CF_3$, —$C_{1-5}$ alkyl or —$OC_{1-5}$ alkyl at one or more hydrogen atoms thereof;

n is 0, 1 or 2; and

Re is hydrogen, halogen, —$CF_3$, —$C_{1-3}$ perfluoroalkyl, —$C_{1-5}$ alkyl, —$OC_{1-5}$ alkyl, —$C_{2-12}$ heterocycloalkyl, —$C_{3-12}$ cycloalkyl, aryl, heteroaryl, —OH, —COOH, —$NH_2$, —$NHC_{1-5}$ alkyl, —$N(C_{1-5}$ alkyl$)_2$, or null, wherein the —$C_{1-5}$ alkyl, —$C_{2-12}$ heterocycloalkyl, —$C_{3-12}$ cycloalkyl, aryl and heteroaryl may each independently be unsubstituted or substituted with halogen, —CN, —$CF_3$, —$OC_{1-5}$ alkyl, —$C_{1-5}$ alkyl, —$CO(O)C_{1-5}$ alkyl, —$C_{2-12}$ heterocycloalkyl, —$C_{1-5}$ alkyl-$C_{2-12}$ heterocycloalkyl, or heteroaryl at one or more hydrogen atoms thereof.

2. The compound of formula I, isomer thereof, or pharmaceutically acceptable salt thereof according to claim 1, wherein A is selected from the group consisting of 3. The compound of formula I, isomer thereof, or pharmaceutically acceptable salt thereof according to claim 2, wherein A is selected from the group consisting of

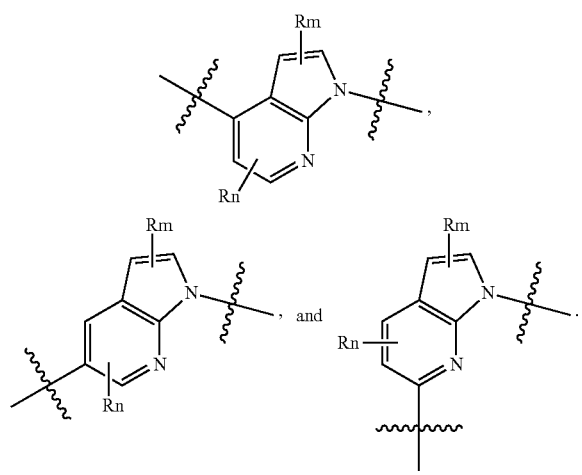

4. The compound of formula I, isomer thereof, or pharmaceutically acceptable salt thereof according to claim 1, wherein B is selected from the group consisting of

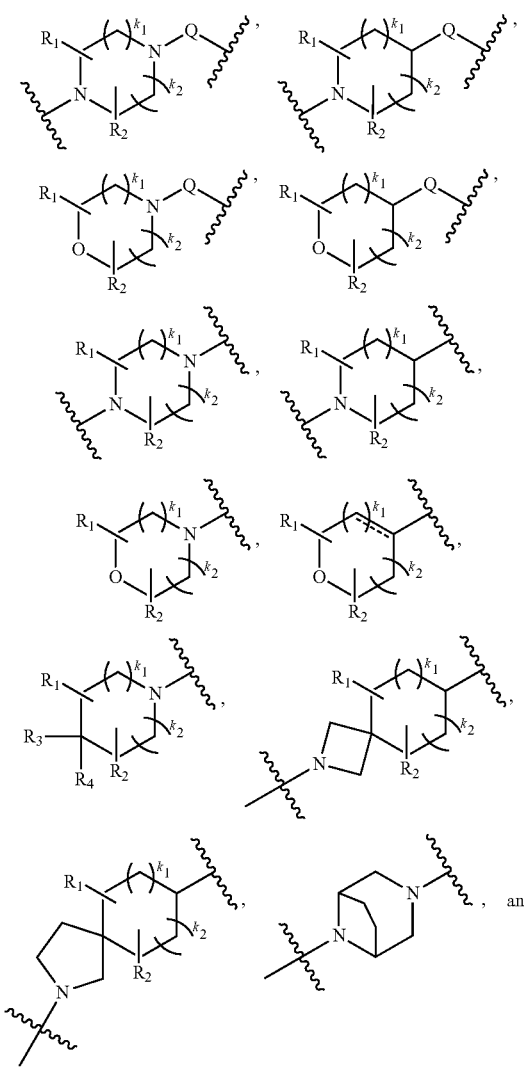

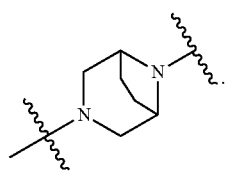

5. The compound of formula I, isomer thereof, or pharmaceutically acceptable salt thereof according to claim 4, wherein B is selected from the group consisting of

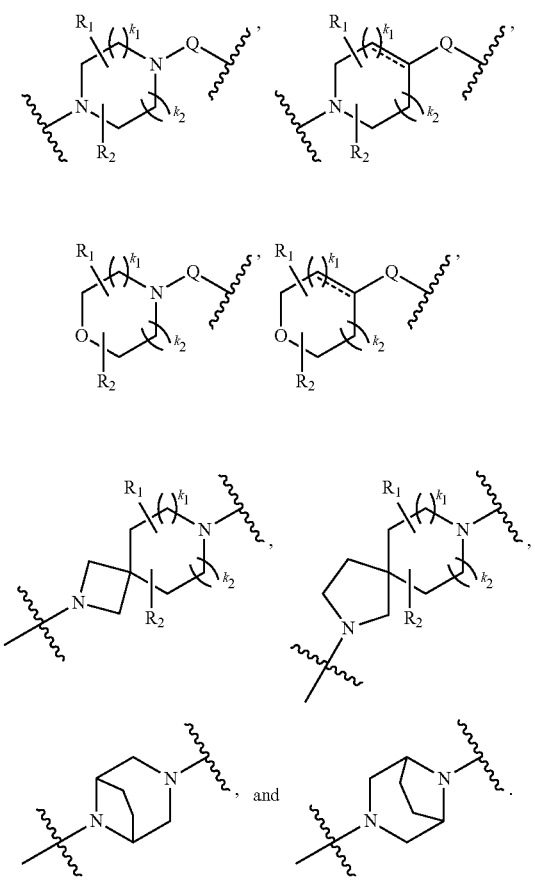

6. The compound of formula I, isomer thereof, or pharmaceutically acceptable salt thereof according to claim 4, wherein X is C;

Rh is hydrogen;

A is selected from the group consisting of

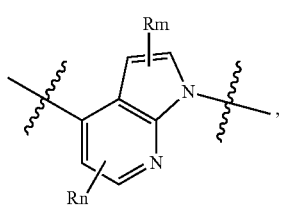

-continued

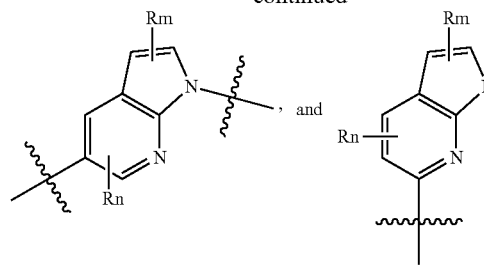

and

-continued

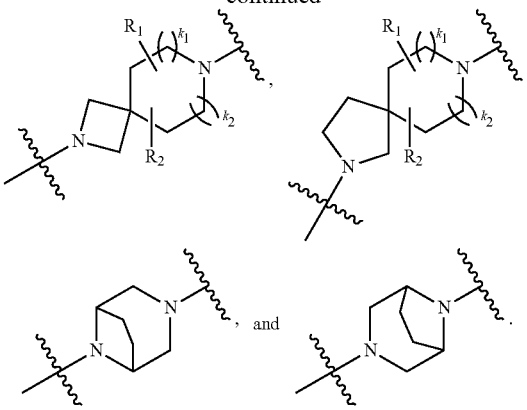

, and

B is selected from the group consisting of

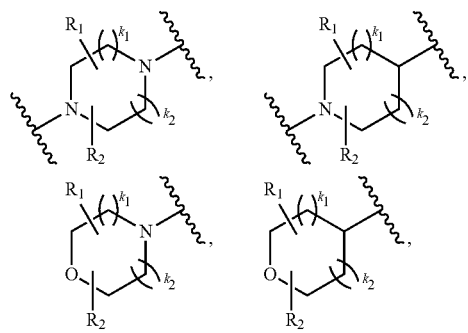

7. The compound of formula I, isomer thereof, or pharmaceutically acceptable salt thereof according to claim 6, wherein
Ra and Rb are each independently hydrogen or —$C_{1-5}$ alkyl;
m is 0 or 1;
Rc and Rd are each independently hydrogen, —$C_{1-5}$ alkyl, or are linked together to form —$C_{3-12}$ cycloalkyl;
n is 0 or 1; and
Re is hydrogen, halogen, —$CF_3$, —$C_{1-5}$ alkyl, —OH, aryl, or heteroaryl wherein the aryl, or heteroaryl may each independently be unsubstituted or substituted with halogen, —$CF_3$, —$OC_{1-5}$ alkyl, —$C_{2-12}$ heterocycloalkyl, or —$C_{1-5}$ alkyl-$C_{2-12}$ heterocycloalkyl at one or more hydrogen atoms thereof.

8. The compound of formula I, isomer thereof, or pharmaceutically acceptable salt thereof according to claim 1, wherein the compound of formula I is selected from the group consisting of the following compounds:

103

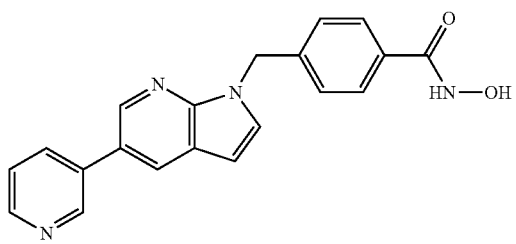

104

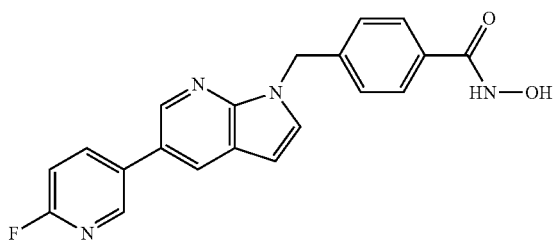

124

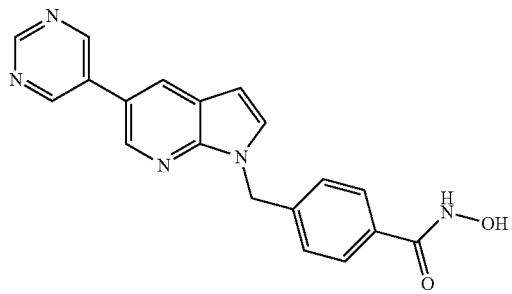

125

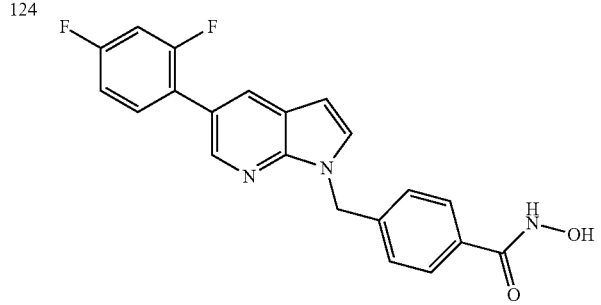

-continued
212
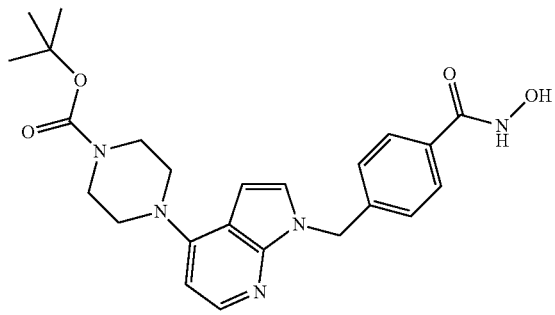
223
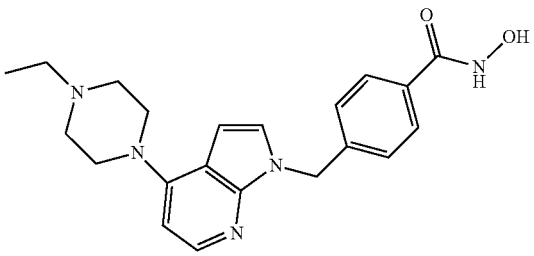
224
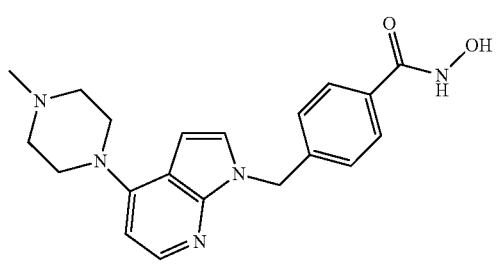
225
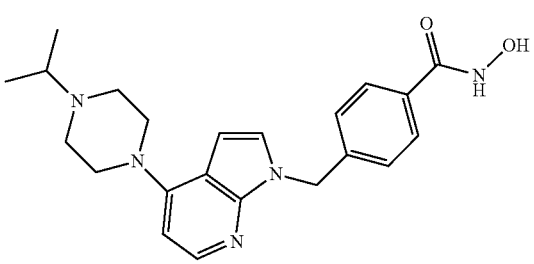
617
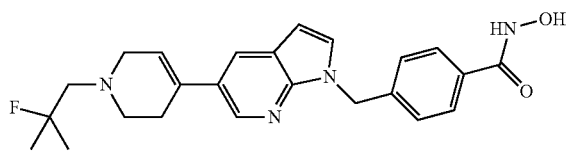
618
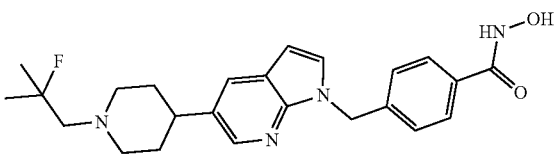
629
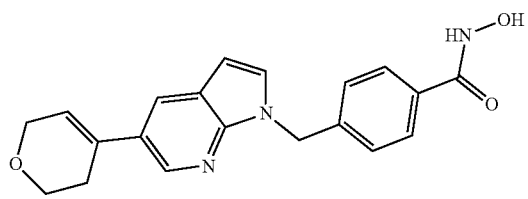
630
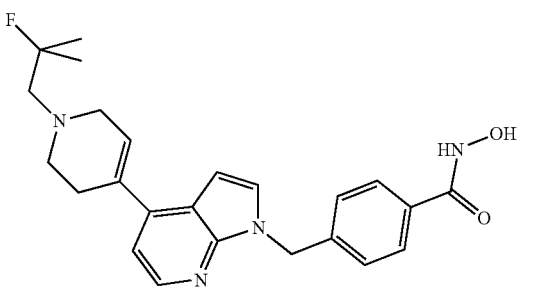
635
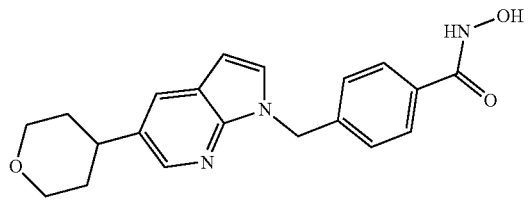
636
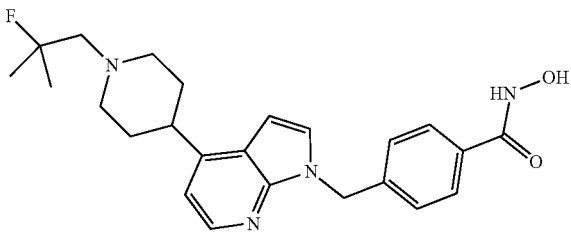
642
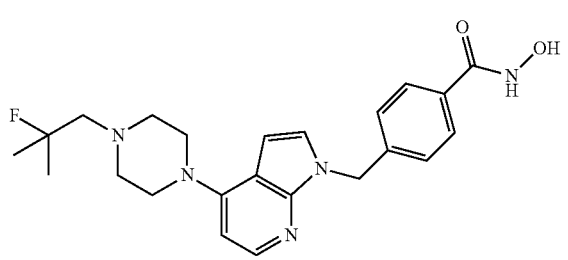
645
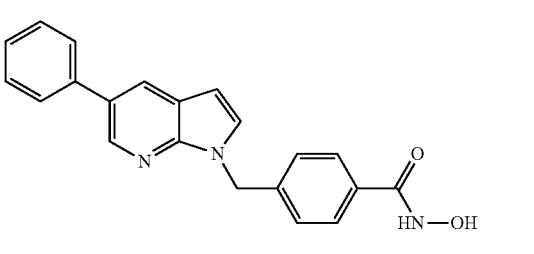

-continued
| 401 | 402 |
|---|---|
| 647 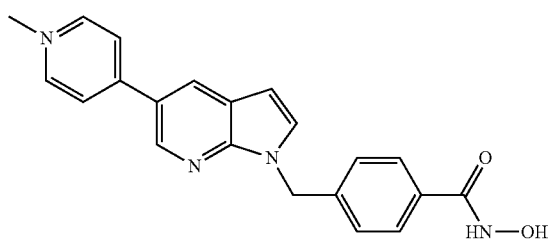 | 648 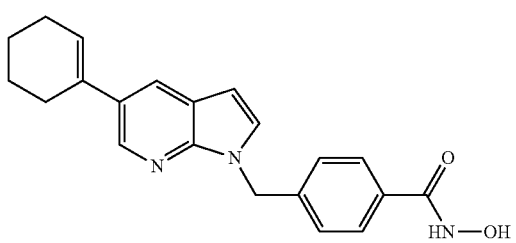 |
| 649 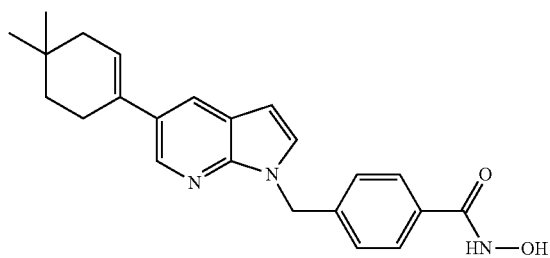 | 650 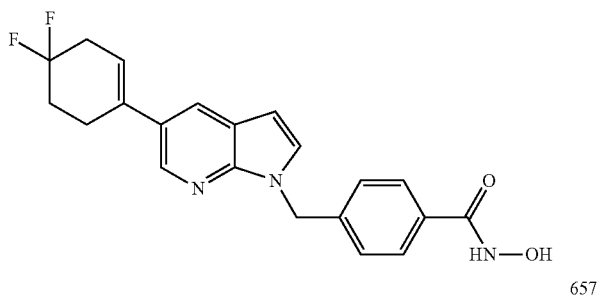 |
| 656 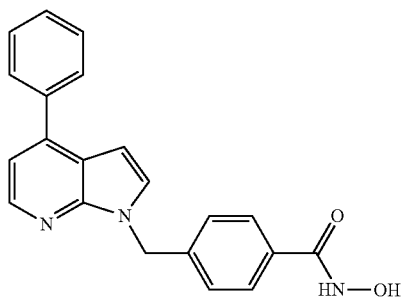 | 657 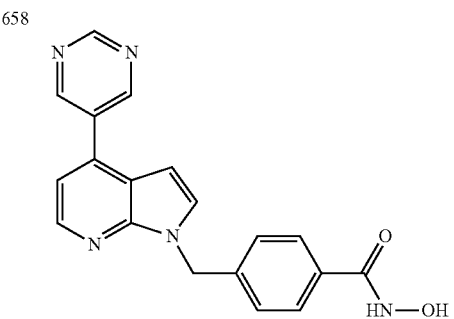 |
| 658 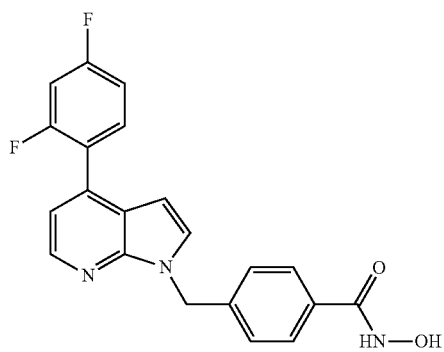 | 659 |
| 685 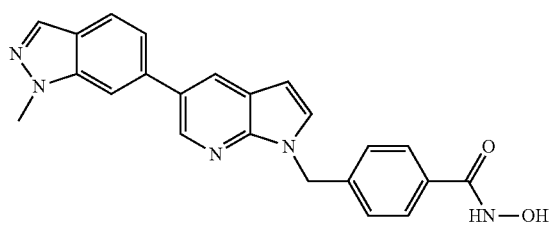 | 686 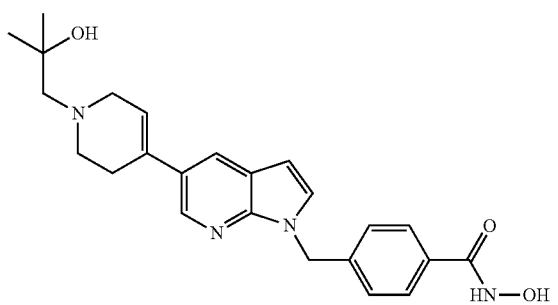 |

-continued
687
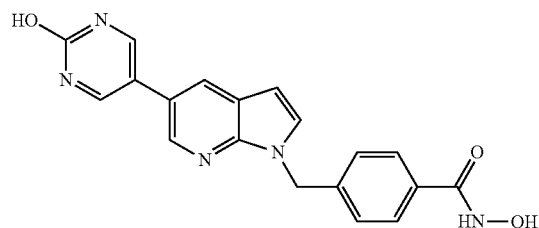
688
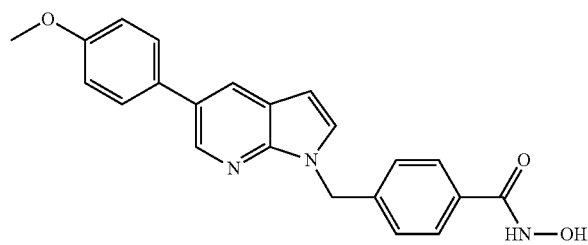 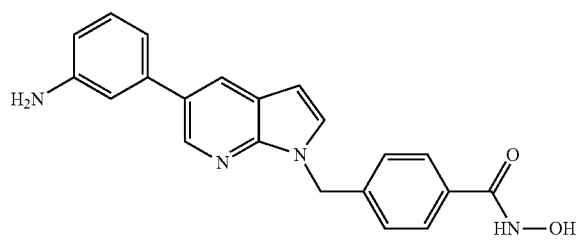
689 690
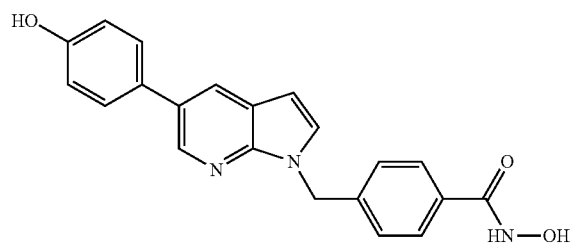 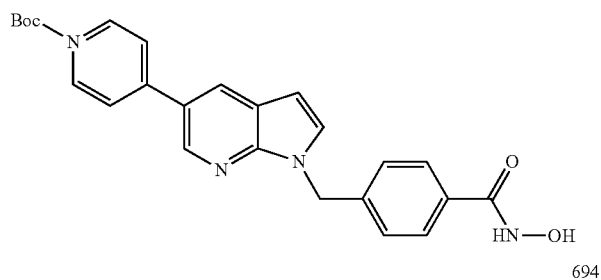
691 692
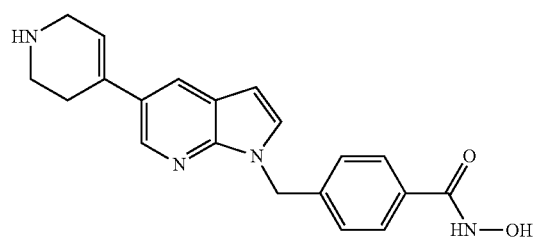 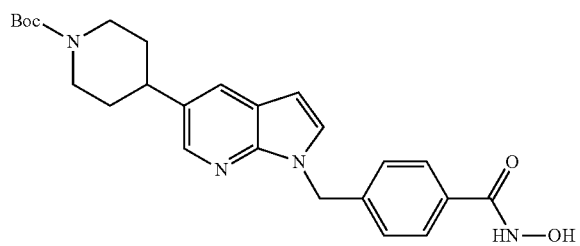
693 694
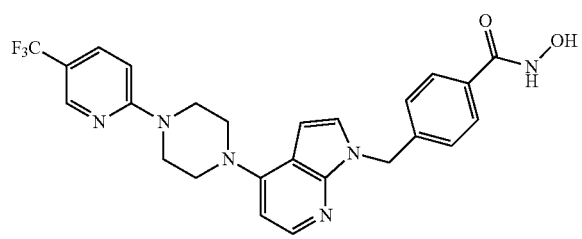 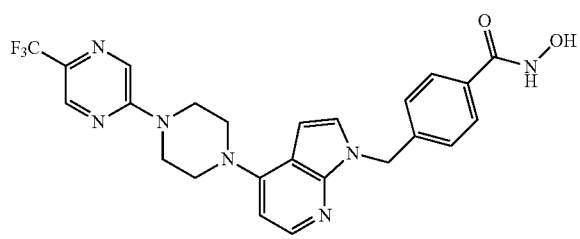
700 701
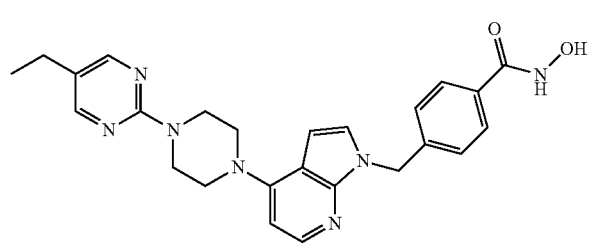 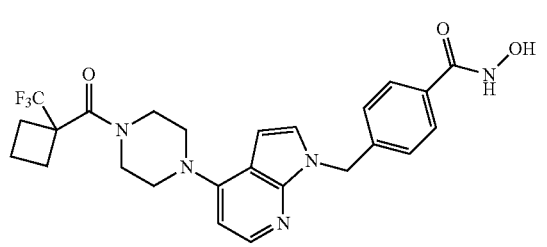
702 703

-continued
| 704 | 705 |
|---|---|
| 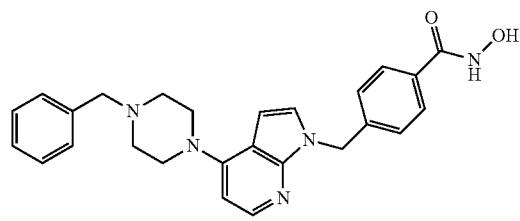 | 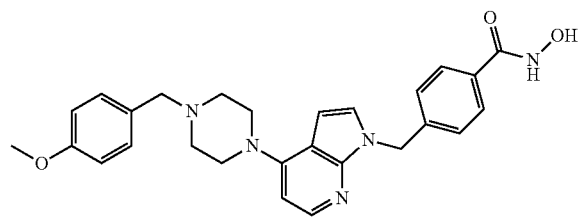 |
| 706 | 714 |
| 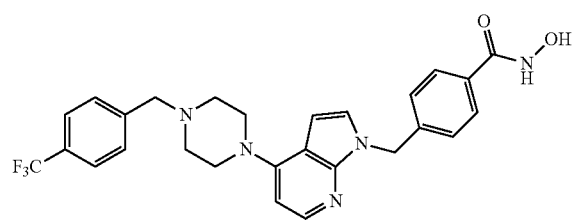 | 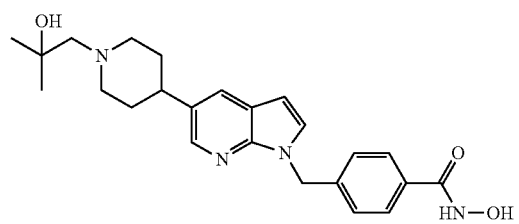 |
| 715 | 721 |
| 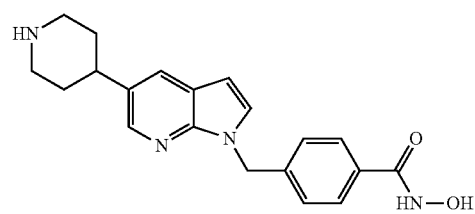 | 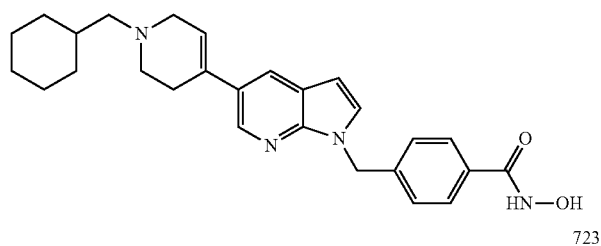 |
| 722 | 723 |
| 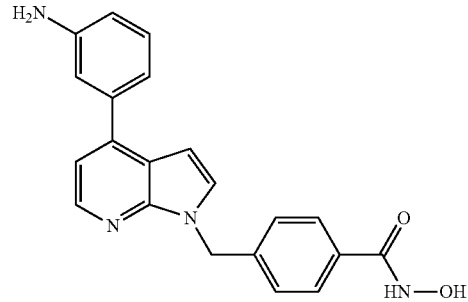 | 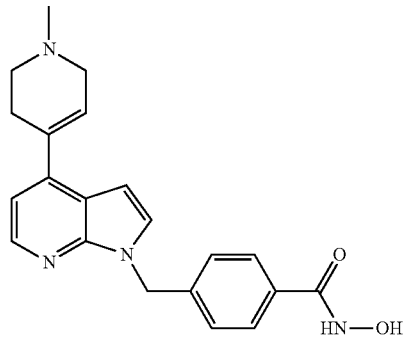 |
| 724 | 743 |
| 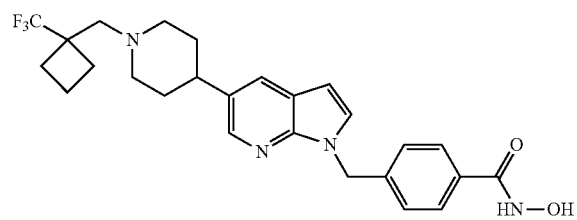 | 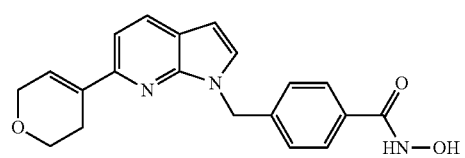 |
| 744 | 746 |
| 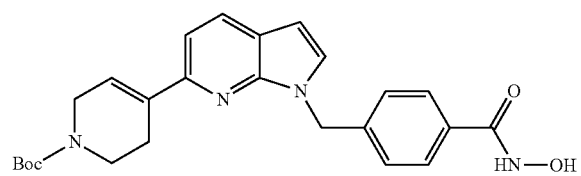 | 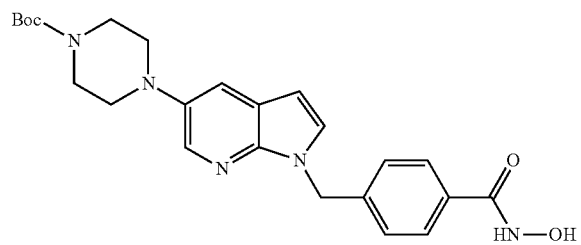 |

407 408
-continued
757 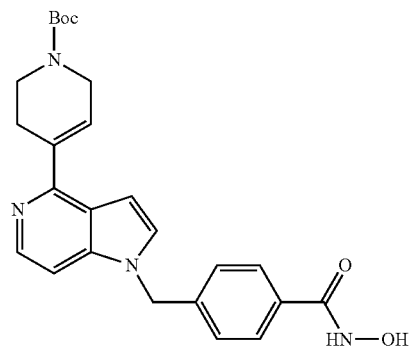 758 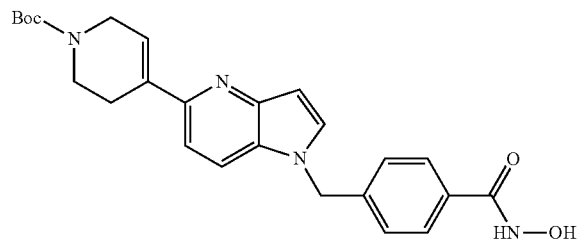
759 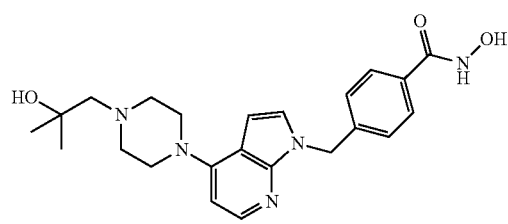 760 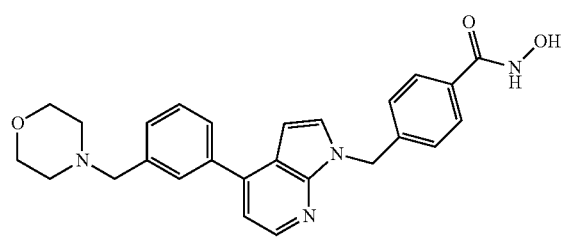
761 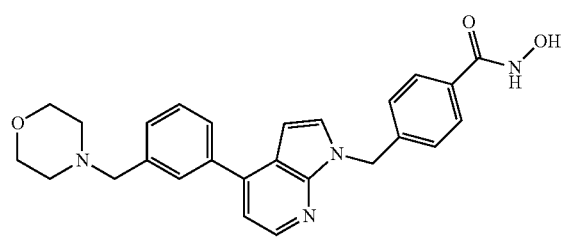 762
763 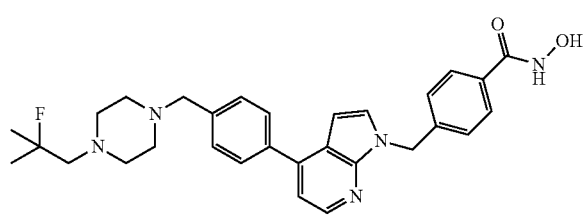 764 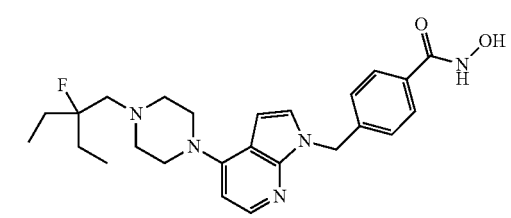
781 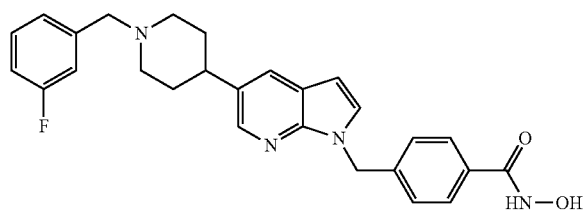 783 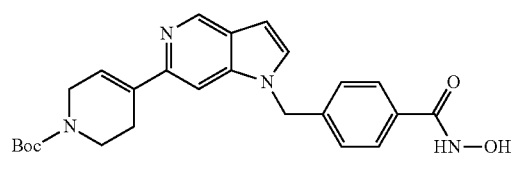

409 410
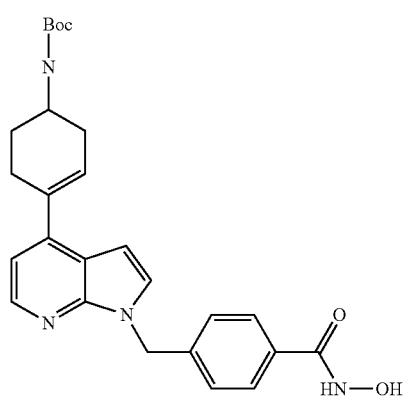
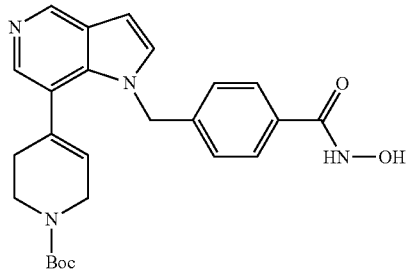
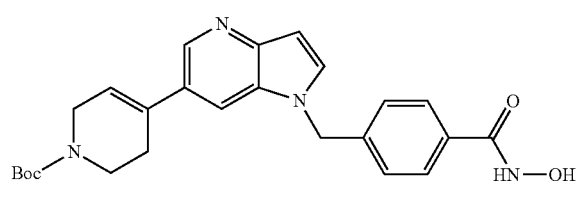
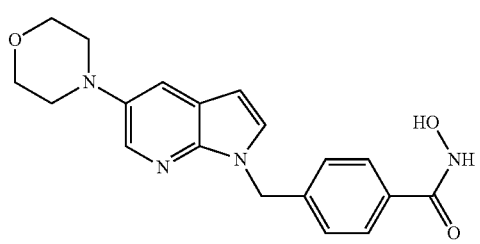
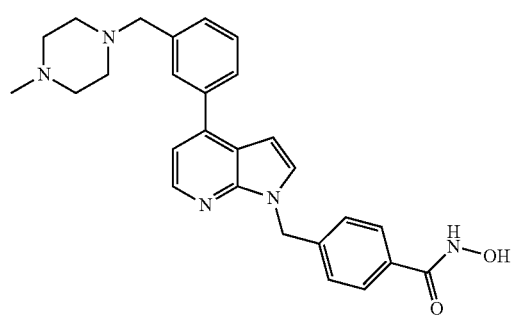
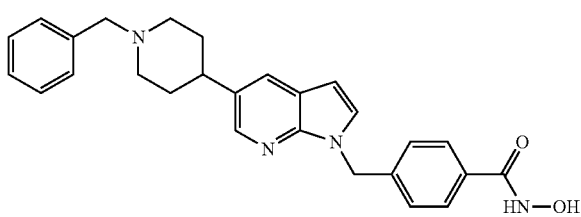
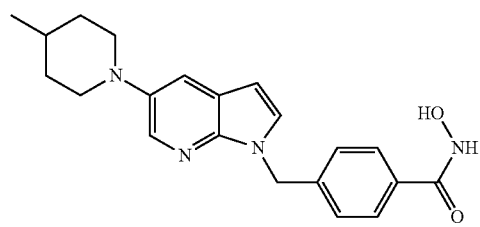
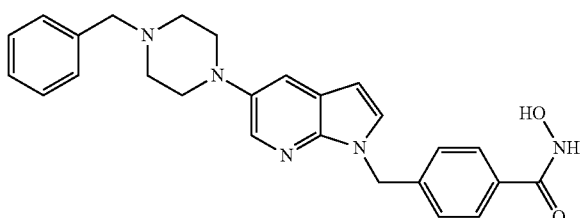
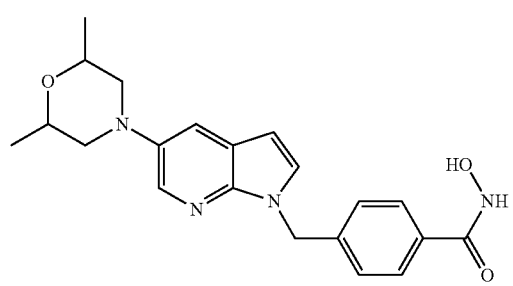
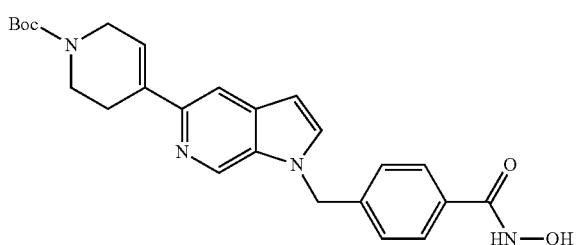

411 412
-continued
809
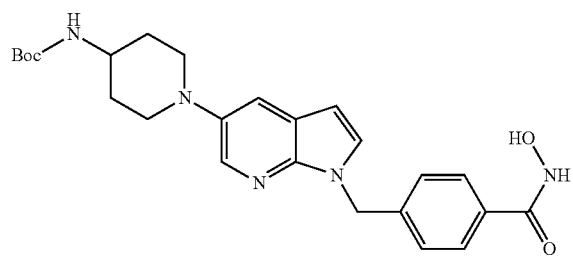
810
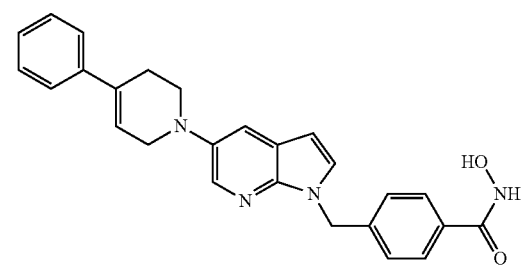
812
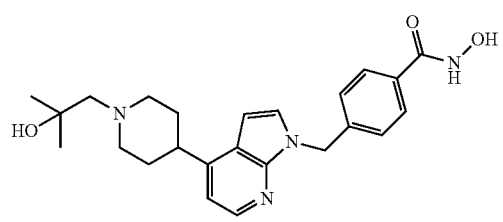
830
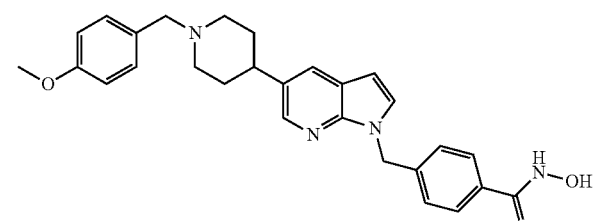
831
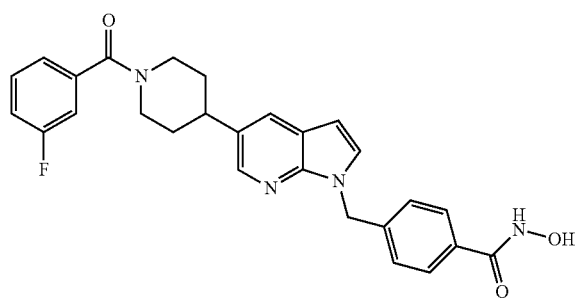
839
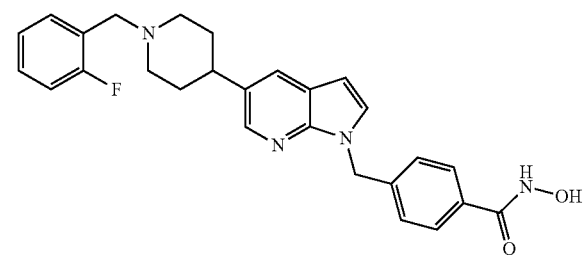
840
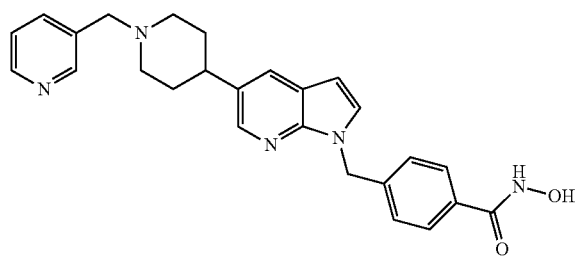
841
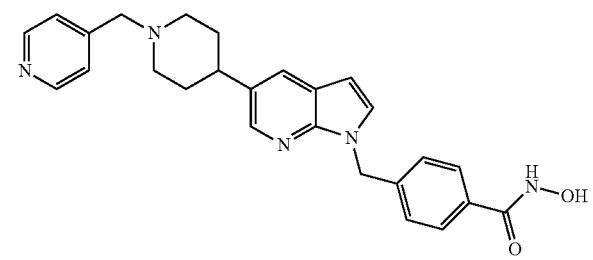
842
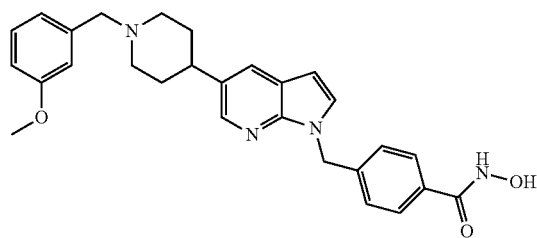
843
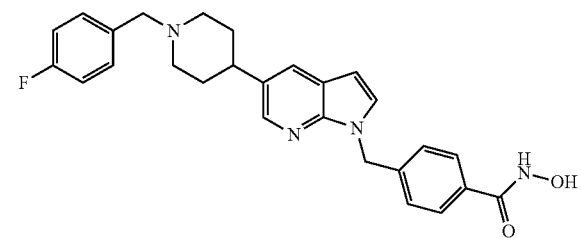

-continued
844
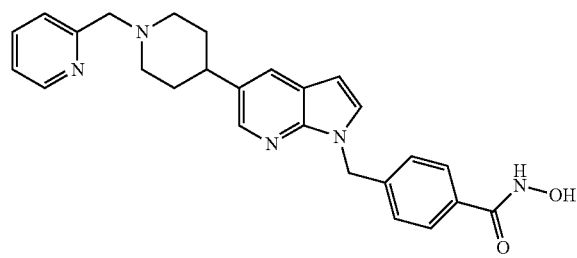
845
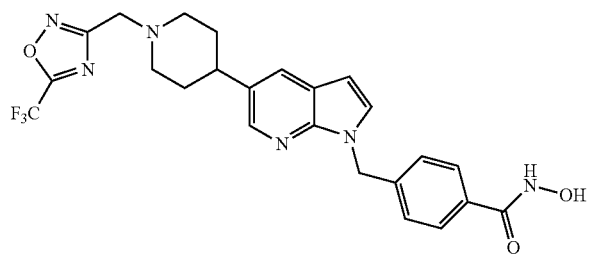
846
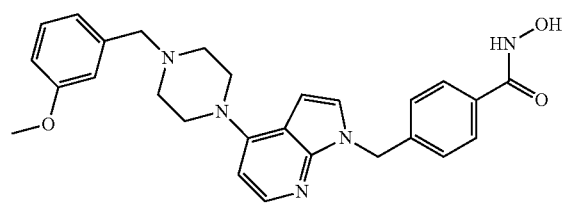
847
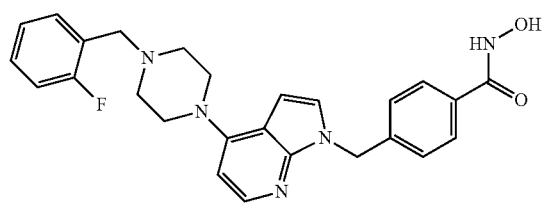
848
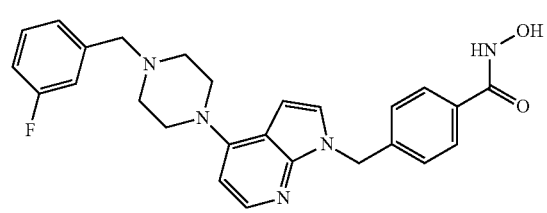
849
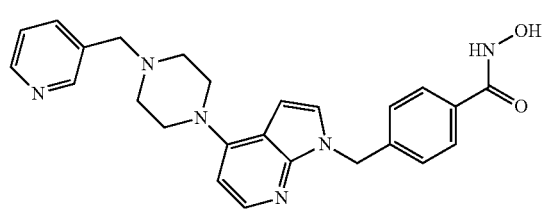
850
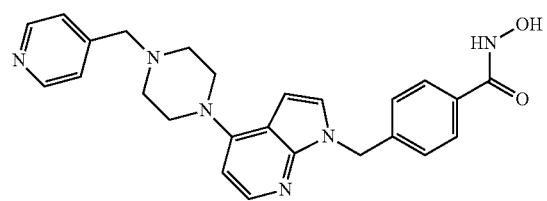
851
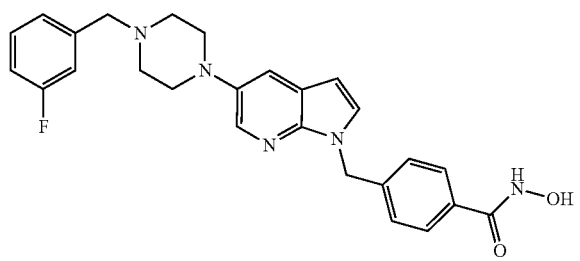
852
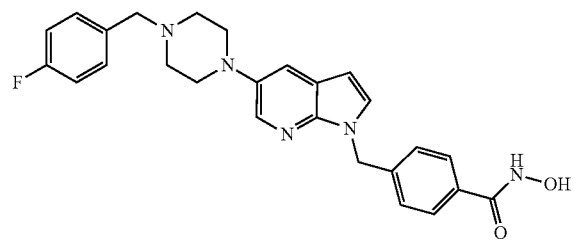
853
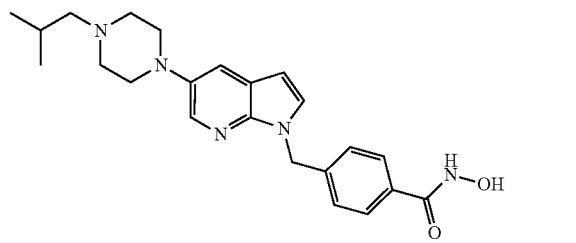
854
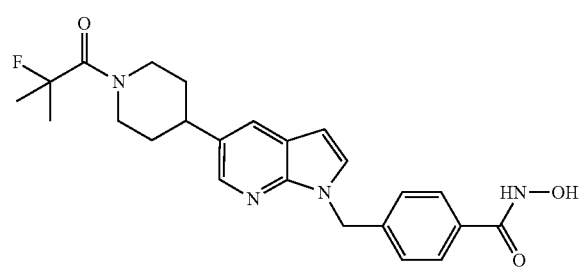
855
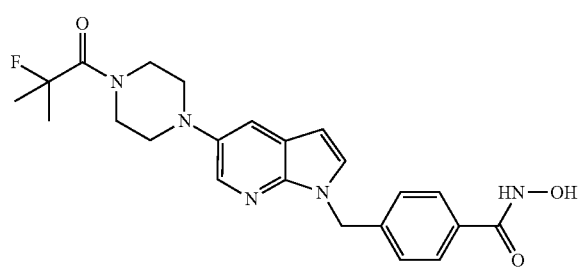

415
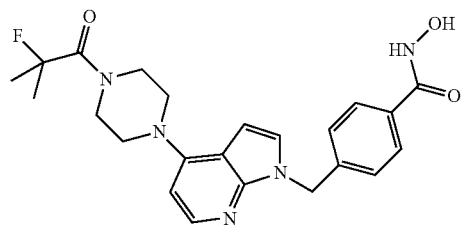
856
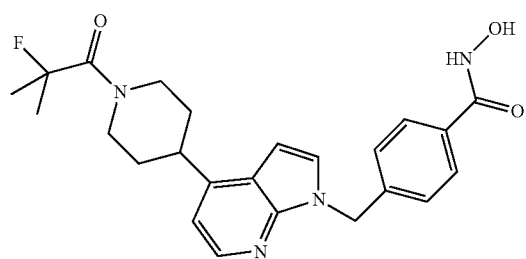
858
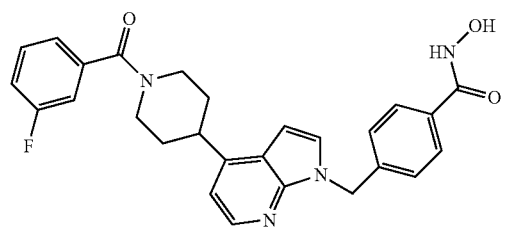
860
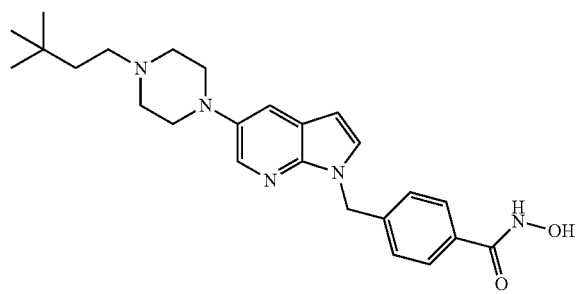
862
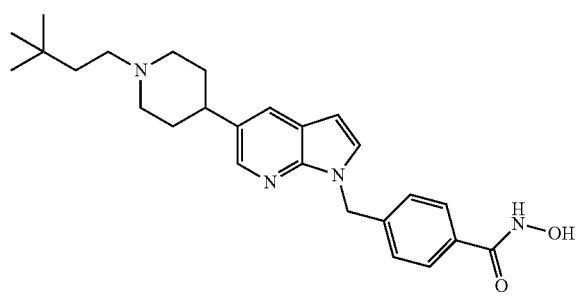
864
416
-continued
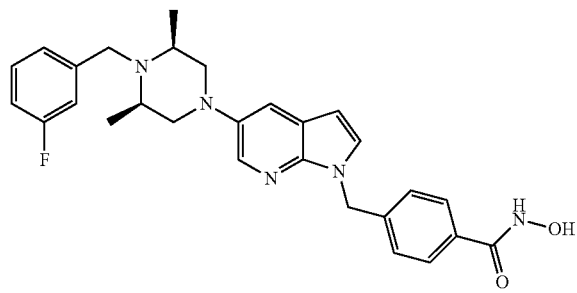
857
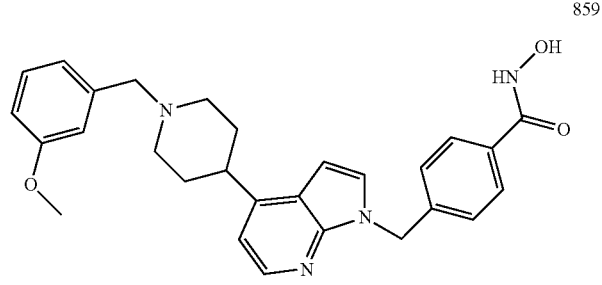
859
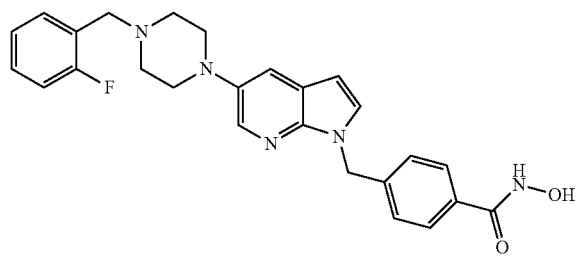
861
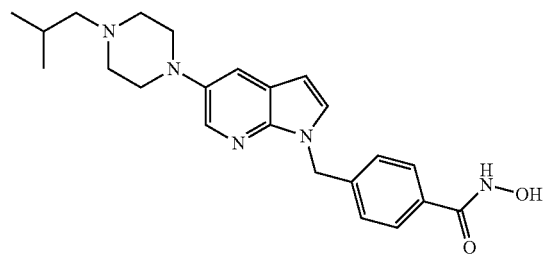
863
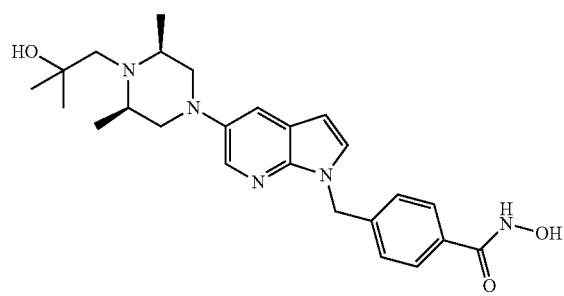
865

417                                          418
-continued
866 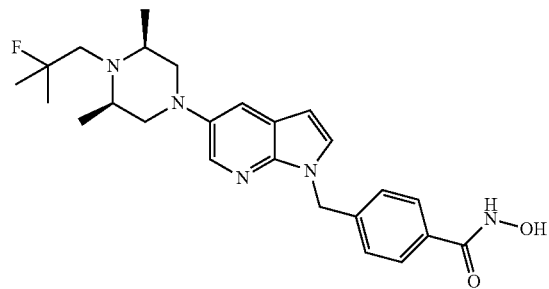  867 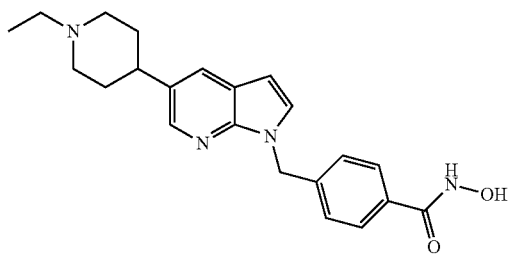
868 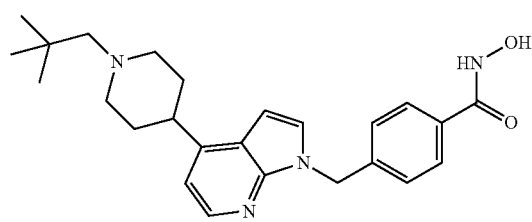  869 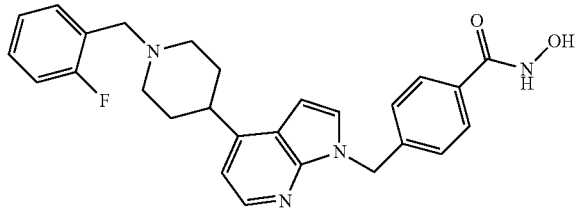
870 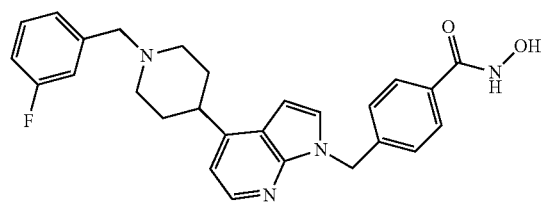  871 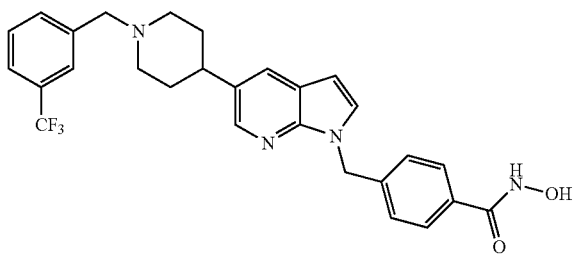
872 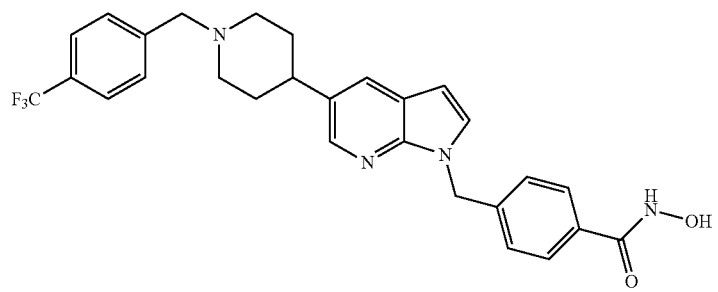
873 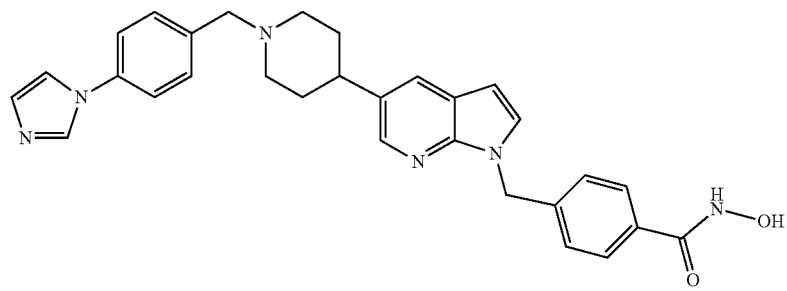

-continued
| | |
|---|---|
| 874 | 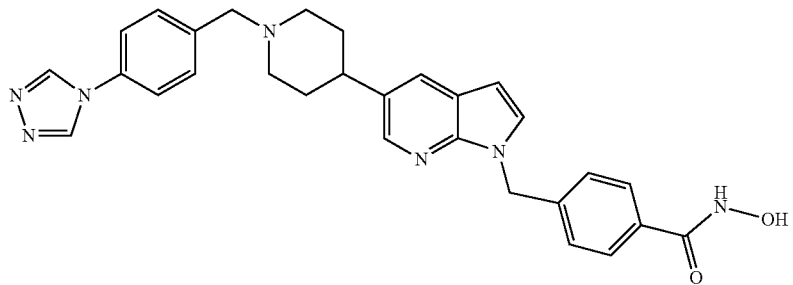 |
| 875 | 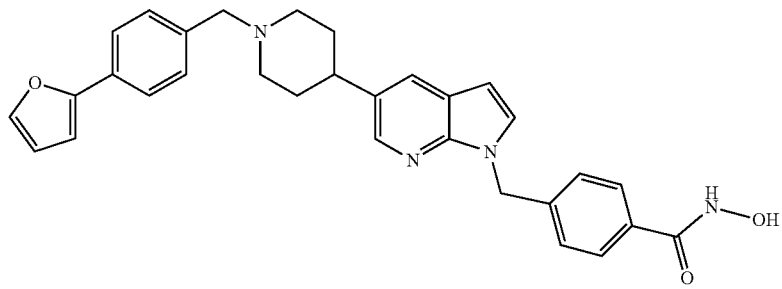 |
| 876 | 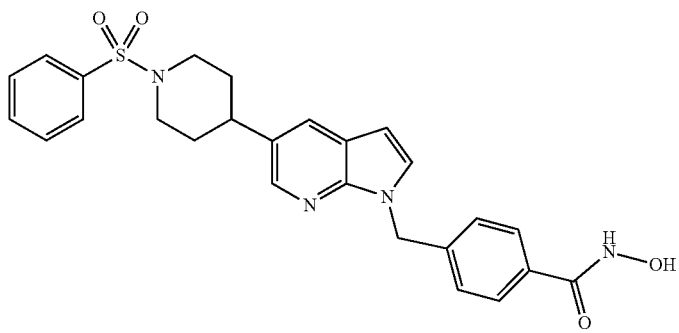 |
| 877 | 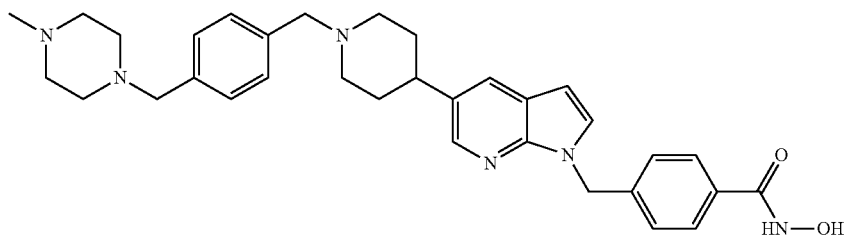 |
| 878 | 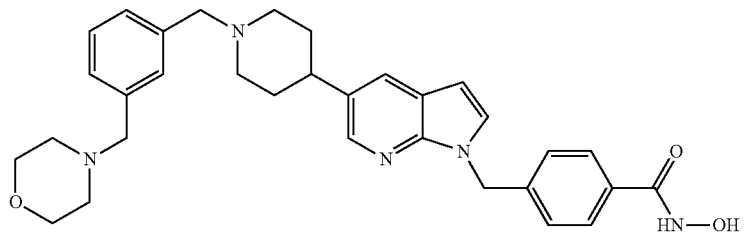 |
| 879 | 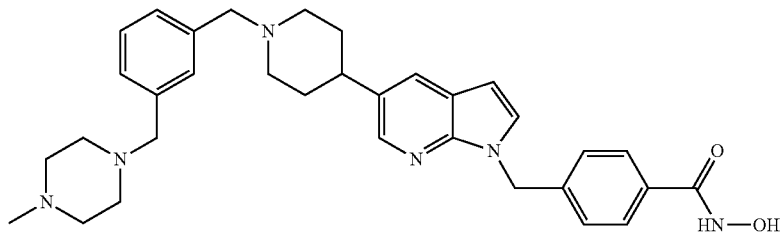 |

880 881
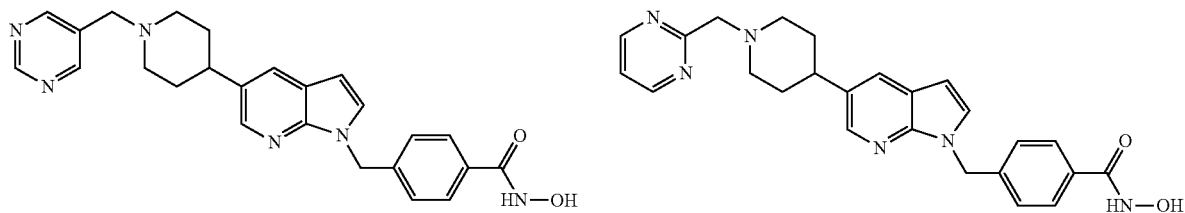
882
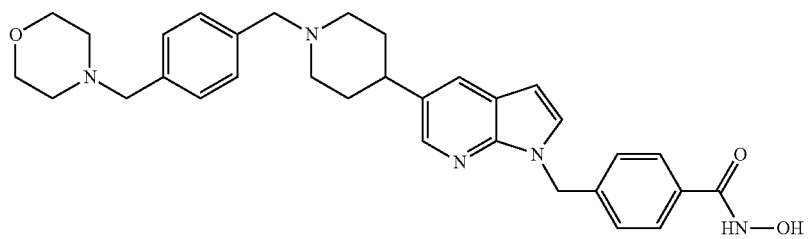
883 884
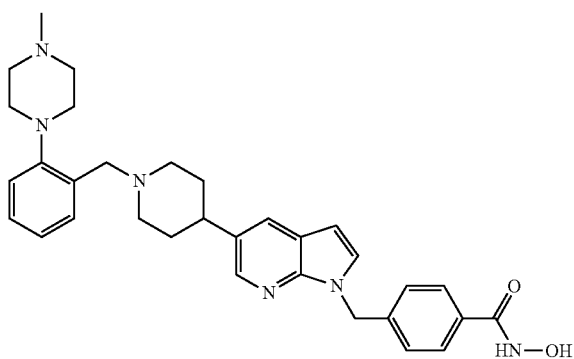
885 886
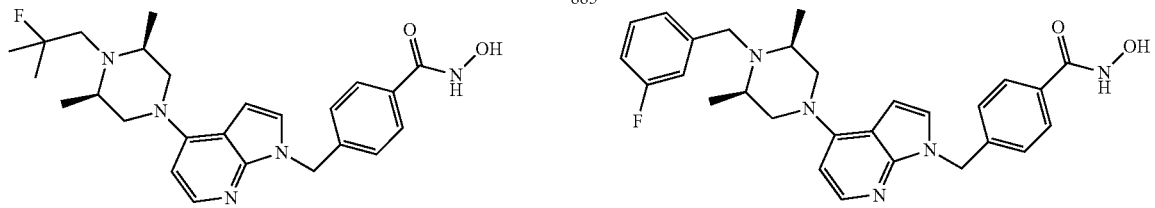
895
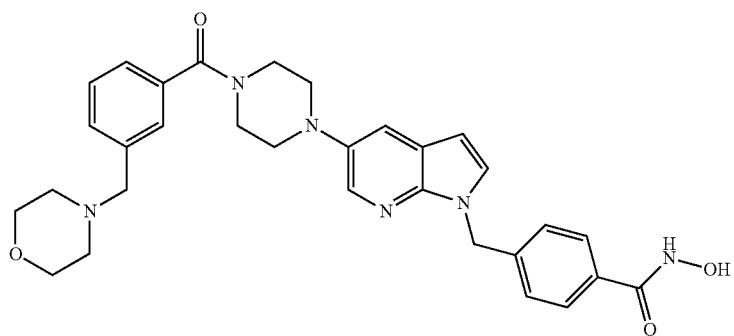

-continued
| | |
|---|---|
| 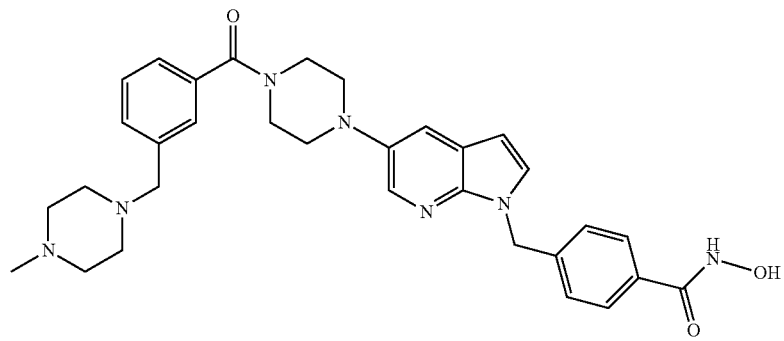 | 896 |
| 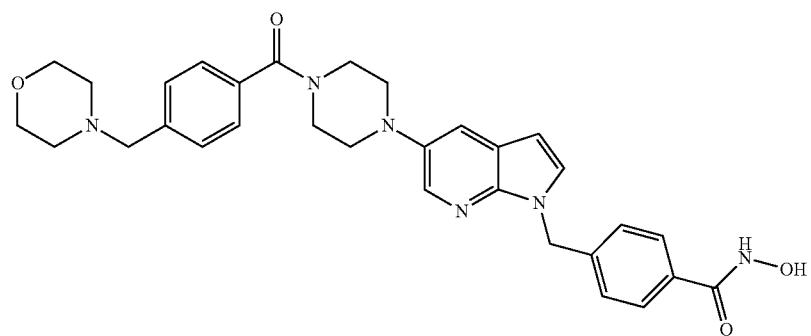 | 897 |
| 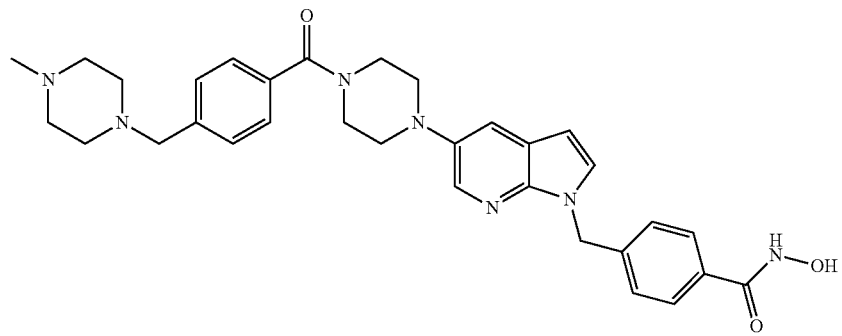 | 898 |
| 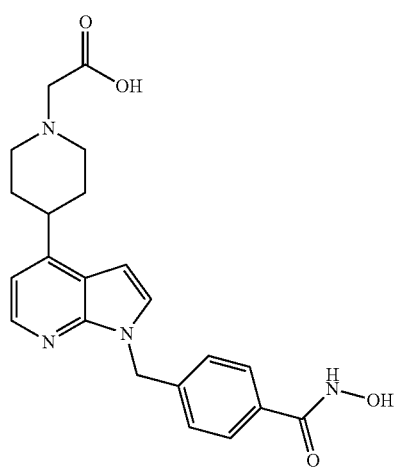  917 | 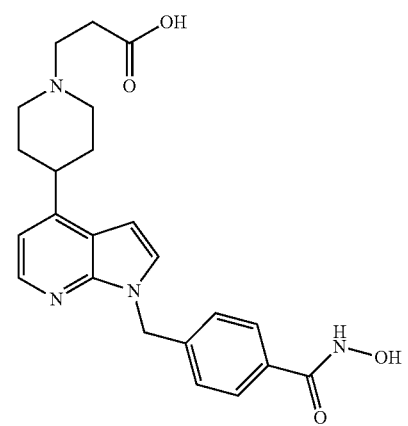  927 |

-continued
930
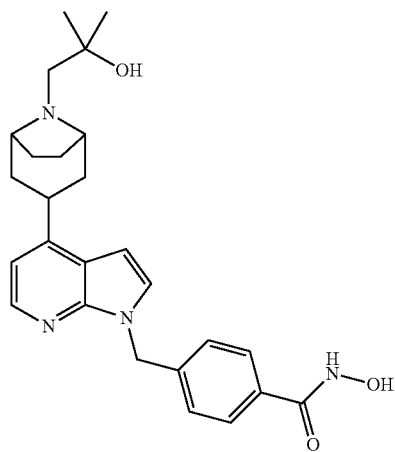
945
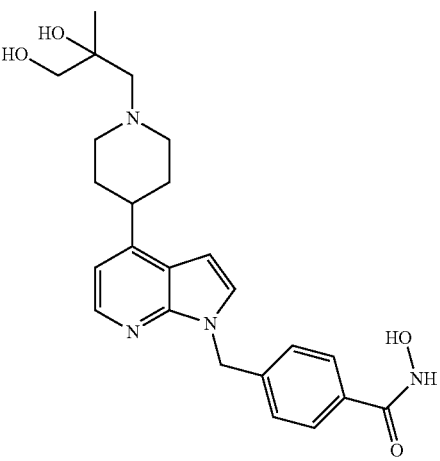
946
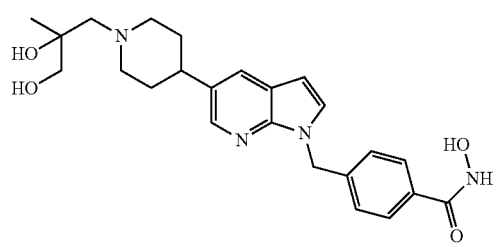
956
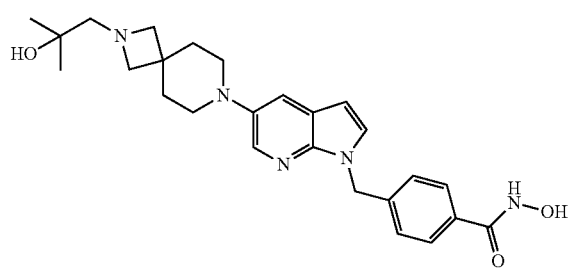
957
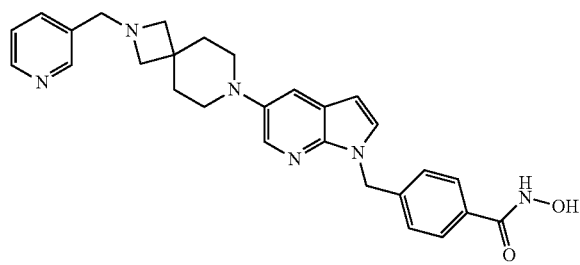
959
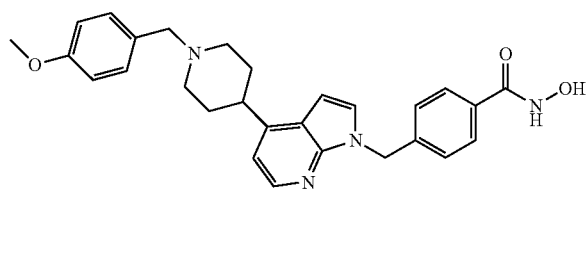
966
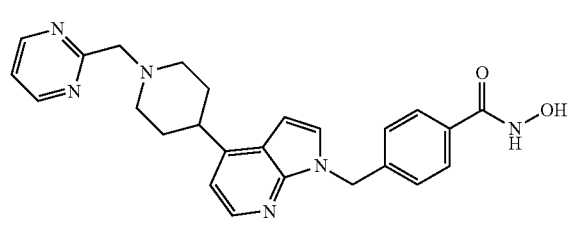
984
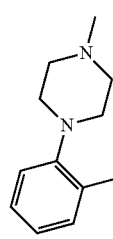
985
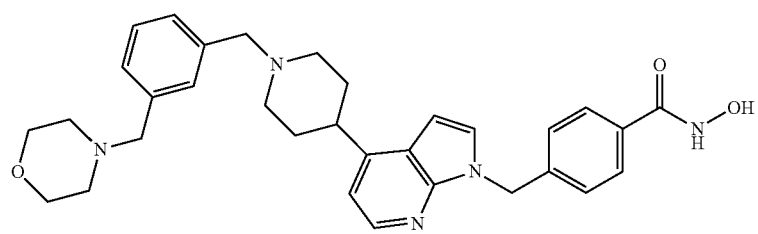

-continued
986
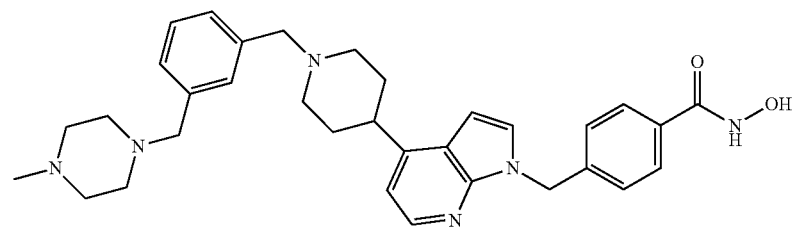
987
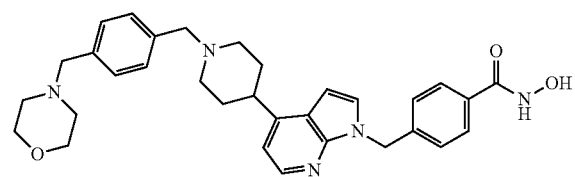
988
990
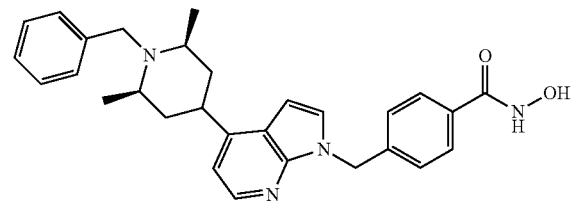
991
992
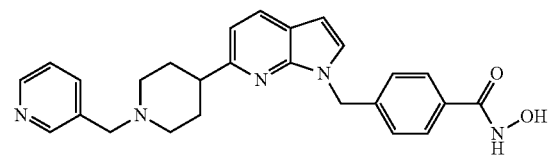
1003
1004
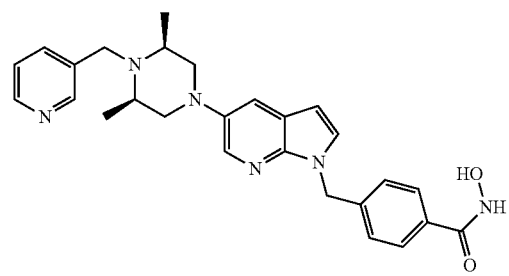
1005
1014
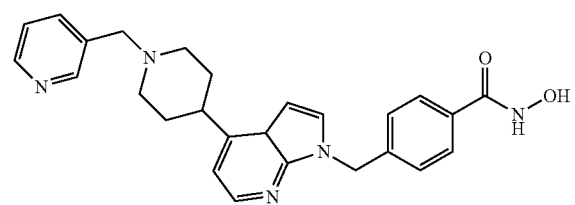
1015
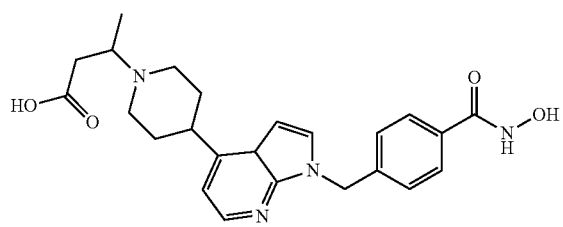

-continued
1017
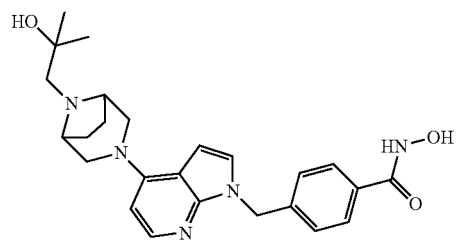
1018
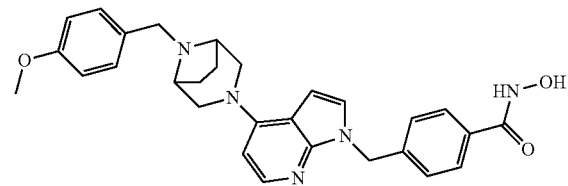
1019
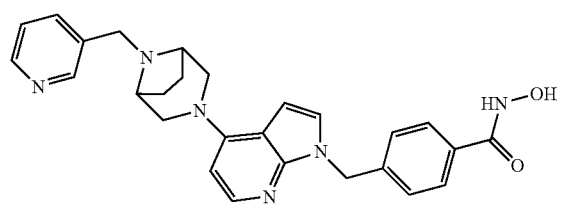
1020
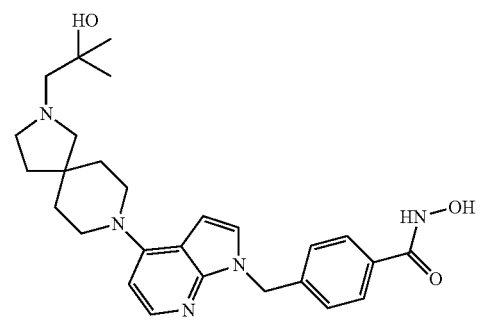
1021
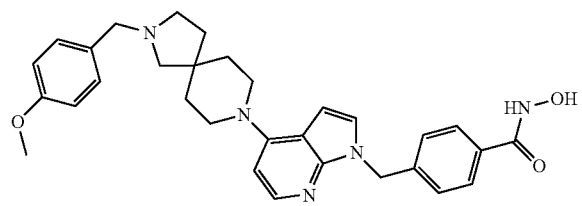
1022
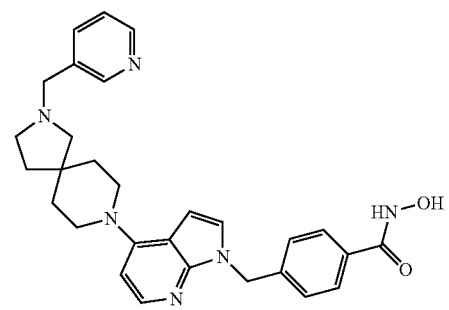
1023
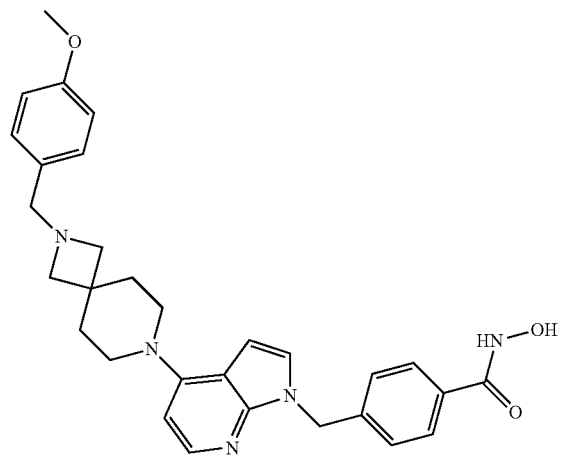
1024
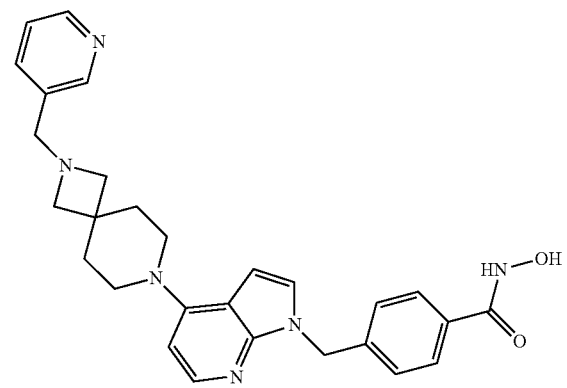

-continued
1025
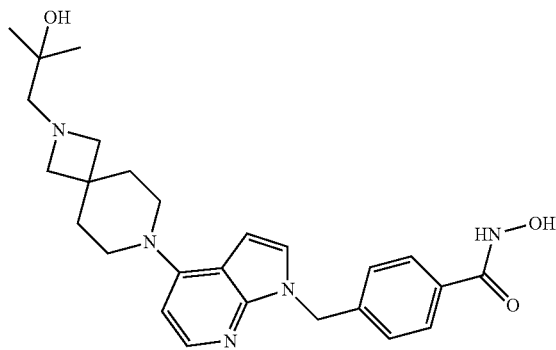
1028
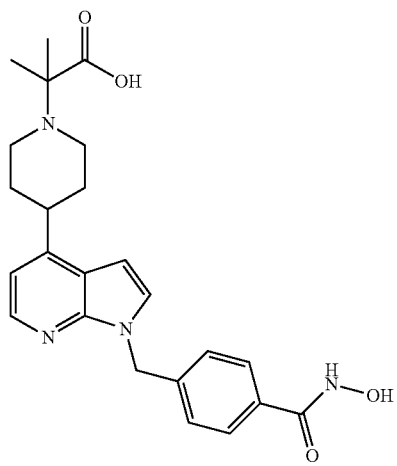
1098
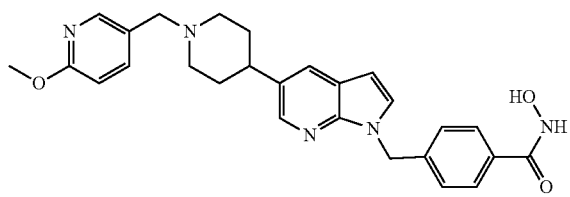
1101
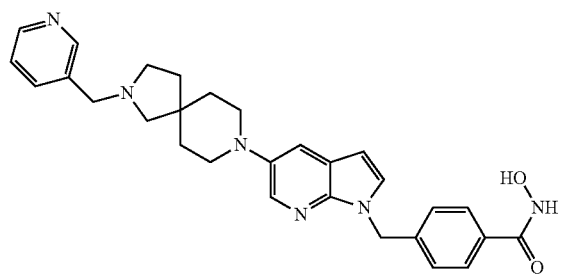
1125
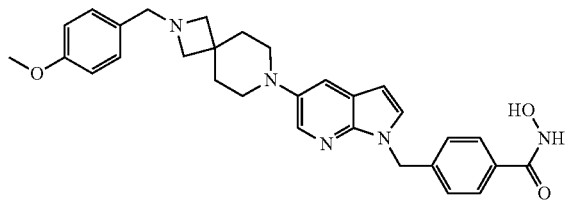
1126
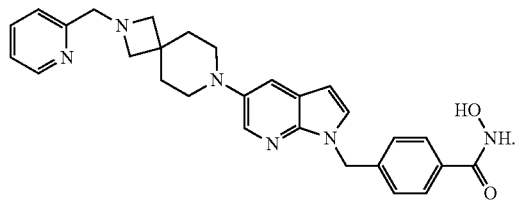
9. The compound of formula I, isomer thereof, or pharmaceutically acceptable salt thereof according to claim 8, wherein the compound of formula I is selected from the group consisting of the following compounds:
223
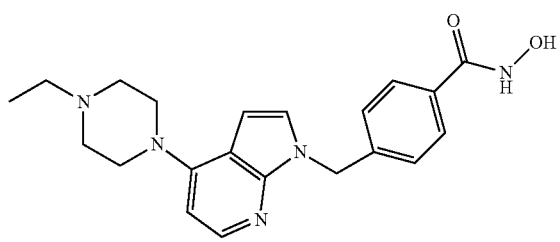
224
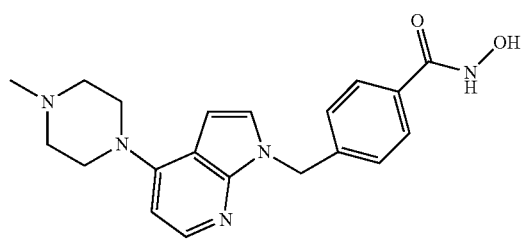
225
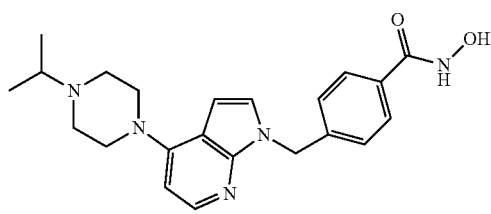
618
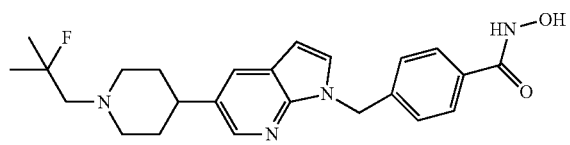

-continued
635
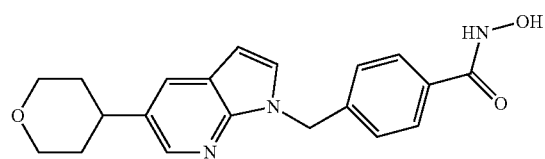
636
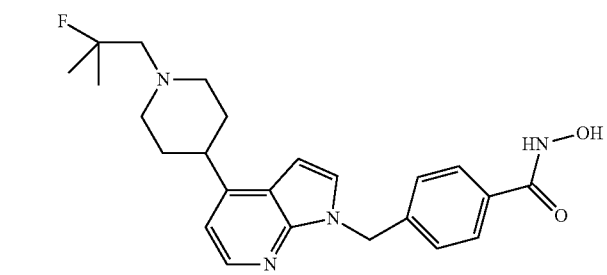
642
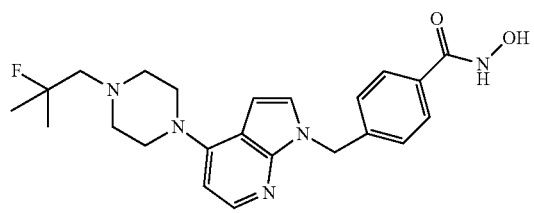
704
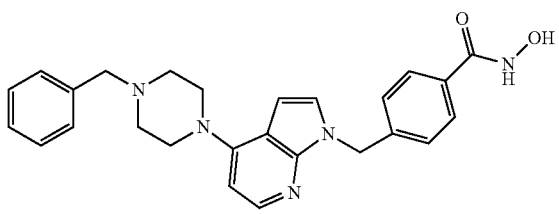
705
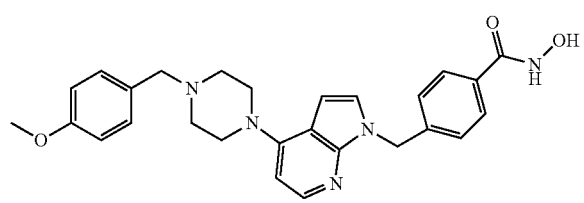
706
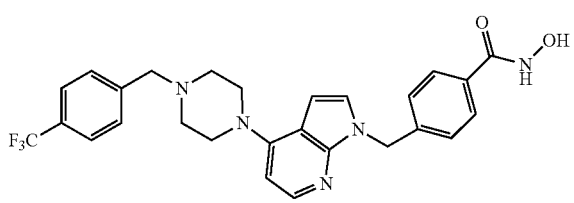
714
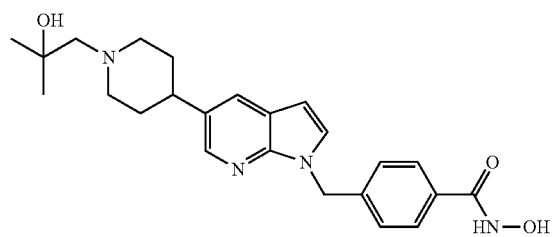
724
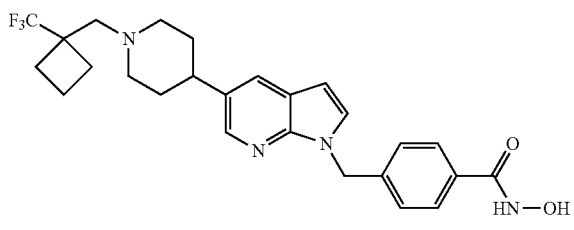
781
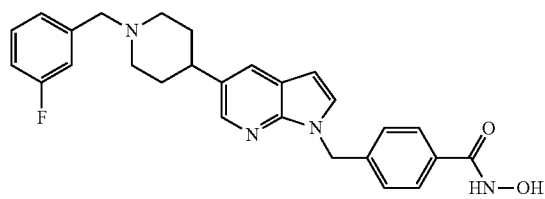
806
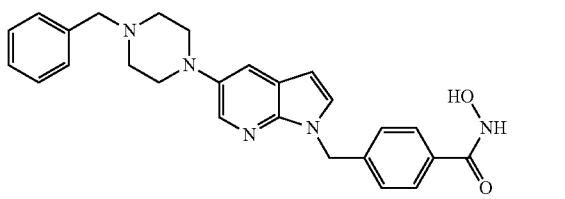
830
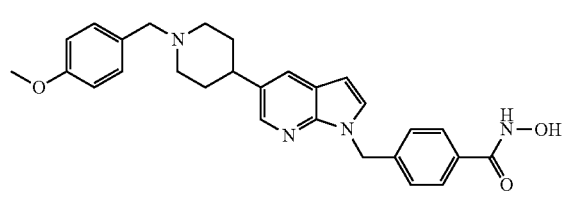
840
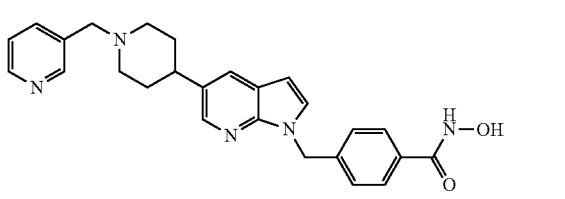
841
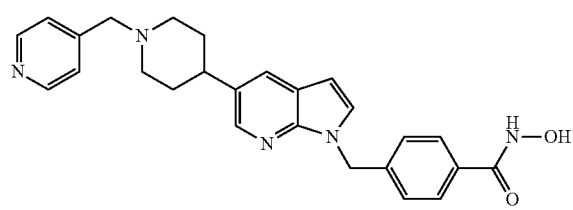
842
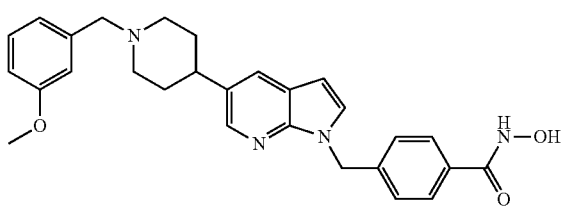

-continued
843
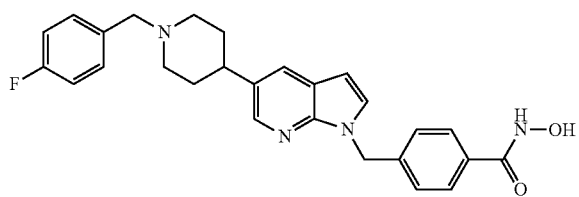
844
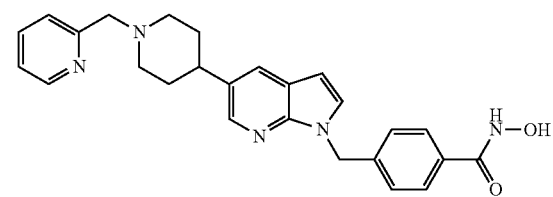
846
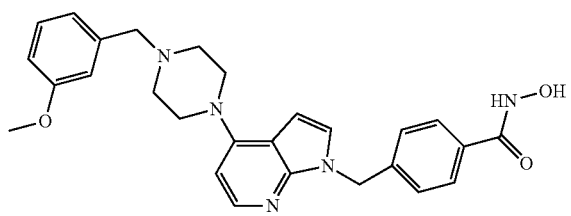
848
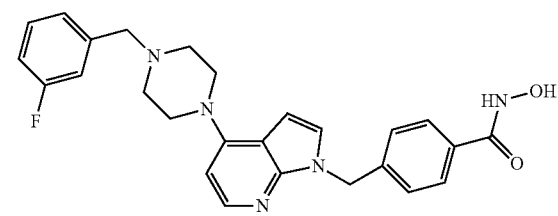
851
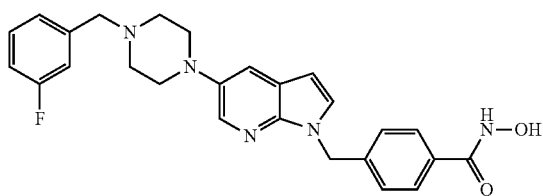
852
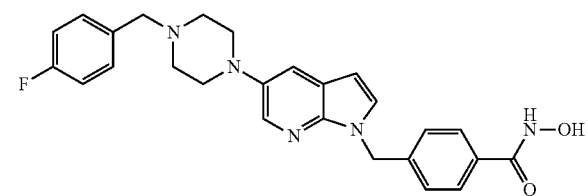
853
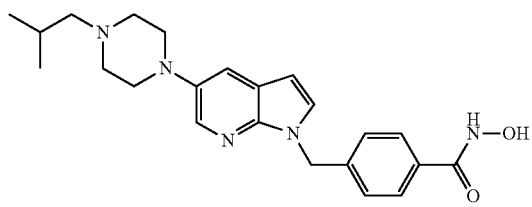
857
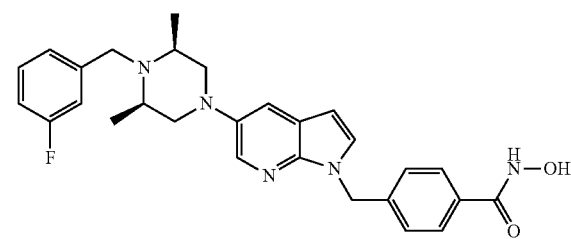
862
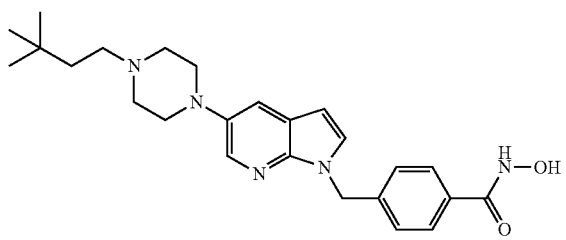
863
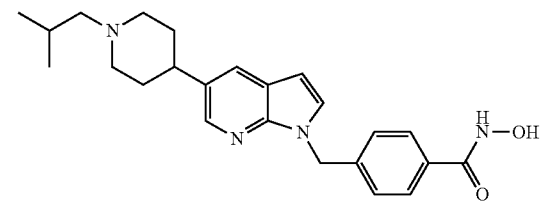
864
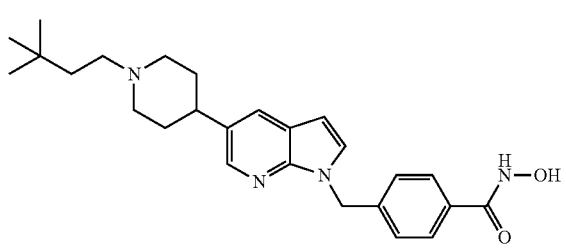
865
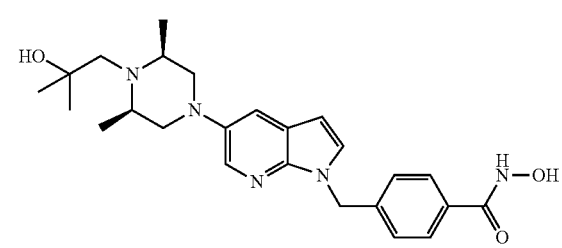

US 9,650,379 B2
437 438
-continued
878
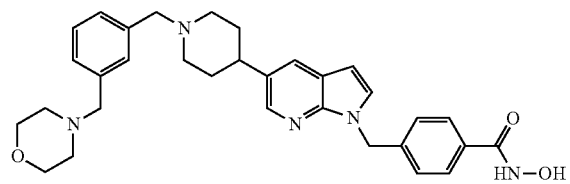
879
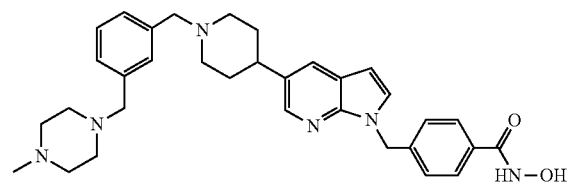
881
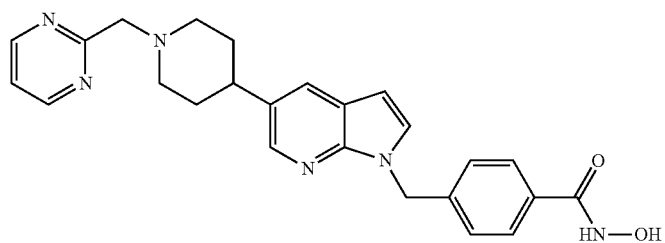
882
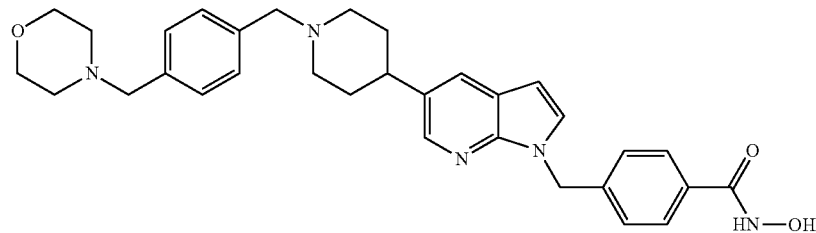
883
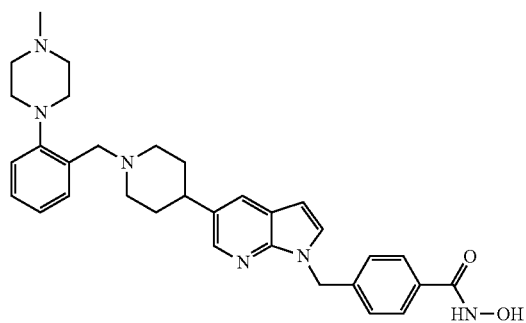
957
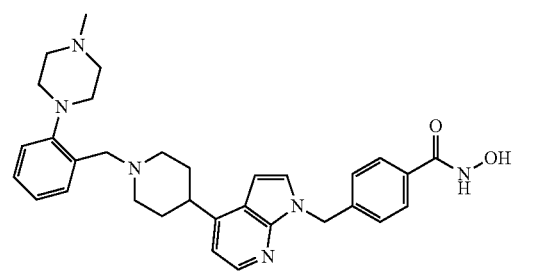
959
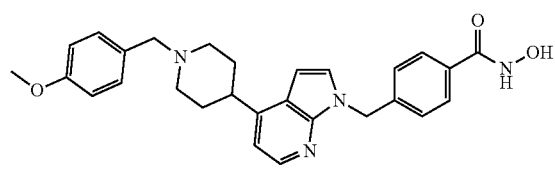
984
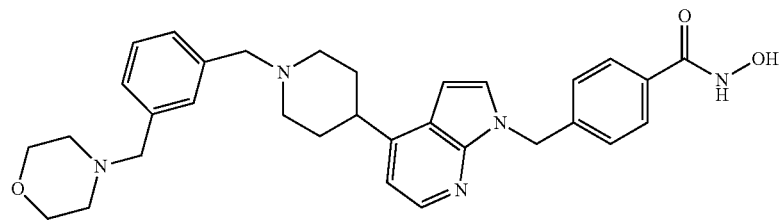
985

-continued

986
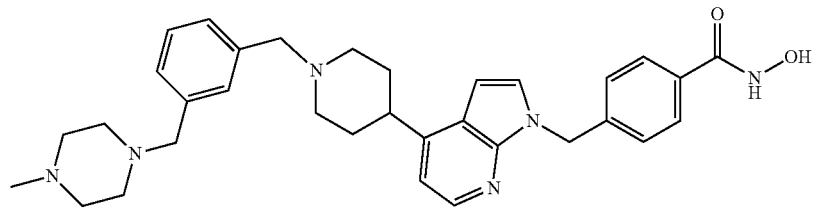

990
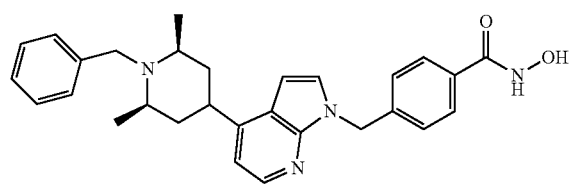

1017
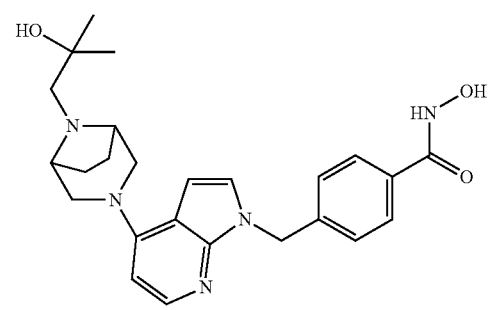

1021
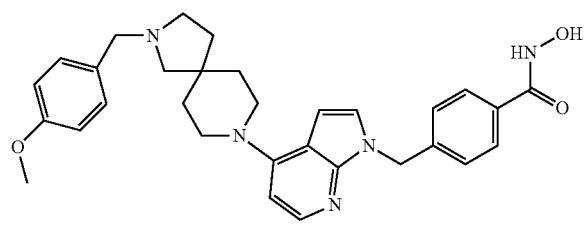

1023
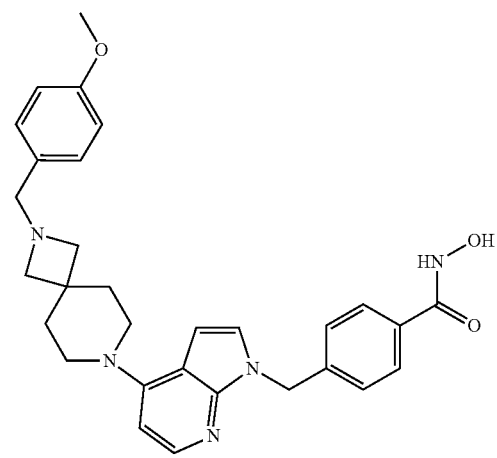

1101
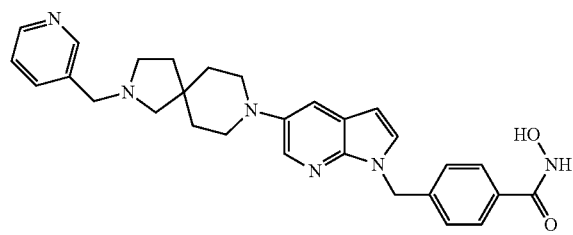

1126
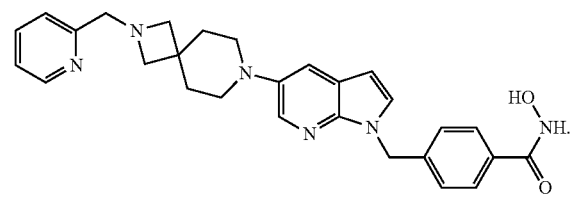

10. A pharmaceutical composition comprising a compound of formula I, isomer thereof, or pharmaceutically acceptable salt thereof according to claim 1, together with a pharmaceutically acceptable carrier.

11. The pharmaceutical composition of claim 10, which is for treatment of malignant tumor diseases, inflammatory diseases, rheumatoid arthritis, or neurodegenerative diseases in a mammal.

12. A method of treating malignant tumor diseases, inflammatory diseases, rheumatoid arthritis, or neurodegenerative diseases in a mammal, the method comprising administering to a mammal in need of such treatment an effective amount of the pharmaceutical composition according to claim 10.

13. The method of claim 11, wherein the mammal is a human.

14. The method of claim 12, wherein the mammal is a human.

* * * * *